(12) United States Patent
Manuguerra et al.

(10) Patent No.: US 10,209,248 B2
(45) Date of Patent: *Feb. 19, 2019

(54) MULTIPLEX IMMUNO SCREENING ASSAY

(71) Applicant: Institut Pasteur, Paris (FR)

(72) Inventors: Jean-Claude Manuguerra, Paris (FR); Jessica Vanhomwegen, Paris (FR); Philippe Despres, La Garenne-Colombes (FR); Sylvie Paulous, Sarcelles (FR)

(73) Assignee: Institut Pasteur, Paris (FR)

( * ) Notice: Subject to any disclaimer, the term of this patent is extended or adjusted under 35 U.S.C. 154(b) by 6 days.

This patent is subject to a terminal disclaimer.

(21) Appl. No.: 15/653,949

(22) Filed: Jul. 19, 2017

(65) Prior Publication Data
US 2017/0336412 A1    Nov. 23, 2017

Related U.S. Application Data

(63) Continuation of application No. 14/396,841, filed as application No. PCT/EP2013/059312 on May 3, 2013.

(Continued)

(30) Foreign Application Priority Data

Dec. 10, 2012 (WO) .................. PCT/EP2012/74986

(51) Int. Cl.
*G01N 33/53* (2006.01)
*C12Q 1/70* (2006.01)
(Continued)

(52) U.S. Cl.
CPC . *G01N 33/54306* (2013.01); *G01N 33/54313* (2013.01); *G01N 33/54353* (2013.01);
(Continued)

(58) Field of Classification Search
None
See application file for complete search history.

(56) References Cited

U.S. PATENT DOCUMENTS

| 5,356,713 A | 10/1994 | Charmot et al. |
| 6,649,414 B1 | 11/2003 | Chandler et al. |

(Continued)

FOREIGN PATENT DOCUMENTS

| WO | 02/083937 A2 | 10/2002 |
| WO | 2012/076715 A1 | 6/2012 |
| WO | 2013/083847 A2 | 6/2013 |

OTHER PUBLICATIONS

Batra et al., "Evaluation of envelope domain III-based single chimeric tetravalent antigen and monovalent antigen mixtures for the detection of anti-gengue antibodies in human sera,"BMC Infectious Diseases 11:64 (Year: 2011).*

(Continued)

*Primary Examiner* — Janet L Andres
*Assistant Examiner* — M Franco G Salvoza
(74) *Attorney, Agent, or Firm* — Arrigo, Lee, Guttmann & Mouta-Bellum LLP

(57) ABSTRACT

The present invention provides an immunoassay leading to the rapid and simultaneous detection of antibodies to a wide range of infectious pathogens in biological fluids of infected patients. This immunoassay involves the covalent and oriented coupling of fusion proteins comprising an AGT enzyme and a viral antigen on an identifiable solid support (e.g. fluorescent microspheres). The thus obtained antigen-coupled microspheres show enhanced capture of specific antibodies as compared to antigen-coupled microspheres produced by standard amine coupling procedures.

Figure 1:
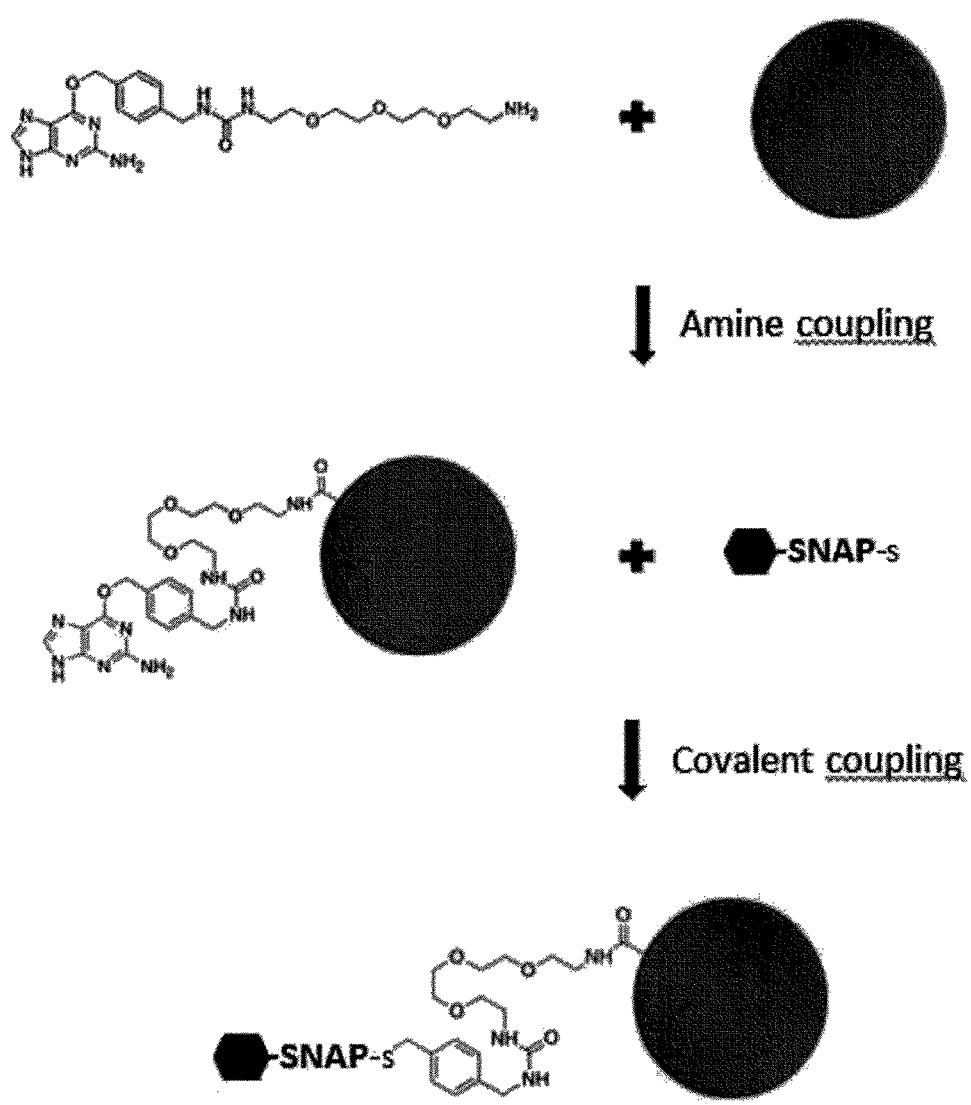

9 Claims, 73 Drawing Sheets
Specification includes a Sequence Listing.

Related U.S. Application Data

(60) Provisional application No. 61/642,924, filed on May 4, 2012.

(51) Int. Cl.

| | |
|---|---|
| *G01N 33/542* | (2006.01) |
| *G01N 33/00* | (2006.01) |
| *G01N 33/536* | (2006.01) |
| *G01N 33/543* | (2006.01) |
| *G01N 33/569* | (2006.01) |
| *G01N 33/564* | (2006.01) |
| *G01N 33/68* | (2006.01) |

(52) U.S. Cl.
CPC ..... *G01N 33/564* (2013.01); *G01N 33/56983* (2013.01); *G01N 33/6845* (2013.01); *G01N 2333/18* (2013.01); *G01N 2333/185* (2013.01); *G01N 2469/20* (2013.01); *Y02A 50/51* (2018.01); *Y02A 50/53* (2018.01); *Y02A 50/56* (2018.01); *Y02A 50/58* (2018.01); *Y02A 50/60* (2018.01)

(56) References Cited

U.S. PATENT DOCUMENTS

| | | | |
|---|---|---|---|
| 8,227,602 | B2 | 7/2012 | Gautier et al. |
| 9,109,219 | B2 | 8/2015 | Despres et al. |
| 9,546,380 | B2 | 1/2017 | Manuguerra et al. |
| 9,638,692 | B2 | 5/2017 | Manuguerra et al. |
| 2006/0188982 | A1* | 8/2006 | Johnson ........... G01N 33/56983 435/345 |
| 2006/0292651 | A1 | 12/2006 | Juillerat |
| 2010/0009872 | A1 | 1/2010 | Eid |
| 2014/0274762 | A1 | 9/2014 | Manuguerra |
| 2015/0099656 | A1 | 4/2015 | Despres et al. |
| 2017/0088843 | A1 | 3/2017 | Despres et al. |
| 2017/0276672 | A1 | 9/2017 | Manuguerra et al. |
| 2018/0038852 | A1 | 2/2018 | Manuguerra et al. |

OTHER PUBLICATIONS

Cho et al., "Expression and Evaluation of Chikungunya Virus E1 and E2 Envelope Proteins for Serodiagnosis of Chikungunya Virus Infection," Yonsei Med J 49(5):828-835 (Year: 2008).*
Avrameas S. immunol. Today May 1991;12(5):154-9.
Damoiseaux et at., ChemBiochem. 4:285-287, 2001.
Xu-Welliver et at., Biochemical Pharmacology 58: 1279-85, 1999.
Lim A. et at, EMBO J. 15: 4050-4060, 1996.
Daniels D.S. et at, EMBO J. 19: 1719-1730, 2000.
Juillerat A. et at, Chemistry & Biology, vol. 10, 313-317, 2003.
Wong et al Journal of Clinical Microbiology 42, No. 1 (Jan. 2004): 65-72.
Wibley J.E.A. et at, Nucleic Acids Research, vol. 28, No. 2, pp. 393-401, 2000.
Feigner et at., Proc. Natl. Acad. Sci. U.S.A., 84:7413-7417, 1987.
Machy et at., Proc. Natl. Acad. Sci. U.S.A., 85:8027-8031, 1988.
Wilson et at., J. Biol. Chem., 267:963-967, 1992.
Wu and Wu, J. Biol. Chem., 263:14621-14624, 1988.
Williams et at., Proc. Natl. Acad. Sci. U.S.A., 88:2726-2730, 1991.
Kolpe A.B. et at, Virus Research 2012; 168:64-72.
Pan W. et at, The Journal of Immunology, 2004), 172:6167-6174.
Sivakolundu S. et at, Journal of Medical Microbiology, 2012.
Pickering et at., Clinical and Diagnostic Laboratory Immunology 9:872-876 (2002).
Anderson et at., Methods Mot. Biol. 723:227-238 (2011).
Tainsky et al., Biomarker Insights 2:261-267 (2007).
Waterboer et al., J. Immunol Methods 309:200-204 (2006).
Burbelo et at., Exp. Rev Vaccines, 9:567-578 (2010).
Ambrosino et at., Malaria Journal 9:317 (2010).
Cham et at., Malaria Journal 7:108 (2008).
Miller and Rosman, BioTechniques, 7:980-990, 1992.
Brinster et at., Nature, 296:39-42, 1982.
Lastowski-Perry et at, J.Biol. Chem. 260: 1527 (1985).
B.J.Bond et at, Mol. Cell. Biol. 6:2080 (1986).
Hellwig, S. al., Nat. Biotechnol.2004; 22(11):1415-22.
Neuman de Vegvar H.E. et al, Clinical Immunology, vol. 111, pp. 196-201 (2004).
Kindermann M. et at, Journal of the American Chemical Society, vol. 125, pp. 7810-7811 (2003).
Kufer K. et at, European Biophysics Journal, vol. 35, pp. 72-78 (2005).
Engin S. et at, Langmuir, vol. 26, No. 9, pp. 6097-6101 (2010).
Brecht et at, SBS 12th annual conference and Exhibtion Advancing Drug Discovery, 2006.
Robinson WH et al, Nature Medicine, vol. 8, No. 3, pp. 292-301 (2002).
Andresen H. et at, Current proteomics, vol. 6, pp. 1-12 (2009).

* cited by examiner

Figure 6

Figure 7
Figure 7A
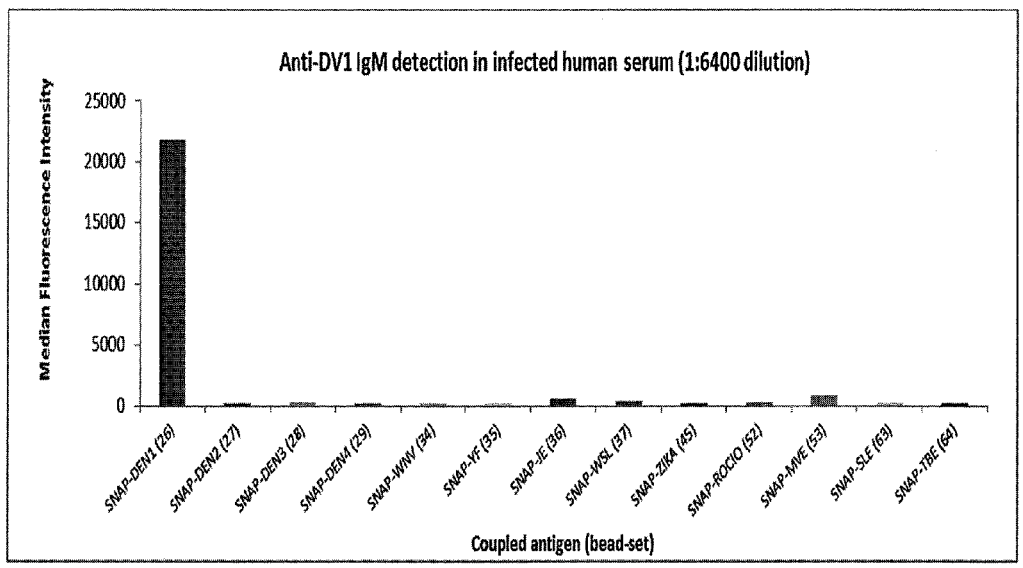
Figure 7B
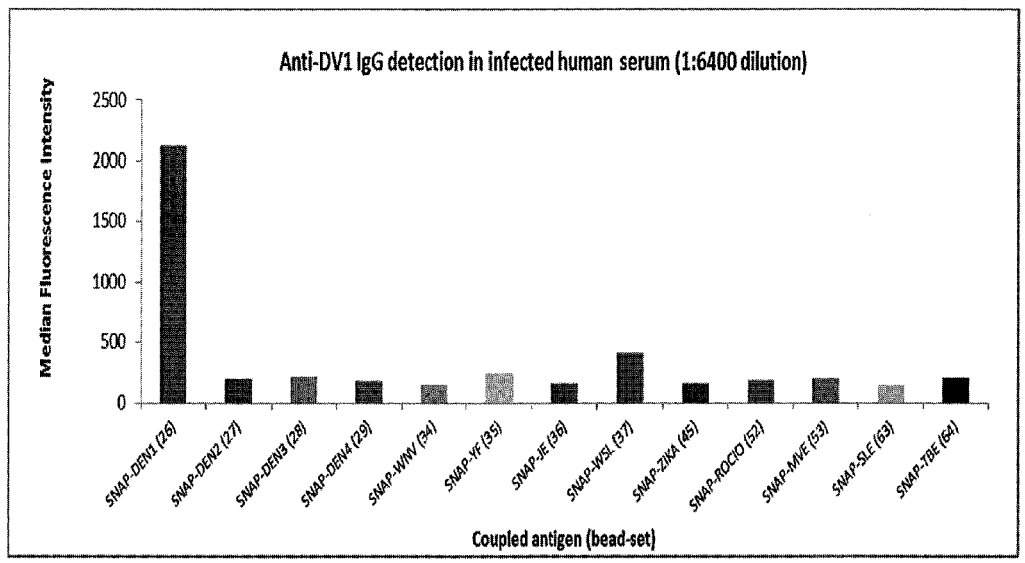

Sequence of chimeric DeSNAPuniv-SARS N protein

Vector:    pDeSNAPuniv. Insertion sites of the SARS N sequence are underlined.

```
BmtI
NruI      NheI                                                              BglII
 |         |                                                                  |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G     < 100
 S   R   A   S   T   M   K   L   C   I   L   L   A   V   V   A   F   V   G   L   S   L   P   T   A   L   A   R   S   D   K   D   C   E
                 10                  20                  30                  40                  50                  60                  70                  80                  90
                 Signal peptide of SNAP                                                                                                                            SNAP sequence >BmrI
                                                                                |
AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC    < 200
 M   K   R   T   T   L   D   S   P   L   G   K   L   E   L   S   G   C   E   Q   G   L   H   E   I   K   L   L   G   K   G   T   S
                 110                 120                 130                 140                 150                 160                 170                 180                 190

PflMI
                                                                      |
T GCT GCT GAT GCA GTT GAA GTT CCA GCA GCA CCA GCA GCT GTT CTT GGA GGT CCT GAG CCC CTC ATG CAA GCC ACA GCC TGG CTT AAC GCA TAT TTC CAC CAG    < 300
 A   A   D   A   V   E   V   P   A   A   P   A   A   V   L   G   G   P   E   P   L   M   Q   A   T   A   W   L   N   A   Y   F   H   Q
                 210                 220                 230                 240                 250                 260                 270                 280                 290

<RpaB5I
                                       |
CCT GAG GCC ATT GAG GAA TTT CCA GAC GTC CCC GCC CTT CAC CAT CCT GTG TTT CAG GAG AGC TTC ACC CGC CAG CTG TTT CAG GAG GTC CTG TGG AAA TTG CTG AAG GTG G    < 400
 P   E   A   I   E   E   F   P   D   V   P   A   L   H   H   P   V   F   Q   E   S   F   T   R   Q   L   F   Q   Q   V   L   W   K   L   L   K   V   V
                 310                 320                 330                 340                 350                 360                 370                 380                 390
```

FIGURE 12A

```
                                                                                                                                                          >AlfI
TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT    < 500
 K  F  G  E  V  I  S  Y  Q  Q  L  A  A  L  A  G  N  P  A  A  T  A  A  V  K  T  A  L  S  G  N  P  V
        410          420          430          440          450          460          470          480          490
                                                     BspEI                                                                           BspHI
                                                      |                                                                                |
G CCC ATC CTG ATC CCT TGT CAC AGA GTC TTC TCA TCT GGA GCT GTA GGT GGC TAT GAA GGA GGA CTG GCA GTT AAG GAG TGG CTG GCT CAT GAA          < 600
 P  I  L  I  P  C  H  R  V  F  S  S  G  A  V  G  G  Y  E  G  G  L  A  V  K  E  W  L  A  H  E
        510          520          530          540          550          560          570          580          590
                <BseYI                       BssHII
                <GsaI                        McaTI                                                                      EcoRV
                 |                           AscI           SanDI                       BamHI                             |
GGT CAT AGA CTT GGA AAG CCT GGG CTG GGT CCT GCT GGT ATA GGC GCG CCA TCC GAA AAC CTG TAC TTC CAG AGC gat atc t              < 700
 G  H  R  L  G  K  P  G  L  G  P  A  G  I  G  A  P  S  E  N  L  Y  F  Q  S  D  I  S
        610          620          630          640          650          660          670          680          690
                                                                                               proTEV cleavage site
ct gat aat gga ccc caa tca aac caa cgt agt gcc cct cgc att aca ttt ggt gga cct aca gat tca act gac aat aac cag aat gga ggt cgc aat gg   < 800
 D  N  G  P  Q  S  N  Q  R  S  A  P  R  I  T  F  G  G  P  T  D  S  T  D  N  N  Q  N  G  G  R  N  G
        710          720          730          740          750          760          770          780          790

Mutated N protein from SARS coronavirus

FIGURE 12B
```

```
                                                                                              XhoI
                                                                                              SciI
                                                                                              PspXI
                                                                                              AbsI
                                                                                              ||
t gca agg cca aag cag cgc cga cct caa ggt tta cct aat aat act gcg tct tgg ttc aca gct ctc act cag cat ggc aag gag gaa ctt aga ttc cct  < 900
  A   R   P   K   Q   R   R   P   Q   G   L   P   N   N   T   A   S   W   F   T   A   L   T   Q   H   G   K   E   E   L   R   F   P
           810             820             830             840             850             860             870             880             890
                          >BsbI                                                                        <SapI               Hpy99I
                                                                                                        |                    |
cga ggc cag ggc gtt cca aac acc atc aac agt ggt cca gat gac caa gat att ggc tac tac cga aga gct acc cga gtt cgt ggt gac ggc aaa a   < 1000
  R   G   Q   G   V   P   N   T   I   N   S   G   P   D   D   Q   D   I   G   Y   Y   R   R   A   T   R   V   R   G   G   D   G   K
           910             920             930             940             950             960             970             980             990
 Eco53kI
 BsiHKAI
 SacI                                                    >FalI                                                                       >CdiI
  |                                                       |                                                                           |
tg gag gag ctc agc cct aga tgg tac ttc tat tac cta gga act ggc cca gaa gcc tca ctt cct tac ggc gct aac aag gaa ggc atc gta tgg gtt gc < 1100
  K   E   L   S   P   R   W   Y   F   Y   Y   L   G   T   G   P   E   A   S   L   P   Y   G   A   N   K   E   G   I   V   W   V   A
         1010            1020            1030            1040            1050            1060            1070            1080            1090
                                                         BanI                                                         <AquIV
                                                          |                                                             |
a act gag gga gcc ttg aat aca cct aag gac cac att ggc acc aat cct cgc aat aac aat gcc acc gtg cta caa cct caa gga aca aca ttg gc  < 1200
  T   E   G   A   L   N   T   P   K   D   H   I   G   T   N   P   R   N   N   N   A   T   V   L   Q   L   P   Q   G   T   T   L
         1110            1120            1130            1140            1150            1160            1170            1180            1190
                                                                             <AquIII
                                                                             <BseRI         BsaAI
                                                                              |               |
cct aag ggc ttc tac gca gag gga ggc agc agt caa gcc tct tct tca tcc tca cgt agt cgt ggt aat tca aga aat tca act cct ggc a  < 1300
  P   K   G   F   Y   A   E   G   G   S   S   Q   A   S   S   S   S   S   R   S   R   G   N   S   R   N   S   T   P   G   S
         1210            1220            1230            1240            1250            1260            1270            1280            1290
```

FIGURE 12C

```
                                                                                                        MscI
                                                                                                         |
gc agt agg gga aat tct cct gct cga atg gcc agc gga ggt ggt gaa act gcc ctc gcg cta ttg ctg cta gac aga ttg aac cag ctt gag agc aaa gt  < 1400
 S  R  R  G  N  S  P  A  R  M  A  S  G  G  G  E  T  A  L  A  L  L  L  D  R  L  N  Q  L  E  S  K  V
      1310         1320         1330         1340         1350         1360         1370         1380         1390

<BbvCI
                                                                      -
t tct ggt aag ggc cag caa cag cag ggc cag caa act gtc act aag aag tct gct gct gag gca tct aag aag cct cgc caa aag cgt act gcc aca aag cag  < 1500
 S  G  K  G  Q  Q  Q  Q  G  Q  Q  T  V  T  K  K  S  A  A  E  A  S  K  K  P  R  Q  K  R  T  A  T  K  Q
      1410         1420         1430         1440         1450         1460         1470         1480         1490

<BmgBI          PasI
                  -               -
tac aac gtc act caa gca ttc ggc aga cgt ggt cca gaa cag acc cag gga aat ttc ggt gac caa gac cta atc aga cag gga act gat tac aag cat t  < 1600
 Y  N  V  T  Q  A  F  G  R  R  G  P  E  Q  T  Q  G  N  F  G  D  Q  D  L  I  R  Q  G  T  D  Y  K  H
      1510         1520         1530         1540         1550         1560         1570         1580         1590

MslI
                                                                     -
gg ccg cag att gca cag ttc gct cca agt gcc tct gca ttc ttc gga atg tca cgc att ggc atg gaa gtc aca cct tcg gga aca tgg ctg act tat ca  < 1700
 P  Q  I  A  Q  F  A  P  S  A  S  A  F  F  G  M  S  R  I  G  M  E  V  T  P  S  G  T  W  L  T  Y  H
      1610         1620         1630         1640         1650         1660         1670         1680         1690

BstXI          >RleAI                                                                 >MaqI
     -              -                                                                     -
t gga gcc att aag ttg gat gac aag gac cca cag ttc aag gac aac aag gac cac att gac ctg aac aag cac att gac gca tac aaa ttc cca aca gag  < 1800
 G  A  I  K  L  D  D  K  D  P  Q  F  K  D  N  K  D  H  I  D  L  N  K  H  I  D  A  Y  K  F  P  P  T  E
      1710         1720         1730         1740         1750         1760         1770         1780         1790
```

FIGURE 12D

```
TCGCGAGCTAGCACCATGAAACTATGTATTCTACTTGCAGTTGTTGCGTTCGTAGGATTGTCCTTACCTACAGCTCTGGC
AAGATCTGACAAAGACTGCGAAATGAAAAGAACTACATTGGATTCACCACTTGGGAAGTTGGAACTGAGTGGATGCGAGC
AAGGATTGCATGAAATTAAGCTACTGGGAAAAGGAACTTCTGCTGATGCAGTTGAAGTTCCAGCACCAGCAGCTGTT
CTTGGAGTCCTGAGCCCCTCATGCAAGCCACAGCCTGGCTTAACGCATATTTCACCAGCCTGAGGCCATTGAGGAATT
TCCAGTCCCCGCCCTTCACCATCCTGTGTTCAGCAGGAGAGCTTCACCCGCCAGTCCTGTGGAAATTGCTGAAGGTGG
TCAAGTTTGGTGAAGTGATTTCATATCAGCAACTTGCTGCATTGGCCGGTAACCCCGCAGCTACAGCTGCCGTGAAAACT
GCTCTCAGCCGGAAATCCTGCCCATCCTGATCCCTTGTCACAGAGTCGTTTCATCTTCCGGAGCTGTAGGTGGCTATGA
AGGAGGACTGCCAGTTAAGGACTGCTGGCTCGTGGCGATCCGAAAACCTGTACTTCCAGACGATATCTCTGATAATGGACCCCAATCA
TAGGCGCGCCAGGGTCCCTAGGTGCCCCTCGCATTACATTTGTGGACCTACAGATTCAACTGACAATAACCAGAATGGAGGTCGCAATGG
AACCAACGTAGTGCGCCCTCGAGGCGCCGACCTCAAGGTTTACCTAATAATACTGCGTCTTGTTCACAGCTCTCACTCAGCATGGCA
TGCAAGGCCAAAGCAGCGCCCTCGAGGCCAGGCGTTCCAATCAACACCAATAGTGTCCAGATGCTCAGCCCTAGATGGTACTTCTATTACCTAGG
AGAGGAACTTAGATTCCCTCGACAGTCGTGGTGACGGCAAAATGAAGGAGCTCAGCCCTAGATGGTTGCAACTGAGGGAGCCTTGAATA
AACTGGGCCAGAAGCCTCACTTCCTTACGGCGCTAATCAGAGCGCAATCCTAATAACAATGCTACACCGTGCTACAACTTCCTCAAGGAACAACATTG
CACCTAAGGACCACATTGGCACCAGAGGAGCAGAGCGGCAGTCAAGCCTCAAGCCTCTCGCTCTCCATCACGTAGTCGCGGTAATTC
CCTAAGGGCTTCAACTCCTGGCAGCAGTAGGGGAAATTCTCCTGCTCGAATGGCCAGCCGAGGTGGTGAACAGCAGGGCCAAACTGTCACT
AAGAAATTCAACTCCTGGCAGCAGTAGGGGAAATTCTCCTGCTCGAATGGCCAGCCGAGGTGGTGAACAGCAGGGCCAAACTGTCACT
TATTGCTGCTAGACAGATTGAACCAGCTTGAAGAAGCCTCGCCAAAAGCGTACTGCCACAAAGCAGTACAACGTCACTCAAGCATT
AAGAAGTCTGCTGCTGAGGCATCTAAGAAGACCCCAGGAAATTTCGGTGACCAAGACCTAATCAGACAGGGAACTGATTACAAGCATT
CGGCAGACCTGGTCCAGAACAGACCCCAGGGAAATTTCGGTGACCAAGACCTAATCAGACAGGGAACTGATTACAAGCATT
GGCCGCAGATTGCACACACTTCGCTCCAAGTGCCTCTGCATTCTTCGGAATGTCACGCATTGGCATGGAAGTCACACCTTCG
GGAACACATGCTGACTTATCATGGAGCCATTAAGTTGGATGACAAGACCCACAGTTCAAGGACAACGTCATACTGCTGAA
CAAGCACATTGACGCATACAAAACATTCCCAACAGAGCCTAAGAGGACCTAAGAAGAACAAGCCTGATGAAGCTCAGC
CTTTGCCAGAGACAAAAGAAGCAGCCCACTCTCTTCCTGCGCTGACATGGATGATTCTCCAGACAACTT
CAGAATTCATGAGTGGAGCTTCTGCTGATTCAACTCAGGCCCCGGAGAGAATCTATATTTTCAAGGGCCCGGGAGG
TAGTCACCATCATCACCATCACTAATGACCGGTGCGGCCGCAAGCTT
```

FIGURE 12F

Sequence of chimeric DeSNAP+SARS S-RBD

Vector: pMT/BiP/SNAP. Insertion sites of the RBD sequence are underlined.

```
BmtI
 NruI                                                              NheI                                                                      BglII
  |                                                                  |                                                                         |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G    < 100
 S   R   A   S   T   M   K   L   C   I   L   L   A   V   V   A   F   V   G   L   S   L   P   T   A   L   A   R   S   D   K   D   C   E
                   10                  20                  30                  40                  50                  60                  70                  80                  90

Signal peptide of chimeric protein                                                      SNAP sequence >BmrI
                                       <MmeI                                                                                                  |
AA ATG AAA AGA ACT ACA TTG GAT TCA CCA CTT GGG AAG CTG GAA CTG AGT GGA TGC GAG CAA GGA TTG CAT GAA ATT AAG CTA CTG GGA AAA GGA ACT TC   < 200
 K   M   K   R   T   T   L   D   S   P   L   G   K   L   E   L   S   G   C   E   Q   G   L   H   E   I   K   L   L   G   K   G   T   S
        110                 120                 130                 140                 150                 160                 170                 180                 190

<PlaDI                            >Bpu10I                                      PflMI
T GCT GCT GAT GCA GTT GAA GTT CCA GCA GCA GCT GTT CTT GGA GGT CCT GAG CCC CTC ATG CAA GCC ACA GCC TGG CTT AAC GCA TAT TTC CAC CAG         < 300
 A   A   D   A   V   E   V   P   A   A   A   V   L   G   G   P   E   P   L   M   Q   A   T   A   W   L   N   A   Y   F   H   Q
      210                 220                 230                 240                 250                 260                 270                 280                 290

>BdaI
 Bsu36I              ApoI    <RpaB5I                                                                                                             |
CCT GAG GCC ATT GAG GAA TTT CCA GTC CCC CTT GCC CTG CAC CAT CCT GTG TTT CAG CAG GAG AGC TTC ACC CGC CAG GTC CTG TGG AAA TTG CTG AAG GTG G   < 400
 P   E   A   I   E   E   F   P   V   P   L   A   L   H   H   P   V   F   Q   Q   E   S   F   T   R   Q   V   L   W   K   L   L   K   V
        310                 320                 330                 340                 350                 360                 370                 380                 390

>AlfI                                        BstEII                      <BceAI
                                                                                                                     <BceFI                    <TstI
                                                                                                                                                 |
TC AAG TTT GGT GAA GTG ATT TCA TAT CAA CAA CTT GCT GCA TTG GCC GGT AAC CCC GCA GTG AAA ACT GCT CTC AGC GCT GTG GGA GAA AAT CCT GT       < 500
 K   F   G   E   V   I   S   Y   Q   Q   L   A   A   L   A   G   N   P   A   V   K   T   A   L   S   A   V   G   E   N   P   V
      410                 420                 430                 440                 450                 460                 470                 480                 490
```

FIGURE 13A

TCGCGAGCTAGCACCATGAAACTATGTATTCTACTTGCAGTTGTTGCGTTCGTAGGATTGTCCTTACCTACAGCTCTGGC
AAGATCTGACAAAGACTGCGAAATGCGAAATGAAAAGAACTACATTGGATTCACCACTTGGGAAGTTGGAACTGAGTGGATGCGAGC
AAGGATTGCATGAAATTAAGCTACTGGGAAAAGGAACTTCTGCTGCTGCTAACGCAGTTGAAGTTCCAGCACCAGCAGCTGTT
CTTGGAGGTCCTGAGCCCCTCAATGCAAGCCACAGCCTGGCTTAACGCATATTTCCACCAGCCTGAGGCCATTGAGGAATT
TCCAGTCCCCGCCCTTCACCATCCTGTGTTCAGCAGGAGAGCTTCACCCGCCAGGTCCTGTGAAATTGCTGAAGGTGG
TCAAGTTTGGTGAAGTGATTTCATATCAGCAACTTGCTGCATTGGCCGGTAACCCCGCAGCTACAGCTGCCGTGAAAACT
GCTCTCAGCGGAGAAATCCTGTGCCCATCCTGATCCCTTGTCACAGAGTCGTTTCATCTTCCGAGCTGTAGGTGGCTATGA
AGGAGGACTGGCAGTTAAGGAGTGGCTCCTGGCTCATGAAGGTCATAGACTTGGAAAGCCTGGGCTCCTCCTGTA
TAGGCGCGCCAGGGTCCCTAGGTGGGCGATCCGAAAAACCTGTACTTCCAGACGCGTAAGAAAATCTCAAATTGCGTGGCCGACTACTC
GAAGTGTTAACGCCACTAGTTCCCCAGCGTTTACGCTTGGAGCGTTACGGAGTTTCGCTACAAAGCTGAACGACCTGTGCTTCA
TGTGCTCTACAACAGCACTTTCTTTTGTGCTCAAGGGGAGACGATGTTCGCCAGAGATGTTCCCCTGGAACACTCGTAATATCGACGCTACCAGTAC
GCAACGTGTACGCTGATAGCTTTGTGGTCAAGGGGAGACGATGTTCGCCAGAGATGTTCCCCTGGAACACTCGTAATATCGACGCTACCAGTAC
GACTACAACTATAAACTGCCAGACGATTTCATGGGCTGTGTCCCTGGAACACTCGTAATATCGACGCTACCAGTAC
AGGAAACTACAATTACAAGTACCGTTACCTGCCGCCCCTGCCCTGAACTGCTACTGGCCACTCAACGACTACGGTTTCTATACCACA
TCTCCCCTGACGGTAAGCCATGTACACCCCCTGCCCTGAACTGCTACTGGCCACTCAACGACTACGGTTTCTATACCACA
ACTGGCATCGGCTACCAACCCTACAGAGTCGTTGTGCTCTCTTTCGAGTTGCTCCTGCCACAGTCCCGGGAGA
GAATCTATATTTTCAAGGGCCCCGGCGGAGGAGTAGTCACCATCATCACCATCACTAATGACCGGTGCGGCCCGCAAGCTT

FIGURE 13D

Sequence of chimeric DeSNAPuniv-huCOV.N (human coronavirus)

Vector: pDeSNAPuniv. Insertion sites of Gene N are underlined.

```
BmtI
 NruI      NheI                                                              BglII
  |         |                                                                  |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G  < 100
 S   R   A   S   T   M   K   L   C   I   L   L   A   V   V   A   F   V   G   L   S   L   P   T   A   L   A   R   S   D   K   D   C   E
                    10                  20                  30                  40                  50                  60                  70                  80                  90
                     Signal peptide of SNAP                                                                                                        SNAP sequence AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC  < 200
 M   K   R   T   T   L   D   S   P   L   G   K   L   E   L   S   G   C   E   Q   G   L   H   E   I   K   L   L   G   K   G   T   S
                   110                 120                 130                 140                 150                 160                 170                 180                 190
                                                                            <DraRI              >Bpu10I                          PflMI T GCT GAT GCA GTT GAA GTT CCA GCA GCA GCT GTT CTT GGA GGT GTT CTT GAG CCC CTC ATG CAA GCC ACA GCC TGG CTT AAC GCA TAT TTC CAC CAG     < 300
 A   A   D   A   V   E   V   P   A   A   A   V   L   G   G   V   L   E   P   L   M   Q   A   T   A   W   L   N   A   Y   F   H   Q
       210                 220                 230                 240                 250                 260                 270                 280                 290
                                                                                                                                                                        >BdaI
      HaeI                                                                                                                                                              >AcuI
 Bsu36I     ApoI            <RpaB5I                                                                                                                                        |
  |          |                |                                                                                                                                            |
CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG V  < 400
 P   E   A   I   E   E   F   P   V   P   A   L   H   H   P   V   F   Q   Q   E   S   F   T   R   Q   V   L   W   K   L   L   K   V   V
       310                 320                 330                 340                 350                 360                 370                 380                 390
                                                                                                                                       <BcefI
                       >AlfI                                           BstEII                                                          <BceAI
                         |                                               |                                                               |
TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT  < 500
 K   F   G   E   V   I   S   Y   Q   Q   L   A   A   L   A   G   N   P   A   A   T   A   A   V   K   T   A   L   S   G   N   P   V
       410                 420                 430                 440                 450                 460                 470                 480                 490
```

FIGURE 14A

```
ac act gga act ggg ccc gaa gca gca ctc cca ttc cgg gct gtt aag gat ggc atc gtt tgg gtc cat gaa gat ggc gcc act gat gct cct tca act tt    < 1100
 T  G  T  G  P  E  A  A  L  P  F  R  A  V  K  D  G  I  V  W  V  H  E  D  G  A  T  D  A  P  S  T  F
        1010         1020         1030         1040         1050         1060         1070         1080         1090
>HgaI                                                                  >CdiI                         SfoI
                                                                                                     NarI
                                                                                                     BsaHI
                                                                                                     BbeI
                                                                                                     HaeII
                                                                                                     KasI
                                                                                              MslI   LpnI  >BsaXI
                                                                                              BstXI
t ggg acg cgg aac cct aac gat tca gct att gtt aca caa ttc gcg ccc ggt act aaa ctt cct aaa aac ttc cac att gag ggg act gga ggc aat    < 1200
 G  T  R  N  P  N  D  S  A  I  V  T  Q  F  A  P  G  T  K  L  P  K  N  F  H  I  E  G  T  G  N
        1110         1120         1130         1140         1150         1160         1170         1180         1190
                              AflII  XmnI
                                    >EarI
agt caa tca tct tca aga gcc tct agc tta agc aga aac tct tcc agg tct agt tca caa ggt tca aga tca gga aac tct cgc act tct cca g    < 1300
 S  Q  S  S  S  R  A  S  S  L  S  R  N  S  S  R  S  S  S  Q  G  S  R  S  G  N  S  T  R  T  S  P  G
        1210         1220         1230         1240         1250         1260         1270         1280         1290
                                                                                                SacII
                                                                                                BtgI
gt cca tct gga atc gga gca gta gga ggt gat cta ctt tac ctt gat ctt ctg aac aga caa gcc ctt gag tct ggc aaa gta aag caa tcg cag cc    < 1400
 P  S  G  I  G  A  V  G  G  D  L  L  Y  L  D  L  L  N  R  Q  A  L  E  S  G  K  V  K  Q  S  Q
        1310         1320         1330         1340         1350         1360         1370         1380         1390
                                                                                                                    <Bbr7I
                                                                                                                    <BbsI
a aaa gta atc act aag aaa gat gct gct gct aaa aat aag atg cgc aag cgc act tcc acc aaa agt ttc aac atg gtg cag gct ttt ggt ctt    < 1500
 K  V  I  T  K  K  D  A  A  A  K  N  K  M  R  K  R  T  S  T  K  S  F  N  M  V  Q  A  F  G  L
        1410         1420         1430         1440         1450         1460         1470         1480         1490
```

FIGURE 14C

```
                                                <BsaI                                     MfeI               <NmeAIII    >Bsp24I                     BlpI
cgc gga cca gga gac ctc cag gga aac ttt ggt gat ctt caa ttg aat aaa ctc ggc act gag gac cca cgt tgg ccc caa att gct gag ctt gct cct a   < 1600
 R   G   P   G   D   L   Q   G   N   F   G   D   L   Q   L   N   K   L   G   T   E   D   P   R   W   P   Q   I   A   E   L   A   P   T
              1510              1520              1530              1540              1550              1560              1570              1580              1590

DraI                                                      BclI
ca gcc agt gct ttt atg ggt atg tcg caa ttt aaa ctt acc cat cag aac aat gat cat ggc aac cct gtg tac ttc ctt cgg tac agt gga gcc at   < 1700
 A   S   A   F   M   G   M   S   Q   F   K   L   T   H   Q   N   N   D   H   G   N   P   V   Y   F   L   R   Y   S   G   A   I
              1610              1620              1630              1640              1650              1660              1670              1680              1690

SspI
t aaa ctt gac cca aag aat ccc aac tac aat aag tgg ttg gag ctt ctt gag caa aat att gat gcc tac aaa acc ttc cct aag aag aaa aaa caa   < 1800
 K   L   D   P   K   N   P   N   Y   N   K   W   L   E   L   L   E   Q   N   I   D   A   Y   K   T   F   P   K   K   K   K   Q
              1710              1720              1730              1740              1750              1760              1770              1780              1790

AhdI
aag gca cca aaa gaa gaa tca aca gac caa atg tct gaa cct cca aag gag cag cgt gtg caa ggt agc atc act cag cgc act cgt cca agt g   < 1900
 K   A   P   K   E   E   S   T   D   Q   M   S   E   P   P   K   E   Q   R   V   Q   G   S   I   T   Q   R   T   R   P   S   V
              1810              1820              1830              1840              1850              1860              1870              1880              1890

HpaI                                                  PspOMI
                              HincII                XmaI                            ApaI
                                                    SmaI
tt cag cct ggt cca atg att gat gtt aac act gat ggc ccg ggA GAG AAT CTA TAT TTT CAA GGG CCC GGG GGA GGT AGT CAT CAC CAT CAC TA   < 2000
 Q   P   G   P   M   I   D   V   N   T   D   G   P   G   E   N   L   Y   F   Q   G   P   G   G   G   S   H   H   H   H   H   H   *
              1910              1920              1930              1940              1950              1960              1970              1980              1990 proTEV cleavage site

EagI
        BsiEI
AgeI    NotI    HindIII
  -      -        -
A TGA CCG GTG CCG CGG CCG CAA GCT T   < 2023
*      P   V   R   P   Q   A
              2010              2020
```

FIGURE 14D

```
TCGCGAGCTAGCACCATGAAACTATGTATTCTACTTGCAGTTGTTGCGTTCGTAGGATTGTCCTTACCTACAGCTCTGGC
AAGATCTGACAAAGACTGCGAAATGAAAAGAACTACATTGGATTCACCACTTGGGAAGTTGGATGCGAGC
AAGGATTGCATGAAATTAAGCTACTGGGAAAAGAACTTCTGCTGCTGATGCAGTTGAAGTTCCAGCACCAGCAGCTGTT
CTTGGAGTCCTGAGCCCCTCAGCCAAGCCACAGCCTGCTTAACGCATATTTCCACCAGCCTGAGGCCATTGAGGAATT
TCCAGTCCCCGCCCTTCACCATCCTGTGTTTCAGCAGGAGAGCTTCACCCGCCAGGTCCTGTGAAATTGCTGAAGGTGG
TCAAGTTTGGTGAAGTGATTTCATATCAGCAACTTGCTGCATTGGCCGGTAACCCCGCAGCTACAGCTGCCGTGAAAACT
GCTCTCAGCGCGAAATCCTGTGCCCATCCTGATCCCTTGTCACAGAGTCGTTTCATCTTCCGGAGCTGTAGGTGGCTATGA
AGGAGGACTGGCAGTTAAGGAGTGGCTCATGAAGCTCATAGACTTGGAAAGCCTGGGCTGGGTCCTGCTGGTA
TAGGCGCGCCAGGGTCCCTAGGTGGGCGATCCGAAAACCTGTACTTCCAGAGCGATATCGCATCCCCTGCTGCACCTCGT
GCTGTTTCCTTTGCCGATAACAATGATATAACAAACCTATCTCGAGGTAGAGACGTAATCAAAACCACGAGC
TGCACCAAATAACACTGTCTCTTGGTACACCCCTGCGCAAAATGCTGGGTATTGCGGAGACAGGACAGCAGCCTTACCGGG
GTGTACCTCTTAATGCCAATTCTACCCCAGTGCGTACTTCTACTACACGTGATGCTCCTCAACTTTTGGACGCGAACCCTAACA
AATGAATTAAGCAACTGGCTCCCCAGTGGCATCGTTTGGGTCCATGAAGATGGCGCCCTAAACTCCTAAAAACTTCCACATTGAGGGGACTGGAGGCAAT
TGTTAAGGATGGCATCGTTTGGGTCCATGAAGATGGCGCCCTAAACTCCTAAAAACTCCTAAAAACTTCCACATTGAGGGGACTGGAGGCAAT
ATGATTCAGCTATTGTTACACAATTCGCGCCCGGTACTAAGCAGAAAACTCTTCCAGTCTAGTTCACAAGTTCAAGATCAGGAAACTC
AGTCAATCATCTTCAAGAGCCCTCTAGCTTAAGCAGAAAACTCTTCCAGTCTAGTTCACAAGTTCAAGATCAGGAAACTC
TACCCGCGGCACTTCTCCAGTCCATCGGAATCGGAGCAGTAGGAGTGATCATCCTATCTTACCTTGATCTTCTGAACAGAC
TACAAGCCCTTGAGTCTGGCAAAGTAACAATCGCAAGCCAAAAGTAATCACTAAGAAAAGATGCTGCTGCTAAAAAT
AAGATGCGCCACAAGCGCACTTCCACCAAAAGTTCAACATGGTGCAGGCTTTTGGTCTTCGCGGACCAGGAGACCTCCA
GGGAAACTTTGGTGATCTTCAATTGAATAAACTCGGCACTGAGGACCCACGTTGCCCCAAATTGCTGAGCTTGCTCCTA
CAGCCAGTGCTTTTATGGTATGTCGCAATTTAAACTTACCCATCAGAACAATGATCATGGCAACCCTGTGTACTTC
CTTCGGTACAGTGGAGCCATTAAAACTTCCCTAAGAAGAGAAAACAAAAGGCACCAATAAGTGTTGAGCTTCTTGAGCAAAATAT
TGATGCCTACAAAACCTTCCCTAAGAAGAGAAAACAAAAGGCACCAATAAGGCACCAATAACAAGACCAAATGTCGAAC
CTCCAAAGGAGCAGCGTGTGCAAGTAGCATCACTCAGCGCATCAGCCGCTCGCACCCGTCCAAGTGTTCAGCCTGTCCAATGATT
GATGTTAACACTGATGGCCCGGAGAGAATCTATATTTTCAAGGGCCCCGGAGGTAGTCACCATCATCACCATCACTA
ATGACCGGTGCGGCCCGAAGCTT
```

FIGURE 14E

Sequence of chimeric huCOV.S1+ DeSNAP (human coronavirus)

Vector: pMT/BiP/SNAP. Insertion sites for Gene S1 are underlined.

```
BglII
      NsiI                                                   Nli3877I
      Ppu10I                                                 AvaI    BstYI
      |                                                      |       |
ATG AAG TTA TGC ATA TTA CTG GCC GTC GTG GCC TTT GTT GGC CTC TCG CTC GGG AGA TCT GTA GGG CCA GAT TCT GTT AAG TCT GCT TGT ATT GAG GTT G  < 100
 M   K   L   C   I   L   L   A   V   V   A   F   V   G   L   S   L   G   R   S   V   G   P   D   S   V   K   S   A   C   I   E   V   D
            10          20          30          40          50          60          70          80          90
```

Signal peptide of chimeric protein (pMT/BiP/HisV5A)    Gene S1 from human betacoronavirus 2cEMC/2012 (G JX869059)

```
                                              <AjuI
                                              |
AT ATA CAA CAG ACT TTC TTT GAT AAA ACT TGG CCT AGG CCA ATT GAT GTT TCT AAG GCT GAC GGT ATT ATA TAC CCT CAA GGC CGT ACA TAT TCT AAC AT  < 200
    I   Q   Q   T   F   F   D   K   T   W   P   R   P   I   D   V   S   K   A   D   G   I   I   Y   P   Q   G   R   T   Y   S   N   I
           110         120         130         140         150         160         170         180         190

NcoI
                                              >SdeOSI
                                          <BsaI                                                             <CspCI
                                          |  | |                                                             |
A ACT ATC ACT TAT CAA GGT CTT TTT CCC TAT CAG GGA GAC CAT GGT GAT ATG TAT GTT TAC TCT GCA GGA CAT GCT ACA GGC ACA ACT CCA CAA AAG TTG  < 300
   T   I   T   Y   Q   G   L   F   P   Y   Q   G   D   H   G   D   M   Y   V   Y   S   A   G   H   A   T   G   T   T   P   Q   K   L
           210         220         230         240         250         260         270         280         290

ZraI
                              AatII                                  <TspGWI
                              |                                      |
TTT GTA GCT AAC TAT TCT CAG GAC GTC AAA CAG TTT GCT AAT GGG TTT GTC GTC CGT ATA GGA GCA GCT GCC AAT TCC ACT GGC ACT GTT ATT ATT AGC C  < 400
 F   V   A   N   Y   S   Q   D   V   K   Q   F   A   N   G   F   V   V   R   I   G   A   A   A   N   S   T   G   T   V   I   I   S   P
           310         320         330         340         350         360         370         380         390
```

```
                                                                                                      >HaeIV                                                          BstBI
                                                                                                        |                                                              |
GC AGA GCT ATA GAC TGT GGT TTT AAT GAT TTG TCA CAA CTC CAC TGC TCA TAT GAA TCC TTC GAT GTT GAA TCT GGA GTT TAT TCA GTT TCG TCT TTC GA     < 1100
 R   A   I   D   C   G   F   N   D   L   S   Q   L   H   C   S   Y   E   S   F   D   V   E   S   G   V   Y   S   V   S   S   F   E

A GCA AAA CCT TCT GGC TCA GTT GTG GAA CAG GCT GAA GGT GTT GAA TGT GAT TTT TCA CCT CTT CTG TCT GGC ACA CCT CCT CAG GTT TAT AAT TTC AAG     < 1200
 A   K   P   S   G   S   V   V   E   Q   A   E   G   V   E   C   D   F   S   P   L   L   S   G   T   P   P   Q   V   Y   N   F   K

CGT TTG GTT TTT ACC AAT TGC AAT TAT AAT CTT ACC AAA TTG CTT TCA CTT TTT TCT GTG AAT GAT TTT ACT TGT AGT CAA ATA TCT CCA GCA GCA ATT G    < 1300
 R   L   V   F   T   N   C   N   Y   N   L   T   K   L   L   S   L   F   S   V   N   D   F   T   C   S   Q   I   S   P   A   A   I

CA AGC AAC TGT TAT TCT CTG ATT TTG GAT TAC TTT TCA TAC CCA CTT AGT ATG AAA TCC GAT CTC AGT GTT AGT CAA GTT TCT GCT GGT CCA ATA TCC CAG TT < 1400
 S   N   C   Y   S   L   I   L   D   Y   F   S   Y   P   L   S   M   K   S   D   L   S   V   S   Q   V   S   A   G   P   I   S   Q

AflIII                                                                                   AflII
                                  PciI                                                                                     |
T AAT TAT AAA CAG TCC TTT TCT AAT CCC ACA TGT TTG ATT TTA GCG ACT GTT CCT CAT AAC CTT ACT ACT ATT ACT AAG CCT CTT AAG TAC AGC TAT ATT    < 1500
 N   Y   K   Q   S   F   S   N   P   T   C   L   I   L   A   T   V   P   H   N   L   T   T   I   T   K   P   L   K   Y   S   Y   I

>BdaI                                                                      >BciVI
                        >BaeI                                                                       |
AAC AAG TGC TCT CGT CTT TTT CTT GAT GAT CGT ACT GAA GTA CCT ACT CAG TTA GTG AAC GCT AAT CAA TAC TCA CCC TGT GTA TCC CCA TCC ACT G         < 1600
 N   K   C   S   R   L   F   L   D   D   R   T   E   V   P   T   Q   L   V   N   A   N   Q   Y   S   P   C   V   S   P   S   T   V
```

FIGURE 15C

```
TG TGG GAA GAC GGT GAT TAT TAT AGG AAA CAA CTA TCT CCA CTT GAA GGT GGT GGC TGG CTT GTT GCT AGT GGC TCA ACT GTT GCC ATG ACT GAG CAA TT  < 1700
 W   E   D   G   D   Y   Y   R   K   Q   L   S   P   L   E   G   G   G   W   L   V   A   S   G   S   T   V   A   M   T   E   Q   L
                   1610            1620            1630            1640            1650            1660            1670            1680            1690

A CAG ATG GGC TTT GGT ATT ACA GTT CAA TAT GGT ACA GAC ACC AAT AGT GTT TGC CCC AAG CTG GAA TTT GCT AAT GAC ACA AAA ATT GCC TCT CAA TTA  < 1800
 Q   M   G   F   G   I   T   V   Q   Y   G   T   D   T   N   S   V   C   P   K   L   E   F   A   N   D   T   K   I   A   S   Q   L
                   1710            1720            1730            1740            1750            1760            1770            1780            1790
           SspI
            |
GGC AAT TGC GTG GAA TAT TCC CTC TAT GGT GTT TCG GGC CGT GTT TTT CAG AAT TGC ACA GCT GGT GTT CGA CAG CAG CGC TTT GTT TAT GAT G  < 1900
 G   N   C   V   E   Y   S   L   Y   G   V   S   G   R   V   F   Q   N   C   T   A   V   R   Q   Q   R   F   V   Y   D   A
                   1810            1820            1830            1840            1850            1860            1870            1880            1890
                                                                                           <DraRI
                                                                                             |
CG TAC CAG AAT TTA GTT GGC TAT TAT TCT GAT GAT GGC AAC TAC TAC TGT TGT CGT GCT TGT GTT AGT GTT CCT GTT TCT GTC ATC TAT GAT AAA GAA AC  < 2000
 Y   Q   N   L   V   G   Y   Y   S   D   D   G   N   Y   Y   C   C   R   A   C   V   S   V   P   V   S   V   I   Y   D   K   E   T
                   1910            1920            1930            1940            1950            1960            1970            1980            1990

T AAA ACC CAC GCT ACT CTA TTT GGT AGT GTT GCA TGT GAA CAC ATT TCT TCT ATG TCT CAA TAC TCC CGT TCT ACG CGA TCA ATG CTT AAA CGG CGA  < 2100
 K   T   H   A   T   L   F   G   S   V   A   C   E   H   I   S   S   T   M   S   Q   Y   S   R   S   T   R   S   M   L   K   R   R
                   2010            2020            2030            2040            2050            2060            2070            2080            2090
       >Bsp24I
         |
GAT TCT ACA TAT GGC CCC CTT CAG ACA CCT GTT TGT GTC CTA GGA CTT GTT AAT TCC TCT TTG TTC GTA GAG GAC TGC AAG TTG CCT CTT GGT CAA T  < 2200
 D   S   T   Y   G   P   L   Q   T   P   V   C   V   L   G   L   V   N   S   S   L   F   V   E   D   C   K   L   P   L   G   Q   S
                   2110            2120            2130            2140            2150            2160            2170            2180            2190
```

```
ATGAAGTTATGCATATTACTGGCCGTCGTGGCCCTTGTTGGCCTCTCGCTCGGAGATCTGTAGGCCAGATTCTGTTAA
GTCTGCCTTGTATTGAGGTTGAATATACCAAGACGACTTTCTTTGATAAAACTTGGCCTAGGCCAATTGATGTTCTAAGGCTG
ACGGTATTATATACCCTCAAGGCCGTACATATTCTAACATAACTATCACTTATCAAGTCTTTTCCTATCAGGGAGAC
CATGGTGATATGTATGTTACTCTGCAGGACACTGCTACAGGCACACTCCACAAAAGTTGTTGTAGTAACTATTCTCA
GGACGTCAAACAGTTGCTAATGGGTTGTCGTCCGTATAGGAGCAGCTGCCAATTCCACTGGCACTGTTATTATTAGCC
CATCTACCAGCCGCTTCTTCAATCATATCTAGTTCTTTTGCCCGTTCTTCAGTTGGTAATTTCTCAGATGGTAAA
ATGGGCCGCTTCTTCAATCATATCTAGTTCTTTTGCCCGATGATGTGGCACTTTACTTAGAGCTTTTTATTGTATTCT
AGAGCCTCGCTCTGGAAATCATTGTCCTGCTGGCAATCCTATACTTCTTTTGCCACTTATCACACTCCTGCAACAGATT
GTTCTGATGGCAATTACAATCGTAATGCCAGTCTGAACTCTTTAAGGAGTATTTAATTTACGTAACTGCACCTTTATG
TACACTTATAACATTACCGAAGATGAGATTTTAGACGTGGTTGGCATTACACAAACGTCTCAAGGTGTTCACCTCTC
ATCTCGTATGTTGATTTGTACGGCGGCAATATGTTCAATTGCCACCTTGCCTGTTTATGATACTATTAAGTATTATT
CTATCATTCCTCACAGTATTCGTTCTGTTGATGGTTATATCGCAGAGCTTATTCAGTTTCGTCTTTCGAAGCAAAACCTTCTGGCTCAG
TTAACTTTCCTGTTGGATTTTTCTGTTGATGGTTATATACGCAGAGCTTATCAGTTTCGTCTTTCGAAGCAAAACCTTCTGGCTCAG
CCACTGCTCATATGAATCCTTCGATGTTGAATGTGAGTTTATTTTCACCTTCGTCTTCACTTTTCTCTGAATGATTTTACTTGTAGTCA
TTGTGAACAGGCTGAAGGTGTTGAATCGTGATTTTCACTGTATTTCTTCACTTTTCTCTGAATGATTTTACTTGTAGTCA
CGTTTGGTTTTCACAATGCAATTATAATCTTACCAAATTGCTTTCACTGTATTTCTCACTGATTTTGATTACTTTTCATACCCACTTAGTATGAAAT
AATATCTCCAGCAGCAATTGCAAGCAACTGTATATTCTTACTGTATTTCTCACTGATTTTGATTACTTTTCATACCCACTTAGTATGAAAT
CCGATCTCAGTGTTAGTTCTGCTGGTCCAATATCCCAGTTTAATATAAACAGTCCTTTTCTAATCCACATGTTTGATT
TTAGCGACTGTTCCTCATAACCTTACTATTACTAAGGGCCTAAGTAACAACAGCTATATTAACAAGTGCTCTCGTCTCT
TTCTGATGATCGTACTGAAGTGCTCAGTTAGTGAACGCTAATCAATACTCACCCGTGTATCCATTGTCCATCACTG
TGTGGAAGACGGTGATTATTATAGGAAACAACTATCTCCACTTGAAGGTGGCTTGGCTTGTTGCTAGTGGCTCAACT
GTTGCCATGACTGAGCAATTCAGATGGGCTTTGGTATTACAGTTCAATATGCGTGGAATATTCCCTCTATGGTGTTCGGGCC
GCTGGAATTTCTAATGACACAAAAAATTGCCTCTCAATTAGGCAATTGCGACAGCAGCCGTTTGTTTATGATGCGTACCAGAATTTAGTTGGC
GTGGTGTTTTTTCAGAATTGCACACGTCTAGGTGTTCGACAGCAGCCGTTTGTTTATGATGCGTACCAGAATTTAGTTGGC
TATTATTCTGATGATGCCAACTACTACTATTTGGTAGTGTTGCATGTGAACACATTTCTCTACCATGTCTCAATACTCCCGTTCTACGC
TAAAACCCACGCTACTCTATTTGGTAGTGTTGCATGTGAACACATTTCTCTACCATGTCTCAATACTCCCGTTCTACGC
GATCAATGCTAACGCGAGATTCTACATATGGCCCCTTGGTTGTGTCCTAGGACTTGTTAATTCC
TCTTTGTTCGTAGAGGACTGCAAGTTGCCTCTTGGCTCATCTCTGCCTCTTCCTGACACACCTAGTACTCTCACACC
TCGCAGTGTGCCTCTGTTCCAGGTGAAATGCCGCTTGGCATCCATCATTGCTTTTAATCATCCTATTCAGGTTGATCAACTTA
ATAGTAGTTATTTTAAATTAAGTATACCCACTAATTTTCCTTTGGTGACTCAGGAGTACATTCAGACAACCATTCAG
AAAGTTACTGTTGATTGTAAACAGTACgcggcccgacgcggaggtagcaaagactgcgaaatgaagcgcaccacct
ggatagccctctggcaagctggaactgtctggtgcgaacaggcctgcgaacaggcctgcacgagatcaagctgctgggcaaaggaacat
ctgccgcgacgcgtggaagtgcctgcccagccgctggaccagagccactgatgcaggccacgcctgg
ctcaacgctacttcaccgcctgaggccatcgaggagttccctgtcccaccagtgttccagcagga
gagctttaccccgcagttgctgtggaaactgctgaaagttgtgaaggtcatcagcagcagctgccg
ccctggccgcaatccgcgccaccgccgcgtgaaaacgccgagccgaaatccgtgccattctgatccctgc
caccggttggttgtctagctctggccgccgtggggcggcttcgaggcgggctgccgtgaaagaggtggctgctggccacga
gggccagactgggcaagcctgggctggctggtccctgacgctgctaggtctggcagagctgctgctggagcatcatcatc
attgatgacgggccc
```

Sequence of chimeric DeSNAP+huCoV.S-RBD

Vector: pMT/BiP/SNAP. Insertion sites of the RBD sequence are underlined.

```
            NheI
NruI        BmtI                                                                                                                  BglII
|           |                                                                                                                     |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G  < 100
S   R   A   S   T   M   K   L   C   I   L   L   A   V   V   A   F   V   G   L   S   L   P   T   A   L   A   R   S   D   K   D   C   E
                10          20          30          40          50          60          70          80              90
```

Signal peptide of chimeric protein

SNAP sequence

```
                                                    <MmeI
                                                    |
AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC  < 200
   M   K   R   T   T   L   D   S   P   L   G   K   L   E   L   S   G   C   E   Q   G   L   H   E   I   K   L   L   G   K   G   T   S
           110         120         130         140         150         160         170         180         190

<PlaDI                                         <DraRI                                          PflMI
      |                                              |                                               |
T GCT GCT GAT GCA GTT GAA GTT CCA GCA CCA GCA GCT GTT CTT GGA GGT CCT GAG CCC CTC ATG CAA GCC ACA GCC TGG CTT AAC GCA TAT TTC CAC CAG  < 300
  A   A   D   A   V   E   V   P   A   P   A   A   V   L   G   G   P   E   P   L   M   Q   A   T   A   W   L   N   A   Y   F   H   Q
              210         220         230         240         250         260         270         280         290

>BdaI
 <PspPRI                                                                                                                   >Eco57MI
Bsu36I             ApoI        <RpaB5I                                                                                     >AcuI
||                 |           |                                                                                           ||
CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG G  < 400
P   E   A   I   E   E   F   P   V   P   A   L   H   H   P   V   F   Q   Q   E   S   F   T   R   Q   V   L   W   K   L   L   K   V   V
            310         320         330         340         350         360         370         380         390
```

FIGURE 16C

TCGCGAGCTAGCACCATGAAACTATGTATTCTACTTGCAGTTGTTGCCGTTCGTAGGATTGTCCTTACCTACAGCTCTGGC
AAGATCTGACAAAGACTGCGAAATGAAAGAACTACATTGGATTCACCACTTGGGAAGTTGGAACTTGAGTGGATGCGAGC
AAGGATTGCATGAAATTAAGCTACTGGGAAAAGAACTTCTGCTGCTGATGCAGTTGAAGTTCCAGCACCAGCAGCTGTT
CTTGGAGGTCCCTGAGCCCCTCATGCAAGCCACAGCCTGGCTTAACGCCATATTTCCACCAGCCTGAGGCCATTGAGGAATT
TCCAGTCCCCGCCCTTCACCATCCTGTGTTTCAGCAGGAGAGCTTCAGGAGCCTCTGTGGAAATTGCTGAAGGTGG
TCAAGTTTGGTGAAGTGATTTCATATCAGCAACTTGCTGCATTGGCCGGTAACCCCGTAACCCCGAGCTACAGCTGCCGTGAAAACT
GCTCTCAGCGGAAATCCTGTGCCCATCCTGATCCCTGTCACAGAGTCGTTTCATCTTCCGGAGCTGGGTCCTGCTATGA
AGGAGGACTGGCAGTTAAGGAGTGCTGCTGGGCTCATGAAGGTCATAGACTTGGAAAGCCTGGGCTGGGTCCTGCTGGTA
TAGGCGCGCCAGGGTCCCTAGGTGCCGGATCCCGAAAACCTGTACTTCCAGAGCGATATCTTGTTGCTGCTTCTACTGC
ATCCTCGAACCTCGTTCTCGGTAACCACTGCTGTAATCGTAACGCCTCCCTTGAAGCTCTTTTAAGGAGTACTTCAACCTGCCAACTGTACCT
TGACTGTAGTGACGGCAACTACACATTACCGAAGACGAAATCCTCGAGTGGTTCGGCATCACAGACAGCTCAGGAGTCCACCTC
TCTCAAGCAGTACGTGGACCTCTATGGTGACCTTGGTAACATGTTTCAATTCGCCATCAGCTCCAGTTCGATACCATCAAGTA
TTACTCCATCATCCCACACTCAATCCGCTCTGATTTCTCCGTGGACGGCTACATTAGACGTGCTATCGATTGCGGTTTCAACGACCTGTCA
AGCCCTCTGACCTTCCTGCTGATTTCTCCGTGGACGGCTACATTAGACGTGCTATCGATTGCGGTTTCAACGACCTGTCA
CAACTCCATTGCTCATACGAATCTTTCGACGTTGAGAGCGGAGTGTACTCCGTTTCCAGCTTGAGGCTAAACCAGTGG
CTCCCCGGGAGAGAATCTATATTTTCAAGGGCCCGGGAGGTAGTCACCATCATCACCATCACTAATGACCGGTGCGGC
CGCAAGCTT

FIGURE 16D

```
G CCC ATC CTG ATC CCT TGT CAC AGA GTC GTT TCA TCT TCC GGA GCT GTA GGT GGC TAT GAA GGA GGA CTG GCA GTT AAG GAG TGG CTG CTG GCT CAT GAA   < 600
P  I   L   I   P   C   H   R   V   V   S   S   S   G   A   V   G   G   Y   E   G   G   L   A   V   K   E   W   L   L   A   H   E
        510                 520                 530                 540                 550                 560                 570                 580                 590
                                                                                                                                                                                              <TsoI
                                                                                                                                                                                              <SdeOSI
                                                                                                                                                                                              BspHI

<GsaaI              BssHII
                                                            <BseYI              McaTI         AvrII
                                                                                AscI          SanDI                    BamHI                                              EcoRV
GGT CAT AGA CTT GGA AAG CCT GGG CTG GGT CCT GCT GGT ATA GGC GCG CCA GGG TCC CTA GGT GGA TCC GGA GAA AAC CTG TAC TTC CAG AGC gat atc g   < 700
G   H   R   L   G   K   P   G   L   G   P   A   G   I   G   A   P   G   S   L   G   G   S   G   E   N   L   Y   F   Q   S   D   I   G
        610                 620                 630                 640                 650                 660                 670                 680                 690

BlpI                                                                                                                                            proTEV cleavage site
 |
ga gct gag ctt cct att gag gag tta agt gat gat gca aag aac tcg atc aca aga gct aag tct gca ggt gct gaa aag tat gct cct tca gag tta gag ga   < 800
 A   E   L   P   I   E   E   L   S   D   D   A   K   N   S   I   T   R   A   K   S   A   G   A   E   K   Y   A   P   S   E   L   E   E
        710                 720                 730                 740                 750                 760                 770                 780                 790
                                                                                                                  <AarI Modified short forms of LruA (genbank: AY741529)

DrdI
                                                                                                                             |
g gcc cgt aag tcc ttc cct gtt gat gat gca cgt aag gct cag gag gag aat ctt aca gag act aag aag tcc gcg ttg tat gca aga gca aag gct tta gac   < 900
 A   R   K   S   F   P   V   D   D   A   R   K   A   Q   E   E   N   L   T   E   T   K   K   S   A   L   Y   A   R   A   K   A   L   D
        810                 820                 830                 840                 850                 860                 870                 880                 890

XmnI                    TaiI
         |                      HpyCH4IV
                                BsaAI           >BpII          >SapI                                                                        StuI
                                 |               |              |                                                                            |
gct tcc gag aag tcc ttc cct tct tct gtt gat gat gca cgt aag gag tcc agc tct tca atc gag tct gca gag gag gcc tat gct tct cag ctt gct t   < 1000
 A   S   E   K   S   F   P   S   S   V   D   D   A   R   K   E   S   S   S   I   E   S   A   E   E   A   Y   A   S   Q   L   A   S
        910                 920                 930                 940                 950                 960                 970                 980                 990
```

FIGURE 17B

```
                        PsiI              BsrGI                                                                                 >BciVI
                         |                   |                                                                                 <DrdIV
                         |                   |                                                                                   |
ct gag cct tat aat act tct gta cag ctt cgc aag gag ggt gat tct cta cgc gag act gct gac cgc act tta gag tcg tat ccg aag gag tcc gga ga  < 1100
 E   P   Y   N   T   S   V   Q   L   R   K   E   G   D   S   L   R   E   T   A   D   R   T   L   E   S   Y   P   K   E   S   G   D
                     1010                1020                1030                1040                1050                1060                1070                1080                1090

<BsmI
                                                                                |
t gac gca aag ctg agg atg aga tta gca gca ttc gat cag tat gag gct tct cgt cag aag tat gcg gat tct aag aag gcc gac gac gag tcc aag gta  < 1200
 D   A   K   L   R   M   R   L   A   A   F   D   Q   Y   E   A   S   R   Q   K   Y   A   D   S   K   K   A   D   E   S   K   V
                     1110                1120                1130                1140                1150                1160                1170                1180                1190

ClaI                                             BsaBI
                                                              |                                                |
tta gct ctt tct cag cag cag cta atc gat tct ttt gca gac att gat aag aat cta gat aag tat gca gat aag gga aag gac ccg gag g  < 1300
 L   A   L   S   Q   Q   Q   L   I   D   S   F   A   D   I   D   K   N   L   D   K   Y   A   E   G   K   D   P   E   V
                     1210                1220                1230                1240                1250                1260                1270                1280                1290

>BsmBI                                                                 >AquIV
                              |                                                                      |
tt tcc gag act aga aat cgt ctc gat tcc tct aag tcc tct aag ata gag gag atc aag cag aag ctt gca gca tct gcg act gat gat att cgt aag aag tc  < 1400
 S   E   T   R   N   R   L   D   S   S   K   S   S   K   I   E   E   G   K   I   K   E   G   Y   S   E   I   D   I   R   K   K   S
                     1310                1320                1330                1340                1350                1360                1370                1380                1390

SspI                                                                                                          >FalI   PvuI
                 |                                                                                                              |       |
c ggc gag ctt gtt gct aag aat att tac gca gag aag cag aag gaa ctt gca gca aag caa agc gta gca tct gcg act aca agg tta gct tcc ttc  < 1500
 G   E   L   V   A   K   N   I   Y   A   E   K   Q   K   E   L   A   A   K   Q   S   V   A   S   A   T   T   R   L   A   S   F
                     1410                1420                1430                1440                1450                1460                1470                1480                1490

XbaI                                                          AflII
            |                                                            SmlI
            |                                                              |
gat cga aat aag atc aat tcc tct aga gat ttt cag gtt tct tac cag aga gca gag gag aac ctt aag gca gct gag gag tcg aga gta gct gca gag g  < 1600
 D   R   N   K   I   N   S   S   R   D   F   Q   V   S   Y   Q   R   A   E   E   N   L   K   A   A   E   E   S   R   V   A   A   E   D
                     1510                1520                1530                1540                1550                1560                1570                1580                1590
```

FIGURE 17C

```
                                                    AccI             >TspRI
                                                     -              BstXI        >NmeAIII
                                                     -               =
at cta tat tct tcg gag aag tac gag gat tct att tcg cgt tct gag gag gca att cgc ctt tcc aga atc gta gac cag gcc act gag ttg gcc ga  < 1700
 L   Y   Y   S   E   K   Y   E   D   S   I   S   R   S   E   E   A   I   R   L   S   R   I   V   D   Q   A   T   E   L   A   E
1610             1620            1630            1640            1650            1660            1670            1680            1690

>TaqII
                                                                -
g aga ata gag aag aga acg act gat aag atc gct ggt cgt gat aca aag gaa aat act aag aac cag tcc aca acc gaa ggc aag                < 1800
 R   I   E   K   R   K   A   T   T   D   K   I   A   G   R   D   T   K   E   N   T   K   N   Q   S   T   T   E   G   K
     1710            1720            1730            1740            1750            1760            1770            1780            1790 aac tct tca tct aag att gga gag gat ggt tta ccg gag gag ggt tgg aag cgt tat gtg gtt cgg aag gtt cct gca gat tgt ctt tgg aga atc gca a   < 1900
 N   S   S   S   K   I   G   E   D   G   L   P   E   E   G   W   K   R   Y   V   V   R   K   V   P   A   D   C   L   W   R   I   A   K
         1810            1820            1830            1840            1850            1860            1870            1880            1890

>BpmI
                   -
ag gat aag aga cat tat gga act tct aag ctc tgg aga aga atc tac gag gca aac cga aac aag atc aag aac cca aac ttg att tat ccg aag cag gt  < 2000
 D   K   R   H   Y   G   T   S   K   L   W   R   R   I   Y   E   A   N   R   N   K   I   K   N   P   N   L   I   Y   P   K   Q   V
     1910            1920            1930            1940            1950            1960            1970            1980            1990

XmaI                                 ApaI                                                  AgeI    EagI
     SmaI                                 PspOMI >CdpI                                           -     NotI    HindIII
     NliI3877I                             -      -                                                     -       -
AseI  AvaI                                 -      -
 -     -
a tta atc ccg gga GAG AAT CTA TAT TTT CAA GGG CCC GGA GGT AGT CAC CAT CAT CAC TAA TGA CCG GTG CGG CCG CAA GCT T   < 2095
 L   L   I   P   G   E   N   L   Y   F   Q   G   P   G   G   S   H   H   H   H   H   H   *   *   P   V   R   P   Q   A
     2010            2020            2030            2040            2050            2060            2070            2080            2090 proTEV cleavage site

FIGURE 17D
```

Sequence of chimeric DeSNAPuniv-shortLruB (leptopsirosis)

Vector: pDeSNAPuniv. Insertion sites of the LruB sequence are underlined.

```
          NheI
NruI      BmtI                                                                                                   BglII
|         |                                                                                                      |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G  < 100
S   R   A   S   T   M   K   L   C   I   L   L   A   V   V   A   F   V   G   L   S   L   P   T   A   L   A   R   S   D   K   D   C   E
            10          20          30          40          50          60          70          80          90
                  Signal peptide of SNAP                                                                         SNAP sequence >BmrI
                                                                                                                  |
AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC  < 200
   M   K   R   T   T   L   D   S   P   L   G   K   L   E   L   S   G   C   E   Q   G   L   H   E   I   K   L   L   G   K   G   T   S
           110         120         130         140         150         160         170         180         190

<PlaDI                                         >Bpu10I              PflMI
     |                                              |                    |
T GCT GCT GAT GCA GTT GAA GTT CCA GCA CCA GCA GCT GTT CTT GGA GGT CCT GAG CCC CTC ATG CAA GCC ACA GCC TGG CTT AAC GCA TAT TTC CAC CAG  < 300
  A   A   D   A   V   E   V   P   A   P   A   A   V   L   G   G   P   E   P   L   M   Q   A   T   A   W   L   N   A   Y   F   H   Q
          210         220         230         240         250         260         270         280         290

HaeI
Bsu36I               <RpaB5I                                                                                     >BdaI
|   |                |                                                                                           |
CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG G  < 400
P   E   A   I   E   E   F   P   V   P   A   L   H   H   P   V   F   Q   Q   E   S   F   T   R   Q   V   L   W   K   L   L   K   V   V
          310         320         330         340         350         360         370         380         390

>AlfI                   BstEII                                                        <TstI
                          |                       |                                                             |
TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT  < 500
   K   F   G   E   V   I   S   Y   Q   Q   L   A   A   L   A   G   N   P   A   A   T   A   A   V   K   T   A   L   S   G   N   P   V
           410         420         430         440         450         460         470         480         490
```

```
                                          >TaqII              AccI                                                                    <BsmBI
gca ttt cgt ttt tca tct gga ccg ata gac aac gta gac att tta ggt tgt gga agt aat gcg gat ggt tcc gga gac gaa gaa tgc gaa gga ctg att a    < 1000
 A   F   R   F   S   S   G   P   I   D   N   V   D   I   L   G   C   G   S   N   A   D   G   S   G   D   E   E   C   E   G   L   I  N
910             920             930             940             950             960             970             980             990

LpnI
                                                    HaeII
                                                    AfeI
ac gga tgg ccg tta gac gaa agc gcg att gat aat tat ata gca aat gca gga aat gca aca act tat gca gcc atc ctc gct aca aat gga gat gca aa    < 1100
 G   W   P   L   D   E   S   A   I   D   N   Y   I   A   N   A   G   N   A   T   T   Y   A   A   I   L   A   T   N   G   D   A  N
         1010            1020            1030            1040            1050            1060            1070            1080            1090
     BclI c gca aat aac gca gat gat caa gat gag aca gcg ctt acg gtc ggt tgg cac gtc gaa tat ata ctc tgg ggt cag gat cta ttt aac gga gga         < 1200
 A   N   N   A   D   D   Q   D   E   T   A   L   T   V   G   W   H   A   I   E   Y   I   L   W   G   Q   D   L   F   N   G   G
    1110            1120            1130            1140            1150            1160            1170            1180            1190

<SapI
                                                               PfoI           <EarI
atc aat caa att tca gga caa cgt aat ata gct gat ctt aca gga gct tct cca gga aca gtt gga ggc aga aga aga gct tat atg aaa gca gtt acg g    < 1300
 I   N   Q   I   S   G   Q   R   N   I   A   D   L   T   G   A   S   P   G   T   V   G   G   R   R   R   A   Y   M   K   A   V   T  D
     1210            1220            1230            1240            1250            1260            1270            1280            1290

>BbsI  BanI                                                                       DrdI
                                                   >Bbr7I
ac gga ctg gtt ctt cag cta aaa ttg att cga gat caa ttt gaa gac ggt gcc aga tat tcg gat gga ctt aaa tcc aat cct gac gca gcg gtc act ta   < 1400
 G   L   V   L   Q   L   K   L   I   R   D   Q   F   E   D   G   A   R   Y   S   D   G   L   K   S   N   P   D   A   A   V   T  Y
     1310            1320            1330            1340            1350            1360            1370            1380            1390
     <BtgZI t atc ttt caa gga ctt ggt aaa ttc atc gct gga gaa tgg gga gaa aga ctt acc gga act ttt ggt gga cag gag gag cat tct tgt ttt                < 1500
 I   F   Q   G   L   G   K   F   I   A   G   E   W   G   E   R   L   T   G   T   F   G   G   Q   E   E   H   S   C   F
      1410            1420            1430            1440            1450            1460            1470            1480            1490

DraIII               <BsbI                         >PsrI                                                    BtgI
agc gat act aca aag gct gac ttc tat tac aac gca cag agt gtg ttg aac att tgg aac gga tct tac gaa ttg aag aag gga acc gta act tcc acg g    < 1600
 S   D   T   T   K   A   D   F   Y   Y   N   A   Q   S   V   L   N   I   W   N   G   S   Y   E   L   K   K   G   T   V   T   S   T  G
     1510            1520            1530            1540            1550            1560            1570            1580            1590

FIGURE 18C
```

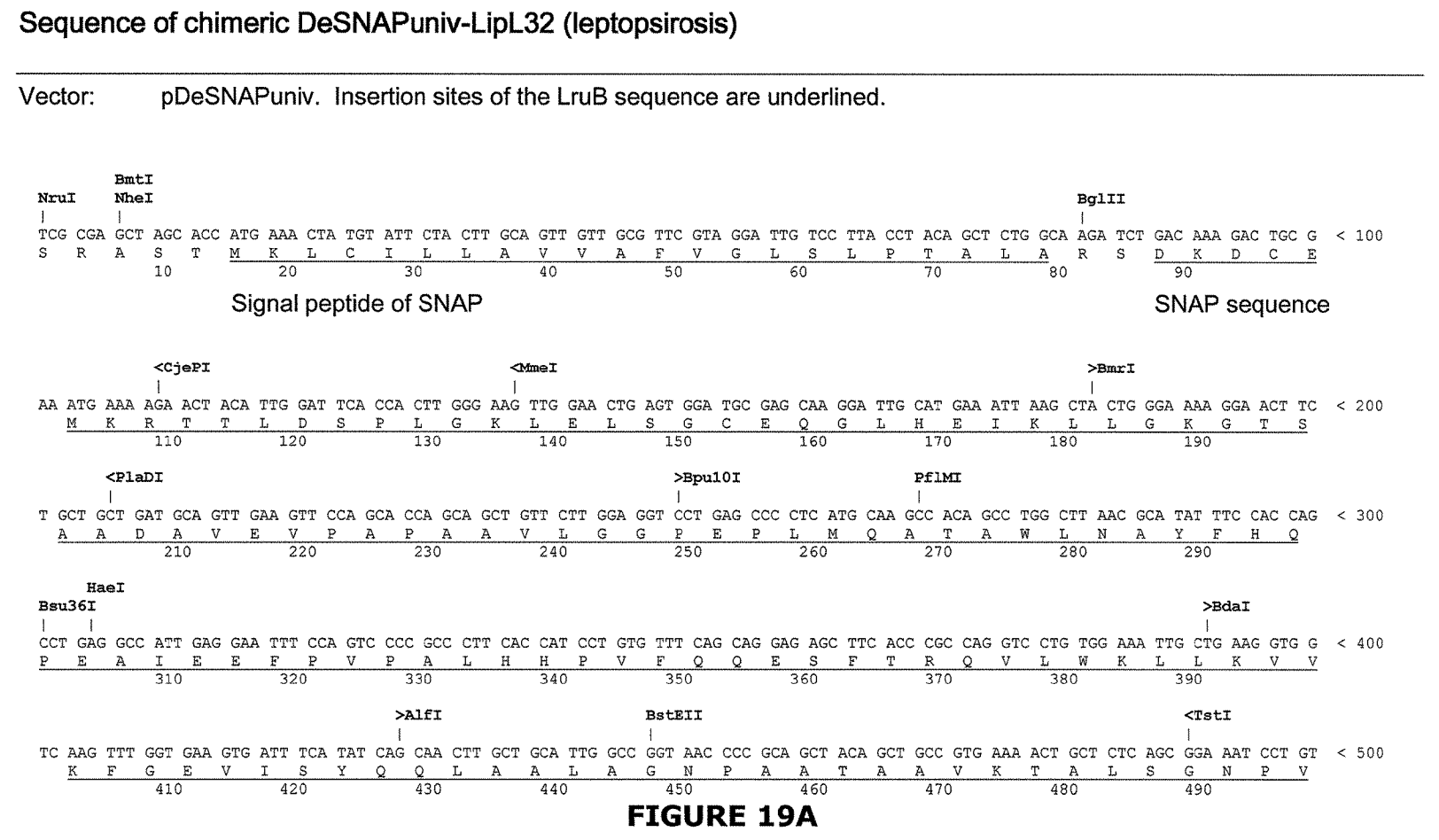

Sequence of chimeric DeSNAPuniv-LipL32 (leptopsirosis)

Vector: pDeSNAPuniv. Insertion sites of the Lru

```
                                                                                                                                                     BspHI
                                        >MlyI                                                                                                         -
                                        >PleI
                                       <BspD6I              BspEI             <TsoI
                                        -                    -                 -
G CCC ATC CTG ATC CCT TGT CAC AGA CTT GGA AAG CCT GGT GTT TCA TCT TCC GGA GCT GTA GGT GGG TAT GAA GGA GGA CTG GCA GTT AAG GAG TGG CTG CTG GCT CAT GAA
P  I   L   I   P   C   H   R   L   G   K   P   G   V   S   S   S   G   A   V   G   G   Y   E   G   G   L   A   V   K   E   W   L   L   A   H   E     < 600
       510         520         530         540         550         560         570         580         590

BssHII        AvrII
                                            McaTI         StyI                                                                            EcoRV
                                   <BseYI    AscI          SanDI                                                     BamHI                 -
                                   <GsaI     -              -                                                          -
GGT CAT AGA CTT GGA AAG CCT GGG CTG GGT CCT GCT GGC GCG CCA GGG TCC CTA GGT GGC TCC GAA AAC CTG TAC TTC CAG AGC GAT ATC a
G   H   R   L   G   K   P   G   L   G   P   A   G   A   P   G   S   L   G   G   S   E   N   L   Y   F   Q   S   D   I   H     < 700
       610         620         630         640         650         660         670         680         690 proTEV cleavage site

PasI                                       AclI
                                                                                       -                                          -
tt acc gct tgt ggt gct ttc ggt ggt ctg cca agc cta aaa agc tct ttt gtt ctg agc gag gac aca atc cca ggg aca aac gaa acc gta aaa acg tt
 T   T   A   C   G   A   F   G   G   L   P   S   L   K   S   S   F   V   L   S   E   D   T   I   P   G   T   N   E   T   V   K   T   L   < 800
       710         720         730         740         750         760         770         780         790

Modified short forms of LipL32 (genbank : AB094433.2)

BsaAI
                             SnaBI                       LpnI
                             <BciVI                      HaeII      DrdI                                                             <Tth111II
             BclI              -                          -          -                                                                 -
a ctt ccc tac gga tct gtg atc aac tat tac gga tac gta aag cca caa gcg ccg gac ggt tta gtc gat gga aac aaa aaa gca tac tat ctc tat
 L   L   P   Y   G   S   V   I   N   Y   Y   G   Y   V   K   P   Q   A   P   D   G   L   V   D   G   N   K   K   A   Y   Y   L   Y     < 900
       810         820         830         840         850         860         870         880         890

>HgaI
                                                                             <BsaXI           >FalI
                                                                              -                -
gtt tgg att cct gcc gtt atc gct gaa atg gga gtt cgt atg att tcc cca aca ggt gag cca ggc gga gac tta gta gtc gac gct t
 V   W   I   P   A   V   I   A   E   M   G   V   R   M   I   S   P   T   G   E   P   G   G   D   L   V   S   D   A   F     < 1000
       910         920         930         940         950         960         970         980         990
```

FIGURE 19B

```
tc aaa gcg gct acc cca gaa gaa aaa tca atg cca cat tgg ttt gat act tgg att cgt gta gaa aga atg tcg gcg att atg cct gac caa atc gcc aa  < 1100
 K   A   A   T   P   E   E   K   S   M   P   H   W   F   D   T   W   I   R   V   E   R   M   S   A   I   M   P   D   Q   I   A   K
        1010            1020            1030            1040            1050            1060            1070            1080            1090
                                                                                                    PsiI     <EarI a gct gcg aaa gca aaa cca gtt caa aaa ttg gac gat gat gat ggt gac gat act tat aaa gaa gag aga cac aac aag tac tct ctt act aga  < 1200
 A   A   A   K   A   K   P   V   Q   K   L   D   D   D   D   G   D   D   T   Y   K   E   E   R   H   N   K   Y   S   L   T   R
        1110            1120            1130            1140            1150            1160            1170            1180            1190 atc aag atc cct aat cct cca aaa tct ttt gac gat ctg aaa aac atc gac act aaa aaa ctt tta gta aga ggt ctt tac aga att tct ttc act acc t  < 1300
 I   K   I   P   N   P   P   K   S   F   D   D   L   K   N   I   D   T   K   K   L   L   V   R   G   L   Y   R   I   S   F   T   T   Y
        1210            1220            1230            1240            1250            1260            1270            1280            1290 ac aaa cca ggt gaa gtg aaa gga tct ttc gtt gca tct gtt ggt ctg ctg ttc cca cca ggt att cca ggt gtg agc ccg ctg atc cac tca aat cct ga  < 1400
 K   P   G   E   V   K   G   S   F   V   A   S   V   G   L   L   F   P   P   G   I   P   G   V   S   P   L   I   H   S   N   P   E
        1310            1320            1330            1340            1350            1360            1370            1380            1390
                        SmaI                                                            PspOMI
                        XmaI                                                            ApaI    >CdpI
                        AvaI                                                                                     AgeI       NotI
                        Nli3877I a gaa ttg caa aaa caa gct atc gct gcC CCC GGA GAG AAT CTA TAT TTT CAA GGG CCC GGC GGA GGT AGT CAC CAT CAT CAC CAT CAC TAA TGA CCG GTG  < 1500
 E   L   Q   K   Q   A   I   A   A   P   G   E   N   L   Y   F   Q   G   P   G   G   G   S   H   H   H   H   H   H   *   *   P   V
        1410            1420            1430            1440            1450            1460            1470            1480            1490
                                                                   proTEV cleavage site BsiEI
EagI     HindIII
 |          |
CGG CCG CAA GCT T  < 1513
 R   P   Q   A
        1510
```

FIGURE 19C

```
TCGCGAGCTAGCACCATGAAACTATGTATTCTACTTGCAGTTGTTGCGTTCGTAGGATTGTCCTTACCTACAGCTCTGGC
AAGATCTGACAAAGACTGCGAAATGAAAAGAACTACATTGGATTCACCACTTGGGAAGTTGGAACTTGAGTGGATGCGAGC
AAGGATTGCATGAAATTAAGCTACTGGGAAAAGGAACTTCTGCTGCTTAACGCATATTTCCACCAGCCTGAAGTTCCAGCACCAGCTGTT
CTTGGAGGTCCTGAGCCCCTCACCATCCTGTGTTTCAGCAGGAGAGCTTCACCCGCCAGGTCCTGTGAAATTGCTGAAGTGG
TCCAGTCCCCGCCCTTCACCATCCTGTGTTTCAGCAGGAGAGCTTCACCCGCCAGGTCCTGTGAAATTGCTGAAGTGG
TCAAGTTTGGTGAAGTGATTTCATATCAGCAACTTGCTGCATTGGCCGGTAACCCCGCAGCTAGACTGCCGTGAAAACT
GCTCTCAGCGGGAAATCCTGTGCCCATCCTGATCCCTGTTGCACAGAGTCGTTTCATCTTCCGGAGCTGTAGGTGGCTATGA
AGGAGGACTGGCAGTTAAGGAGTGGCTGCTTGGCTCATGAAGTCATAGACTTGGAAAGCCTGGGCTGGGTCCTGCTGGTA
TAGGCGCGCCAGGGTCCCTAGGTGGCCGATCCGAAAACCTGTACTTCCAGAGCCATATCATTACCGCTTGTGTGCTTTC
GGTGGTCTGCCAAGCCTAAAAGCTCTTTTGTTCTGAGCGGACACAATCCCAGGACAACAAGCGAAACGTAAAAACGTT
ACTTCCCTACGGATCTGTGATCAACTATTACGGATACGTAAAGCCTGAAATGCTCGGACGTTCGTATGATTTCCCAACAGGCGAA
AAAAGCATACTATCTCTATGTTTGGATTCCTGCCGTAATCGCTGAAAGCGGCTACCCCAGAAGAAAATCAATGCCACATTG
ATCGGTGAGCCAGGCGACGGAGACTTAGTAAGCGACGCCTTCAAAGCTGACCAAATGCCGACCAAATCGCCAAAGCTGCAAAGCAAAACCAG
GTTTGATACTTGGATTCGTGTAGAAAGAATGTCGGCGATTATGCCTGACCAAATGCCGACCAAATCGCCAAAGCTACAACTCTCTTACTAGA
TTCAAAAATTGGACGATGATGATGGTGACGATACTTTATAAAGAAGAGACACAACAAGTACAACATCTCTTACTAGA
ATCAAGATCCCTAATCCTCACTACAAACCAGGTGATCTTTGACGATCGAAAAAACATCGACACTAAAAAACTTTTAGTAAGAGGTCTTTA
CAGAATTTCTTTCACTACTGCCGCTGAGCCCGCTGATCCACTCAAAAACCAGGTGATCCACATCGTTGCTCTTTTCCCACCAG
GTATTCCAGGTGTGAGCCCGCCGGAGTGAGGTAGTCACCATCATCACCATCAATCCTGAAGAATTGCAAAAACAAGCTATCGCTGCCCGGGAGAGAAT
CTATATTTTCAAGGGCCCCGGCGGAGTGAGCCCGCCAAGCTT
```

FIGURE 19D

Sequence of chimeric DeSNAPuniv-HEV.C protein

Vector: pDeSNAPuniv. Insertion sites of the HEV.C sequence are underlined.

```
       NheI
NruI   BmtI                                                                           BglIII
 |      |                                                                               |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G   < 100
 S   R   A   S   T   M   K   L   C   I   L   L   A   V   V   A   F   V   G   L   S   L   P   T   A   L   A   R   S   D   K   D   C   E
                     10                  20                  30                  40                  50                  60                  70                  80                  90
                         Signal peptide of SNAP                                                                                                  SNAP sequence AA ATG AAA AGA ACT ACA TTG GAT TCA CCA CTT GGG AAG TTG GAA CTG TCT GGA TGC GAG CAA GGA TTG CAT GAA ATT AAG CTA CTG GGA AAA GGA ACT TC   < 200
 E   M   K   R   T   T   L   D   S   P   L   G   K   L   E   L   S   G   C   E   Q   G   L   H   E   I   K   L   L   G   K   G   T   S
                    110                 120                 130                 140                 150                 160                 170                 180                 190
                                                                                              >Bpu10I T GCT GCT GAT GCA GTT GAA GTT CCA GAA GCA CCA GCA GCT GTT CTT GGA GGT CCT GAG CCC CTC ATG CAA GCC ACA GCC TGG CTT AAC GCA TAT TTC CAC CAG   < 300
 A   A   A   D   A   V   E   V   P   E   A   P   A   A   V   L   G   G   P   E   P   L   M   Q   A   T   A   W   L   N   A   Y   F   H   Q
                    210                 220                 230                 240                 250                 260                 270                 280                 290
Bsu36I
 |
CCT GAG GCC ATT GAG GAA TTT CCA GTC CCC GCC CTT CAC CAT CCT GTT CAG CAG GAG AGC TTC ACC CGC CAG GTC CTG TGG AAA TTG CTG AAG GTG G   < 400
 P   E   A   I   E   E   F   P   V   P   A   L   H   H   P   V   Q   Q   E   S   F   T   R   Q   V   L   W   K   L   L   K   V   V
                    310                 320                 330                 340                 350                 360                 370                 380                 390
                                                                                                                                                 <TstI
                                                                                                                                                   |
TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT   < 500
 S   K   F   G   E   V   I   S   Y   Q   Q   L   A   A   L   A   G   N   P   A   A   T   A   A   V   K   T   A   L   S   G   N   P   V
                    410                 420                 430                 440                 450                 460                 470                 480                 490
```

FIGURE 20A

```
                                                    BspEI                                                                                  BspHI
                                                 <MboII                                                                                    <SdeOSI
G CCC ATC CTG ATC CCT TGT CAC AGA GTC GTT TCA TCT TCC GGA GCT GTA GGT GGC TAT GAA GGA GGA CTG GCA GTT AAG GAG TGG CTG CTG GCT CAT GAA  < 600
  P   I   L   I   P   C   H   R   V   V   S   S   S   G   A   V   G   G   Y   E   G   G   L   A   V   K   E   W   L   L   A   H   E
          510         520         530         540         550         560         570         580         590

McaTI
                                                         BssHII          AvrII
                                                        AscI     SanDI               BamHI        TatI          EcoRV
GGT CAT AGA CTT GGA AAG CCT GGG CTG GGT CCT GCT GGT ATA GGC GCG CCA GGG TCC CTA GGT GGC GGA TCC GAA AAC CTG TAC TTC CAG AGC gat atc a  < 700
 G   H   R   L   G   K   P   G   L   G   P   A   G   I   G   A   P   G   S   L   G   G   G   S   E   N   L   Y   F   Q   S   D   I   N
         610         620         630         640         650         660         670         680         690
``` proTEV cleavage site

```
   NspI
   PciI                 MslI
at aac atg ttc ttt tgc tct gtg cat gga gat gcc acc atg cgc tct cgg gct ttc ctg ttc ttg ttc ctc gtg ttt ctg cct atg ctg cca gcg cca cc  < 800
    N   M   F   F   C   S   V   H   G   D   A   T   M   R   S   R   A   F   L   F   L   F   L   V   F   L   P   M   L   P   A   P   P
          710         720         730         740         750         760         770         780         790
```

Mutated C protein from Hepatitiis E virus genbank access AB29196

```
                                   AccI
                          DrdI     SalI
a gcc ggt cag cct tct ggc cga cgt cga ggt cga cgt agc gga ggt gca ggt ggt ggt ttc tgg ggt gac cgt att gat tct cag cca ttc gct ctc cct  < 900
   A   G   Q   P   S   G   R   R   R   G   R   R   S   G   G   A   G   G   G   F   W   G   D   R   I   D   S   Q   P   F   A   L   P
          810         820         830         840         850         860         870         880         890

BglI
tat att cat cca acc aac cca ttc gca cct gac att cca gcc gca gct ggt gct gga gct cga cct cgg cag cca gcc cgc cca ctc ggc tcc gct tgg c  < 1000
 Y   I   H   P   T   N   P   F   A   P   D   I   P   A   A   A   G   A   G   A   R   P   R   Q   P   A   R   P   L   G   S   A   W   R
         910         920         930         940         950         960         970         980         990
```

FIGURE 20B

```
                                                  >PspOMII        >BmgBI
gt gac caa tcc cag cgc cca gcc act tcc gca cgt cgt cga tct gca cgt cgt cga tct act gtt cc   < 1100
 D   Q   S   Q   R   P   A   T   S   A   R   R   S   A   R   R   S   P   L   T   A   V   P
    1010        1020        1030        1040        1050        1060        1070        1080        1090 t gtt cct gat gtc gat tct cga ggt gct ata tta cga cgt cag tat aat tca aca tca cta aca tct act att gcc act ctt gtt   < 1200
 V   P   D   V   D   S   R   G   A   I   L   R   R   Q   Y   N   L   S   T   S   P   L   T   S   T   I   A   T   G   L   V
    1110        1120        1130        1140        1150        1160        1170        1180        1190
                                                                                MscI cta tat gct gct ccg ctg agc cct ttg cta cca ctc caa gat gga act aac act cac att atg gcc act gaa gca tca aat tat gcc cag tac cgt gtt g   < 1300
 L   Y   A   A   P   L   S   P   L   L   P   L   Q   D   G   T   N   T   H   I   M   A   T   E   A   S   N   Y   A   Q   Y   R   V
    1210        1220        1230        1240        1250        1260        1270        1280        1290
                                                                <BciVI tc cgc gct acc atc cgg tac cgt ccg ctt gtg ccg aac gtc ggc gga tac gct ata tct atc tct ttc tgg cct cag aca act acc ccg aca tc   < 1400
 R   A   T   I   R   Y   R   P   L   V   P   N   A   V   G   G   Y   A   I   S   I   S   F   W   P   Q   T   T   T   P   T   S
    1310        1320        1330        1340        1350        1360        1370        1380        1390
                                                                                        >AloI t gtg gac atg aac tct atc acc tcc acg gat gtc cga gat gtc cga atc ctt gtc cag cct att gct gca gaa ctt gtg atc ccc agt gag cgc ctg cat tat cgt   < 1500
 V   D   M   N   S   I   T   S   T   D   V   R   I   L   V   Q   P   G   I   A   S   E   L   V   I   P   S   E   R   L   H   Y   R
    1410        1420        1430        1440        1450        1460        1470        1480        1490
                          <BsaI                            >BplI aac caa ggc tgg cgc tct gtt gag acc tct ggt gtt gcg gag gag gcg acc tcc ggc ctt gtc atg ctt tgc atc gga tca cct gta aat tct t   < 1600
 N   Q   G   W   R   S   V   E   T   S   G   V   A   E   E   A   T   S   G   L   V   M   L   C   I   H   G   S   P   V   N   S   Y
    1510        1520        1530        1540        1550        1560        1570        1580        1590
                   <Tth111II                                                                 SexAI           PmlI ac acc aat acg cct tat act ggt gcc ctt ggc ttg ctt gat ttc gca ctc gag ctc gag ttc cgc aat ttg aca cct ggt aac acg aca cgt gtt tc   < 1700
 T   N   T   P   Y   T   G   A   L   G   L   L   D   F   A   L   E   L   E   F   R   N   L   T   P   G   N   T   N   T   R   V   S
    1610        1620        1630        1640        1650        1660        1670        1680        1690
```

FIGURE 20C

FIGURE 20D

```
                                                ApaLI
                                                  |
c cgc tac tcg agt gca cga cac aag cta cgc cga gga cct gat ggc act gct gag tta act acg act gct gct aca cgc ttt atg aag gac ctt cat  < 1800
  R   Y   S   S   A   R   H   K   L   R   R   G   P   D   G   T   A   E   L   T   T   T   A   A   T   R   F   M   K   D   L   H
      1710              1720              1730              1740              1750              1760              1770              1780              1790
                                                            <TaqII                AfeI                                  <BtsI         HpaI
                                                              |                    |                                      |            |
ttt aca ggg act aat gga gtt ggt gaa gtc cgt ggt ata gcg cta act ctg ttc aac ctt gct gat acg ctt ctc ggt gga ctc ccg aca gaa ttg a   < 1900
  F   T   G   T   N   G   V   G   E   V   R   G   I   A   L   T   L   F   N   L   A   D   T   L   L   G   G   L   P   T   E   L
      1810              1820              1830              1840              1850              1860              1870              1880              1890
                                                                          >BsmBI
                                                                            |
tt tcg tcg gct ggt gca ttc tat tct cgc ccc gtc tca gcc aat ggc gag gag ctc gtg aag ctc tac act tca gtc gag aac gct cag ca          < 2000
  S   S   A   G   Q   L   F   Y   S   R   P   V   V   S   A   N   G   E   E   P   T   V   K   L   Y   T   S   V   E   N   A   Q
      1910              1920              1930              1940              1950              1960              1970              1980              1990
                      >RleAI      BsaBI                                                                                                  >BsaXI
                          |          |                                                                                                      |
g gat aag ggt ata gct atc cca cat gat att gat ctt ggt gag tcc cgt gtt gtc att cag gat tat gat aac caa cat gag cag gat cgt cca act cct       < 2100
  D   K   G   I   A   I   P   H   D   I   D   L   G   E   S   R   V   V   I   Q   D   Y   D   N   Q   H   E   Q   D   R   P   T   P
      2010              2020              2030              2040              2050              2060              2070              2080              2090
                                                                                                                BclI
                                                                                                                  |
tct cct gct cca tct cct cga cct tta tct gtc gtc gct aat gat gtg cta tgg ctt tca ctt aca gca gct gag tat gat cag act acc tat ggc tcc t       < 2200
  S   P   A   P   S   R   P   L   S   V   V   A   N   D   V   L   W   L   S   L   T   A   A   E   Y   D   Q   T   T   Y   G   S
      2110              2120              2130              2140              2150              2160              2170              2180              2190
                              PshAI              <MaqI                                              PasI
                                  |                  |                                                |
ct act aat cca atg tat tct gat acc gtg aat gtt gct act ttt gtc aat gtt gct act ggt gcc cag ggt gta tct cgc ctg gac tgg tct aaa gtc acc ct   < 2300
  T   N   P   M   Y   V   V   S   D   T   V   T   F   V   N   V   A   T   G   A   Q   G   V   S   R   L   D   W   S   K   V   T   L
      2210              2220              2230              2240              2250              2260              2270              2280              2290
                                              DraIII
                                                |
t gat gga cga cca ctt atg act atc cag cag tat tct atg gtt gtt ttt ctg cca cta cgt ggc aag ctc tcc ttc tgg gag gcc ggt acc act aag          < 2400
  D   G   R   P   L   M   T   I   Q   Q   Y   S   M   V   V   F   L   P   L   R   G   K   L   S   F   W   E   A   G   T   T   K
      2310              2320              2330              2340              2350              2360              2370              2380              2390
```

```
NaeI                                                                                          NsiI
NgoMIV                                                         >BsmI                          PpuI0I
 |                                                              |                              |
gcc ggc tac cct tat aat tat aat act gcc agt gac cag att tta att gag aat gca gct ggt cac cgt gta tgc atc tca acc tac act act aat c  < 2500
 A   G   Y   P   Y   N   Y   N   T   T   A   S   D   Q   I   L   I   E   N   A   A   G   H   R   V   C   I   S   T   Y   T   T   N   L
    2410        2420        2430        2440        2450        2460        2470        2480        2490 tt gga tct ggc cct gtt tct att tct gtt ggt gtc ctc gca cct cac tct gcg ttg gcc gct tta gag gac act gac tat cct gtt gct ca        < 2600
 G   S   G   P   V   S   I   S   V   G   V   L   A   P   H   S   A   L   A   A   L   E   D   T   D   Y   P   V   A   H
    2510        2520        2530        2540        2550        2560        2570        2580        2590

<HgaI
                                                                                               |
c act ttt gat gat ttc tgc cct gag tgc cgt aca ctc ggt cag ggt tgt gct ttc caa tca act gtt gct gag cta cag cgt ctt aaa atg aag gtg < 2700
 T   F   D   D   F   C   P   E   C   R   T   L   G   Q   G   C   A   F   Q   S   T   V   A   E   L   Q   R   L   K   M   K   V
    2610        2620        2630        2640        2650        2660        2670        2680        2690

XmaI                                   PspOMI                              EagI
            SmaI                                   ApaI                         AgeI   NotI       HindIII
             |                                      |                            |      |          |
ggt aaa act cgg gag tac ccg ggA GAG AAT CTA TAT TTT CAA GGG CCC GGC GGA GGT AGT CAC CAT CAC TAA TGA CCG GTG CGG CCG CAA G         < 2800
 G   K   T   R   E   Y   P   G   E   N   L   Y   F   Q   G   P   G   G   G   S   H   H   H   *   *   P   V   R   P   Q   A
    2710        2720        2730        2740        2750        2760        2770        2780        2790
                          proTEV cleavage site

CT T < 2803
```

FIGURE 20E

```
TCGCGAGCTAGCACCATGAAAACTATGATTCTACTTGCCAGTTGTTGCGTTCGTAGGATTGTCCTTACCTACAGCTCTGGC
AAGATCTGACAAAGACTCGGAAATGAAAAGAACATTGGATTCACCACTTGGGAAGTTGGAACTGAGTGGATGCGAGC
AAGGATTGCATGAAATTAAGCTACTGGGAAAAGGAACTTCTGCTGATGCAGTTGAAGTTCCAGCACCAGCAGCTGTT
CTTGGAGGTCCTGAGCCCCTCATGCAAGCCACAGCCTCAAGCCCATATTTCACCAGCCTGAAGTTCCAGCCATTGAGGAATT
TCCAGTCCCCCCCCCTTCACCATCCTGTGTTCAGCAGGAGAGCTTCACCCGCCAGGTCCTGTGGAAATTGCTGAGGTGG
TCAAGTTTGGTGAAGTGATTTCATATCAGCAACTTGCTGCATTGGCCGTCATTGGCATTGCTGCGTAAGCTACAGCTGCCGTGAAAACT
GCTCTCAGCGGAAATCCTGTGCCCATCCTGATCCCTGTCACAGAGTCGTTTCATCTTCCGGAGCTGTAGGTGGCTATGA
AGGAGGACTGGCAGTTAAGGAGTGGCTGCTGGCTCATGAAGGTCATAGACTTGGAAAGCCTGGGCTGGGTCCTGCTGGTA
TAGGCGCGCCAGGGTCCCTAGGTGGGCGATCCGAAAACCTGTACTTCCAGAGCGATATCAATAACATGTTCTTTTGCTCT
GTGCATGGAGATGCCACCATGCGCCTTCTGGCCAACGTCGAGGTGCGAGGTGCAGGTGCGTTTCTGGGGTGACCGTATTGATT
AGCCGGTCAGCCTTCTGGCCGACGTCGAGGTGCCGAGGTGCAGGTGCGTTTCTGGGGTGACCGTATTGATT
CTCAGCCATTCGCTCTCCCTTATATTCATCAACCAACCATTCGACCATTCGACCAATTCCAGCGCCCAGCCCACTTCCGCACGTCGTCG
CGACCTCGGCAGCCAGCCCGCCACTCGGCTCCGTTGGCGTGACATCCGGCGCAGCACCCAGCCCAGCTGGTGCTGAGCT
ATCTGCACCAGCTGGAGCTTCGCCACTGCTGCTGAGGTGCCACCTGCTCCAGATACTGTTCCTGTTCCTGATGTCGATTCTC
GAGGTGCTATATTACGACGTCAGTATAATTATTCAACATCACCGCTAACATCTACTATTGCCACTGTACTAACCTTGTT
CTATATGCTCCGCGCTGAGCCCTTTGCTACCACTCCAAGATGGAACTAAACACTCACATTATGGCCACTGAAGCATCAAA
TTATGCCCAGTACCGTGTTGTCCGCCTAACCCGGCAGACACTCCGCTGTGCCGAACGTGTCCAAGCTGCGGATAGCCTATAT
CTATCTTTCTGGCCTCAGACAACTACTACCGCGACATCTGTGGACATGAACTCATCACCTCACGATGTCGAATC
CTTGTCCAGCCTGGTATTGCTTCAGAACTTGTGATCCGCAGTGAGCGCCTGCATTATCGTAACCAAGGCTGGCGCTCGT
TGAGACCCTCGGTGTTGCGGAGGAGGCGACCTCGGCTTGCGTTGCTGAACCTCAGCAAAGTGGCACTGCTGAGTT
ACACCAATACGCCTTATACTGGTGCCCTTACTCGAGTAGTGCACGACACAAGCTCATTTACAGGACTAATGGCATCCGAAGTCGGTCGGTA
AACTAGGACTGCTACAGCGTGTTCCCGCGTACATCGAGTAGTGCACGACACAAGCTCATTTACAGGACTAATGGAGTTGGTGAAGTCGGTCGGTA
TAGCGCTAACTCTGTTCAACCTTGCTGATACGCTTCGCGGTGACTCCCGACAGAATTGATTTCGTCGCGTGGTGTCAG
CTATTCTATTCTCGCCCCGTCTCTCAGCCAATGGCGAGCCAACGGTGAAGCTCTACACTTCAGTCGAGAACGCTCAGCA
GGATAAGGGTATAGCTATCCCACATGATATTGATCTTGGTGAGCTCCCGTGTTGTCATTCAGGATTATGATAATAACAATG
AGCAGGATCGTCCAACTCCTTCTCCCTGCTCCATCTGACCCTTTATCTGTCCTTCGTCGTAATGATGTCATGCCTTTCA
CTTACAGCAGCTGAGTATGATCAGACTACCTATGGCTCCTCTACTAATCCAATGTATGTCTCTGATACCGTGACATTTGT
CAATGTTGCTACTGGTGCCAGGTGATCCGCGCTCTCTGGACTGGTCTAAAGTCACCTTGATGACGACCACTTATGA
CTATCCAGCAGTATTCTAAGACTTTCTTTCTTGTTCTGCCCAGTGACCAGATTTTAATTGAGAATGCAGCTGGTCACCGTGTATGCAT
GCCGGCTACCCTTATAATTATATAACTACTGCCAGTGACCAGATTTTAATTGAGAATGCAGCTGGTCACCGTGTATGCAT
CTCAACCTACACTACAATCTTGGATCTGGCCCTGTTTCTATTCTGCGTGTCGGTGTCCTCGCACCTCACTCTGCGTTGG
CCGCTTTAGGGTTGCTTTCAATCAATCCTGCTATCCTGCTGAGCTACAGCGTCTTACAGCGTCCACACTTTGATGATTCTGCCCTGAGTCCCGTACACTCGGC
CTTCAGGGTTGTGCTTTGCAATCAATGCTGTCTGAGCTACAGCGTCTTACAGCGTCTTACAGCGTCCACACTTTGATGATTCTGCCCTGAGTCCCGTACACTCGGC
GGGAGAGAATCTATATTTTCAAGGGGCCCGGCAGGTAGTCACCATCACCATCAATGACCGGTGCGGCCCGAAG
CTT
```

FIGURE 20F

Sequence of chimeric DeSNAPuniv-HEV.C protein central domain

Vector:    pDeSNAPuniv. Insertion sites of the HEV.C sequence are underlined

```
   NruI    BmtI
    |     NheI                                                                                 BglII
    |      |                                                                                    |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G    < 100
 S   R   A   S   T   M   K   L   C   I   L   L   A   V   V   A   F   V   G   L   S   L   P   T   A   L   A   R   S   D   K   D   C   E
                     10              20              30              40              50              60              70              80              90
                         Signal peptide of SNAP                                                                                    SNAP sequence AA ATG AAA AGA ACT ACA TTG GAT TCA CCA CTT GGG AAG CTT GAA CTG AGT GGA TGC GAG CAA GGA TTG CAT GAA ATT AAG CTA CTG GGA AAA GGA ACT TC  < 200
 M   K   R   T   T   L   D   S   P   L   G   K   L   E   L   S   G   C   E   Q   G   L   H   E   I   K   L   L   G   K   G   T   S
             110             120             130             140             150             160             170             180             190
                                                     <DraRI           >Bpu10I T GCT GCT GAT GAA GTT CCA GCA GCA CCA GCT GTT CTT GGA GGT CCT GAG CCC CTC ATG CAA GCC ACA GCC TGG CTT AAC GCA TAT TTC CAC CAG     < 300
 A   A   A   D   E   V   P   A   A   P   A   V   L   G   G   P   E   P   L   M   Q   A   T   A   W   L   N   A   Y   F   H   Q
     210             220             230             240             250             260             270             280             290
Bsu36I
 |
CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG G  < 400
 P   E   A   I   E   E   F   P   V   P   A   L   H   H   P   V   F   Q   Q   E   S   F   T   R   Q   V   L   W   K   L   L   K   V
             310             320             330             340             350             360             370             380             390
                                 >AlfI                                                           <BceAI
                                                                                                 <BcefI TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT   < 500
 K   F   G   E   V   I   S   Y   Q   Q   L   A   A   L   A   G   N   P   A   A   T   A   A   V   K   T   A   L   S   G   N   P   V
         410             420             430             440             450             460             470             480             490
                                                                                                                         <TstI
```

```
                     XmaI                                                                 ApaI
                     SmaI                                                                 PspOMI
                     |                                                                    |
t cac tct gcC CCG GGA GAG AAT CTA TAT TTT CAA GGG CCC GGC GGA GGT AGT CAC CAT CAC CAT CAC TAA
  H   S   A   P   G   E   N   L   Y   F   Q   G   P   G   G   G   S   H   H   H   H   H   H   *
              2310                2320                2330                2340                2350                2360                2370
```

```
                                                                                                AgeI
                                                                                                |
                                                                                                TGA CCG
                                                                                                 *   P
                                                                                                   2380
```

```
                                                                                                          EagI
                                                                                                          NotI                HindIII
                                                                                                          |                   |
                                                                                                          GTG CGG CCG CAA GCT T  < 2395
                                                                                                           V   R   P   Q   A
                                                                                                                 2390
``` proTEV cleavage site

```
TCGCGAGCTAGCACCATGAAACTATGTATTCTACTTGCAGTTGTTGCGTTCGTAGGATTGTCCTTACCTACAGCTCTGGC
AAGATCTGACAAAGACTGCGAAATGAAAAGAACTACATTGGATTCACCACCTTGGGAAGTTGGAACTGAGTGATGCGAGC
AAGGATTGCATGAAATTAAGCTACTGGGAAAAGGAACTTCTGCTGCTGAAGTTCCAGCACCAGCAGCTGTT
CTTGGAGTCCTGAGCCCCTTCACCATCCTGTGTTTCAGCAGGAGCTTCACCCGCAGCTCCAGCGCCAGCCATTGAGGAATT
TCCAGTTCCCCGCCCTTCACCATCCTGTGTTTCAGCAGGAGCTTCACCCGCAGCTCCAGCGCCAGCCATTGCTGAAGGTGG
TCAAGTTTGGTGAAAATCCTGTGCCCATCCTGCATTCAGCAACCTGTCTGCATTGTCACAGAGTCGTTTCATCTTCCGAGCTGTAGGTGGCTATGA
GCTCTCAGCAGGACTGCAGTTAAGGAGTGGCTGTGCTTGGCTCATGAAGGTCATAGACTTGGAAAGCCTGGCTGGGTCCTGTCCTGGTA
AGGAGGACTGGCAGTTAAGGAGTGGCTGTGCTTGGCTCATGAAGGTCATAGACTTGGAAAGCCTGGCTGGGTCCTGTCCTGGTA
TAGGCGGCCAGGGTCCCTAGGTGGCGGATCCGAAAACCTGTACTTCCAGAGCGATATCgttgtgctggagctcgacct
cggcagccagcccgccactgcctggccttggccctcgcgtgtgctggcacctgctccagacgcccattccgcacgtcgatctgc
accagtggagcttgccactgactgctgtgggcacctgctgtcctccagatactgttcctgatgtgactacctgttctatat
gctccgcctagccctttgctactactccaaagatgaactaacacatcacattatgccactgaagcatcaaattatgc
ccagtaccgtgttgtccgcgaccatccgtaccgtccttgtgccaacgctgtggccggatacgctatatctatct
ctttctgccctcagacaactactaccccgacatctgtgacatgaactctatcacctccacggatgtccgaatccttgtc
cccctggtattgctcagaacttgctccagtgagccgtgcattatcgtaaccaagctgcgctgtgtgagac
ctctgtgtttgcggaggaggcgaccctcgggccttgttcatccacggatcacctgtaaattcttacacca
atacgcctatactgtgccctgctactcgagatagcaacgaccaagtacgccgagaccctgagttccgcaattgacacctgtaacacg
aacacagtgttccgctactcgagtatgcaacgaccaagtacgccgagaccctgagttccgcaattgacacctgtaacacg
gactgctgctacacgctttatgaaggaccctcatttacagggactaatgagttgctggagtcggtcgtggtatagcgc
taactctgttcaactgtgatacgccttctgggacccccgacagaattgtttgtcgctgttggtcagctattc
tattctccccccgtgtctcagccaatgcgagccgaagctctcacatttcagtgcagaccctcagaggataagcgccttc
gggtatgctatccacatgatttgatcttggtagtcccgttgtcattcaggattatgataaccaacatgacgagg
atcgtccaactcctttctcctgctccatccgacctttatctgtcctttgtgtaatgatgtgctatggcttccacttaca
gcagtcgagtatgatcgactactagactcccctctaatccaatccaatggatgttctctataccgtgacattgctcaatgt
tgctactggtgcccaggtgtatctcgctctcctgactgtcctaaagtcaccccttgatggaccacttatgactatcc
agcagtattcaagacttcctttttgttctgccactacgtggcaagctcttaattgaagatgcgctgtcaccgtgtatgcatccaac
taccctatataattatataacctcttgatctgccctgatttctatttctgctcgtgtgtcggtgtctctatgatccaagagccgc
ctacactactaatcttgatctgccctgatttctatttctgctcgtgtgtcggtgtctctcaagcacctcactctgCCCCGGGAGAGA
ATCTATATTTTCAAGGGCCCGGGAGGTAGTCACCATCATCACTAATGACCGGTGCGGCCGCAAGCTT
```

FIGURE 21E

Sequence of chimeric DeSNAPuniv- HCV Core antigen

Vector: pDeSNAPuniv. Insertion sites of the HCV C sequence are underlined.

```
     NruI  BmtI                                                           BglII
           NheI
     |     |                                                              |
     TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G  < 100
     S   R   A   S   T   M   K   L   C   I   L   L   A   V   V   A   F   V   G   L   S   L   P   T   A   L   A   R   S   D   K   D   C   E
                         10                      20                      30                      40                      50                      60                      70                      80                      90
                         Signal peptide of SNAP                                                                                                              SNAP sequence <CjePI                                              <MmeI                                                                       >BmrI
     |                                                   |                                                                           |
     AA ATG AAA AGA ACT ACA TTG GAT TCA CCA CTT GGG AAG CTA GAA CTG AGT GGA TGC GAG CAA GGA TTG CAT GAA ATT AAG CTA CTG GGA AAA GGA ACT TC  < 200
     M   K   R   T   T   L   D   S   P   L   G   K   L   E   L   S   G   C   E   Q   G   L   H   E   I   K   L   L   G   K   G   T   S
                         110                     120                     130                     140                     150                     160                     170                     180                     190

<PlaDI                                                        >Bpu10I
     |                                                             |
     T GCT GCT GAT GCA GTT GAA GTT CCA GCA CCA GCA GCT GTT CTT GGA GGT CCT GAG CCC CTC ATG CAA GCC ACA GCC TGG CTT AAC GCA TAT TTC CAC CAG  < 300
     A   A   D   A   V   E   V   P   A   P   A   A   V   L   G   G   P   E   P   L   M   Q   A   T   A   W   L   N   A   Y   F   H   Q
                         210                     220                     230                     240                     250                     260                     270                     280                     290

HaeI
     <PspPRI  ApoI                                                                                                      >BdaI
     Bsu36I   |                                                                                                         |
     |        |
     CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG G  < 400
     P   E   A   I   E   E   F   P   V   P   A   L   H   H   P   V   F   Q   Q   E   S   F   T   R   Q   V   L   W   K   L   L   K   V
                         310                     320                     330                     340                     350                     360                     370                     380                     390
```

FIGURE 22A

FIGURE 22C

Sequence of chimeric DeSNAPuniv-short HCV Core (C)

Vector: pDeSNAPuniv. Insertion sites of the HCV C sequence are underlined.

```
BmtI
 NruI    NheI                                                                                                                    BglII
 |       |                                                                                                                       |
 TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G  < 100
 S   R   A   S   T   M   K   L   C   I   L   L   A   V   V   A   F   V   G   L   S   L   P   T   A   L   A   R   S   D   K   D   C   E
             10          20          30          40          50          60          70          80          90
```

Signal peptide of SNAP

SNAP sequence

```
            <CjePI                                   <MmeI                                                                      >BmrI
            |                                        |                                                                          |
 AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC  < 200
    M   K   R   T   T   L   D   S   P   L   G   K   L   E   L   S   G   C   E   Q   G   L   H   E   I   K   L   L   G   K   G   T   S
             110         120         130         140         150         160         170         180         190
```

```
       <PlaDI
       |
 T GCT GCT GAT GCA GTT GAA GTT CCA GCA CCA GCA GCT GTT CTT GGA GGT CCT GAG CCC CTC ATG CAA GCC ACA GCC TGG CTT AAC GCA TAT TTC CAC CAG  < 300
   A   A   D   A   V   E   V   P   A   P   A   A   V   L   G   G   P   E   P   L   M   Q   A   T   A   W   L   N   A   Y   F   H   Q
             210         220         230         240         250         260         270         280         290
```

```
     HaeI
  <PspPRI
 Bsu36I                  ApoI                                                                                                       >BdaI
 ||   |                  |                                                                                                          |
 CCT GAG GCC ATT GAG GAA TTT CCA GTC CCC GCC CTT CAC CAT CCT GTG TTT CAG CAG GAG AGC TTC ACC CGC CAG GTC CTG TGG AAA TTG CTG AAG GTG G  < 400
 P   E   A   I   E   E   F   P   V   P   A   L   H   H   P   V   F   Q   Q   E   S   F   T   R   Q   V   L   W   K   L   L   K   V   V
             310         320         330         340         350         360         370         380         390
```

FIGURE 23A

```
                                                              >AlfI                    BstEII                                <BceAI
                                                              |                        |                                     <BcefI
TC AAG TTT GGT GAA GTG ATT TCA TAT CAG CAA CTT GCT GCA TTG GCC GGT AAC CCC GCA GCT ACA GCT GCC GTG AAA ACT GCT CTC AGC GGA AAT CCT GT  < 500
 K   F   G   E   V   I   S   Y   Q   Q   L   A   A   L   A   G   N   P   A   A   T   A   A   V   K   T   A   L   S   G   N   P   V
       410             420             430             440             450             460             470             480             490

>MlyI
                 <BspD6I
                 >PleI                                                       McaTI                                                               <NgoAVIII
                 |                                                           BsshII                                                              <SdeOSI
                 |           BspEI                                   <BseYI  AscI   SanDI                                                        BspHI
                 |           |                                       <GsaI   | |    |                                                            |
G CCC ATC CTG ATC CCT TGT CAC AGA GTC GTT TCA TCT CCA GGA GCT GTA GGT GGC TAT GAA GGA GGA CTG GCA GTT AAG GAG TGG CTG CTG GCT CAT GAA
 P   I   L   I   P   C   H   R   V   V   S   S   P   G   A   V   G   G   Y   E   G   G   L   A   V   K   E   W   L   L   A   H   E     < 600
       510             520             530             540             550             560             570             580             590

AvrII
                                                                             StyI
                                                                             |                    BamHI              TatI                EcoRV
                                                                             |                    |                  |                   |
GGT CAT AGA CTT GGA AAG CCT GGG CTG GGT CCT GCT GGG CTG GGC CCA GGG TCC CTA GGT GGC TCC GAA AAC CTG TAC TTC CAG AGC GAT ATC A
 G   H   R   L   G   K   P   G   L   G   P   A   G   L   G   P   G   S   L   G   G   S   E   N   L   Y   F   Q   S   D   I   S     < 700
       610             620             630             640             650             660             670             680             690
                                                                                                           proTEV cleavage site GT ACg AAT CCT AAg CCT CAA cgt AAg ACT AAg CGc AAT ACT AAT CGT CCA GAT GTT AAG TTT CCG GGt GGc CAA ATT GTT GGT GGA GTT TA    < 800
 T   N   P   K   P   Q   R   K   T   K   R   N   T   N   R   P   D   V   K   F   P   G   G   Q   I   V   G   G   V   Y
       710             720             730             740             750             760             770             780             790

>Bbr7I
                                                                                                             >BbsI
              EcoNI                         XmnI
              |                             |
C CTA TTG CCG CGA AGA GGT CCT CGT TTA GGT GTT CGA GCA ACT TCT GAA AAg ACT CGA GCT ACA TCA CAA CCT CGT GGA AGA CGA CAA CCT ATT tTT AAG GCT A   < 900
 L   L   L   P   R   R   G   P   R   L   G   V   R   A   T   S   E   R   T   R   A   T   S   Q   P   R   G   R   R   Q   P   I   F   K   A
       810             820             830             840             850             860             870             880             890

Short form of the HCV Core protein from viral strain TCHM-R2/03 of genotype 1b (genbank access GQ913864)

FIGURE 23B
```

```
TCGCGAGCTAGCACCATGAAACTATGTATTCTACTTGCAGTTGTTGCGTTCGTTCGTAGGATTGTCCTTACCTACAGCTCTGGC
AAGATCTGACAAAGACTGCGAAATGCGAAAAGAACTACATTGGATTCACCACTTGGGAACTTGGAACTTGAGTGGATGCGAGC
AAGGATTGCATGAAATTAAGCTACTGGGAAAAGAACTTCTGCTGCTGAAGTTCCAGCACCAGCAGCTGTT
CTTGGAGGTCCTGACCCCCTTCACGCAAGCCACAGCTTCTGGCTTAACGCCATATTTCCACCAGCCATTGAGGAATT
TCCAGTCCCCGCCCTTCACCATCCTGTGTTTCAGCAGGAGAGCTTCACCGCCAGGTCCTGTGGAAATTGCTGAAGGTGG
TCAAGTTTGGTGAAGTGATTTCATATCAGCAACTTGCTGCATTGGCCGGTAACCCGCAGCTACAGCTGCCGTGAAAACT
GCTCTCAGCGGAAATCCTGTGCCCATCCTGATCCCTTGTCACAGAGTCGTTTCATCTTCCGGAGCTGTAGGTGGCTATGA
AGGAGGACTGGCAGTTAAGGAGTGGCTGCTGCTGCGGATCCATGAAGGTCATAGACTTGGAAAGCCTGGGCTGGGCTCCTGCTGGTA
TAGGCGCGCCAGGGTCCCTAGGTGGCGGATCCGAAAACCTGTACTTCCAGAGCGATATCAGTACGAATCCTAAgCCTCAA
cgtAagACTAAgCGCAATACTAATCGTCGTCCACAAGATGTTAAGTTTCCGGGtGgCcGGtCAAATTGTTGGTGGAGTTTA
CCTATTGCCGGAAGAGGTCCTCGTTTAGGTGTTCGAGCAACTAGAAAgACTTCTGGACGATCACAACCTCGTGAAGAC
GACAACCTATTtttAAGGCTCGtCGtGTACTATCACCTCGTGGTTCTCGACCTAGTGGTTATCCTatgCCTCTATATGGTAAT
GAAGGAtgcGGTaatGCAGGAatgCTAGGAAGTAGAaCTatgCCTCAGCCTGGTTATCCTcctactGACCCTCGACGAAG
ATCACGTAATTTAGGTagaGTAATTGATACACTTACATGTGGTTTGCTGATCTTATGGATATATTCCACTAGTAGGTG
CTCCACTAGGTGGAGCTGCAAGAGCTCTTGCACATGGTGTACGAGTTCTTGAAGATGAGTGAACTATGCAACAGGTAAT
CTCCCGGGAGAGAATCTATATTTTCAAGGGCCCGGCGGAGGTAGTCACCATCATCACCACTAATGACCGGTGCGGCC
GCAAGCTT
```

FIGURE 23D

Sequence of chimeric DeSNAPuniv-Schmallenberg NSs protein

Vector: pDeSNAPuniv. Insertion sites of the Schmallenberg NSs gene are underlined.

```
         BmtI
NruI     NheI                                                              BglII
 |        |                                                                  |
TCG CGA GCT AGC ACC ATG AAA CTA TGT ATT CTA CTT GCA GTT GTT GCG TTC GTA GGA TTG TCC TTA CCT ACA GCT CTG GCA AGA TCT GAC AAA GAC TGC G   < 100
 S   R   A   S   T   M   K   L   C   I   L   L   A   V   V   A   F   V   G   L   S   L   P   T   A   L   A   R   S   D   K   D   C  E
            10                  20                  30                  40                  50                  60                  70                  80                  90
             Signal peptide of SNAP                                                                                                          SNAP sequence <VmeI                                                                           >BmrI
AA ATG AAA AGA ACT ACA TTG GAT TCA CCA CTT GGG AAG TTG GAA CTG AGT GGA TGC GAG CAA GGA TTG CAT GAA ATT AAG CTA CTG GGA AAA GGA ACT TC   < 200
 M   K   R   T   T   L   D   S   P   L   G   K   L   E   L   S   G   C   E   Q   G   L   H   E   I   K   L   L   G   K   G   T   S
             110                 120                 130                 140                 150                 160                 170                 180                 190

<PlaDI                                  <DraRI         >Bpu10I                                          PflMI
T GCT GCT GAT GCA GTT GAA GTT CCA GCA GCA GTT CTT GGT GTT CTT GAG CCC CTC ATG CAA GCC ACA GCC TGG CTT AAC GCA TAT TTC CAC CAG          < 300
 A   A   D   A   V   E   V   P   A   A   V   L   G   V   L   E   P   L   M   Q   A   T   A   W   L   N   A   Y   F   H   Q
           210                 220                 230                 240                 250                 260                 270                 280                 290

>BdaI
<PspP2RI                                                                                                                           >AcuI
Bsu36I                       <RpaB5I                                                                                               >Eco57MI
   |                           |                                                                                                    ||
CCT GAG GCC ATT GAG GAA TTT CCA GTC CCC GCC CTT CAC CAT CCT GTG TTT CAG CAG GAG AGC TTC ACC CGC CTG TGG AAA TTG CTG AAG GTG G          < 400
 P   E   A   I   E   E   F   P   V   P   A   L   H   H   P   V   F   Q   Q   E   S   F   T   R   L   W   K   L   L   K   V
           310                 320                 330                 340                 350                 360                 370                 380                 390
```

FIGURE 24A

| Agent | | | Antigen-coupled microspheres | | Microsphere panels | | | | | | | | | |
|---|---|---|---|---|---|---|---|---|---|---|---|---|---|---|
| | | | | | Geographical | | | | | Syndromic | | | Veterinary | |
| Genus | Species | | Abbreviation | Description | Africa | Asia | Europe | Americas | Oceania | Flu-like | Encephalitis | Hemorrhagic fever | Bovine disease | Equine disease |
| Flavivirus | Dengue virus type 1 | | SNAP+DEN1.EDIII | Enveloppe Domain III | x | x | x | x | x | x | | x | | |
| | Dengue virus type 2 | | SNAP+DEN2.EDIII | Enveloppe Domain III | x | x | x | x | x | x | | x | | |
| | Dengue virus type 3 | | SNAP+DEN3.EDIII | Enveloppe Domain III | x | x | x | x | x | x | | x | | |
| | Dengue virus type 4 | | SNAP+DEN4.EDIII | Enveloppe Domain III | x | x | x | x | x | x | | x | | |
| | Yellow fever virus | | SNAP+YF.EDIII | Enveloppe Domain III | x | x | | x | | x | | x | | |
| | West-Nile virus | | SNAP+WNV.EDIII | Enveloppe Domain III | x | x | x | x | x | x | x | | | x |
| | | | WNV.prM-sE+SNAP | Soluble form of secreted Enveloppe protein | x | x | x | x | x | x | x | | | x |
| | Usutu virus | | SNAP+USU.EDIII | Enveloppe Domain III | x | x | x | | | | x | | | |
| | Japanese encephalitis virus genotype 3 | | JE.prM-sE+SNAP | Soluble form of secreted Enveloppe protein | | x | | | x | x | x | | | x |
| | Japanese encephalitis virus genotype 1 | | SNAP+JE-1.EDIII | Enveloppe Domain III | | x | | | x | x | x | | | x |
| | Japanese encephalitis virus genotype 2 | | SNAP+JE-2.EDIII | Enveloppe Domain III | | x | | | x | x | x | | | x |
| | Japanese encephalitis virus genotype 3 | | SNAP+JE-3.EDIII | Enveloppe Domain III | | x | | | x | x | x | | | x |
| | Japanese encephalitis virus genotype 4 | | SNAP+JE-4.EDIII | Enveloppe Domain III | | x | | | x | x | x | | | x |
| | Japanese encephalitis virus genotype 5 | | SNAP+JE-5.EDIII | Enveloppe Domain III | | x | | | x | x | x | | | x |
| | Murray Valley encephalitis virus | | SNAP+MVE.EDIII | Enveloppe Domain III | | x | | | x | x | x | | | |
| | Saint-Louis encephalitis virus | | SNAP+SLE.EDIII | Enveloppe Domain III | | | | x | x | x | x | | | |
| | Zika virus | | SNAP+ZIKV.EDIII | Enveloppe Domain III | x | x | | | | x | x | | | |
| | Wesselsbron virus | | SNAP+WSL.EDIII | Enveloppe Domain III | x | | | | | x | x | | | |
| | Rocio virus | | SNAP+ROCV.EDIII | Enveloppe Domain III | | | | x | | | x | | | |
| | Rabensburg virus | | SNAP+RabV.EDIII | Enveloppe Domain III | | | x | | | | x | | | |
| | Insectivore flavivirus (coll.La Timone) | | SNAP+Insectflavi.EDIII | Enveloppe Domain III | | | x | | | | x | | | |
| | Tickborne encephalitis virus | | SNAP+TBE.EDIII | Enveloppe Domain III | | x | x | | | | x | | | |
| | Omsk Hemorrhagic Fever virus | | SNAP+OMSK.EDIII | Enveloppe Domain III | | x | | | | | | x | x | |
| | Kyasanur Forest Disease virus | | SNAP+KAS.EDIII | Enveloppe Domain III | | x | | | | | | x | x | |
| | Alkhurma virus | | SNAP+ALK.EDIII | Enveloppe Domain III | | x | | | | | | x | x | |
| Orthobunyavirus | Schmallenberg virus | | SNAP+SBV.N | Nucleoprotein N | | | x | | | | | | x | |
| | Akabane virus | | SNAP+AKA.N | Nucleoprotein N | | | x | | x | | | | x | |
| | Aino virus | | SNAP+AIN.N | Nucleoprotein N | | | x | | x | | | | x | |
| | Shamonda virus | | SNAP+SHA.N | Nucleoprotein N | x | | x | | | | | | x | |
| Bunyavirus | Rift Valley fever virus | | SNAP+RVF.N | Nucleoprotein N | x | x | x | x | | x | | x | x | |
| Alphavirus | Chikungunya virus | | CHIK.sE2+SNAP | Soluble form of secreted E2 glycoprotein | x | x | | x | x | x | | | | |
| | Ross River virus | | RR.sE2+SNAP | Soluble form of secreted E2 glycoprotein | | | | | x | x | | | | |
| | Mayaro virus | | MAY.sE2+SNAP | Soluble form of secreted E2 glycoprotein | | | | x | | x | | | | x |

FIGURE 25A

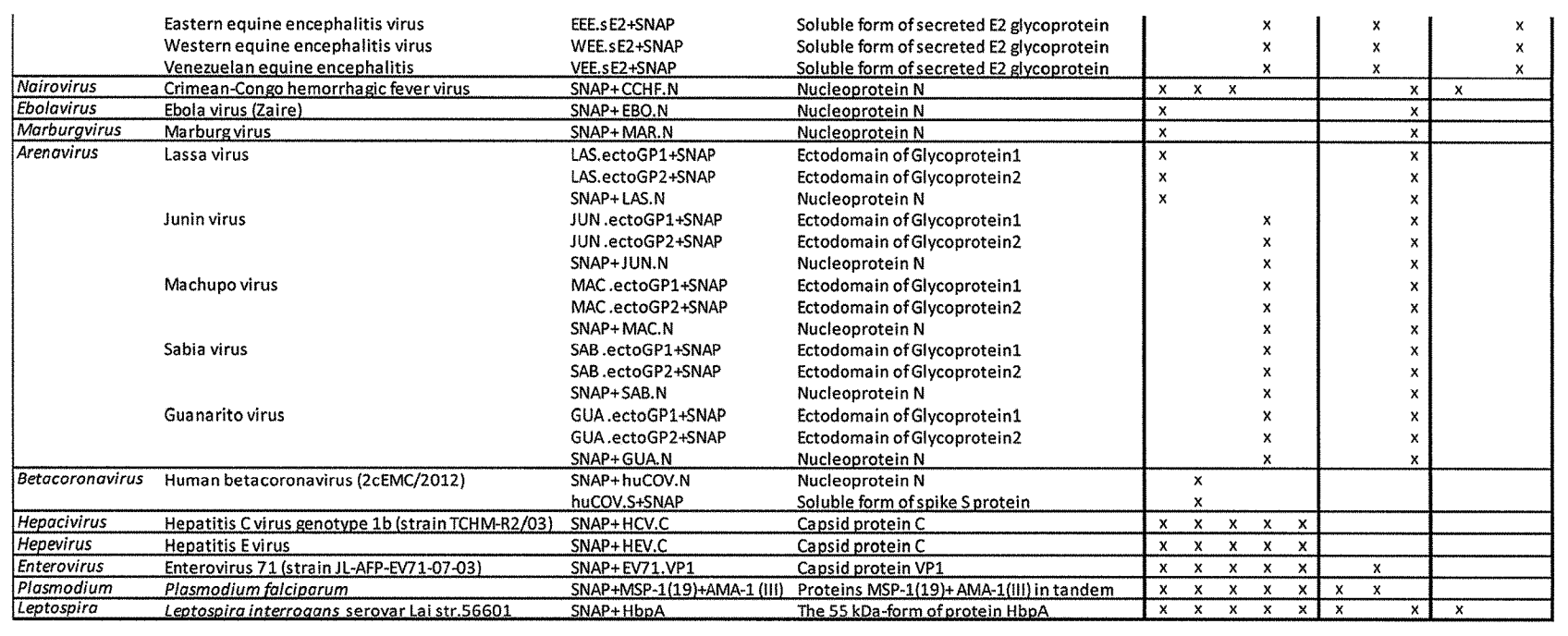

| | | | | | | | | | | | | | |
|---|---|---|---|---|---|---|---|---|---|---|---|---|---|
| | Eastern equine encephalitis virus | EEE.sE2+SNAP | Soluble form of secreted E2 glycoprotein | | | | x | | | x | | | x |
| | Western equine encephalitis virus | WEE.sE2+SNAP | Soluble form of secreted E2 glycoprotein | | | | x | | | x | | | x |
| | Venezuelan equine encephalitis | VEE.sE2+SNAP | Soluble form of secreted E2 glycoprotein | | | | x | | | x | | | x |
| *Nairovirus* | Crimean-Congo hemorrhagic fever virus | SNAP+CCHF.N | Nucleoprotein N | x | x | x | | | | | x | x | |
| *Ebolavirus* | Ebola virus (Zaire) | SNAP+EBO.N | Nucleoprotein N | x | | | | | | | x | | |
| *Marburgvirus* | Marburg virus | SNAP+MAR.N | Nucleoprotein N | x | | | | | | | x | | |
| *Arenavirus* | Lassa virus | LAS.ectoGP1+SNAP | Ectodomain of Glycoprotein1 | x | | | | | | | x | | |
| | | LAS.ectoGP2+SNAP | Ectodomain of Glycoprotein2 | x | | | | | | | x | | |
| | | SNAP+LAS.N | Nucleoprotein N | x | | | | | | | x | | |
| | Junin virus | JUN.ectoGP1+SNAP | Ectodomain of Glycoprotein1 | | | | x | | | | x | | |
| | | JUN.ectoGP2+SNAP | Ectodomain of Glycoprotein2 | | | | x | | | | x | | |
| | | SNAP+JUN.N | Nucleoprotein N | | | | x | | | | x | | |
| | Machupo virus | MAC.ectoGP1+SNAP | Ectodomain of Glycoprotein1 | | | | x | | | | x | | |
| | | MAC.ectoGP2+SNAP | Ectodomain of Glycoprotein2 | | | | x | | | | x | | |
| | | SNAP+MAC.N | Nucleoprotein N | | | | x | | | | x | | |
| | Sabia virus | SAB.ectoGP1+SNAP | Ectodomain of Glycoprotein1 | | | | x | | | | x | | |
| | | SAB.ectoGP2+SNAP | Ectodomain of Glycoprotein2 | | | | x | | | | x | | |
| | | SNAP+SAB.N | Nucleoprotein N | | | | x | | | | x | | |
| | Guanarito virus | GUA.ectoGP1+SNAP | Ectodomain of Glycoprotein1 | | | | x | | | | x | | |
| | | GUA.ectoGP2+SNAP | Ectodomain of Glycoprotein2 | | | | x | | | | x | | |
| | | SNAP+GUA.N | Nucleoprotein N | | | | x | | | | x | | |
| *Betacoronavirus* | Human betacoronavirus (2cEMC/2012) | SNAP+huCOV.N | Nucleoprotein N | | x | | | | | | | | |
| | | huCOV.S+SNAP | Soluble form of spike S protein | | x | | | | | | | | |
| *Hepacivirus* | Hepatitis C virus genotype 1b (strain TCHM-R2/03) | SNAP+HCV.C | Capsid protein C | x | x | x | x | x | | | | | |
| *Hepevirus* | Hepatitis E virus | SNAP+HEV.C | Capsid protein C | x | x | x | x | x | | | | | |
| *Enterovirus* | Enterovirus 71 (strain JL-AFP-EV71-07-03) | SNAP+EV71.VP1 | Capsid protein VP1 | x | x | x | x | x | | x | | | |
| *Plasmodium* | *Plasmodium falciparum* | SNAP+MSP-1(19)+AMA-1 (III) | Proteins MSP-1(19)+AMA-1(III) in tandem | x | x | x | x | x | x | x | | | |
| *Leptospira* | *Leptospira interrogans* serovar Lai str.56601 | SNAP+HbpA | The 55 kDa-form of protein HbpA | x | x | x | x | x | x | | x | x | |

FIGURE 25B

SEQUENCE LISTING

<160> NUMBER OF SEQ ID NOS: 179

<210> SEQ ID NO 1
<211> LENGTH: 238
<212> TYPE: PRT
<213> ORGANISM: homo sapiens

<400> SEQUENCE: 1

Met Leu Gly Gln Pro Ala Pro Leu Glu Arg Phe Ala Ser Arg Arg Pro
1               5                   10                  15

Gln Val Leu Ala Val Arg Thr Val Cys Asp Leu Val Leu Gly Lys Met
            20                  25                  30

Asp Lys Asp Cys Glu Met Lys Arg Thr Thr Leu Asp Ser Pro Leu Gly
         35                  40                  45

Lys Leu Glu Leu Ser Gly Cys Glu Gln Gly Leu His Glu Ile Lys Leu
 50                  55                  60

Leu Gly Lys Gly Thr Ser Ala Ala Asp Ala Val Glu Val Pro Ala Pro
 65                  70                  75                  80

Ala Ala Val Leu Gly Gly Pro Glu Pro Leu Met Gln Cys Thr Ala Trp
                 85                  90                  95

Leu Asn Ala Tyr Phe His Gln Pro Glu Ala Ile Glu Glu Phe Pro Val
                100                 105                 110

Pro Ala Leu His His Pro Val Phe Gln Gln Glu Ser Phe Thr Arg Gln
                115                 120                 125

Val Leu Trp Lys Leu Leu Lys Val Val Lys Phe Gly Glu Val Ile Ser
 130                 135                 140

Tyr Gln Gln Leu Ala Ala Leu Ala Gly Asn Pro Lys Ala Ala Arg Ala
145                 150                 155                 160

Val Gly Gly Ala Met Arg Gly Asn Pro Val Pro Ile Leu Ile Pro Cys
                165                 170                 175

His Arg Val Val Cys Ser Ser Gly Ala Val Gly Asn Tyr Ser Gly Gly
                180                 185                 190

Leu Ala Val Lys Glu Trp Leu Leu Ala His Glu Gly His Arg Leu Gly
                195                 200                 205

Lys Pro Gly Leu Gly Gly Ser Ser Gly Leu Ala Gly Ala Trp Leu Lys
                210                 215                 220

Gly Ala Gly Ala Thr Ser Gly Ser Pro Pro Ala Gly Arg Asn
225                 230                 235

<210> SEQ ID NO 2
<211> LENGTH: 193
<212> TYPE: PRT
<213> ORGANISM: artificial
<220> FEATURE:
<223> OTHER INFORMATION: Amino acid sequence of SNAP

<400> SEQUENCE: 2

Arg Ser Asp Lys Asp Cys Glu Met Lys Arg Thr Thr Leu Asp Ser Pro
 1               5                  10                  15

Leu Gly Lys Leu Glu Leu Ser Gly Cys Glu Gln Gly Leu His Glu Ile
                 20                  25                  30

Lys Leu Leu Gly Lys Gly Thr Ser Ala Ala Asp Ala Val Glu Val Pro
                 35                  40                  45

Ala Pro Ala Ala Val Leu Gly Gly Pro Glu Pro Leu Met Gln Ala Thr
 50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
                100                 105                 110

Ile Ser Tyr Gln Gln Leu Ala Ala Leu Ala Gly Asn Pro Ala Ala Thr
                115                 120                 125

Ala Ala Val Lys Thr Ala Leu Ser Gly Asn Pro Val Pro Ile Leu Ile
                130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
            165                 170                 175

Leu Gly Lys Pro Gly Leu Gly Pro Ala Gly Ile Gly Ala Pro Gly Ser
        180                 185                 190

Leu

<210> SEQ ID NO 3
<211> LENGTH: 404
<212> TYPE: DNA
<213> ORGANISM: Dengue virus 1

<400> SEQUENCE: 3
taggcgcgcc agggtccctg gagggaggtg gcgggtctct gactttaaaa gggatgtcat    60
atgtgatgtg cacaggctca tttaagctag agaaggaagt ggctgagacc cagcatggaa   120
ctgtcctagt gcaggttaaa tacgaaggaa cagatgcgcc atgcaagatc ccctttcga    180 cccaagatga aaaggagtg acccagaatg ggagattgat aacagccaat cccatagtta   240
ctgacaaaga aaaccaatc aacattgaga cagaaccacc ttttggtgag agctacatca   300
tagtaggggc aggtgaaaaa gctttgaaac taagctggtt caagaaagga agcagcatag   360
ggaaaggagg tggccatcac catcaccatc actgatgacc ggtt                    404

<210> SEQ ID NO 4
<211> LENGTH: 404
<212> TYPE: DNA
<213> ORGANISM: Dengue virus 2

<400> SEQUENCE: 4
taggcgcgcc agggtccctg gagggaggtg gcgggtctct acagctcaaa ggaatgtcat    60
attctatgtg tacaggaaag tttaaagttg tgaaggaaat agcagaaaca caacatggaa   120
caatagttct cagagtacaa tatgaagggg acggttctcc gtgcaagatc ccttttgaaa   180
taatggattt ggaaaaaaga catgtcttag gtcgcttgat cacagtcaac ccaattgtta   240
cagaaataga cagcccagtc aacatagaag cagaacctcc attcggagac agctacatca   300
ttataggagt agaaccggga caactgaagc tcagctggtt taagaaagga agttccattg   360
gccaaggagg tggccatcac catcaccatc actgatgacc ggtt                    404

<210> SEQ ID NO 5
<211> LENGTH: 401
<212> TYPE: DNA
<213> ORGANISM: Dengue virus 3

<400> SEQUENCE: 5
taggcgcgcc agggtccctg gagggaggtg gcgggtctga actcaagggg atgagctatg    60
caatgtgctt gaatacctt tgttgaaga aagaagtctc cgaaacgcag catgggacaa    120
tactcattaa ggttgagtac aaaggggaag atgcaccttg caagattcct ttctccacag   180
aggatggaca agggaaagcc cacaatggta gactgatcac agccaaccca gtggttacta   240
agaaggagga gcctgtcaac attgaggctg aacctccttt tggggaaagc aacatagtga   300
ttggagttgg agacaaagcc ttgaaaatta ctggtacaa gaagggaagc tcgattggga   360
agggaggtgg ccatcaccat caccatcact gatgaccggt t                       401

<210> SEQ ID NO 6
<211> LENGTH: 401
<212> TYPE: DNA
<213> ORGANISM: Dengue virus 4

<400> SEQUENCE: 6

```
taggcgcgcc agggtccctg gagggaggtg gcgggtctag aatcaaggga atgtcataca    60
cgatgtgctc aggaaagttc tcaattgaca aagagatggc agaaacacag catgggacaa   120
cagtggtgaa agtcaagtat gaaggtgctg gagctccgtg taaagtcccc atagagatac   180
gagatgtaaa taaggaaaaa gtggttgggc gtgtcatctc atccacccct ctagctgaga   240
ataccaacag tgtgaccaac atagaactgg aacccccctt tggggacagt tacatagtca   300
taggtgttgg gaacagtgca ttgacactcc attggttcag gaaaggaagt tctattggca   360
agggaggtgg ccatcaccat caccatcact gatgaccggt t                       401
```

<210> SEQ ID NO 7
<211> LENGTH: 398
<212> TYPE: DNA
<213> ORGANISM: West Nile Virus

<400> SEQUENCE: 7

```
taggcgcgcc aggaggtggc gggtctcagt tgaagggaac aacctatggc gtctgttcaa    60
aggctttcaa gtttcttggg actcccgcag acacaggtca cggcactgtg gtgttggaat   120
tgcagtacac tggcacggat ggaccttgca aagttcctat ctcgtcagtg gcttcattga   180
acgacctaac gccagtgggc agattggtca ctgtcaaccc ttttgtttca gtggccacgg   240
ccaacgctaa ggtcctgatt gaattggaac cacccttt gg agactcatac atagtggtgg   300
gcagaggaga acaacagatc aatcaccatt ggcacaagtc tggaagcagc attggcaaag   360
gaggtggcca tcaccatcac catcactgat gaccggtt                            398
```

<210> SEQ ID NO 8
<211> LENGTH: 410
<212> TYPE: DNA
<213> ORGANISM: Yellow fever virus

<400> SEQUENCE: 8

```
taggcgcgcc agggtccctg gagggaggtg gcgggtcttc agctttgaca ctcaagggga    60
catcctacaa aatgtgcact gacaaaatgt cttttgtcaa gaacccaact gacactggcc   120
atggcactgt tgtgatgcag gtgaaagtgc caaaaggagc ccctgcaag attccagtga    180
tagtagctga tgatcttaca gcggcaatca ataaaggcat tttggttaca gttaaccccca   240
tcgcctcaac caatgatgat gaagtgctga ttgaggtgaa cccaccttt ggagacagct    300
acattatcgt tgggacagga gattcacgtc tcacttacca gtggcacaaa gagggaagct   360
caataggaaa gggaggtggc catcaccatc accatcactg atgaccggtt              410
```

<210> SEQ ID NO 9
<211> LENGTH: 410
<212> TYPE: DNA
<213> ORGANISM: Japanese encephalitis virus

<400> SEQUENCE: 9

```
taggcgcgcc agggtccctg gagggaggtg gcgggtctgc tctgaaaggc acaacctatg    60
gcatgtgtac agaaaaattc tcgttcgcga aaaatccggc ggacactggt cacggaacag   120
ttgtcattga actctcctac tctgggagtg atggcccctg caaaattccg attgtctccg   180
tcgcgagcct caatgacatg actcctgttg ggcggctggt gacagtgaac ccctttgtcg   240
cggcttccag tgccaactca aaggtgctgg tcgagatgga accccccttc ggagactcct   300
```

```
atatcgtggt tggaagggga gacaagcaga tcaaccacca ttggcacaga gctggaagca      360
cgctgggcaa gggaggtggc catcaccatc accatcactg atgaccggtt                 410

<210> SEQ ID NO 10
<211> LENGTH: 397
<212> TYPE: DNA
<213> ORGANISM: Zika virus

<400> SEQUENCE: 10
gcgcgccagg aggtggcggg tctcttagat tgaagggcgt gtcatactcc ttgtgtaccg      60
cagcgttcac attccccaag atcccggctg aaacactgca cgggacagtc acagtggagg     120
tacagtacgc agggacagat ggaccctgca aggttccagc tcagatggcg gtggacatgc     180
aaactctgac cccagttggg aggctgataa ccgctaaccc tgtaatcact gaaagcactg     240
agaactctaa gatgatgctg gaacttgatc caccatttgg ggactcttac attgtcatag     300
gagtcgggga gaagaagatc acccatcact ggcacaggag tggcagcacc attggaaaag     360
gaggtggcca tcaccatcac catcactgat gaccggt                              397

<210> SEQ ID NO 11
<211> LENGTH: 385
<212> TYPE: DNA
<213> ORGANISM: Wesselbron virus

<400> SEQUENCE: 11
gcgcgccagg aggtggcggg ctcatcctga aaggttcaac ctactcaatg tgcaaaagag      60
ggatgtcctt tgctaagcaa ccagttgaga cagaccatgg aacagcagtg atgcagataa     120
aagttacaac tggagctccg tgcagaattc cagtgattgc agcagattcc atggcgggaa     180
cagaaaaccg tggaagcgtc atcacaacca atcctattgc tgcgtcaaac aatgatgaag     240
tgttggtgga gatcagtcca ccatttggag agagttacat catcgttggt aatggagatg     300
ataaacttac ataccactgg caaagatcag gaagcaccat cgggaatgga ggtggccatc     360
accatcacca tcactgatga ccggt                                            385

<210> SEQ ID NO 12
<211> LENGTH: 397
<212> TYPE: DNA
<213> ORGANISM: Rocio virus

<400> SEQUENCE: 12
gcgcgccagg aggtggcggg tctctcaaaa tcaagggtc aacatacctg atgtgcaagg      60
acaaatttgc ttttgccaag aacccagttg acacaggaca cggcacaatc gtgacggagg     120
tacagtacgc tggttctgat gggccatgca ggattccaat caccatgacc gagaacctac     180
atgatctcac tcccatcgga cgattggtga cggtcaatcc atttgttccc tcatccgaga     240
cggcacaaaa aatttttgatt gaactcgagc ccccctttgg gacatccttc atactggtgg     300
gtacaggtcc caaccaggtg aaataccagt ggcataagtc tggtagtgtg atcggaaaag     360
gaggtggcca tcaccatcac catcactgat gaccggt                              397

<210> SEQ ID NO 13
<211> LENGTH: 397
<212> TYPE: DNA
<213> ORGANISM: Murray encephalitis virus

<400> SEQUENCE: 13
gcgcgccagg aggtggcggg tctttgaaac tgaaaggaac cacttatggg atgtgcacag      60
```

```
aaaaatttac tttctcaaag aatccagccg acaccggaca tggcacggta gtactagaac    120
tgcagtacac cgggagtgat ggaccatgca aaattccaat atcctctgta gcaagtctca    180
atgacatgac gcctgtcgga agaatggtga cagctaatcc atatgtagct tcatcaactg    240
ccaatgctaa agttctggtg gagattgaac caccccttcgg agactcatac attgtggtag    300 gcagggagaga caagcagatc aatcaccact ggcataagga gggtagttca attggcaaag    360
gaggtggcca tcaccatcac catcactgat gaccggt                              397

<210> SEQ ID NO 14
<211> LENGTH: 397
<212> TYPE: DNA
<213> ORGANISM: Saint-Louis encephalitis virus

<400> SEQUENCE: 14
gcgcgccagg aggtggcggg tctgttaaaa tcaagggggac gacatatggt atgtgtgact     60
ctgctttcac cttcagcaag aaccctgctg acacagggca tgggacagtg atcgtggaac    120
tgcagtacac tggaagcaac ggaccatgcc gggttcccat ttctgtgact gcaaacctca    180
tggacttgac accagttgga agactggtca cggtcaatcc ctttattagc acaggggggag    240 cgaacaacaa ggtcatgatc gaagttgaac cacccttttgg cgactcttac atcgtcgtcg    300
gaagaggcac cacccagatc aactaccact ggcacaaaga gggaagcagc attgggaagg    360
gaggtggcca tcaccatcac catcactgat gaccggt                              397

<210> SEQ ID NO 15
<211> LENGTH: 579
<212> TYPE: DNA
<213> ORGANISM: artificial
<220> FEATURE:
<223> OTHER INFORMATION: DNA encoding original SNAP (normal G/C content)

<400> SEQUENCE: 15
agatctgaca aagactgcga aatgaagcgc accaccctgg atagccctct gggcaagctg     60
gaactgtctg gtgcgaaca gggcctgcac gagatcaagc tgctgggcaa aggaacatct    120
gccgccgacg ccgtggaagt gcctgcccca gccgccgtgc tgggcggacc agagccactg    180
atgcaggcca ccgcctggct caacgcctac tttcaccagc ctgaggccat cgaggagttc    240
cctgtgccag ccctgcacca cccagtgttc cagcaggaga gctttacccg ccaggtgctg    300
tggaaactgc tgaaagtggt gaagttcgga gaggtcatca gctaccagca gctggccgcc    360
ctggccggca tcccgccgc caccgccgcc gtgaaaaccg ccctgagcgg aaatcccgtg    420
cccattctga tcccctgcca ccgggtggtg tctagctctg cgccgtggg gggctacgag    480 ggcgggctcg ccgtgaaaga gtggctgctg gcccacgagg ccacagact gggcaagcct    540 gggctgggtc ctgcaggtat aggcgcgcca gggtcccta                            579

<210> SEQ ID NO 16
<211> LENGTH: 235
<212> TYPE: PRT
<213> ORGANISM: artificial
<220> FEATURE:
<223> OTHER INFORMATION: mutated N protein of schmallenberg virus

<400> SEQUENCE: 16

Asp Ile Ser Ser Gln Phe Ile Phe Glu Asp Val Pro Gln Arg Asn Ala
1               5                   10                  15

Ala Thr Phe Asn Pro Glu Val Gly Tyr Val Ala Phe Ile Gly Lys Tyr
```

```
                    20                  25                  30
Gly Gln Gln Leu Asn Phe Gly Val Ala Arg Val Phe Leu Asn Gln
             35                  40                  45
Lys Lys Ala Lys Met Val Leu His Lys Thr Ala Gln Pro Ser Val Asp
 50                  55                  60
Leu Thr Phe Gly Gly Val Lys Phe Thr Val Val Asn Asn His Phe Pro
 65                  70                  75                  80
Gln Tyr Val Ser Asn Pro Val Pro Asp Asn Ala Ile Thr Leu His Arg
                 85                  90                  95
Met Ser Gly Tyr Leu Ala Arg Trp Ile Ala Asp Thr Cys Lys Ala Ser
             100                 105                 110
Val Leu Lys Leu Ala Glu Ala Ser Ala Gln Ile Val Met Pro Leu Ala
             115                 120                 125
Glu Val Lys Gly Cys Thr Trp Ala Asp Gly Tyr Thr Met Tyr Leu Gly
             130                 135                 140
Phe Ala Pro Gly Ala Glu Met Phe Leu Asp Ala Phe Asp Phe Tyr Pro
145                 150                 155                 160
Leu Val Ile Glu Met His Arg Val Leu Lys Asp Asn Met Asp Val Asn
                 165                 170                 175
Phe Met Lys Lys Val Leu Arg Gln Arg Tyr Gly Thr Met Thr Ala Glu
             180                 185                 190
Glu Trp Met Thr Gln Lys Ile Thr Glu Ile Lys Ala Ala Phe Asn Ser
             195                 200                 205
Val Gly Gln Leu Ala Trp Ala Lys Ser Gly Phe Ser Pro Ala Ala Arg
             210                 215                 220
Thr Phe Leu Gln Gln Phe Gly Ile Asn Ile Pro
225                 230                 235

<210> SEQ ID NO 17
<211> LENGTH: 707
<212> TYPE: DNA
<213> ORGANISM: artificial
<220> FEATURE:
<223> OTHER INFORMATION: Mutated DNA sequence encoding the N protein of
      schmallenberg virus

<400> SEQUENCE: 17
gatatctcaa gccaattcat ttttgaagat gtaccacaac ggaatgcagc tacatttaac      60
ccggaggtcg ggtatgtggc atttattggt aagtatgggc aacaactcaa cttcggtgtt     120
gctagagtct tcttcctcaa ccagaagaag gccaagatgg tcctacataa gacggcacaa     180
ccaagtgtcg atcttacttt tggtggggtc aaatttacag tggttaataa ccattttccc     240
caatatgtct caaatcctgt gccagacaat gccattacac ttcacaggat gtcaggttat     300
ctagcacgtt ggattgctga tacatgcaag gctagtgtcc tcaaactagc tgaagctagt     360
gctcagattg tcatgcccct tgctgaggtt aagggatgca cctgggccga tggttataca     420
atgtatcttg gatttgcacc tggggccgaa atgttccttg atgcttttga cttctatcca     480
ctagttattg aaatgcatag ggtcctcaag gacaatatgg atgtaaattt tatgaaaaaa     540
gtcctccgcc aacgctatgg aacaatgact gctgaagaat ggatgactca gaaaataaca     600
gaaataaaag ctgcttttaa ttctgttgga cagcttgcct gggccaaatc tggattctct     660
cctgctgcta gaaccttctt gcagcaattc ggtatcaaca tcccggg                   707

<210> SEQ ID NO 18
<211> LENGTH: 211
```

<212> TYPE: PRT
<213> ORGANISM: mus musculus

<400> SEQUENCE: 18

Met Ala Glu Thr Cys Lys Met Lys Tyr Ser Val Leu Asp Ser Pro Leu
1               5                   10                  15

Gly Lys Met Glu Leu Ser Gly Cys Glu Arg Gly Leu His Gly Ile Arg
            20                  25                  30

Leu Leu Ser Gly Lys Thr Pro Asn Thr Asp Pro Thr Glu Ala Pro Ala
        35                  40                  45

Thr Pro Glu Val Leu Gly Gly Pro Glu Gly Val Pro Glu Pro Leu Val
    50                  55                  60

Gln Cys Thr Ala Trp Leu Glu Ala Tyr Phe Arg Glu Pro Ala Ala Thr
65                  70                  75                  80

Glu Gly Leu Pro Leu Pro Ala Leu His His Pro Val Phe Gln Gln Asp
                85                  90                  95

Ser Phe Thr Arg Gln Val Leu Trp Lys Leu Leu Lys Val Val Lys Phe
            100                 105                 110

Gly Glu Thr Val Ser Tyr Gln Gln Leu Ala Ala Leu Ala Gly Asn Pro
        115                 120                 125

Lys Ala Ala Arg Ala Val Gly Ala Met Arg Ser Asn Pro Val Pro
130                 135                 140

Ile Leu Ile Pro Cys His Arg Val Val Arg Ser Asp Gly Ala Ile Gly
145                 150                 155                 160

His Tyr Ser Gly Gly Gly Gln Ala Val Lys Glu Trp Leu Leu Ala His
                165                 170                 175

Glu Gly Ile Pro Thr Gly Gln Pro Ala Ser Lys Gly Leu Gly Leu Thr
            180                 185                 190

Gly Thr Trp Leu Lys Ser Ser Phe Glu Ser Thr Ser Ser Glu Pro Ser
        195                 200                 205

Gly Arg Asn
    210

<210> SEQ ID NO 19
<211> LENGTH: 209
<212> TYPE: PRT
<213> ORGANISM: Rattus norvegicus

<400> SEQUENCE: 19

Met Ala Glu Ile Cys Lys Met Lys Tyr Thr Val Leu Asp Ser Pro Leu
1               5                   10                  15

Gly Lys Ile Glu Leu Ser Gly Cys Glu Arg Gly Leu His Gly Ile Arg
            20                  25                  30

Phe Leu Ser Gly Lys Thr Pro Asn Thr Asp Pro Thr Glu Ala Pro Ala
        35                  40                  45

Cys Pro Glu Val Leu Gly Gly Pro Glu Gly Val Pro Glu Pro Leu Val
    50                  55                  60

Gln Cys Thr Ala Trp Leu Glu Ala Tyr Phe His Glu Pro Ala Ala Thr
65                  70                  75                  80

Glu Gly Leu Pro Leu Pro Ala Leu His His Pro Val Phe Gln Gln Asp
                85                  90                  95

Ser Phe Thr Arg Gln Val Leu Trp Lys Leu Leu Lys Val Val Lys Phe
            100                 105                 110

Gly Glu Met Val Ser Tyr Gln Gln Leu Ala Ala Leu Ala Gly Asn Pro
        115                 120                 125

-continued

```
Lys Ala Ala Arg Ala Val Gly Gly Ala Met Arg Ser Asn Pro Val Pro
    130                 135                 140

Ile Leu Ile Pro Cys His Arg Val Ile Arg Ser Asp Gly Ala Ile Gly
145                 150                 155                 160

Asn Tyr Ser Gly Gly Gly Gln Thr Val Lys Glu Trp Leu Leu Ala His
                165                 170                 175

Glu Gly Ile Pro Thr Gly Gln Pro Ala Ser Lys Gly Leu Gly Leu Ile
            180                 185                 190

Gly Ser Trp Leu Lys Pro Ser Phe Glu Ser Ser Ser Pro Lys Pro Ser
        195                 200                 205

Gly

<210> SEQ ID NO 20
<211> LENGTH: 963
<212> TYPE: DNA
<213> ORGANISM: artificial
<220> FEATURE:
<223> OTHER INFORMATION: DNA sequence coding for SNAP - linker - DEN1
      EDIII - linker- Histag

<400> SEQUENCE: 20
agatctgaca aagactgcga aatgaagcgc accaccctgg atagccctct gggcaagctg     60
gaactgtctg ggtgcgaaca gggcctgcac gagatcaagc tgctgggcaa aggaacatct    120
gccgccgacg ccgtggaagt gcctgcccca gccgccgtgc tgggcggacc agagccactg    180
atgcaggcca ccgcctggct caacgcctac tttcaccagc ctgaggccat cgaggagttc    240
cctgtgccag ccctgcacca cccagtgttc cagcaggaga gctttacccg ccaggtgctg    300
tggaaactgc tgaaagtggt gaagttcgga gaggtcatca gctaccagca gctggccgcc    360
ctggccggca atcccgccgc caccgccgcc gtgaaaaccg ccctgagcgg aaatcccgtg    420
cccattctga tcccctgcca ccgggtggtg tctagctctg gcgccgtggg gggctacgag    480
ggcgggctcg ccgtgaaaga gtggctgctg gcccacgagg gccacagact gggcaagcct    540
gggctgggtc ctgcaggtat aggcgcgcca gggtccctgg agggaggtgg cgggtctctg    600
actttaaaag ggatgtcata tgtgatgtgc acaggctcat ttaagctaga gaaggaagtg    660
gctgagaccc agcatggaac tgtcctagtg caggttaaat acgaaggaac agatgcgcca    720
tgcaagatcc ccttttcgac ccaagatgag aaaggagtga cccagaatgg gagattgata    780
acagccaatc ccatagttac tgacaaagaa aaaccaatca acattgagac agaaccacct    840
tttggtgaga gctacatcat agtaggggca ggtgaaaaag ctttgaaact aagctggttc    900
aagaaaggaa gcagcatagg gaaaggaggt ggccatcacc atcaccatca ctgatgaccg    960
gtt                                                                  963

<210> SEQ ID NO 21
<211> LENGTH: 316
<212> TYPE: PRT
<213> ORGANISM: artificial
<220> FEATURE:
<223> OTHER INFORMATION: SNAP - linker - DEN1 EDIII - linker- Histag

<400> SEQUENCE: 21

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Gly Lys Gly Thr Ser Ala Ala Asp Ala Val Glu Val Pro Ala
```

```
                35                  40                  45
Pro Ala Val Leu Gly Gly Pro Glu Pro Leu Met Gln Ala Thr Ala
     50                  55                  60
Trp Leu Asn Ala Tyr Phe His Gln Pro Glu Ala Ile Glu Glu Phe Pro
 65                  70                  75                  80
Val Pro Ala Leu His His Pro Val Phe Gln Gln Glu Ser Phe Thr Arg
                 85                  90                  95
Gln Val Leu Trp Lys Leu Leu Lys Val Val Lys Phe Gly Glu Val Ile
                100                 105                 110
Ser Tyr Gln Gln Leu Ala Ala Leu Ala Gly Asn Pro Ala Ala Thr Ala
                115                 120                 125
Ala Val Lys Thr Ala Leu Ser Gly Asn Pro Val Pro Ile Leu Ile Pro
    130                 135                 140
Cys His Arg Val Val Ser Ser Gly Ala Val Gly Tyr Glu Gly
145                 150                 155                 160
Gly Leu Ala Val Lys Glu Trp Leu Leu Ala His Glu Gly His Arg Leu
                165                 170                 175
Gly Lys Pro Gly Leu Gly Pro Ala Gly Ile Gly Ala Pro Gly Ser Leu
            180                 185                 190
Glu Gly Gly Gly Ser Leu Thr Leu Lys Gly Met Ser Tyr Val Met
        195                 200                 205
Cys Thr Gly Ser Phe Lys Leu Glu Lys Glu Val Ala Glu Thr Gln His
    210                 215                 220
Gly Thr Val Leu Val Gln Val Lys Tyr Glu Gly Thr Asp Ala Pro Cys
225                 230                 235                 240
Lys Ile Pro Phe Ser Thr Gln Asp Glu Lys Gly Val Thr Gln Asn Gly
                245                 250                 255
Arg Leu Ile Thr Ala Asn Pro Ile Val Thr Asp Lys Glu Lys Pro Ile
                260                 265                 270
Asn Ile Glu Thr Glu Pro Pro Phe Gly Glu Ser Tyr Ile Ile Val Gly
            275                 280                 285
Ala Gly Glu Lys Ala Leu Lys Leu Ser Trp Phe Lys Lys Gly Ser Ser
    290                 295                 300
Ile Gly Lys Gly Gly Gly His His His His His
305                 310                 315

<210> SEQ ID NO 22
<211> LENGTH: 54
<212> TYPE: DNA
<213> ORGANISM: artificial
<220> FEATURE:
<223> OTHER INFORMATION: DNA sequence encoding the ssBiP sequence

<400> SEQUENCE: 22
atgaagttat gcatattact ggccgtcgtg gcctttgttg gcctctcgct cggg          54

<210> SEQ ID NO 23
<211> LENGTH: 66
<212> TYPE: DNA
<213> ORGANISM: artificial
<220> FEATURE:
<223> OTHER INFORMATION: DNA artificial encoding BiP-like signal =
      insect ssBiP signal peptide + cleavage site DEN1prM signal
      sequence

<400> SEQUENCE: 23
atgaaactat gtattctact tgcagttgtt gcgttcgtag gattgtccttacctacagct      60
```

```
ctggca                                                              66

<210> SEQ ID NO 24
<211> LENGTH: 22
<212> TYPE: PRT
<213> ORGANISM: artificial
<220> FEATURE:
<223> OTHER INFORMATION: BiP-like signal = insect ssBiP signal peptide +
      cleavage site DEN1prM signal sequence

<400> SEQUENCE: 24

Met Lys Leu Cys Ile Leu Leu Ala Val Val Ala Phe Val Gly Leu Ser
1               5                   10                  15

Leu Pro Thr Ala Leu Ala
            20

<210> SEQ ID NO 25
<211> LENGTH: 4
<212> TYPE: PRT
<213> ORGANISM: artificial
<220> FEATURE:
<223> OTHER INFORMATION: Amino acid sequence of the spacer

<400> SEQUENCE: 25

Gly Gly Gly Ser
1

<210> SEQ ID NO 26
<211> LENGTH: 12
<212> TYPE: DNA
<213> ORGANISM: artificial
<220> FEATURE:
<223> OTHER INFORMATION: DNA sequence of the spacer

<400> SEQUENCE: 26
ggtggcggat ct                                                       12

<210> SEQ ID NO 27
<211> LENGTH: 6
<212> TYPE: PRT
<213> ORGANISM: artificial
<220> FEATURE:
<223> OTHER INFORMATION: Amino acid sequence of HIS TAG

<400> SEQUENCE: 27

His His His His His His
1               5

<210> SEQ ID NO 28
<211> LENGTH: 18
<212> TYPE: DNA
<213> ORGANISM: artificial
<220> FEATURE:
<223> OTHER INFORMATION: DNA sequence encoding His Tag

<400> SEQUENCE: 28
catcatcatc atcatcat                                                 18

<210> SEQ ID NO 29
<211> LENGTH: 21
<212> TYPE: DNA
<213> ORGANISM: artificial
<220> FEATURE:
<223> OTHER INFORMATION: DNA encoding pro-TEV cleavage site 1

<400> SEQUENCE: 29
```
gaaaacctgt acttccagag c                                           21

<210> SEQ ID NO 30
<211> LENGTH: 21
<212> TYPE: DNA
<213> ORGANISM: artificial
<220> FEATURE:
<223> OTHER INFORMATION: DNA encoding pro-TEV cleavage site 2

<400> SEQUENCE: 30
gagaatctat attttcaagg g                                           21

<210> SEQ ID NO 31
<211> LENGTH: 530
<212> TYPE: DNA
<213> ORGANISM: artificial
<220> FEATURE:
<223> OTHER INFORMATION: SNAP-like sequence G/C low content

<400> SEQUENCE: 31
gacaaagact gcgaaatgaa agaactaca ttggattcac cacttgggaa gttggaactg    60
agtggatgcg agcaaggatt gcatgaaatt aagctactgg gaaaaggaac ttctgctgct   120
gatgcagttg aagttccagc accagcagct gttcttggag tcctgagcc cctcatgcaa    180 gccacagcct ggcttaacgc atatttccac cagcctgagg ccattgagga atttccagtc   240
cccgcccttc accatcctgt gtttcagcag gagagcttca cccgccaggt cctgtggaaa   300
ttgctgaagg tggtcaagtt tggtgaagtg atttcatatc agcaacttgc tgcattggcc   360
ggtaaccccg cagctacagc tgccgtgaaa actgctctca gcggaaatcc tgtgcccatc   420
ctgatccctt gtcacagagt cgtttcatct tccggagctg taggtggcta tgaaggagga   480
ctggcagtta aggagtggct gctggctcat gaaggtcata gacttggaaa              530

<210> SEQ ID NO 32
<211> LENGTH: 7
<212> TYPE: PRT
<213> ORGANISM: artificial
<220> FEATURE:
<223> OTHER INFORMATION: Pro-TEV cleavage site 1

<400> SEQUENCE: 32

Glu Asn Leu Tyr Phe Gln Ser
1               5

<210> SEQ ID NO 33
<211> LENGTH: 7
<212> TYPE: PRT
<213> ORGANISM: artificial
<220> FEATURE:
<223> OTHER INFORMATION: Pro-TEV cleavage site 2

<400> SEQUENCE: 33

Glu Asn Leu Tyr Phe Gln Gly
1               5

<210> SEQ ID NO 34
<211> LENGTH: 798
<212> TYPE: DNA
<213> ORGANISM: artificial
<220> FEATURE:
<223> OTHER INFORMATION: Cassette DNA pDeSNAP Univ (BIPlike - SNAPlike-
      proTEV/Histag)

<400> SEQUENCE: 34

| | |
|---|---:|
| gatcgcgagc tagcaccatg aaactatgta ttctacttgc agttgttgcg ttcgtaggat | 60 |
| tgtccttacc tacagctctg gcaagatctg acaaagactg cgaaatgaaa agaactacat | 120 |
| tggattcacc acttgggaag ttggaactga gtggatgcga gcaaggattg catgaaatta | 180 |
| agctactggg aaaaggaact tctgctgctg atgcagttga agttccagca ccagcagctg | 240 |
| ttcttggagg tcctgagccc ctcatgcaag ccacagcctg gcttaacgca tatttccacc | 300 |
| agcctgaggc cattgaggaa tttccagtcc ccgcccttca ccatcctgtg tttcagcagg | 360 |
| agagcttcac ccgccaggtc ctgtggaaat tgctgaaggt ggtcaagttt ggtgaagtga | 420 |
| tttcatatca gcaacttgct gcattggccg gtaaccccgc agctacagct gccgtgaaaa | 480 |
| ctgctctcag cggaaatcct gtgcccatcc tgatcccttg tcacagagtc gtttcatctt | 540 |
| ccggagctgt aggtggctat gaaggaggac tggcagttaa ggagtggctg ctggctcatg | 600 |
| aaggtcatag acttggaaag cctgggctgg gtcctgctgg tataggcgcg ccagggtccc | 660 |
| taggtggcgg atccgaaaac ctgtacttcc agagcgatat cggaggtgga ggcccgggag | 720 |
| agaatctata ttttcaaggg cccggcggag gtagtcacca tcatcaccat cactaatgac | 780 |
| cggtgcggcc gcaagctt | 798 |

<210> SEQ ID NO 35
<211> LENGTH: 1439
<212> TYPE: DNA
<213> ORGANISM: artificial
<220> FEATURE:
<223> OTHER INFORMATION: Cassette DNA pDeSNAP Univ +SBV.N (ssBIP - SNAPlike- SBV.N- proTEV/Histag)

<400> SEQUENCE: 35

| | |
|---|---:|
| atgaagttat gcatattact ggccgtcgtg gcctttgttg cctctcgct cgggagatct | 60 |
| gacaaagact gcgaaatgaa agaactaca ttggattcac acttgggaa gttggaactg | 120 |
| agtggatgcg agcaaggatt gcatgaaatt aagctactgg gaaaaggaac ttctgctgct | 180 |
| gatgcagttg aagttccagc accagcagct gttcttggag gtcctgagcc ctcatgcaa | 240 |
| gccacagcct ggcttaacgc atatttccac cagcctgagg ccattgagga atttccagtc | 300 |
| cccgccctt ccatcctgt gtttcagcag gagagcttca cccgccaggt cctgtggaaa | 360 |
| ttgctgaagg tggtcaagtt tggtgaagtg atttcatatc agcaacttgc tgcattggcc | 420 |
| ggtaaccccg cagctacagc tgccgtgaaa actgctctca gcggaaatcc tgtgcccatc | 480 |
| ctgatccctt gtcacagagt cgtttcatct tccggagctg taggtggcta tgaaggagga | 540 |
| ctggcagtta aggagtggct gctggctcat gaaggtcata gacttggaaa gcctgggctg | 600 |
| ggtcctgctg gtataggcgc gccagggtcc ctaggtggcg gatccgaaaa cctgtacttc | 660 |
| cagagcgata tctcaagcca attcattttt gaagatgtac acaacgaaa tgcagctaca | 720 |
| tttaacccgg aggtcgggta tgtggcattt attggtaagt atgggcaaca actcaacttc | 780 |
| ggtgttgcta gagtcttctt cctcaaccag aagaaggcca agatggtcct acataagacg | 840 |
| gcacaaccaa gtgtcgatct tacttttggt ggggtcaaat ttacagtggt taataaccat | 900 |
| tttccccaat atgtctcaaa tcctgtgcca gacaatgcca ttacacttca caggatgtca | 960 |
| ggttatctga cacgttggat tgctgataca tgcaaggcta gtgtcctcaa actagctgaa | 1020 |
| gctagtgctc agattgtcat gcccttgct gaggttaagg gatgcacctg gccgatggt | 1080 |
| tatacaatgt atcttggatt tgcacctggg gccgaaatgt ccttgatgc ttttgacttc | 1140 |
| tatccactag ttattgaaat gcatagggtc ctcaaggaca atatggatgt aaattttatg | 1200 |

```
aaaaaagtcc tccgccaacg ctatggaaca atgactgctg aagaatggat gactcagaaa    1260
ataacagaaa taaagctgc ttttaattct gttggacagc ttgcctgggc caaatctgga     1320
ttctctcctg ctgctagaac cttcttgcag caattcggta tcaacatccc gggagagaat   1380
ctatattttc aagggcccgg cggaggtagt caccatcatc accatcacta atgaccggt    1439
```

<210> SEQ ID NO 36
<211> LENGTH: 1480
<212> TYPE: DNA
<213> ORGANISM: artificial
<220> FEATURE:
<223> OTHER INFORMATION: Cassette DNA pDeSNAP Univ +SBV.N (BIPlike -
      SNAPlike-SBV.N -proTEV/Histag)

<400> SEQUENCE: 36

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag      360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt ttcatcttcc     540
ggagctgtag gtggctatga aggaggactg gcagttaagg agtggctgct ggctcatgaa     600
ggtcatagac ttgaaaagcc tgggctgggt cctgctggta taggcgcgcc agggtcccta     660
ggtggcggat ccgaaaacct gtacttccag agcgatatct caagccaatt cattttttgaa    720 gatgtaccac aacggaatgc agctacattt aaccccgagg tcgggtatgt ggcatttatt     780
ggtaagtatg gcaacaact caacttcggt gttgctagag tcttcttcct caaccagaag     840
aaggccaaga tggtcctaca taagacggca caaccaagtg tcgatcttac ttttggtggg    900
gtcaaattta cagtggttaa taaccatttt ccccaatatg tctcaaatcc tgtgccagac    960
aatgccatta cacttcacag gatgtcaggt tatctagcac gttggattgc tgatacatgc   1020
aaggctagtg tcctcaaact agctgaagct agtgctcaga ttgtcatgcc ccttgctgag   1080
gttaagggat gcacctgggc cgatggttat acaatgtatc ttggatttgc acctggggcc   1140
gaaatgttcc ttgatgcttt tgacttctat ccactagtta ttgaaatgca tagggtcctc   1200
aaggacaata tggatgtaaa ttttatgaaa aaagtcctcc gccaacgcta tggaacaatg   1260
actgctgaag aatggatgac tcagaaaata acagaaataa agctgctttt taattctgtt    1320
ggacagcttg cctgggccaa atctggattc tctcctgctg ctagaacctt cttgcagcaa   1380
ttcggtatca acatcccggg agagaatcta tattttcaag ggcccggcgg aggtagtcac   1440
catcatcacc atcactaatg accggtgcgg ccgcaagctt                         1480
```

<210> SEQ ID NO 37
<211> LENGTH: 18
<212> TYPE: PRT
<213> ORGANISM: artificial
<220> FEATURE:
<223> OTHER INFORMATION: Amino acid sequence of the ssBiP sequence

<400> SEQUENCE: 37

Met Lys Leu Cys Ile Leu Leu Ala Val Val Ala Phe Val Gly Leu Ser
1               5                   10                  15

Leu Gly

<210> SEQ ID NO 38
<211> LENGTH: 17
<212> TYPE: PRT
<213> ORGANISM: West Nile virus strain IS-98-ST1

<400> SEQUENCE: 38

Met Val Val Phe Val Val Leu Leu Leu Val Ala Pro Ala Tyr Ser
1               5                   10                  15

Leu

<210> SEQ ID NO 39
<211> LENGTH: 5
<212> TYPE: PRT
<213> ORGANISM: Dengue virus

<400> SEQUENCE: 39

Pro Thr Ala Leu Ala
1               5

<210> SEQ ID NO 40
<211> LENGTH: 6
<212> TYPE: PRT
<213> ORGANISM: artificial
<220> FEATURE:
<223> OTHER INFORMATION: Cleavage site of enterokinase

<400> SEQUENCE: 40

Asp Asp Asp Asp Lys Asp
1               5

<210> SEQ ID NO 41
<211> LENGTH: 480
<212> TYPE: PRT
<213> ORGANISM: artificial
<220> FEATURE:
<223> OTHER INFORMATION: Amino acid sequence of
      BiPlike+SNAPlike+proTEV+SBV.N+proTEV+Histag

<400> SEQUENCE: 41

Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
                20                  25                  30

Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Ala
    50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
                100                 105                 110

Gln Gln Glu Ser Phe Thr Arg Gln Val Leu Trp Lys Leu Leu Lys Val
            115                 120                 125

Val Lys Phe Gly Glu Val Ile Ser Tyr Gln Gln Leu Ala Ala Leu Ala
        130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Ser Ser Ser Gly
            165                 170                 175

Ala Val Gly Gly Tyr Glu Gly Gly Leu Ala Val Lys Glu Trp Leu Leu
            180                 185                 190

Ala His Glu Gly His Arg Leu Gly Lys Pro Gly Leu Gly Pro Ala Gly
        195                 200                 205

Ile Gly Ala Pro Gly Ser Leu Gly Gly Ser Glu Asn Leu Tyr Phe
    210                 215                 220

Gln Ser Asp Ile Ser Ser Gln Phe Ile Phe Glu Asp Val Pro Gln Arg
225                 230                 235                 240

Asn Ala Ala Thr Phe Asn Pro Glu Val Gly Tyr Val Ala Phe Ile Gly
                245                 250                 255

Lys Tyr Gly Gln Gln Leu Asn Phe Gly Val Ala Arg Val Phe Phe Leu
            260                 265                 270

Asn Gln Lys Lys Ala Lys Met Val Leu His Lys Thr Ala Gln Pro Ser
        275                 280                 285

Val Asp Leu Thr Phe Gly Gly Val Lys Phe Thr Val Val Asn Asn His
    290                 295                 300

Phe Pro Gln Tyr Val Ser Asn Pro Val Pro Asp Asn Ala Ile Thr Leu
305                 310                 315                 320

His Arg Met Ser Gly Tyr Leu Ala Arg Trp Ile Ala Asp Thr Cys Lys
                325                 330                 335

Ala Ser Val Leu Lys Leu Ala Glu Ala Ser Ala Gln Ile Val Met Pro
            340                 345                 350

Leu Ala Glu Val Lys Gly Cys Thr Trp Ala Asp Gly Tyr Thr Met Tyr
        355                 360                 365

Leu Gly Phe Ala Pro Gly Ala Glu Met Phe Leu Asp Ala Phe Asp Phe
    370                 375                 380

Tyr Pro Leu Val Ile Glu Met His Arg Val Leu Lys Asp Asn Met Asp
385                 390                 395                 400

Val Asn Phe Met Lys Lys Val Leu Arg Gln Arg Tyr Gly Thr Met Thr
                405                 410                 415

Ala Glu Glu Trp Met Thr Gln Lys Ile Thr Glu Ile Lys Ala Ala Phe
            420                 425                 430

Asn Ser Val Gly Gln Leu Ala Trp Ala Lys Ser Gly Phe Ser Pro Ala
        435                 440                 445

Ala Arg Thr Phe Leu Gln Gln Phe Gly Ile Asn Ile Pro Gly Glu Asn
    450                 455                 460

Leu Tyr Phe Gln Gly Pro Gly Gly Gly Ser His His His His His
465                 470                 475                 480

<210> SEQ ID NO 42
<211> LENGTH: 438
<212> TYPE: PRT
<213> ORGANISM: artificial
<220> FEATURE:
<223> OTHER INFORMATION: Amino acid sequence of the fusion protein
      SNAP+SCHM.N (without BiPlike + HisTag

<400> SEQUENCE: 42

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile

```
            20                  25                  30
Lys Leu Leu Gly Lys Gly Thr Ser Ala Ala Asp Ala Val Glu Val Pro
            35                  40                  45

Ala Pro Ala Ala Val Leu Gly Gly Pro Glu Pro Leu Met Gln Ala Thr
 50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
                100                 105                 110

Ile Ser Tyr Gln Gln Leu Ala Ala Leu Ala Gly Asn Pro Ala Ala Thr
                115                 120                 125

Ala Ala Val Lys Thr Ala Leu Ser Gly Asn Pro Val Pro Ile Leu Ile
                130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
                180                 185                 190

Leu Gly Gly Gly Ser Glu Asn Leu Tyr Phe Gln Ser Asp Ile Ser Ser
                195                 200                 205

Gln Phe Ile Phe Glu Asp Val Pro Gln Arg Asn Ala Ala Thr Phe Asn
                210                 215                 220

Pro Glu Val Gly Tyr Val Ala Phe Ile Gly Lys Tyr Gly Gln Gln Leu
225                 230                 235                 240

Asn Phe Gly Val Ala Arg Val Phe Phe Leu Asn Gln Lys Lys Ala Lys
                245                 250                 255

Met Val Leu His Lys Thr Ala Gln Pro Ser Val Asp Leu Thr Phe Gly
                260                 265                 270

Gly Val Lys Phe Thr Val Val Asn Asn His Phe Pro Gln Tyr Val Ser
                275                 280                 285

Asn Pro Val Pro Asp Asn Ala Ile Thr Leu His Arg Met Ser Gly Tyr
                290                 295                 300

Leu Ala Arg Trp Ile Ala Asp Thr Cys Lys Ala Ser Val Leu Lys Leu
305                 310                 315                 320

Ala Glu Ala Ser Ala Gln Ile Val Met Pro Leu Ala Glu Val Lys Gly
                325                 330                 335

Cys Thr Trp Ala Asp Gly Tyr Thr Met Tyr Leu Gly Phe Ala Pro Gly
                340                 345                 350

Ala Glu Met Phe Leu Asp Ala Phe Asp Phe Tyr Pro Leu Val Ile Glu
                355                 360                 365

Met His Arg Val Leu Lys Asp Asn Met Asp Val Asn Phe Met Lys Lys
                370                 375                 380

Val Leu Arg Gln Arg Tyr Gly Thr Met Thr Ala Glu Glu Trp Met Thr
385                 390                 395                 400

Gln Lys Ile Thr Glu Ile Lys Ala Ala Phe Asn Ser Val Gly Gln Leu
                405                 410                 415

Ala Trp Ala Lys Ser Gly Phe Ser Pro Ala Ala Arg Thr Phe Leu Gln
                420                 425                 430

Gln Phe Gly Ile Asn Ile
                435
```

<210> SEQ ID NO 43
<211> LENGTH: 4194
<212> TYPE: DNA
<213> ORGANISM: artificial
<220> FEATURE:
<223> OTHER INFORMATION: pMT/BiP/SNAP-Histag avec cassette DeSNAP Univ

<400> SEQUENCE: 43

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccag | tgaattttaa | cgttgcagga | 420 |
| caggatgtgg | tgcccgatgt | gactagctct | ttgctgcagg | ccgtcctatc | ctctggttcc | 480 |
| gataagagac | ccagaactcc | ggcccccac | cgcccaccgc | cacccccata | catatgtggt | 540 |
| acgcaagtaa | gagtgcctgc | gcatgcccca | tgtgccccac | caagagtttt | gcatcccata | 600 |
| caagtcccca | aagtggagaa | ccgaaccaat | tcttcgcggg | cagaacaaaa | gcttctgcac | 660 |
| acgtctccac | tcgaatttgg | agccggccgg | cgtgtgcaaa | agaggtgaat | cgaacgaaag | 720 |
| acccgtgtgt | aaagccgcgt | ttccaaaatg | tataaaaccg | agagcatctg | gccaatgtgc | 780 |
| atcagttgtg | gtcagcagca | aaatcaagtg | aatcatctca | gtgcaactaa | aggggggatc | 840 |
| cgatctcaat | atgaagttat | gcatattact | ggccgtcgtg | gcctttgttg | gcctctcgct | 900 |
| cgggagatct | gacaaagact | gcgaaatgaa | agaactaca | ttggattcac | cacttgggaa | 960 |
| gttggaactg | agtggatgcg | agcaaggatt | gcatgaaatt | aagctactgg | gaaaaggaac | 1020 |
| ttctgctgct | gatgcagttg | aagttccagc | accagcagct | gttcttggag | tcctgagcc | 1080 |
| cctcatgcaa | gccacagcct | ggcttaacgc | atatttccac | cagcctgagg | ccattgagga | 1140 |
| atttccagtc | cccgcccttc | accatcctgt | gtttcagcag | gagagcttca | cccgccaggt | 1200 |
| cctgtggaaa | ttgctgaagg | tggtcaagtt | tggtgaagtg | atttcatatc | agcaacttgc | 1260 |
| tgcattggcc | ggtaaccccg | cagctacagc | tgccgtgaaa | actgctctca | gcggaaatcc | 1320 |
| tgtgcccatc | ctgatccctt | gtcacagagt | cgtttcatct | tccggagctg | taggtggcta | 1380 |
| tgaaggagga | ctggcagtta | aggagtggct | gctggctcat | gaaggtcata | gacttggaaa | 1440 |
| gcctgggctg | ggtcctgctg | gtataggcgc | gccagggtcc | ctaggtggcg | gatccgaaaa | 1500 |
| cctgtacttc | cagagcgata | tcggaggtgg | aggcccggga | gagaatctat | attttcaagg | 1560 |
| gcccggcgga | ggtagtcacc | atcatcacca | tcactaatga | ccggtcatca | tcaccatcac | 1620 |
| cattgagttt | aaacccgctg | atcagcctcg | actgtgcctt | ctaaggcctg | agctcgctga | 1680 |
| tcagcctcga | tcgaggatcc | agacatgata | agatacattg | atgagtttgg | acaaaccaca | 1740 |
| actagaatgc | agtgaaaaaa | atgctttatt | tgtgaaattt | gtgatgctat | tgctttattt | 1800 |
| gtaaccatta | taagctgcaa | taaacaagtt | aacaacaaca | attgcattca | ttttatgttt | 1860 |
| caggttcagg | gggaggtgtg | ggaggttttt | taaagcaagt | aaaacctcta | caaatgtggt | 1920 |
| atggctgatt | atgatcagtc | gacctgcagg | catgcaagct | tggcgtaatc | atggtcatag | 1980 |
| ctgtttcctg | tgtgaaattg | ttatccgctc | acaattccac | acaacatacg | agccggaagc | 2040 |

```
ataaagtgta aagcctgggg tgcctaatga gtgagctaac tcacattaat tgcgttgcgc   2100
tcactgcccg ctttccagtc gggaaacctg tcgtgccagc tgcattaatg aatcggccaa   2160
cgcgcgggga gaggcggttt gcgtattggg cgctcttccg cttcctcgct cactgactcg   2220
ctgcgctcgg tcgttcggct gcggcgagcg gtatcagctc actcaaaggc ggtaatacgg   2280
ttatccacag aatcagggga taacgcagga agaacatgt gagcaaaagg ccagcaaaag   2340
gccaggaacc gtaaaaaggc cgcgttgctg gcgtttttcc ataggctccg ccccctgac   2400
gagcatcaca aaaatcgacg ctcaagtcag aggtggcgaa acccgacagg actataaaga   2460
taccaggcgt ttccccctgg aagctccctc gtgcgctctc ctgttccgac cctgccgctt   2520
accggatacc tgtccgcctt tctcccttcg ggaagcgtgg cgctttctca tagctcacgc   2580
tgtaggtatc tcagttcggt gtaggtcgtt cgctccaagc tgggctgtgt gcacgaaccc   2640
cccgttcagc ccgaccgctg cgccttatcc ggtaactatc gtcttgagtc caacccggta   2700
agacacgact tatcgccact ggcagcagcc actggtaaca ggattagcag agcgaggtat   2760
gtaggcggtg ctacagagtt cttgaagtgg tggcctaact acggctacac tagaaggaca   2820
gtatttggta tctgcgctct gctgaagcca gttaccttcg gaaaaagagt tggtagctct   2880
tgatccggca aacaaaccac cgctggtagc ggtggttttt ttgtttgcaa gcagcagatt   2940
acgcgcagaa aaaaggatc tcaagaagat cctttgatct tttctacggg gtctgacgct   3000
cagtggaacg aaaactcacg ttaagggatt ttggtcatga gattatcaaa aaggatcttc   3060
acctagatcc ttttaaatta aaaatgaagt tttaaatcaa tctaaagtat atatgagtaa   3120
acttggtctg acagttacca atgcttaatc agtgaggcac ctatctcagc gatctgtcta   3180
tttcgttcat ccatagttgc ctgactcccc gtcgtgtaga taactacgat acgggagggc   3240
ttaccatctg gccccagtgc tgcaatgata ccgcgagacc cacgctcacc ggctccagat   3300
ttatcagcaa taaaccagcc agccggaagg gccgagcgca gaagtggtcc tgcaacttta   3360
tccgcctcca tccagtctat taattgttgc cgggaagcta gagtaagtag ttcgccagtt   3420
aatagtttgc gcaacgttgt tgccattgct acaggcatcg tggtgtcacg ctcgtcgttt   3480
ggtatggctt cattcagctc cggttcccaa cgatcaaggc gagttacatg atcccccatg   3540
ttgtgcaaaa aagcggttag ctccttcggt cctccgatcg ttgtcagaag taagttggcc   3600
gcagtgttat cactcatggt tatggcagca ctgcataatt ctcttactgt catgccatcc   3660
gtaagatgct tttctgtgac tggtgagtac tcaaccaagt cattctgaga atagtgtatg   3720
cggcgaccga gttgctcttg cccggcgtca tacgggata taccgcgcc acatagcaga   3780
actttaaaag tgctcatcat tggaaaacgt tcttcgggc gaaaactctc aaggatctta   3840
ccgctgttga tccagttc gatgtaaccc actcgtgcac ccaactgatc ttcagcatct   3900
tttactttca ccagcgtttc tgggtgagca aaaacaggaa ggcaaaatgc cgcaaaaaag   3960
ggaataaggg cgacacggaa atgttgaata ctcatactct cctttttca atattattga   4020
agcatttatc agggttattg tctcatgagc ggatacatat ttgaatgtat ttagaaaaat   4080
aaacaaatag gggttccgcg cacatttccc cgaaaagtgc cacctgacgt ctaagaaacc   4140
attattatca tgacattaac ctataaaaat aggcgtatca cgaggccctt tcgt         4194
```

<210> SEQ ID NO 44
<211> LENGTH: 3458
<212> TYPE: DNA
<213> ORGANISM: artificial
<220> FEATURE:
<223> OTHER INFORMATION: pUC57 with DeSNAP Univ cassette

<400> SEQUENCE: 44

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta cgccagggt     360
tttcccagtc acgacgttgt aaaacgacgg ccagtgaatt cgagctcggt acctcgcgaa     420
tgcatctaga tcgagctagc accatgaaac tatgtattct acttgcagtt gttgcgttcg     480
taggattgtc cttacctaca gctctggcaa gatctgacaa agactgcgaa atgaaaagaa     540
ctacattgga ttcaccactt gggaagttgg aactgagtgg atgcgagcaa ggattgcatg     600
aaattaagct actgggaaaa ggaacttctg ctgctgatgc agttgaagtt ccagcaccag     660
cagctgttct tggaggtcct gagcccctca tgcaagccac agcctggctt aacgcatatt     720
tccaccagcc tgaggccatt gaggaatttc cagtccccgc ccttcaccat cctgtgtttc     780
agcaggagag cttcacccgc caggtcctgt ggaaattgct gaaggtggtc aagtttggtg     840
aagtgatttc atatcagcaa cttgctgcat tggccggtaa ccccgcagct acagctgccg     900
tgaaaactgc tctcagcgga aatcctgtgc ccatcctgat cccttgtcac agagtcgttt     960
catcttccgg agctgtaggt ggctatgaag gaggactggc agttaaggag tggctgctgg    1020
ctcatgaagg tcatagactt ggaaagcctg gctgggtcc tgctggtata ggcgcgccag     1080
ggtccctagg tggcggatcc gaaaacctgt acttccagag cgatatcgga ggtggaggcc    1140
cgggagagaa tctatatttt caagggcccg gcggaggtag tcaccatcat caccatcact    1200
aatgaccggt gcggccgcaa gcttggcgta atcatggtca tagctgtttc ctgtgtgaaa    1260
ttgttatccg ctcacaattc cacacaacat acgagccgga agcataaagt gtaaagcctg    1320
gggtgcctaa tgagtgagct aactcacatt aattgcgttg cgctcactgc ccgctttcca    1380
gtcgggaaac ctgtcgtgcc agctgcatta atgaatcggc caacgcgcgg ggagaggcgg    1440
tttgcgtatt gggcgctctt ccgcttcctc gctcactgac tcgctgcgct cggtcgttcg    1500
gctgcggcga gcggtatcag ctcactcaaa ggcggtaata cggttatcca cagaatcagg    1560
ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta cactagaaga acagtatttg gtatctgcgc    2100
tctgctgaag ccagttacct tcggaaaaag agttggtagc tcttgatccg gcaaacaaac    2160
caccgctggt agcggtggtt tttttgtttg caagcagcag attacgcgca gaaaaaaagg    2220
atctcaagaa gatcctttga tcttttctac ggggtctgac gctcagtgga acgaaaactc    2280
```

| acgttaaggg | atttttggtca | tgagattatc | aaaaaggatc | ttcacctaga | tccttttaaa | 2340 |
| ttaaaaatga | agtttttaaat | caatctaaag | tatatatgag | taaacttggt | ctgacagtta | 2400 |
| ccaatgctta | atcagtgagg | cacctatctc | agcgatctgt | ctatttcgtt | catccatagt | 2460 |
| tgcctgactc | cccgtcgtgt | agataactac | gatacgggag | ggcttaccat | ctggccccag | 2520 |
| tgctgcaatg | ataccgcgag | acccacgctc | accggctcca | gatttatcag | caataaacca | 2580 |
| gccagccgga | agggccgagc | gcagaagtgg | tcctgcaact | ttatccgcct | ccatccagtc | 2640 |
| tattaattgt | tgccgggaag | ctagagtaag | tagttcgcca | gttaatagtt | tgcgcaacgt | 2700 |
| tgttgccatt | gctacaggca | tcgtggtgtc | acgctcgtcg | tttggtatgg | cttcattcag | 2760 |
| ctccggttcc | caacgatcaa | ggcgagttac | atgatccccc | atgttgtgca | aaaaagcggt | 2820 |
| tagctccttc | ggtcctccga | tcgttgtcag | aagtaagttg | gccgcagtgt | tatcactcat | 2880 |
| ggttatggca | gcactgcata | attctcttac | tgtcatgcca | tccgtaagat | gcttttctgt | 2940 |
| gactggtgag | tactcaacca | agtcattctg | agaatagtgt | atgcggcgac | cgagttgctc | 3000 |
| ttgcccggcg | tcaatacggg | ataataccgc | gccacatagc | agaactttaa | aagtgctcat | 3060 |
| cattggaaaa | cgttcttcgg | ggcgaaaact | ctcaaggatc | ttaccgctgt | tgagatccag | 3120 |
| ttcgatgtaa | cccactcgtg | cacccaactg | atcttcagca | tctttactt | tcaccagcgt | 3180 |
| ttctgggtga | gcaaaaacag | gaaggcaaaa | tgccgcaaaa | aagggaataa | gggcgacacg | 3240 |
| gaaatgttga | atactcatac | tcttcctttt | tcaatattat | tgaagcattt | atcagggtta | 3300 |
| ttgtctcatg | agcggataca | tatttgaatg | tatttagaaa | aataaacaaa | taggggttcc | 3360 |
| gcgcacattt | ccccgaaaag | tgccacctga | cgtctaagaa | accattatta | tcatgacatt | 3420 |
| aacctataaa | aataggcgta | tcacgaggcc | ctttcgtc | | | 3458 |

<210> SEQ ID NO 45
<211> LENGTH: 6365
<212> TYPE: DNA
<213> ORGANISM: artificial
<220> FEATURE:
<223> OTHER INFORMATION: pcDNA3 with DeSNAP Univ cassette

<400> SEQUENCE: 45

| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccaccccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |

```
accatgaaac tatgtattct acttgcagtt gttgcgttcg taggattgtc cttacctaca    960
gctctggcaa gatctgacaa agactgcgaa atgaaaagaa ctacattgga ttcaccactt   1020
gggaagttgg aactgagtgg atgcgagcaa ggattgcatg aaattaagct actgggaaaa   1080
ggaacttctg ctgctgatgc agttgaagtt ccagcaccag cagctgttct tggaggtcct   1140
gagcccctca tgcaagccac agcctggctt aacgcatatt ccaccagcc tgaggccatt    1200
gaggaatttc cagtccccgc ccttcaccat cctgtgtttc agcaggagag cttcacccgc   1260
caggtcctgt ggaaattgct gaaggtggtc aagtttggtg aagtgatttc atatcagcaa   1320
cttgctgcat tggccggtaa ccccgcagct acagctgccg tgaaaactgc tctcagcgga   1380
aatcctgtgc ccatcctgat cccttgtcac agagtcgttt catcttccgg agctgtaggt   1440
ggctatgaag gaggactggc agttaaggag tggctgctgg ctcatgaagg tcatagactt   1500
ggaaagcctg gctgggtcc tgctggtata ggcgcgccag ggtccctagg tggcggatcc    1560
gaaaacctgt acttccagag cgatatcgga ggtggaggcc cgggagagaa tctatatttt   1620
caagggcccg gcggaggtag tcaccatcat caccatcact aatgaccggt gcggccgcaa   1680
gcttggtacc gagctcggat ccactagtcc agtgtggtgg aattctgcag atatccagca   1740
cagtggcggc cgctcgagtc tagagggccc gtttaaaccc gctgatcagc ctcgactgtg   1800
ccttctagtt gccagccatc tgttgtttgc cctcccccg tgccttcctt gaccctggaa    1860
ggtgccactc ccactgtcct ttcctaataa aatgaggaaa ttgcatcgca ttgtctgagt   1920
aggtgtcatt ctattctggg gggtggggtg ggcaggaca gcaaggggga ggattgggaa    1980
gacaatagca ggcatgctgg ggatgcggtg gctctatgg cttctgaggc ggaaagaacc    2040
agctggggct ctaggggta tccccacgcg ccctgtagcg cgcattaag cgcggcgggt     2100
gtggtggtta cgcgcagcgt gaccgctaca cttgccagcg ccctagcgcc cgctcctttc   2160
gctttcttcc cttcctttct cgccacgttc gccggctttc cccgtcaagc tctaaatcgg   2220
gggctccctt tagggttccg atttagtgct ttacggcacc tcgaccccaa aaaacttgat   2280
tagggtgatg gttcacgtag tgggccatcg ccctgataga cggttttcg ccctttgacg    2340
ttggagtcca cgttctttaa tagtggactc ttgttccaaa ctggacaac actcaaccct    2400
atctcggtct attcttttga tttataaggg attttgccga tttcggccta ttggttaaaa   2460
aatgagctga tttaacaaaa atttaacgcg aattaattct gtggaatgtg tgtcagttag   2520
ggtgtggaaa gtccccaggc tccccagcag gcagaagtat gcaaagcatg catctcaatt   2580
agtcagcaac caggtgtgga aagtccccag gctccccagc aggcagaagt atgcaaagca   2640
tgcatctcaa ttagtcagca accatagtcc cgcccctaac tccgcccatc ccgcccctaa   2700
ctccgcccag ttccgcccat tctccgcccc atggctgact aatttttttt atttatgcag   2760
aggccgaggc cgcctctgcc tctgagctat tccagaagta gtgaggaggc ttttttggag   2820
gcctaggctt ttgcaaaaag ctcccgggag cttgtatatc catttcgga tctgatcagc    2880
acgtgatgaa aaagcctgaa ctcaccgcga cgtctgtcga agtttctg atcgaaaagt     2940
tcgacagcgt ctccgacctg atgcagctct cggagggcga agaatctcgt gctttcagct   3000
tcgatgtagg agggcgtgga tatgtcctgc gggtaaatag ctgcgccgat ggtttctaca   3060
aagatcgtta tgtttatcgg cactttgcat cggccgcgct cccgattccg aagtgcttg    3120
acattgggga attcagcgag agcctgacct attgcatctc ccgccgtgca cagggtgtca   3180
cgttgcaaga cctgcctgaa accgaactgc ccgctgttct gcagccggtc gcggaggcca   3240
```

```
tggatgcgat cgctgcggcc gatcttagcc agacgagcgg gttcggccca ttcggaccgc    3300
aaggaatcgg tcaatacact acatggcgtg atttcatatg cgcgattgct gatccccatg    3360
tgtatcactg gcaaactgtg atggacgaca ccgtcagtgc gtccgtcgcg caggctctcg    3420
atgagctgat gctttgggcc gaggactgcc ccgaagtccg gcacctcgtg cacgcggatt    3480
tcggctccaa caatgtcctg acggacaatg gccgcataac agcggtcatt gactggagcg    3540
aggcgatgtt cggggattcc caatacgagg tcgccaacat cttcttctgg aggccgtggt    3600
tggcttgtat ggagcagcag acgcgctact tcgagcggag gcatccggag cttgcaggat    3660
cgccgcggct ccgggcgtat atgctccgca ttggtcttga ccaactctat cagagcttgg    3720
ttgacggcaa tttcgatgat gcagcttggg cgcagggtcg atgcgacgca atcgtccgat    3780
ccggagccgg gactgtcggg cgtacacaaa tcgcccgcag aagcgcggcc gtctggaccg    3840
atggctgtgt agaagtactc gccgatagtg gaaaccgacg ccccagcact cgtccgaggg    3900
caaaggaata gcacgtgcta cgagatttcg attccaccgc cgccttctat gaaaggttgg    3960
gcttcggaat cgttttccgg gacgccggct ggatgatcct ccagcgcggg gatctcatgc    4020
tggagttctt cgcccacccc aacttgttta ttgcagctta taatggttac aaataaagca    4080
atagcatcac aaatttcaca aataaagcat ttttttcact gcattctagt tgtggtttgt    4140
ccaaactcat caatgtatct tatcatgtct gtataccgtc gacctctagc tagagcttgg    4200
cgtaatcatg gtcatagctg tttcctgtgt gaaattgtta tccgctcaca attccacaca    4260
acatacgagc cggaagcata aagtgtaaag cctggggtgc ctaatgagtg agctaactca    4320
cattaattgc gttgcgctca ctgcccgctt tccagtcggg aaacctgtcg tgccagctgc    4380
attaatgaat cggccaacgc gcggggagag gcggtttgcg tattgggcgc tcttccgctt    4440
cctcgctcac tgactcgctg cgctcggtcg ttcggctgcg gcgagcggta tcagctcact    4500
caaaggcggt aatacggtta tccacagaat caggggataa cgcaggaaag aacatgtgag    4560
caaaaggcca gcaaaaggcc aggaaccgta aaaaggccgc gttgctggcg ttttcccata    4620
ggctccgccc ccctgacgag catcacaaaa atcgacgctc aagtcagagg tggcgaaacc    4680
cgacaggact ataaagatac caggcgtttc ccccctggaag ctccctcgtg cgctctcctg    4740
ttccgaccct gccgcttacc ggatacctgt ccgcctttct cccttcggga agcgtggcgc    4800
tttctcatag ctcacgctgt aggtatctca gttcggtgta ggtcgttcgc tccaagctgg    4860
gctgtgtgca cgaaccccccc gttcagcccg accgctgcgc cttatccggt aactatcgtc    4920
ttgagtccaa cccggtaaga cacgacttat cgccactggc agcagccact ggtaacagga    4980
ttagcagagc gaggtatgta ggcggtgcta cagagttctt gaagtggtgg cctaactacg    5040
gctacactag aagaacagta tttggtatct gcgctctgct gaagccagtt accttcggaa    5100
aaagagttgg tagctcttga tccggcaaac aaaccaccgc tggtagcggt ttttttgttt    5160
gcaagcagca gattacgcgc agaaaaaaag gatctcaaga agatcctttg atcttttcta    5220
cggggtctga cgctcagtgg aacgaaaact cacgttaagg gattttggtc atgagattat    5280
caaaaaggat cttcacctag atccttttaa attaaaaatg aagttttaaa tcaatctaaa    5340
gtatatatga gtaaacttgg tctgacagtt accaatgctt aatcagtgag gcacctatct    5400
cagcgatctg tctatttcgt tcatccatag ttgcctgact ccccgtcgtg tagataacta    5460
cgatacggga gggcttacca tctggcccca gtgctgcaat gataccgcga gacccacgct    5520
caccggctcc agatttatca gcaataaacc agccagccgg aagggccgag cgcagaagtg    5580
gtcctgcaac tttatccgcc tccatccagt ctattaattg ttgccgggaa gctagagtaa    5640
```

-continued

```
gtagttcgcc agttaatagt ttgcgcaacg ttgttgccat tgctacaggc atcgtggtgt   5700
cacgctcgtc gtttggtatg gcttcattca gctccggttc ccaacgatca aggcgagtta   5760
catgatcccc catgttgtgc aaaaaagcgg ttagctcctt cggtcctccg atcgttgtca   5820
gaagtaagtt ggccgcagtg ttatcactca tggttatggc agcactgcat aattctctta   5880
ctgtcatgcc atccgtaaga tgcttttctg tgactggtga gtactcaacc aagtcattct   5940
gagaatagtg tatgcggcga ccgagttgct cttgcccggc gtcaatacgg gataataccg   6000
cgccacatag cagaacttta aaagtgctca tcattggaaa acgttcttcg gggcgaaaac   6060
tctcaaggat cttaccgctg ttgagatcca gttcgatgta acccactcgt gcacccaact   6120
gatcttcagc atcttttact ttcaccagcg tttctgggtg agcaaaaaca ggaaggcaaa   6180
atgccgcaaa aaagggaata agggcgacac ggaaatgttg aatactcata ctcttccttt   6240
ttcaatatta ttgaagcatt tatcagggtt attgtctcat gagcggatac atatttgaat   6300
gtatttagaa aaataaacaa ataggggttc cgcgcacatt tccccgaaaa gtgccacctg   6360
acgtc                                                                6365
```

```

<210> SEQ ID NO 46
<211> LENGTH: 476
<212> TYPE: PRT
<213> ORGANISM: artificial
<220> FEATURE:
<223> OTHER INFORMATION: Amino acid sequence of
      ssBiP+SNAPlike+proTEV+SBV.N+proTEV+Histag
      (encoded by SEQ ID NO:35)

<400> SEQUENCE: 46

Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Gly Ser Glu Asn Leu Tyr Phe Gln Ser Asp Ile
```

```
                210               215               220
Ser Ser Gln Phe Ile Phe Glu Asp Val Pro Gln Arg Asn Ala Ala Thr
225               230               235               240

Phe Asn Pro Glu Val Gly Tyr Val Ala Phe Ile Gly Lys Tyr Gly Gln
              245               250               255

Gln Leu Asn Phe Gly Val Ala Arg Val Phe Phe Leu Asn Gln Lys Lys
              260               265               270

Ala Lys Met Val Leu His Lys Thr Ala Gln Pro Ser Val Asp Leu Thr
          275               280               285

Phe Gly Gly Val Lys Phe Thr Val Val Asn Asn His Phe Pro Gln Tyr
      290               295               300

Val Ser Asn Pro Val Pro Asp Asn Ala Ile Thr Leu His Arg Met Ser
305               310               315               320

Gly Tyr Leu Ala Arg Trp Ile Ala Asp Thr Cys Lys Ala Ser Val Leu
              325               330               335

Lys Leu Ala Glu Ala Ser Ala Gln Ile Val Met Pro Leu Ala Glu Val
              340               345               350

Lys Gly Cys Thr Trp Ala Asp Gly Tyr Thr Met Tyr Leu Gly Phe Ala
          355               360               365

Pro Gly Ala Glu Met Phe Leu Asp Ala Phe Asp Phe Tyr Pro Leu Val
      370               375               380

Ile Glu Met His Arg Val Leu Lys Asp Asn Met Asp Val Asn Phe Met
385               390               395               400

Lys Lys Val Leu Arg Gln Arg Tyr Gly Thr Met Thr Ala Glu Glu Trp
              405               410               415

Met Thr Gln Lys Ile Thr Glu Ile Lys Ala Ala Phe Asn Ser Val Gly
              420               425               430

Gln Leu Ala Trp Ala Lys Ser Gly Phe Ser Pro Ala Ala Arg Thr Phe
          435               440               445

Leu Gln Gln Phe Gly Ile Asn Ile Pro Gly Glu Asn Leu Tyr Phe Gln
      450               455               460

Gly Pro Gly Gly Gly Ser His His His His His
465               470               475
```

<210> SEQ ID NO 47
<211> LENGTH: 891
<212> TYPE: DNA
<213> ORGANISM: artificial
<220> FEATURE:
<223> OTHER INFORMATION: Modified DNA sequence encoding enterovirus 71
      VP1 (strain JL-AFP-EV71-07-03)

<400> SEQUENCE: 47

```
ggagataggg tggcagacgt gattgaaagt tccaaaggaa atagtgtgag cagagccctc    60
actcaagctc taccagcacc cacaggtcag aacacacagg tgagcagtca tcgactggat   120
acaggcaagg ttccagcact ccaagctgct gaaattggag catcatcaaa tgctagtgat   180
gagagcatga tcgagacacg ctgtgttctt aactcgcata gcacagctga ccactctt    240
gatagtttct tcagcagagc ggggttagtt ggagagattg atctccctct tgaaggcaca   300
actaacccaa atggttatgc caactgggac atagatataa caggttacgc gcaaatgcgt   360
agaaaggtgg agctattcac ctacatgcgc tttgatgcag agttcacttt tgttgcgtgc   420
acacccaccg gggaagttgt cccacaattg ctccaataca tgtttgtgcc acctggagcc   480
cctaagccag attccaggga atccctcgca tggcaaactc ccaccaaccc ctcagttttt   540
```

```
gtcaagctgt cagaccctcc agcacaagtt tcagtaccat tcatgtcacc tgcgagtgct    600
taccaatggt tttatgacgg ttatcccaca ttcggagaac acaaacagga gaaggatctc    660
gaatatgggg catgtcctaa caacatgatg ggcacgttct cagtgcggac tgtagggacc    720
tccaagtcca agtacccttt agtggttagg atttacatga gaatgaagca cgtcagggcg    780
tggataccct gcccgatgcg caaccaaaac tacctattca aagccaaccc aaattatgct    840
ggcaactcca ttaagccaac tggtaccagt cgcacagcga tcactactct c             891
```

<210> SEQ ID NO 48
<211> LENGTH: 1643
<212> TYPE: DNA
<213> ORGANISM: artificial
<220> FEATURE:
<223> OTHER INFORMATION: DNA Sequence of chimeric DeSNAPuniv-EV71.VP1
      (ssBiP-SNAPlike- proTEVcleavage site - modified EV71-VP1-
      proTEVcleavage site -Histag) for expression in S2 cells

<400> SEQUENCE: 48

```
atgaagttat gcatattact ggccgtcgtg gtggcctttg ttggcctctc gctcgggaga     60
tctagatctg acaaagactg cgaaatgaaa agaactacat tggattcacc acttgggaag    120
ttggaactga gtggatgcga gcaaggattg catgaaatta gctactggga aaaggaact     180 tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cggagatagg gtggcagacg tgattgaaag ttccaaagga    720
aatagtgtga gcagagccct cactcaagct ctaccagcac ccacaggtca gaacacacag    780
gtgagcagtc atcgactgga tacaggcaag gttccagcac tccaagctgc tgaaattgga    840
gcatcatcaa atgctagtga tgagagcatg atcgagacag ctgtgttct taactcgcat    900 agcacagctg agaccactct tgatagtttc ttcagcagag cggggttagt tggagagatt    960
gatctccctc ttgaaggcac aactaaccca aatggttatg ccaactggga catagatata   1020
acaggttacg cgcaaatgcg tagaaaggtg gagctattca cctacatgcg ctttgatgca   1080
gagttcactt ttgttgcgtg cacacccacc ggggaagttg tcccacaatt gctccaatac   1140
atgtttgtgc cacctggagc ccctaagcca gattccaggg aatccctcgc atggcaaact   1200
gccaccaacc cctcagtttt tgtcaagctg tcagaccctc cagcacaagt ttcagtacca   1260
ttcatgtcac ctgcgagtgc ttaccaatgg tttatgacg gttatcccac attcggagaa    1320
cacaaacagg agaaggatct cgaatatggg gcatgtccta caacatgat gggcacgttc    1380 tcagtgcgga ctgtagggac ctccaagtcc aagtacccct tagtggttag gatttacatg   1440
agaatgaagc acgtcagggc gtggatacct cgcccgatgc gcaaccaaaa ctacctattc   1500
aaagccaacc caaattatgc tggcaactcc attaagccaa ctggtaccag tcgcacagcg   1560
atcactactc tcccgggaga gaatctatat tttcaagggc cggcggagg tagtcaccat   1620 catcaccatc actaatgacc ggt                                           1643
```

<210> SEQ ID NO 49
<211> LENGTH: 523
<212> TYPE: PRT
<213> ORGANISM: artificial
<220> FEATURE:
<223> OTHER INFORMATION: Amino acid sequence of fusion protein
      [SNAPlike - proTEV - VP1 EV71 - proTEV- Histag]

<400> SEQUENCE: 49

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Gly Asp
        195                 200                 205

Arg Val Ala Asp Val Ile Glu Ser Ser Lys Gly Asn Ser Val Ser Arg
    210                 215                 220

Ala Leu Thr Gln Ala Leu Pro Ala Pro Thr Gly Gln Asn Thr Gln Val
225                 230                 235                 240

Ser Ser His Arg Leu Asp Thr Gly Lys Val Pro Ala Leu Gln Ala Ala
                245                 250                 255

Glu Ile Gly Ala Ser Ser Asn Ala Ser Asp Glu Ser Met Ile Glu Thr
            260                 265                 270

Arg Cys Val Leu Asn Ser His Ser Thr Ala Glu Thr Thr Leu Asp Ser
        275                 280                 285

Phe Phe Ser Arg Ala Gly Leu Val Gly Glu Ile Asp Leu Pro Leu Glu
    290                 295                 300

Gly Thr Thr Asn Pro Asn Gly Tyr Ala Asn Trp Asp Ile Asp Ile Thr
305                 310                 315                 320

Gly Tyr Ala Gln Met Arg Arg Lys Val Glu Leu Phe Thr Tyr Met Arg
                325                 330                 335

Phe Asp Ala Glu Phe Thr Phe Val Ala Cys Thr Pro Thr Gly Glu Val
            340                 345                 350

Val Pro Gln Leu Leu Gln Tyr Met Phe Val Pro Pro Gly Ala Pro Lys
```

|  |  |  | 355 |  |  |  | 360 |  |  |  | 365 |  |  |
|---|---|---|---|---|---|---|---|---|---|---|---|---|---|
| Pro | Asp | Ser | Arg | Glu | Ser | Leu | Ala | Trp | Gln | Thr | Ala | Thr | Asn | Pro | Ser |
| 370 |  |  |  |  | 375 |  |  |  |  | 380 |  |  |  |  |
| Val | Phe | Val | Lys | Leu | Ser | Asp | Pro | Pro | Ala | Gln | Val | Ser | Val | Pro | Phe |
| 385 |  |  |  |  | 390 |  |  |  |  | 395 |  |  |  |  | 400 |
| Met | Ser | Pro | Ala | Ser | Ala | Tyr | Gln | Trp | Phe | Tyr | Asp | Gly | Tyr | Pro | Thr |
|  |  |  |  | 405 |  |  |  |  | 410 |  |  |  |  | 415 |  |
| Phe | Gly | Glu | His | Lys | Gln | Glu | Lys | Asp | Leu | Glu | Tyr | Gly | Ala | Cys | Pro |
|  |  |  | 420 |  |  |  |  | 425 |  |  |  |  | 430 |  |  |
| Asn | Asn | Met | Met | Gly | Thr | Phe | Ser | Val | Arg | Thr | Val | Gly | Thr | Ser | Lys |
|  |  |  | 435 |  |  |  |  | 440 |  |  |  |  | 445 |  |  |
| Ser | Lys | Tyr | Pro | Leu | Val | Val | Arg | Ile | Tyr | Met | Arg | Met | Lys | His | Val |
|  | 450 |  |  |  |  | 455 |  |  |  |  | 460 |  |  |  |  |
| Arg | Ala | Trp | Ile | Pro | Arg | Pro | Met | Arg | Asn | Gln | Asn | Tyr | Leu | Phe | Lys |
| 465 |  |  |  |  | 470 |  |  |  |  | 475 |  |  |  |  | 480 |
| Ala | Asn | Pro | Asn | Tyr | Ala | Gly | Asn | Ser | Ile | Lys | Pro | Thr | Gly | Thr | Ser |
|  |  |  |  | 485 |  |  |  |  | 490 |  |  |  |  | 495 |  |
| Arg | Thr | Ala | Ile | Thr | Thr | Leu | Pro | Gly | Glu | Asn | Leu | Tyr | Phe | Gln | Gly |
|  |  |  |  | 500 |  |  |  |  | 505 |  |  |  |  | 510 |  |
| Pro | Gly | Gly | Gly | Ser | His | His | His | His | His |  |  |  |  |  |  |
|  |  |  |  | 515 |  |  |  |  | 520 |  |  |  |  |  |  |

```
<210> SEQ ID NO 50
<211> LENGTH: 2386
<212> TYPE: DNA
<213> ORGANISM: artificial
<220> FEATURE:
<223> OTHER INFORMATION: DNA Sequence encoding chimeric DeSNAPuniv-
      JE.-sE (ssBiP- sE from JEV strain SA-14 -SNAPlike) for expression
      in S2 cells

<400> SEQUENCE: 50
atgaagttat gcatattact ggccgtcgtg gcctttgttg cctctcgct  cgggagatct     60
atgaagttgt cgaatttcca ggggaagctt ttgatgacca tcaacaacac ggacattgca    120
gacgttatcg tgattcccac ctcaaaagga gagaacagat gctgggtccg gcaatcgac    180
gtcggctaca tgtgtgagga cactatcacg tacgaatgtc ctaagcttac catgggcaat    240
gatccagagg atgtggattg ctggtgtgac aaccaagaag tctacgtcca atatggacgg    300
tgcacgcgga ccaggcattc aagcgaagc aggagatccg tgtcggtcca acacatggg     360
gagagttcac tagtgaataa aaagaggct tggctggatt caacgaaagc cacacgtat     420
ctcatgaaaa ctgagaactg gatcataagg aatcctggct atgctttcct ggcggcggta    480
cttggctgga tgcttggcag taacaacggt caacgcgtgg tatttaccat cctcctgctg    540
ttggtcgctc cggcttacag tttttaattgt ctgggaatgg gcaatcgtga cttcatagaa    600
ggagccagtg gagccacttg ggtggacttg gtgctagaag agatagctg cttgacaatc    660
atggcaaacg acaaaccaac attggacgtc cgcatgatta acatcgaagc tagccaactt    720
gctgaggtca gaagttactg ctatcatgct tcagtcactg acatctcgac ggtggctcgg    780
tgccccacga ctggagaagc tcacaacgag aagcgagctg atagtagcta tgtgtgcaaa    840
caaggcttca ctgaccgtgg gtggggcaac ggatgtggac ttttcgggaa gggaagcatt    900
gacacatgtg caaaattctc ctgcaccagt aaagcgattg ggagaacaat ccagccagaa    960
aacatcaaat acgaagttgg cattttttgt catggaacca ccacttccgga aaaccatggg   1020
aattattcag cgcaagttgg ggcgtcccag gcggcaaagt ttacagtaac acccaatgct   1080
```

```
ccttcgataa ccctcaaact tggtgactac ggagaagtca cactggactg tgagccaagg   1140
agtggactga acactgaagc gttttacgtc atgaccgtgg ggtcaaagtc atttctggtc   1200
catagggagt ggtttcatga cctcgctctc ccctggacgt cccctcgag cacagcgtgg   1260 agaaacagag aactcctcat ggaatttgaa ggggcgcacg ccacaaaaca gtccgttgtt   1320
gctcttgggt cacaggaagg aggcctccat caggcgttgg caggagccat cgtggtggag   1380
tactcaagct cagtgaagtt aacatcaggc cacctgaaat gtaggctgaa aatggacaaa   1440
ctggctctga aaggcacaac ctatggcatg tgtacagaaa aattctcgtt cgcgaaaaat   1500
ccggcggaca ctggtcacgg aacagttgtc attgaactct cctactctgg gagtgatggc   1560
tcctgcaaaa ttccgattgt ttccgttgcg agcctcaatg acatgacccc cgttgggcgg   1620
ctggtgacag tgaacccctt cgtcgcgact tccagtgcca actcaaaggt gctggtcgag   1680
atggaacccc ccttcggaga ctcctacatc gtagttggaa ggggagacaa gcagatcaac   1740
caccattggc acaaagctgg gcggccgcac ggcggaggta gcaaagactg cgaaatgaag   1800
cgcaccaccc tggatagccc tctgggcaag ctggaactgt ctgggtgcga acagggcctg   1860
cacgagatca agctgctggg caaaggaaca tctgccgccg acgccgtgga agtgcctgcc   1920
ccagccgccg tgctgggcgg accagagcca ctgatgcagg ccaccgcctg gctcaacgcc   1980
tactttcacc agcctgaggc catcgaggag ttccctgtgc cagccctgca ccacccagtg   2040
ttccagcagg agagctttac ccgccaggtg ctgtggaaac tgctgaaagt ggtgaagttc   2100
ggagaggtca tcagctacca gcagctggcc gccctggccg gcaatcccgc cgccaccgcc   2160
gccgtgaaaa ccgccctgag cggaaatccc gtgcccattc tgatcccctg ccaccgggtg   2220
gtgtctagct ctggcgccgt gggggctac gagggcgggc tcgccgtgaa agagtggctg   2280
ctggcccacg agggccacag actgggcaag cctgggctgg gtcctgcagg tatagcgcg   2340 ccagggtccc tggagcatca tcatcatcat cattgatgac gggccc                 2386
```

```

<210> SEQ ID NO 51
<211> LENGTH: 773
<212> TYPE: PRT
<213> ORGANISM: artificial
<220> FEATURE:
<223> OTHER INFORMATION: Amino acid Sequence of fusion protein [sE from
      JEV strain SA-14 - SNAPlike - Histag]

<400> SEQUENCE: 51

Arg Ser Met Lys Leu Ser Asn Phe Gln Gly Lys Leu Leu Met Thr Ile
1               5                   10                  15

Asn Asn Thr Asp Ile Ala Asp Val Ile Val Ile Pro Thr Ser Lys Gly
            20                  25                  30

Glu Asn Arg Cys Trp Val Arg Ala Ile Asp Val Gly Tyr Met Cys Glu
        35                  40                  45

Asp Thr Ile Thr Tyr Glu Cys Pro Lys Leu Thr Met Gly Asn Asp Pro
    50                  55                  60

Glu Asp Val Asp Cys Trp Cys Asp Asn Gln Glu Val Tyr Val Gln Tyr
65                  70                  75                  80

Gly Arg Cys Thr Arg Thr Arg His Ser Lys Arg Ser Arg Arg Ser Val
                85                  90                  95

Ser Val Gln Thr His Gly Glu Ser Ser Leu Val Asn Lys Lys Glu Ala
            100                 105                 110

Trp Leu Asp Ser Thr Lys Ala Thr Arg Tyr Leu Met Lys Thr Glu Asn
        115                 120                 125
```

```
Trp Ile Ile Arg Asn Pro Gly Tyr Ala Phe Leu Ala Ala Val Leu Gly
    130                 135                 140

Trp Met Leu Gly Ser Asn Asn Gly Gln Arg Val Val Phe Thr Ile Leu
145                 150                 155                 160

Leu Leu Leu Val Ala Pro Ala Tyr Ser Phe Asn Cys Leu Gly Met Gly
                165                 170                 175

Asn Arg Asp Phe Ile Glu Gly Ala Ser Gly Ala Thr Trp Val Asp Leu
            180                 185                 190

Val Leu Glu Gly Asp Ser Cys Leu Thr Ile Met Ala Asn Asp Lys Pro
        195                 200                 205

Thr Leu Asp Val Arg Met Ile Asn Ile Glu Ala Ser Gln Leu Ala Glu
    210                 215                 220

Val Arg Ser Tyr Cys Tyr His Ala Ser Val Thr Asp Ile Ser Thr Val
225                 230                 235                 240

Ala Arg Cys Pro Thr Thr Gly Glu Ala His Asn Glu Lys Arg Ala Asp
                245                 250                 255

Ser Ser Tyr Val Cys Lys Gln Gly Phe Thr Asp Arg Gly Trp Gly Asn
            260                 265                 270

Gly Cys Gly Leu Phe Gly Lys Gly Ser Ile Asp Thr Cys Ala Lys Phe
        275                 280                 285

Ser Cys Thr Ser Lys Ala Ile Gly Arg Thr Ile Gln Pro Glu Asn Ile
    290                 295                 300

Lys Tyr Glu Val Gly Ile Phe Val His Gly Thr Thr Thr Ser Glu Asn
305                 310                 315                 320

His Gly Asn Tyr Ser Ala Gln Val Gly Ala Ser Gln Ala Ala Lys Phe
                325                 330                 335

Thr Val Thr Pro Asn Ala Pro Ser Ile Thr Leu Lys Leu Gly Asp Tyr
            340                 345                 350

Gly Glu Val Thr Leu Asp Cys Glu Pro Arg Ser Gly Leu Asn Thr Glu
        355                 360                 365

Ala Phe Tyr Val Met Thr Val Gly Ser Lys Ser Phe Leu Val His Arg
    370                 375                 380

Glu Trp Phe His Asp Leu Ala Leu Pro Trp Thr Ser Pro Ser Ser Thr
385                 390                 395                 400

Ala Trp Arg Asn Arg Glu Leu Leu Met Glu Phe Glu Gly Ala His Ala
                405                 410                 415

Thr Lys Gln Ser Val Val Ala Leu Gly Ser Gln Glu Gly Gly Leu His
            420                 425                 430

Gln Ala Leu Ala Gly Ala Ile Val Val Glu Tyr Ser Ser Ser Val Lys
        435                 440                 445

Leu Thr Ser Gly His Leu Lys Cys Arg Leu Lys Met Asp Lys Leu Ala
    450                 455                 460

Leu Lys Gly Thr Thr Tyr Gly Met Cys Thr Glu Lys Phe Ser Phe Ala
465                 470                 475                 480

Lys Asn Pro Ala Asp Thr Gly His Gly Thr Val Val Ile Glu Leu Ser
                485                 490                 495

Tyr Ser Gly Ser Asp Gly Ser Cys Lys Ile Pro Ile Val Ser Val Ala
            500                 505                 510

Ser Leu Asn Asp Met Thr Pro Val Gly Arg Leu Val Thr Val Asn Pro
        515                 520                 525

Phe Val Ala Thr Ser Ser Ala Asn Ser Lys Val Leu Val Glu Met Glu
    530                 535                 540
```

```
Pro Pro Phe Gly Asp Ser Tyr Ile Val Val Gly Arg Gly Asp Lys Gln
545                 550                 555                 560

Ile Asn His His Trp His Lys Ala Gly Arg Pro His Gly Gly Gly Ser
                565                 570                 575

Lys Asp Cys Glu Met Lys Arg Thr Thr Leu Asp Ser Pro Leu Gly Lys
            580                 585                 590

Leu Glu Leu Ser Gly Cys Glu Gln Gly Leu His Glu Ile Lys Leu Leu
        595                 600                 605

Gly Lys Gly Thr Ser Ala Ala Asp Ala Val Glu Val Pro Ala Pro Ala
    610                 615                 620

Ala Val Leu Gly Gly Pro Glu Pro Leu Met Gln Ala Thr Ala Trp Leu
625                 630                 635                 640

Asn Ala Tyr Phe His Gln Pro Glu Ala Ile Glu Glu Phe Pro Val Pro
                645                 650                 655

Ala Leu His His Pro Val Phe Gln Gln Glu Ser Phe Thr Arg Gln Val
            660                 665                 670

Leu Trp Lys Leu Leu Lys Val Val Lys Phe Gly Glu Val Ile Ser Tyr
        675                 680                 685

Gln Gln Leu Ala Ala Leu Ala Gly Asn Pro Ala Ala Thr Ala Ala Val
    690                 695                 700

Lys Thr Ala Leu Ser Gly Asn Pro Val Pro Ile Leu Ile Pro Cys His
705                 710                 715                 720

Arg Val Val Ser Ser Ser Gly Ala Val Gly Gly Tyr Glu Gly Gly Leu
                725                 730                 735

Ala Val Lys Glu Trp Leu Leu Ala His Glu Gly His Arg Leu Gly Lys
            740                 745                 750

Pro Gly Leu Gly Pro Ala Gly Ile Gly Ala Pro Gly Ser Leu Glu His
        755                 760                 765

His His His His His
    770

<210> SEQ ID NO 52
<211> LENGTH: 1020
<212> TYPE: DNA
<213> ORGANISM: artificial
<220> FEATURE:
<223> OTHER INFORMATION: DNA Sequence encoding the fusion protein
      BiPlike-SNAPlike-EDIII from Japanese encephalitis virus genotype I
      cloned into pMT/BiP/SNAP for expression in S2 cells

<400> SEQUENCE: 52
atgaaactat gtattctact tgcagttgtt gcgttcgtag gattgtcctt aagatctgac    60
aaagactgcg aaatgaaaag aactacattg gattcaccac ttgggaagtt ggaactgagt   120
ggatgcgagc aaggattgca tgaaattaag ctactgggaa aaggaacttc tgctgctgat   180
gcagttgaag ttccagcacc agcagctgtt cttggaggtc ctgagcccct catgcaagcc   240
acagcctggc ttaacgcata tttccaccag cctgaggcca ttgaggaatt tccagtcccc   300
gcccttcacc atcctgtgtt tcagcaggag agcttcaccc gccaggtcct gtggaaattg   360
ctgaaggtgg tcaagtttgg tgaagtgatt tcatatcagc aacttgctgc attggccggt   420
aaccccgcag ctacagctgc cgtgaaaact gctctcagcg aaatcctgt gcccatcctg   480 atcccttgtc acagagtcgt ttcatcttcc ggagctgtag gtggctatga aggaggactg   540
gcagttaagg agtggctgct ggctcatgaa ggtcatagac ttggaaagcc tgggctgggt   600
cctgctggta taggcgcgcc agggtccctg gagggaggtg gcgggtctgc tctgaagggc   660
```

```
acgacttacg gcatgtgtac agaaaaattc tcgttcgcga aaaatccagc ggacacaggc    720
catggaacag ttgtcattga gctcacatac tctggaagcg atggtccctg taaaattccg    780
attgtctcag tcgcgagttt aaacgacatg accctgtgg ggaggctggt aacagtaaac    840
cccttcgtcg cgacatctag ctccaactca aggtgctgg ttgagatgga acctcccttc    900
ggagactctt acatcgtggt tggaagaggg gataagcaga ttaaccatca ctggcacaaa    960
gctggaagca cgctgggtaa aggaggtggc catcaccatc accatcactg atgaccggtt   1020
```

<210> SEQ ID NO 53
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype I -
      Histag

<400> SEQUENCE: 53

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Ser Ala Leu Lys Gly Thr Thr Tyr Gly Met
        195                 200                 205

Cys Thr Glu Lys Phe Ser Phe Ala Lys Asn Pro Ala Asp Thr Gly His
    210                 215                 220

Gly Thr Val Val Ile Glu Leu Thr Tyr Ser Gly Ser Asp Gly Pro Cys
225                 230                 235                 240

Lys Ile Pro Ile Val Ser Val Ala Ser Leu Asn Asp Met Thr Pro Val
                245                 250                 255

Gly Arg Leu Val Thr Val Asn Pro Phe Val Ala Thr Ser Ser Asn
            260                 265                 270

Ser Lys Val Leu Val Glu Met Glu Pro Pro Phe Gly Asp Ser Tyr Ile
        275                 280                 285

Val Val Gly Arg Gly Asp Lys Gln Ile Asn His His Trp His Lys Ala
```

```
                  290                 295                 300
Gly Ser Thr Leu Gly Lys Gly Gly His His His His His
305                 310                 315

<210> SEQ ID NO 54
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 1
      (JE-1.EDIII)

<400> SEQUENCE: 54
gcgcgccagg gtccctggag ggaggtggcg ggtctgctct gaagggcacg acttacggca      60
tgtgtacaga aaaattctcg ttcgcgaaaa atccagcgga cacaggccat ggaacagttg     120
tcattgagct cacatactct ggaagcgatg gtccctgtaa aattccgatt gtctcagtcg     180
cgagtttaaa cgacatgacc cctgtgggga ggctggtaac agtaaacccc ttcgtcgcga     240
catctagctc caactcaaag gtgctggttg agatggaacc tcccttcgga gactcttaca     300
tcgtggttgg aagaggggat aagcagatta accatcactg cacaaagct ggaagcacgc      360 tgggtaaagg aggtggccat caccatcacc atcactgatg accggt                    406

<210> SEQ ID NO 55
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 2
      (JE-2.EDIII)

<400> SEQUENCE: 55
gcgcgccagg gtccctggag ggaggtggcg ggtctgctct gaaaggcaca acctatggta      60
tgtgcacaga aaactcctcg ttccgaaaaa atccagcgga cacaggccat ggaacagttg     120
tcattgagct cacatactct gggagtgatg gtccctgtaa gattccaaat gtctccgttg     180
cgagcctgaa tgacatgacc cctgtaggga ggctggtaac agtaaacccc tttgtcgcga     240
catccagcgc caactcaaaa gtgctggttg aaatggaacc cccttttgga gattcttaca     300
tcgtggtcgg aagaggtgac aagcagatca atcatcactg cacaaagct ggaagcacgc      360 tgggcaaagg aggtggccat caccatcacc atcactgatg accggt                    406

<210> SEQ ID NO 56
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 4
      (JE-4.EDIII)

<400> SEQUENCE: 56
gcgcgccagg gtccctggag ggaggtggcg ggtctgctct gaaaggcaca acctatggaa      60
tgtgcacaga aaagttctcg tttgcaaaga atccagcaga cactggtcat ggaacagttg     120
tcattgaact cctgtattct ggaagtgacg gcccctgtaa catcccaatt gtctcagtgg     180
tcagtctaaa cgacatgact ccagttgaa ggttggtgac agtgaacccc ttcgttgcca      240
catccagttc caattcaaag gtcttagttg agatggaacc tccttttgga gactcctaca     300
```
ttgtggtcgg gagaggagaa aaacaaatca accaccactg gcacaaacct ggaagcacat        360
tgggcaaagg aggtggccat caccatcacc atcactgatg accggt                     406

<210> SEQ ID NO 57
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 5
      (JE-5.EDIII)

<400> SEQUENCE: 57
gcgcgccagg gtccctggag ggaggtggcg ggtctgcgtt gaaagggacc acctatggta        60
tgtgcacaga gaagttctct ttttccaaga atccagctga cactggtcat ggtacggttg       120
tcatagaatt gcagtacacc ggcactgacg gaccttgcaa gatacccatc tcttcggtgg       180
ccagtctgaa tgatttaact ccagttggta gattggtgac agtcaatcct tttgttgcca       240
catccaccgc caattcgaag gttttggtag aattggaacc accatttgga gattcattca       300
ttgttgtcgg aagaggagat aagcagatca atcaccattg cacaaggct ggcagttcac        360 tgggaaaggg aggtggccat caccatcacc atcactgatg accggt                     406

<210> SEQ ID NO 58
<211> LENGTH: 394
<212> TYPE: DNA
<213> ORGANISM: artificial
<220> FEATURE:
<223> OTHER INFORMATION: DNA sequence of Domain III encoding envelope E
      protein from Rabensburg virus (RabV.EDIII)

<400> SEQUENCE: 58
gcgcgccagg aggtggcggg tctcagctca aggaacgac ctatggagta tgcgcaaaag        60
ccttcaagtt ttctgggaat ccagctgaca cagggcatgg caccgtggtc ttagagttgc      120
aatacaccgg aaccgatggt ccttgtaagg tgcctgtctc ttccgtggct tcactcaacg      180
acctaactcc cgttgggaga ctggtgacag tgaatccctt tgttgctgca gctactgcta      240
attcaaaggt tctgatagaa ctggaacctc cattcggtga ctcatacatt gtggtaggta      300
gaggagaaca ccagataaac caccattggc acaagtctgg aagcagtatt ggaaagggag      360
gtggccatca ccatcaccat cactgatgac cggt                                  394

<210> SEQ ID NO 59
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      2 cloned into pMT/BiP/SNAP for expression in S2 cells

<400> SEQUENCE: 59
atgaaactat gtattctact tgcagttgtt gcgttcgtag gattgtcctt aagatctgac        60
aaagactgcg aaatgaaaag aactacattg gattcaccac ttgggaagtt ggaactgagt      120
ggatgcgagc aaggattgca tgaaattaag ctactgggaa aaggaacttc tgctgctgat      180
gcagttgaag ttccagcacc agcagctgtt cttggaggtc ctgagcccct catgcaagcc      240
acagcctggc ttaacgcata tttccaccag cctgaggcca ttgaggaatt ccagtcccc       300 gcccttcacc atcctgtgtt tcagcaggag agcttcaccc gccaggtcct gtggaaattg      360

-continued

```
ctgaaggtgg tcaagtttgg tgaagtgatt tcatatcagc aacttgctgc attggccggt    420
aaccccgcag ctacagctgc cgtgaaaact gctctcagcg aaatcctgt gcccatcctg     480
atccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctgc tctgaaaggc    660
acaacctatg gtatgtgcac agaaaactcc tcgttccgaa aaaatccagc ggacacaggc    720
catggaacag ttgtcattga gctcacatac tctggagtg atggtccctg taagattcca     780
aatgtctccg ttgcgagcct gaatgacatg acccctgtag gaggctggt aacagtaaac     840
cccttttgtcg cgacatccag cgccaactca aaagtgctgg ttgaaatgga accccttttt   900
ggagattctt acatcgtggt cggaagaggt gacaagcaga tcaatcatca ctggcacaaa    960
gctggaagca cgctgggcaa aggaggtggc catcaccatc accatcactg atgaccggtt   1020
```

<210> SEQ ID NO 60
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype 2 -
      Histag

<400> SEQUENCE: 60

```
Arg Ser Asp Lys Asp Cys Glu Met Lys Arg Thr Thr Leu Asp Ser Pro
  1               5                  10                  15

Leu Gly Lys Leu Glu Leu Ser Gly Cys Glu Gln Gly Leu His Glu Ile
             20                  25                  30

Lys Leu Leu Gly Lys Gly Thr Ser Ala Ala Asp Ala Val Glu Val Pro
         35                  40                  45

Ala Pro Ala Ala Val Leu Gly Gly Pro Glu Pro Leu Met Gln Ala Thr
     50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Asn Ser Ser Phe Arg Lys Asn Pro Ala Asp Thr Gly His
    210                 215                 220

Gly Thr Val Val Ile Glu Leu Thr Tyr Ser Gly Ser Asp Gly Pro Cys
225                 230                 235                 240
```

```
Lys Ile Pro Asn Val Ser Val Ala Ser Leu Asn Asp Met Thr Pro Val
            245                 250                 255

Gly Arg Leu Val Thr Val Asn Pro Phe Val Ala Thr Ser Ser Ala Asn
        260                 265                 270

Ser Lys Val Leu Val Glu Met Glu Pro Pro Phe Gly Asp Ser Tyr Ile
    275                 280                 285

Val Val Gly Arg Gly Asp Lys Gln Ile Asn His His Trp His Lys Ala
    290                 295                 300

Gly Ser Thr Leu Gly Lys Gly Gly His His His His His His
305                 310                 315
```

<210> SEQ ID NO 61
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      4 cloned into pMT/BiP/SNAP for expression in S2 cells

<400> SEQUENCE: 61

```
atgaaactat gtattctact tgcagttgtt gcgttcgtag gattgtcctt aagatctgac      60
aaagactgcg aaatgaaaag aactacattg gattcaccac ttgggaagtt ggaactgagt    120
ggatgcgagc aaggattgca tgaaattaag ctactgggaa aaggaacttc tgctgctgat    180
gcagttgaag ttccagcacc agcagctgtt cttggaggtc ctgagcccct catgcaagcc    240
acagcctggc ttaacgcata tttccaccag cctgaggcca ttgaggaatt tccagtcccc    300
gcccttcacc atcctgtgtt tcagcaggag agcttcaccc gccaggtcct gtggaaattg    360
ctgaaggtgg tcaagtttgg tgaagtgatt tcatatcagc aacttgctgc attggccggt    420
aaccccgcag ctacagctgc cgtgaaaact gctctcagcg gaaatcctgt gcccatcctg    480
atcccttgtc acagagtcgt tcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctgc tctgaaaggc    660
acaacctatg gaatgtgcac agaaaagttc tcgtttgcaa agaatccagc agacactggt    720
catggaacag ttgtcattga actcctgtat tctggaagtg acggcccctg taacatccca    780
attgtctcag tggtcagtct aaacgacatg actccagttg aaggttggt gacagtgaac    840
ccttcgttg ccacatccag ttccaattca aggtcttag ttgagatgga acctccttt      900
ggagactcct acattgtggt cgggagagga gaaaaacaaa tcaaccacca ctggcacaaa    960
cctggaagca cattgggcaa aggaggtggc catcaccatc accatcactg atgaccggtt   1020
```

<210> SEQ ID NO 62
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype 4 -
      Histag

<400> SEQUENCE: 62

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30
```

-continued

```
Lys Leu Leu Gly Lys Gly Thr Ser Ala Ala Asp Ala Val Glu Val Pro
         35                  40                  45
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Leu Lys Val Val Lys Phe Gly Glu Val
                100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Glu Gly Gly Gly Gly Ser Ala Leu Lys Gly Thr Thr Tyr Gly Met
        195                 200                 205
Cys Thr Glu Lys Phe Ser Phe Ala Lys Asn Pro Ala Asp Thr Gly His
210                 215                 220
Gly Thr Val Val Ile Glu Leu Leu Tyr Ser Gly Ser Asp Gly Pro Cys
225                 230                 235                 240
Asn Ile Pro Ile Val Ser Val Val Ser Leu Asn Asp Met Thr Pro Val
                245                 250                 255
Gly Arg Leu Val Thr Val Asn Pro Phe Val Ala Thr Ser Ser Ser Asn
            260                 265                 270
Ser Lys Val Leu Val Glu Met Glu Pro Pro Phe Gly Asp Ser Tyr Ile
        275                 280                 285
Val Val Gly Arg Gly Glu Lys Gln Ile Asn His His Trp His Lys Pro
290                 295                 300
Gly Ser Thr Leu Gly Lys Gly Gly His His His His His His
305                 310                 315
```

<210> SEQ ID NO 63
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      5 cloned into pMT/BiP/SNAP for expression in S2 cells

<400> SEQUENCE: 63

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
```

-continued

```
aaccccgcag ctacagctgc cgtgaaaact gctctcagcg aaatcctgt gcccatcctg    480 atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctgc gttgaaaggg    660
accacctatg gtatgtgcac agagaagttc tcttttttcca agaatccagc tgacactggt    720
catggtacgg ttgtcataga attgcagtac accggcactg acggaccttg caagataccc    780
atctcttcgg tggccagtct gaatgattta actccagttg gtagattggt gacagtcaat    840
ccttttgttg ccacatccac cgccaattcg aaggttttgg tagaattgga accaccattt    900
ggagattcat tcattgttgt cggaagagga gataagcaga tcaatcacca ttggcacaag    960
gctggcagtt cactgggaaa gggaggtggc catcaccatc accatcactg atgaccggtt   1020
```

<210> SEQ ID NO 64
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype 5 -
      Histag

<400> SEQUENCE: 64

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Lys Phe Ser Phe Ser Lys Asn Pro Ala Asp Thr Gly His
    210                 215                 220

Gly Thr Val Val Ile Glu Leu Gln Tyr Thr Gly Thr Asp Gly Pro Cys
225                 230                 235                 240

Lys Ile Pro Ile Ser Ser Val Ala Ser Leu Asn Asp Leu Thr Pro Val
```

Gly Arg Leu Val Thr Val Asn Pro Phe Val Ala Thr Ser Thr Ala Asn
            245                 250                 255

Ser Lys Val Leu Val Glu Leu Glu Pro Pro Phe Gly Asp Ser Phe Ile
    260                 265                 270

Val Val Gly Arg Gly Asp Lys Gln Ile Asn His His Trp His Lys Ala
275                 280                 285

Gly Ser Ser Leu Gly Lys Gly Gly His His His His His His
    290                 295                 300

305             310             315

<210> SEQ ID NO 65
<211> LENGTH: 1008
<212> TYPE: DNA
<213> ORGANISM: artificial
<220> FEATURE:
<223> OTHER INFORMATION: DNA Sequence encoding the fusion protein
      BiPlike -SNAPlike-EDIII from Rabensburg virus cloned into
      pMT/BiP/SNAP for expression in S2 cells

<400> SEQUENCE: 65
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg aaatcctgt gcccatcctg      480 atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc aggaggtggc gggtctcagc tcaaaggaac gacctatgga     660
gtatgcgcaa aagccttcaa gttttctggg aatccagctg acacagggca tggcaccgtg     720
gtcttagagt tgcaatacac cggaaccgat ggtccttgta aggtgcctgt ctcttccgtg     780
gcttcactca cgacctaac tcccgttggg agactggtga cagtgaatcc ctttgttgct     840
gcagctactg ctaattcaaa ggttctgata gaactggaac ctccattcgg tgactcatac     900
attgtggtag gtagaggaga caccagata aaccaccatt ggcacaagtc tggaagcagt     960
attggaaagg gaggtggcca tcaccatcac catcactgat gaccggtt              1008

<210> SEQ ID NO 66
<211> LENGTH: 314
<212> TYPE: PRT
<213> ORGANISM: artificial
<220> FEATURE:
<223> OTHER INFORMATION: Amino acid Sequence of the fusion protein
      SNAPlike-EDIII from Rabensburg virus - Histag

<400> SEQUENCE: 66

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

```
Ala Pro Ala Ala Val Leu Gly Gly Pro Glu Pro Leu Met Gln Ala Thr
        50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
                100                 105                 110

Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
                180                 185                 190

Gly Gly Ser Gln Leu Lys Gly Thr Thr Tyr Gly Val Cys Ala Lys Ala
            195                 200                 205

Phe Lys Phe Ser Gly Asn Pro Ala Asp Thr Gly His Gly Thr Val Val
210                 215                 220

Leu Glu Leu Gln Tyr Thr Gly Thr Asp Gly Pro Cys Lys Val Pro Val
225                 230                 235                 240

Ser Ser Val Ala Ser Leu Asn Asp Leu Thr Pro Val Gly Arg Leu Val
                245                 250                 255

Thr Val Asn Pro Phe Val Ala Ala Thr Ala Asn Ser Lys Val Leu
                260                 265                 270

Ile Glu Leu Glu Pro Pro Phe Gly Asp Ser Tyr Ile Val Val Gly Arg
            275                 280                 285

Gly Glu His Gln Ile Asn His His Trp His Lys Ser Gly Ser Ser Ile
290                 295                 300

Gly Lys Gly Gly Gly His His His His His
305                 310
```

<210> SEQ ID NO 67
<211> LENGTH: 977
<212> TYPE: DNA
<213> ORGANISM: artificial
<220> FEATURE:
<223> OTHER INFORMATION: DNA Sequence encoding the fusion protein ssBiP-SNAPlike-EDIII from an insect flavivirus virus cloned into pMT/BiP/SNAP for expression in S2 cells

<400> SEQUENCE: 67

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aggaacttc tgctgctgat      180 gcagttgaag ttccagcacc agcagctgtt cttggaggtc ctgagcccct catgcaagcc     240
acagcctggc ttaacgcata tttccaccag cctgaggcca ttgaggaatt ccagtcccc     300 gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg gaaatcctgt gcccatcctg     480
```

```
atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc aggaggtggc ggggaagcgc agacagtgtt ctctcaatcc    660
ccttgggggt tcgaaggaat agcggagata acactaaaag aggcccaaaa gagcatttgt    720
tcactacctt tgtcttgtgt gggctgtagc ttgttgtctt ccaaggtcgt tttccttgag    780
acaacaacga aagctgccgt ccacgttgga tgtgggaatg gaacttctgt tctaacagtt    840
ggaactactc ctgtgagtat cgactgtgta gtaacgcccc tgtcgcaggt gtggaggctc    900
gtgtcgcacg tcaccggaag atacaccaaa cttgggtttg gaggtggcca tcaccatcac    960
catcactgat gaccggt                                                   977
```

<210> SEQ ID NO 68
<211> LENGTH: 305
<212> TYPE: PRT
<213> ORGANISM: artificial
<220> FEATURE:
<223> OTHER INFORMATION: Amino acid Sequence of the fusion protein
      SNAPlike-EDIII from a insect flavivirus - Histag

<400> SEQUENCE: 68

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Glu Ala Gln Thr Val Phe Ser Gln Ser Pro Trp Gly Phe Glu
        195                 200                 205

Gly Ile Ala Glu Ile Thr Leu Lys Glu Ala Gln Lys Ser Ile Cys Ser
    210                 215                 220

Leu Pro Leu Ser Cys Val Gly Cys Ser Leu Leu Ser Ser Lys Val Val
225                 230                 235                 240

Phe Leu Glu Thr Thr Thr Lys Ala Ala Val His Val Gly Cys Gly Asn
                245                 250                 255

Gly Thr Ser Val Leu Thr Val Gly Thr Thr Pro Val Ser Ile Asp Cys
```

```
                    260                 265                 270
Val Val Thr Pro Leu Ser Gln Val Trp Arg Leu Val Ser His Val Thr
            275                 280                 285

Gly Arg Tyr Thr Lys Leu Gly Phe Gly Gly Gly His His His His His
            290                 295                 300

His
305

<210> SEQ ID NO 69
<211> LENGTH: 1783
<212> TYPE: DNA
<213> ORGANISM: artificial
<220> FEATURE:
<223> OTHER INFORMATION: DNA sequence encoding ssBiP-sE2 from Ross River
      virus strain QML-1 -SNAPlike-Histag for expression in S2 cells

<400> SEQUENCE: 69
atgaagttat gcatattact ggccgtcgtg gcctttgttg gcctctcgct cgggagatct      60
agtgtaacag agcacttcaa tgtgtataag gctactagac ataccctagc acattgcgct    120
gattgcgggg acgggtactt ctgctatagc ccagttgcca tcgagaagat ccgagatgag    180
gcgtctgatg catgctcaa gatccaagtc tccgcccaaa taggtctgga caaggcaggc    240
acccacgccc acacgaagct ccgatatatg gctggtcacg atgttcagga atctaagaga    300
gattccttga gggtgtacac gtccgcagcg tgctccatac atgggacgat gggacacttc    360
atcgtcgcac actgtccacc aggcgactac ctcaaggttt cgttcgagga cgcagattcg    420
cacgtgaagg catgtaaggt ccaatacaag cacaatccat gccggtgggt agagagaag    480 ttcgtggtta gaccacactt tggcgtagag ctgccatgca cctcatacca gctgacaacg    540
gctcccaccg acgaggagat tgacatgcat acaccgccag atataccgga tcgcaccctg    600
ctatcacaga cggcgggcaa cgtcaaaata acagcaggcg gcaggactat caggtacaat    660
tgtacctgcg gccgtgacaa cgtaggcact accagtactg acaagaccat caacacatgc    720
aagattgacc aatgccatgc tgccgtcacc agccatgaca atggcaatt tacctctcca    780 tttgttccca gggctgatca gacagctagg aaaggcaagg tacacgttcc gttccctctg    840
actaacgtca cctgccgagt gccgttggct cgagcgccgg atgtcaccta tggtaagaag    900
gaggtgaccc tgagattaca cccagatcat ccgacactct tctcctatag gagtttagga    960
gccgaaccgc acccgtacga ggaatgggtt gacaagttct ctgagcgcat catcccagtg   1020
acggaagaag ggattgaata ccagtggggc aacaacccgc cggtccgcct gtgggcgcaa   1080
ctgacgaccg agggcaaacc ccatggatgg ccacatgaaa tcattcagta ctattatgga   1140 ctatacccg ccgccacgcg gccgcacggc ggaggtagca aagactgcga atgaagcgc    1200 accaccctgg atagccctct gggcaagctg aactgtctg ggtgcgaaca gggcctgcac   1260
gagatcaagc tgctgggcaa aggaacatct gccgccgacg ccgtggaagt gcctgcccca   1320
gccgccgtgc tgggcggacc agagccactg atgcaggcca ccgcctggct caacgcctac   1380
tttcaccagc ctgaggccat cgaggagttc cctgtgccag ccctgcacca cccagtgttc   1440
cagcaggaga gctttacccg ccaggtgctg tggaaactgc tgaaagtggt gaagttcgga   1500
gaggtcatca gctaccagca gctggccgcc ctggccggca tcccgccgc caccgccgcc   1560 gtgaaaaccg cccctgagcgg aaatcccgtg cccattctga tccctgcca ccgggtggtg   1620 tctagctctg gcgccgtggg gggctacgag ggcgggctcg ccgtgaaaga gtggctgctg   1680
gcccacgagg gccacagact gggcaagcct gggctgggtc ctgcaggtat aggcgcgcca   1740
```
gggtccctgg agcatcatca tcatcatcat tgatgacggg ccc     1783

```
<210> SEQ ID NO 70
<211> LENGTH: 572
<212> TYPE: PRT
<213> ORGANISM: artificial
<220> FEATURE:
<223> OTHER INFORMATION: Amino acid sequence of the fusion protein [sE2
      from Ross River virus strain QML-1 -SNAPlike-Histag]

<400> SEQUENCE: 70

Arg Ser Ser Val Thr Glu His Phe Asn Val Tyr Lys Ala Thr Arg Pro
1               5                   10                  15

Tyr Leu Ala His Cys Ala Asp Cys Gly Asp Gly Tyr Phe Cys Tyr Ser
            20                  25                  30

Pro Val Ala Ile Glu Lys Ile Arg Asp Glu Ala Ser Asp Gly Met Leu
        35                  40                  45

Lys Ile Gln Val Ser Ala Gln Ile Gly Leu Asp Lys Ala Gly Thr His
    50                  55                  60

Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
            100                 105                 110

Leu Lys Val Ser Phe Glu Asp Ala Asp Ser His Val Lys Ala Cys Lys
        115                 120                 125

Val Gln Tyr Lys His Asn Pro Leu Pro Val Gly Arg Glu Lys Phe Val
    130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
            180                 185                 190

Thr Ala Gly Gly Arg Thr Ile Arg Tyr Asn Cys Thr Cys Gly Arg Asp
        195                 200                 205

Asn Val Gly Thr Thr Ser Thr Asp Lys Thr Ile Asn Thr Cys Lys Ile
    210                 215                 220

Asp Gln Cys His Ala Ala Val Thr Ser His Asp Lys Trp Gln Phe Thr
225                 230                 235                 240

Ser Pro Phe Val Pro Arg Ala Asp Gln Thr Ala Arg Lys Gly Lys Val
                245                 250                 255

His Val Pro Phe Pro Leu Thr Asn Val Thr Cys Arg Val Pro Leu Ala
            260                 265                 270

Arg Ala Pro Asp Val Thr Tyr Gly Lys Lys Glu Val Thr Leu Arg Leu
        275                 280                 285

His Pro Asp His Pro Thr Leu Phe Ser Tyr Arg Ser Leu Gly Ala Glu
    290                 295                 300

Pro His Pro Tyr Glu Glu Trp Val Asp Lys Phe Ser Glu Arg Ile Ile
305                 310                 315                 320

Pro Val Thr Glu Glu Gly Ile Glu Tyr Gln Trp Gly Asn Asn Pro Pro
                325                 330                 335

Val Arg Leu Trp Ala Gln Leu Thr Thr Glu Gly Lys Pro His Gly Trp
            340                 345                 350
```

```
Pro His Glu Ile Ile Gln Tyr Tyr Gly Leu Tyr Pro Ala Ala Thr
    355                 360                 365

Arg Pro His Gly Gly Gly Ser Lys Asp Cys Glu Met Lys Arg Thr Thr
370                 375                 380

Leu Asp Ser Pro Leu Gly Lys Leu Glu Leu Ser Gly Cys Glu Gln Gly
385                 390                 395                 400

Leu His Glu Ile Lys Leu Leu Gly Lys Gly Thr Ser Ala Ala Asp Ala
                405                 410                 415

Val Glu Val Pro Ala Pro Ala Ala Val Leu Gly Gly Pro Glu Pro Leu
            420                 425                 430

Met Gln Ala Thr Ala Trp Leu Asn Ala Tyr Phe His Gln Pro Glu Ala
        435                 440                 445

Ile Glu Glu Phe Pro Val Pro Ala Leu His His Pro Val Phe Gln Gln
    450                 455                 460

Glu Ser Phe Thr Arg Gln Val Leu Trp Lys Leu Leu Lys Val Val Lys
465                 470                 475                 480

Phe Gly Glu Val Ile Ser Tyr Gln Gln Leu Ala Ala Leu Ala Gly Asn
                485                 490                 495

Pro Ala Ala Thr Ala Ala Val Lys Thr Ala Leu Ser Gly Asn Pro Val
            500                 505                 510

Pro Ile Leu Ile Pro Cys His Arg Val Val Ser Ser Gly Ala Val
        515                 520                 525

Gly Gly Tyr Glu Gly Gly Leu Ala Val Lys Glu Trp Leu Leu Ala His
    530                 535                 540

Glu Gly His Arg Leu Gly Lys Pro Gly Leu Gly Pro Ala Gly Ile Gly
545                 550                 555                 560

Ala Pro Gly Ser Leu Glu His His His His His His
                565                 570

<210> SEQ ID NO 71
<211> LENGTH: 1783
<212> TYPE: DNA
<213> ORGANISM: artificial
<220> FEATURE:
<223> OTHER INFORMATION: DNA sequence encoding ssBiP-sE2 from Mayaro
      virus strain IQD2668 -SNAPlike-Histag for expression in S2 cells

<400> SEQUENCE: 71
atgaagttat gcatattact ggccgtcgtg gcctttgttg gcctctcgct cgggagatct      60
agtgtaacag agcacttcaa tgtgtataag gctactagac ataccctagc acattgcgct     120
gattgcgggg acgggtactt ctgctatagc ccagttgcca tcgagaagat ccgagatgag     180
gcgtctgatg gcatgctcaa gatccaagtc tccgcccaaa taggtctgga caaggcaggc     240
acccacgccc acacgaagct ccgatatatg gctggtcacg atgttcagga atctaagaga     300
gattccttga gggtgtacac gtccgcagcg tgctccatac atgggacgat gggacacttc     360
atcgtcgcac actgtccacc aggcgactac ctcaaggttt cgttcgagga cgcagattcg     420
cacgtgaagg catgtaaggt ccaatacaag cacaatccat tgccggtggg tagagagaag     480
ttcgtggtta gaccacactt tggcgtagag ctgccatgca cctcatacca gctgacaacg     540
gctcccaccg acgaggagat tgacatgcat acaccgccag atataccgga tcgcaccctg     600
ctatcacaga cggcgggcaa cgtcaaaata acagcaggcg gcaggactat caggtacaat     660
tgtacctgcg gccgtgacaa cgtaggcact accagtactg acaagaccat caacacatgc     720
aagattgacc aatgccatgc tgccgtcacc agccatgaca aatggcaatt tacctctcca     780
```

```
tttgttccca gggctgatca gacagctagg aaaggcaagg tacacgttcc gttccctctg    840
actaacgtca cctgccgagt gccgttggct cgagcgccgg atgtcaccta tggtaagaag    900
gaggtgaccc tgagattaca cccagatcat ccgacactct tctcctatag gagtttagga    960
gccgaaccgc acccgtacga ggaatggggtt gacaagttct ctgagcgcat catcccagtg   1020
acggaagaag ggattgaata ccagtggggc aacaacccgc cggtccgcct gtgggcgcaa   1080
ctgacgaccg agggcaaacc ccatggatgg ccacatgaaa tcattcagta ctattatgga   1140
ctataccccg ccgccacgcg gccgcacggc ggaggtagca aagactgcga aatgaagcgc   1200
accaccctgg atagccctct gggcaagctg aactgtctg gtgcgaaca gggcctgcac     1260 gagatcaagc tgctgggcaa aggaacatct gccgccgacg ccgtggaagt gcctgcccca   1320
gccgccgtgc tgggcggacc agagccactg atgcaggcca ccgcctggct caacgcctac   1380
tttcaccagc tgaggccat cgaggagttc cctgtgccag ccctgcacca cccagtgttc    1440
cagcaggaga gctttacccg ccaggtgctg tggaaactgc tgaaagtggt gaagttcgga   1500
gaggtcatca gctaccagca gctggccgcc ctggccggca tcccgccgc caccgccgcc   1560 gtgaaaaccg ccctgagcgg aaatcccgtg cccattctga tccctgcca ccgggtggtg    1620 tctagctctg gcgccgtggg gggctacgag ggcgggctcg ccgtgaaaga gtggctgctg   1680
gcccacgagg ccacagact gggcaagcct gggctgggtc ctgcaggtat aggcgcgcca   1740
gggtccctgg agcatcatca tcatcatcat tgatgacggg ccc                     1783
```

<210> SEQ ID NO 72
<211> LENGTH: 572
<212> TYPE: PRT
<213> ORGANISM: artificial
<220> FEATURE:
<223> OTHER INFORMATION: Amino acid sequence of the fusion protein [sE2
      from Mayaro virus strain IQD2668 -SNAPlike-Histag]

<400> SEQUENCE: 72

Arg Ser Ser Val Thr Glu His Phe Asn Val Tyr Lys Ala Thr Arg Pro
1               5                   10                  15

Tyr Leu Ala His Cys Ala Asp Cys Gly Asp Gly Tyr Phe Cys Tyr Ser
            20                  25                  30

Pro Val Ala Ile Glu Lys Ile Arg Asp Glu Ala Ser Asp Gly Met Leu
        35                  40                  45

Lys Ile Gln Val Ser Ala Gln Ile Gly Leu Asp Lys Ala Gly Thr His
    50                  55                  60

Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
            100                 105                 110

Leu Lys Val Ser Phe Glu Asp Ala Asp Ser His Val Lys Ala Cys Lys
        115                 120                 125

Val Gln Tyr Lys His Asn Pro Leu Pro Val Gly Arg Glu Lys Phe Val
    130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
                180                 185                 190

Thr Ala Gly Gly Arg Thr Ile Arg Tyr Asn Cys Thr Cys Gly Arg Asp
            195                 200                 205

Asn Val Gly Thr Thr Ser Thr Asp Lys Thr Ile Asn Thr Cys Lys Ile
210                 215                 220

Asp Gln Cys His Ala Ala Val Thr Ser His Asp Lys Trp Gln Phe Thr
225                 230                 235                 240

Ser Pro Phe Val Pro Arg Ala Asp Gln Thr Ala Arg Lys Gly Lys Val
                245                 250                 255

His Val Pro Phe Pro Leu Thr Asn Val Thr Cys Arg Val Pro Leu Ala
            260                 265                 270

Arg Ala Pro Asp Val Thr Tyr Gly Lys Lys Glu Val Thr Leu Arg Leu
        275                 280                 285

His Pro Asp His Pro Thr Leu Phe Ser Tyr Arg Ser Leu Gly Ala Glu
    290                 295                 300

Pro His Pro Tyr Glu Glu Trp Val Asp Lys Phe Ser Glu Arg Ile Ile
305                 310                 315                 320

Pro Val Thr Glu Glu Gly Ile Glu Tyr Gln Trp Gly Asn Asn Pro Pro
                325                 330                 335

Val Arg Leu Trp Ala Gln Leu Thr Thr Glu Gly Lys Pro His Gly Trp
            340                 345                 350

Pro His Glu Ile Ile Gln Tyr Tyr Tyr Gly Leu Tyr Pro Ala Ala Thr
        355                 360                 365

Arg Pro His Gly Gly Gly Ser Lys Asp Cys Glu Met Lys Arg Thr Thr
    370                 375                 380

Leu Asp Ser Pro Leu Gly Lys Leu Glu Leu Ser Gly Cys Glu Gln Gly
385                 390                 395                 400

Leu His Glu Ile Lys Leu Leu Gly Lys Gly Thr Ser Ala Ala Asp Ala
                405                 410                 415

Val Glu Val Pro Ala Pro Ala Ala Val Leu Gly Gly Pro Glu Pro Leu
            420                 425                 430

Met Gln Ala Thr Ala Trp Leu Asn Ala Tyr Phe His Gln Pro Glu Ala
        435                 440                 445

Ile Glu Glu Phe Pro Val Pro Ala Leu His His Pro Val Phe Gln Gln
    450                 455                 460

Glu Ser Phe Thr Arg Gln Val Leu Trp Lys Leu Leu Lys Val Val Lys
465                 470                 475                 480

Phe Gly Glu Val Ile Ser Tyr Gln Gln Leu Ala Ala Leu Ala Gly Asn
                485                 490                 495

Pro Ala Ala Thr Ala Ala Val Lys Thr Ala Leu Ser Gly Asn Pro Val
            500                 505                 510

Pro Ile Leu Ile Pro Cys His Arg Val Val Ser Ser Ser Gly Ala Val
        515                 520                 525

Gly Gly Tyr Glu Gly Gly Leu Ala Val Lys Glu Trp Leu Leu Ala His
    530                 535                 540

Glu Gly His Arg Leu Gly Lys Pro Gly Leu Gly Pro Ala Gly Ile Gly
545                 550                 555                 560

Ala Pro Gly Ser Leu Glu His His His His His His
                565                 570

<210> SEQ ID NO 73
<211> LENGTH: 1786
<212> TYPE: DNA

<213> ORGANISM: artificial
<220> FEATURE:
<223> OTHER INFORMATION: DNA sequence encoding ssBiP-sE2 from Western Equine Encephalitis virus -SNAPlike-Histag for expression in S2 cells

<400> SEQUENCE: 73

```
atgaagttat gcatattact ggccgtcgtg gcctttgttg gcctctcgct cgggagatct      60
agcattaccg atgacttcac actgaccagt ccctacctgg ggttctgccc gtattgcaga     120
cactcaacgc cgtgtttcag cccaataaaa attgagaacg tgtgggacga atctgatgat     180
ggatcgatta gaatccaggt ctcggcacaa ttcggctaca atcaggcagg cactgcggat     240
gtcaccaaat tccgttacat gtctttcgac cacgaccatg acatcaagga agacagtatg     300
gagaaaatag ctatcagcac atctggaccc tgccgtcgtc ttggccacaa agggtacttc     360
ctgttagctc aatgtcctcc aggtgacagt gtaaccgtca gtatcacgag cggagcatct     420
gagaattcat gcaccgtgga gaaaaagatc aggaggaagt tgtcggtag agaggagtac     480
ttgttcccac ccgtccatgg aaagctggta agtgccacg tttacgatca cttgaaggag     540
acgtctgccg ggtacataac catgcacagg ccaggcccac acgcgtataa gtcctatctg     600
gaggaagcgt caggcgaagt gtacattaaa ccaccttctg caagaacgt cacctacgaa     660
tgtaagtgtg gcgactacag cacaggtatc gtgagcacgc aacgaagat aacggctgc     720
actaaagcaa aacagtgcat tgcctacaag agcgaccaaa cgaaatgggt cttcaactcg     780
ccggatctta ttaggcacac agaccactca gtgcaaggta aattgcacat tccattccgc     840
ttgacaccga cagtctgccc ggttccgtta gctcacacgc ctacagtcac gaagtggttc     900
aaaggcatca ccctccacct gactgcaatg cgaccaacat tgctgacaac gagaaaattg     960
gggctgcgag cagacgcaac agcagaatgg attacagggt ctacatccag gaattttct    1020
gtggggcgag aagggctgga gtacgtatgg ggtaaccatg aaccagtcag agtctgggcc    1080
caggagtcgg caccaggcga cccacatgga tggccgcatg agatcatcat ccactattat    1140
catcggcatc cagtctacac gcggccgcac ggcggaggta gcaaagactg gaaatgaag    1200
cgcaccaccc tggatagccc tctgggcaag ctggaactgt ctgggtgcga acagggcctg    1260
cacgagatca agctgctggg caaaggaaca tctgccgccg acgccgtgga agtgcctgcc    1320
ccagccgccg tgctgggcgg accagagcca ctgatgcagg ccaccgcctg gctcaacgcc    1380
tactttcacc agcctgaggc catcgaggag ttccctgtgc agcccctgca ccacccagtg    1440
ttccagcagg agagctttac ccgccaggtg ctgtggaaac tgctgaaagt ggtgaagttc    1500
ggagaggtca tcagctacca gcagctggcc gccctggccg gcaatcccgc cgccaccgcc    1560
gccgtgaaaa ccgccctgag cggaaatccc gtgcccattc tgatcccctg ccaccggtg    1620
gtgtctagct ctggcgccgt ggggggctac gagggcgggc tcgccgtgaa agagtggctg    1680
ctggcccacg agggccacag actgggcaag cctgggctgg tcctgcagg tataggcgcg    1740
ccagggtccc tggagcatca tcatcatcat cattgatgac gggccc                 1786
```

<210> SEQ ID NO 74
<211> LENGTH: 573
<212> TYPE: PRT
<213> ORGANISM: artificial
<220> FEATURE:
<223> OTHER INFORMATION: Amino acid sequence of the fusion protein [sE2 from Western Equine Encephalitis -SNAPlike-Histag]

<400> SEQUENCE: 74

```
Arg Ser Ser Ile Thr Asp Asp Phe Thr Leu Thr Ser Pro Tyr Leu Gly
1               5                   10                  15
Phe Cys Pro Tyr Cys Arg His Ser Thr Pro Cys Phe Ser Pro Ile Lys
            20                  25                  30
Ile Glu Asn Val Trp Asp Glu Ser Asp Asp Gly Ser Ile Arg Ile Gln
        35                  40                  45
Val Ser Ala Gln Phe Gly Tyr Asn Gln Ala Gly Thr Ala Asp Val Thr
50                  55                  60
Lys Phe Arg Tyr Met Ser Phe Asp His Asp His Asp Ile Lys Glu Asp
65                  70                  75                  80
Ser Met Glu Lys Ile Ala Ile Ser Thr Ser Gly Pro Cys Arg Arg Leu
                85                  90                  95
Gly His Lys Gly Tyr Phe Leu Leu Ala Gln Cys Pro Pro Gly Asp Ser
            100                 105                 110
Val Thr Val Ser Ile Thr Ser Gly Ala Ser Glu Asn Ser Cys Thr Val
        115                 120                 125
Glu Lys Lys Ile Arg Arg Lys Phe Val Gly Arg Glu Glu Tyr Leu Phe
130                 135                 140
Pro Pro Val His Gly Lys Leu Val Lys Cys His Val Tyr Asp His Leu
145                 150                 155                 160
Lys Glu Thr Ser Ala Gly Tyr Ile Thr Met His Arg Pro Gly Pro His
                165                 170                 175
Ala Tyr Lys Ser Tyr Leu Glu Glu Ala Ser Gly Glu Val Tyr Ile Lys
            180                 185                 190
Pro Pro Ser Gly Lys Asn Val Thr Tyr Glu Cys Lys Cys Gly Asp Tyr
        195                 200                 205
Ser Thr Gly Ile Val Ser Thr Arg Thr Lys Met Asn Gly Cys Thr Lys
210                 215                 220
Ala Lys Gln Cys Ile Ala Tyr Lys Ser Asp Gln Thr Lys Trp Val Phe
225                 230                 235                 240
Asn Ser Pro Asp Leu Ile Arg His Thr Asp His Ser Val Gln Gly Lys
                245                 250                 255
Leu His Ile Pro Phe Arg Leu Thr Pro Thr Val Cys Pro Val Pro Leu
            260                 265                 270
Ala His Thr Pro Thr Val Thr Lys Trp Phe Lys Gly Ile Thr Leu His
        275                 280                 285
Leu Thr Ala Met Arg Pro Thr Leu Leu Thr Thr Arg Lys Leu Gly Leu
290                 295                 300
Arg Ala Asp Ala Thr Ala Glu Trp Ile Thr Gly Ser Thr Ser Arg Asn
305                 310                 315                 320
Phe Ser Val Gly Arg Glu Gly Leu Glu Tyr Val Trp Gly Asn His Glu
                325                 330                 335
Pro Val Arg Val Trp Ala Gln Glu Ser Ala Pro Gly Asp Pro His Gly
            340                 345                 350
Trp Pro His Glu Ile Ile His Tyr Tyr His Arg His Pro Val Tyr
        355                 360                 365
Thr Arg Pro His Gly Gly Gly Ser Lys Asp Cys Glu Met Lys Arg Thr
370                 375                 380
Thr Leu Asp Ser Pro Leu Gly Lys Leu Glu Leu Ser Gly Cys Glu Gln
385                 390                 395                 400
Gly Leu His Glu Ile Lys Leu Leu Gly Lys Gly Thr Ser Ala Ala Asp
                405                 410                 415
Ala Val Glu Val Pro Ala Pro Ala Ala Val Leu Gly Gly Pro Glu Pro
```

```
                420           425           430
Leu Met Gln Ala Thr Ala Trp Leu Asn Ala Tyr Phe His Gln Pro Glu
            435                 440                 445
Ala Ile Glu Glu Phe Pro Val Pro Ala Leu His His Pro Val Phe Gln
        450                 455                 460
Gln Glu Ser Phe Thr Arg Gln Val Leu Trp Lys Leu Leu Lys Val Val
465                 470                 475                 480
Lys Phe Gly Glu Val Ile Ser Tyr Gln Gln Leu Ala Ala Leu Ala Gly
                485                 490                 495
Asn Pro Ala Ala Thr Ala Ala Val Lys Thr Ala Leu Ser Gly Asn Pro
            500                 505                 510

```
ccgttaacca caattatcgg gcggccgcac ggcggaggta gcaaagactg cgaaatgaag    1200
cgcaccaccc tggatagccc tctgggcaag ctggaactgt ctgggtgcga acagggcctg    1260
cacgagatca agctgctggg caaaggaaca tctgccgccg acgccgtgga agtgcctgcc    1320
ccagccgccg tgctgggcgg accagagcca ctgatgcagg ccaccgcctg gctcaacgcc    1380
tactttcacc agcctgaggc catcgaggag ttccctgtgc agccctgca ccacccagtg     1440 ttccagcagg agagctttac ccgccaggtg ctgtggaaac tgctgaaagt ggtgaagttc    1500
ggagaggtca tcagctacca gcagctggcc gccctggccg gcaatcccgc cgccaccgcc    1560
gccgtgaaaa ccgccctgag cggaaatccc gtgcccattc tgatcccctg ccaccgggtg    1620
gtgtctagct ctggcgccgt gggggggctac gagggcgggc tcgccgtgaa agagtggctg    1680
ctggcccacg agggccacag actgggcaag cctgggctgg gtcctgcagg tataggcgcg    1740
ccagggtccc tggagcatca tcatcatcat cattgatgac gggccc                   1786
```

<210> SEQ ID NO 76
<211> LENGTH: 573
<212> TYPE: PRT
<213> ORGANISM: artificial
<220> FEATURE:
<223> OTHER INFORMATION: Amino acid sequence of the fusion protein [sE2 from Eastern Equine Encephalitis -SNAPlike-Histag]

<400> SEQUENCE: 76

```
Arg Ser Asp Leu Asp Thr His Phe Thr Gln Tyr Lys Leu Ala Arg Pro
1               5                   10                  15

Tyr Ile Ala Asp Cys Pro Asn Cys Gly His Ser Arg Cys Asp Ser Pro
            20                  25                  30

Ile Ala Ile Glu Glu Val Arg Gly Asp Ala His Ala Gly Val Ile Arg
        35                  40                  45

Ile Gln Thr Ser Ala Met Phe Gly Leu Lys Thr Asp Gly Val Asp Leu
    50                  55                  60

Ala Tyr Met Ser Phe Met Asn Gly Lys Thr Gln Lys Ser Ile Lys Ile
65                  70                  75                  80

Asp Asn Leu His Val Arg Thr Ser Ala Pro Cys Ser Leu Val Ser His
                85                  90                  95

His Gly Tyr Tyr Ile Leu Ala Gln Cys Pro Pro Gly Asp Thr Val Thr
            100                 105                 110

Val Gly Phe His Asp Gly Pro Asn Arg His Thr Cys Thr Val Ala His
        115                 120                 125

Lys Val Glu Phe Arg Pro Val Gly Arg Glu Lys Tyr Arg His Pro Pro
    130                 135                 140

Glu His Gly Val Glu Leu Pro Cys Asn Arg Tyr Thr His Lys Arg Ala
145                 150                 155                 160

Asp Gln Gly His Tyr Val Glu Met His Gln Pro Gly Leu Val Ala Asp
                165                 170                 175

His Ser Leu Leu Ser Ile His Ser Ala Lys Val Lys Ile Thr Val Pro
            180                 185                 190

Ser Gly Ala Gln Val Lys Tyr Tyr Cys Lys Cys Pro Asp Val Arg Glu
        195                 200                 205

Gly Ile Thr Ser Ser Asp His Thr Thr Thr Cys Thr Asp Val Lys Gln
    210                 215                 220

Cys Arg Ala Tyr Leu Ile Asp Asn Lys Lys Trp Val Tyr Asn Ser Gly
225                 230                 235                 240

Arg Leu Pro Arg Gly Glu Gly Asp Thr Phe Lys Gly Lys Leu His Val
```

```
                    245                 250                 255
Pro Phe Val Pro Val Lys Ala Lys Cys Ile Ala Thr Leu Ala Pro Glu
                260                 265                 270

Pro Leu Val Glu His Lys His Arg Thr Leu Ile Leu His Leu His Pro
            275                 280                 285

Asp His Pro Thr Leu Leu Thr Thr Arg Ser Leu Gly Ser Asp Ala Asn
        290                 295                 300

Pro Thr Arg Gln Trp Ile Glu Arg Pro Thr Thr Val Asn Phe Thr Val
305                 310                 315                 320

Thr Gly Glu Gly Leu Glu Tyr Thr Trp Gly Asn His Pro Pro Lys Arg
                325                 330                 335

Val Trp Ala Gln Glu Ser Gly Glu Gly Asn Pro His Gly Trp Pro His
            340                 345                 350

Glu Val Val Val Tyr Tyr Asn Arg Tyr Pro Leu Thr Thr Ile Ile
        355                 360                 365

Gly Arg Pro His Gly Gly Ser Lys Asp Cys Glu Met Lys Arg Thr
    370                 375                 380

Thr Leu Asp Ser Pro Leu Gly Lys Leu Glu Leu Ser Gly Cys Glu Gln
385                 390                 395                 400

Gly Leu His Glu Ile Lys Leu Leu Gly Lys Gly Thr Ser Ala Ala Asp
                405                 410                 415

Ala Val Glu Val Pro Ala Pro Ala Ala Val Leu Gly Gly Pro Glu Pro
            420                 425                 430

Leu Met Gln Ala Thr Ala Trp Leu Asn Ala Tyr Phe His Gln Pro Glu
        435                 440                 445

Ala Ile Glu Glu Phe Pro Val Pro Ala Leu His His Pro Val Phe Gln
    450                 455                 460

Gln Glu Ser Phe Thr Arg Gln Val Leu Trp Lys Leu Leu Lys Val Val
465                 470                 475                 480

Lys Phe Gly Glu Val Ile Ser Tyr Gln Gln Leu Ala Ala Leu Ala Gly
                485                 490                 495

Asn Pro Ala Ala Thr Ala Val Lys Thr Ala Leu Ser Gly Asn Pro
            500                 505                 510

Val Pro Ile Leu Ile Pro Cys His Arg Val Val Ser Ser Ser Gly Ala
        515                 520                 525

Val Gly Gly Tyr Glu Gly Gly Leu Ala Val Lys Glu Trp Leu Leu Ala
    530                 535                 540

His Glu Gly His Arg Leu Gly Lys Pro Gly Leu Gly Pro Ala Gly Ile
545                 550                 555                 560

Gly Ala Pro Gly Ser Leu Glu His His His His His His
                565                 570

<210> SEQ ID NO 77
<211> LENGTH: 1792
<212> TYPE: DNA
<213> ORGANISM: artificial
<220> FEATURE:
<223> OTHER INFORMATION: DNA sequence encoding ssBiP-sE2 from Venezuelan
      Equine Encephalitis virus -SNAPlike-Histag for expression in S2
      cells

<400> SEQUENCE: 77
atgaagttat gcatattact ggccgtcgtg gcctttgttg gcctctcgct cgggagatct      60
agatcttcta ccgaggagct gtttaaggag tataagctaa cgcgccctta catggccaga    120
tgcatcagat gtgccgttgg gagctgccat agtccaatag caattgaggc agtgaagagc    180
```

```
gacgggcacg acggctatgt tagacttcag acttcctcgc agtatggcct ggattcctct    240
ggcaacttaa agggaaggac tatgcggtat gatatgcacg ggaccattga agagatacca    300
ctacatcaag tgtcactcca cacatctcgc ccgtgtcaca ttgtggatgg catggttat    360
tttctgcttg ctaggtgccc ggcagggac tccatcacca tggaatttaa aaaggttca    420
gtcacacact cctgctcagt gccgtatgaa gtgaaattta atcctgtagg cagagaactc    480
tacactcatc caccgaaaca cggagcagag caagcgtgcc aagtctacgc gcacgatgca    540
cagaacagag gagcttatgt cgagatgcac ctcccgggct cagaagtgga cagcagtttg    600
atttccttga gcggcagttc agtcaccgtg acacctcctg tcgggactag cgccttggtg    660
aaatgcaagt gcggcggcac aaagatctcc gaaaccatca acaaggcaaa acagttcagc    720
cagtgcacaa agaaggagca gtgcagagca tatcgactgc agaatgacaa gtgggtgtat    780
aattctgaca aactgcccaa agcagcggga gccaccctaa aaggaaaact cacgtcccg    840
ttcttgctgg cagacggcaa atgcaccgtg cctctagcac cggaacctat gataaccttc    900
ggtttccgat cagtgtcact gaaactgcac cctaagaatc cacatatctc gaccactcgc    960
caacttgctg atgagcctca ttacacgcac gagctctat ctgaaccagc tgttaggaat    1020
tttaccgtca ctgaaaaggg gtgggagttt gtatggggaa accatccgcc gaaaaggttt    1080
tgggcacagg aaacagcacc cggaaatcca catgggctgc acatgaggt gataactcat    1140
tattaccaca gatacctat gtccacgcgg ccgcacggcg gaggtagcaa agactgcgaa    1200
atgaagcgca ccaccctgga tagccctctg ggcaagctgg aactgtctgg gtgcgaacag    1260
ggcctgcacg agatcaagct gctgggcaaa ggaacatctg ccgccgacgc cgtggaagtg    1320
cctgccccag ccgccgtgct gggcggacca gagccactga tgcaggccac cgcctggctc    1380
aacgcctact ttcaccagcc tgaggccatc gaggagttcc ctgtgccagc cctgcaccac    1440
ccagtgttcc agcaggagag ctttacccgc caggtgctgt ggaaactgct gaaagtggtg    1500
aagttcggag aggtcatcag ctaccagcag ctggccgccc tggccggcaa tcccgccgcc    1560
accgccgccg tgaaaaccgc cctgagcgga atcccgtgc ccattctgat cccctgccac    1620
cgggtggtgt ctagctctgg cgccgtgggg ggctacgagg gcgggctcgc cgtgaaagag    1680
tggctgctgg cccacgaggg ccacagactg ggcaagcctg gctgggtcc tgcaggtata    1740
ggcgcgccag gtccctgga gcatcatcat catcatcatt gatgacgggc cc    1792

<210> SEQ ID NO 78
<211> LENGTH: 575
<212> TYPE: PRT
<213> ORGANISM: artificial
<220> FEATURE:
<223> OTHER INFORMATION: Amino acid sequence of the fusion protein [sE2
      from Venezuelan Equine Encephalitis -SNAPlike-Histag]

<400> SEQUENCE: 78

Arg Ser Arg Ser Ser Thr Glu Glu Leu Phe Lys Glu Tyr Lys Leu Thr
1               5                   10                  15

Arg Pro Tyr Met Ala Arg Cys Ile Arg Cys Ala Val Gly Ser Cys His
                20                  25                  30

Ser Pro Ile Ala Ile Glu Ala Val Lys Ser Asp Gly His Asp Gly Tyr
            35                  40                  45

Val Arg Leu Gln Thr Ser Ser Gln Tyr Gly Leu Asp Ser Ser Gly Asn
        50                  55                  60

Leu Lys Gly Arg Thr Met Arg Tyr Asp Met His Gly Thr Ile Glu Glu
```

```
                65                  70                  75                  80
        Ile Pro Leu His Gln Val Ser Leu His Thr Ser Arg Pro Cys His Ile
                        85                  90                  95
        Val Asp Gly His Gly Tyr Phe Leu Leu Ala Arg Cys Pro Ala Gly Asp
                       100                 105                 110
        Ser Ile Thr Met Glu Phe Lys Lys Gly Ser Val Thr His Ser Cys Ser
                       115                 120                 125
        Val Pro Tyr Glu Val Lys Phe Asn Pro Val Gly Arg Glu Leu Tyr Thr
                       130                 135                 140
        His Pro Pro Glu His Gly Ala Glu Gln Ala Cys Gln Val Tyr Ala His
        145                 150                 155                 160
        Asp Ala Gln Asn Arg Gly Ala Tyr Val Glu Met His Leu Pro Gly Ser
                            165                 170                 175
        Glu Val Asp Ser Ser Leu Ile Ser Leu Ser Gly Ser Ser Val Thr Val
                        180                 185                 190
        Thr Pro Pro Val Gly Thr Ser Ala Leu Val Lys Cys Lys Cys Gly Gly
                        195                 200                 205
        Thr Lys Ile Ser Glu Thr Ile Asn Lys Ala Lys Gln Phe Ser Gln Cys
                        210                 215                 220
        Thr Lys Lys Glu Gln Cys Arg Ala Tyr Arg Leu Gln Asn Asp Lys Trp
        225                 230                 235                 240
        Val Tyr Asn Ser Asp Lys Leu Pro Lys Ala Ala Gly Ala Thr Leu Lys
                        245                 250                 255
        Gly Lys Leu His Val Pro Phe Leu Leu Ala Asp Gly Lys Cys Thr Val
                        260                 265                 270
        Pro Leu Ala Pro Glu Pro Met Ile Thr Phe Gly Phe Arg Ser Val Ser
                        275                 280                 285
        Leu Lys Leu His Pro Lys Asn Pro Thr Tyr Leu Thr Thr Arg Gln Leu
                        290                 295                 300
        Ala Asp Glu Pro His Tyr Thr His Glu Leu Ile Ser Glu Pro Ala Val
        305                 310                 315                 320
        Arg Asn Phe Thr Val Thr Glu Lys Gly Trp Glu Phe Val Trp Gly Asn
                        325                 330                 335
        His Pro Pro Lys Arg Phe Trp Ala Gln Glu Thr Ala Pro Gly Asn Pro
                        340                 345                 350
        His Gly Leu Pro His Glu Val Ile Thr His Tyr Tyr His Arg Tyr Pro
                        355                 360                 365
        Met Ser Thr Arg Pro His Gly Gly Ser Lys Asp Cys Glu Met Lys
        370                 375                 380
        Arg Thr Thr Leu Asp Ser Pro Leu Gly Lys Leu Glu Leu Ser Gly Cys
        385                 390                 395                 400
        Glu Gln Gly Leu His Glu Ile Lys Leu Leu Gly Lys Gly Thr Ser Ala
                        405                 410                 415
        Ala Asp Ala Val Glu Val Pro Ala Pro Ala Ala Val Leu Gly Gly Pro
                        420                 425                 430
        Glu Pro Leu Met Gln Ala Thr Ala Trp Leu Asn Ala Tyr Phe His Gln
                        435                 440                 445
        Pro Glu Ala Ile Glu Glu Phe Pro Val Pro Ala Leu His His Pro Val
                        450                 455                 460
        Phe Gln Gln Glu Ser Phe Thr Arg Gln Val Leu Trp Lys Leu Leu Lys
        465                 470                 475                 480
        Val Val Lys Phe Gly Glu Val Ile Ser Tyr Gln Gln Leu Ala Ala Leu
                        485                 490                 495
```

```
Ala Gly Asn Pro Ala Ala Thr Ala Ala Val Lys Thr Ala Leu Ser Gly
                500                 505                 510

Asn Pro Val Pro Ile Leu Ile Pro Cys His Arg Val Ser Ser Ser
            515                 520                 525

Gly Ala Val Gly Gly Tyr Glu Gly Leu Ala Val Lys Glu Trp Leu
        530                 535                 540

Leu Ala His Glu Gly His Arg Leu Gly Lys Pro Gly Leu Gly Pro Ala
545                 550                 555                 560

Gly Ile Gly Ala Pro Gly Ser Leu Glu His His His His His
                565                 570                 575
```

<210> SEQ ID NO 79
<211> LENGTH: 1442
<212> TYPE: DNA
<213> ORGANISM: artificial
<220> FEATURE:
<223> OTHER INFORMATION: DNA sequence encoding ssBiP- SNAPlike-Akabane N
<211> LENGTH: 458
<212> TYPE: PRT
<213> ORGANISM: artificial
<220> FEATURE:
<223> OTHER INFORMATION: Amino acid sequence of fusion protein
      [SNAPlike-Akabane N protein-Histag]

<400> SEQUENCE: 80

Arg Ser Asp Lys Asp Cys Gl

```
                370             375             380
Val Leu Arg Gln Arg Tyr Gly Gln Leu Thr Ala Glu Glu Trp Met Thr
385                 390                 395                 400

Ser Lys Leu Asp Ala Val Lys Ala Ala Phe Ser Ser Val Ala Gln Ile
                405                 410                 415

Ser Trp Ala Lys Ser Gly Phe Ser Pro Ala Ala Arg Ala Phe Leu Ala
                420                 425                 430

Gln Phe Gly Ile Gln Ile Pro Gly Glu Asn Leu Tyr Phe Gln Gly Pro
            435                 440                 445

Gly Gly Gly Ser His His His His His His
450                 455

<210> SEQ ID NO 81
<211> LENGTH: 1451
<212> TYPE: DNA
<213> ORGANISM: artificial
<220> FEATURE:
<223> OTHER INFORMATION: DNA sequence encoding ssBiP- SNAPlike-Aino N
      protein-proTEV cleavage site-Histag for expression in S2 cells

<400> SEQUENCE: 81
atgaagttat gcatattact ggccgtcgtg gtggcctttg ttggcctctc gctcgggaga       60
tctagatctg acaaagactg cgaaatgaaa agaactacat ggattcacc acttgggaag      120 ttggaactga gtggatgcga gcaaggattg catgaaatta gctactggg aaaaggaact      180 tctgctgctg atgcagttga agttccagca ccagcagctg ttcttggagg tcctgagccc      240
ctcatgcaag ccacagcctg gcttaacgca tatttccacc agcctgaggc cattgaggaa      300
tttccagtcc ccgcccttca ccatcctgtg tttcagcagg agagcttcac ccgccaggtc      360
ctgtggaaat tgctgaaggt ggtcaagttt ggtgaagtga tttcatatca gcaacttgct      420
gcattggccg gtaaccccgc agctacagct gccgtgaaaa ctgctctcag cggaaatcct      480
gtgcccatcc tgatcccttg tcacagagtc gtttcatctt ccggagctgt aggtggctat      540
gaaggaggac tggcagttaa ggagtggctg ctggctcatg aaggtcatag acttggaaag      600
cctgggctgg tcctgctgg tataggcgcg ccagggtccc taggtggcgg atccgaaaac      660
ctgtacttcc agagcgatat cgcaaaccaa tttatttcc aagatgttcc tcaacggaat      720
ctcgctacat taacccgga ggtcgggtat gtggcattta ttgctaaaca tgggtcccaa      780
ctcaatttcg ataccgttag agtcttcttc ctcaatcaga agaaggccaa gatggtgctc      840
agtaagacgg cacaaccaag tgttgatctt acatttggtg gcatcaaatt tacactggtt      900
aataaccatt tcccccaata cacagcaaat cctgtgccag acactgccct cactctccac      960
cgtctctcag gttatctagc aaaatggggtt gcagaccaat gcaaaacaaa tcagattaaa     1020
ctggctgagg ccatggaaaa aattgtcatg ccacttgctg aagtgaaagg ttgcacctgg     1080
actgaaggac tgactatgta tctgggattt gcaccaggcg ctgaaatgtt tttagaaaca     1140
tttgagttct accctttggt tattgacatg cacagagtgc tgaaagatgg aatggatgtc     1200
aactttatga gaaaggtcct tcgccagcgc tatggcacat tgactgcaga acagtggatg     1260
actcaaaaaa tagatgctgt ccgtgcagcc ttcaatgctg ttgggcagct aagttgggct     1320
aaatcaggat tctcaccagc tgccagagcc ttccttgccc aattcggcat aaacatgatc     1380
ccgggagaga atctatattt tcaagggccc ggcggaggta gtcaccatca tcaccatcac     1440
taatgaccgg t                                                          1451
```

<210> SEQ ID NO 82
<211> LENGTH: 459
<212> TYPE: PRT
<213> ORGANISM: artificial
<220> FEATURE:
<223> OTHER INFORMATION: Amino acid sequence of fusion protein [SNAPlike-Aino N protein-Histag]

<400> SEQUENCE: 82

| | | | | | | | | | | | | | | |
|---|---|---|---|---|---|---|---|---|---|---|---|---|---|---|
| Arg | Ser | Asp | Lys | Asp | Cys | Glu | Met | Lys | Arg | Thr | Thr | Leu | Asp | Ser | Pro |
| 1 | | | | 5 | | | | | 10 | | | | | 15 | |

Leu Gly Lys Leu Glu Leu Ser Gly Cys Glu Gln Gly Leu His Glu Ile
           20                  25                  30

Lys Leu Leu Gly Lys Gly Thr Ser Ala Ala Asp Ala Val Glu Val Pro
           35                  40                  45

Ala Pro Ala Ala Val Leu Gly Gly Pro Glu Pro Leu Met Gln Ala Thr
 50                      55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
                100                 105                 110

Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala Asn
        195                 200                 205

Gln Phe Ile Phe Gln Asp Val Pro Gln Arg Asn Leu Ala Thr Phe Asn
210                 215                 220

Pro Glu Val Gly Tyr Val Ala Phe Ile Ala Lys His Gly Ser Gln Leu
225                 230                 235                 240

Asn Phe Asp Thr Val Arg Val Phe Phe Leu Asn Gln Lys Lys Ala Lys
                245                 250                 255

Met Val Leu Ser Lys Thr Ala Gln Pro Ser Val Asp Leu Thr Phe Gly
            260                 265                 270

Gly Ile Lys Phe Thr Leu Val Asn Asn His Phe Pro Gln Tyr Thr Ala
        275                 280                 285

Asn Pro Val Pro Asp Thr Ala Leu Thr Leu His Arg Leu Ser Gly Tyr
290                 295                 300

Leu Ala Lys Trp Val Ala Asp Gln Cys Lys Thr Asn Gln Ile Lys Leu
305                 310                 315                 320

Ala Glu Ala Met Glu Lys Ile Val Met Pro Leu Ala Glu Val Lys Gly
                325                 330                 335

Cys Thr Trp Thr Glu Gly Leu Thr Met Tyr Leu Gly Phe Ala Pro Gly
            340                 345                 350

Ala Glu Met Phe Leu Glu Thr Phe Glu Phe Tyr Pro Leu Val Ile Asp
        355                 360                 365

```
Met His Arg Val Leu Lys Asp Gly Met Asp Val Asn Phe Met Arg Lys
    370                 375                 380

Val Leu Arg Gln Arg Tyr Gly Thr Leu Thr Ala Glu Gln Trp Met Thr
385                 390                 395                 400

Gln Lys Ile Asp Ala Val Arg Ala Ala Phe Asn Ala Val Gly Gln Leu
                405                 410                 415

Ser Trp Ala Lys Ser Gly Phe Ser Pro Ala Ala Arg Ala Phe Leu Ala
                420                 425                 430

Gln Phe Gly Ile Asn Met Ile Pro Gly Glu Asn Leu Tyr Phe Gln Gly
                435                 440                 445

Pro Gly Gly Gly Ser His His His His His His
    450                 455
```

<210> SEQ ID NO 83
<211> LENGTH: 1448
<212> TYPE: DNA
<213> ORGANISM: artificial
<220> FEATURE:
<223> OTHER INFORMATION: DNA sequence encoding ssBiP - SNAPlike-Shamonda
      N protein-proTEV cleavage site-Histag for expression in S2 cells

<400> SEQUENCE: 83

```
atgaagttat gcatattact ggccgtcgtg gtggcctttg ttggcctctc gctcgggaga      60
tctagatctg acaaagactg cgaaatgaaa agaactacat ggattcacc  acttgggaag    120
ttggaactga gtggatgcga gcaaggattg catgaaatta gctactggg  aaaaggaact    180
tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg taaccccgc  agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat ctcaagccaa ttcattttg aagatgtacc acaacggaat     720
gcagctacat taacccgga aggtgggtat gtggcattta ttggtaagta tgggcaacaa     780
ctcaatttcg gggttgctaa agtcttcttc ctcaaccaga agaaggccaa aatggtccta    840
cataagacgg acaaccaag  tgtcgatctt acttttggtg gggtcaaatt cacagtggtt   900
aataaccatt tccccaata  tgtctcaaat cctgtgccag acaatgccat tacacttcac    960
aggatgtcag ttatctagc  acgctggatt gctgatacat gcaaggctag tgtcctcaaa   1020
ctagctgaag ctagtgctca aattgtcatg ccccttgctg aggttaaggg atgtacctgg   1080
gctgatggtt atacaatgta tcttggattt gcacctgggg ccgaaatgtt ccttgatgct   1140
tttgattttt atccgctagt tatcgaaatg catagggtcc ttaaggacaa tatggatgta   1200
aattttatga aaaagtcct  ccgccaacgc tatggaacaa tgactgctga agaatggatg   1260
actcagaaaa taccagaaat aaaggctgct ttcaattctg ttgacaact  tgcctgggct   1320
aaatctggat tctctcctgc tgctagaact ttcttgcagc aatttggtat caacatcccg   1380
ggagagaatc tatatttca  agggcccggc ggaggtagtc accatcatca ccatcactaa   1440
tgaccggt                                                            1448
```

<210> SEQ ID NO 84
<211> LENGTH: 458
<212> TYPE: PRT
<213> ORGANISM: artificial
<220> FEATURE:
<223> OTHER INFORMATION: Amino acid sequence of fusion protein [SNAPlike-Shamonda N protein-Histag]

<400> SEQUENCE: 84

```
Arg Ser Asp Lys Asp Cys Glu Met Lys Arg Thr Thr Leu Asp Ser Pro
1               5                   10                  15

Leu Gly Lys Leu Glu Leu Ser

```
Met His Arg Val Leu Lys Asp Asn Met Asp Val Asn Phe Met Lys Lys
        370                 375                 380

Val Leu Arg Gln Arg Tyr Gly Thr Met Thr Ala Glu Glu Trp Met Thr
385                 390                 395                 400

Gln Lys Ile Pro Glu Ile Lys Ala Ala Phe Asn Ser Val Gly Gln Leu
                405                 410                 415

Ala Trp Ala Lys Ser Gly Phe Ser Pro Ala Ala Arg Thr Phe Leu Gln
                420                 425                 430

Gln Phe Gly Ile Asn Ile Pro Gly Glu Asn Leu Tyr Phe Gln Gly Pro
        435                 440                 445

Gly Gly Gly Ser His His His His His His
        450                 455

<210> SEQ ID NO 85
<211> LENGTH: 1991
<212> TYPE: DNA
<213> ORGANISM: artificial
<220> FEATURE:
<223> OTHER INFORMATION: DNA sequence encoding ssBiP -SNAPlike-proTEV
      cleavage site-N protein from human betacoronavirus strain
      2cEMC/2012- Histag for expression in S2 cells

<400> SEQUENCE: 85
atgaagttat gcatattact ggccgtcgtg gtggcctttg ttggcctctc gctcgggaga      60
tctagatctg acaaagactg cgaaatgaaa agaactacat tggattcacc acttgggaag    120
ttggaactga gtggatgcga gcaaggattg catgaaatta agctactggg aaaaggaact    180
tctgctgctg atgcagttga agttccagca ccagcagctg ttcttggagg tcctgagccc    240
ctcatgcaag ccacagcctg cttaacgca tatttccacc agcctgaggc cattgaggaa     300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cgcatcccct gctgcacctc gtgctgtttc ctttgccgat    720
aacaatgata taacaaatac aaacctatct cgaggtagag acgtaatccc aaaaccacga    780
gctgcaccaa ataacactgt ctcttggtac actgggctta cccaacacgg aaagtccct    840 cttacctttc cacctgggca gggtgtacct cttaatgcca attctacccc tgcgcaaaat    900
gctgggtatt ggcggagaca ggacagaaaa attaataccg ggaatggaat taagcaactg    960
gctcccaggt ggtacttcta ctacactgga actggacccg aagcagcact cccattccgg   1020
gctgttaagg atggcatcgt ttgggtccat gaagatggcg ccactgatgc tccttcaact   1080
tttgggacgc ggaaccctaa caatgattca gctattgtta cacaattcgc gcccggtact   1140
aaacttccta aaacttccca cattgagggg actggaggca atagtcaatc atcttcaaga   1200
gcctctagct taagcagaaa ctcttccagg tctagttcac aaggttcaag atcaggaaac   1260
tctacccgcg gcacttctcc aggtccatct ggaatcggag cagtaggagg tgatctactt   1320
taccttgatc tttctgaacag actacaagcc cttgagtctg caaagtaaa gcaatcgcag   1380 ccaaaagtaa tcactaagaa agatgctgct gctgctaaaa ataagatgcg ccacaagcgc   1440
```

-continued

```
acttccacca aaagtttcaa catggtgcag gcttttggtc ttcgcggacc aggagacctc    1500
cagggaaact ttggtgatct tcaattgaat aaactcggca ctgaggaccc acgttggccc    1560
caaattgctg agcttgctcc tacagccagt gcttttatgg gtatgtcgca atttaaactt    1620
acccatcaga acaatgatga tcatggcaac cctgtgtact tccttcggta cagtggagcc    1680
attaaacttg acccaaagaa tcccaactac aataagtggt tggagcttct tgagcaaaat    1740
attgatgcct acaaaacctt ccctaagaag gaaagaaac aaaaggcacc aaaagaagaa    1800
tcaacagacc aaatgtctga acctccaaag gagcagcgtg tgcaaggtag catcactcag    1860
cgcactcgca cccgtccaag tgttcagcct ggtccaatga ttgatgttaa cactgatggc    1920
ccgggagaga atctatattt tcaagggccc ggcggaggta gtcaccatca tcaccatcac    1980
taatgaccgg t                                                          1991
```

<210> SEQ ID NO 86
<211> LENGTH: 639
<212> TYPE: PRT
<213> ORGANISM: artificial
<220> FEATURE:
<223> OTHER INFORMATION: Amino acid sequence of fusion protein
      [SNAPlike-proTEV-COV N protein-Histag]

<400> SEQUENCE: 86

```
Arg Ser Asp Lys Asp Cys Glu Met Lys Arg Thr Thr Leu Asp Ser Pro
1               5

Lys Val Pro Leu Thr Phe Pro Pro Gln Gly Val Pro Leu Asn Ala
        260                 265                 270

Asn Ser Thr Pro Ala Gln Asn Ala Gly Tyr Trp Arg Arg Gln Asp Arg
        275                 280                 285

Lys Ile Asn Thr Gly Asn Gly Ile Lys Gln Leu Ala Pro Arg Trp Tyr
        290                 295                 300

Phe Tyr Tyr Thr Gly Thr Gly Pro Glu Ala Ala Leu Pro Phe Arg Ala
305                 310                 315                 320

Val Lys Asp Gly Ile Val Trp Val His Glu Asp Gly Ala Thr Asp Ala
                325                 330                 335

Pro Ser Thr Phe Gly Thr Arg Asn Pro Asn Asn Asp Ser Ala Ile Val
                340                 345                 350

Thr Gln Phe Ala Pro Gly Thr Lys Leu Pro Lys Asn Phe His Ile Glu
        355                 360                 365

Gly Thr Gly Gly Asn Ser Gln Ser Ser Ser Arg Ala Ser Ser Leu Ser
        370                 375                 380

Arg Asn Ser Ser Arg Ser Ser Gln Gly Ser Arg Ser Gly Asn Ser
385                 390                 395                 400

Thr Arg Gly Thr Ser Pro Gly Pro Ser Gly Ile Gly Ala Val Gly Gly
                405                 410                 415

Asp Leu Leu Tyr Leu Asp Leu Leu Asn Arg Leu Gln Ala Leu Glu Ser
                420                 425                 430

Gly Lys Val Lys Gln Ser Gln Pro Lys Val Ile Thr Lys Lys Asp Ala
        435                 440                 445

Ala Ala Ala Lys Asn Lys Met Arg His Lys Arg Thr Ser Thr Lys Ser
450                 455                 460

Phe Asn Met Val Gln Ala Phe Gly Leu Arg Gly Pro Gly Asp Leu Gln
465                 470                 475                 480

Gly Asn Phe Gly Asp Leu Gln Leu Asn Lys Leu Gly Thr Glu Asp Pro
                485                 490                 495

Arg Trp Pro Gln Ile Ala Glu Leu Ala Pro Thr Ala Ser Ala Phe Met
        500                 505                 510

Gly Met Ser Gln Phe Lys Leu Thr His Gln Asn Asn Asp Asp His Gly
        515                 520                 525

Asn Pro Val Tyr Phe Leu Arg Tyr Ser Gly Ala Ile Lys Leu Asp Pro
        530                 535                 540

Lys Asn Pro Asn Tyr Asn Lys Trp Leu Glu Leu Leu Glu Gln Asn Ile
545                 550                 555                 560

Asp Ala Tyr Lys Thr Phe Pro Lys Lys Glu Lys Gln Lys Ala Pro
                565                 570                 575

Lys Glu Glu Ser Thr Asp Gln Met Ser Glu Pro Pro Lys Glu Gln Arg
                580                 585                 590

Val Gln Gly Ser Ile Thr Gln Arg Thr Arg Thr Arg Pro Ser Val Gln
        595                 600                 605

Pro Gly Pro Met Ile Asp Val Asn Thr Asp Gly Pro Gly Glu Asn Leu
        610                 615                 620

Tyr Phe Gln Gly Pro Gly Gly Ser His His His His His
625                 630                 635

<210> SEQ ID NO 87
<211> LENGTH: 4465
<212> TYPE: DNA
<213> ORGANISM: artificial
<220> FEATURE:
<223> OTHER INFORMATION: DNA sequence encoding ssBiP- S protein from human betacoronavirus strain 2cEMC/2012- SNAPlike - Histag for
expression in S2 cells

<400> SEQUENCE: 87

| | | | | | |
|---|---|---|---|---|---|
| atgaagttat | gcatattact | ggccgtcgtg | gtggcctttg | ttggcctctc | gctcgggaga | 60 |
| tctagatctg | tagggccaga | ttctgttaag | tctgcttgta | ttgaggttga | tatacaacag | 120 |
| actttctttg | ataaaacttg | gcctaggcca | attgatgttt | ctaaggctga | cggtattata | 180 |
| taccctcaag | gccgtacata | ttctaacata | actatcactt | atcaaggtct | ttttccctat | 240 |
| cagggagacc | atggtgatat | gtatgtttac | tctgcaggac | atgctacagg | cacaactcca | 300 |
| caaaagttgt | tgtagctaa | ctattctcag | gacgtcaaac | agtttgctaa | tgggtttgtc | 360 |
| gtccgtatag | gagcagctgc | caattccact | ggcactgtta | ttattagccc | atctaccagc | 420 |
| gctactatac | gaaaaattta | ccctgctttt | atgctgggtt | cttcagttgg | taatttctca | 480 |
| gatggtaaaa | tgggccgctt | cttcaatcat | actctagttc | ttttgcccga | tggatgtggc | 540 |
| acttactta | gagcttttta | ttgtattcta | gagcctcgct | ctggaaatca | ttgtcctgct | 600 |
| ggcaattcct | atacttcttt | tgccacttat | cacactcctg | caacagattg | ttctgatggc | 660 |
| aattacaatc | gtaatgccag | tctgaactct | tttaaggagt | attttaattt | acgtaactgc | 720 |
| acctttatgt | acacttataa | cattaccgaa | gatgagattt | tagagtggtt | tggcattaca | 780 |
| caaactgctc | aaggtgttca | cctcttctca | tctcggtatg | ttgatttgta | cggcggcaat | 840 |
| atgtttcaat | ttgccacctt | gcctgtttat | gatactatta | agtattattc | tatcattcct | 900 |
| cacagtattc | gttctatcca | aagtgataga | aaggcttggg | ctgccttcta | cgtatataaa | 960 |
| cttcaaccgt | taactttcct | gttggatttt | tctgttgatg | gttatatacg | cagagctata | 1020 |
| gactgtggtt | ttaatgattt | gtcacaactc | cactgctcat | atgaatcctt | cgatgttgaa | 1080 |
| tctggagttt | attcagtttc | gtcttttcgaa | gcaaaacctt | ctggctcagt | tgtggaacag | 1140 |
| gctgaaggtg | ttgaatgtga | ttttttcacct | cttctgtctg | gcacacctcc | tcaggtttat | 1200 |
| aatttcaagc | gtttggtttt | taccaattgc | aattataatc | ttaccaaatt | gctttcactt | 1260 |
| ttttctgtga | atgattttac | ttgtagtcaa | atatctccag | cagcaattgc | aagcaactgt | 1320 |
| tattcttcac | tgattttgga | ttacttttca | tacccactta | gtatgaaatc | cgatctcagt | 1380 |
| gttagttctg | ctggtccaat | atcccagttt | aattataaac | agtccttttc | taatcccaca | 1440 |
| tgtttgattt | tagcgactgt | tcctcataac | cttactacta | ttactaagcc | tcttaagtac | 1500 |
| agctatatta | acaagtgctc | tcgtcttctt | tctgatgatc | gtactgaagt | acctcagtta | 1560 |
| gtgaacgcta | atcaatactc | accctgtgta | tccattgtcc | catccactgt | gtgggaagac | 1620 |
| ggtgattatt | ataggaaaca | actatctcca | cttgaaggtg | gtggctggct | tgttgctagt | 1680 |
| ggctcaactg | ttgccatgac | tgagcaatta | cagatgggct | ttggtattac | agttcaatat | 1740 |
| ggtacagaca | ccaatagtgt | ttgccccaag | ctggaatttg | ctaatgacac | aaaaattgcc | 1800 |
| tctcaattag | gcaattgcgt | ggaatattcc | ctctatggtg | tttcgggccg | tggtgttttt | 1860 |
| cagaattgca | cagctgtagg | tgttcgacag | cagcgctttg | tttatgatgc | gtaccagaat | 1920 |
| ttagttggct | attattctga | tgatggcaac | tactactgtt | tgcgtgcttg | tgttagtgtt | 1980 |
| cctgtttctg | tcatctatga | taaagaaact | aaaacccacg | ctactctatt | tggtagtgtt | 2040 |
| gcatgtgaac | acatttcttc | taccatgtct | caatactccc | gttctacgcg | atcaatgctt | 2100 |
| aaacggcgag | attctacata | tggccccctt | cagacacctg | ttggttgtgt | cctaggactt | 2160 |
| gttaattcct | ctttgttcgt | agaggactgc | aagttgcctc | ttggtcaatc | tctctgtgct | 2220 |

-continued

```
cttcctgaca cacctagtac tctcacacct cgcagtgtgc gctctgttcc aggtgaaatg   2280
cgcttggcat ccattgcttt taatcatcct attcaggttg atcaacttaa tagtagttat   2340
tttaaattaa gtatacccac taatttttcc tttggtgtga ctcaggagta cattcagaca   2400
accattcaga aagttactgt tgattgtaaa cagtacgttt gcaatggttt ccagaagtgt   2460
gagcaattac tgcgcgagta tggccagttt tgttccaaaa taaaccaggc tctccatggt   2520
gccaatttac gccaggatga ttctgtacgt aatttgtttg cgagcgtgaa aagctctcaa   2580
tcatctccta tcataccagg ttttggaggt gactttaatt tgacacttct agaacctgtt   2640
tctatatcta ctggcagtcg tagtgcacgt agtgctattg aggatttgct atttgacaaa   2700
gtcactatag ctgatcctgg ttatatgcaa ggttacgatg attgcatgca gcaaggtcca   2760
gcatcagctc gtgatcttat ttgtgctcaa tatgtggctg gttacaaagt attacctcct   2820
cttatggatg ttaatatgga agccgcgtat acttcatctt tgcttggcag catagcaggt   2880
gttggctgga ctgctggctt atcctccttt gctgctattc catttgcaca gagtatcttt   2940
tataggttaa acggtgttgg cattactcaa caggttcttt cagagaacca aaagctcatt   3000
gccaataagt ttaatcaggc tctgggagct atgcaaacag gcttcactac aactaatgaa   3060
gcctttcaga aggttcagga tgctgtgaac aacaatgcac aggctctatc caaattagcg   3120
agcgagctat ctaatacttt tggtgctatt tccgcctcta ttggagacat catacaacgt   3180
cttgatgttc tcgaacagga cgcccaaata gacagactta ttaatggccg tttgacaaca   3240
ctaaatgctt ttgttgcaca gcagcttgtt cgttccgaat cagctgctct ttccgctcaa   3300
ttggctaaag ataaagtcaa tgagtgtgtc aaggcacaat ccaagcgttc tggattttgc   3360
ggtcaaggca cacatatagt gtcctttgtt gtaaatgccc ctaatggcct ttacttcatg   3420
catgttggtt attaccctag caaccacatt gaggttgttt ctgcttatgg tctttgcgat   3480
gcagctaacc ctactaattg tatagcccct gttaatggct actttattaa aactaataac   3540
actaggattg ttgatgagtg gtcatatact ggctcgtcct tctatgcacc tgagcccatt   3600
acctccctta atactaagta tgttgcacca caggtgacat accaaaacat ttctactaac   3660
ctccctcctc ctcttctcgg caattccacc gggattgact tccaagatga gttggatgag   3720
tttttcaaaa atgttagcac cagtatacct aattttggtt ccctaacaca gattaatact   3780
acattactcg atcttaccta cgagatgttg tctcttcaac aagttgttaa agcccttaag   3840
cggccgcacg gcggaggtag caaagactgc gaaatgaagc gcaccaccct ggatagccct   3900
ctgggcaagc tggaactgtc tgggtgcgaa cagggcctgc acgagatcaa gctgctgggc   3960
aaaggaacat ctgccgccga cgccgtggaa gtgcctgccc cagccgccgt gctgggcgga   4020
ccagagccac tgatgcaggc caccgcctgg ctcaacgcct actttcacca gcctgaggcc   4080
atcgaggagt tccctgtgcc agccctgcac cacccagtgt tccagcagga gagctttacc   4140
cgccaggtgc tgtggaaact gctgaaagtg gtgaagttcg gagaggtcat cagctaccag   4200
cagctggccg ccctggccgg caatcccgcc gccaccgccg ccgtgaaaac cgccctgagc   4260
ggaaatcccg tgcccattct gatcccctgc caccgggtgg tgtctagctc tggcgccgtg   4320
gggggctacg agggcgggct cgccgtgaaa gagtggctgc tggcccacga gggccacaga   4380
ctgggcaagc ctgggctggg tcctgcaggt ataggcgcgc cagggtccct ggagcatcat   4440
catcatcatc attgatgacg ggccc                                         4465
```

<210> SEQ ID NO 88
<211> LENGTH: 1463

-continued

<212> TYPE: PRT
<213> ORGANISM: artificial
<220> FEATURE:
<223> OTHER INFORMATION: Amino acid sequence of fusion protein [huCOV.S protein -SNAPlike-Histag]

<400> SEQUENCE: 88

```
Arg Ser Val Gly Pro Asp Ser Val Lys Ser Ala Cys Ile Glu Val Asp
1               5                   10                  15

Ile Gln Gln Thr Phe Phe Asp Lys Thr Trp Pro Arg Pro Ile Asp Val
            20                  25                  30

Ser Lys Ala Asp Gly Ile Ile Tyr Pro Gln Gly Arg Thr Tyr Ser Asn
        35                  40                  45

Ile Thr Ile Thr Tyr Gln Gly Leu Phe Pro Tyr Gln Gly Asp His Gly
    50                  55                  60

Asp Met Tyr Val Tyr Ser Ala Gly His Ala Thr Gly Thr Thr Pro Gln
65                  70                  75                  80

Lys Leu Phe Val Ala Asn Tyr Ser Gln Asp Val Lys Gln Phe Ala Asn
                85                  90                  95

Gly Phe Val Val Arg Ile Gly Ala Ala Ala Asn Ser Thr Gly Thr Val
            100                 105                 110

Ile Ile Ser Pro Ser Thr Ser Ala Thr Ile Arg Lys Ile Tyr Pro Ala
        115                 120                 125

Phe Met Leu Gly Ser Ser Val Gly Asn Phe Ser Asp Gly Lys Met Gly
    130                 135                 140

Arg Phe Phe Asn His Thr Leu Val Leu Leu Pro Asp Gly Cys Gly Thr
145                 150                 155                 160

Leu Leu Arg Ala Phe Tyr Cys Ile Leu Glu Pro Arg Ser Gly Asn His
                165                 170                 175

Cys Pro Ala Gly Asn Ser Tyr Thr Ser Phe Ala Thr Tyr His Thr Pro
            180                 185                 190

Ala Thr Asp Cys Ser Asp Gly Asn Tyr Asn Arg Asn Ala Ser Leu Asn
        195                 200                 205

Ser Phe Lys Glu Tyr Phe Asn Leu Arg Asn Cys Thr Phe Met Tyr Thr
    210                 215                 220

Tyr Asn Ile Thr Glu Asp Glu Ile Leu Glu Trp Phe Gly Ile Thr Gln
225                 230                 235                 240

Thr Ala Gln Gly Val His Leu Phe Ser Ser Arg Tyr Val Asp Leu Tyr
                245                 250                 255

Gly Gly Asn Met Phe Gln Phe Ala Thr Leu Pro Val Tyr Asp Thr Ile
            260                 265                 270

Lys Tyr Tyr Ser Ile Ile Pro His Ser Ile Arg Ser Ile Gln Ser Asp
        275                 280                 285

Arg Lys Ala Trp Ala Ala Phe Tyr Val Tyr Lys Leu Gln Pro Leu Thr
    290                 295                 300

Phe Leu Leu Asp Phe Ser Val Asp Gly Tyr Ile Arg Arg Ala Ile Asp
305                 310                 315                 320

Cys Gly Phe Asn Asp Leu Ser Gln Leu His Cys Ser Tyr Glu Ser Phe
                325                 330                 335

Asp Val Glu Ser Gly Val Tyr Ser Val Ser Ser Phe Glu Ala Lys Pro
            340                 345                 350

Ser Gly Ser Val Val Glu Gln Ala Glu Gly Val Glu Cys Asp Phe Ser
        355                 360                 365

Pro Leu Leu Ser Gly Thr Pro Pro Gln Val Tyr Asn Phe Lys Arg Leu
    370                 375                 380
```

```
Val Phe Thr Asn Cys Asn Tyr Asn Leu Thr Lys Leu Leu Ser Leu Phe
385                 390                 395                 400

Ser Val Asn Asp Phe Thr Cys Ser Gln Ile Ser Pro Ala Ala Ile Ala
            405                 410                 415

Ser Asn Cys Tyr Ser Ser Leu Ile Leu Asp Tyr Phe Ser Tyr Pro Leu
            420                 425                 430

Ser Met Lys Ser Asp Leu Ser Val Ser Ser Ala Gly Pro Ile Ser Gln
            435                 440                 445

Phe Asn Tyr Lys Gln Ser Phe Ser Asn Pro Thr Cys Leu Ile Leu Ala
            450                 455                 460

Thr Val Pro His Asn Leu Thr Thr Ile Thr Lys Pro Leu Lys Tyr Ser
465                 470                 475                 480

Tyr Ile Asn Lys Cys Ser Arg Leu Leu Ser Asp Asp Arg Thr Glu Val
            485                 490                 495

Pro Gln Leu Val Asn Ala Asn Gln Tyr Ser Pro Cys Val Ser Ile Val
            500                 505                 510

Pro Ser Thr Val Trp Glu Asp Gly Asp Tyr Tyr Arg Lys Gln Leu Ser
            515                 520                 525

Pro Leu Glu Gly Gly Gly Trp Leu Val Ala Ser Gly Ser Thr Val Ala
            530                 535                 540

Met Thr Glu Gln Leu Gln Met Gly Phe Gly Ile Thr Val Gln Tyr Gly
545                 550                 555                 560

Thr Asp Thr Asn Ser Val Cys Pro Lys Leu Glu Phe Ala Asn Asp Thr
            565                 570                 575

Lys Ile Ala Ser Gln Leu Gly Asn Cys Val Glu Tyr Ser Leu Tyr Gly
            580                 585                 590

Val Ser Gly Arg Gly Val Phe Gln Asn Cys Thr Ala Val Gly Val Arg
            595                 600                 605

Gln Gln Arg Phe Val Tyr Asp Ala Tyr Gln Asn Leu Val Gly Tyr Tyr
            610                 615                 620

Ser Asp Asp Gly Asn Tyr Tyr Cys Leu Arg Ala Cys Val Ser Val Pro
625                 630                 635                 640

Val Ser Val Ile Tyr Asp Lys Glu Thr Lys Thr His Ala Thr Leu Phe
            645                 650                 655

Gly Ser Val Ala Cys Glu His Ile Ser Ser Thr Met Ser Gln Tyr Ser
            660                 665                 670

Arg Ser Thr Arg Ser Met Leu Lys Arg Arg Asp Ser Thr Tyr Gly Pro
            675                 680                 685

Leu Gln Thr Pro Val Gly Cys Val Leu Gly Leu Val Asn Ser Ser Leu
            690                 695                 700

Phe Val Glu Asp Cys Lys Leu Pro Leu Gly Gln Ser Leu Cys Ala Leu
705                 710                 715                 720

Pro Asp Thr Pro Ser Thr Leu Thr Pro Arg Ser Val Arg Ser Val Pro
            725                 730                 735

Gly Glu Met Arg Leu Ala Ser Ile Ala Phe Asn His Pro Ile Gln Val
            740                 745                 750

Asp Gln Leu Asn Ser Ser Tyr Phe Lys Leu Ser Ile Pro Thr Asn Phe
            755                 760                 765

Ser Phe Gly Val Thr Gln Glu Tyr Ile Gln Thr Thr Ile Gln Lys Val
            770                 775                 780

Thr Val Asp Cys Lys Gln Tyr Val Cys Asn Gly Phe Gln Lys Cys Glu
785                 790                 795                 800
```

```
Gln Leu Leu Arg Glu Tyr Gly Gln Phe Cys Ser Lys Ile Asn Gln Ala
            805                 810                 815
Leu His Gly Ala Asn Leu Arg Asp Asp Ser Val Arg Asn Leu Phe
        820                 825                 830
Ala Ser Val Lys Ser Ser Gln Ser Ser Pro Ile Ile Pro Gly Phe Gly
            835                 840                 845
Gly Asp Phe Asn Leu Thr Leu Leu Glu Pro Val Ser Ile Ser Thr Gly
    850                 855                 860
Ser Arg Ser Ala Arg Ser Ala Ile Glu Asp Leu Leu Phe Asp Lys Val
865                 870                 875                 880
Thr Ile Ala Asp Pro Gly Tyr Met Gln Gly Tyr Asp Asp Cys Met Gln
                885                 890                 895
Gln Gly Pro Ala Ser Ala Arg Asp Leu Ile Cys Ala Gln Tyr Val Ala
            900                 905                 910
Gly Tyr Lys Val Leu Pro Pro Leu Met Asp Val Asn Met Glu Ala Ala
            915                 920                 925
Tyr Thr Ser Ser Leu Leu Gly Ser Ile Ala Gly Val Gly Trp Thr Ala
    930                 935                 940
Gly Leu Ser Ser Phe Ala Ala Ile Pro Phe Ala Gln Ser Ile Phe Tyr
945                 950                 955                 960
Arg Leu Asn Gly Val Gly Ile Thr Gln Gln Val Leu Ser Glu Asn Gln
                965                 970                 975
Lys Leu Ile Ala Asn Lys Phe Asn Gln Ala Leu Gly Ala Met Gln Thr
            980                 985                 990
Gly Phe Thr Thr Thr Asn Glu Ala Phe Gln Lys Val Gln Asp Ala Val
        995                 1000                1005
Asn Asn Asn Ala Gln Ala Leu Ser Lys Leu Ala Ser Glu Leu Ser
    1010                1015                1020
Asn Thr Phe Gly Ala Ile Ser Ala Ser Ile Gly Asp Ile Ile Gln
    1025                1030                1035
Arg Leu Asp Val Leu Glu Gln Asp Ala Gln Ile Asp Arg Leu Ile
    1040                1045                1050
Asn Gly Arg Leu Thr Thr Leu Asn Ala Phe Val Ala Gln Gln Leu
    1055                1060                1065
Val Arg Ser Glu Ser Ala Ala Leu Ser Ala Gln Leu Ala Lys Asp
    1070                1075                1080
Lys Val Asn Glu Cys Val Lys Ala Gln Ser Lys Arg Ser Gly Phe
    1085                1090                1095
Cys Gly Gln Gly Thr His Ile Val Ser Phe Val Val Asn Ala Pro
    1100                1105                1110
Asn Gly Leu Tyr Phe Met His Val Gly Tyr Tyr Pro Ser Asn His
    1115                1120                1125
Ile Glu Val Val Ser Ala Tyr Gly Leu Cys Asp Ala Ala Asn Pro
    1130                1135                1140
Thr Asn Cys Ile Ala Pro Val Asn Gly Tyr Phe Ile Lys Thr Asn
    1145                1150                1155
Asn Thr Arg Ile Val Asp Glu Trp Ser Tyr Thr Gly Ser Ser Phe
    1160                1165                1170
Tyr Ala Pro Glu Pro Ile Thr Ser Leu Asn Thr Lys Tyr Val Ala
    1175                1180                1185
Pro Gln Val Thr Tyr Gln Asn Ile Ser Thr Asn Leu Pro Pro Pro
    1190                1195                1200
Leu Leu Gly Asn Ser Thr Gly Ile Asp Phe Gln Asp Glu Leu Asp
```

-continued

|       |       |       |       |       |       |       |       |       |       |       |       |
|-------|-------|-------|-------|-------|-------|-------|-------|-------|-------|-------|-------|
|       |       | 1205  |       |       |       | 1210  |       |       |       | 1215  |       |
| Glu   | Phe   | Phe   | Lys   | Asn   | Val   | Ser   | Thr   | Ser   | Ile   | Pro   | Asn   | Phe   | Gly   | Ser   |
|       |       | 1220  |       |       |       | 1225  |       |       |       | 1230  |       |

Glu Phe Phe Lys Asn Val Ser Thr Ser Ile Pro Asn Phe Gly Ser
                1220                1225                1230

Leu Thr Gln Ile Asn Thr Thr Leu Leu Asp Leu Thr Tyr Glu Met
        1235                1240                1245

Leu Ser Leu Gln Gln Val Val Lys Ala Leu Lys Arg Pro His Gly
        1250                1255                1260

Gly Gly Ser Lys Asp Cys Glu Met Lys Arg Thr Thr Leu Asp Ser
    1265                1270                1275

Pro Leu Gly Lys Leu Glu Leu Ser Gly Cys Glu Gln Gly Leu His
    1280                1285                1290

Glu Ile Lys Leu Leu Gly Lys Gly Thr Ser Ala Ala Asp Ala Val
    1295                1300                1305

Glu Val Pro Ala Pro Ala Ala Val Leu Gly Gly Pro Glu Pro Leu
    1310                1315                1320

Met Gln Ala Thr Ala Trp Leu Asn Ala Tyr Phe His Gln Pro Glu
    1325                1330                1335

Ala Ile Glu Glu Phe Pro Val Pro Ala Leu His His Pro Val Phe
    1340                1345                1350

Gln Gln Glu Ser Phe Thr Arg Gln Val Leu Trp Lys Leu Leu Lys
    1355                1360                1365

Val Val Lys Phe Gly Glu Val Ile Ser Tyr Gln Gln Leu Ala Ala
    1370                1375                1380

Leu Ala Gly Asn Pro Ala Ala Thr Ala Ala Val Lys Thr Ala Leu
    1385                1390                1395

Ser Gly Asn Pro Val Pro Ile Leu Ile Pro Cys His Arg Val Val
    1400                1405                1410

Ser Ser Ser Gly Ala Val Gly Gly Tyr Glu Gly Gly Leu Ala Val
    1415                1420                1425

Lys Glu Trp Leu Leu Ala His Glu Gly His Arg Leu Gly Lys Pro
    1430                1435                1440

Gly Leu Gly Pro Ala Gly Ile Gly Ala Pro Gly Ser Leu Glu His
    1445                1450                1455

His His His His His
    1460

<210> SEQ ID NO 89
<211> LENGTH: 1325
<212> TYPE: DNA
<213> ORGANISM: artificial
<220> FEATURE:
<223> OTHER INFORMATION: DNA sequence encoding ssBiP - SNAPlike -proTEV-
      C protein from hepatitis C virus strain TCHM-R2/03 of genotype
      1b - -proTEV - Histag for expression in S2 cells

<400> SEQUENCE: 89
atgaagttat gcatattact ggccgtcgtg gtggcctttg ttggcctctc gctcgggaga      60
tctagatctg acaaagactg cgaaatgaaa agaactacat ggattcacc acttgggaag     120 ttggaactga gtggatgcga gcaaggattg catgaaatta gctactggg aaaaggaact     180 tctgctgctg atgcagttga agttccagca ccagcagctg ttcttggagg tcctgagccc     240
ctcatgcaag ccacagcctg cttaacgca tatttccacc agcctgaggc cattgaggaa     300
tttccagtcc cgcccttca ccatcctgtg tttcagcagg agagcttcac ccgccaggtc     360
ctgtggaaat tgctgaaggt ggtcaagttt ggtgaagtga tttcatatca gcaacttgct     420

```
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cagtacaaat cctaaacctc aaagaaaaac taaacgaaat    720
actaatcgtc gtccacaaga tgttaagttt ccgggaggag acaaattgt tggtggagtt     780 tacctattgc cgcgaagagg tcctcgttta ggtgttcgag caactagaaa aacttctgaa    840
cgatcacaac tcgtggaag acgacaacct attcctaagg ctcgtcagcc tgaaggtaga     900
gcttgggctc agcctggtta tccttggcct ctatatggta atgaaggaat gggttgggca    960
ggatggctac tatcacctcg tggttctcga cctagttggg gtgcaaatga ccctcgacga   1020
agatcacgta atttaggtaa ggtaattgat acacttacat gtggttttgc tgatcttatg   1080
ggatatattc cactagtagg tgctccacta ggtggagctg caagagttct tgcacatggt   1140
gtacgagttc ttgaagatgg agtgaactat gcaacaggta atcttcctgg atgttcattt   1200 tctattttc tattagcttt gctatcatgt ctgactattc agcttcagc tggcccggga    1260 gagaatctat attttcaagg gcccggcgga ggtagtcacc atcatcacca tcactaatga   1320
ccggt                                                                1325
```

<210> SEQ ID NO 90
<211> LENGTH: 417
<212> TYPE: PRT
<213> ORGANISM: artificial
<220> FEATURE:
<223> OTHER INFORMATION: Amino acid sequence of fusion protein
      [SNAPlike-proTEV-C protein of HCV-proTEV-Histag]

<400> SEQUENCE: 90

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190
```

```
Leu Gly Gly Gly Ser Glu Asn Leu Tyr Phe Gln Ser Asp Ile Ser Thr
            195                 200                 205

Asn Pro Lys Pro Gln Arg Lys Thr Lys Arg Asn Thr Asn Arg Arg Pro
210                 215                 220

Gln Asp Val Lys Phe Pro Gly Gly Gln Ile Val Gly Gly Val Tyr
225                 230                 235                 240

Leu Leu Pro Arg Arg Gly Pro Arg Leu Gly Val Arg Ala Thr Arg Lys
                245                 250                 255

Thr Ser Glu Arg Ser Gln Pro Arg Gly Arg Arg Gln Pro Ile Pro Lys
            260                 265                 270

Ala Arg Gln Pro Glu Gly Arg Ala Trp Ala Gln Pro Gly Tyr Pro Trp
        275                 280                 285

Pro Leu Tyr Gly Asn Glu Gly Met Gly Trp Ala Gly Trp Leu Leu Ser
290                 295                 300

Pro Arg Gly Ser Arg Pro Ser Trp Gly Ala Asn Asp Pro Arg Arg Arg
305                 310                 315                 320

Ser Arg Asn Leu Gly Lys Val Ile Asp Thr Leu Thr Cys Gly Phe Ala
                325                 330                 335

Asp Leu Met Gly Tyr Ile Pro Leu Val Gly Ala Pro Leu Gly Gly Ala
            340                 345                 350

Ala Arg Val Leu Ala His Gly Val Arg Val Leu Glu Asp Gly Val Asn
        355                 360                 365

Tyr Ala Thr Gly Asn Leu Pro Gly Cys Ser Phe Ser Ile Phe Leu Leu
370                 375                 380

Ala Leu Leu Ser Cys Leu Thr Ile Pro Ala Ser Ala Gly Pro Gly Glu
385                 390                 395                 400

Asn Leu Tyr Phe Gln Gly Pro Gly Gly Gly Ser His His His His
                405                 410                 415

His

<210> SEQ ID NO 91
<211> LENGTH: 1376
<212> TYPE: DNA
<213> ORGANISM: artificial
<220> FEATURE:
<223> OTHER INFORMATION: DNA sequence encoding ssBiP- SNAPlike -
      MSP1(19) antigen from Plasmodium falciparum - proTEV - AMA-1(III)
      antigen from Plasmodium falciparum - Histag for expression in S2
      cells

<400> SEQUENCE: 91
atgaagttat gcatattact ggccgtcgtg gtggcctttg ttggcctctc gctcgggaga      60
tctagatctg acaaagactg cgaaatgaaa agaactacat ggattcacc acttgggaag     120 ttggaactga gtggatgcga gcaaggattg catgaaatta agctactggg aaaaggaact    180
tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
```

```
ctgtacttcc agagcgatat caaacaatgt ccacaaaatt ctggatgttt cagacattta    720
gatgaaagag aagaatgtaa atgtttatta aattacaaac aagaaggtga taaatgtgtt    780
gaaaatccaa atcttacttg taacgaaaat aatggtggat gtgatgcaga tgccaaatgt    840
accgaagaag attcaggcag caacggaaag aaaatcacat gtgaatgtac taaacctgat    900
tcttatccac ttttcgatgg tattttcgga ggtggctctg agaatctata ttttcaaggg    960
cccggtggag cgaagttga aaacaatttt ccatgttcat tatataaaga tgaaataatg   1020
aaagaaatcg aaagagaatc aaaacgaatt aaattaaatg ataatgatga tgaagggaat   1080
aaaaaaatta tagctccaag aatttttatt tcagatgata agacagtttt aaaatgccca   1140
tgtgaccctg aaatggtaag taatagtaca tgtcgtttct ttgtatgtaa atgtgtagaa   1200
agaagggcag aagtaacatc aaataatgaa gttgtagtta agaagaata taaagatgaa   1260 tatgcagata ttcctgaaca taaaccaact tatgataaaa tgctcccggg agagaatcta   1320
tattttcaag ggcccggcgg aggtagtcac catcatcacc atcactaatg accggt       1376
```

<210> SEQ ID NO 92
<211> LENGTH: 434
<212> TYPE: PRT
<213> ORGANISM: artificial
<220> FEATURE:
<223> OTHER INFORMATION: Amino acid sequence of fusion protein [SNAPlike-MSP1-proTEV-AMA1-Histag]

<400> SEQUENCE: 92

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
                20                  25                  30

Lys Leu Leu Gly Lys Gly Thr Ser Ala Ala Asp Ala Val Glu Val Pro
            35                  40                  45

Ala Pro Ala Ala Val Leu Gly Gly Pro Glu Pro Leu Met Gln Ala Thr
        50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Lys Gln
        195                 200                 205

Cys Pro Gln Asn Ser Gly Cys Phe Arg His Leu Asp Glu Arg Glu Glu
    210                 215                 220

Cys Lys Cys Leu Leu Asn Tyr Lys Gln Glu Gly Asp Lys Cys Val Glu
225                 230                 235                 240
```

Asn Pro Asn Leu Thr Cys Asn Glu Asn Gly Gly Cys Asp Ala Asp
                245                 250                 255

Ala Lys Cys Thr Glu Glu Asp Ser Gly Ser Asn Gly Lys Lys Ile Thr
            260                 265                 270

Cys Glu Cys Thr Lys Pro Asp Ser Tyr Pro Leu Phe Asp Gly Ile Phe
            275                 280                 285

Gly Gly Gly Ser Glu Asn Leu Tyr Phe Gln Gly Pro Gly Gly Gly Glu
            290                 295                 300

Val Glu Asn Asn Phe Pro Cys Ser Leu Tyr Lys Asp Glu Ile Met Lys
305                 310                 315                 320

Glu Ile Glu Arg Glu Ser Lys Arg Ile Lys Leu Asn Asp Asn Asp Asp
                325                 330                 335

Glu Gly Asn Lys Lys Ile Ile Ala Pro Arg Ile Phe Ile Ser Asp Asp
            340                 345                 350

Lys Asp Ser Leu Lys Cys Pro Cys Asp Pro Glu Met Val Ser Asn Ser
            355                 360                 365

Thr Cys Arg Phe Phe Val Cys Lys Cys Val Glu Arg Arg Ala Glu Val
            370                 375                 380

Thr Ser Asn Asn Glu Val Val Val Lys Glu Glu Tyr Lys Asp Glu Tyr
385                 390                 395                 400

Ala Asp Ile Pro Glu His Lys Pro Thr Tyr Asp Lys Met Leu Pro Gly
                405                 410                 415

Glu Asn Leu Tyr Phe Gln Gly Pro Gly Gly Gly Ser His His His
            420                 425                 430

His His

<210> SEQ ID NO 93
<211> LENGTH: 2195
<212> TYPE: DNA
<213> ORGANISM: artificial
<220> FEATURE:
<223> OTHER INFORMATION: DNA sequence encoding ssBiP- SNAPlike -proTEV-
      modified short form of HbpA from Leptospira interrogans serovar
      Lai str.56601 - proTEV- Histag for expression in S2 cells

<400> SEQUENCE: 93
atgaagttat gcatattact ggccgtcgtg gtggcctttg ttggcctctc gctcgggaga      60
tctagatctg acaaagactg cgaaatgaaa agaactacat ggattcacc acttgggaag     120 ttggaactga gtggatgcga gcaaggattg catgaaatta agctactggg aaaaggaact    180
tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg taaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cttcaacacc acggccaaca tgggcttcag gaacgagtac    720
gtgagcggcg cggtgtccgc aggttacaat aagaaccccg cgtacaggtt ggtcccaaac    780
tctcaggcga ctactgggaa cgcctatcag gacttgaaca cgggcatcaa cctgaccttc    840

|  |  |  |  |  |  |
|---|---|---|---|---|---|
| aacccggacg | gcaagttcaa | ggggaagacg | aggattctct | accagcacag | ggaccagaac | 900 |
| ggggtggacg | tgacccagtc | caaggccgtc | ttcgaccgga | caacaagac | gcacgacttc | 960 |
| ttggcgacgg | ggtcgttgga | gtacgggtta | gggaagagga | acttgatctc | cttcaggggg | 1020 |
| aacatctcca | agtgggagaa | caagtactac | aacaaccaga | ggggggtcgga | cgagttggac | 1080 |
| gtgaagcagt | tgaactcgga | gttgacgtcg | caggggaccg | tgcagttgga | catggaggcc | 1140 |
| tctgagaagc | acttcatcac | tgtaggtgcg | gagtccttcg | cgaacgagtt | ggagtcggac | 1200 |
| cgcttgcaga | gcaggtacgt | gtacaggacg | aggaaggcgg | tgttcttcca | ggacgagtgg | 1260 |
| accgtgtccc | ggtcgccgag | gattcgggtg | gtgccaggag | tgaggtacga | cgacgactcg | 1320 |
| cagttcggga | accagacgac | gccgaagctg | gcggcccggt | acgacatatt | gcagaacttg | 1380 |
| gtgtggaggg | cgagctacgg | gaggggatta | cggccgccga | gcttgcagga | gttgtacctg | 1440 |
| cggttcgaga | acccggccgt | gggttacgtg | gtggagggta | acccgaactt | gaagccggag | 1500 |
| cggtcgatca | cgatcaactc | ggacttggag | tacagcccgt | tcagcttctt | gacgttctcc | 1560 |
| ttgagcgtgt | accggaacga | catcatcaac | ctgatccagt | acaagttcga | ctcgaacaag | 1620 |
| gggagggagt | tcgcggagtt | ccagctgcag | aacatcgcga | aggcgtacac | gagaggagga | 1680 |
| gagttcggcg | tgcagtacag | gttcttgaag | tacttcacgc | tggagttggg | gtacaaccac | 1740 |
| acggacacga | gggacctgag | ctcggacagg | ccgttggagg | cagggcgct | gcaccaggcg | 1800 |
| tcggcgaact | tcatctacaa | ctcgcccgga | ggattccaat | tcaacctgag | gggcaagcac | 1860 |
| ttggacaaga | ggccgttcta | cagctcgacc | aacaacctgt | cggcggccgg | acaggactac | 1920 |
| atccccagcg | aggtgaagtt | gaacgagaac | ccgcccgtga | tctacgggaa | gccgttcacg | 1980 |
| atcttgaacg | tgaggatcga | gcagaagttc | ttcaacaagc | acttcgcgct | gttcttgggc | 2040 |
| gtggacaact | gctcaacca | gtacgagctg | gcgtacaacc | ccacgcggcc | gaggttctac | 2100 |
| tacggcggct | tctcggccca | gttcccggga | gagaatctat | attttcaagg | gcccggcgga | 2160 |
| ggtagtcacc | atcatcacca | tcactaatga | ccggt |  |  | 2195 |

<210> SEQ ID NO 94
<211> LENGTH: 707
<212> TYPE: PRT
<213> ORGANISM: artificial
<220> FEATURE:
<223> OTHER INFORMATION: Amino acid sequence of fusion protein
      [SNAPlike-proTEV-HbPA1-proTEV-Histag]

<400> SEQUENCE: 94

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr

-continued

```
            115                 120                 125
Ala Ala Val Lys Thr Ala Leu Ser Gly Asn Pro Val Pro Ile Leu Ile
        130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Phe Asn
        195                 200                 205

Thr Thr Ala Asn Met Gly Phe Arg Asn Glu Tyr Val Ser Gly Ala Val
    210                 215                 220

Ser Ala Gly Tyr Asn Lys Asn Pro Gly Tyr Arg Leu Val Pro Asn Ser
225                 230                 235                 240

Gln Ala Thr Thr Gly Asn Ala Tyr Gln Asp Leu Asn Thr Gly Ile Asn
                245                 250                 255

Leu Thr Phe Asn Pro Asp Gly Lys Phe Lys Gly Lys Thr Arg Ile Leu
            260                 265                 270

Tyr Gln His Arg Asp Gln Asn Gly Val Asp Val Thr Gln Ser Lys Ala
        275                 280                 285

Val Phe Asp Arg Asn Asn Lys Thr His Asp Phe Leu Ala Thr Gly Ser
    290                 295                 300

Leu Glu Tyr Gly Leu Gly Lys Arg Asn Leu Ile Ser Phe Arg Gly Asn
305                 310                 315                 320

Ile Ser Lys Trp Glu Asn Lys Tyr Tyr Asn Asn Gln Arg Gly Ser Asp
                325                 330                 335

Glu Leu Asp Val Lys Gln Leu Asn Ser Glu Leu Thr Ser Gln Gly Thr
            340                 345                 350

Val Gln Leu Asp Met Glu Ala Ser Glu Lys His Phe Ile Thr Val Gly
        355                 360                 365

Ala Glu Ser Phe Ala Asn Glu Leu Glu Ser Asp Arg Leu Gln Ser Arg
    370                 375                 380

Tyr Val Tyr Arg Thr Arg Lys Ala Val Phe Phe Gln Asp Glu Trp Thr
385                 390                 395                 400

Val Ser Arg Ser Pro Arg Ile Arg Val Val Pro Gly Val Arg Tyr Asp
                405                 410                 415

Asp Asp Ser Gln Phe Gly Asn Gln Thr Thr Pro Lys Leu Ala Ala Arg
            420                 425                 430

Tyr Asp Ile Leu Gln Asn Leu Val Trp Arg Ala Ser Tyr Gly Arg Gly
        435                 440                 445

Leu Arg Pro Pro Ser Leu Gln Glu Leu Tyr Leu Arg Phe Glu Asn Pro
    450                 455                 460

Ala Val Gly Tyr Val Val Glu Gly Asn Pro Asn Leu Lys Pro Glu Arg
465                 470                 475                 480

Ser Ile Thr Ile Asn Ser Asp Leu Glu Tyr Ser Pro Phe Ser Phe Leu
                485                 490                 495

Thr Phe Ser Leu Ser Val Tyr Arg Asn Asp Ile Ile Asn Leu Ile Gln
            500                 505                 510

Tyr Lys Phe Asp Ser Asn Lys Gly Arg Glu Phe Ala Glu Phe Gln Leu
        515                 520                 525

Gln Asn Ile Ala Lys Ala Tyr Thr Arg Gly Gly Glu Phe Gly Val Gln
    530                 535                 540
```

Tyr Arg Phe Leu Lys Tyr Phe Thr Leu Glu Leu Gly Tyr Asn His Thr
545                 550                 555                 560

Asp Thr Arg Asp Leu Ser Ser Asp Arg Pro Leu Glu Gly Arg Ala Leu
            565                 570                 575

His Gln Ala Ser Ala Asn Phe Ile Tyr Asn Ser Pro Gly Gly Phe Gln
        580                 585                 590

Phe Asn Leu Arg Gly Lys His Leu Asp Lys Arg Pro Phe Tyr Ser Ser
    595                 600                 605

Thr Asn Asn Leu Ser Ala Ala Gly Gln Asp Tyr Ile Pro Ser Glu Val
610                 615                 620

Lys Leu Asn Glu Asn Pro Pro Val Ile Tyr Gly Lys Pro Phe Thr Ile
625                 630                 635                 640

Leu Asn Val Arg Ile Glu Gln Lys Phe Phe Asn Lys His Phe Ala Leu
            645                 650                 655

Phe Leu Gly Val Asp Asn Leu Leu Asn Gln Tyr Glu Leu Ala Tyr Asn
        660                 665                 670

Pro Thr Arg Pro Arg Phe Tyr Tyr Gly Gly Phe Ser Ala Gln Phe Pro
    675                 680                 685

Gly Glu Asn Leu Tyr Phe Gln Gly Pro Gly Gly Ser His His His
    690                 695                 700

His His His
705

<210> SEQ ID NO 95
<211> LENGTH: 968
<212> TYPE: DNA
<213> ORGANISM: artificial
<220> FEATURE:
<223> OTHER INFORMATION: DNA sequence encoding ssBiP- SNAPlike -proTEV-
      MUB40 - proTEV- Histag for expression in S2 cells

<400> SEQUENCE: 95
atgaagttat gcatattact ggccgtcgtg gtggcctttg ttggcctctc gctcgggaga      60
tcttcgcgag ctagcaccat gaaactatgt attctacttg cagttgttgc gttcgtagga    120
ttgtccttac ctacagctct ggcaagatct gacaaagact cgcaaatgaa agaactaca     180 ttggattcac cacttgggaa gttggaactg agtggatgcg agcaaggatt gcatgaaatt    240
aagctactgg gaaaaggaac ttctgctgct gatgcagttg aagttccagc accagcagct    300
gttcttggag tcctgagcc cctcatgcaa gccacagcct ggcttaacgc atatttccac     360
cagcctgagg ccattgagga atttccagtc ccgcccttc accatcctgt gtttcagcag     420
gagagcttca cccgccaggt cctgtggaaa ttgctgaagg tggtcaagtt tggtgaagtg    480
atttcatatc agcaacttgc tgcattggcc ggtaaccccg cagctacagc tgccgtgaaa    540
actgctctca gcggaaatcc tgtgcccatc ctgatccctt gtcacagagt cgtttcatct    600
tccggagctg taggtggcta tgaaggagga ctggcagtta aggagtggct gctggctcat    660
gaaggtcata gacttggaaa gcctgggctg gtcctgctg gtataggcgc gccagggtcc    720
ctaggtggcg atccgaaaa cctgtacttc cagagcgata tcacggctga aggcatcaag    780
aagtttgaag cgacggtta tgaactgttc aaggacaact tcccagctgg tgagaagttc    840
gataacgatg acaccaacga tcaattctac acggtaatct tcaagcacca tcgtggcccg    900
ggagagaatc tatattttca agggcccggc ggaggtagtc accatcatca ccatcactaa    960
tgaccggt                                                             968

<210> SEQ ID NO 96
<211> LENGTH: 298
<212> TYPE: PRT
<213> ORGANISM: artificial
<220> FEATURE:
<223> OTHER INFORMATION: Amino acid sequence of fusion protein
    [SNAPlike-proTEV-MUB40-proTEV-Histag]

<400> SEQUENCE: 96

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
                20                  25                  30

Cys Glu Met Lys Arg Thr Thr Leu Asp Ser Pro Leu Gly Lys Leu Glu
            35                  40                  45

Leu Ser Gly Cys Glu Gln Gly Leu His Glu Ile Lys Leu Leu Gly Lys
        50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
                100                 105                 110

His His Pro Val Phe Gln Gln Glu Ser Phe Thr Arg Gln Val Leu Trp
            115                 120                 125

Lys Leu Leu Lys Val Val Lys Phe Gly Glu Val Ile Ser Tyr Gln Gln
        130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
                180                 185                 190

Lys Glu Trp Leu Leu Ala His Glu Gly His Arg Leu Gly Lys Pro Gly
            195                 200                 205

Leu Gly Pro Ala Gly Ile Gly Ala Pro Gly Ser Leu Gly Gly Gly Ser
        210                 215                 220

Glu Asn Leu Tyr Phe Gln Ser Asp Ile Thr Ala Glu Gly Ile Lys Lys
225                 230                 235                 240

Phe Glu Gly Asp Gly Tyr Glu Leu Phe Lys Asp Asn Phe Pro Ala Gly
                245                 250                 255

Glu Lys Phe Asp Asn Asp Asp Thr Asn Asp Gln Phe Tyr Thr Val Ile
            260                 265                 270

Phe Lys His His Arg Gly Pro Gly Glu Asn Leu Tyr Phe Gln Gly Pro
        275                 280                 285

Gly Gly Gly Ser His His His His His His
    290                 295

<210> SEQ ID NO 97
<211> LENGTH: 1238
<212> TYPE: DNA
<213> ORGANISM: artificial
<220> FEATURE:
<223> OTHER INFORMATION: DNA sequence encoding ssBiP- SNAPlike -proTEV-
    soluble form of mouse C-type like lectin (CLEC5A) - proTEV- Histag
    for expression in S2 cells

<400> SEQUENCE: 97

```
atgaagttat gcatattact ggccgtcgtg gtggcctttg ttggcctctc gctcgggaga      60
tctagatctg acaaagactg cgaaatgaaa agaactacat ggattcacc acttgggaag     120
ttggaactga gtggatgcga gcaaggattg catgaaatta agctactggg aaaaggaact    180
tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg taaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cgttttggc aaaagtaatg atggcttcgt ccccacggag    720
agctacggaa ccactagtgt gcagaatgtc tcacaaatct tgggagaaa tgacgaaagt    780
accatgccta caaggagcta tgaacagtc tgtcccagaa actgggattt tcaccaagga    840
aaatgctttt tcttctcctt ctccgaatca ccttggaaag acagcatgga ttattgtgca    900
acacaagggt ccacactggc aattgtcaac actccagaga aactgaagta tcttcaggac    960
atagctggta ttgagaatta ctttattggt ttggtacgtc agcctggaga gaaaaagtgg   1020
cgctggatca acaactctgt gttcaatggc aatgttacca atcaggacca gaacttcgac   1080
tgtgtcacta taggtctgac gaagacatat gatgctgcat catgtgaagt cagctatcgc   1140
tggatctgcg aaatgaatgc caaaggcccg ggagagaatc tatattttca agggcccggc   1200
ggaggtagtc accatcatca ccatcactaa tgaccggt                            1238
```

<210> SEQ ID NO 98
<211> LENGTH: 388
<212> TYPE: PRT
<213> ORGANISM: artificial
<220> FEATURE:
<223> OTHER INFORMATION: Amino acid sequence of fusion protein
      [SNAPlike-proTEV-moCLEC5A-proTEV-Histag]

<400> SEQUENCE: 98

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile

```
                130            135             140
    Pro Cys His Arg Val Val Ser Ser Gly Ala Val Gly Gly Tyr Glu
    145             150             155             160
    Gly Gly Leu Ala Val Lys Glu Trp Leu Leu Ala His Glu Gly His Arg
                165             170             175
    Leu Gly Lys Pro Gly Leu Gly Pro Ala Gly Ile Gly Ala Pro Gly Ser
                180             185             190
    Leu Gly Gly Gly Ser Glu Asn Leu Tyr Phe Gln Ser Asp Ile Val Phe
                195             200             205
    Gly Lys Ser Asn Asp Gly Phe Val Pro Thr Glu Ser Tyr Gly Thr Thr
    210             215             220
    Ser Val Gln Asn Val Ser Gln Ile Phe Gly Arg Asn Asp Glu Ser Thr
    225             230             235             240
    Met Pro Thr Arg Ser Tyr Gly Thr Val Cys Pro Arg Asn Trp Asp Phe
                245             250             255
    His Gln Gly Lys Cys Phe Phe Phe Ser Phe Ser Glu Ser Pro Trp Lys
                260             265             270
    Asp Ser Met Asp Tyr Cys Ala Thr Gln Gly Ser Thr Leu Ala Ile Val
                275             280             285
    Asn Thr Pro Glu Lys Leu Lys Tyr Leu Gln Asp Ile Ala Gly Ile Glu
    290             295             300
    Asn Tyr Phe Ile Gly Leu Val Arg Gln Pro Gly Glu Lys Lys Trp Arg
    305             310             315             320
    Trp Ile Asn Asn Ser Val Phe Asn Gly Asn Val Thr Asn Gln Asp Gln
                325             330             335
    Asn Phe Asp Cys Val Thr Ile Gly Leu Thr Lys Thr Tyr Asp Ala Ala
                340             345             350
    Ser Cys Glu Val Ser Tyr Arg Trp Ile Cys Glu Met Asn Ala Lys Gly
                355             360             365
    Pro Gly Glu Asn Leu Tyr Phe Gln Gly Pro Gly Gly Ser His His
                370             375             380
    His His His His
    385
```

<210> SEQ ID NO 99
<211> LENGTH: 1229
<212> TYPE: DNA
<213> ORGANISM: artificial
<220> FEATURE:
<223> OTHER INFORMATION: DNA sequence encoding ssBiP- SNAPlike -proTEV-
      soluble form of human C-type like lectin (CLEC5A) - proTEV- Histag
      for expression in S2 cells

<400> SEQUENCE: 99

```
atgaagttat gcatattact ggccgtcgtg gtggcctttg ttggcctctc gctcgggaga     60
tctagatctg acaaagactg cgaaatgaaa agaactacat ggattcacc acttgggaag    120 ttggaactga gtggatgcga gcaaggattg catgaaatta gctactggg aaaaggaact    180 tctgctgctg atgcagttga agttccagca ccagcagctg ttcttggagg tcctgagccc   240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg taaccccgc agctacagct gccgtgaaaa ctgctctcag cggaaatcct    480
gtgcccatcc tgatcccttg tcacagagtc gtttcatctt ccggagctgt aggtggctat    540
```

```
gaaggaggac tggcagttaa ggagtggctg ctggctcatg aaggtcatag

-continued

```
225                 230                 235                 240

Arg Ser Tyr Gly Thr Val Cys Pro Lys Asp Trp Glu Phe Tyr Gln Ala
                245                 250                 255

Arg Cys Phe Phe Leu Ser Thr Ser Glu Ser Ser Trp Asn Glu Ser Arg
            260                 265                 270

Asp Phe Cys Lys Gly Lys Gly Ser Thr Leu Ala Ile Val Asn Thr Pro
        275                 280                 285

Glu Lys Leu Lys Phe Leu Gln Asp Ile Thr Asp Ala Glu Lys Tyr Phe
    290                 295                 300

Ile Gly Leu Ile Tyr His Arg Glu Glu Lys Arg Trp Arg Trp Ile Asn
305                 310                 315                 320

Asn Ser Val Phe Asn Gly Asn Val Thr Asn Gln Asn Gln Asn Phe Asn
                325                 330                 335

Cys Ala Thr Ile Gly Leu Thr Lys Thr Phe Asp Ala Ala Ser Cys Asp
            340                 345                 350

Ile Ser Tyr Arg Arg Ile Cys Glu Lys Asn Ala Lys Gly Pro Gly Glu
        355                 360                 365

Asn Leu Tyr Phe Gln Gly Pro Gly Gly Gly Ser His His His His His
    370                 375                 380

His
385
```

<210> SEQ ID NO 101
<211> LENGTH: 962
<212> TYPE: DNA
<213> ORGANISM: artificial
<220> FEATURE:
<223> OTHER INFORMATION: DNA sequence encoding BiPlike- SNAPlike- cxVAGO protein from Culex quinquefasciatus - Histag for expression in S2 cells

<400> SEQUENCE: 101

```
atgaaactat gtattctact tgcagttgtt gcgttcgtag gattgtcctt aagatctgac     60
aaagactgcg aaatgaaaag aactacattg gattcaccac ttgggaagtt ggaactgagt    120
ggatgcgagc aaggattgca tgaaattaag ctactgggaa aaggaacttc tgctgctgat    180
gcagttgaag ttccagcacc agcagctgtt cttggaggtc ctgagcccct catgcaagcc    240
acagcctggc ttaacgcata tttccaccag cctgaggcca ttgaggaatt tccagtcccc    300
gcccttcacc atcctgtgtt tcagcaggag agcttcaccc gccaggtcct gtggaaattg    360
ctgaaggtgg tcaagtttgg tgaagtgatt tcatatcagc aacttgctgc attggccggt    420
aaccccgcag ctacagctgc cgtgaaaact gctctcagcg gaaatcctgt gcccatcctg    480
atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctga agccgttcta    660
caaaatgccg agcatccaga ttaccctgga aagtgttacg acgaaggtac gcagaccgtt    720
gtagctcccc tagaaagtgc gaagctacca aaatcgtgta caaaggtatt ctgctcgact    780
aacctttcac tgacctatac tacgtgtggg tcagtacttg tcaatgaccc gcactgcgag    840
aagatcgaac aagacctgac taaagacttc ccagagtgct gtcacaagta taaatgtgaa    900
ctggagggag tagtcacgta ccacggaggt ggccatcacc atcaccatca ctgatgaccg    960
gt                                                                   962
```

```
<210> SEQ ID NO 102
<211> LENGTH: 300
<212> TYPE: PRT
<213> ORGANISM: artificial
<220> FEATURE:
<223> OTHER INFORMATION: Amino acid sequence of fusion protein
      [SNAPlike-cxVAGO-Histag]

<400> SEQUENCE: 102

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65              70                  75                  80

Pro Val Pro Ala Leu His His Pro Val Phe Gln Gln Glu Ser Phe Thr
                85                  90                  95

Arg Gln Val Leu Trp Lys Leu Lys Val Val Lys Phe Gly Glu Val
            100                 105                 110

Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Ser Glu Ala Val Leu Gln Asn Ala Glu His
        195                 200                 205

Pro Asp Tyr Pro Gly Lys Cys Tyr Asp Glu Gly Thr Gln Thr Val Val
    210                 215                 220

Ala Pro Leu Glu Ser Ala Lys Leu Pro Lys Ser Cys Thr Lys Val Phe
225                 230                 235                 240

Cys Ser Thr Asn Leu Ser Leu Thr Tyr Thr Thr Cys Gly Ser Val Leu
                245                 250                 255

Val Asn Asp Pro His Cys Glu Lys Ile Glu Gln Asp Leu Thr Lys Asp
            260                 265                 270

Phe Pro Glu Cys Cys His Lys Tyr Lys Cys Glu Leu Glu Gly Val Val
        275                 280                 285

Thr Tyr His Gly Gly Gly His His His His His
    290                 295                 300

<210> SEQ ID NO 103
<211> LENGTH: 962
<212> TYPE: DNA
<213> ORGANISM: artificial
<220> FEATURE:
<223> OTHER INFORMATION: DNA sequence encoding BiPlike- SNAPlike- aaVAGO
      protein from Aedes albopictus - Histag for expression in S2 cells

<400> SEQUENCE: 103
atgaaactat gtattctact tgcagttgtt gcgttcgtag gattgtcctt aagatctgac     60
```

-continued

```
aaagactgcg aaatgaaaag aactacattg gattcaccac ttgggaagtt ggaactgagt    120
ggatgcgagc aaggattgca tgaaattaag ctactgggaa aaggaacttc tgctgctgat    180
gcagttgaag ttccagcacc agcagctgtt cttggaggtc ctgagcccct catgcaagcc    240
acagcctggc ttaacgcata tttccaccag cctgaggcca ttgaggaatt tccagtcccc    300
gcccttcacc atcctgtgtt tcagcaggag agcttcaccc gccaggtcct gtggaaattg    360
ctgaaggtgg tcaagtttgg tgaagtgatt tcatatcagc aacttgctgc attggccggt    420
aaccccgcag ctacagctgc cgtgaaaact gctctcagcg aaatcctgt gcccatcctg     480
atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctac ggctatcttc    660
ccaaattcgg agaacaaaga tttcccaggc gaatgctatg acacggagac taagattcat    720
ttcaagccag gggaaaatcg tcaacgacct ggcaactgtg aagagatgtc atgcggaact    780
gacttctcga ttcactttt cggatgcgga ctagctatac tagacgatga cccggattgc    840
gagatcccag ttcaggattt cacaaaggac acgcagtgtt gccataagta caagtgtgtg    900
cgtaacggtg aagtcaatta cattggaggt ggccatcacc atcaccatca ctgatgaccg    960
gt                                                                  962
```

<210> SEQ ID NO 104
<211> LENGTH: 300
<212> TYPE: PRT
<213> ORGANISM: artificial
<220> FEATURE:
<223> OTHER INFORMATION: Amino acid sequence of fusion protein [SNAPlike-aaVAGO-Histag]

<400> SEQUENCE: 104

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190
```

```
Leu Gly Gly Gly Gly Ser Thr Ala Ile Phe Pro Asn Ser Glu Asn
        195                 200                 205
Lys Asp Phe Pro Gly Glu Cys Tyr Asp Thr Glu Thr Lys Ile His Phe
    210                 215                 220
Lys Pro Gly Glu Asn Arg Gln Arg Pro Gly Asn Cys Glu Glu Met Ser
225                 230                 235                 240
Cys Gly Thr Asp Phe Ser Ile His Phe Phe Gly Cys Gly Leu Ala Ile
                245                 250                 255
Leu Asp Asp Asp Pro Asp Cys Glu Ile Pro Val Gln Asp Phe Thr Lys
            260                 265                 270
Asp Thr Gln Cys Cys His Lys Tyr Lys Cys Val Arg Asn Gly Glu Val
        275                 280                 285
Asn Tyr Ile Gly Gly Gly His His His His His His
        290                 295                 300
```

<210> SEQ ID NO 105
<211> LENGTH: 4108
<212> TYPE: DNA
<213> ORGANISM: artificial
<220> FEATURE:
<223> OTHER INFORMATION: DNA sequence of OpIE2SP-SNAP cloned into pUC57
      for constitutive expression of secreted chimeric SNAP-target
      protein in invertebrate cells

<400> SEQUENCE: 105

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtggaat tctcatgatg ataaacaatg     420
tatggtgcta atgttgcttc aacaacaatt ctgttgaact gtgttttcat gtttgccaac     480
aagcaccttt atactcggtg gcctccccac caccaacttt tttgcactgc aaaaaaacac     540
gcttttgcac gcgggcccat acatagtaca aactctacgt ttcgtagact atttttacata    600
aatagtctac accgttgtat acgctccaaa tacactacca cacattgaac cttttttgcag    660
tgcaaaaaag tacgtgtcgg cagtcacgta ggccggcctt atcgggtcgc gtcctgtcac     720
gtacgaatca cattatcgga ccggacgagt gttgtcttat cgtgacagga cgccagcttc     780
ctgtgttgct aaccgcagcc ggacgcaact ccttatcgga acaggacgcg cctccatatc     840
agccgcgcgt tatctcatgc gcgtgaccgg acacgaggcg cccgtcccgc ttatcgcgcc     900
tataaataca gcccgcaacg atctggtaaa cacagttgaa cagcatctgt tcgaaggatc     960
cttgatcgag ctagcatgaa actatgtatt ctacttgcag ttgttgcgtt cgtaggattg    1020
tccttaagat ctgacaaaga ctgcgaaatg aaaagaacta cattggattc accacttggg    1080
aagttggaac tgagtggatg cgagcaagga ttgcatgaaa ttaagctact gggaaaagga    1140
acttctgctg ctgatgcagt tgaagttcca gcaccagcag ctgttcttgg aggtcctgag    1200
cccctcatgc aagccacagc ctggcttaac gcatatttcc accagcctga ggccattgag    1260
gaatttccag tccccgccct tcaccatcct gtgtttcagc aggagagctt cacccgccag    1320
gtcctgtgga aattgctgaa ggtggtcaag tttggtgaag tgatttcata tcagcaactt    1380
```

```
gctgcattgg ccggtaaccc cgcagctaca gctgccgtga aaactgctct cagcggaaat    1440
cctgtgccca tcctgatccc ttgtcacaga gtcgtttcat cttccggagc tgtaggtggc    1500
tatgaaggag gactggcagt taaggagtgg ctgctggctc atgaaggtca tagacttgga    1560
aagcctgggc tgggtcctgc tggtataggc gcgccaggt ccctaggtgg cggatccgaa     1620
aacctgtact tccagagcga tatcggaggt ggaggcccgg gaggtggcgg aagtgactat    1680
aaagatgacg acgataagtg ataagcggcc gcaaaaccgg ttgagtttat ctgactaaat    1740
cttagtttgt attgtcatgt tttaatacaa tatgttatgt ttaaatatgt ttttaataaa    1800
ttttataaaa taatttcaac ttttattgta acaacattgt ccatttacac actcctttca    1860
agcgcgtgaa gcttggcgta atcatggtca tagctgtttc ctgtgtgaaa ttgttatccg    1920
ctcacaattc cacacaacat acgagccgga agcataaagt gtaaagcctg gggtgcctaa    1980
tgagtgagct aactcacatt aattgcgttg cgctcactgc ccgctttcca gtcgggaaac    2040
ctgtcgtgcc agctgcatta atgaatcggc caacgcgcgg ggagaggcgg tttgcgtatt    2100
gggcgctctt ccgcttcctc gctcactgac tcgctgcgct cggtcgttcg ctgcggcga    2160
gcggtatcag ctcactcaaa ggcggtaata cggttatcca cagaatcagg ggataacgca    2220
ggaaagaaca tgtgagcaaa aggccagcaa aaggccagga accgtaaaaa ggccgcgttg    2280
ctggcgtttt tccataggct ccgcccccct gacgagcatc acaaaaatcg acgctcaagt    2340
cagaggtggc gaaacccgac aggactataa agataccagg cgtttccccc tggaagctcc    2400
ctcgtgcgct ctcctgttcc gaccctgccg cttaccggat acctgtccgc ctttctccct    2460
tcgggaagcg tggcgctttc tcatagctca cgctgtaggt atctcagttc ggtgtaggtc    2520
gttcgctcca agctgggctg tgtgcacgaa ccccccgttc agcccgaccg ctgcgcctta    2580
tccggtaact atcgtcttga gtccaacccg gtaagacacg acttatcgcc actggcagca    2640
gccactggta acaggattag cagagcgagg tatgtaggcg gtgctacaga gttcttgaag    2700
tggtggccta actacggcta cactagaaga acagtatttg gtatctgcgc tctgctgaag    2760
ccagttacct tcggaaaaag agttggtagc tcttgatccg gcaaacaaac caccgctggt    2820
agcggtggtt tttttgtttg caagcagcag attacgcgca gaaaaaaagg atctcaagaa    2880
gatcctttga tcttttctac ggggtctgac gctcagtgga acgaaaactc acgttaaggg    2940
attttggtca tgagattatc aaaaaggatc ttcacctaga tccttttaaa ttaaaaatga    3000
agttttaaat caatctaaag tatatatgag taaacttggt ctgacagtta ccaatgctta    3060
atcagtgagg cacctatctc agcgatctgt ctatttcgtt catccatagt tgcctgactc    3120
cccgtcgtgt agataactac gatacgggag ggcttaccat ctggccccag tgctgcaatg    3180
ataccgcgag acccacgctc accggctcca gatttatcag caataaacca gccagccgga    3240
agggccgagc gcagaagtgg tcctgcaact ttatccgcct ccatccagtc tattaattgt    3300
tgccgggaag ctagagtaag tagttcgcca gttaatagtt tgcgcaacgt tgttgccatt    3360
gctacaggca tcgtggtgtc acgctcgtcg tttggtatgg cttcattcag ctccggttcc    3420
caacgatcaa ggcgagttac atgatccccc atgttgtgca aaaaagcggt tagctccttc    3480
ggtcctccga tcgttgtcag aagtaagttg gccgcagtgt tatcactcat ggttatggca    3540
gcactgcata attctcttac tgtcatgcca tccgtaagat gcttttctgt gactggtgag    3600
tactcaacca agtcattctg agaatagtgt atgcggcgac cgagttgctc ttgcccggcg    3660
tcaatacggg ataataccgc gccacatagc agaactttaa aagtgctcat cattggaaaa    3720
```

```
cgttcttcgg ggcgaaaact ctcaaggatc ttaccgctgt tgagatccag ttcgatgtaa    3780
cccactcgtg cacccaactg atcttcagca tcttttactt tcaccagcgt ttctgggtga    3840
gcaaaaacag gaaggcaaaa tgccgcaaaa aagggaataa gggcgacacg gaaatgttga    3900
atactcatac tcttcctttt tcaatattat tgaagcattt atcagggtta ttgtctcatg    3960
agcggataca tatttgaatg tatttagaaa aataaacaaa taggggttcc gcgcacattt    4020
ccccgaaaag tgccacctga cgtctaagaa accattatta tcatgacatt aacctataaa    4080
aataggcgta tcacgaggcc ctttcgtc                                      4108
```

<210> SEQ ID NO 106
<211> LENGTH: 24
<212> TYPE: DNA
<213> ORGANISM: artificial
<220> FEATURE:
<223> OTHER INFORMATION: DNA sequence of C-term peptide tag of OpIE2SP-
      SNAP

<400> SEQUENCE: 106

```
gactataaag atgacgacga taag                                            24
```

<210> SEQ ID NO 107
<211> LENGTH: 8
<212> TYPE: PRT
<213> ORGANISM: artificial
<220> FEATURE:
<223> OTHER INFORMATION: Amino acid sequence of C-term peptide tag of
      OpIE2SP-SNAP

<400> SEQUENCE: 107

Asp Tyr Lys Asp Asp Asp Asp Lys
1               5

<210> SEQ ID NO 108
<211> LENGTH: 2200
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Crimean-Congo hemorragic fever virus-proTEV2-
      Histag for expression in S2 cells

<400> SEQUENCE: 108

```
atgaagttat gcatattact ggccgtcgtg gcctttgttg cctctcgct cgggagatct      60 gacaaagact gcgaaatgaa aagaactaca ttggattcac cacttgggaa gttggaactg    120
agtggatgcg agcaaggatt gcatgaaatt aagctactgg gaaaaggaac ttctgctgct    180
gatgcagttg aagttccagc accagcagct gttcttggag tcctgagcc cctcatgcaa    240 gccacagcct ggcttaacgc atatttccac cagcctgagg ccattgagga atttccagtc    300 cccgccttc accatcctgt gtttcagcag gagagcttca cccgccaggt cctgtggaaa    360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata gacttggaaa gcctgggctg    600
ggtcctgctg gtataggcgc gccagggtcc ctaggtggcg gatccgaaaa cctgtacttc    660
cagagcgata tcgaaaacaa gatcgaggtg aataacaaag atgagatgaa caggtggttt    720
gaagagttca aaaaggaaa tggacttgtg gacaccttca caaactccta ttccttttgc    780
```

-continued

| | |
|---|---|
| gagagtgttc ccaatttgga caggtttgtg tttcagatgg ccagtgccac cgatgatgca | 840 |
| cagaaggact ccatctacgc atctgctctg gtggaggcaa caaagttttg tgcacctata | 900 |
| tatgagtgcg catgggttag ctccactggc attgtaaaaa agggacttga atggttcgag | 960 |
| aaaaatgcag gaaccattaa gtcctgggat gaaagttata ctgagctaaa ggtcgacgtc | 1020 |
| ccgaaaatag agcagcttac gggttaccaa caagctgcct tgaagtggag aaaagacata | 1080 |
| ggtttccgtg tcaatgccaa cacagcagct ctgagcaaca agtcctcgc agaatacaaa | 1140 |
| gtccctggtg agattgtgat gtctgtcaaa gagatgctgt cagacatgat taggagaagg | 1200 |
| aacctgattc taaacagggg tggtgatgag aacccacgtg gcccagtgag ccatgagcat | 1260 |
| gtagactggt gcagggagtt tgtcaaaggc aaatacatca tggccttcaa cccaccatgg | 1320 |
| ggggacatca acaagtcagg ccgttcagga atagcacttg ttgcaacagg ccttgctaag | 1380 |
| cttgcagaga ctgaaggaaa gggaatattt gatgaagcca aaagactgt ggaggccctc | 1440 |
| aacgggtatc tggacaagca taaggacgaa gttgatagag caagcgccga cagcatgata | 1500 |
| acaaaccttc ttaagcatat tgccaaggca caggagctct ataaaaattc atctgcactt | 1560 |
| cgtgcacaaa gcgcacagat tgacactgct ttcagctcat actattggct ttacaaggct | 1620 |
| ggcgtgactc ctgaaaacctt cccgacggtg tcacagttcc tctttgagct agggaaacag | 1680 |
| ccaagaggta ccaagaaaat gaagaaggct cttctgagca ccccaatgaa gtgggggaag | 1740 |
| aagctttatg agctctttgc cgatgattct ttccagcaga acaggattta catgcatcct | 1800 |
| gccgtgctta cagctggtag aatcagtgaa atgggagtct gctttgggac aatccctgtg | 1860 |
| gccaatcctg atgatgctgc ccaaggatct ggacacacta agtctattct caacctccgt | 1920 |
| accaacactg agaccaataa tccgtgtgcc aaaaccatcg tcaagctatt tgaagttcaa | 1980 |
| aaaacagggt tcaacattca ggacatggac atagtggcct ctgagcactt gctacaccaa | 2040 |
| tcccttgttg gcaagcaatc cccattccag aacgcctaca acgtcaaggg caatgccacc | 2100 |
| agtgctaaca tcatcccggg agagaatcta tattttcaag ggcccggcgg aggtagtcac | 2160 |
| catcatcacc atcactaatg accggtgcgg ccgcaagctt | 2200 |

<210> SEQ ID NO 109
<211> LENGTH: 707
<212> TYPE: PRT
<213> ORGANISM: artificial
<220> FEATURE:
<223> OTHER INFORMATION: Amino acid sequence of fusion protein
      [SNAPlike-proTEV1-CCHF.N-proTEV2-Histag]

<400> SEQUENCE: 109

Arg Ser Asp Lys Asp Cys Glu Met Lys Arg Thr Thr Leu Asp Ser Pro
1               5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

```
Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
        130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
                180                 185                 190

Leu Gly Gly Gly Ser Glu Asn Leu Tyr Phe Gln Ser Asp Ile Glu Asn
                195                 200                 205

Lys Ile Glu Val Asn Asn Lys Asp Glu Met Asn Arg Trp Phe Glu Glu
        210                 215                 220

Phe Lys Lys Gly Asn Gly Leu Val Asp Thr Phe Thr Asn Ser Tyr Ser
225                 230                 235                 240

Phe Cys Glu Ser Val Pro Asn Leu Asp Arg Phe Val Phe Gln Met Ala
                245                 250                 255

Ser Ala Thr Asp Asp Ala Gln Lys Asp Ser Ile Tyr Ala Ser Ala Leu
        260                 265                 270

Val Glu Ala Thr Lys Phe Cys Ala Pro Ile Tyr Glu Cys Ala Trp Val
        275                 280                 285

Ser Ser Thr Gly Ile Val Lys Lys Gly Leu Glu Trp Phe Glu Lys Asn
        290                 295                 300

Ala Gly Thr Ile Lys Ser Trp Asp Glu Ser Tyr Thr Glu Leu Lys Val
305                 310                 315                 320

Asp Val Pro Lys Ile Glu Gln Leu Thr Gly Tyr Gln Gln Ala Ala Leu
                325                 330                 335

Lys Trp Arg Lys Asp Ile Gly Phe Arg Val Asn Ala Asn Thr Ala Ala
                340                 345                 350

Leu Ser Asn Lys Val Leu Ala Glu Tyr Lys Val Pro Gly Glu Ile Val
        355                 360                 365

Met Ser Val Lys Glu Met Leu Ser Asp Met Ile Arg Arg Arg Asn Leu
        370                 375                 380

Ile Leu Asn Arg Gly Gly Asp Glu Asn Pro Arg Gly Pro Val Ser His
385                 390                 395                 400

Glu His Val Asp Trp Cys Arg Glu Phe Val Lys Gly Lys Tyr Ile Met
                405                 410                 415

Ala Phe Asn Pro Pro Trp Gly Asp Ile Asn Lys Ser Gly Arg Ser Gly
                420                 425                 430

Ile Ala Leu Val Ala Thr Gly Leu Ala Lys Leu Ala Glu Thr Glu Gly
        435                 440                 445

Lys Gly Ile Phe Asp Glu Ala Lys Lys Thr Val Glu Ala Leu Asn Gly
        450                 455                 460

Tyr Leu Asp Lys His Lys Asp Glu Val Asp Arg Ala Ser Ala Asp Ser
465                 470                 475                 480

Met Ile Thr Asn Leu Leu Lys His Ile Ala Lys Ala Gln Glu Leu Tyr
                485                 490                 495

Lys Asn Ser Ser Ala Leu Arg Ala Gln Ser Ala Gln Ile Asp Thr Ala
                500                 505                 510

Phe Ser Ser Tyr Tyr Trp Leu Tyr Lys Ala Gly Val Thr Pro Glu Thr
        515                 520                 525
```

```
Phe Pro Thr Val Ser Gln Phe Leu Phe Glu Leu Gly Lys Gln Pro Arg
        530                 535                 540

Gly Thr Lys Lys Met Lys Lys Ala Leu Leu Ser Thr Pro Met Lys Trp
545                 550                 555                 560

Gly Lys Lys Leu Tyr Glu Leu Phe Ala Asp Asp Ser Phe Gln Gln Asn
                565                 570                 575

Arg Ile Tyr Met His Pro Ala Val Leu Thr Ala Gly Arg Ile Ser Glu
            580                 585                 590

Met Gly Val Cys Phe Gly Thr Ile Pro Val Ala Asn Pro Asp Asp Ala
        595                 600                 605

Ala Gln Gly Ser Gly His Thr Lys Ser Ile Leu Asn Leu Arg Thr Asn
610                 615                 620

Thr Glu Thr Asn Asn Pro Cys Ala Lys Thr Ile Val Lys Leu Phe Glu
625                 630                 635                 640

Val Gln Lys Thr Gly Phe Asn Ile Gln Asp Met Asp Ile Val Ala Ser
                645                 650                 655

Glu His Leu Leu His Gln Ser Leu Val Gly Lys Gln Ser Pro Phe Gln
            660                 665                 670

Asn Ala Tyr Asn Val Lys Gly Asn Ala Thr Ser Ala Asn Ile Ile Pro
        675                 680                 685

Gly Glu Asn Leu Tyr Phe Gln Gly Pro Gly Gly Ser His His His
690                 695                 700

His His His
705

<210> SEQ ID NO 110
<211> LENGTH: 2974
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Ebola virus-proTEV2-Histag for expression in
      S2 cells

<400> SEQUENCE: 110
atgaagttat gcatattact ggccgtcgtg gcctttgttg cctctcgct  cgggagatct      60 gacaaagact gcgaaatgaa agaactaca  ttggattcac cacttgggaa gttggaactg     120
agtggatgcg agcaaggatt gcatgaaatt aagctactgg aaaaggaac  ttctgctgct     180 gatgcagttg aagttccagc accagcagct gttcttggag gtcctgagcc cctcatgcaa     240
gccacagcct ggcttaacgc atatttccac cagcctgagg ccattgagga atttccagtc     300 cccgccttc  accatcctgt gtttcagcag gagagcttca cccgccaggt cctgtggaaa     360
ttgctgaagg tggtcaagtt tggtgaagtg atttcatatc agcaacttgc tgcattggcc     420 ggtaacccg  cagctacagc tgccgtgaaa actgctctca gcggaaatcc tgtgcccatc     480
ctgatccctt gtcacagagt cgtttcatct tccggagctg taggtggcta tgaaggagga     540
ctggcagtta aggagtggct gctggctcat gaaggtcata gacttggaaa gcctgggctg     600
ggtcctgctg gtataggcgc gccagggtcc ctaggtggcg atccgaaaa  cctgtacttc     660 cagagcgata tcgattctcg tcctcagaaa atctggatgg cgccgagtct cactgaatct     720
gacatggatt accacaaaat cttgacagca ggtctgtccg ttcaacaggg gattgttcgg     780
caaagagtca tcccagtgta tcaagtaaac aatcttgaag aaatttgcca acttatcata     840
caggcctttg aagcaggtgt tgattttcaa gagagtgcgg acagtttcct tctcatgctt     900
tgtcttcatc atgcgtacca gggagattac aaacttttct tggaaagtgg cgcagtcaag     960
```

```
tatttggaag ggcacgggtt ccgttttgaa gtcaagaagc gtgatggagt gaagcgcctt    1020
gaggaattgc tgccagcagt atctagtgga aaaaacatta gagaacact tgctgccatg    1080
ccggaagagg agacaactga agctaatgcc ggtcagtttc tctcctttgc aagtctattc    1140
cttccgaaat tggtagtagg agaaaaggct tgccttgaga aggttcaaag gcaaattcaa    1200
gtacatgcag agcaaggact gatacaatat ccaacagctt ggcaatcagt aggacacatg    1260
atggtgattt tccgtttgat gcgaacaaat tttctgatca aatttctcct aatacaccaa    1320
gggatgcaca tggttgccgg gcatgatgcc aacgatgctg tgatttcaaa ttcagtggct    1380
caagctcgtt tttcaggctt attgattgtc aaaacagtac ttgatcatat cctacaaaag    1440
acagaacgag gagttcgtct ccatcctctt gcaaggaccg ccaaggtaaa aaatgaggtg    1500
aactccttta aggctgcact cagctccctg gccaagcatg gagagtatgc tcctttcgcc    1560
cgacttttga acctttctgg agtaaataat cttgagcatg gtcttttccc tcaactatcg    1620
gcaattgcac tcggagtcgc cacagcacac gggagtaccc tcgcaggagt aaatgttgga    1680
gaacagtatc aacaactcag agaggctgcc actgaggctg agaagcaact ccaacaatat    1740
gcagagtctc gcgaacttga ccatcttgga cttgatgatc aggaaaagaa aattcttatg    1800
aacttccatc agaaaaagaa cgaaatcagc ttccagcaaa caaacgctat ggtaactcta    1860
agaaaagagc gcctggccaa gctgacagaa gctatcactg ctgcgtcact gcccaaaaca    1920
agtggacatt acgatgatga tgacgacatt cccttccag gacccatcaa tgatgacgac    1980
aatcctggcc atcaagatga tgatccgact gactcacagg atacgaccat tcccgatgtg    2040
gtggttgatc ccgatgatgg aagctacggc gaataccaga gttactcgga aaacggcatg    2100
aatgcaccag atgacttggt cctattcgat ctggacgagg acgacgagga cactaagcca    2160
gtgcctaata gatcgaccaa gggtggacaa cagaagaaca gtcaaaaggg ccagcatata    2220
gagggcagac agacacaatc caggccaatt caaaatgtcc caggccctca cagaacaatc    2280
caccacgcca gtgcgccact cacggacaat gacagaagaa atgaaccctc cggctcaacc    2340
agccctcgca tgctgacacc aattaacgaa gaggcagacc cactggacga tgccgacgac    2400
gagacgtcta gccttccgcc cttggagtca gatgatgaag agcaggacag ggacggaact    2460
tccaaccgca cacccactgt cgccccaccg gctcccgtat acagagatca ctctgaaaag    2520
aaagaactcc cgcaagacga gcaacaagat caggaccaca ctcaagaggc aggaaccag    2580
gacagtgaca cacccagtc agaacactct tttgaggaga tgtatcgcca cattctaaga    2640
tcacaggggc catttgatgc tgttttgtat tatcatatga tgaaggatga gcctgtagtt    2700
ttcagtacca gtgatggcaa agagtacacg tatccagact cccttgaaga ggaatatcca    2760
ccatggctca ctgaaaaaga ggctatgaat gaagagaata gatttgttac attggatggt    2820
caacaatttt attggccggt gatgaatcac aagaataaat tcatggcaat cctgcaacat    2880
catcagggcc cggagagaa tctatatttt caagggcccg gcggaggtag tcaccatcat    2940
caccatcact aatgaccggt gcggccgcaa gctt                                  2974
```

<210> SEQ ID NO 111
<211> LENGTH: 965
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 111

```
Arg Ser Asp Lys Asp Cys Glu Met Lys Arg Thr Thr Leu Asp Ser Pro
1               5                   10                  15
Leu Gly Lys Leu Glu Leu Ser Gly Cys Glu Gln Gly Leu His Glu Ile
            20                  25                  30
Lys Leu Leu Gly Lys Gly Thr Ser Ala Ala Asp Ala Val Glu Val Pro
            35                  40                  45
Ala Pro Ala Ala Val Leu Gly Gly Pro Glu Pro Leu Met Gln Ala Thr
50                  55                  60
Ala Trp Leu Asn Ala Tyr Phe His Gln Pro Glu Ala Ile Glu Glu Phe
65                  70                  75                  80
Pro Val Pro Ala Leu His His Pro Val Phe Gln Gln Glu Ser Phe Thr
                85                  90                  95
Arg Gln Val Leu Trp Lys Leu Leu Lys Val Val Lys Phe Gly Glu Val
                100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Gly Ser Glu Asn Leu Tyr Phe Gln Ser Asp Ile Asp Ser
            195                 200                 205
Arg Pro Gln Lys Ile Trp Met Ala Pro Ser Leu Thr Glu Ser Asp Met
210                 215                 220
Asp Tyr His Lys Ile Leu Thr Ala Gly Leu Ser Val Gln Gln Gly Ile
225                 230                 235                 240
Val Arg Gln Arg Val Ile Pro Val Tyr Gln Val Asn Asn Leu Glu Glu
                245                 250                 255
Ile Cys Gln Leu Ile Ile Gln Ala Phe Glu Ala Gly Val Asp Phe Gln
            260                 265                 270
Glu Ser Ala Asp Ser Phe Leu Leu Met Leu Cys Leu His His Ala Tyr
            275                 280                 285
Gln Gly Asp Tyr Lys Leu Phe Leu Glu Ser Gly Ala Val Lys Tyr Leu
            290                 295                 300
Glu Gly His Gly Phe Arg Phe Glu Val Lys Lys Arg Asp Gly Val Lys
305                 310                 315                 320
Arg Leu Glu Glu Leu Leu Pro Ala Val Ser Ser Gly Lys Asn Ile Lys
                325                 330                 335
Arg Thr Leu Ala Ala Met Pro Glu Glu Thr Thr Glu Ala Asn Ala
                340                 345                 350
Gly Gln Phe Leu Ser Phe Ala Ser Leu Phe Leu Pro Lys Leu Val Val
            355                 360                 365
Gly Glu Lys Ala Cys Leu Glu Lys Val Gln Arg Gln Ile Gln Val His
370                 375                 380
Ala Glu Gln Gly Leu Ile Gln Tyr Pro Thr Ala Trp Gln Ser Val Gly
385                 390                 395                 400
His Met Met Val Ile Phe Arg Leu Met Arg Thr Asn Phe Leu Ile Lys
                405                 410                 415
```

```
Phe Leu Leu Ile His Gln Gly Met His Met Val Ala Gly His Asp Ala
                420                 425                 430

Asn Asp Ala Val Ile Ser Asn Ser Val Ala Gln Ala Arg Phe Ser Gly
            435                 440                 445

Leu Leu Ile Val Lys Thr Val Leu Asp His Ile Leu Gln Lys Thr Glu
        450                 455                 460

Arg Gly Val Arg Leu His Pro Leu Ala Arg Thr Ala Lys Val Lys Asn
465                 470                 475                 480

Glu Val Asn Ser Phe Lys Ala Ala Leu Ser Ser Leu Ala Lys His Gly
                485                 490                 495

Glu Tyr Ala Pro Phe Ala Arg Leu Leu Asn Leu Ser Gly Val Asn Asn
            500                 505                 510

Leu Glu His Gly Leu Phe Pro Gln Leu Ser Ala Ile Ala Leu Gly Val
        515                 520                 525

Ala Thr Ala His Gly Ser Thr Leu Ala Gly Val Asn Val Gly Glu Gln
530                 535                 540

Tyr Gln Gln Leu Arg Glu Ala Ala Thr Glu Ala Glu Lys Gln Leu Gln
545                 550                 555                 560

Gln Tyr Ala Glu Ser Arg Glu Leu Asp His Leu Gly Leu Asp Asp Gln
                565                 570                 575

Glu Lys Lys Ile Leu Met Asn Phe His Gln Lys Asn Glu Ile Ser
            580                 585                 590

Phe Gln Gln Thr Asn Ala Met Val Thr Leu Arg Lys Glu Arg Leu Ala
        595                 600                 605

Lys Leu Thr Glu Ala Ile Thr Ala Ala Ser Leu Pro Lys Thr Ser Gly
610                 615                 620

His Tyr Asp Asp Asp Asp Ile Pro Phe Pro Gly Pro Ile Asn Asp
625                 630                 635                 640

Asp Asp Asn Pro Gly His Gln Asp Asp Pro Thr Asp Ser Gln Asp
                645                 650                 655

Thr Thr Ile Pro Asp Val Val Asp Pro Asp Gly Ser Tyr Gly
            660                 665                 670

Glu Tyr Gln Ser Tyr Ser Glu Asn Gly Met Asn Ala Pro Asp Asp Leu
        675                 680                 685

Val Leu Phe Asp Leu Asp Glu Asp Glu Asp Thr Lys Pro Val Pro
690                 695                 700

Asn Arg Ser Thr Lys Gly Gly Gln Gln Lys Asn Ser Gln Lys Gly Gln
705                 710                 715                 720

His Ile Glu Gly Arg Gln Thr Gln Ser Arg Pro Ile Gln Asn Val Pro
                725                 730                 735

Gly Pro His Arg Thr Ile His His Ala Ser Ala Pro Leu Thr Asp Asn
            740                 745                 750

Asp Arg Arg Asn Glu Pro Ser Gly Ser Thr Ser Pro Arg Met Leu Thr
        755                 760                 765

Pro Ile Asn Glu Glu Ala Asp Pro Leu Asp Ala Asp Glu Thr
770                 775                 780

Ser Ser Leu Pro Pro Leu Glu Ser Asp Asp Glu Gln Asp Arg Asp
785                 790                 795                 800

Gly Thr Ser Asn Arg Thr Pro Thr Val Ala Pro Pro Ala Pro Val Tyr
                805                 810                 815

Arg Asp His Ser Glu Lys Lys Glu Leu Pro Gln Asp Glu Gln Gln Asp
            820                 825                 830

Gln Asp His Thr Gln Glu Ala Arg Asn Gln Asp Ser Asp Asn Thr Gln
```

|     |     |     |     | 835 |     |     |     |     | 840 |     |     |     |     | 845 |     |
| --- | --- | --- | --- | --- | --- | --- | --- | --- | --- | --- | --- | --- | --- | --- | --- |

Ser Glu His Ser Phe Glu Glu Met Tyr Arg His Ile Leu Arg Ser Gln
            850                  855                860

Gly Pro Phe Asp Ala Val Leu Tyr Tyr His Met Met Lys Asp Glu Pro
865              870                  875              880

Val Val Phe Ser Thr Ser Asp Gly Lys Glu Tyr Thr Tyr Pro Asp Ser
                  885                  890              895

Leu Glu Glu Tyr Pro Pro Trp Leu Thr Glu Lys Glu Ala Met Asn
            900                  905              910

Glu Glu Asn Arg Phe Val Thr Leu Asp Gly Gln Gln Phe Tyr Trp Pro
            915                  920              925

Val Met Asn His Lys Asn Lys Phe Met Ala Ile Leu Gln His His Gln
            930                  935              940

Gly Pro Gly Glu Asn Leu Tyr Phe Gln Gly Pro Gly Gly Gly Ser His
945              950                  955              960

His His His His His
            965

<210> SEQ ID NO 112
<211> LENGTH: 2842
<212> TYPE: DNA
<213> ORGANISM: artificial
<220> FEATURE:
<223> OTHER INFORMATION: DNA sequence encoding ssBiP-SNAPlike-proTEV1-N
    nucleoprotein of the Marburg virus-proTEV2-Histag for expression
    in S2 cells

<400> SEQUENCE: 112

| | |
|---|---|
| atgaagttat gcatattact ggccgtcgtg gcctttgttg gcctctcgct cgggagatct | 60 |
| gacaaagact gcgaaatgaa agaactaca ttggattcac cacttgggaa gttggaactg | 120 |
| agtggatgcg agcaaggatt gcatgaaatt aagctactgg aaaaggaac ttctgctgct | 180 |
| gatgcagttg aagttccagc accagcagct gttcttggag gtcctgagcc cctcatgcaa | 240 |
| gccacagcct ggcttaacgc atatttccac cagcctgagg ccattgagga atttccagtc | 300 |
| cccgcccttc accatcctgt gtttcagcag gagagcttca cccgccaggt cctgtggaaa | 360 |
| ttgctgaagg tggtcaagtt tggtgaagtg atttcatatc agcaacttgc tgcattggcc | 420 |
| ggtaaccccg cagctacagc tgccgtgaaa actgctctca gcggaaatcc tgtgcccatc | 480 |
| ctgatcccttt gtcacagagt cgtttcatct tccggagctg taggtggcta tgaaggagga | 540 |
| ctggcagtta aggagtggct gctggctcat gaaggtcata gacttggaaa gcctgggctg | 600 |
| ggtcctgctg gtataggcgc gccagggtcc ctaggtggcg atccgaaaa cctgtacttc | 660 |
| cagagcgata tcgatttaca gtttgttg gagttgggta caaacccac tgcccctcat | 720 |
| gttcgtaata agaaagtgat attatttgac acaaatcatc aggttagtat ctgtaatcag | 780 |
| ataatagatg caataaactc agggattgat cttggtgatc tcctagaagg gggtttgctg | 840 |
| acgttgtgtg ttgagcatta ctataattct gataaggata aattcaacac aagtcctatc | 900 |
| gcgaagtact acgtgatgc gggctatgaa tttgatgtca tcaagaatgc agatgcaacc | 960 |
| cgctttctgg atgtgattcc taatgaacct cattacagcc ctttaattct agcccttaag | 1020 |
| acattggaaa gtactgaatc tcagaggggg agaattgggc tctttttatc attttgcagt | 1080 |
| cttttcctcc caaaacttgt cgtcggagac cgagctagta tcgaaaaggc tttaagacaa | 1140 |
| gtaacagtgc atcaagaaca ggggatcgtc atacccta atcattggct taccacaggc | 1200 |
| cacatgaaag taattttcgg gattttgagg tccagcttca ttttaaagtt tgtgttgatt | 1260 |

```
catcaaggag taaatttggt gacaggtcat gatgcctatg acagtatcat tagtaattca   1320
gtaggtcaaa ctagattctc aggacttctt atcgtgaaaa cagttctgga gttcatcttg   1380
caaaaaactg attcaggggt gacactacat cctttggtgc ggacctccaa agtaaaaaat   1440
gaagttgcta gtttcaagca ggcgttgagc aacctagccc gacatgggga atacgcacca   1500
tttgcacggg ttctgaattt atcagggatt aacaacctcg aacatggact ctatcctcag   1560
ctttcagcaa ttgcgctggg tgtggcaaca gcacacggca gtacattggc tggtgtcaat   1620
gttggcgaac aatatcaaca actacgagag gcggcacatg atgcggaagt aaaactacaa   1680
aggcgacatg aacatcagga aattcaagct attgccgagg atgacgagga aaggaagata   1740
ttagaacaat tccaccttca gaaaactgaa atcacacaca gtcagacact agccgtcctc   1800
agccagaaac gagaaaaatt agctcgtctc gctgcagaaa ttgaaaacaa tattgtggaa   1860
gatcagggat ttaagcaatc acagaatcgg gtgtcacagt cgtttttgaa tgaccctaca   1920
cctgtggaag taacggttca agccaggccc atgaatcgac caactgctct gcctccccca   1980
gttgacgaca agattgagca tgaatctaca gaagatagct cttcttcaag tagctttgtt   2040
gacttgaatg atccatttgc actgctgaat gaggacgagg atactcttga tgacagtgtc   2100
atgatccccg gcacaacatc gagagaattt caagggattc ctgaaccgcc aagacaatcc   2160
caagacctca ataacagcca aggaaagcag gaagatgaat ccacaaatcc gattaagaaa   2220
cagtttctga gataccaaga attgcctcct gttcaagagg atgatgaatc ggaatacaca   2280
actgactctc aagaaagcat cgaccaacca ggttccgaca atgaacaagg agttgatctt   2340
ccacctcctc cgttgtacgc tcaggaaaaa agacaggacc caatacagca cccagcagca   2400
aaccctcaag atcccttcgg cagtattggt gatgtaaatg gtgacatctt agaacctata   2460
agatcacctt cttcaccatc tgctcctcag gaagacacaa ggatgaggga agcctatgaa   2520
ttgtcgcctg atttcacaaa tgatgaggat aatcagcaga attggccaca aagagtggtg   2580
acaaagaagg gtagaacttt cctttatcct aatgatcttc tgcaaacaaa tcctccagag   2640
tcacttataa cagccctcgt tgaggaatac caaaatcctg tctcagctaa ggagcttcaa   2700
gcagattggc ccgacatgtc atttgatgaa aggagacatg ttgcgatgaa cttgggcccg   2760
ggagagaatc tatattttca agggcccggc ggaggtagtc accatcatca ccatcactaa   2820
tgaccggtgc ggccgcaagc tt                                            2842
```

```

<210> SEQ ID NO 113
<211> LENGTH: 921
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 113

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
```

```
                65                  70                  75                  80
        Pro Val Pro Ala Leu His His Pro Val Phe Gln Gln Glu Ser Phe Thr
                        85                  90                  95

Arg Gln Val Leu Trp Lys Leu Leu Lys Val Lys Phe Gly Glu Val
                    100                 105                 110

Ile Ser Tyr Gln Gln Leu Ala Ala Leu Ala Gly Asn Pro Ala Ala Thr
                        115                 120                 125

Ala Ala Val Lys Thr Ala Leu Ser Gly Asn Pro Val Pro Ile Leu Ile
                    130                 135                 140

Pro Cys His Arg Val Val Ser Ser Gly Ala Val Gly Gly Tyr Glu
        145                 150                 155                 160

Gly Gly Leu Ala Val Lys Glu Trp Leu Leu Ala His Glu Gly His Arg
                        165                 170                 175

Leu Gly Lys Pro Gly Leu Gly Pro Ala Gly Ile Gly Ala Pro Gly Ser
                    180                 185                 190

Leu Gly Gly Gly Ser Glu Asn Leu Tyr Phe Gln Ser Asp Ile Asp Leu
                    195                 200                 205

His Ser Leu Leu Glu Leu Gly Thr Lys Pro Thr Ala Pro His Val Arg
                210                 215                 220

Asn Lys Lys Val Ile Leu Phe Asp Thr Asn His Gln Val Ser Ile Cys
        225                 230                 235                 240

Asn Gln Ile Ile Asp Ala Ile Asn Ser Gly Ile Asp Leu Gly Asp Leu
                        245                 250                 255

Leu Glu Gly Gly Leu Leu Thr Leu Cys Val Glu His Tyr Tyr Asn Ser
                    260                 265                 270

Asp Lys Asp Lys Phe Asn Thr Ser Pro Ile Ala Lys Tyr Leu Arg Asp
                    275                 280                 285

Ala Gly Tyr Glu Phe Asp Val Ile Lys Asn Ala Asp Ala Thr Arg Phe
                    290                 295                 300

Leu Asp Val Ile Pro Asn Glu Pro His Tyr Ser Pro Leu Ile Leu Ala
        305                 310                 315                 320

Leu Lys Thr Leu Glu Ser Thr Glu Ser Gln Arg Gly Arg Ile Gly Leu
                        325                 330                 335

Phe Leu Ser Phe Cys Ser Leu Phe Leu Pro Lys Leu Val Val Gly Asp
                    340                 345                 350

Arg Ala Ser Ile Glu Lys Ala Leu Arg Gln Val Thr Val His Gln Glu
                    355                 360                 365

Gln Gly Ile Val Thr Tyr Pro Asn His Trp Leu Thr Thr Gly His Met
                370                 375                 380

Lys Val Ile Phe Gly Ile Leu Arg Ser Ser Phe Ile Leu Lys Phe Val
        385                 390                 395                 400

Leu Ile His Gln Gly Val Asn Leu Val Thr Gly His Asp Ala Tyr Asp
                        405                 410                 415

Ser Ile Ile Ser Asn Ser Val Gly Gln Thr Arg Phe Ser Gly Leu Leu
                    420                 425                 430

Ile Val Lys Thr Val Leu Glu Phe Ile Leu Gln Lys Thr Asp Ser Gly
                    435                 440                 445

Val Thr Leu His Pro Leu Val Arg Thr Ser Lys Val Lys Asn Glu Val
                450                 455                 460

Ala Ser Phe Lys Gln Ala Leu Ser Asn Leu Ala Arg His Gly Glu Tyr
        465                 470                 475                 480

Ala Pro Phe Ala Arg Val Leu Asn Leu Ser Gly Ile Asn Asn Leu Glu
                        485                 490                 495
```

```
His Gly Leu Tyr Pro Gln Leu Ser Ala Ile Ala Leu Gly Val Ala Thr
            500                 505                 510

Ala His Gly Ser Thr Leu Ala Gly Val Asn Val Gly Glu Gln Tyr Gln
            515                 520                 525

Gln Leu Arg Glu Ala Ala His Asp Ala Glu Val Lys Leu Gln Arg Arg
            530                 535                 540

His Glu His Gln Glu Ile Gln Ala Ile Ala Glu Asp Glu Glu Arg
545                 550                 555                 560

Lys Ile Leu Glu Gln Phe His Leu Gln Lys Thr Glu Ile Thr His Ser
                    565                 570                 575

Gln Thr Leu Ala Val Leu Ser Gln Lys Arg Glu Lys Leu Ala Arg Leu
                    580                 585                 590

Ala Ala Glu Ile Glu Asn Asn Ile Val Glu Asp Gln Gly Phe Lys Gln
            595                 600                 605

Ser Gln Asn Arg Val Ser Gln Ser Phe Leu Asn Asp Pro Thr Pro Val
            610                 615                 620

Glu Val Thr Val Gln Ala Arg Pro Met Asn Arg Pro Thr Ala Leu Pro
625                 630                 635                 640

Pro Pro Val Asp Asp Lys Ile Glu His Glu Ser Thr Glu Asp Ser Ser
                    645                 650                 655

Ser Ser Ser Ser Phe Val Asp Leu Asn Asp Pro Phe Ala Leu Leu Asn
            660                 665                 670

Glu Asp Glu Asp Thr Leu Asp Asp Ser Val Met Ile Pro Gly Thr Thr
            675                 680                 685

Ser Arg Glu Phe Gln Gly Ile Pro Glu Pro Arg Gln Ser Gln Asp
            690                 695                 700

Leu Asn Asn Ser Gln Gly Lys Gln Glu Asp Glu Ser Thr Asn Pro Ile
705                 710                 715                 720

Lys Lys Gln Phe Leu Arg Tyr Gln Glu Leu Pro Pro Val Gln Glu Asp
                    725                 730                 735

Asp Glu Ser Glu Tyr Thr Thr Asp Ser Gln Glu Ser Ile Asp Gln Pro
            740                 745                 750

Gly Ser Asp Asn Glu Gln Gly Val Asp Leu Pro Pro Pro Leu Tyr
            755                 760                 765

Ala Gln Glu Lys Arg Gln Asp Pro Ile Gln His Pro Ala Ala Asn Pro
            770                 775                 780

Gln Asp Pro Phe Gly Ser Ile Gly Asp Val Asn Gly Asp Ile Leu Glu
785                 790                 795                 800

Pro Ile Arg Ser Pro Ser Ser Pro Ser Ala Pro Gln Glu Asp Thr Arg
                    805                 810                 815

Met Arg Glu Ala Tyr Glu Leu Ser Pro Asp Phe Thr Asn Asp Glu Asp
            820                 825                 830

Asn Gln Gln Asn Trp Pro Gln Arg Val Val Thr Lys Lys Gly Arg Thr
            835                 840                 845

Phe Leu Tyr Pro Asn Asp Leu Leu Gln Thr Asn Pro Pro Glu Ser Leu
            850                 855                 860

Ile Thr Ala Leu Val Glu Glu Tyr Gln Asn Pro Val Ser Ala Lys Glu
865                 870                 875                 880

Leu Gln Ala Asp Trp Pro Asp Met Ser Phe Asp Glu Arg Arg His Val
                    885                 890                 895

Ala Met Asn Leu Gly Pro Gly Glu Asn Leu Tyr Phe Gln Gly Pro Gly
            900                 905                 910
```

Gly Gly Ser His His His His His His
    915                 920

<210> SEQ ID NO 114
<211> LENGTH: 2461
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Lassa virus-proTEV2-Histag for expression in
      S2 cells

<400> SEQUENCE: 114

```
atgaagttat gcatattact ggccgtcgtg gcctttgttg cctctcgct cgggagatct      60
gacaaagact gcgaaatgaa agaactaca ttggattcac cacttgggaa gttggaactg     120
agtggatgcg agcaaggatt gcatgaaatt aagctactgg gaaaaggaac ttctgctgct    180
gatgcagttg aagttccagc accagcagct gttcttggag gtcctgagcc cctcatgcaa    240
gccacagcct ggcttaacgc atatttccac cagcctgagg ccattgagga atttccagtc    300
cccgccttc accatcctgt gtttcagcag agagcttca cccgccaggt cctgtggaaa      360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata acttggaaa gcctgggctg    600
ggtcctgctg gtataggcgc gccagggtcc ctaggtggcg gatccgaaaa cctgtacttc    660
cagagcgata tcagtgcctc aaaggaaata aaatccttt tgtggacaca atctttgagg    720
agggaattat ctggttactg ctccaacatc aaactacagg tggtgaaaga tgcccaggct    780
cttttacatg gacttgactt ctccgaagtc agtaatgttc aacggttgat gcgcaaggag    840
agaagggatg acaatgattt gaacggttg agggacctaa atcaagcggt caacaatctt    900
gttgaattaa aatcaactca acaaaagagt atactgagag ttgggactct aacctcagat    960
gacttattaa tcttagccgc tgacctagag aagttaaagt caaaggtgat cagaacagaa   1020
aggccattaa gtgcaggtgt ctatatgggc aacctaagct cacagcaact tgaccaaaga   1080
agagctctcc tgaatatgat aggaatgagt ggtggtaatc aaggggctcg ggctgggaga   1140
gatggagtgg tgagagtttg ggatgtgaaa aatgcagagt tgctcaataa tcagttcggg   1200
accatgccaa gtctgacact ggcatgtctg acaaaacagg ggcaggttga cttgaatgat   1260
gcagtacaag cattgacaga tttgggtttg atctacacag caaagtatcc caacacttca   1320
gacttagaca ggctgactca aagtcatccc atcctaaata tgattgacac caagaaaagc   1380
tctttgaata tctcaggtta taattttagc ttgggtgcag ctgtgaaggc aggagcttgc   1440
atgctggatg gtggcaatat gttggagaca atcaaggtgt cacctcagac aatggatggt   1500
atcctcaaat ccattttaaa ggtcaagaag gctcttggaa tgttcatttc agacacccct   1560
ggtgaaagga atccttatga aaacatactc tacaagattt gtttgtcagg agatggatgg   1620
ccatatattg catcaagaac ctcaataaca ggaagggcct gggaaaacac tgtcgttgat   1680
ctggaatcag atgggaagcc acagaaagct gacagcaaca attccagtaa atccctgcag   1740
tcggcagggt ttaccgctgg gcttacctat tctcagctga tgacccctcaa ggatgcaatg   1800
ctgcaacttg acccaaatgc taagacctgg atggacattg aaggaagacc tgaagatcca   1860
gtggaaattg ccctctatca accaagttca ggctgctaca tacacttctt ccgtgaacct   1920
```

```
actgatttaa agcagttcaa gcaggatgct aagtactcac atgggattga tgtcacagac    1980
ctcttcgcta cacaaccggg cttgaccagt gctgtcattg atgcactccc ccggaatatg    2040
gtcattacct gtcagggtgc cgatgacata aggaaactcc ttgaatcaca aggaagaaaa    2100
gacattaaac taattgatat tgccctcagc aaaactgatt ccaggaagta tgaaaatgca    2160
gtctgggacc agtataaaga cttatgccac atgcacacag gtgtcgttgt tgaaaagaag    2220
aaaagaggcg gtaaagagga aataacccct cactgtgcac taatggactg catcatgttt    2280
gatgcagcag tgtcaggagg actgaacaca tcggttttga gagcagtgct gcccagagat    2340
atggtgttca gaacatcgac acctagagtc gttctcccgg gagagaatct atattttcaa    2400
gggcccggcg gaggtagtca ccatcatcac catcactaat gaccggtgcg gccgcaagct    2460
t                                                                    2461
```

<210> SEQ ID NO 115
<211> LENGTH: 794
<212> TYPE: PRT
<213> ORGANISM: artificial
<220> FEATURE:
<223> OTHER INFORMATION: Amino acid sequence of fusion protein
      [SNAPlike-proTEV1-LAS.N-proTEV2-Histag]

<400> SEQUENCE: 115

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ala
        195                 200                 205

Ser Lys Glu Ile Lys Ser Phe Leu Trp Thr Gln Ser Leu Arg Arg Glu
    210                 215                 220

Leu Ser Gly Tyr Cys Ser Asn Ile Lys Leu Gln Val Val Lys Asp Ala
225                 230                 235                 240

Gln Ala Leu Leu His Gly Leu Asp Phe Ser Glu Val Ser Asn Val Gln
                245                 250                 255
```

```
Arg Leu Met Arg Lys Glu Arg Arg Asp Asn Asp Leu Lys Arg Leu
            260                 265                 270

Arg Asp Leu Asn Gln Ala Val Asn Asn Leu Val Glu Leu Lys Ser Thr
        275                 280                 285

Gln Gln Lys Ser Ile Leu Arg Val Gly Thr Leu Thr Ser Asp Asp Leu
    290                 295                 300

Leu Ile Leu Ala Ala Asp Leu Glu Lys Leu Lys Ser Lys Val Ile Arg
305                 310                 315                 320

Thr Glu Arg Pro Leu Ser Ala Gly Val Tyr Met Gly Asn Leu Ser Ser
                325                 330                 335

Gln Gln Leu Asp Gln Arg Arg Ala Leu Leu Asn Met Ile Gly Met Ser
    340                 345                 350

Gly Gly Asn Gln Gly Ala Arg Ala Gly Arg Asp Gly Val Val Arg Val
            355                 360                 365

Trp Asp Val Lys Asn Ala Glu Leu Leu Asn Asn Gln Phe Gly Thr Met
    370                 375                 380

Pro Ser Leu Thr Leu Ala Cys Leu Thr Lys Gln Gly Gln Val Asp Leu
385                 390                 395                 400

Asn Asp Ala Val Gln Ala Leu Thr Asp Leu Gly Leu Ile Tyr Thr Ala
                405                 410                 415

Lys Tyr Pro Asn Thr Ser Asp Leu Asp Arg Leu Thr Gln Ser His Pro
            420                 425                 430

Ile Leu Asn Met Ile Asp Thr Lys Lys Ser Ser Leu Asn Ile Ser Gly
        435                 440                 445

Tyr Asn Phe Ser Leu Gly Ala Ala Val Lys Ala Gly Ala Cys Met Leu
    450                 455                 460

Asp Gly Gly Asn Met Leu Glu Thr Ile Lys Val Ser Pro Gln Thr Met
465                 470                 475                 480

Asp Gly Ile Leu Lys Ser Ile Leu Lys Val Lys Lys Ala Leu Gly Met
                485                 490                 495

Phe Ile Ser Asp Thr Pro Gly Glu Arg Asn Pro Tyr Glu Asn Ile Leu
            500                 505                 510

Tyr Lys Ile Cys Leu Ser Gly Asp Gly Trp Pro Tyr Ile Ala Ser Arg
        515                 520                 525

Thr Ser Ile Thr Gly Arg Ala Trp Glu Asn Thr Val Val Asp Leu Glu
    530                 535                 540

Ser Asp Gly Lys Pro Gln Lys Ala Asp Ser Asn Ser Ser Lys Ser
545                 550                 555                 560

Leu Gln Ser Ala Gly Phe Thr Ala Gly Leu Thr Tyr Ser Gln Leu Met
                565                 570                 575

Thr Leu Lys Asp Ala Met Leu Gln Leu Asp Pro Asn Ala Lys Thr Trp
            580                 585                 590

Met Asp Ile Glu Gly Arg Pro Glu Asp Pro Val Glu Ile Ala Leu Tyr
        595                 600                 605

Gln Pro Ser Ser Gly Cys Tyr Ile His Phe Phe Arg Glu Pro Thr Asp
    610                 615                 620

Leu Lys Gln Phe Lys Gln Asp Ala Lys Tyr Ser His Gly Ile Asp Val
625                 630                 635                 640

Thr Asp Leu Phe Ala Thr Gln Pro Gly Leu Thr Ser Ala Val Ile Asp
                645                 650                 655

Ala Leu Pro Arg Asn Met Val Ile Thr Cys Gln Gly Ser Asp Asp Ile
            660                 665                 670

Arg Lys Leu Leu Glu Ser Gln Gly Arg Lys Asp Ile Lys Leu Ile Asp
```

|  |  |  | 675 |  |  |  | 680 |  |  |  | 685 |  |
|---|---|---|---|---|---|---|---|---|---|---|---|---|
| Ile | Ala | Leu | Ser | Lys | Thr | Asp | Ser | Arg | Lys | Tyr | Glu | Asn | Ala | Val | Trp |
|  |  |  | 690 |  |  |  | 695 |  |  |  | 700 |  |

| Asp | Gln | Tyr | Lys | Asp | Leu | Cys | His | Met | His | Thr | Gly | Val | Val | Val | Glu |
|---|---|---|---|---|---|---|---|---|---|---|---|---|---|---|---|
| 705 |  |  |  | 710 |  |  |  | 715 |  |  |  |  |  |  | 720 |

| Lys | Lys | Lys | Arg | Gly | Gly | Lys | Glu | Glu | Ile | Thr | Pro | His | Cys | Ala | Leu |
|---|---|---|---|---|---|---|---|---|---|---|---|---|---|---|---|
|  |  |  |  | 725 |  |  |  |  | 730 |  |  |  |  | 735 |  |

| Met | Asp | Cys | Ile | Met | Phe | Asp | Ala | Ala | Val | Ser | Gly | Gly | Leu | Asn | Thr |
|---|---|---|---|---|---|---|---|---|---|---|---|---|---|---|---|
|  |  |  |  | 740 |  |  |  |  | 745 |  |  |  | 750 |  |  |

| Ser | Val | Leu | Arg | Ala | Val | Leu | Pro | Arg | Asp | Met | Val | Phe | Arg | Thr | Ser |
|---|---|---|---|---|---|---|---|---|---|---|---|---|---|---|---|
|  |  |  | 755 |  |  |  | 760 |  |  |  |  | 765 |  |  |  |

| Thr | Pro | Arg | Val | Val | Leu | Pro | Gly | Glu | Asn | Leu | Tyr | Phe | Gln | Gly | Pro |
|---|---|---|---|---|---|---|---|---|---|---|---|---|---|---|---|
| 770 |  |  |  |  | 775 |  |  |  |  | 780 |  |  |  |  |  |

| Gly | Gly | Gly | Ser | His | His | His | His | His | His |
|---|---|---|---|---|---|---|---|---|---|
| 785 |  |  |  |  | 790 |  |  |  |  |

<210> SEQ ID NO 116
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Junin virus-proTEV2-Histag for expression in S2 cells

<400> SEQUENCE: 116

| atgaagttat gcatattact ggccgtcgtg gcctttgttg gcctctcgct cgggagatct | 60 |
|---|---|
| gacaaagact gcgaaatgaa agaactaca ttggattcac cacttgggaa gttggaactg | 120 |
| agtggatgcg agcaaggatt gcatgaaatt aagctactgg aaaaggaac ttctgctgct | 180 |
| gatgcagttg aagttccagc accagcagct gttcttggag gtcctgagcc cctcatgcaa | 240 |
| gccacagcct ggcttaacgc atatttccac cagcctgagg ccattgagga atttccagtc | 300 |
| cccgcccttc accatcctgt gtttcagcag gagagcttca cccgccaggt cctgtggaaa | 360 |
| ttgctgaagg tggtcaagtt tggtgaagtg atttcatatc agcaacttgc tgcattggcc | 420 |
| ggtaaccccg cagctacagc tgccgtgaaa actgctctca gcggaaatcc tgtgcccatc | 480 |
| ctgatcccctt gtcacagagt cgtttcatct tccggagctg taggtggcta tgaaggagga | 540 |
| ctggcagtta aggagtggct gctggctcat gaaggtcata gacttggaaa gcctgggctg | 600 |
| ggtcctgctg gtataggcgc gccagggtcc ctaggtggcg atccgaaaa cctgtacttc | 660 |
| cagagcgata tcgcacactc caaggaggtt cctagcttta gatggactca gtccttaagg | 720 |
| agaggtttga gccaattcac tcagactgtc aagtcagatg ttttgaagga cgccaagcta | 780 |
| attgctgaca gcatcgactt caaccaagtg gcacaggtgc agcgggcact cagaaagact | 840 |
| aaaaaggggg aagaagacct caataagttg agggacctga taaagaggt tgacagactc | 900 |
| atgtccatga gagtgttca acgaaacaca gtttcaagg tgggtgatct ggggagggat | 960 |
| gaactgatgg agttggcgtc tgaccttgag aaattaaaaa acaagataag aagagcagag | 1020 |
| acaggctctc aggggggttta catgggtaac ttgtcccagt cacaacttgc taaaagatca | 1080 |
| gagatattga acactgggg atttcaacag caagggactg ggggaaatgg tgtggtgagg | 1140 |
| atatgggatg ttaaagaccc ttcaaagcta acaatcagt ttggctctgt tcctgcattg | 1200 |
| acaattgcat gcatgactgt tcaaggaggt gagacaatga acagtgtcat acaggcttta | 1260 |
| acctcacttg ggcttctata cactgtgaag tatccaaact taagtgacct tgacagactg | 1320 |

```
actcaggaac atgactgcct tcagattgtg actaaagatg aaagctccat caatatttct   1380
ggttacaact tcagtctttc agctgcagta aaggctggag catctattct tgatggtgga   1440
aacatgttgg aaacaatcag agtcacccca gaaaacttct cttccctcat aaaatcaacc   1500
attcaggtta aacgaagaga aggcatgttt attgatgaga accaggcaa tagaaatcct    1560
tatgaaaacc ttttgtacaa actttgtctt tctggcgatg gttggcctta tattggttca   1620
agatcacaaa tcacaggcag gtcatgggac aacacaagta ttgatctgac aaggaaacca   1680
gttgctggtc ctagacagcc ggaaaaaaac ggtcagaatt tgagattggc taacttgaca   1740
gagatacaag aagctgtcat cagagaggca gtggggaaac tcgaccccac caacacccttt  1800
tggctcgaca ttgaaggacc agccactgac cctgttgaga tggcattatt ccaacctgca   1860
ggtaagcagt acattcactg cttcagaaaa ccacatgatg agaaagggtt taaaaatggt   1920
agcagacact ctcacggcat cttaatgaag gacatagaag atgcaatgcc aggagttctt   1980
agttacgtga tcggcttgct gcctccagac atggttgtga ctactcaagg ttccgatgac   2040
atcaggaagt tgtttgacct ccatggaaga agggatctta aactggttga tgttaagctc   2100
acatctgaac aagccaggca gtttgatcaa caggtctggg agaaatatgg tcacttatgc   2160
aaatatcaca atggagtggt tgtcaataag aaaaagaggg aaaaggatac tcccttcaag   2220
ttggcctcca gtgaaccaca ctgtgctctg ctagactgca taatgtttca gtcagtgcta   2280
gatgggaagc tctatgagga ggaacctaca cctctattac caccgagctt gctgttcctc   2340
ccgaaggcag cctatgcact cccgggagag aatctatatt ttcaagggcc cggcggaggt   2400
agtcaccatc atcaccatca ctaatgaccg gtgcggccgc aagctt                  2446
```

<210> SEQ ID NO 117
<211> LENGTH: 789
<212> TYPE: PRT
<213> ORGANISM: artificial
<220> FEATURE:
<223> OTHER INFORMATION: Aa sequence of fusion protein
      [SNAPlike-proTEV1-JUN.N-proTEV2-Histag]

<400> SEQUENCE: 117

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160
```

```
Gly Gly Leu Ala Val Lys Glu Trp Leu Leu Ala His Glu Gly His Arg
            165                 170                 175
Leu Gly Lys Pro Gly Leu Gly Pro Ala Gly Ile Gly Ala Pro Gly Ser
        180                 185                 190
Leu Gly Gly Gly Ser Glu Asn Leu Tyr Phe Gln Ser Asp Ile Ala His
        195                 200                 205
Ser Lys Glu Val Pro Ser Phe Arg Trp Thr Gln Ser Leu Arg Arg Gly
    210                 215                 220
Leu Ser Gln Phe Thr Gln Thr Val Lys Ser Asp Val Leu Lys Asp Ala
225                 230                 235                 240
Lys Leu Ile Ala Asp Ser Ile Asp Phe Asn Gln Val Ala Gln Val Gln
                245                 250                 255
Arg Ala Leu Arg Lys Thr Lys Lys Gly Glu Glu Asp Leu Asn Lys Leu
            260                 265                 270
Arg Asp Leu Asn Lys Glu Val Asp Arg Leu Met Ser Met Arg Ser Val
        275                 280                 285
Gln Arg Asn Thr Val Phe Lys Val Gly Asp Leu Gly Arg Asp Glu Leu
    290                 295                 300
Met Glu Leu Ala Ser Asp Leu Glu Lys Leu Lys Asn Lys Ile Arg Arg
305                 310                 315                 320
Ala Glu Thr Gly Ser Gln Gly Val Tyr Met Gly Asn Leu Ser Gln Ser
                325                 330                 335
Gln Leu Ala Lys Arg Ser Glu Ile Leu Arg Thr Leu Gly Phe Gln Gln
            340                 345                 350
Gln Gly Thr Gly Asn Gly Val Val Arg Ile Trp Asp Val Lys Asp
        355                 360                 365
Pro Ser Lys Leu Asn Asn Gln Phe Gly Ser Val Pro Ala Leu Thr Ile
    370                 375                 380
Ala Cys Met Thr Val Gln Gly Gly Glu Thr Met Asn Ser Val Ile Gln
385                 390                 395                 400
Ala Leu Thr Ser Leu Gly Leu Leu Tyr Thr Val Lys Tyr Pro Asn Leu
                405                 410                 415
Ser Asp Leu Asp Arg Leu Thr Gln Glu His Asp Cys Leu Gln Ile Val
            420                 425                 430
Thr Lys Asp Glu Ser Ser Ile Asn Ile Ser Gly Tyr Asn Phe Ser Leu
        435                 440                 445
Ser Ala Ala Val Lys Ala Gly Ala Ser Ile Leu Asp Gly Gly Asn Met
    450                 455                 460
Leu Glu Thr Ile Arg Val Thr Pro Glu Asn Phe Ser Ser Leu Ile Lys
465                 470                 475                 480
Ser Thr Ile Gln Val Lys Arg Arg Glu Gly Met Phe Ile Asp Glu Lys
                485                 490                 495
Pro Gly Asn Arg Asn Pro Tyr Glu Asn Leu Leu Tyr Lys Leu Cys Leu
            500                 505                 510
Ser Gly Asp Gly Trp Pro Tyr Ile Gly Ser Arg Ser Gln Ile Thr Gly
        515                 520                 525
Arg Ser Trp Asp Asn Thr Ser Ile Asp Leu Thr Arg Lys Pro Val Ala
    530                 535                 540
Gly Pro Arg Gln Pro Glu Lys Asn Gly Gln Asn Leu Arg Leu Ala Asn
545                 550                 555                 560
Leu Thr Glu Ile Gln Glu Ala Val Ile Arg Glu Ala Val Gly Lys Leu
                565                 570                 575
Asp Pro Thr Asn Thr Leu Trp Leu Asp Ile Glu Gly Pro Ala Thr Asp
```

```
              580                 585                 590
Pro Val Glu Met Ala Leu Phe Gln Pro Ala Gly Lys Gln Tyr Ile His
                595                 600                 605

Cys Phe Arg Lys Pro His Asp Glu Lys Gly Phe Lys Asn Gly Ser Arg
            610                 615                 620

His Ser His Gly Ile Leu Met Lys Asp Ile Glu Asp Ala Met Pro Gly
625                 630                 635                 640

Val Leu Ser Tyr Val Ile Gly Leu Leu Pro Pro Asp Met Val Val Thr
                645                 650                 655

Thr Gln Gly Ser Asp Asp Ile Arg Lys Leu Phe Asp Leu His Gly Arg
            660                 665                 670

Arg Asp Leu Lys Leu Val Asp Val Lys Leu Thr Ser Glu Gln Ala Arg
                675                 680                 685

Gln Phe Asp Gln Gln Val Trp Glu Lys Tyr Gly His Leu Cys Lys Tyr
            690                 695                 700

His Asn Gly Val Val Val Asn Lys Lys Arg Glu Lys Asp Thr Pro
705                 710                 715                 720

Phe Lys Leu Ala Ser Ser Glu Pro His Cys Ala Leu Leu Asp Cys Ile
                725                 730                 735

Met Phe Gln Ser Val Leu Asp Gly Lys Leu Tyr Glu Glu Pro Thr
            740                 745                 750

Pro Leu Leu Pro Pro Ser Leu Leu Phe Leu Pro Lys Ala Ala Tyr Ala
                755                 760                 765

Leu Pro Gly Glu Asn Leu Tyr Phe Gln Gly Pro Gly Gly Ser His
            770                 775                 780

His His His His His
785
```

<210> SEQ ID NO 118
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Machupo virus-proTEV2-Histag for expression in S2 cells

<400> SEQUENCE: 118

```
atgaagttat gcatattact ggccgtcgtg gcctttgttg cctctcgct cgggagatct      60 gacaaagact gcgaaatgaa aagaactaca ttggattcac cacttgggaa gttggaactg     120
agtggatgcg agcaaggatt gcatgaaatt aagctactgg aaaaggaac ttctgctgct     180 gatgcagttg aagttccagc accagcagct gttcttggag gtcctgagcc cctcatgcaa     240
gccacagcct ggcttaacgc atatttccac cagcctgagg ccattgagga atttccagtc     300
cccgcccttc accatcctgt gtttcagcag gagagcttca cccgccaggt cctgtggaaa     360
ttgctgaagg tggtcaagtt tggtgaagtg atttcatatc agcaacttgc tgcattggcc     420 ggtaacccg cagctacagc tgccgtgaaa actgctctca gcggaaatcc tgtgcccatc     480
ctgatccctt gtcacagagt cgtttcatct tccggagctg taggtggcta tgaaggagga     540
ctggcagtta aggagtggct gctggctcat gaaggtcata gacttggaaa gcctgggctg     600
ggtcctgctg gtataggcgc gccagggtcc ctaggtggcg atccgaaaa cctgtacttc     660 cagagcgata tcgctcactc caaggaaatt cccagctttc ggtggactca gtcactgaga     720
agaggcctga gtcagttcac ccacactgtg aaaacagatg tgttgaaaga tgccaagctc     780
```

|   |   |
|---|---|
| atagctgaca gcatcgactt caaccaggtt tcacaagtgc agagggctct cagaaagaac | 840 |
| aaaaggggtg aagaggatct gaacaagctg agggatttaa acaaagaagt ggataggctc | 900 |
| atgtctatga aaagcatcca gaaaacacc atattcaaga ttggtgatct ggggagagat | 960 |
| gaattgatgg agcttgcatc agacttggaa aaactgaaga caagataaa gaggactgag | 1020 |
| tcaggtcccc aagggctgta catgggtaat ttgtcacagc tgcaactgac aaagaggtca | 1080 |
| gaaatcttga agaccctggg attccaacag cagagaggtg ctggaaatgg tgtggttaga | 1140 |
| atctgggatg tctcagatcc atcaaaactg aataatcagt ttggttccat gccagctctc | 1200 |
| acaatcgctt gtatgactgt ccagggtgga gaaacgatga atagtgtggt ccaagcgttg | 1260 |
| acatctctgg gcctgttata cactgttaaa tatccgaatt taaatgacct tgacaagcta | 1320 |
| acactagagc acgaatgctt gcagatcgta actaaggacg agagctccat caacatctct | 1380 |
| ggctataact tcagtctgtc agctgctgtg aaagctggcg cctcaatact tgacggtggg | 1440 |
| aacatgctgg aaacaattag ggtcactcct gataatttct ccagcttgat taaatcaact | 1500 |
| ctgcaagtca agcgaaaaga ggggatgttt atagacgaga aacctgggaa tcgaaatcct | 1560 |
| tatgagaacc ttctgtataa attgtgtctc tcaggtgacg ggtggcctta cattggttcc | 1620 |
| agatcacaaa ttcttgggag gtcttgggac aacacaagtg ttgatctaac aaagaaacct | 1680 |
| caagttggac cgagacaacc cgagaaaaac ggtcagaatc taagactagc aaacctgact | 1740 |
| gaaatgcaag aagcagtgat taagaggct gtaaagaagt tagaccccac taatacactg | 1800 |
| tggcttgaca ttgaagggcc tccaacagac cctgtggaat tggcactata tcagccagcc | 1860 |
| aacaagcatt atattcattg ttttagaaag ccacatgatg agaagggctt caaaaatggc | 1920 |
| agcagacatt cacatggcat cttgatgcaa gacatcgagg atgcaatgcc aggagtatta | 1980 |
| agttatgtaa taggtttact accacaagat atggtgatta caactcaagg ttctgacgac | 2040 |
| ataaggaaac ttttagacat tcatggacgg aaggatttaa agctggtaga tgtgaaactc | 2100 |
| acatctgatc aagcaagact ctatgatcag caaatttggg agaagtttgg acatctttgc | 2160 |
| aaacatcata atggagttgt tgtcaacaag aaaaagagag aaaaagactc tccattcaaa | 2220 |
| ttgagttctg gtgaacctca ctgtgctctg ttggattgta tcatgtatca atcagtgatg | 2280 |
| gatggcaaaa tggtagatga agaaccagtg gcactttac ctctcagcct tctatttcta | 2340 |
| cccaaggcag cctttgcact cccggggagag aatctatatt ttcaagggcc cggcggaggt | 2400 |
| agtcaccatc atcaccatca ctaatgaccg gtgcggccgc aagctt | 2446 |

<210> SEQ ID NO 119
<211> LENGTH: 789
<212> TYPE: PRT
<213> ORGANISM: artificial
<220> FEATURE:
<223> OTHER INFORMATION: Amino acid sequence of fusion protein
      [SNAPlike-proTEV1-MAC.N-proTEV2-Histag]

<400> SEQUENCE: 119

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

-continued

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
            165                 170                 175

Leu Gly Lys Pro Gly Leu Gly Pro Ala Gly Ile Gly Ala Pro Gly Ser
        180                 185                 190

Leu Gly Gly Gly Ser Glu Asn Leu Tyr Phe Gln Ser Asp Ile Ala His
    195                 200                 205

Ser Lys Glu Ile Pro Ser Phe Arg Trp Thr Gln Ser Leu Arg Arg Gly
210                 215                 220

Leu Ser Gln Phe Thr His Thr Val Lys Thr Asp Val Leu Lys Asp Ala
225                 230                 235                 240

Lys Leu Ile Ala Asp Ser Ile Asp Phe Asn Gln Val Ser Gln Val Gln
                245                 250                 255

Arg Ala Leu Arg Lys Asn Lys Arg Gly Glu Glu Asp Leu Asn Lys Leu
            260                 265                 270

Arg Asp Leu Asn Lys Glu Val Asp Arg Leu Met Ser Met Lys Ser Ile
        275                 280                 285

Gln Lys Asn Thr Ile Phe Lys Ile Gly Asp Leu Gly Arg Asp Glu Leu
    290                 295                 300

Met Glu Leu Ala Ser Asp Leu Glu Lys Leu Lys Asn Lys Ile Lys Arg
305                 310                 315                 320

Thr Glu Ser Gly Pro Gln Gly Leu Tyr Met Gly Asn Leu Ser Gln Leu
                325                 330                 335

Gln Leu Thr Lys Arg Ser Glu Ile Leu Lys Thr Leu Gly Phe Gln Gln
            340                 345                 350

Gln Arg Gly Ala Gly Asn Gly Val Val Arg Ile Trp Asp Val Ser Asp
        355                 360                 365

Pro Ser Lys Leu Asn Asn Gln Phe Gly Ser Met Pro Ala Leu Thr Ile
    370                 375                 380

Ala Cys Met Thr Val Gln Gly Gly Glu Thr Met Asn Ser Val Val Gln
385                 390                 395                 400

Ala Leu Thr Ser Leu Gly Leu Leu Tyr Thr Val Lys Tyr Pro Asn Leu
                405                 410                 415

Asn Asp Leu Asp Lys Leu Thr Leu Glu His Gly Cys Leu Gln Ile Val
            420                 425                 430

Thr Lys Asp Glu Ser Ser Ile Asn Ile Ser Gly Tyr Asn Phe Ser Leu
        435                 440                 445

Ser Ala Ala Val Lys Ala Gly Ala Ser Ile Leu Asp Gly Gly Asn Met
    450                 455                 460

Leu Glu Thr Ile Arg Val Thr Pro Asp Asn Phe Ser Ser Leu Ile Lys
465                 470                 475                 480

Ser Thr Leu Gln Val Lys Arg Lys Glu Gly Met Phe Ile Asp Glu Lys

Pro Gly Asn Arg Asn Pro Tyr Glu Asn Leu Leu Tyr Lys Leu Cys Leu
            500                 505                 510

Ser Gly Asp Gly Trp Pro Tyr Ile Gly Ser Arg Ser Gln Ile Leu Gly
            515                 520                 525

Arg Ser Trp Asp Asn Thr Ser Val Asp Leu Thr Lys Lys Pro Gln Val
            530                 535                 540

Gly Pro Arg Gln Pro Glu Lys Asn Gly Gln Asn Leu Arg Leu Ala Asn
545                 550                 555                 560

Leu Thr Glu Met Gln Glu Ala Val Ile Lys Glu Ala Val Lys Lys Leu
                565                 570                 575

Asp Pro Thr Asn Thr Leu Trp Leu Asp Ile Glu Gly Pro Pro Thr Asp
                580                 585                 590

Pro Val Glu Leu Ala Leu Tyr Gln Pro Ala Asn Lys His Tyr Ile His
                595                 600                 605

Cys Phe Arg Lys Pro His Asp Glu Lys Gly Phe Lys Asn Gly Ser Arg
            610                 615                 620

His Ser His Gly Ile Leu Met Gln Asp Ile Glu Asp Ala Met Pro Gly
625                 630                 635                 640

Val Leu Ser Tyr Val Ile Gly Leu Leu Pro Gln Asp Met Val Ile Thr
                645                 650                 655

Thr Gln Gly Ser Asp Asp Ile Arg Lys Leu Leu Asp Ile His Gly Arg
                660                 665                 670

Lys Asp Leu Lys Leu Val Asp Val Lys Leu Thr Ser Asp Gln Ala Arg
            675                 680                 685

Leu Tyr Asp Gln Gln Ile Trp Glu Lys Phe Gly His Leu Cys Lys His
            690                 695                 700

His Asn Gly Val Val Val Asn Lys Lys Arg Glu Lys Asp Ser Pro
705                 710                 715                 720

Phe Lys Leu Ser Ser Gly Glu Pro His Cys Ala Leu Leu Asp Cys Ile
                725                 730                 735

Met Tyr Gln Ser Val Met Asp Gly Lys Met Val Asp Glu Glu Pro Val
                740                 745                 750

Ala Leu Leu Pro Leu Ser Leu Leu Phe Leu Pro Lys Ala Ala Phe Ala
            755                 760                 765

Leu Pro Gly Glu Asn Leu Tyr Phe Gln Gly Pro Gly Gly Ser His
            770                 775                 780

His His His His His
785

<210> SEQ ID NO 120
<211> LENGTH: 2434
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Guanarito virus-proTEV2-Histag for expression
      in S2 cells

<400> SEQUENCE: 120
atgaagttat gcatattact ggccgtcgtg gcctttgttg cctctcgct cgggagatct      60 gacaaagact gcgaaatgaa agaactaca ttggattcac cacttgggaa gttggaactg     120
agtggatgcg agcaaggatt gcatgaaatt aagctactgg aaaaggaac ttctgctgct     180 gatgcagttg aagttccagc accagcagct gttcttggag gtcctgagcc cctcatgcaa     240

```
gccacagcct ggcttaacgc atatttccac cagcctgagg ccattgagga atttccagtc    300
cccgcccttc accatcctgt gtttcagcag gagagcttca cccgccaggt cctgtggaaa    360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata gacttggaaa gcctgggctg    600
ggtcctgctg gtataggcgc gccagggtcc ctaggtggcg gatccgaaaa cctgtacttc    660
cagagcgata tcgctcactc caaagaaatc cccagcttcc gctggactca atctctaagg    720
agagaactag ggatgttcac agaaccaacc aaatcaagtg ttcttaatga tgcaaagctc    780
attgcagact cccttgattt cacacaagtt tctcaagttc aaagactcct acgtaagtcc    840
aaacgaggag acactgatct tgataaactt agggacttaa ataaagaagt tgatagactg    900
atgagcatga aaagtgttca gaacaacaca gttctgaaag ttggtgattt gggcaaagat    960
gaattaatgg acttggcctc tgacctagaa aaactaaaga agaagattgg agatagggaa   1020
agcaatagtc caaggatgta catgggaaac ttgacgcagt cacaattgga aaaagagca    1080
gggattctta gaaccctggg attccaacaa caaggggggg ctgcaggtgg ggttgtcagg   1140
ttgtgggatg tatctgatcc ctccaaactg aataaccaat tggttcaat gccagctctt    1200
accattgcct gcatgacagt tcagggagga gaaacaatga acaatgttgt gcaggcacta   1260
acatcacttg gtcttctcta cactgtcaaa tatcccaatc ttgatgacct ggaaaaacta   1320
actttagaac acgactgcct acagattata acaaaggatg agagtgcact caacatatct   1380
ggttataact tcagtctttc agctgctgta aaagctggtg catcacttat agatggtggc   1440
aacatgctgg agacaataaa agtcacaccc aacaacttct cttctattgt caaggccgca   1500
ttgaacgtca aaagaagaga aggcatgttc atagatgaga gaccgggcaa tagaaaccct   1560
tatgagaacc ttctctacaa gctgtgtttg tctggggagg gttggccata tattggatca   1620
aggtcacaaa tactcgggag gtcttgggac aacacaagtg tcgatttaaa tgcaagacct   1680
gtaacaggtc cccgagctcc tgaaaagaat ggacaaaata tcagactatc aaatctttct   1740
gaaatgcaag aagcgatcgt aaaggaagca atgaggaaat tagattcatc agacacaatc   1800
tggatggaca ttgaaggccc gccaactgat cctgtggagt tggcagtttt ccaaccttct   1860
tcaggaaact atgtacactg tttcagaaaa cctcatgatg agaaaggttt taaaaatgga   1920
agtaggcact cacacggcat actattaaag gaccttgaag atgctcaacc tggtctattg   1980
agttacgtca ttggcttatt gccacagggt tcagttatca ctgttcaagg ggcagatgac   2040
atcaaaaagc tattcgacat acatggaagg aaagatttaa aacttgttga tgtcagactg   2100
actggggaac agtccagaat ttttgaacag gaagtttggg aaaaatttgg ccacctctgc   2160
agagcacaca atggtgtcat tgttcctaag aagaaaaaca aggaggctaa ctccacgaag   2220
gagccacact gtgctcttct cgattgcatc atgtttcagt ctgttcttga tggtcatctt   2280
cccgacacca ttcccattca actgctacca aacacattag tgttccaagc caagagcgca   2340
tttgtgatcc cggagagaa tctatatttt caagggcccg gcggaggtag tcaccatcat   2400
caccatcact aatgaccggt gcggccgcaa gctt                               2434
```

<210> SEQ ID NO 121
<211> LENGTH: 785
<212> TYPE: PRT
<213> ORGANISM: artificial

```
<220> FEATURE:
<223> OTHER INFORMATION: Amino acid sequence of fusion protein
      [SNAPlike-proTEV1-GUA.N-proTEV2-Histag]

<400> SEQUENCE: 121

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Ile Pro Ser Phe Arg Trp Thr Gln Ser Leu Arg Arg Glu
210                 215                 220

Leu Gly Met Phe Thr Glu Pro Thr Lys Ser Ser Val Leu Asn Asp Ala
225                 230                 235                 240

Lys Leu Ile Ala Asp Ser Leu Asp Phe Thr Gln Val Ser Gln Val Gln
                245                 250                 255

Arg Leu Leu Arg Lys Ser Lys Arg Gly Asp Thr Asp Leu Asp Lys Leu
            260                 265                 270

Arg Asp Leu Asn Lys Glu Val Asp Arg Leu Met Ser Met Lys Ser Val
        275                 280                 285

Gln Asn Asn Thr Val Leu Lys Val Gly Asp Leu Gly Lys Asp Glu Leu
290                 295                 300

Met Asp Leu Ala Ser Asp Leu Glu Lys Leu Lys Lys Ile Gly Asp
305                 310                 315                 320

Arg Glu Ser Asn Ser Pro Arg Met Tyr Met Gly Asn Leu Thr Gln Ser
                325                 330                 335

Gln Leu Glu Lys Arg Ala Gly Ile Leu Arg Thr Leu Gly Phe Gln Gln
            340                 345                 350

Gln Arg Gly Ala Ala Gly Gly Val Val Arg Leu Trp Asp Val Ser Asp
        355                 360                 365

Pro Ser Lys Leu Asn Asn Gln Phe Gly Ser Met Pro Ala Leu Thr Ile
370                 375                 380

Ala Cys Met Thr Val Gln Gly Gly Glu Thr Met Asn Asn Val Val Gln
```

```
            385                 390                 395                 400
Ala Leu Thr Ser Leu Gly Leu Tyr Thr Val Lys Tyr Pro Asn Leu
                405                 410                 415

Asp Asp Leu Glu Lys Leu Thr Leu Glu His Asp Cys Leu Gln Ile Ile
            420                 425                 430

Thr Lys Asp Glu Ser Ala Leu Asn Ile Ser Gly Tyr Asn Phe Ser Leu
            435                 440                 445

Ser Ala Ala Val Lys Ala Gly Ala Ser Leu Ile Asp Gly Gly Asn Met
450                 455                 460

Leu Glu Thr Ile Lys Val Thr Pro Asn Asn Phe Ser Ser Ile Val Lys
465                 470                 475                 480

Ala Ala Leu Asn Val Lys Arg Arg Glu Gly Met Phe Ile Asp Glu Arg
                485                 490                 495

Pro Gly Asn Arg Asn Pro Tyr Glu Asn Leu Leu Tyr Lys Leu Cys Leu
                500                 505                 510

Ser Gly Glu Gly Trp Pro Tyr Ile Gly Ser Arg Ser Gln Ile Leu Gly
                515                 520                 525

Arg Ser Trp Asp Asn Thr Ser Val Asp Leu Asn Ala Arg Pro Val Thr
            530                 535                 540

Gly Pro Arg Ala Pro Glu Lys Asn Gly Gln Asn Ile Arg Leu Ser Asn
545                 550                 555                 560

Leu Ser Glu Met Gln Glu Ala Ile Val Lys Glu Ala Met Arg Lys Leu
                565                 570                 575

Asp Ser Ser Asp Thr Ile Trp Met Asp Ile Glu Gly Pro Pro Thr Asp
            580                 585                 590

Pro Val Glu Leu Ala Val Phe Gln Pro Ser Ser Gly Asn Tyr Val His
            595                 600                 605

Cys Phe Arg Lys Pro His Asp Glu Lys Gly Phe Lys Asn Gly Ser Arg
610                 615                 620

His Ser His Gly Ile Leu Leu Lys Asp Leu Glu Asp Ala Gln Pro Gly
625                 630                 635                 640

Leu Leu Ser Tyr Val Ile Gly Leu Leu Pro Gln Gly Ser Val Ile Thr
                645                 650                 655

Val Gln Gly Ala Asp Asp Ile Lys Lys Leu Phe Asp Ile His Gly Arg
                660                 665                 670

Lys Asp Leu Lys Leu Val Asp Val Arg Leu Thr Gly Glu Gln Ser Arg
            675                 680                 685

Ile Phe Glu Gln Glu Val Trp Glu Lys Phe Gly His Leu Cys Arg Ala
            690                 695                 700

His Asn Gly Val Ile Val Pro Lys Lys Asn Lys Glu Ala Asn Ser
705                 710                 715                 720

Thr Lys Glu Pro His Cys Ala Leu Leu Asp Cys Ile Met Phe Gln Ser
                725                 730                 735

Val Leu Asp Gly His Leu Pro Asp Thr Ile Pro Ile Gln Leu Leu Pro
            740                 745                 750

Asn Thr Leu Val Phe Gln Ala Lys Ser Ala Phe Val Ile Pro Gly Glu
                755                 760                 765

Asn Leu Tyr Phe Gln Gly Pro Gly Gly Gly Ser His His His His
            770                 775                 780

His
785

<210> SEQ ID NO 122
```

<211> LENGTH: 2440
<212> TYPE: DNA
<213> ORGANISM: artificial
<220> FEATURE:
<223> OTHER INFORMATION: DNA sequence encoding ssBiP-SNAPlike-proTEV1-N
nucleoprotein of the Sabia virus-proTEV2-Histag for expression in
S2 cells

<400> SEQUENCE: 122

| | | | | | |
|---|---|---|---|---|---|
| atgaagttat | gcatattact | ggccgtcgtg | gcctttgttg | gcctctcgct | cgggagatct | 60 |
| gacaaagact | gcgaaatgaa | agaactaca | ttggattcac | cacttgggaa | gttggaactg | 120 |
| agtggatgcg | agcaaggatt | gcatgaaatt | aagctactgg | gaaaaggaac | ttctgctgct | 180 |
| gatgcagttg | aagttccagc | accagcagct | gttcttggag | gtcctgagcc | cctcatgcaa | 240 |
| gccacagcct | ggcttaacgc | atatttccac | cagcctgagg | ccattgagga | atttccagtc | 300 |
| cccgcccttc | accatcctgt | gtttcagcag | agagcttca | cccgccaggt | cctgtggaaa | 360 |
| ttgctgaagg | tggtcaagtt | tggtgaagtg | atttcatatc | agcaacttgc | tgcattggcc | 420 |
| ggtaaccccg | cagctacagc | tgccgtgaaa | actgctctca | gcggaaatcc | tgtgcccatc | 480 |
| ctgatccctt | gtcacagagt | cgtttcatct | tccggagctg | taggtggcta | tgaaggagga | 540 |
| ctggcagtta | aggagtggct | gctggctcat | gaaggtcata | gacttggaaa | gcctgggctg | 600 |
| ggtcctgctg | gtataggcgc | gccagggtcc | ctaggtggcg | gatccgaaaa | cctgtacttc | 660 |
| cagagcgata | tcagcaactc | aaaggaaatc | cccagcttca | gatggactca | atccctgaga | 720 |
| agagggctca | gtgagttcac | aacaccgtg | aagaccgatg | ttctgaggga | tgccaaaatg | 780 |
| atacttgatg | gtcttgattt | caatcaagtc | tctcttgttc | aaagaatcct | tagaaagtct | 840 |
| aaaaggaatg | atggtgatct | tgataaactg | agagacctaa | ataagaagt | ggacaacctg | 900 |
| atgagcatga | gagttccca | aagagacaca | atcttaaaac | ttggtgatct | caacaaatct | 960 |
| gaactgatgg | atcttgcatc | agacctggag | aaactgaaaa | gaaagttgg | acaaacagaa | 1020 |
| agatcagcct | caggaggtgt | gtacctggga | aacctttccc | aatcacagct | caccaaaagg | 1080 |
| tctgatcttt | taaggaaact | tggttttcaa | cagcagcaag | tgaggtctcc | aggggttgta | 1140 |
| aggatttggg | acgtagctga | tccgaacagg | ctgaataatc | aatttggatc | tgtccctgca | 1200 |
| ctgacaatcg | cttgtatgac | taaacaaagt | gacaatacca | tgggggatgt | tgttcaggca | 1260 |
| ctaacatctt | tgggacttct | ttatacagtt | aagttcccca | acctgattga | cctagaaaaa | 1320 |
| cttacagcag | aacatgactg | tcttcaaata | gtgactaaag | atgagagcgg | cttgaacatc | 1380 |
| tcaggatata | actatagtct | ttctgcagct | gttaaagctg | gtgcaacgct | tctggatggt | 1440 |
| ggtaacatgc | tggaaaccat | aaggatcact | cctgacaact | tttctcagat | cataaagaca | 1500 |
| accctatcca | taagaaaaa | ggaaggcatg | tttgtagatg | agaaacctgg | aaatagaaac | 1560 |
| ccttatgaaa | accttctgta | caaaatctgc | cttttcaggag | aaggttggcc | ttacattggc | 1620 |
| tccagatccc | agatcaaggg | taggtcatgg | gaaaacacca | ctgttgattt | aagcacaaag | 1680 |
| ccccaacaag | ggccgagaac | accagaaaag | gcaggtcaga | acattagact | ctcccacttg | 1740 |
| actgagttgc | aagagtcagt | tgtgagagag | gcaatgggta | agattgaccc | aactctgaca | 1800 |
| acatggattg | acattgaggg | taccagtaat | gatccggttg | aattagcatt | gtaccaacca | 1860 |
| gacacaggta | attatatcct | ctgttatagg | aaaccacatg | atgagaaggg | gttcaaaaat | 1920 |
| ggtagcaggc | attcacatgg | gatgttgcta | aaggacctag | aatctgcaca | gccaggcttg | 1980 |
| ctcagctatg | ttatagggct | ccttcctcaa | aacatggtcc | tcaccaccca | aggttcgat | 2040 |
| gatataaggc | gcttagtaga | tacacacggt | cgcaaagact | taaagattgt | cgacattaaa | 2100 |

```
ttggcatctg aacaggcgag aaagtttgag gagccaatct ggtcagattt tggtcaccto    2160 tgtaagaaac acaatggagt tattgtgcca agaaaaaga aagacaaaga catcccacag    2220
tcctcagagc acactgtgc cctacttgat tgtctaatgt ttcagtcagc catagcaggc    2280
caaccacctc aaaccaaact ggaaggttta ttgcctgatg cattgctctt cacactggag    2340
gcagcattca ccatcccggg agagaatcta tattttcaag ggcccggcgg aggtagtcac    2400
catcatcacc atcactaatg accggtgcgg ccgcaagctt                         2440
```

<210> SEQ ID NO 123
<211> LENGTH: 787
<212> TYPE: PRT
<213> ORGANISM: artificial
<220> FEATURE:
<223> OTHER INFORMATION: Amino acid sequence of fusion protein
      [SNAPlike-proTEV1-SAB.N-proTEV2-Histag]

<400> SEQUENCE: 123

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Asn
        195                 200                 205

Ser Lys Glu Ile Pro Ser Phe Arg Trp Thr Gln Ser Leu Arg Arg Gly
    210                 215                 220

Leu Ser Glu Phe Thr Thr Pro Val Lys Thr Asp Val Leu Arg Asp Ala
225                 230                 235                 240

Lys Met Ile Leu Asp Gly Leu Asp Phe Asn Gln Val Ser Leu Val Gln
                245                 250                 255

Arg Ile Leu Arg Lys Ser Lys Arg Asn Asp Gly Asp Leu Asp Lys Leu
            260                 265                 270

Arg Asp Leu Asn Lys Glu Val Asp Asn Leu Met Ser Met Lys Ser Ser
        275                 280                 285

Gln Arg Asp Thr Ile Leu Lys Leu Gly Asp Leu Asn Lys Ser Glu Leu

```
            290                 295                 300
Met Asp Leu Ala Ser Asp Leu Glu Lys Leu Lys Arg Lys Val Gly Gln
305                 310                 315                 320

Thr Glu Arg Ser Ala Ser Gly Gly Val Tyr Leu Gly Asn Leu Ser Gln
                325                 330                 335

Ser Gln Leu Thr Lys Arg Ser Asp Leu Leu Arg Lys Leu Gly Phe Gln
                340                 345                 350

Gln Gln Gln Val Arg Ser Pro Gly Val Val Arg Ile Trp Asp Val Ala
                355                 360                 365

Asp Pro Asn Arg Leu Asn Asn Gln Phe Gly Ser Val Pro Ala Leu Thr
370                 375                 380

Ile Ala Cys Met Thr Lys Gln Ser Asp Asn Thr Met Gly Asp Val Val
385                 390                 395                 400

Gln Ala Leu Thr Ser Leu Gly Leu Leu Tyr Thr Val Lys Phe Pro Asn
                405                 410                 415

Leu Ile Asp Leu Glu Lys Leu Thr Ala Glu His Asp Cys Leu Gln Ile
                420                 425                 430

Val Thr Lys Asp Glu Ser Gly Leu Asn Ile Ser Gly Tyr Asn Tyr Ser
                435                 440                 445

Leu Ser Ala Ala Val Lys Ala Gly Ala Thr Leu Leu Asp Gly Gly Asn
450                 455                 460

Met Leu Glu Thr Ile Arg Ile Thr Pro Asp Asn Phe Ser Gln Ile Ile
465                 470                 475                 480

Lys Thr Thr Leu Ser Ile Lys Lys Glu Gly Met Phe Val Asp Glu
                485                 490                 495

Lys Pro Gly Asn Arg Asn Pro Tyr Glu Asn Leu Leu Tyr Lys Ile Cys
                500                 505                 510

Leu Ser Gly Glu Gly Trp Pro Tyr Ile Gly Ser Arg Ser Gln Ile Lys
                515                 520                 525

Gly Arg Ser Trp Glu Asn Thr Thr Val Asp Leu Ser Thr Lys Pro Gln
                530                 535                 540

Gln Gly Pro Arg Thr Pro Glu Lys Ala Gly Gln Asn Ile Arg Leu Ser
545                 550                 555                 560

His Leu Thr Glu Leu Gln Glu Ser Val Val Arg Glu Ala Met Gly Lys
                565                 570                 575

Ile Asp Pro Thr Leu Thr Thr Trp Ile Asp Ile Glu Gly Thr Ser Asn
                580                 585                 590

Asp Pro Val Glu Leu Ala Leu Tyr Gln Pro Asp Thr Gly Asn Tyr Ile
                595                 600                 605

Leu Cys Tyr Arg Lys Pro His Asp Glu Lys Gly Phe Lys Asn Gly Ser
610                 615                 620

Arg His Ser His Gly Met Leu Leu Lys Asp Leu Glu Ser Ala Gln Pro
625                 630                 635                 640

Gly Leu Leu Ser Tyr Val Ile Gly Leu Leu Pro Gln Asn Met Val Leu
                645                 650                 655

Thr Thr Gln Gly Ser Asp Asp Ile Arg Arg Leu Val Asp Thr His Gly
                660                 665                 670

Arg Lys Asp Leu Lys Ile Val Asp Ile Lys Leu Ala Ser Glu Gln Ala
                675                 680                 685

Arg Lys Phe Glu Glu Pro Ile Trp Ser Asp Phe Gly His Leu Cys Lys
                690                 695                 700

Lys His Asn Gly Val Ile Val Pro Lys Lys Lys Asp Lys Asp Ile
705                 710                 715                 720
```

```
Pro Gln Ser Ser Glu Pro His Cys Ala Leu Leu Asp Cys Leu Met Phe
                725                 730                 735

Gln Ser Ala Ile Ala Gly Gln Pro Pro Gln Thr Lys Leu Glu Gly Leu
            740                 745                 750

Leu Pro Asp Ala Leu Leu Phe Thr Leu Glu Ala Ala Phe Thr Ile Pro
        755                 760                 765

Gly Glu Asn Leu Tyr Phe Gln Gly Pro Gly Gly Ser His His His
    770                 775                 780

His His His
785

<210> SEQ ID NO 124
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Omsk virus-Histag for expression in S2 cells

<400> SEQUENCE: 124
atgaaactat g

```
                35                  40                  45
Ala Pro Ala Ala Val Leu Gly Gly Pro Glu Pro Leu Met Gln Ala Thr
            50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                85                  90                  95
Arg Gln Val Leu Trp Lys Leu Lys Val Lys Phe Gly Glu Val
            100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
            130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Gly
            180                 185                 190
Gly Gly Leu Glu Lys Leu Lys Met Lys Gly Leu Thr Tyr Thr Met Cys
        195                 200                 205
Asp Lys Ala Lys Phe Thr Trp Lys Arg Ala Pro Thr Asp Ser Gly His
210                 215                 220
Asp Thr Val Val Met Glu Val Ala Phe Ser Gly Thr Lys Pro Cys Arg
225                 230                 235                 240
Ile Pro Val Arg Ala Val Ala His Gly Ser Pro Asp Val Asp Val Ala
                245                 250                 255
Met Leu Ile Thr Pro Asn Pro Thr Ile Glu Asn Asn Gly Gly Gly Phe
            260                 265                 270
Ile Glu Met Gln Leu Pro Pro Gly Asp Asn Ile Ile Tyr Val Gly Glu
        275                 280                 285
Leu Lys His Gln Trp Phe Gln Lys Gly Ser Ser Ile Gly Gly Gly Gly
    290                 295                 300
His His His His His His
305                 310

<210> SEQ ID NO 126
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Kyasanur Forest Disease virus-Histag for expression
      in S2 cells

<400> SEQUENCE: 126
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttgagggtc ctgagcccct catgcaagcc     240
acagcctggc ttaacgcata tttccaccag cctgaggcca ttgaggaatt ccagtccccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
```

```
aaccccgcag ctacagctgc cgtgaaaact gctctcagcg aaatcctgt gcccatcctg    480 atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc aggaggtggc gggcttgaaa aacttaagat gaaagggatg    660
acatacacgg tttgtgaggg atcaaaattt gcttggaaaa ggccgccaac cgacagtgga    720
catgataccg tagtcatgga ggtgacttac accgggagca agccatgcag ataccagtg    780 agagccgtgg cccatggaga acccaatgtt aacgtggcaa gtctaataac cccaaaccca    840
tccatggaaa caactggagg agggttcgtt gagctacagc taccaccagg agacaacatc    900
atctatgttg gtgagctgag ccaccagtgg tttcagaagg gcagcacaat tggcggaggt    960
ggccatcacc atcaccatca ctgatgaccg gt    992
```

<210> SEQ ID NO 127
<211> LENGTH: 310
<212> TYPE: PRT
<213> ORGANISM: artificial
<220> FEATURE:
<223> OTHER INFORMATION: Amino acid sequence of fusion protein [SNAPlike-KYA.EDIII-Histag]

<400> S

Ser Leu Ile Thr Pro Asn Pro Ser Met Glu Thr Gly Gly Gly Phe
            260                 265                 270

Val Glu Leu Gln Leu Pro Pro Gly Asp Asn Ile Ile Tyr Val Gly Glu
        275                 280                 285

Leu Ser His Gln Trp Phe Gln Lys Gly Ser Thr Ile Gly Gly Gly Gly
    290                 295                 300

His His His His His His
305                 310

<210> SEQ ID NO 128
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Alkhumra virus-Histag for expression in S2 cells

<400> SEQUENCE: 128
atgaaactat gtattctact tgcagttgtt gcgttcgtag gattgtcctt aagatctgac      60
aaagactgcg aaatgaaaag aactacattg gattcaccac ttgggaagtt ggaactgagt    120
ggatgcgagc aaggattgca tgaaattaag ctactgggaa aaggaacttc tgctgctgat    180
gcagttgaag ttccagcacc agcagctgtt cttggaggtc ctgagcccct catgcaagcc    240
acagcctggc ttaacgcata tttccaccag cctgaggcca ttgaggaatt tccagtcccc    300
gcccttcacc atcctgtgtt tcagcaggag agcttcaccc gccaggtcct gtggaaattg    360
ctgaaggtgg tcaagtttgg tgaagtgatt tcatatcagc aacttgctgc attggccggt    420
aaccccgcag ctacagctgc cgtgaaaact gctctcagcg aaatcctgt gcccatcctg     480 atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc aggaggtggc gggcttgaaa aactcaagat gaaaggaatg    660
acatacacgg tctgtgaggg atcaaagttt gcttggaaga ggccgccaac cgacagtggg    720
catgacactg tggtcatgga agtgacttac actgggagca agccatgcag aataccagtg    780
agagccgtgg cccatggaga acctaatgtc aatgtagcta gcctgataac tccaaatcca    840
tccatggaga caactggagg aggtttcgtt gaactgcagc tgccaccagg agacaacatc    900
atctatgttg gtgagctgag tcaccagtgg tttcagaagg gtagtacaat aggcggaggt    960
ggccatcacc atcaccatca ctgatgaccg gt                                  992

<210> SEQ ID NO 129
<211> LENGTH: 310
<212> TYPE: PRT
<213> ORGANISM: artificial
<220> FEATURE:
<223> OTHER INFORMATION: Amino acid sequence of fusion protein
      [SNAPlike-ALK.EDIII-Histag]

<400> SEQUENCE: 129

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
             85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
            165                 170                 175

Leu Gly Lys Pro Gly Leu Gly Pro Ala Gly Ile Gly Ala Pro Gly Gly
            180                 185                 190

Gly Gly Leu Glu Lys Leu Lys Met Lys Gly Met Thr Tyr Thr Val Cys
            195                 200                 205

Glu Gly Ser Lys Phe Ala Trp Lys Arg Pro Pro Thr Asp Ser Gly His
210                 215                 220

Asp Thr Val Val Met Glu Val Thr Tyr Thr Gly Ser Lys Pro Cys Arg
225                 230                 235                 240

Ile Pro Val Arg Ala Val Ala His Gly Glu Pro Asn Val Asn Val Ala
            245                 250                 255

Ser Leu Ile Thr Pro Asn Pro Ser Met Glu Thr Gly Gly Gly Phe
            260                 265                 270

Val Glu Leu Gln Leu Pro Pro Gly Asp Asn Ile Ile Tyr Val Gly Glu
            275                 280                 285

Leu Ser His Gln Trp Phe Gln Lys Gly Ser Thr Ile Gly Gly Gly Gly
            290                 295                 300

His His His His His His
305                 310

<210> SEQ ID NO 130
<211> LENGTH: 1288
<212> TYPE: DNA
<213> ORGANISM: artificial
<220> FEATURE:
<223> OTHER INFORMATION: DNA sequence encoding ssBiP- Glycoprotein GP1
      from Lassa virus- SNAPlike-Histag for expression in S2 cells

<400> SEQUENCE: 130
atgaagttat gcatattact ggccgtcgtg gcctttgttg gcctctcgct cgggagatct      60
accagtctgt acaagggggt gtacgagctt cagactctgg aactgaacat ggagacactc     120
aacatgacca tgcctctctc ctgcacaaag aacaacagtc atcattacat aatggtgggc     180
aatgagacag gactggaact gaccttgacc aacacgagca tcatcaatca caagttctgc     240
aacctgtctg atgcccacaa gaagaacctc tacgaccacg ctctgatgag cataatctca     300
actttccact tgtccatccc caacttcaac cagtacgagg caatgagctg cgatttcaat     360
gggggcaaga tcagtgtgca gtacaacctg agtcacagct acgctgggga tgcagccaac     420
cattgtggca ctgtggcaaa cggtgtgttg cagactttca tgaggatggc ttggggcggg     480
agctacatcg ctcttgactc aggccgtggc aactgggact gtatcatgac tagttaccaa     540
tacctgataa tccagaacac aacctgggaa gatcactgcc aattctccag accatctccc     600

```
atcggctacc tcgggctcct ctcacaaagg actagagata tttacatcag tagaagattg      660
ctgcggccgc acggcggagg tagcaaagac tgcgaaatga agcgcaccac cctggatagc      720
cctctgggca agctggaact gtctgggtgc gaacagggcc tgcacgagat caagctgctg      780
ggcaaaggaa catctgccgc cgacgccgtg aagtgcctg ccccagccgc cgtgctgggc       840
ggaccagagc cactgatgca ggccaccgcc tggctcaacg cctactttca ccagcctgag      900
gccatcgagg agttccctgt gccagccctg caccacccag tgttccagca ggagagcttt      960
acccgccagg tgctgtggaa actgctgaaa gtggtgaagt cggagaggt catcagctac      1020 cagcagctgg ccgccctggc cggcaatccc gccgccaccg ccgccgtgaa aaccgccctg     1080
agcggaaatc ccgtgcccat tctgatcccc tgccaccggg tggtgtctag ctctggcgcc     1140 gtgggggggct acgagggcgg gctcgccgtg aaagagtggc tgctggccca cgagggccac     1200
agactgggca gcctgggct gggtcctgca ggtataggcg cgccagggtc cctggagcat      1260
catcatcatc atcattgatg acgggccc                                         1288
```

<210> SEQ ID NO 131
<211> LENGTH: 407
<212> TYPE: PRT
<213> ORGANISM: artificial
<220> FEATURE:
<223> OTHER INFORMATION: Amino acid sequence of fusion protein
      [LAS.ectoGP1- SNAPlike-Histag]

<400> SEQUENCE: 131

```
Arg Ser Thr Ser Leu Tyr Lys Gly Val Tyr Glu Leu Gln Thr Leu Glu
1               5                   10                  15

Leu Asn Met Glu Thr Leu Asn Met Thr Met Pro Leu Ser Cys Thr Lys
                20                  25                  30

Asn Asn Ser His His Tyr Ile Met Val Gly Asn Glu Thr Gly Leu Glu
            35                  40                  45

Leu Thr Leu Thr Asn Thr Ser Ile Ile Asn His Lys Phe Cys Asn Leu
        50                  55                  60

Ser Asp Ala His Lys Lys Asn Leu Tyr Asp His Ala Leu Met Ser Ile
65                  70                  75                  80

Ile Ser Thr Phe His Leu Ser Ile Pro Asn Phe Asn Gln Tyr Glu Ala
                85                  90                  95

Met Ser Cys Asp Phe Asn Gly Gly Lys Ile Ser Val Gln Tyr Asn Leu
                100                 105                 110

Ser His Ser Tyr Ala Gly Asp Ala Ala Asn His Cys Gly Thr Val Ala
            115                 120                 125

Asn Gly Val Leu Gln Thr Phe Met Arg Met Ala Trp Gly Gly Ser Tyr
        130                 135                 140

Ile Ala Leu Asp Ser Gly Arg Gly Asn Trp Asp Cys Ile Met Thr Ser
145                 150                 155                 160

Tyr Gln Tyr Leu Ile Ile Gln Asn Thr Thr Trp Glu Asp His Cys Gln
                165                 170                 175

Phe Ser Arg Pro Ser Pro Ile Gly Tyr Leu Gly Leu Ser Gln Arg
                180                 185                 190

Thr Arg Asp Ile Tyr Ile Ser Arg Arg Leu Leu Arg Pro His Gly Gly
            195                 200                 205

Gly Ser Lys Asp Cys Glu Met Lys Arg Thr Thr Leu Asp Ser Pro Leu
        210                 215                 220

Gly Lys Leu Glu Leu Ser Gly Cys Glu Gln Gly Leu His Glu Ile Lys
```

```
                225                 230                 235                 240
Leu Leu Gly Lys Gly Thr Ser Ala Ala Asp Ala Val Glu Val Pro Ala
                    245                 250                 255
Pro Ala Ala Val Leu Gly Gly Pro Glu Pro Leu Met Gln Ala Thr Ala
                260                 265                 270
Trp Leu Asn Ala Tyr Phe His Gln Pro Glu Ala Ile Glu Glu Phe Pro
                275                 280                 285
Val Pro Ala Leu His His Pro Val Phe Gln Gln Glu Ser Phe Thr Arg
            290                 295                 300
Gln Val Leu Trp Lys Leu Leu Lys Val Val Lys Phe Gly Glu Val Ile
305                 310                 315                 320
Ser Tyr Gln Gln Leu Ala Ala Leu Ala Gly Asn Pro Ala Ala Thr Ala
                    325                 330                 335
Ala Val Lys Thr Ala Leu Ser Gly Asn Pro Val Pro Ile Leu Ile Pro
                340                 345                 350
Cys His Arg Val Val Ser Ser Gly Ala Val Gly Gly Tyr Glu Gly
                355                 360                 365
Gly Leu Ala Val Lys Glu Trp Leu Leu Ala His Glu Gly His Arg Leu
            370                 375                 380
Gly Lys Pro Gly Leu Gly Pro Ala Gly Ile Gly Ala Pro Gly Ser Leu
385                 390                 395                 400
Glu His His His His His His
            405

<210> SEQ ID NO 132
<211> LENGTH: 1264
<212> TYPE: DNA
<213> ORGANISM: artificial
<220> FEATURE:
<223> OTHER INFORMATION: DNA sequence encoding ssBiP- Glycoprotein GP1
      from Junin virus- SNAPlike-Histag for expression in S2 cells

<400> SEQUENCE: 132
atgaagttat gcatattact ggccgtcgtg gcctttgttg gcctctcgct cgggagatct      60
gaggaggctt tcaagatcgg cctgcacacc gagttccaga cggtgtcctt ctcgatggtg     120
ggcctcttct ccaacaaccc acacgacctg cctttgttgt gtaccttgaa caagagccat     180
ctgtacatta aggggggcaa cgcttcattc cagatcagct cgacgacat cgcggtgttg      240
ttgccacagt acgacgttat catccagcac ccagcagaca tgagctggtg ctccaagagt     300
gatgatcaga tttggttgtc tcagtggttc atgaatgctg tgggacatga ttggcaccta     360
gacccaccat tcctgtgtag aaccgtaca aagacagaag gcttcatctt ccaagtcaac      420
acctccaaga ctggtgttaa tgaaaattat gctaagaagt tcaagactgg catgcaccac     480
ttgtatagag agtaccctga ctcttgcccg aacggcaagc tgtgcttaat gaaggcacaa     540
cctaccagtt ggcctctcca atgtccactc gaccacgtca acacattaca cttccttaca     600
agaggcaaga acattcagct tccaaggagg tccttgaagc ggccgcacgg cggaggtagc     660
aaagactgcg aaatgaagcg caccaccctg gatagccctc tgggcaagct ggaactgtct     720
gggtgcgaac agggcctgca cgagatcaag ctgctgggca aggaacatc tgccgccgac     780
gccgtggaag tgcctgcccc agccgccgtg ctgggcggac agagccact gatgcaggcc     840
accgcctggc tcaacgccta ctttcaccag cctgaggcca tcgaggagtt ccctgtgcca     900
gccctgcacc acccagtgtt ccagcaggag agctttaccc gccaggtgct gtggaaactg     960
ctgaaagtgg tgaagttcgg agaggtcatc agctaccagc agctggccgc cctggccggc    1020
```

```
aatcccgccg ccaccgccgc cgtgaaaacc gccctgagcg gaaatcccgt gcccattctg    1080
atcccctgcc accgggtggt gtctagctct ggcgccgtgg ggggctacga gggcgggctc    1140
gccgtgaaag agtggctgct ggcccacgag ggccacagac tgggcaagcc tgggctgggt    1200
cctgcaggta taggcgcgcc agggtccctg gagcatcatc atcatcatca ttgatgacgg    1260
gccc                                                                1264
```

```
<210> SEQ ID NO 133
<211> LENGTH: 399
<212> TYPE: PRT
<213> ORGANISM: artificial
<220> FEATURE:
<223> OTHER INFORMATION: Amino acid sequence of fusion protein
      [JUN.ectoGP1- SNAPlike-Histag]

<400> SEQUENCE: 133
```

```
Arg Ser Glu Glu Ala Phe Lys Ile Gly Leu His Thr Glu Phe Gln Thr
1               5                   10                  15

Val Ser Phe Ser Met Val Gly Leu Phe Ser Asn Asn Pro His Asp Leu
            20                  25                  30

Pro Leu Leu Cys Thr Leu Asn Lys Ser His Leu Tyr Ile Lys Gly Gly
        35                  40                  45

Asn Ala Ser Phe Gln Ile Ser Phe Asp Asp Ile Ala Val Leu Leu Pro
50                  55                  60

Gln Tyr Asp Val Ile Ile Gln His Pro Ala Asp Met Ser Trp Cys Ser
65                  70                  75                  80

Lys Ser Asp Asp Gln Ile Trp Leu Ser Gln Trp Phe Met Asn Ala Val
            85                  90                  95

Gly His Asp Trp His Leu Asp Pro Pro Phe Leu Cys Arg Asn Arg Thr
        100                 105                 110

Lys Thr Glu Gly Phe Ile Phe Gln Val Asn Thr Ser Lys Thr Gly Val
    115                 120                 125

Asn Glu Asn Tyr Ala Lys Lys Phe Lys Thr Gly Met His His Leu Tyr
130                 135                 140

Arg Glu Tyr Pro Asp Ser Cys Pro Asn Gly Lys Leu Cys Leu Met Lys
145                 150                 155                 160

Ala Gln Pro Thr Ser Trp Pro Leu Gln Cys Pro Leu Asp His Val Asn
            165                 170                 175

Thr Leu His Phe Leu Thr Arg Gly Lys Asn Ile Gln Leu Pro Arg Arg
        180                 185                 190

Ser Leu Lys Arg Pro His Gly Gly Ser Lys Asp Cys Glu Met Lys
    195                 200                 205

Arg Thr Thr Leu Asp Ser Pro Leu Gly Lys Leu Glu Leu Ser Gly Cys
210                 215                 220

Glu Gln Gly Leu His Glu Ile Lys Leu Leu Gly Lys Gly Thr Ser Ala
225                 230                 235                 240

Ala Asp Ala Val Glu Val Pro Ala Pro Ala Ala Val Leu Gly Gly Pro
            245                 250                 255

Glu Pro Leu Met Gln Ala Thr Ala Trp Leu Asn Ala Tyr Phe His Gln
        260                 265                 270

Pro Glu Ala Ile Glu Glu Phe Pro Val Pro Ala Leu His His Pro Val
    275                 280                 285

Phe Gln Gln Glu Ser Phe Thr Arg Gln Val Leu Trp Lys Leu Leu Lys
290                 295                 300
```

```
Val Val Lys Phe Gly Glu Val Ile Ser Tyr Gln Gln Leu Ala Ala Leu
305                 310                 315                 320

Ala Gly Asn Pro Ala Ala Thr Ala Ala Val Lys Thr Ala Leu Ser Gly
            325                 330                 335

Asn Pro Val Pro Ile Leu Ile Pro Cys His Arg Val Val Ser Ser Ser
            340                 345                 350

Gly Ala Val Gly Gly Tyr Glu Gly Gly Leu Ala Val Lys Glu Trp Leu
            355                 360                 365

Leu Ala His Glu Gly His Arg Leu Gly Lys Pro Gly Leu Gly Pro Ala
        370                 375                 380

Gly Ile Gly Ala Pro Gly Ser Leu Glu His His His His His
385                 390                 395
```

<210> SEQ ID NO 134
<211> LENGTH: 1297
<212> TYPE: DNA
<213> ORGANISM: artificial
<220> FEATURE:
<223> OTHER INFORMATION: DNA sequence encoding ssBiP- Glycoprotein GP1 from Machupo virus- SNAPlike-Histag for expression in S2 cells

<400> SEQUENCE: 134

```
atgaagttat gcatattact ggccgtcgtg gcctttgttg gcctctcgct cgggagatct      60
gacggcacat tcaagatcgg cctgcacacg gagttccagt cagtcaccct caccatgcag     120
agactttgg ctaaccattc aaacgagctc ccgtctctct gcatgctgaa caacagtttc     180
tattatatga ggggaggtgt gaacaccttc ctgatccgtg tttctgatat ttcagtcctc     240
atgaaggagt acgatgtatc aatctacgag ccagaggacc tcggaaactg tctgaacaag     300
tctgactcaa gctgggctat ccattggttc tcaaacgctt tgggacatga ctggctgatg     360
gaccctccaa tgctctgtag aaacaagaca agaaggagg gatctaacat ccaattcaac     420
atcagcaagg ctgatgatgc cagagtgtat ggaaagaaga tcagaaacgg tatgaggcat     480
ctcttcaggg gcttccatga cccgtgtgag gaagggaagg tgtgctacct gaccatcaac     540
cagtgtggtg accccagttc cttcgactac tgtggcgtga accatctgtc caagtgtcag     600
ttcgaccatg tgaacaccct gcatttcctg gtgagaagta agacacatct caacttcgag     660
aggtctttga gcggccgca cggcggaggt agcaaagact gcgaaatgaa gcgcaccacc     720
ctggatagcc ctctgggcaa gctggaactg tctgggtgcg aacagggcct gcacgagatc     780
aagctgctgg caaaggaac atctgccgcc gacgccgtgg aagtgcctgc cccagccgcc     840
gtgctgggcg accagagcc actgatgcag gccaccgcct ggctcaacgc ctactttcac     900
cagcctgagg ccatcgagga gttccctgtg ccagccctgc accaccagt gttccagcag     960
gagagcttta cccgccaggt gctgtggaaa ctgctgaaag tggtgaagtt cggagaggtc    1020
atcagctacc agcagctggc cgccctggcc ggcaatcccg ccgccaccgc cgccgtgaaa    1080
accgccctga gcggaaatcc cgtgcccatt ctgatcccct gccaccgggt ggtgtctagc    1140
tctggcgccg tggggggcta cgagggcggg ctcgccgtga agagtggct gctggcccac    1200
gagggccaca gactgggcaa gcctgggctg gtcctgcag gtataggcgc gccagggtcc    1260
ctggagcatc atcatcatca tcattgatga cgggccc                           1297
```

<210> SEQ ID NO 135
<211> LENGTH: 410
<212> TYPE: PRT
<213> ORGANISM: artificial
<220> FEATURE:

-continued

<223> OTHER INFORMATION: Amino acid sequence of fusion protein
[MAC.ectoGP1- SNAPlike-Histag]

<400> SEQUENCE: 135

Arg Ser Asp Gly Thr Phe Lys Ile Gly Leu His Thr Glu Phe Gln Ser
1 5 10 15

Val Thr Leu Thr Met Gln Arg Leu Leu Ala Asn His Ser Asn Glu Leu
20 25 30

Pro Ser Leu Cys Met Leu Asn Asn Ser Phe Tyr Tyr Met Arg Gly Gly
35 40 45

Val Asn Thr Phe Leu Ile Arg Val Ser Asp Ile Ser Val Leu Met Lys
50 55 60

Glu Tyr Asp Val Ser Ile Tyr Glu Pro Glu Asp Leu Gly Asn Cys Leu
65 70 75 80

Asn Lys Ser Asp Ser Ser Trp Ala Ile His Trp Phe Ser Asn Ala Leu
85 90 95

Gly His Asp Trp Leu Met Asp Pro Pro Met Leu Cys Arg Asn Lys Thr
100 105 110

Lys Lys Glu Gly Ser Asn Ile Gln Phe Asn Ile Ser Lys Ala Asp Asp
115 120 125

Ala Arg Val Tyr Gly Lys Lys Ile Arg Asn Gly Met Arg His Leu Phe
130 135 140

Arg Gly Phe His Asp Pro Cys Glu Glu Gly Lys Val Cys Tyr Leu Thr
145 150 155 160

Ile Asn Gln Cys Gly Asp Pro Ser Ser Phe Asp Tyr Cys Gly Val Asn
165 170 175

His Leu Ser Lys Cys Gln Phe Asp His Val Asn Thr Leu His Phe Leu
180 185 190

Val Arg Ser Lys Thr His Leu Asn Phe Glu Arg Ser Leu Lys Arg Pro
195 200 205

His Gly Gly Gly Ser Lys Asp Cys Glu Met Lys Arg Thr Thr Leu Asp
210 215 220

Ser Pro Leu Gly Lys Leu Glu Leu Ser Gly Cys Glu Gln Gly Leu His
225 230 235 240

Glu Ile Lys Leu Leu Gly Lys Gly Thr Ser Ala Ala Asp Ala Val Glu
245 250 255

Val Pro Ala Pro Ala Ala Val Leu Gly Gly Pro Glu Pro Leu Met Gln
260 265 270

Ala Thr Ala Trp Leu Asn Ala Tyr Phe His Gln Pro Glu Ala Ile Glu
275 280 285

Glu Phe Pro Val Pro Ala Leu His His Pro Val Phe Gln Gln Glu Ser
290 295 300

Phe Thr Arg Gln Val Leu Trp Lys Leu Leu Lys Val Val Lys Phe Gly
305 310 315 320

Glu Val Ile Ser Tyr Gln Gln Leu Ala Ala Leu Ala Gly Asn Pro Ala
325 330 335

Ala Thr Ala Ala Val Lys Thr Ala Leu Ser Gly Asn Pro Val Pro Ile
340 345 350

Leu Ile Pro Cys His Arg Val Val Ser Ser Ser Gly Ala Val Gly Gly
355 360 365

Tyr Glu Gly Gly Leu Ala Val Lys Glu Trp Leu Leu Ala His Glu Gly
370 375 380

His Arg Leu Gly Lys Pro Gly Leu Gly Pro Ala Gly Ile Gly Ala Pro
385 390 395 400

Gly Ser Leu Glu His His His His His His
            405                 410

<210> SEQ ID NO 136
<211> LENGTH: 1246
<212> TYPE: DNA
<213> ORGANISM: artificial
<220> FEATURE:
<223> OTHER INFORMATION: DNA sequence encoding ssBiP- Glycoprotein GP1
      from Guanarito virus- SNAPlike-Histag for expression in S2 cells

<400> SEQUENCE: 136

```
atgaagttat gcatattact ggccgtcgtg gcctttgttg cctctcgct cgggagatct      60
ttcaaggttg gtcatcatac gaacttcgag tcgttcacgg ttaagctggg aggtgtcttc    120
catgaattgc cttcgctgtg tagggtcaac aactcctaca gtctgatcag gctctcccat    180
aacagtaacc aggcattgtc ggttgagtac gtggatgtgc accctgtcct ctgttcgtcc    240
agtccaacca tcctcgacaa ctacacgcaa tgtatcaagg ctcgccaga gttcgattgg    300
attctcgggt ggacgatcaa gggattggga catgacttct tgagagatcc aagaatctgc    360
tgtgagccta agaagacgac taacgctgag ttcacgttcc aattgaactt gacggatagt    420
cctgagaccc atcactacag gagcaagatt gaggtaggca tccgacactt gttcgggaac    480
tacatcacca cgatagcta ctcgaagatg tccgtggtta tgaggaacac cacctgggaa    540
ggtcaatgct cgaacagtca tgtgaacacg ctgagattcc tcgttaagaa cgcaggttac    600
ctcgttggaa ggaagccact gcggccgcac ggcggaggta gcaaagactg cgaaatgaag    660
cgcaccaccc tggatagccc tctgggcaag ctggaactgt ctgggtgcga acagggcctg    720
cacgagatca agctgctggg caaaggaaca tctgccgccg acgccgtgga agtgcctgcc    780
ccagccgccg tgctgggcgg accagagcca ctgatgcagg ccaccgcctg gctcaacgcc    840
tactttcacc agcctgaggc catcgaggag ttccctgtgc agcccctgca ccacccagtg    900
ttccagcagg agagctttac ccgccaggtg ctgtggaaac tgctgaaagt ggtgaagttc    960
ggagaggtca tcagctacca gcagctggcc gccctggccg gcaatcccgc cgccaccgcc   1020
gccgtgaaaa ccgccctgag cggaaatccc gtgcccattc tgatcccctg ccaccgggtg   1080
gtgtctagct ctggcgccgt ggggggctac gagggcgggc tcgccgtgaa agagtggctg   1140
ctggcccacg agggccacag actgggcaag cctgggctgg tcctgcagg tataggcgcg   1200
ccagggtccc tggagcatca tcatcatcat cattgatgac gggccc               1246
```

<210> SEQ ID NO 137
<211> LENGTH: 393
<212> TYPE: PRT
<213> ORGANISM: artificial
<220> FEATURE:
<223> OTHER INFORMATION: Amino acid sequence of fusion protein
      [GUA.ectoGP1- SNAPlike-Histag]

<400> SEQUENCE: 137

Arg Ser Phe Lys Val Gly His His Thr Asn Phe Glu Ser Phe Thr Val
1               5                   10                  15

Lys Leu Gly Gly Val Phe His Glu Leu Pro Ser Leu Cys Arg Val Asn
            20                  25                  30

Asn Ser Tyr Ser Leu Ile Arg Leu Ser His Asn Ser Asn Gln Ala Leu
        35                  40                  45

Ser Val Glu Tyr Val Asp Val His Pro Val Leu Cys Ser Ser Ser Pro
    50                  55                  60

Thr Ile Leu Asp Asn Tyr Thr Gln Cys Ile Lys Gly Ser Pro Glu Phe
65                  70                  75                  80

Asp Trp Ile Leu Gly Trp Thr Ile Lys Gly Leu Gly His Asp Phe Leu
            85                  90                  95

Arg Asp Pro Arg Ile Cys Cys Glu Pro Lys Lys Thr Thr Asn Ala Glu
            100                 105                 110

Phe Thr Phe Gln Leu Asn Leu Thr Asp Ser Pro Glu Thr His His Tyr
            115                 120                 125

Arg Ser Lys Ile Glu Val Gly Ile Arg His Leu Phe Gly Asn Tyr Ile
            130                 135                 140

Thr Asn Asp Ser Tyr Ser Lys Met Ser Val Val Met Arg Asn Thr Thr
145                 150                 155                 160

Trp Glu Gly Gln Cys Ser Asn Ser His Val Asn Thr Leu Arg Phe Leu
            165                 170                 175

Val Lys Asn Ala Gly Tyr Leu Val Gly Arg Lys Pro Leu Arg Pro His
            180                 185                 190

Gly Gly Gly Ser Lys Asp Cys Glu Met Lys Arg Thr Thr Leu Asp Ser
            195                 200                 205

Pro Leu Gly Lys Leu Glu Leu Ser Gly Cys Glu Gln Gly Leu His Glu
210                 215                 220

Ile Lys Leu Leu Gly Lys Gly Thr Ser Ala Ala Asp Ala Val Glu Val
225                 230                 235                 240

Pro Ala Pro Ala Ala Val Leu Gly Gly Pro Glu Pro Leu Met Gln Ala
            245                 250                 255

Thr Ala Trp Leu Asn Ala Tyr Phe His Gln Pro Glu Ala Ile Glu Glu
            260                 265                 270

Phe Pro Val Pro Ala Leu His His Pro Val Phe Gln Gln Glu Ser Phe
            275                 280                 285

Thr Arg Gln Val Leu Trp Lys Leu Leu Lys Val Val Lys Phe Gly Glu
            290                 295                 300

Val Ile Ser Tyr Gln Gln Leu Ala Ala Leu Ala Gly Asn Pro Ala Ala
305                 310                 315                 320

Thr Ala Ala Val Lys Thr Ala Leu Ser Gly Asn Pro Val Pro Ile Leu
            325                 330                 335

Ile Pro Cys His Arg Val Val Ser Ser Ser Gly Ala Val Gly Gly Tyr
            340                 345                 350

Glu Gly Gly Leu Ala Val Lys Glu Trp Leu Leu Ala His Glu Gly His
            355                 360                 365

Arg Leu Gly Lys Pro Gly Leu Gly Pro Ala Gly Ile Gly Ala Pro Gly
            370                 375                 380

Ser Leu Glu His His His His His His
385                 390

<210> SEQ ID NO 138
<211> LENGTH: 1273
<212> TYPE: DNA
<213> ORGANISM: artificial
<220> FEATURE:
<223> OTHER INFORMATION: DNA sequence encoding ssBiP- Glycoprotein GP1 from Sabia virus- SNAPlike-Histag for expression in S2 cells

<400> SEQUENCE: 138
atgaagttat gcatattact ggccgtcgtg gcctttgttg gcctctcgct cgggagatct    60
ttcagaatcg gaaggagcac agaattgcag aacatcacgt tcgatatgtt gaaggtgttc   120

-continued

```
gaggaccacc ccacatcctg catggtgaac cattccacct actacgtcca tgagaacaag    180
aacgccactt ggtgtctgga ggtgtccgtg actgatgtta ccctgctcat ggctgaacat    240
gatcgtcaag tcctcaacaa cctgtcgaac tgtgtgcacc ctgcagtcga gcacagaagc    300
aggatggttg gcttgctgga gtggatcttc agagccctga agtacgactt caaccatgat    360
ccaacaccgt tgtgtcagaa gcagacttcg acagtgaacg agacacgtgt gcagatcaac    420
atcactgagg ggttcgggtc ccacgggttc gaagatacca tcctccagag actcggggtt    480
ctgttcggtt cgagaattgc attctcgaac atccaggact tgggtaagaa gaggttcttg    540
ttgatcagga actcgacttg gaagaaccaa tgcgagatga accatgtgaa ctccatgcac    600
ttgatgttgg cgaacgctgg tcgctcgtcc ggttcgagaa gaccactgcg gccgcacggc    660
ggaggtagca aagactgcga aatgaagcgc accaccctgg atagccctct gggcaagctg    720
gaactgtctg ggtgcgaaca gggcctgcac gagatcaagc tgctgggcaa aggaacatct    780
gccgccgacg ccgtggaagt gcctgcccca gccgccgtgc tgggcggacc agagccactg    840
atgcaggcca ccgcctggct caacgcctac tttcaccagc ctgaggccat cgaggagttc    900
cctgtgccag ccctgcacca cccagtgttc cagcaggaga gctttacccg ccaggtgctg    960
tggaaactgc tgaaagtggt gaagttcgga gaggtcatca gctaccagca gctggccgcc   1020
ctggccggca atcccgccgc caccgccgcc gtgaaaaccg ccctgagcgg aaatcccgtg   1080
cccattctga tcccctgcca ccgggtggtg tctagctctg gcgccgtggg gggctacgag   1140
ggcgggctcg ccgtgaaaga gtggctgctg gcccacgagg gccacagact gggcaagcct   1200
gggctgggtc ctgcaggtat aggcgcgcca gggtccctgg agcatcatca tcatcatcat   1260
tgatgacggg ccc                                                       1273
```

```

<210> SEQ ID NO 139
<211> LENGTH: 396
<212> TYPE: PRT
<213> ORGANISM: artificial
<220> FEATURE:
<223> OTHER INFORMATION: Amino acid sequence of fusion protein
      [SAB.ectoGP1- SNAPlike-Histag]

<400> SEQUENCE: 139

Arg Ser Thr Glu Leu Gln Asn Ile Thr Phe Asp Met Leu Lys Val Phe
1               5                   10                  15

Glu Asp His Pro Thr Ser Cys Met Val Asn His Ser Thr Tyr Tyr Val
            20                  25                  30

His Glu Asn Lys Asn Ala Thr Trp Cys Leu Glu Val Ser Val Thr Asp
        35                  40                  45

Val Thr Leu Leu Met Ala Glu His Asp Arg Gln Val Leu Asn Asn Leu
    50                  55                  60

Ser Asn Cys Val His Pro Ala Val Glu His Arg Ser Arg Met Val Gly
65                  70                  75                  80

Leu Leu Glu Trp Ile Phe Arg Ala Leu Lys Tyr Asp Phe Asn His Asp
                85                  90                  95

Pro Thr Pro Leu Cys Gln Lys Gln Thr Ser Thr Val Asn Glu Thr Arg
            100                 105                 110

Val Gln Ile Asn Ile Thr Glu Gly Phe Gly Ser His Gly Phe Glu Asp
        115                 120                 125

Thr Ile Leu Gln Arg Leu Gly Val Leu Phe Gly Ser Arg Ile Ala Phe
    130                 135                 140

Ser Asn Ile Gln Asp Leu Gly Lys Lys Arg Phe Leu Leu Ile Arg Asn
```

```
                    145                 150                 155                 160
Ser Thr Trp Lys Asn Gln Cys Glu Met Asn His Val Asn Ser Met His
                165                 170                 175
Leu Met Leu Ala Asn Ala Gly Arg Ser Gly Ser Arg Arg Pro Leu
            180                 185                 190
Arg Pro His Gly Gly Ser Lys Asp Cys Glu Met Lys Arg Thr Thr
        195                 200                 205
Leu Asp Ser Pro Leu Gly Lys Leu Glu Leu Ser Gly Cys Glu Gln Gly
    210                 215                 220
Leu His Glu Ile Lys Leu Leu Gly Lys Gly Thr Ser Ala Ala Asp Ala
225                 230                 235                 240
Val Glu Val Pro Ala Pro Ala Ala Val Leu Gly Gly Pro Glu Pro Leu
                245                 250                 255
Met Gln Ala Thr Ala Trp Leu Asn Ala Tyr Phe His Gln Pro Glu Ala
                260                 265                 270
Ile Glu Glu Phe Pro Val Pro Ala Leu His His Pro Val Phe Gln Gln
            275                 280                 285
Glu Ser Phe Thr Arg Gln Val Leu Trp Lys Leu Leu Lys Val Val Lys
        290                 295                 300
Phe Gly Glu Val Ile Ser Tyr Gln Gln Leu Ala Ala Leu Ala Gly Asn
305                 310                 315                 320
Pro Ala Ala Thr Ala Ala Val Lys Thr Ala Leu Ser Gly Asn Pro Val
                325                 330                 335
Pro Ile Leu Ile Pro Cys His Arg Val Val Ser Ser Gly Ala Val
                340                 345                 350
Gly Gly Tyr Glu Gly Gly Leu Ala Val Lys Glu Trp Leu Leu Ala His
            355                 360                 365
Glu Gly His Arg Leu Gly Lys Pro Gly Leu Gly Pro Ala Gly Ile Gly
        370                 375                 380
Ala Pro Gly Ser Leu Glu His His His His His His
385                 390                 395

<210> SEQ ID NO 140
<211> LENGTH: 1189
<212> TYPE: DNA
<213> ORGANISM: artificial
<220> FEATURE:
<223> OTHER INFORMATION: DNA sequence encoding ssBiP- Glycoprotein GP2
      from Lassa virus- SNAPlike-Histag for expression in S2 cells

<400> SEQUENCE: 140
atgaagttat gcatattact ggccgtcgtg gcctttgttg cctctcgct cgggagatct      60 ggcacattca catggacact gtcggattct gaaggtaagg acacaccagg gggatactgt     120
ctgaccaggt ggatgctgat cgaggctgaa ctgaagtgct cgggaacac agctgtggcg     180 aagtgtaacg agaagcatga tgaggagttc tgtgacatgc tgaggctgtt cgacttcaac     240
aagcaagcca tccagaggtt gaaggctgaa gcacagatga gcatccagtt gatcaacaag     300
gcagtgaatg ccttgatcaa cgaccaactg atcatgaaga accatctgcg ggacatcatg     360
ggtatcccat actgtaacta cagcaagtac tggtacctca accacacaac tactgggaga     420
acatcgctgc ccaagtgttg gctggtgtcg aacggttcgt acttgaacga dacccacttc     480
tccgatgaca tcgaacaaca agctgacaac atgatcactg agatgttgca gaaggagtac     540
atggagaggc aggggaagac accgcggccg cacggcggag gtagcaaaga ctgcgaaatg     600
aagcgcacca ccctggatag ccctctgggc aagctggaac tgtctgggtg cgaacagggc     660
```

```
ctgcacgaga tcaagctgct gggcaaagga acatctgccg ccgacgccgt ggaagtgcct    720
gccccagccg ccgtgctggg cggaccagag ccactgatgc aggccaccgc ctggctcaac    780
gcctactttc accagcctga ggccatcgag gagttccctg tgccagccct gcaccaccca    840
gtgttccagc aggagagctt tacccgccag gtgctgtgga aactgctgaa agtggtgaag    900
ttcggagagg tcatcagcta ccagcagctg gccgccctgg ccggcaatcc cgccgccacc    960
gccgccgtga aaaccgccct gagcggaaat cccgtgccca ttctgatccc ctgccaccgg   1020
gtggtgtcta gctctggcgc cgtgggggc tacgagggcg ggctcgccgt gaaagagtgg    1080
ctgctggccc acgagggcca cagactgggc aagcctgggc tgggtcctgc aggtataggc   1140
gcgccagggt ccctggagca tcatcatcat catcattgat gacgggccc                1189
```

<210> SEQ ID NO 141
<211> LENGTH: 374
<212> TYPE: PRT
<213> ORGANISM: artificial
<220> FEATURE:
<223> OTHER INFORMATION: Amino acid sequence of fusion protein
      [LAS.ectoGP2- SNAPlike-Histag]

<400> SEQUENCE: 141

```
Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45

Asp Glu Glu Phe Cys Asp Met Leu Arg Leu Phe Asp Phe Asn Lys Gln
    50                  55                  60

Ala Ile Gln Arg Leu Lys Ala Glu Ala Gln Met Ser Ile Gln Leu Ile
65                  70                  75                  80

Asn Lys Ala Val Asn Ala Leu Ile Asn Asp Gln Leu Ile Met Lys Asn
                85                  90                  95

His Leu Arg Asp Ile Met Gly Ile Pro Tyr Cys Asn Tyr Ser Lys Tyr
            100                 105                 110

Trp Tyr Leu Asn His Thr Thr Thr Gly Arg Thr Ser Leu Pro Lys Cys
        115                 120                 125

Trp Leu Val Ser Asn Gly Ser Tyr Leu Asn Glu Thr His Phe Ser Asp
    130                 135                 140

Asp Ile Glu Gln Gln Ala Asp Asn Met Ile Thr Glu Met Leu Gln Lys
145                 150                 155                 160

Glu Tyr Met Glu Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
```

```
                260                 265                 270
Val Leu Trp Lys Leu Leu Lys Val Lys Phe Gly Glu Val Ile Ser
            275                 280                 285

Tyr Gln Gln Leu Ala Ala Leu Ala Gly Asn Pro Ala Ala Thr Ala Ala
            290                 295                 300

Val Lys Thr Ala Leu Ser Gly Asn Pro Val Pro Ile Leu Ile Pro Cys
305                 310                 315                 320

His Arg Val Val Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
            355                 360                 365

His His His His His His
    370

<210> SEQ ID NO 142
<211> LENGTH: 1189
<212> TYPE: DNA
<213> ORGANISM: artificial
<220> FEATURE:
<223> OTHER INFORMATION: DNA sequence encoding ssBiP- Glycoprotein GP2
      from Junin virus- SNAPlike-Histag for expression in S2 cells

<400> SEQUENCE: 142
atgaagttat gcatattact ggccgtcgtg gcctttgttg gcctctcgct cgggagatct      60
gcattcttct cctggtcgtt gacagactca tccggcaagg ataccctgg aggctactgc     120 ctggaagagt ggatgctcgt ggcagccaag atgaagtgct tcggcaacac tgctgtggcc    180
aagtgcaact tgaaccatga ctcggagttc tgtgacatgt tgaggctgtt cgattacaac    240
aagaacgcta tcaagaccct gaacgatgag actaagaagc aagtgaacct gatggggcag    300
acaatcaacg ccctgatctc ggacaacttg ttgatgaaga caagatcag ggaactgatg     360 agtgtcccct actgcaacta cacgaagttc tggtacgtca accacacact ctccggacaa    420
cactcgttgc caaggtgctg gttgatcaag aacaacagct acttgaacat ctccgacttc    480
cgtaacgact ggatcttgga gagtgacttc ttgatctccg agatgctgag caaggagtac    540
tcggacaggc agggtaagac tccgcggccg cacggcggag gtagcaaaga ctgcgaaatg    600
aagcgcacca cccctggatag ccctctgggc aagctggaac tgtctgggtg cgaacagggc    660
ctgcacgaga tcaagctgct gggcaaagga acatctgccg ccgacgccgt ggaagtgcct    720
gccccagccg ccgtgctggg cggaccagag ccactgatgc aggccaccgc ctggctcaac    780
gcctactttc accagcctga ggccatcgag gagttccctg tgccagccct gcaccaccca    840
gtgttccagc aggagagctt tacccgccag gtgctgtgga aactgctgaa agtggtgaag    900
ttcggagagg tcatcagcta ccagcagctg gccgccctgg ccggcaatcc cgccgccacc    960
gccgccgtga aaaccgccct gagcggaaat cccgtgccca ttctgatccc ctgccaccgg    1020
gtggtgtcta gctctggcgc cgtggggggc tacgagggcg gctcgccgt gaaagagtgg    1080 ctgctggccc acgagggcca cagactgggc aagcctgggc tggtcctgc aggtataggc     1140 gcgccagggt ccctggagca tcatcatcat catcattgat gacgggccc              1189

<210> SEQ ID NO 143
<211> LENGTH: 374
<212> TYPE: PRT
<213> ORGANISM: artificial
```

```
<220> FEATURE:
<223> OTHER INFORMATION: Amino acid sequence of fusion protein
      [JUN.ectoGP2- SNAPlike-Histag]

<400> SEQUENCE: 143

Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45

Asp Glu Glu Phe Cys Asp Met Leu Arg Leu Phe Asp Phe Asn Lys Gln
    50                  55                  60

Ala Ile Gln Arg Leu Lys Ala Glu Ala Gln Met Ser Ile Gln Leu Ile
65                  70                  75                  80

Asn Lys Ala Val Asn Ala Leu Ile Asn Asp Gln Leu Ile Met Lys Asn
                85                  90                  95

His Leu Arg Asp Ile Met Gly Ile Pro Tyr Cys Asn Tyr Ser Lys Tyr
            100                 105                 110

Trp Tyr Leu Asn His Thr Thr Thr Gly Arg Thr Ser Leu Pro Lys Cys
        115                 120                 125

Trp Leu Val Ser Asn Gly Ser Tyr Leu Asn Glu Thr His Phe Ser Asp
130                 135                 140

Asp Ile Glu Gln Gln Ala Asp Asn Met Ile Thr Glu Met Leu Gln Lys
145                 150                 155                 160

Glu Tyr Met Glu Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
290                 295                 300

Val Lys Thr Ala Leu Ser Gly Asn Pro Val Pro Ile Leu Ile Pro Cys
305                 310                 315                 320

His Arg Val Val Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 144
<211> LENGTH: 1189
<212> TYPE: DNA
<213> ORGANISM: artificial
<220> FEATURE:
<223> OTHER INFORMATION: DNA sequence encoding ssBiP-Glycoprotein GP2 from Machupo virus- SNAPlike-Histag for expression in S2 cells

<400> SEQUENCE: 144

```
atgaagttat gcatattact ggccgtcgtg gcctttgttg gcctctcgct cgggagatct      60
gcattcttct catggtcgct gaccgactcc tccggcaagg acatgccagg aggttactgt     120
ctggaggaat ggatgttgat cgcagccaag atgaagtgct tcggcaacac cgctgtcgct     180
aagtgtaacc agaaccatga ctcagagttc tgtgatatgc tgaggctatt cgactacaac     240
aagaacgcaa tcaagaccct caacgatgaa tcgaagaagg agatcaacct gctaagccag     300
accgtgaacg ccttgatctc ggataacttg ttaatgaaga acaagatcaa ggagctaatg     360
agcatcccgtt actgtaatta cacgaagttc tggtacgtca accatatccct gacagggcag     420
```

```
atgaagttat gcatattact ggccgtcgtg gcctttgttg gcctctcgct cgggagatct      60
gcattcttct catggtcgct gaccgactcc tccggcaagg acatgccagg aggttactgt     120
ctggaggaat ggatgttgat cgcagccaag atgaagtgct tcggcaacac cgctgtcgct     180
aagtgtaacc agaaccatga ctcagagttc tgtgatatgc tgaggctatt cgactacaac     240
aagaacgcaa tcaagaccct caacgatgaa tcgaagaagg agatcaacct gctaagccag     300
accgtgaacg ccttgatctc ggataacttg ttaatgaaga acaagatcaa ggagctaatg     360
agcatcccctt actgtaatta cacgaagttc tggtacgtca accataccct gacagggcag     420
cacacgctgc caaggtgttg gttgatcagg aacggaagtt acctcaacac ctcggagttc     480
aggaacgact ggatcttgga gagtgatcac ctcatctcgg agatgttgag taaggaatac     540
gctgagaggc aaggcaagac cccgcggccg cacggcggag gtagcaaaga ctgcgaaatg     600
aagcgcacca ccctggatag ccctctgggc aagctggaac tgtctgggtg cgaacaggc     660
ctgcacgaga tcaagctgct gggcaaagga catctgccg ccgacgccgt ggaagtgcct     720
gccccagccg ccgtgctggg cggaccagag ccactgatgc aggccaccgc ctggctcaac     780
gcctactttc accagcctga ggccatcgag gagttccctg tgccagccct gcaccaccca     840
gtgttccagc aggagagctt acccgccag tgctgtgga aactgctgaa agtggtgaag     900
ttcggagagg tcatcagcta ccagcagctg gccgccctgg ccggcaatcc cgccgccacc     960
gccgccgtga aaccgccct gagcggaaat cccgtgccca ttctgatccc ctgccaccgg    1020
gtggtgtcta gctctggcgc cgtgggggc tacgagggcg ggctcgccgt gaaagagtgg    1080
ctgctggccc acgagggcca cagactgggc aagcctgggc tgggtcctgc aggtataggc    1140
gcgccagggt ccctggagca tcatcatcat catcattgat gacgggccc                1189
```

<210> SEQ ID NO 145
<211> LENGTH: 374
<212> TYPE: PRT
<213> ORGANISM: artificial
<220> FEATURE:
<223> OTHER INFORMATION: Amino acid sequence of fusion protein [MAC.ectoGP2- SNAPlike-Histag]

<400> SEQUENCE: 145

```
Arg Ser Ala Phe Phe Ser Trp Ser Leu Thr Asp Ser Ser Gly Lys Asp
 1               5                  10                  15

Met Pro Gly Gly Tyr Cys Leu Glu Glu Trp Met Leu Ile Ala Ala Lys
            20                  25                  30

Met Lys Cys Phe Gly Asn Thr Ala Val Ala Lys Cys Asn Gln Asn His
        35                  40                  45

Asp Ser Glu Phe Cys Asp Met Leu Arg Leu Phe Asp Tyr Asn Lys Asn
    50                  55                  60

Ala Ile Lys Thr Leu Asn Asp Glu Ser Lys Lys Glu Ile Asn Leu Leu
65                  70                  75                  80

Ser Gln Thr Val Asn Ala Leu Ile Ser Asp Asn Leu Leu Met Lys Asn
                85                  90                  95
```

| | | | | | | | | | | | |
|---|---|---|---|---|---|---|---|---|---|---|---|
|Lys|Ile|Lys|Glu|Leu|Met|Ser|Ile|Pro|Tyr|Cys|Asn|Tyr|Thr|Lys|Phe|
| | | |100| | | |105| | | |110|

Trp Tyr Val Asn His Thr Leu Thr Gly Gln His Thr Leu Pro Arg Cys
              115                 120              125

Trp Leu Ile Arg Asn Gly Ser Tyr Leu Asn Thr Ser Glu Phe Arg Asn
          130                 135              140

Asp Trp Ile Leu Glu Ser Asp His Leu Ile Ser Glu Met Leu Ser Lys
145             150              155              160

Glu Tyr Ala Glu Arg Gln Gly Lys Thr Pro Arg Pro His Gly Gly Gly
              165                 170              175

Ser Lys Asp Cys Glu Met Lys Arg Thr Thr Leu Asp Ser Pro Leu Gly
          180                 185              190

Lys Leu Glu Leu Ser Gly Cys Glu Gln Gly Leu His Glu Ile Lys Leu
              195                 200              205

Leu Gly Lys Gly Thr Ser Ala Ala Asp Ala Val Glu Val Pro Ala Pro
          210                 215              220

Ala Ala Val Leu Gly Gly Pro Glu Pro Leu Met Gln Ala Thr Ala Trp
225             230              235              240

Leu Asn Ala Tyr Phe His Gln Pro Glu Ala Ile Glu Glu Phe Pro Val
              245                 250              255

Pro Ala Leu His His Pro Val Phe Gln Gln Glu Ser Phe Thr Arg Gln
          260                 265              270

Val Leu Trp Lys Leu Lys Val Lys Phe Gly Glu Val Ile Ser
              275                 280              285

Tyr Gln Gln Leu Ala Ala Leu Ala Gly Asn Pro Ala Ala Thr Ala Ala
          290                 295              300

Val Lys Thr Ala Leu Ser Gly Asn Pro Val Pro Ile Leu Ile Pro Cys
305             310              315              320

His Arg Val Val Ser Ser Gly Ala Val Gly Gly Tyr Glu Gly Gly
              325                 330              335

Leu Ala Val Lys Glu Trp Leu Leu Ala His Glu Gly His Arg Leu Gly
          340                 345              350

Lys Pro Gly Leu Gly Pro Ala Gly Ile Gly Ala Pro Gly Ser Leu Glu
          355                 360              365

His His His His His His
      370

<210> SEQ ID NO 146
<211> LENGTH: 1189
<212> TYPE: DNA
<213> ORGANISM: artificial
<220> FEATURE:
<223> OTHER INFORMATION: DNA sequence encoding ssBiP-Glycoprotein GP2
      from Guanarito virus- SNAPlike-Histag for expression in S2 cells

<400> SEQUENCE: 146
atgaagttat gcatattact ggccgtcgtg gcctttgttg gcctctcgct cgggagatct      60
gcattcttca gttggtcgct gtctgacccg aagggtaatg acatgccagg tggttactgt     120
ctggagaggt ggatgttggt cgctggggac ttgaagtgct tcggcaacac agctgtcgcc     180
aagtgtaact tgaaccatga ttccgagttc tgtgacatgt tgaggctgtt cgacttcaac     240
aagaacgcca tcgagaagct gaacaaccag actaagactg ctgtcaacat gttgactcac     300
tcgatcaaca gtctgatctc cgataacttg ttgatgagga caagctgaa ggagattttg      360 aaggtcccat actgcaacta cacaagattc tggtacatca ccacacgaa gtccggcgag      420

```
cactcgctgc ctcggtgttg gctggtcagt aacggttcct acttgaacga gagtgacttc    480
aggaacgagt ggatcttgga gagtgatcac ctgatcgcag agatgttgag caaggaatac    540
caagataggc aggggaagac tccgcggccg cacggcggag gtagcaaaga ctgcgaaatg    600
aagcgcacca ccctggatag ccctctgggc aagctggaac tgtctgggtg cgaacagggc    660
ctgcacgaga tcaagctgct gggcaaagga acatctgccg ccgacgccgt ggaagtgcct    720
gccccagccg ccgtgctggg cggaccagag ccactgatgc aggccaccgc ctggctcaac    780
gcctactttc accagcctga ggccatcgag gagttccctg tgccagccct gcaccaccca    840
gtgttccagc aggagagctt tacccgccag gtgctgtgga aactgctgaa agtggtgaag    900
ttcggagagg tcatcagcta ccagcagctg gccgccctgg ccggcaatcc cgccgccacc    960
gccgccgtga aaaccgccct gagcggaaat cccgtgccca ttctgatccc ctgccaccgg   1020
gtggtgtcta gctctggcgc cgtgggggc tacgagggcg gctcgccgt gaaagagtgg     1080 ctgctggccc acgagggcca cagactgggc aagcctgggc tgggtcctgc aggtataggc   1140
gcgccagggt ccctggagca tcatcatcat catcattgat gacgggccc               1189
```

<210> SEQ ID NO 147
<211> LENGTH: 374
<212> TYPE: PRT
<213> ORGANISM: artificial
<220> FEATURE:
<223> OTHER INFORMATION: Amino acid sequence of fusion protein
     [GUA.ectoGP2- SNAPlike-Histag]

<400> SEQUENCE: 147

```
Arg Ser Ala Phe Phe Ser Trp Ser Leu Ser Asp Pro Lys Gly Asn Asp
  1               5                  10                  15

Met Pro Gly Gly Tyr Cys Leu Glu Arg Trp Met Leu Val Ala Gly Asp
             20                  25                  30

Leu Lys Cys Phe Gly Asn Thr Ala Val Ala Lys Cys Asn Leu Asn His
         35                  40                  45

Asp Ser Glu Phe Cys Asp Met Leu Arg Leu Phe Asp Phe Asn Lys Asn
     50                  55                  60

Ala Ile Glu Lys Leu Asn Asn Gln Thr Lys Thr Ala Val Asn Met Leu
 65                  70                  75                  80

Thr His Ser Ile Asn Ser Leu Ile Ser Asp Asn Leu Leu Met Arg Asn
                 85                  90                  95

Lys Leu Lys Glu Ile Leu Lys Val Pro Tyr Cys Asn Tyr Thr Arg Phe
            100                 105                 110

Trp Tyr Ile Asn His Thr Lys Ser Gly Glu His Ser Leu Pro Arg Cys
        115                 120                 125

Trp Leu Val Ser Asn Gly Ser Tyr Leu Asn Glu Ser Asp Phe Arg Asn
    130                 135                 140

Glu Trp Ile Leu Glu Ser Asp His Leu Ile Ala Glu Met Leu Ser Lys
145                 150                 155                 160

Glu Tyr Gln Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220
```

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
            245                 250                 255

Pro Ala Leu His His Pro Val Phe Gln Gln Glu Ser Phe Thr Arg Gln
        260                 265                 270

Val Leu Trp Lys Leu Lys Val Val Lys Phe Gly Glu Val Ile Ser
    275                 280                 285

Tyr Gln Gln Leu Ala Ala Leu Ala Gly Asn Pro Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370

<210> SEQ ID NO 148
<211> LENGTH: 1189
<212> TYPE: DNA
<213> ORGANISM: artificial
<220> FEATURE:
<223> OTHER INFORMATION: DNA sequence encoding ssBiP-Glycoprotein GP2
      from Sabia virus- SNAPlike-Histag for expression in S2 cells

<400> SEQUENCE: 148
atgaagttat gcatattact ggccgtcgtg gcctttgttg cctctcgct cgggagatct        60 ggcatcttct cctggacgat cacggatgca gtgggcaacg acatgcctgg tggttactgt      120
ctggagagat ggatgctggt gacgtcggat cttaagtgct cggcaacac ggcactggcg      180 aagtgtaacc tcgaccacga ttcggagttc tgtgacatgt tgaagttgtt cgagttcaac      240
aagaaggcga tcgagacatt gaacgacaac acgaagaaca aggtgaactt gctgacccac      300
tcgatcaacg cattgatctc cgacaacttg ctgatgaaga accgactcaa ggaattgttg      360
aacacgcctt actgtaacta caccaagttc tggtatgtca accacacggc atccggggag      420
cactcattgc cacggtgctg gctggttagg aacaatagct acttgaacga gagtgagttc      480
aggaatgatt ggatcatcga gagtgatcac ttgttgtccg agatgctcaa caaggaatac      540
atcgatagac agggcaagac gccgcggccg cacggcggag gtagcaaaga ctgcgaaatg      600
aagcgcacca ccctggatag ccctctgggc aagctggaac tgtctgggtg cgaacagggc      660
ctgcacgaga tcaagctgct gggcaaagga acatctgccg ccgacgccgt ggaagtgcct      720
gccccagccg ccgtgctggg cggaccagag ccactgatgc aggccaccgc ctggctcaac      780
gcctactttc accagcctga ggccatcgag gagttccctg tgccagccct gcaccaccca      840
gtgttccagc aggagagctt tacccgccag gtgctgtgga aactgctgaa agtggtgaag      900
ttcggagagg tcatcagcta ccagcagctg gccgccctgg ccggcaatcc cgccgccacc      960
gccgccgtga aaaccgccct gagcggaaat cccgtgccca ttctgatccc ctgccaccgg     1020
gtggtgtcta gctctggcgc cgtgggggc tacgagggcg gctcgccgt gaaagagtgg     1080 ctgctggccc acgagggcca cagactgggc aagcctgggc tgggtcctgc aggtataggc     1140

```
gcgccagggt ccctggagca tcatcatcat catcattgat gacgggccc          1189
```

<210> SEQ ID NO 149
<211> LENGTH: 374
<212> TYPE: PRT
<213> ORGANISM: artificial
<220> FEATURE:
<223> OTHER INFORMATION: Amino acid sequence of fusion protein
    [SAB.ectoGP2- SNAPlike-Histag]

<400> SEQUENCE: 149

```
Arg Ser Gly Ile Phe Ser Trp Thr Ile Thr Asp Ala Val Gly Asn Asp
1               5                   10                  15

Met Pro Gly Gly Tyr Cys Leu Glu Arg Trp Met Leu Val Thr Ser Asp
            20                  25                  30

Leu Lys Cys Phe Gly Asn Thr Ala Leu Ala Lys Cys Asn Leu Asp His
        35                  40                  45

Asp Ser Glu Phe Cys Asp Met Leu Lys Leu Phe Glu Phe Asn Lys Lys
    50                  55                  60

Ala Ile Glu Thr Leu Asn Asp Asn Thr Lys Asn Lys Val Asn Leu Leu
65                  70                  75                  80

Thr His Ser Ile Asn Ala Leu Ile Ser Asp Asn Leu Leu Met Lys Asn
                85                  90                  95

Arg Leu Lys Glu Leu Leu Asn Thr Pro Tyr Cys Asn Tyr Thr Lys Phe
            100                 105                 110

Trp Tyr Val Asn His Thr Ala Ser Gly Glu His Ser Leu Pro Arg Cys
        115                 120                 125

Trp Leu Val Arg Asn Asn Ser Tyr Leu Asn Glu Ser Glu Phe Arg Asn
    130                 135                 140

Asp Trp Ile Ile Glu Ser Asp His Leu Leu Ser Glu Met Leu Asn Lys
145                 150                 155                 160

Glu Tyr Ile Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350
```

Lys Pro Gly Leu Gly Pro Ala Gly Ile Gly Ala Pro Gly Ser Leu Glu
    355                 360                 365

His His His His His His
    370

<210> SEQ ID NO 150
<211> LENGTH: 2774
<212> TYPE: DNA
<213> ORGANISM: artificial
<220> FEATURE:
<223> OTHER INFORMATION: DNA sequence encoding BiPlike-
    SNAPlike-proTEV1-C protein of Hepatitis E virus- proTEV2-Histag
    for expression in S2 cells

<400> SEQUENCE: 150

| | | | |
|---|---|---|---|
| atgaaactat gtattctact tgcagttgtt gcgttcgtag gattgtcctt acctacagct | | | 60 |
| ctggcaagat ctgacaaaga ctgcgaaatg aaaagaacta cattggattc accacttggg | | | 120 |
| aagttggaac tgagtggatg cgagcaagga ttgcatgaaa ttaagctact gggaaaagga | | | 180 |
| acttctgctg ctgatgcagt tgaagttcca gcaccagcac tgttcttgg aggtcctgag | | | 240 |
| cccctcatgc aagccacagc ctggcttaac gcatatttcc accagcctga ggccattgag | | | 300 |
| gaatttccag tccccgccct tcaccatcct gtgtttcagc aggagagctt cacccgccag | | | 360 |
| gtcctgtgga aattgctgaa ggtggtcaag tttggtgaag tgatttcata tcagcaactt | | | 420 |
| gctgcattgg ccggtaaccc cgcagctaca gctgccgtga aaactgctct cagcggaaat | | | 480 |
| cctgtgccca tcctgatccc ttgtcacaga gtcgtttcat cttccggagc tgtaggtggc | | | 540 |
| tatgaaggag actggcagt taaggagtgg ctgctggctc atgaaggtca tagacttgga | | | 600 |
| aagcctgggc tgggtcctgc tggtataggc gcgccagggt ccctaggtgg cggatccgaa | | | 660 |
| aacctgtact ccagagcga tatcaataac atgttctttt gctctgtgca tggagatgcc | | | 720 |
| accatgcgct ctcgggcttt tctgtttttg ttcctcgtgt ttctgcctat gctgcccgcg | | | 780 |
| ccaccggccg gtcagccgtc tggccgccg cgcgggcggc gcagcggcgg tgccggcggt | | | 840 |
| ggtttctggg gtgaccggat tgattctcag cccttcgccc tcccctatat tcatccaacc | | | 900 |
| aaccccttcg cacctgacat tccagccgca gccggggctg gagctcgccc tcggcagcca | | | 960 |
| gcccgcccac tcggctccgc ttggcgtgac caatcccagc gccccgccac ttccgcccgt | | | 1020 |
| cgtcgatctg ccccagctgg ggcttcgccg ctgactgctg tggccccggc cccgatact | | | 1080 |
| gttcctgttc ccgatgtcga ttctcgcggc gctatattac gccgccagta taatttatca | | | 1140 |
| acatccccgc taacatctac tattgccact ggtactaacc ttgttctata tgctgctccg | | | 1200 |
| ctgagcccctt tgcttccgct ccaagatgga actaacactc acattatggc cactgaagca | | | 1260 |
| tcaaattatg cccagtaccg tgttgtccgc gctaccatcc ggtaccgtcc gcttgtgccg | | | 1320 |
| aacgctgtcg gcggatacgc tatatctatc tctttctggc ctcagacaac tactacccg | | | 1380 |
| acatctgtgg acatgaactc tatcacctcc acggatgtcc gaatccttgt ccagcctggt | | | 1440 |
| attgcttcag aacttgtgat ccccagtgag cgcctgcatt atcgtaacca aggctggcgc | | | 1500 |
| tctgttgaga cctctggtgt tgcggaggag gaggcgacct ccggccttgt catgcttttgc | | | 1560 |
| atccacggat cacctgtaaa ttcttacacc aatacgcctt atactggtgc ccttggcttg | | | 1620 |
| cttgatttcg cactcgagct cgagttccgc aatttgacac ctggtaacac gaacacacgt | | | 1680 |
| gtttcccgct actcgagtag tgcgcgccac aagctacgcc gagggcctga tggcactgct | | | 1740 |
| gagttaacta cgactgctgc tacacgcttt atgaaggacc ttcatttac agggactaat | | | 1800 |
| ggagttggtg aagtcggtcg tggtatagcg ctaactctgt tcaaccttgc tgatacgctt | | | 1860 |

-continued

```
ctcggcgggc tcccgacaga attgatttcg tcggctggtg gtcagctatt ttattctcgc    1920
cccgtcgtct cagccaatgg cgagccgacg gtgaagctct acacttcagt cgagaacgct    1980
cagcaggata agggtatagc tatcccacat gatattgatc ttggtgagtc ccgtgttgtc    2040
attcaggatt atgataacca acatgagcag gatcgtccca cccttctcc tgctccctct     2100
cggcctttt ctgtccttcg tgctaatgat gtgctatggc tttcacttac agcagctgag     2160
tatgatcaga ctacctatgg ctcctctact aatcccatgt atgtctctga taccgtgaca    2220
tttgtcaatg ttgctactgg tgcccagggg gtatctcgct ctctggactg gtctaaagtc    2280
acccttgatg gcgcccact tatgactatc cagcagtatt ctaagacttt ctttgttctg    2340
cccctccgtg gcaagctctc cttctgggag gccggtacca ctaaggccgg ctacccttat    2400
aattataata ctactgccag tgaccagatt ttaattgaga atgcagctgg tcaccgtgta    2460
tgcatctcaa cctacactac taatcttgga tctggccctg tttctatttc tgctgtcggt    2520
gtcctcgcac tcactctgc gttggccgct ttagaggaca ctgttgacta tcctgctcgt    2580
gctcacactt tgatgattt ctgccctgag tgccgtacac tcggccttca gggttgtgct    2640
ttccaatcaa ctgttgctga gctacagcgt cttaaaatga aggtgggtaa aactcgggag    2700
tacccgggag agaatctata ttttcaaggg cccggcggag gtagtcacca tcatcaccat    2760
cactaatgac cggt                                                     2774
```

<210> SEQ ID NO 151
<211> LENGTH: 899
<212> TYPE: PRT
<213> ORGANISM: artificial
<220> FEATURE:
<223> OTHER INFORMATION: Aa sequence of fusion protein
      [SNAPlike-proTEV1-HEV.C-proTEV2-Histag]

<400> SEQUENCE: 151

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
                20                  25                  30

Lys Leu Leu Gly Lys Gly Thr Ser Ala Ala Asp Ala Val Glu Val Pro
            35                  40                  45

Ala Pro Ala Ala Val Leu Gly Gly Pro Glu Pro Leu Met Gln Ala Thr
        50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

```
Leu Gly Gly Gly Ser Glu Asn Leu Tyr Phe Gln Ser Asp Ile Asn Asn
            195                 200                 205
Met Phe Phe Cys Ser Val His Gly Asp Ala Thr Met Arg Ser Arg Ala
210                 215                 220
Phe Leu Phe Leu Phe Leu Val Phe Leu Pro Met Leu Pro Ala Pro Pro
225                 230                 235                 240
Ala Gly Gln Pro Ser Gly Arg Arg Gly Arg Arg Ser Gly Gly Ala
                245                 250                 255
Gly Gly Gly Phe Trp Gly Asp Arg Ile Asp Ser Gln Pro Phe Ala Leu
            260                 265                 270
Pro Tyr Ile His Pro Thr Asn Pro Phe Ala Pro Asp Ile Pro Ala Ala
            275                 280                 285
Ala Gly Ala Gly Ala Arg Pro Arg Gln Pro Ala Arg Pro Leu Gly Ser
            290                 295                 300
Ala Trp Arg Asp Gln Ser Gln Arg Pro Ala Thr Ser Ala Arg Arg Arg
305                 310                 315                 320
Ser Ala Pro Ala Gly Ala Ser Pro Leu Thr Ala Val Ala Pro Ala Pro
                325                 330                 335
Asp Thr Val Pro Val Pro Asp Val Asp Ser Arg Gly Ala Ile Leu Arg
            340                 345                 350
Arg Gln Tyr Asn Leu Ser Thr Ser Pro Leu Thr Ser Thr Ile Ala Thr
            355                 360                 365
Gly Thr Asn Leu Val Leu Tyr Ala Ala Pro Leu Ser Pro Leu Leu Pro
            370                 375                 380
Leu Gln Asp Gly Thr Asn Thr His Ile Met Ala Thr Glu Ala Ser Asn
385                 390                 395                 400
Tyr Ala Gln Tyr Arg Val Val Arg Ala Thr Ile Arg Tyr Arg Pro Leu
                405                 410                 415
Val Pro Asn Ala Val Gly Gly Tyr Ala Ile Ser Ile Ser Phe Trp Pro
            420                 425                 430
Gln Thr Thr Thr Thr Pro Thr Ser Val Asp Met Asn Ser Ile Thr Ser
            435                 440                 445
Thr Asp Val Arg Ile Leu Val Gln Pro Gly Ile Ala Ser Glu Leu Val
    450                 455                 460
Ile Pro Ser Glu Arg Leu His Tyr Arg Asn Gln Gly Trp Arg Ser Val
465                 470                 475                 480
Glu Thr Ser Gly Val Ala Glu Glu Ala Thr Ser Gly Leu Val Met
                485                 490                 495
Leu Cys Ile His Gly Ser Pro Val Asn Ser Tyr Thr Asn Thr Pro Tyr
            500                 505                 510
Thr Gly Ala Leu Gly Leu Leu Asp Phe Ala Leu Glu Leu Glu Phe Arg
            515                 520                 525
Asn Leu Thr Pro Gly Asn Thr Asn Thr Arg Val Ser Arg Tyr Ser Ser
    530                 535                 540
Ser Ala Arg His Lys Leu Arg Arg Gly Pro Asp Gly Thr Ala Glu Leu
545                 550                 555                 560
Thr Thr Thr Ala Ala Thr Arg Phe Met Lys Asp Leu His Phe Thr Gly
                565                 570                 575
Thr Asn Gly Val Gly Glu Val Gly Arg Gly Ile Ala Leu Thr Leu Phe
            580                 585                 590
Asn Leu Ala Asp Thr Leu Leu Gly Gly Leu Pro Thr Glu Leu Ile Ser
    595                 600                 605
```

```
Ser Ala Gly Gly Gln Leu Phe Tyr Ser Arg Pro Val Ser Ala Asn
    610                 615                 620

Gly Glu Pro Thr Val Lys Leu Tyr Thr Ser Val Glu Asn Ala Gln Gln
625                 630                 635                 640

Asp Lys Gly Ile Ala Ile Pro His Asp Ile Asp Leu Gly Ser Arg
                645                 650                 655

Val Val Ile Gln Asp Tyr Asp Asn Gln His Glu Gln Asp Arg Pro Thr
            660                 665                 670

Pro Ser Pro Ala Pro Ser Arg Pro Phe Ser Val Leu Arg Ala Asn Asp
                675                 680                 685

Val Leu Trp Leu Ser Leu Thr Ala Ala Glu Tyr Asp Gln Thr Thr Tyr
    690                 695                 700

Gly Ser Ser Thr Asn Pro Met Tyr Val Ser Asp Thr Val Thr Phe Val
705                 710                 715                 720

Asn Val Ala Thr Gly Ala Gln Gly Val Ser Arg Ser Leu Asp Trp Ser
                725                 730                 735

Lys Val Thr Leu Asp Gly Arg Pro Leu Met Thr Ile Gln Tyr Ser
                740                 745                 750

Lys Thr Phe Phe Val Leu Pro Leu Arg Gly Lys Leu Ser Phe Trp Glu
    755                 760                 765

Ala Gly Thr Thr Lys Ala Gly Tyr Pro Tyr Asn Tyr Asn Thr Thr Ala
770                 775                 780

Ser Asp Gln Ile Leu Ile Glu Asn Ala Ala Gly His Arg Val Cys Ile
785                 790                 795                 800

Ser Thr Tyr Thr Thr Asn Leu Gly Ser Gly Pro Val Ser Ile Ser Ala
                805                 810                 815

Val Gly Val Leu Ala Pro His Ser Ala Leu Ala Ala Leu Glu Asp Thr
    820                 825                 830

Val Asp Tyr Pro Ala Arg Ala His Thr Phe Asp Asp Phe Cys Pro Glu
    835                 840                 845

Cys Arg Thr Leu Gly Leu Gln Gly Cys Ala Phe Gln Ser Thr Val Ala
    850                 855                 860

Glu Leu Gln Arg Leu Lys Met Lys Val Gly Lys Thr Arg Glu Tyr Pro
865                 870                 875                 880

Gly Glu Asn Leu Tyr Phe Gln Gly Pro Gly Gly Ser His His
                885                 890                 895

His His His

<210> SEQ ID NO 152
<211> LENGTH: 51
<212> TYPE: DNA
<213> ORGANISM: artificial
<220> FEATURE:
<223> OTHER INFORMATION: DNA encoding biPlike sequence

<400> SEQUENCE: 152
atgaaactat gtattctact tgcagttgtt gcgttcgtag gattgtcctt a        51

<210> SEQ ID NO 153
<211> LENGTH: 17
<212> TYPE: PRT
<213> ORGANISM: artificial
<220> FEATURE:
<223> OTHER INFORMATION: Amino acid of BIPlike sequence

<400> SEQUENCE: 153

Met Lys Leu Cys Ile Leu Leu Ala Val Val Ala Phe Val Gly Leu Ser
```

Leu

<210> SEQ ID NO 154
<211> LENGTH: 2047
<212> TYPE: DNA
<213> ORGANISM: Artificial Sequence
<220> FEATURE:
<223> OTHER INFORMATION: nucleotide sequence of a SNAP construct containing the SARS virus N gene

<400> SEQUENCE: 154

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt ttcatcttcc     540
ggagctgtag gtggctatga aggaggactg gcagttaagg agtggctgct ggctcatgaa     600
ggtcatagac ttggaaagcc tgggctgggt cctgctggta taggcgcgcc agggtcccta     660
ggtggcggat ccgaaaacct gtacttccag agcgatatct ctgataatgg accccaatca     720
aaccaacgta gtgccctcg cattacattt ggtggaccta cagattcaac tgacaataac     780
cagaatggag gtcgcaatgg tgcaaggcca agcagcgcc gacctcaagg tttacctaat     840
aatactgcgt cttggttcac agctctcact cagcatggca aggaggaact tagattccct     900
cgaggccagg gcgttccaat caacaccaat agtggtccag atgaccaaat tggctactac     960
cgaagagcta cccgacgagt tcgtggtggt gacggcaaaa tgaaggagct cagccctaga    1020
tggtacttct attacctagg aactgggcca gaagcctcac ttccttacgg cgctaacaag    1080
gaaggcatcg tatgggttgc aactgaggga gccttgaata cacctaagga ccacattggc    1140
acccgcaatc ctaataacaa tgctgccacc gtgctacaac ttcctcaagg aacaacattg    1200
cctaagggct ctacgcaga gggaagcaga ggcggcagtc aagcctcttc tcgctcctca    1260
tcacgtagtc gcggtaattc aagaaattca actcctggca gcagtagggg aaattctcct    1320
gctcgaatgg ccagcggagg tggtgaaact gccctcgcgc tattgctgct agacagattg    1380
aaccagcttg agagcaaagt ttctggtaag gccagcaac agcagggcca aactgtcact    1440
aagaagtctg ctgctgaggc atctaagaag cctcgccaaa agcgtactgc cacaaagcag    1500
tacaacgtca ctcaagcatt cggcagacgt ggtccagaac agaccagggg aaatttcggt    1560
gaccaagacc taatcagaca gggaactgat tacaagcatt ggccgcagat tgcacagttc    1620
gctccaagtg cctctgcatt cttcggaatg tcacgcattg gcatggaagt cacaccttcg    1680
ggaacatggc tgacttatca tggagccatt aagttggatg acaaggaccc acagttcaag    1740
gacaacgtca tactgctgaa caagcacatt gacgcataca aaacattccc accaacagag    1800
cctaagaagg acaagaagaa gaagactgat gaagctcagc ctttgccgca gagacaaaag    1860
aagcagccca ctgtgactct tcttcctgcg gctgacatgg atgatttctc cagacaactt    1920
```
cagaattcca tgagtggagc ttctgctgat tcaactcagg ccccgggaga gaatctatat    1980
tttcaagggc cggcggagg tagtcaccat catcaccatc actaatgacc ggtgcggccg    2040
caagctt                                                              2047

<210> SEQ ID NO 155
<211> LENGTH: 674
<212> TYPE: PRT
<213> ORGANISM: Artificial Sequence
<220> FEATURE:
<223> OTHER INFORMATION: Amino acid sequence of a SNAP construct
      containing the SARS virus N gene

<400> SEQUENCE: 155

```
Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
                20                  25                  30

Cys Glu Met Lys Arg Thr Thr Leu Asp Ser Pro Leu Gly Lys Leu Glu
            35                  40                  45

Leu Ser Gly Cys Glu Gln Gly Leu His Glu Ile Lys Leu Leu Gly Lys
        50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
                100                 105                 110

His His Pro Val Phe Gln Gln Glu Ser Phe Thr Arg Gln Val Leu Trp
            115                 120                 125

Lys Leu Leu Lys Val Val Lys Phe Gly Glu Val Ile Ser Tyr Gln Gln
        130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
                180                 185                 190

Lys Glu Trp Leu Leu Ala His Glu Gly His Arg Leu Gly Lys Pro Gly
            195                 200                 205

Leu Gly Pro Ala Gly Ile Gly Ala Pro Gly Ser Leu Gly Gly Gly Ser
        210                 215                 220

Glu Asn Leu Tyr Phe Gln Ser Asp Ile Ser Asp Asn Gly Pro Gln Ser
225                 230                 235                 240

Asn Gln Arg Ser Ala Pro Arg Ile Thr Phe Gly Gly Pro Thr Asp Ser
                245                 250                 255

Thr Asp Asn Asn Gln Asn Gly Gly Arg Asn Gly Ala Arg Pro Lys Gln
            260                 265                 270

Arg Arg Pro Gln Gly Leu Pro Asn Asn Thr Ala Ser Trp Phe Thr Ala
        275                 280                 285

Leu Thr Gln His Gly Lys Glu Glu Leu Arg Phe Pro Arg Gly Gln Gly
        290                 295                 300

Val Pro Ile Asn Thr Asn Ser Gly Pro Asp Asp Gln Ile Gly Tyr Tyr
305                 310                 315                 320

Arg Arg Ala Thr Arg Arg Val Arg Gly Gly Asp Gly Lys Met Lys Glu
                325                 330                 335
```

```
Leu Ser Pro Arg Trp Tyr Phe Tyr Leu Gly Thr Gly Pro Glu Ala
        340                 345                 350

Ser Leu Pro Tyr Gly Ala Asn Lys Glu Gly Ile Val Trp Val Ala Thr
            355                 360                 365

Glu Gly Ala Leu Asn Thr Pro Lys Asp His Ile Gly Thr Arg Asn Pro
370                 375                 380

Asn Asn Asn Ala Ala Thr Val Leu Gln Leu Pro Gln Gly Thr Thr Leu
385                 390                 395                 400

Pro Lys Gly Phe Tyr Ala Glu Gly Ser Arg Gly Gly Ser Gln Ala Ser
                405                 410                 415

Ser Arg Ser Ser Arg Ser Arg Gly Asn Ser Arg Asn Ser Thr Pro
            420                 425                 430

Gly Ser Ser Arg Gly Asn Ser Pro Ala Arg Met Ala Ser Gly Gly Gly
            435                 440                 445

Glu Thr Ala Leu Ala Leu Leu Leu Leu Asp Arg Leu Asn Gln Leu Glu
    450                 455                 460

Ser Lys Val Ser Gly Lys Gly Gln Gln Gln Gln Gly Gln Thr Val Thr
465                 470                 475                 480

Lys Lys Ser Ala Ala Glu Ala Ser Lys Lys Pro Arg Gln Lys Arg Thr
            485                 490                 495

Ala Thr Lys Gln Tyr Asn Val Thr Gln Ala Phe Gly Arg Arg Gly Pro
                500                 505                 510

Glu Gln Thr Gln Gly Asn Phe Gly Asp Gln Asp Leu Ile Arg Gln Gly
            515                 520                 525

Thr Asp Tyr Lys His Trp Pro Gln Ile Ala Gln Phe Ala Pro Ser Ala
    530                 535                 540

Ser Ala Phe Phe Gly Met Ser Arg Ile Gly Met Glu Val Thr Pro Ser
545                 550                 555                 560

Gly Thr Trp Leu Thr Tyr His Gly Ala Ile Lys Leu Asp Asp Lys Asp
                565                 570                 575

Pro Gln Phe Lys Asp Asn Val Ile Leu Leu Asn Lys His Ile Asp Ala
            580                 585                 590

Tyr Lys Thr Phe Pro Pro Thr Glu Pro Lys Lys Asp Lys Lys Lys Lys
            595                 600                 605

Thr Asp Glu Ala Gln Pro Leu Pro Gln Arg Gln Lys Lys Gln Pro Thr
610                 615                 620

Val Thr Leu Leu Pro Ala Ala Asp Met Asp Asp Phe Ser Arg Gln Leu
625                 630                 635                 640

Gln Asn Ser Met Ser Gly Ala Ser Ala Asp Ser Thr Gln Ala Pro Gly
                645                 650                 655

Glu Asn Leu Tyr Phe Gln Gly Pro Gly Gly Gly Ser His His His
            660                 665                 670

His His

<210> SEQ ID NO 156
<211> LENGTH: 1357
<212> TYPE: DNA
<213> ORGANISM: Artificial Sequence
<220> FEATURE:
<223> OTHER INFORMATION: Nucleotide sequence of a SNAP construct
      containing the SARS virus S gene receptor binding domain

<400> SEQUENCE: 156
tcgcgagcta gcaccatgaa actatgtatt ctacttgcag ttgttgcgtt cgtaggattg    60
```

```
tccttaccta cagctctggc aagatctgac aaagactgcg aaatgaaaag aactacattg      120
gattcaccac ttgggaagtt ggaactgagt ggatgcgagc aaggattgca tgaaattaag      180
ctactgggaa aaggaacttc tgctgctgat gcagttgaag ttccagcacc agcagctgtt      240
cttggaggtc ctgagcccct catgcaagcc acagcctggc ttaacgcata tttccaccag      300
cctgaggcca ttgaggaatt tccagtcccc gcccttcacc atcctgtgtt tcagcaggag      360
agcttcaccc gccaggtcct gtggaaattg ctgaaggtgg tcaagtttgg tgaagtgatt      420
tcatatcagc aacttgctgc attggccggt aaccccgcag ctacagctgc cgtgaaaact      480
gctctcagcg gaaatcctgt gcccatcctg atcccttgtc acagagtcgt ttcatcttcc      540
ggagctgtag gtggctatga aggaggactg gcagttaagg agtggctgct ggctcatgaa      600
ggtcatagac ttggaaagcc tgggctgggt cctgctggta taggcgcgcc agggtcccta      660
ggtggcggat ccgaaaacct gtacttccag agcgatatca ccaacctctg tcctttcggt      720
gaagtgttta acgccactaa gttccccagc gtttacgctt gggagcgtaa gaaaatctca      780
aattgcgtgg ccgactactc tgtgctctac aacagcactt tctttccac cttcaagtgt      840 tacggagttt ccgctacaaa gctgaacgac ctgtgcttca gcaacgtgta cgctgatagc      900
tttgtggtca agggagacga tgttcgccag attgcccctg acagaccgg cgttatcgct      960 gactacaact ataaactgcc agacgatttc atgggctgtg tcctggcctg aacactcgt      1020 aatatcgacg ctaccagtac aggaaactac aattacaagt accgttacct gcgccacggt      1080
aagttgaggc cattcgaacg cgacatctca aacgtccctt ctcccctga cggtaagcca      1140 tgtacacccc ctgccctgaa ctgctactgg ccactcaacg actacggttt ctataccaca      1200
actggcatcg gctaccaacc ctacagagtc gttgtgctct ctttcgagtt gctcaacgct      1260
cctgccacag tcccgggaga gaatctatat tttcaagggc ccggcggagg tagtcaccat      1320
catcaccatc actaatgacc ggtgcggccg caagctt                               1357
```

<210> SEQ ID NO 157
<211> LENGTH: 444
<212> TYPE: PRT
<213> ORGANISM: Artificial Sequence
<220> FEATURE:
<223> OTHER INFORMATION: Amino acid sequence of a SNAP construct
      containing the SARS virus S gene receptor binding domain.

<400> SEQUENCE: 157

```
Ser Arg Ala Ser Thr Met Lys Leu Cys Ile Leu Leu Ala Val Val Ala
1               5                  10                   15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125
```

Lys Leu Leu Lys Val Val Lys Phe Gly Glu Val Ile Ser Tyr Gln Gln
130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
            165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
210                 215                 220

Glu Asn Leu Tyr Phe Gln Ser Asp Ile Thr Asn Leu Cys Pro Phe Gly
225                 230                 235                 240

Glu Val Phe Asn Ala Thr Lys Phe Pro Ser Val Tyr Ala Trp Glu Arg
                245                 250                 255

Lys Lys Ile Ser Asn Cys Val Ala Asp Tyr Ser Val Leu Tyr Asn Ser
            260                 265                 270

Thr Phe Phe Ser Thr Phe Lys Cys Tyr Gly Val Ser Ala Thr Lys Leu
        275                 280                 285

Asn Asp Leu Cys Phe Ser Asn Val Tyr Ala Asp Ser Phe Val Val Lys
290                 295                 300

Gly Asp Asp Val Arg Gln Ile Ala Pro Gly Gln Thr Gly Val Ile Ala
305                 310                 315                 320

Asp Tyr Asn Tyr Lys Leu Pro Asp Asp Phe Met Gly Cys Val Leu Ala
                325                 330                 335

Trp Asn Thr Arg Asn Ile Asp Ala Thr Ser Thr Gly Asn Tyr Asn Tyr
            340                 345                 350

Lys Tyr Arg Tyr Leu Arg His Gly Lys Leu Arg Pro Phe Glu Arg Asp
        355                 360                 365

Ile Ser Asn Val Pro Phe Ser Pro Asp Gly Lys Pro Cys Thr Pro Pro
370                 375                 380

Ala Leu Asn Cys Tyr Trp Pro Leu Asn Asp Tyr Gly Phe Tyr Thr Thr
385                 390                 395                 400

Thr Gly Ile Gly Tyr Gln Pro Tyr Arg Val Val Val Leu Ser Phe Glu
                405                 410                 415

Leu Leu Asn Ala Pro Ala Thr Val Pro Gly Glu Asn Leu Tyr Phe Gln
            420                 425                 430

Gly Pro Gly Gly Gly Ser His His His His His
        435                 440

<210> SEQ ID NO 158
<211> LENGTH: 2023
<212> TYPE: DNA
<213> ORGANISM: Artificial Sequence
<220> FEATURE:
<223> OTHER INFORMATION: Nucleotide sequence of a SNAP construct
      containing the human coronavirus N gene

<400> SEQUENCE: 158
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag    180
ctactgggaa aaggaacttc tgctgctgat gcagttgaag ttccagcacc agcagctgtt    240

| | |
|---|---|
| cttggaggtc ctgagcccct catgcaagcc acagcctggc ttaacgcata tttccaccag | 300 |
| cctgaggcca ttgaggaatt tccagtcccc gcccttcacc atcctgtgtt tcagcaggag | 360 |
| agcttcaccc gccaggtcct gtggaaattg ctgaaggtgg tcaagtttgg tgaagtgatt | 420 |
| tcatatcagc aacttgctgc attggccggt aaccccgcag ctacagctgc cgtgaaaact | 480 |
| gctctcagcg gaaatcctgt gcccatcctg atcccttgtc acagagtcgt ttcatcttcc | 540 |
| ggagctgtag gtggctatga aggaggactg cagttaagg agtggctgct ggctcatgaa | 600 |
| ggtcatagac ttggaaagcc tgggctgggt cctgctggta taggcgcgcc agggtcccta | 660 |
| ggtggcggat ccgaaaacct gtacttccag agcgatatcg catccctgc tgcacctcgt | 720 |
| gctgtttcct ttgccgataa caatgatata acaaatacaa acctatctcg aggtagagga | 780 |
| cgtaatccaa aaccacgagc tgcaccaaat aacactgtct cttggtacac tgggcttacc | 840 |
| caacacggga aagtccctct tacctttcca cctgggcagg gtgtacctct taatgccaat | 900 |
| tctaccctg cgcaaaatgc tgggtattgg cggagacagg acagaaaaat taataccggg | 960 |
| aatggaatta agcaactggc tcccaggtgg tacttctact acactggaac tggacccgaa | 1020 |
| gcagcactcc cattccgggc tgttaaggat ggcatcgttt gggtccatga agatggcgcc | 1080 |
| actgatgctc cttcaacttt tgggacgcgg aaccctaaca atgattcagc tattgttaca | 1140 |
| caattcgcgc ccggtactaa acttcctaaa aacttccaca ttgaggggac tggaggcaat | 1200 |
| agtcaatcat cttcaagagc ctctagctta agcagaaact cttccaggtc tagttcacaa | 1260 |
| ggttcaagat caggaaactc tacccgcggc acttctccag gtccatctgg aatcggagca | 1320 |
| gtaggaggtg atctactta ccttgatctt ctgaacagac tacaagccct tgagtctggc | 1380 |
| aaagtaaagc aatcgcagcc aaaagtaatc actaagaaag atgctgctgc tgctaaaaat | 1440 |
| aagatgcgcc acaagcgcac ttccaccaaa agtttcaaca tggtgcaggc ttttggtctt | 1500 |
| cgcggaccag gagacctcca gggaaacttt ggtgatcttc aattgaataa actcggcact | 1560 |
| gaggacccac gttggcccca aattgctgag cttgctccta cagccagtgc ttttatgggt | 1620 |
| atgtcgcaat ttaaacttac ccatcagaac aatgatgatc atggcaaccc tgtgtacttc | 1680 |
| cttcggtaca gtggagccat taaacttgac ccaaagaatc caactacaa taagtggttg | 1740 |
| gagcttcttg agcaaaatat tgatgcctac aaaaccttcc ctaagaagga aagaaacaa | 1800 |
| aaggcaccaa aagaagaatc aacagaccaa atgtctgaac ctccaaagga gcagcgtgtg | 1860 |
| caaggtagca tcactcagcg cactcgcacc cgtccaagtg ttcagcctgg tccaatgatt | 1920 |
| gatgttaaca ctgatggccc gggagagaat ctatattttc aagggcccgg cggaggtagt | 1980 |
| caccatcatc accatcacta atgaccggtg cggccgcaag ctt | 2023 |

<210> SEQ ID NO 159
<211> LENGTH: 666
<212> TYPE: PRT
<213> ORGANISM: Artificial Sequence
<220> FEATURE:
<223> OTHER INFORMATION: Amino acid sequence of a SNAP construct
containing the human coronavirus N gene.

<400> SEQUENCE: 159

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

```
Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
                100                 105                 110

His His Pro Val Phe Gln Gln Glu Ser Phe Thr Arg Gln Val Leu Trp
            115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
                180                 185                 190

Lys Glu Trp Leu Leu Ala His Glu Gly His Arg Leu Gly Lys Pro Gly
    195                 200                 205

Leu Gly Pro Ala Gly Ile Gly Ala Pro Gly Ser Leu Gly Gly Gly Ser
210                 215                 220

Glu Asn Leu Tyr Phe Gln Ser Asp Ile Ala Ser Pro Ala Ala Pro Arg
225                 230                 235                 240

Ala Val Ser Phe Ala Asp Asn Asn Asp Ile Thr Asn Thr Asn Leu Ser
                245                 250                 255

Arg Gly Arg Gly Arg Asn Pro Lys Pro Arg Ala Ala Pro Asn Asn Thr
                260                 265                 270

Val Ser Trp Tyr Thr Gly Leu Thr Gln His Gly Lys Val Pro Leu Thr
    275                 280                 285

Phe Pro Pro Gly Gln Gly Val Pro Leu Asn Ala Asn Ser Thr Pro Ala
290                 295                 300

Gln Asn Ala Gly Tyr Trp Arg Arg Gln Asp Arg Lys Ile Asn Thr Gly
305                 310                 315                 320

Asn Gly Ile Lys Gln Leu Ala Pro Arg Trp Tyr Phe Tyr Tyr Thr Gly
                325                 330                 335

Thr Gly Pro Glu Ala Ala Leu Pro Phe Arg Ala Val Lys Asp Gly Ile
                340                 345                 350

Val Trp Val His Glu Asp Gly Ala Thr Asp Ala Pro Ser Thr Phe Gly
    355                 360                 365

Thr Arg Asn Pro Asn Asn Asp Ser Ala Ile Val Thr Gln Phe Ala Pro
    370                 375                 380

Gly Thr Lys Leu Pro Lys Asn Phe His Ile Glu Gly Thr Gly Gly Asn
385                 390                 395                 400

Ser Gln Ser Ser Ser Arg Ala Ser Ser Leu Ser Arg Asn Ser Ser Arg
                405                 410                 415

Ser Ser Ser Gln Gly Ser Arg Ser Gly Asn Ser Thr Arg Gly Thr Ser
                420                 425                 430

Pro Gly Pro Ser Gly Ile Gly Ala Val Gly Gly Asp Leu Leu Tyr Leu
            435                 440                 445

Asp Leu Leu Asn Arg Leu Gln Ala Leu Glu Ser Gly Lys Val Lys Gln
    450                 455                 460
```

Ser Gln Pro Lys Val Ile Thr Lys Lys Asp Ala Ala Ala Lys Asn
465                 470                 475                 480

Lys Met Arg His Lys Arg Thr Ser Thr Lys Ser Phe Asn Met Val Gln
            485                 490                 495

Ala Phe Gly Leu Arg Gly Pro Gly Asp Leu Gln Gly Asn Phe Gly Asp
                500                 505                 510

Leu Gln Leu Asn Lys Leu Gly Thr Glu Asp Pro Arg Trp Pro Gln Ile
        515                 520                 525

Ala Glu Leu Ala Pro Thr Ala Ser Ala Phe Met Gly Met Ser Gln Phe
    530                 535                 540

Lys Leu Thr His Gln Asn Asn Asp Asp His Gly Asn Pro Val Tyr Phe
545                 550                 555                 560

Leu Arg Tyr Ser Gly Ala Ile Lys Leu Asp Pro Lys Asn Pro Asn Tyr
                565                 570                 575

Asn Lys Trp Leu Glu Leu Leu Glu Gln Asn Ile Asp Ala Tyr Lys Thr
            580                 585                 590

Phe Pro Lys Lys Glu Lys Lys Gln Lys Ala Pro Lys Glu Glu Ser Thr
        595                 600                 605

Asp Gln Met Ser Glu Pro Pro Lys Glu Gln Arg Val Gln Gly Ser Ile
    610                 615                 620

Thr Gln Arg Thr Arg Thr Arg Pro Ser Val Gln Pro Gly Pro Met Ile
625                 630                 635                 640

Asp Val Asn Thr Asp Gly Pro Gly Glu Asn Leu Tyr Phe Gln Gly Pro
                645                 650                 655

Gly Gly Gly Ser His His His His His His
            660                 665

<210> SEQ ID NO 160
<211> LENGTH: 3055
<212> TYPE: DNA
<213> ORGANISM: Artificial Sequence
<220> FEATURE:
<223> OTHER INFORMATION: Nucleotide sequence of a SNAP construct
      containing the human coronavirus S1 gene.

<400> SEQUENCE: 160
atgaagttat gcatattact ggccgtcgtg gcctttgttg gcctctcgct cgggagatct       60
gtagggccag attctgttaa gtctgcttgt attgaggttg atatacaaca gactttcttt      120
gataaaactt ggcctaggcc aattgatgtt tctaaggctg acggtattat ataccctcaa      180
ggccgtacat attctaacat aactatcact tatcaaggtc ttttttccct atcagggagac     240 catggtgata tgtatgttta ctctgcagga catgctacag gcacaactcc acaaaagttg      300
tttgtagcta actattctca ggacgtcaaa cagtttgcta tgggtttgt cgtccgtata       360 ggagcagctg ccaattccac tggcactgtt attattagcc atctaccag cgctactata      420 cgaaaaattt accctgcttt tatgctgggt tcttcagttg gtaatttctc agatggtaaa      480
atgggccgct tcttcaatca tactctagtt cttttgcccg atggatgtgg cactttactt      540
agagcttttt attgtattct agagcctcgc tctggaaatc attgtcctgc tggcaattcc      600
tatacttctt tgccacttta tcacactcct gcaacagatt gttctgatgg caattacaat      660
cgtaatgcca gtctgaactc ttttaaggag tattttaatt acgtaactg caccttttatg     720 tacacttata acattaccga agatgagatt ttagagtggt ttggcattac acaaactgct      780
caaggtgttc acctcttctc atctcggtat gttgattgt acggcggcaa tatgtttcaa      840
tttgccacct gcctgtttta tgatactatt aagtattatt ctatcattcc tcacagtatt      900

```
cgttctatcc aaagtgatag aaaggcttgg gctgccttct acgtatataa acttcaaccg    960
ttaactttcc tgttggattt ttctgttgat ggttatatac gcagagctat agactgtggt   1020
tttaatgatt tgtcacaact ccactgctca tatgaatcct tcgatgttga atctggagtt   1080
tattcagttt cgtctttcga agcaaaacct tctggctcag ttgtggaaca ggctgaaggt   1140
gttgaatgtg attttcacc tcttctgtct ggcacacctc ctcaggttta taatttcaag   1200
cgtttggttt ttaccaattg caattataat cttaccaaat tgctttcact tttttctgtg   1260
aatgatttta cttgtagtca aatatctcca gcagcaattg caagcaactg ttattcttca   1320
ctgattttgg attacttttc atacccactt agtatgaaat ccgatctcag tgttagttct   1380
gctggtccaa tatcccagtt taattataaa cagtccttt ctaatcccac atgtttgatt   1440
ttagcgactg ttcctcataa ccttactact attactaagc ctcttaagta cagctatatt   1500
aacaagtgct ctcgtcttct ttctgatgat cgtactgaag tacctcagtt agtgaacgct   1560
aatcaatact caccctgtgt atccattgtc ccatccactg tgtgggaaga cggtgattat   1620
tataggaaac aactatctcc acttgaaggt ggtggctggc ttgttgctag tggctcaact   1680
gttgccatga ctgagcaatt acagatgggc tttggtatta cagttcaata tggtacagac   1740
accaatagtg tttgccccaa gctggaattt gctaatgaca caaaaattgc ctctcaatta   1800
ggcaattgcg tggaatattc cctctatggt gtttcgggcc gtggtgtttt tcagaattgc   1860
acagctgtag gtgttcgaca gcagcgcttt gtttatgatg cgtaccagaa tttagttggc   1920
tattattctg atgatggcaa ctactactgt ttgcgtgctt gtgttagtgt tcctgtttct   1980
gtcatctatg ataaagaaac taaaacccac gctactctat ttggtagtgt tgcatgtgaa   2040
cacatttctt ctaccatgtc tcaatactcc cgttctacgc gatcaatgct taaacggcga   2100
gattctacat atggcccct tcagacacct gttggttgtg tcctaggact tgttaattcc   2160
tctttgttcg tagaggactg caagttgcct cttggtcaat ctctctgtgc tcttcctgac   2220
acacctagta ctctcacacc tcgcagtgtg cgctctgttc caggtgaaat gcgcttggca   2280
tccattgctt ttaatcatcc tattcaggtt gatcaactta atagtagtta ttttaaatta   2340
agtataccca ctaatttttc ctttggtgtg actcaggagt acattcagac aaccattcag   2400
aaagttactg ttgattgtaa acagtacgcg cggccgcacg gcggaggtag caaagactgc   2460
gaaatgaagc gcaccaccct ggatagccct ctgggcaagc tggaactgtc tgggtgcgaa   2520
cagggcctgc acgagatcaa gctgctgggc aaaggaacat ctgccgccga cgccgtggaa   2580
gtgcctgccc cagccgccgt gctgggcgga ccagagccac tgatgcaggc caccgcctgg   2640
ctcaacgcct actttcacca gcctgaggcc atcgaggagt ccctgtgcc agccctgcac   2700 cacccagtgt tccagcagga gagctttacc cgccagtgtc tgtggaaact gctgaaagtg   2760
gtgaagttcg gagaggtcat cagctaccag cagctggccg ccctggccgg caatcccgcc   2820
gccaccgccg ccgtgaaaac cgccctgagc ggaaatcccg tgcccattct gatccctgc   2880 caccgggtgg tgtctagctc tggcgccgtg gggggctacg agggcgggct cgccgtgaaa   2940
gagtggctgc tggcccacga gggccacaga ctgggcaagc ctgggctggg tcctgcaggt   3000
ataggcgcgc cagggtccct ggagcatcat catcatcatc attgatgacg ggccc         3055
```

<210> SEQ ID NO 161  
<211> LENGTH: 1014  
<212> TYPE: PRT  
<213> ORGANISM: Artificial Sequence  
<220> FEATURE:

<223> OTHER INFORMATION: Amino acid sequence of a SNAP construct containing the human coronavirus S1 gene.

<400> SEQUENCE: 161

```
Met Lys Leu Cys Ile Leu Ala Val Val Ala Phe Val Gly Leu Ser
1               5                   10                  15

Leu Gly Arg Ser Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400
```

-continued

```
Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
        530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
        610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Ala Arg Pro His Gly Gly Gly
                805                 810                 815
```

```
Ser Lys Asp Cys Glu Met Lys Arg Thr Thr Leu Asp Ser Pro Leu Gly
            820                 825                 830
Lys Leu Glu Leu Ser Gly Cys Glu Gln Gly Leu His Glu Ile Lys Leu
        835                 840                 845
Leu Gly Lys Gly Thr Ser Ala Ala Asp Ala Val Glu Val Pro Ala Pro
850                 855                 860
Ala Ala Val Leu Gly Gly Pro Glu Pro Leu Met Gln Ala Thr Ala Trp
865                 870                 875                 880
Leu Asn Ala Tyr Phe His Gln Pro Glu Ala Ile Glu Glu Phe Pro Val
                885                 890                 895
Pro Ala Leu His His Pro Val Phe Gln Gln Glu Ser Phe Thr Arg Gln
            900                 905                 910
Val Leu Trp Lys Leu Leu Lys Val Val Lys Phe Gly Glu Val Ile Ser
        915                 920                 925
Tyr Gln Gln Leu Ala Ala Leu Ala Gly Asn Pro Ala Ala Thr Ala Ala
930                 935                 940
Val Lys Thr Ala Leu Ser Gly Asn Pro Val Pro Ile Leu Ile Pro Cys
945                 950                 955                 960
His Arg Val Val Ser Ser Gly Ala Val Gly Gly Tyr Glu Gly Gly
                965                 970                 975
Leu Ala Val Lys Glu Trp Leu Leu Ala His Glu Gly His Arg Leu Gly
            980                 985                 990
Lys Pro Gly Leu Gly Pro Ala Gly  Ile Gly Ala Pro Gly  Ser Leu Glu
        995                 1000                1005
His His  His His His His
    1010
```

<210> SEQ ID NO 162
<211> LENGTH: 1369
<212> TYPE: DNA
<213> ORGANISM: Artificial Sequence
<220> FEATURE:
<223> OTHER INFORMATION: Nucleotide sequence of a SNAP construct
      containing the human coronavirus S1 gene receptor binding domain
      (RBD)

<400> SEQUENCE: 162

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttaggaattt ccagtcccc gccttcacc atcctgtgtt tcagcaggag       360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt tcatcttcc      540
ggagctgtag gtggctatga aggaggactg gcagttaagg agtggctgct ggctcatgaa     600
ggtcatagac ttgaaagcc tgggctgggt cctgctggta taggcgcgcc agggtcccta     660
ggtggcggat ccgaaaacct gtacttccag agcgatatct gttgcgtgc tttctactgc     720
atcctcgaac tcgttctgg taaccactgt cctgccggaa atagctacac tagcttcgcc     780
acttaccaca cacccgccac tgactgtagt gacggcaact acaatcgtaa cgcctccttg     840
```

```
aactcttttta aggagtactt caacctgcgc aactgtacct tcatgtacac ttacaacatt    900
accgaagacg aaatcctcga gtggttcggc atcacacaga cagctcaggg agtccacctc    960
ttctcaagca ggtacgtgga cctctatggt ggtaacatgt ttcaattcgc cacactgcca   1020
gtctacgata ccatcaagta ttactccatc atcccacact caatccgctc tatccaaagc   1080
gaccgcaagg cctgggctgc ttttttacgtg tacaagctgc agcctctgac cttcctgctg   1140
gatttctccg tggacggcta cattagacgt gctatcgatt gcggtttcaa cgacctgtca   1200
caactccatt gctcatacga atctttcgac gttgagagcg gagtgtactc cgtttccagc   1260
ttcgaggcta aacccagtgg ctcccccggga gagaatctat attttcaagg gcccggcgga   1320
ggtagtcacc atcatcacca tcactaatga ccggtgcggc cgcaagctt              1369
```

<210> SEQ ID NO 163
<211> LENGTH: 448
<212> TYPE: PRT
<213> ORGANISM: Artificial Sequence
<220> FEATURE:
<223> OTHER INFORMATION: Amino acid sequence of a SNAP construct containing the human coronavirus S1 gene receptor binding domain (RBD)

<400> SEQUENCE: 163

```
Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Leu Leu Arg Ala Phe Tyr Cys
225                 230                 235                 240

Ile Leu Glu Pro Arg Ser Gly Asn His Cys Pro Ala Gly Asn Ser Tyr
                245                 250                 255

Thr Ser Phe Ala Thr Tyr His Thr Pro Ala Thr Asp Cys Ser Asp Gly
```

```
                260             265              270
Asn Tyr Asn Arg Asn Ala Ser Leu Asn Ser Phe Lys Glu Tyr Phe Asn
            275             280             285

Leu Arg Asn Cys Thr Phe Met Tyr Thr Tyr Asn Ile Thr Glu Asp Glu
            290             295             300

Ile Leu Glu Trp Phe Gly Ile Thr Gln Thr Ala Gln Gly Val His Leu
305             310             315             320

Phe Ser Ser Arg Tyr Val Asp Leu Tyr Gly Gly Asn Met Phe Gln Phe
            325             330             335

Ala Thr Leu Pro Val Tyr Asp Thr Ile Lys Tyr Tyr Ser Ile Ile Pro
            340             345             350

His Ser Ile Arg Ser Ile Gln Ser Asp Arg Lys Ala Trp Ala Ala Phe
            355             360             365

Tyr Val Tyr Lys Leu Gln Pro Leu Thr Phe Leu Leu Asp Phe Ser Val
            370             375             380

Asp Gly Tyr Ile Arg Arg Ala Ile Asp Cys Gly Phe Asn Asp Leu Ser
385             390             395             400

Gln Leu His Cys Ser Tyr Glu Ser Phe Asp Val Glu Ser Gly Val Tyr
            405             410             415

Ser Val Ser Ser Phe Glu Ala Lys Pro Ser Gly Ser Pro Gly Glu Asn
            420             425             430

Leu Tyr Phe Gln Gly Pro Gly Gly Gly Ser His His His His His His
            435             440             445
```

<210> SEQ ID NO 164
<211> LENGTH: 2095
<212> TYPE: DNA
<213> ORGANISM: Artificial Sequence
<220> FEATURE:
<223> OTHER INFORMATION: Nucleotide sequence of a SNAP construct
      containing the LruA gene of Leptospirosis

<400> SEQUENCE: 164

```
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttaggaatt tccagtcccc gcccttcacc atcctgtgtt tcagcaggag      360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt tcatcttcc     540
ggagctgtag gtggctatga aggaggactg cagttaagg agtggctgct ggctcatgaa      600
ggtcatagac ttgaaaagcc tgggctgggt cctgctggta taggcgcgcc agggtcccta    660
ggtggcggat ccgaaaacct gtacttccag agcgatatcg agctgagct tcctattgag      720
gagttaagtg atgcaaagaa ctcgatcaca agagctaagt ctgcaggtgc tgaaaagtat     780
gctccttcag agttagagga ggcccgtaag aacttactca cagctcatca gaaggcttcg     840
gaggagaatc ttacagagac taagaagtcc gcgttgtatg caagagcaaa ggctttagac     900
gcttccgaga gtccttccc ttcttctgtt gatgatgcac gtaaggagtc cagctcttca      960
atcgagtctg cagaggaggc ctatgcttct cagcttgctt ctgagcctta taatacttct    1020
```

-continued

```
gtacagcttc gcaaggaggg tgattctcta cgcgagactg ctgaccgcac tttagagtcg    1080
tatccgaagg agtccggaga tgacgcaaag ctgaggatga gattagcagc attcgatcag    1140
tatgaggctt ctcgtcagaa gtatgcggat tctaagaagg ccgcagacga gtccaaggta    1200
ttagctcttt ctcagaagca gcagctaatc gattcttttg cagacataga taagaatcta    1260
aatgatgcag ataagtatgc agagggaaag gacccggagg tttccgagac tagaaatcgt    1320
ctcgattcct ctaagtccaa gatagaggag gggaagatca aggagggata ttccgagata    1380
gatgatattc gtaagaagtc cggcgagctt gttgctaaga atattaagat ttacgcagag    1440
aagcagaagg aacttgcaaa gcaaagcgta gcatctgcga ctacaaggtt agcttccttc    1500
gatcgaaata agatcaattc ctctagagat tttcaggttt cttaccagag agcagaggag    1560
aaccttaagg cagctgagga gtcgagagta gctgcagagg atctatattc ttcggagaag    1620
tacgaggatt ctatttcgcg ttctgaggag gcaattcgcc tttccagaat cgtagtagac    1680
caggccactg agttggccga gagaatagag agaaaggcaa cgactgataa gatcgctggt    1740
cgtgatacaa agaccgaagg gaataagaat actaagaacc agtccacaac cgaaggcaag    1800
aactcttcat ctaagattgg agaggatggt ttaccggagg gttggaagcg ttatgtggtt    1860
cggaagaagg ttcctgcaga ttgtctttgg agaatcgcaa aggataagag acattatgga    1920
acttctaagc tctggagaag aatctacgag gcaaaccgaa acaagatcaa gaacccaaac    1980
ttgatttatc cgaagcaggt attattaatc ccgggagaga atctatattt tcaagggccc    2040
ggcggaggta gtcaccatca tcaccatcac taatgaccgg tgcggccgca agctt         2095
```

<210> SEQ ID NO 165
<211> LENGTH: 690
<212> TYPE: PRT
<213> ORGANISM: Artificial Sequence
<220> FEATURE:
<223> OTHER INFORMATION: Amino acid sequence of a SNAP construct containing the LruA gene of Leptospirosis

<400> SEQUENCE: 165

```
Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
```

-continued

```
                165                 170                 175
Val Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
            195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Gly Ala Glu Leu Pro Ile Glu
225                 230                 235                 240

Glu Leu Ser Asp Ala Lys Asn Ser Ile Thr Arg Ala Lys Ser Ala Gly
                245                 250                 255

Ala Glu Lys Tyr Ala Pro Ser Glu Leu Glu Ala Arg Lys Asn Leu
            260                 265                 270

Leu Thr Ala His Gln Lys Ala Ser Glu Glu Asn Leu Thr Glu Thr Lys
            275                 280                 285

Lys Ser Ala Leu Tyr Ala Arg Ala Lys Ala Leu Asp Ala Ser Glu Lys
    290                 295                 300

Ser Phe Pro Ser Ser Val Asp Asp Ala Arg Lys Glu Ser Ser Ser
305                 310                 315                 320

Ile Glu Ser Ala Glu Glu Ala Tyr Ala Ser Gln Leu Ala Ser Glu Pro
                325                 330                 335

Tyr Asn Thr Ser Val Gln Leu Arg Lys Glu Gly Asp Ser Leu Arg Glu
            340                 345                 350

Thr Ala Asp Arg Thr Leu Glu Ser Tyr Pro Lys Glu Ser Gly Asp Asp
            355                 360                 365

Ala Lys Leu Arg Met Arg Leu Ala Ala Phe Asp Gln Tyr Glu Ala Ser
    370                 375                 380

Arg Gln Lys Tyr Ala Asp Ser Lys Lys Ala Ala Asp Glu Ser Lys Val
385                 390                 395                 400

Leu Ala Leu Ser Gln Lys Gln Leu Ile Asp Ser Phe Ala Asp Ile
                405                 410                 415

Asp Lys Asn Leu Asn Asp Ala Asp Lys Tyr Ala Glu Gly Lys Asp Pro
            420                 425                 430

Glu Val Ser Glu Thr Arg Asn Arg Leu Asp Ser Ser Lys Ser Lys Ile
            435                 440                 445

Glu Glu Gly Lys Ile Lys Glu Gly Tyr Ser Glu Ile Asp Asp Ile Arg
    450                 455                 460

Lys Lys Ser Gly Glu Leu Val Ala Lys Asn Ile Lys Ile Tyr Ala Glu
465                 470                 475                 480

Lys Gln Lys Glu Leu Ala Lys Gln Ser Val Ala Ser Ala Thr Thr Arg
                485                 490                 495

Leu Ala Ser Phe Asp Arg Asn Lys Ile Asn Ser Ser Arg Asp Phe Gln
            500                 505                 510

Val Ser Tyr Gln Arg Ala Glu Glu Asn Leu Lys Ala Ala Glu Glu Ser
            515                 520                 525

Arg Val Ala Ala Glu Asp Leu Tyr Ser Ser Glu Lys Tyr Glu Asp Ser
    530                 535                 540

Ile Ser Arg Ser Glu Glu Ala Ile Arg Leu Ser Arg Ile Val Val Asp
545                 550                 555                 560

Gln Ala Thr Glu Leu Ala Glu Arg Ile Glu Arg Lys Ala Thr Asp
                565                 570                 575

Lys Ile Ala Gly Arg Asp Thr Lys Thr Glu Gly Asn Lys Asn Thr Lys
            580                 585                 590
```

```
Asn Gln Ser Thr Thr Glu Gly Lys Asn Ser Ser Ser Lys Ile Gly Glu
        595                 600                 605

Asp Gly Leu Pro Glu Gly Trp Lys Arg Tyr Val Val Arg Lys Lys Val
    610                 615                 620

Pro Ala Asp Cys Leu Trp Arg Ile Ala Lys Asp Lys Arg His Tyr Gly
625                 630                 635                 640

Thr Ser Lys Leu Trp Arg Arg Ile Tyr Glu Ala Asn Arg Asn Lys Ile
                645                 650                 655

Lys Asn Pro Asn Leu Ile Tyr Pro Lys Gln Val Leu Leu Ile Pro Gly
            660                 665                 670

Glu Asn Leu Tyr Phe Gln Gly Pro Gly Gly Gly Ser His His His His
        675                 680                 685

His His
    690
```

<210> SEQ ID NO 166
<211> LENGTH: 1711
<212> TYPE: DNA
<213> ORGANISM: Artificial Sequence
<220> FEATURE:
<223> OTHER INFORMATION: Nucleotide sequence of a SNAP construct containing the LruB gene of Leptospirosis.

<400> SEQUENCE: 166

```
tcgcgagcta gcaccatgaa actatgtatt ctacttgcag ttgttgcgtt cgtaggattg     60
tccttaccta cagctctggc aagatctgac aaagactgcg aaatgaaaag aactacattg    120
gattcaccac ttgggaagtt ggaactgagt ggatgcgagc aaggattgca tgaaattaag    180
ctactgggaa aaggaacttc tgctgctgat gcagttgaag ttccagcacc agcagctgtt    240
cttggaggtc ctgagcccct catgcaagcc acagcctggc ttaacgcata tttccaccag    300
cctgaggcca ttgaggaatt tccagtcccc gcccttcacc atcctgtgtt tcagcaggag    360
agcttcaccc gccaggtcct gtggaaattg ctgaaggtgg tcaagtttgg tgaagtgatt    420
tcatatcagc aacttgctgc attggccggt aaccccgcag ctacagctgc cgtgaaaact    480
gctctcagcg gaaatcctgt gcccatcctg atcccttgtc acagagtcgt ttcatcttcc    540
ggagctgtag gtggctatga aggaggactg gcagttaagg agtggctgct ggctcatgaa    600
ggtcatagac ttggaaagcc tgggctgggt cctgctggta taggcgcgcc agggtcccta    660
ggtggcggat ccgaaaacct gtacttccag agcgatatcc aacccactgc gacaagagct    720
caagtcgtag atcgttatct tcaactcggc tacgaatcct acgatcagag ctataaagac    780
gcagtcgctt ttcagaccgc agtcacagcc tttgctgcca ataacaaccc gaccgcagcg    840
gatcatatca atcttaagaa tttatacgta gtagcaagag cttcttattt aactacggaa    900
gcatttcgtt tttcatctgg accgatagac aacgtagaca ttttaggttg tggaagtaat    960
gcggatggtt ccggagacga agaatgcgaa ggactgatta acggatggcc gttagacgaa   1020
agcgcgattg ataattatat agcaaatgca ggaaatgcaa caacttatgc agccatccta   1080
gctacaaatg gagatgcaaa cgcaaataac gcagatgatc aagacgatga gacagcgctt   1140
acggtcggtt ggcacgccat cgaatatata ctctggggtc aggatctatt taacggagga   1200
atcaatcaaa tttcaggaca acgtaatata gctgatctta caggagcttc tccaggaaca   1260
gttggaggca gaagaagagc ttatatgaaa gcagttacgg acggactggt tcttcagcta   1320
aaattgattc gagatcaatt tgaagacggt gccagatatt cggatggact taaatccaat   1380
```

```
cctgacgcag cggtcactta tatctttcaa ggacttggta aattcatcgc tggagaatgg   1440
ggaggagaaa gacttaccgg aacttttggt ggacagcagg aggaggagca ttcttgtttt   1500
agcgatacta caaaggctga cttctattac aacgcacaga gtgtgttgaa catttggaac   1560
ggatcttacg aattgaagaa gggaaccgta acttccacgg gtccgggttt aaagaatctt   1620
tttggcccgg gagagaatct atattttcaa gggcccggcg gaggtagtca ccatcatcac   1680
catcactaat gaccggtgcg gccgcaagct t                                  1711
```

<210> SEQ ID NO 167
<211> LENGTH: 562
<212> TYPE: PRT
<213> ORGANISM: Artificial Sequence
<220> FEATURE:
<223> OTHER INFORMATION: Amino acid sequence of a SNAP construct containing the LruB gene of Leptospirosis.

<400> SEQUENCE: 167

```
Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
                20                  25                  30

Cys Glu Met Lys Arg Thr Thr Leu Asp Ser Pro Leu Gly Lys Leu Glu
            35                  40                  45

Leu Ser Gly Cys Glu Gln Gly Leu His Glu Ile Lys Leu Leu Gly Lys
        50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Gln Pro Thr Ala Thr Arg Ala
225                 230                 235                 240

Gln Val Val Asp Arg Tyr Leu Gln Leu Gly Tyr Glu Ser Tyr Asp Gln
                245                 250                 255

Ser Tyr Lys Asp Ala Val Ala Phe Gln Thr Ala Val Thr Ala Phe Ala
            260                 265                 270

Ala Asn Asn Asn Pro Thr Ala Ala Asp His Ile Asn Leu Lys Asn Leu
        275                 280                 285

Tyr Val Val Ala Arg Ala Ser Tyr Leu Thr Thr Glu Ala Phe Arg Phe
    290                 295                 300
```

Ser Ser Gly Pro Ile Asp Asn Val Asp Ile Leu Gly Cys Gly Ser Asn
305                 310                 315                 320

Ala Asp Gly Ser Gly Asp Glu Glu Cys Glu Gly Leu Ile Asn Gly Trp
            325                 330                 335

Pro Leu Asp Glu Ser Ala Ile Asp Asn Tyr Ile Ala Asn Ala Gly Asn
        340                 345                 350

Ala Thr Thr Tyr Ala Ala Ile Leu Ala Thr Asn Gly Asp Ala Asn Ala
    355                 360                 365

Asn Asn Ala Asp Asp Gln Asp Asp Glu Thr Ala Leu Thr Val Gly Trp
370                 375                 380

His Ala Ile Glu Tyr Ile Leu Trp Gly Gln Asp Leu Phe Asn Gly Gly
385                 390                 395                 400

Ile Asn Gln Ile Ser Gly Gln Arg Asn Ile Ala Asp Leu Thr Gly Ala
            405                 410                 415

Ser Pro Gly Thr Val Gly Gly Arg Arg Arg Ala Tyr Met Lys Ala Val
        420                 425                 430

Thr Asp Gly Leu Val Leu Gln Leu Lys Leu Ile Arg Asp Gln Phe Glu
    435                 440                 445

Asp Gly Ala Arg Tyr Ser Asp Gly Leu Lys Ser Asn Pro Asp Ala Ala
450                 455                 460

Val Thr Tyr Ile Phe Gln Gly Leu Gly Lys Phe Ile Ala Gly Glu Trp
465                 470                 475                 480

Gly Gly Glu Arg Leu Thr Gly Thr Phe Gly Gly Gln Glu Glu Glu
            485                 490                 495

His Ser Cys Phe Ser Asp Thr Thr Lys Ala Asp Phe Tyr Tyr Asn Ala
        500                 505                 510

Gln Ser Val Leu Asn Ile Trp Asn Gly Ser Tyr Glu Leu Lys Lys Gly
    515                 520                 525

Thr Val Thr Ser Thr Gly Pro Gly Leu Lys Asn Leu Phe Gly Pro Gly
    530                 535                 540

Glu Asn Leu Tyr Phe Gln Gly Pro Gly Gly Gly Ser His His His
545                 550                 555                 560

His His

<210> SEQ ID NO 168
<211> LENGTH: 1513
<212> TYPE: DNA
<213> ORGANISM: Artificial Sequence
<220> FEATURE:
<223> OTHER INFORMATION: Nucleotide sequence of a SNAP construct
      containing the LipL32 gene of Leptospirosis.

<400> SEQUENCE: 168
tcgcgagcta gcaccatgaa actatgtatt ctacttgcag ttgttgcgtt cgtaggattg 60
tccttaccta cagctctggc aagatctgac aaagactgcg aaatgaaaag aactacattg 120
gattcaccac ttgggaagtt ggaactgagt ggatgcgagc aaggattgca tgaaattaag 180
ctactgggaa aaggaacttc tgctgctgat gcagttgaag ttccagcacc agcagctgtt 240
cttggaggtc ctgagcccct catgcaagcc acagcctggc ttaacgcata tttccaccag 300
cctgaggcca ttgaggaatt tccagtcccc gcccttcacc atcctgtgtt tcagcaggag 360
agcttcaccc gccaggtcct gtggaaattg ctgaaggtgg tcaagtttgg tgaagtgatt 420
tcatatcagc aacttgctgc attggccggt aaccccgcag ctacagctgc cgtgaaaact 480
gctctcagcg gaaatcctgt gcccatcctg atcccttgtc acagagtcgt ttcatcttcc 540

-continued

```
ggagctgtag gtggctatga aggaggactg gcagttaagg agtggctgct ggctcatgaa      600
ggtcatagac ttggaaagcc tgggctgggt cctgctggta taggcgcgcc agggtcccta      660
ggtggcggat ccgaaaacct gtacttccag agcgatatca ttaccgcttg tggtgctttc      720
ggtggtctgc caagcctaaa aagctctttt gttctgagcg aggacacaat cccagggaca      780
aacgaaaccg taaaaacgtt acttccctac ggatctgtga tcaactatta cggatacgta      840
aagccaggac aagcgccgga cggtttagtc gatggaaaca aaaagcata ctatctctat       900
gtttggattc ctgccgtaat cgctgaaatg ggagttcgta tgatttcccc aacaggcgaa      960
atcggtgagc aggcgacgg agacttagta agcgacgctt tcaaagcggc taccccagaa      1020
gaaaaatcaa tgccacattg gtttgatact tggattcgtg tagaaagaat gtcggcgatt     1080
atgcctgacc aaatcgccaa agctgcgaaa gcaaaaccag ttcaaaaatt ggacgatgat     1140
gatgatggtg acgatactta taagaagag agacacaaca agtacaactc tcttactaga     1200
atcaagatcc ctaatcctcc aaaatctttt gacgatctga aaacatcga cactaaaaaa     1260
cttttagtaa gaggtctta cagaatttct ttcactacct acaaaccagg tgaagtgaaa     1320
ggatctttcg ttgcatctgt tggtctgctt ttcccaccag gtattccagg tgtgagcccg     1380
ctgatccact caaatcctga agaattgcaa aaacaagcta tcgctgcccc gggagagaat     1440
ctatattttc aagggcccgg cggaggtagt caccatcatc accatcacta atgaccggtg     1500
cggccgcaag ctt                                                         1513

<210> SEQ ID NO 169
<211> LENGTH: 496
<212> TYPE: PRT
<213> ORGANISM: Artificial Sequence
<220> FEATURE:
<223> OTHER INFORMATION: Amino acid sequence of a SNAP construct
      containing the LipL32 gene of Leptospirosis.

<400> SEQUENCE: 169

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175
```

Val Ser Ser Ser Gly Ala Val Gly Gly Tyr Glu Gly Gly Leu Ala Val
            180                 185                 190
Lys Glu Trp Leu Leu Ala His Glu Gly His Arg Leu Gly Lys Pro Gly
            195                 200                 205
Leu Gly Pro Ala Gly Ile Gly Ala Pro Gly Ser Leu Gly Gly Gly Ser
            210                 215                 220
Glu Asn Leu Tyr Phe Gln Ser Asp Ile Ile Thr Ala Cys Gly Ala Phe
225                 230                 235                 240
Gly Gly Leu Pro Ser Leu Lys Ser Ser Phe Val Leu Ser Glu Asp Thr
            245                 250                 255
Ile Pro Gly Thr Asn Glu Thr Val Lys Thr Leu Leu Pro Tyr Gly Ser
            260                 265                 270
Val Ile Asn Tyr Tyr Gly Tyr Val Lys Pro Gly Gln Ala Pro Asp Gly
            275                 280                 285
Leu Val Asp Gly Asn Lys Lys Ala Tyr Tyr Leu Tyr Val Trp Ile Pro
            290                 295                 300
Ala Val Ile Ala Glu Met Gly Val Arg Met Ile Ser Pro Thr Gly Glu
305                 310                 315                 320
Ile Gly Glu Pro Gly Asp Gly Asp Leu Val Ser Asp Ala Phe Lys Ala
            325                 330                 335
Ala Thr Pro Glu Glu Lys Ser Met Pro His Trp Phe Asp Thr Trp Ile
            340                 345                 350
Arg Val Glu Arg Met Ser Ala Ile Met Pro Asp Gln Ile Ala Lys Ala
            355                 360                 365
Ala Lys Ala Lys Pro Val Gln Lys Leu Asp Asp Asp Asp Gly Asp
            370                 375                 380
Asp Thr Tyr Lys Glu Glu Arg His Asn Lys Tyr Asn Ser Leu Thr Arg
385                 390                 395                 400
Ile Lys Ile Pro Asn Pro Pro Lys Ser Phe Asp Asp Leu Lys Asn Ile
            405                 410                 415
Asp Thr Lys Lys Leu Leu Val Arg Gly Leu Tyr Arg Ile Ser Phe Thr
            420                 425                 430
Thr Tyr Lys Pro Gly Glu Val Lys Gly Ser Phe Val Ala Ser Val Gly
            435                 440                 445
Leu Leu Phe Pro Pro Gly Ile Pro Gly Val Ser Pro Leu Ile His Ser
            450                 455                 460
Asn Pro Glu Glu Leu Gln Lys Gln Ala Ile Ala Ala Pro Gly Glu Asn
465                 470                 475                 480
Leu Tyr Phe Gln Gly Pro Gly Gly Gly Ser His His His His His
            485                 490                 495

<210> SEQ ID NO 170
<211> LENGTH: 2803
<212> TYPE: DNA
<213> ORGANISM: Artificial Sequence
<220> FEATURE:
<223> OTHER INFORMATION: Nucleotide sequence of a SNAP construct
      containing the C gene of Hepatitis E

<400> SEQUENCE: 170
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240

```
cttggaggtc ctgagcccct catgcaagcc acagcctggc ttaacgcata tttccaccag    300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt    420
tcatatcagc aacttgctgc attggccggt aaccccgcag ctacagctgc cgtgaaaact    480
gctctcagcg gaaatcctgt gcccatcctg atcccttgtc acagagtcgt ttcatcttcc    540
ggagctgtag gtggctatga aggaggactg cagttaagg agtggctgct ggctcatgaa     600
ggtcatagac ttggaaagcc tgggctgggt cctgctggta taggcgcgcc agggtcccta    660
ggtggcggat ccgaaaacct gtacttccag agcgatatca ataacatgtt cttttgctct    720
gtgcatggag atgccaccat cgctctcgg gctttcctgt tcttgttcct cgtgtttctg     780
cctatgctgc cagcgccacc agccggtcag ccttctggcc gacgtcgagg tcgacgtagc    840
ggaggtgcag gtggtggttt ctggggtgac cgtattgatt ctcagccatt cgctctccct    900
tatattcatc caaccaaccc attcgcacct gacattccag ccgcagctgg tgctggagct    960
cgacctcggc agccagcccg cccactcggc tccgcttggc gtgaccaatc ccagcgccca   1020
gccacttccg cacgtcgtcg atctgcacca gctggagctt cgccactgac tgctgtggca   1080
cctgctccag atactgttcc tgttcctgat gtcgattctc gaggtgctat attacgacgt   1140
cagtataatt tatcaacatc accgctaaca tctactattg ccactggtac taaccttgtt   1200
ctatatgctg ctccgctgag ccctttgcta ccactccaag atggaactaa cactcacatt   1260
atggccactg aagcatcaaa ttatgcccag taccgtgttg ccgcgctac catccggtac    1320 cgtccgcttg tgccgaacgc tgtcggcgga tacgctatat ctatctcttt ctggcctcag   1380
acaactacta ccccgacatc tgtggacatg aactctatca cctccacgga tgtccgaatc   1440
cttgtccagc ctggtattgc ttcagaactt gtgatcccca gtgagcgcct gcattatcgt   1500
aaccaaggct ggcgctctgt tgagacctct ggtgttgcgg aggaggaggc gacctccggc   1560
cttgtcatgc tttgcatcca cggatcacct gtaaattctt acaccaatac gccttatact   1620
ggtgcccttg gcttgcttga tttcgcactc gagctcgagt tccgcaattt gacacctggt   1680
aacacgaaca cacgtgtttc ccgctactcg agtagtgcac gacacaagct acgccgagga   1740
cctgatggca ctgctgagtt aactacgact gctgctacac gctttatgaa ggaccttcat   1800
tttacaggga ctaatggagt tggtgaagtc ggtcgtggta tagcgctaac tctgttcaac   1860
cttgctgata cgcttctcgg tggactcccg acagaattga tttcgtcggc tggtggtcag   1920
ctattctatt ctcgccccgt cgtctcagcc aatggcgagc caacggtgaa gctctacact   1980
tcagtcgaga acgctcagca ggataagggt atagctatcc cacatgatat tgatcttggt   2040
gagtcccgtg ttgtcattca ggattatgat aaccaacatg agcaggatcg tccaactcct   2100
tctcctgctc catctcgacc tttatctgtc cttcgtgcta atgatgtgct atggctttca   2160
cttacagcag ctgagtatga tcagactacc tatggctcct ctactaatcc aatgtatgtc   2220
tctgataccg tgacatttgt caatgttgct actggtgccc agggtgtatc tcgctctctg   2280
gactggtcta aagtcacccct tgatggacga ccacttatga ctatccagca gtattctaag   2340
actttctttg ttctgccact acgtggcaag ctctccttct gggaggccgg taccactaag   2400
gccggctacc cttataatta taatactact gccagtgacc agatttttaat tgagaatgca   2460 gctggtcacc gtgtatgcat ctcaacctac actactaatc ttggatctgg ccctgttttct   2520 atttctgctc tcggtgtcct cgcacctcac tctgcgttgg ccgctttaga ggacactgtt   2580
gactatcctg ctcgtgctca cacttttgat gatttctgcc ctgagtgccg tacactcggc   2640
```

```
cttcagggtt gtgctttcca atcaactgtt gctgagctac agcgtcttaa aatgaaggtg    2700
ggtaaaactc gggagtaccc gggagagaat ctatattttc aagggcccgg cggaggtagt    2760
caccatcatc accatcacta atgaccggtg cggccgcaag ctt                      2803
```

<210> SEQ ID NO 171
<211> LENGTH: 926
<212> TYPE: PRT
<213> ORGANISM: Artificial Sequence
<220> FEATURE:
<223> OTHER INFORMATION: Amino acid sequence of a SNAP construct
      containing the C gene of Hepatitis E

<400> SEQUENCE: 171

```
Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
                20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Asn Asn Met Phe Phe Cys Ser
225                 230                 235                 240

Val His Gly Asp Ala Thr Met Arg Ser Arg Ala Phe Leu Phe Leu Phe
                245                 250                 255

Leu Val Phe Leu Pro Met Leu Pro Ala Pro Ala Gly Gln Pro Ser
            260                 265                 270

Gly Arg Arg Gly Arg Arg Ser Gly Gly Ala Gly Gly Phe Trp
        275                 280                 285

Gly Asp Arg Ile Asp Ser Gln Pro Phe Ala Leu Pro Tyr Ile His Pro
    290                 295                 300

Thr Asn Pro Phe Ala Pro Asp Ile Pro Ala Ala Gly Ala Gly Ala
305                 310                 315                 320

Arg Pro Arg Gln Pro Ala Arg Pro Leu Gly Ser Ala Trp Arg Asp Gln
```

```
                    325                 330                 335
Ser Gln Arg Pro Ala Thr Ser Ala Arg Arg Ser Ala Pro Ala Gly
                340                 345                 350
Ala Ser Pro Leu Thr Ala Val Ala Pro Ala Pro Asp Thr Val Pro Val
            355                 360                 365
Pro Asp Val Asp Ser Arg Gly Ala Ile Leu Arg Arg Gln Tyr Asn Leu
        370                 375                 380
Ser Thr Ser Pro Leu Thr Ser Thr Ile Ala Thr Gly Thr Asn Leu Val
385                 390                 395                 400
Leu Tyr Ala Ala Pro Leu Ser Pro Leu Leu Pro Leu Gln Asp Gly Thr
                405                 410                 415
Asn Thr His Ile Met Ala Thr Glu Ala Ser Asn Tyr Ala Gln Tyr Arg
            420                 425                 430
Val Val Arg Ala Thr Ile Arg Tyr Arg Pro Leu Val Pro Asn Ala Val
        435                 440                 445
Gly Gly Tyr Ala Ile Ser Ile Ser Phe Trp Pro Gln Thr Thr Thr Thr
    450                 455                 460
Pro Thr Ser Val Asp Met Asn Ser Ile Thr Ser Thr Asp Val Arg Ile
465                 470                 475                 480
Leu Val Gln Pro Gly Ile Ala Ser Glu Leu Val Ile Pro Ser Glu Arg
                485                 490                 495
Leu His Tyr Arg Asn Gln Gly Trp Arg Ser Val Glu Thr Ser Gly Val
            500                 505                 510
Ala Glu Glu Ala Thr Ser Gly Leu Val Met Leu Cys Ile His Gly
        515                 520                 525
Ser Pro Val Asn Ser Tyr Thr Asn Thr Pro Tyr Thr Gly Ala Leu Gly
    530                 535                 540
Leu Leu Asp Phe Ala Leu Glu Leu Glu Phe Arg Asn Leu Thr Pro Gly
545                 550                 555                 560
Asn Thr Asn Thr Arg Val Ser Arg Tyr Ser Ser Ser Ala Arg His Lys
                565                 570                 575
Leu Arg Arg Gly Pro Asp Gly Thr Ala Glu Leu Thr Thr Thr Ala Ala
            580                 585                 590
Thr Arg Phe Met Lys Asp Leu His Phe Thr Gly Thr Asn Gly Val Gly
        595                 600                 605
Glu Val Gly Arg Gly Ile Ala Leu Thr Leu Phe Asn Leu Ala Asp Thr
    610                 615                 620
Leu Leu Gly Gly Leu Pro Thr Glu Leu Ile Ser Ser Ala Gly Gly Gln
625                 630                 635                 640
Leu Phe Tyr Ser Arg Pro Val Val Ser Ala Asn Gly Glu Pro Thr Val
                645                 650                 655
Lys Leu Tyr Thr Ser Val Glu Asn Ala Gln Gln Asp Lys Gly Ile Ala
            660                 665                 670
Ile Pro His Asp Ile Asp Leu Gly Glu Ser Arg Val Val Ile Gln Asp
        675                 680                 685
Tyr Asp Asn Gln His Glu Gln Asp Arg Pro Thr Pro Ser Pro Ala Pro
    690                 695                 700
Ser Arg Pro Leu Ser Val Leu Arg Ala Asn Asp Val Leu Trp Leu Ser
705                 710                 715                 720
Leu Thr Ala Ala Glu Tyr Asp Gln Thr Thr Tyr Gly Ser Ser Thr Asn
                725                 730                 735
Pro Met Tyr Val Ser Asp Thr Val Thr Phe Val Asn Val Ala Thr Gly
            740                 745                 750
```

```
Ala Gln Gly Val Ser Arg Ser Leu Asp Trp Ser Lys Val Thr Leu Asp
        755                 760                 765
Gly Arg Pro Leu Met Thr Ile Gln Gln Tyr Ser Lys Thr Phe Phe Val
    770                 775                 780
Leu Pro Leu Arg Gly Lys Leu Ser Phe Trp Glu Ala Gly Thr Thr Lys
785                 790                 795                 800
Ala Gly Tyr Pro Tyr Asn Tyr Asn Thr Thr Ala Ser Asp Gln Ile Leu
                805                 810                 815
Ile Glu Asn Ala Ala Gly His Arg Val Cys Ile Ser Thr Tyr Thr Thr
                820                 825                 830
Asn Leu Gly Ser Gly Pro Val Ser Ile Ser Ala Val Gly Val Leu Ala
                835                 840                 845
Pro His Ser Ala Leu Ala Ala Leu Glu Asp Thr Val Asp Tyr Pro Ala
        850                 855                 860
Arg Ala His Thr Phe Asp Asp Phe Cys Pro Glu Cys Arg Thr Leu Gly
865                 870                 875                 880
Leu Gln Gly Cys Ala Phe Gln Ser Thr Val Ala Glu Leu Gln Arg Leu
                885                 890                 895
Lys Met Lys Val Gly Lys Thr Arg Glu Tyr Pro Gly Glu Asn Leu Tyr
                900                 905                 910
Phe Gln Gly Pro Gly Gly Ser His His His His His
        915                 920                 925

<210> SEQ ID NO 172
<211> LENGTH: 2395
<212> TYPE: DNA
<213> ORGANISM: Artificial Sequence
<220> FEATURE:
<223> OTHER INFORMATION: Nucleotide sequence of a SNAP construct
      containing the core sequence of the C gene of Hepatitis E

<400> SEQUENCE: 172
tcgcgagcta gcaccatgaa actatgtatt ctacttgcag ttgttgcgtt cgtaggattg      60
tccttaccta cagctctggc aagatctgac aaagactgcg aaatgaaaag aactacattg    120
gattcaccac ttgggaagtt ggaactgagt ggatgcgagc aaggattgca tgaaattaag    180
ctactgggaa aaggaacttc tgctgctgat gcagttgaag ttccagcacc agcagctgtt    240
cttggaggtc ctgagcccct catgcaagcc acagcctggc ttaacgcata tttccaccag    300
cctgaggcca ttgaggaatt ccagtcccc gcccttcacc atcctgtgtt tcagcaggag    360
agcttcaccc gccaggtcct gtggaaattg ctgaaggtgg tcaagtttgg tgaagtgatt    420
tcatatcagc aacttgctgc attggccggt aaccccgcag ctacagctgc cgtgaaaact    480
gctctcagcg gaaatcctgt gcccatcctg atcccttgtc acagagtcgt tcatcttcc    540 ggagctgtag gtggctatga aggaggactg gcagttaagg agtggctgct ggctcatgaa    600
ggtcatagac ttgaaaagcc tgggctgggt cctgctggta taggcgcgcc agggtcccta    660
ggtggcggat ccgaaaacct gtacttccag agcgatatcg ctggtgctgg agctcgacct    720
cggcagccag cccgcccact cggctccgct tggcgtgacc aatcccagcg cccagccact    780
tccgcacgtc gtcgatctgc accagctgga gcttcgccac tgactgctgt ggcacctgct    840
ccagatactg ttcctgttcc tgatgtcgat tctcgaggtg ctatattacg acgtcagtat    900
aatttatcaa catcaccgct aacatctact attgccactg gtactaacct tgttctatat    960
gctgctccgc tgagcccttt gctaccactc caagatggaa ctaacactca cattatggcc   1020
```

```
actgaagcat caaattatgc ccagtaccgt gttgtccgcg ctaccatccg gtaccgtccg    1080
cttgtgccga acgctgtcgg cggatacgct atatctatct ctttctggcc tcagacaact    1140
actacccga catctgtgga catgaactct atcacctcca cggatgtccg aatccttgtc     1200
cagcctggta ttgcttcaga acttgtgatc cccagtgagc gcctgcatta tcgtaaccaa    1260
ggctggcgct ctgttgagac ctctggtgtt gcggaggagg aggcgacctc cggccttgtc    1320
atgctttgca tccacggatc acctgtaaat tcttacacca atacgcctta tactggtgcc    1380
cttggcttgc ttgatttcgc actcgagctc gagttccgca atttgacacc tggtaacacg    1440
aacacacgtg tttcccgcta ctcgagtagt gcacgacaca agctacgccg aggacctgat    1500
ggcactgctg agttaactac gactgctgct acacgcttta tgaaggacct tcattttaca    1560
gggactaatg gagttggtga agtcggtcgt ggtatagcgc taactctgtt caaccttgct    1620
gatacgcttc tcggtggact cccgacagaa ttgatttcgt cggctggtgg tcagctattc    1680
tattctcgcc ccgtcgtctc agccaatggc gagccaacgg tgaagctcta cacttcagtc    1740
gagaacgctc agcaggataa gggtatagct atcccacatg atattgatct tggtgagtcc    1800
cgtgttgtca ttcaggatta tgataaccaa catgagcagg atcgtccaac tccttctcct    1860
gctccatctc gacctttatc tgtccttcgt gctaatgatg tgctatggct ttcacttaca    1920
gcagctgagt atgatcagac tacctatggc tcctctacta atccaatgta tgtctctgat    1980
accgtgacat ttgtcaatgt tgctactggt gcccagggtg tatctcgctc tctggactgg    2040
tctaaagtca cccttgatgg acgaccactt atgactatcc agcagtattc taagactttc    2100
tttgttctgc cactacgtgg caagctctcc ttctgggagg ccggtaccac taaggccggc    2160
tacccttata attataatac tactgccagt gaccagattt taattgagaa tgcagctggt    2220
caccgtgtat gcatctcaac ctacactact aatcttggat ctggccctgt ttctatttct    2280
gctgtcggtg tcctcgcacc tcactctgcc ccgggagaga atctatattt tcaagggccc    2340
ggcggaggta gtcaccatca tcaccatcac taatgaccgg tgcggccgca agctt         2395
```

<210> SEQ ID NO 173
<211> LENGTH: 790
<212> TYPE: PRT
<213> ORGANISM: Artificial Sequence
<220> FEATURE:
<223> OTHER INFORMATION: Amino acid sequence of a SNAP construct
containing the core sequence of the C gene of Hepatitis E

<400> SEQUENCE: 173

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp

-continued

```
            115                 120                 125
Lys Leu Leu Lys Val Val Lys Phe Gly Glu Val Ile Ser Tyr Gln Gln
            130                 135                 140
Leu Ala Leu Ala Gly Asn Pro Ala Thr Ala Ala Val Lys Thr
145                 150                 155                 160
Ala Leu Ser Gly Asn Pro Val Pro Ile Leu Ile Pro Cys His Arg Val
                    165                 170                 175
Val Ser Ser Ser Gly Ala Val Gly Gly Tyr Glu Gly Gly Leu Ala Val
                    180                 185                 190
Lys Glu Trp Leu Leu Ala His Glu Gly His Arg Leu Gly Lys Pro Gly
                195                 200                 205
Leu Gly Pro Ala Gly Ile Gly Ala Pro Gly Ser Leu Gly Gly Gly Ser
            210                 215                 220
Glu Asn Leu Tyr Phe Gln Ser Asp Ile Ala Gly Ala Gly Ala Arg Pro
225                 230                 235                 240
Arg Gln Pro Ala Arg Pro Leu Gly Ser Ala Trp Arg Asp Gln Ser Gln
                    245                 250                 255
Arg Pro Ala Thr Ser Ala Arg Arg Ser Ala Pro Ala Gly Ala Ser
                260                 265                 270
Pro Leu Thr Ala Val Ala Pro Ala Pro Asp Thr Val Pro Val Pro Asp
                275                 280                 285
Val Asp Ser Arg Gly Ala Ile Leu Arg Arg Gln Tyr Asn Leu Ser Thr
290                 295                 300
Ser Pro Leu Thr Ser Thr Ile Ala Thr Gly Thr Asn Leu Val Leu Tyr
305                 310                 315                 320
Ala Ala Pro Leu Ser Pro Leu Leu Pro Leu Gln Asp Gly Thr Asn Thr
                325                 330                 335
His Ile Met Ala Thr Glu Ala Ser Asn Tyr Ala Gln Tyr Arg Val Val
                340                 345                 350
Arg Ala Thr Ile Arg Tyr Arg Pro Leu Val Pro Asn Ala Val Gly Gly
                355                 360                 365
Tyr Ala Ile Ser Ile Ser Phe Trp Pro Gln Thr Thr Thr Pro Thr
370                 375                 380
Ser Val Asp Met Asn Ser Ile Thr Ser Thr Asp Val Arg Ile Leu Val
385                 390                 395                 400
Gln Pro Gly Ile Ala Ser Glu Leu Val Ile Pro Ser Glu Arg Leu His
                405                 410                 415
Tyr Arg Asn Gln Gly Trp Arg Ser Val Glu Thr Ser Gly Val Ala Glu
                420                 425                 430
Glu Glu Ala Thr Ser Gly Leu Val Met Leu Cys Ile His Gly Ser Pro
                435                 440                 445
Val Asn Ser Tyr Thr Asn Pro Tyr Thr Gly Ala Leu Gly Leu Leu
                450                 455                 460
Asp Phe Ala Leu Glu Leu Glu Phe Arg Asn Leu Thr Pro Gly Asn Thr
465                 470                 475                 480
Asn Thr Arg Val Ser Arg Tyr Ser Ser Ala Arg His Lys Leu Arg
                    485                 490                 495
Arg Gly Pro Asp Gly Thr Ala Glu Leu Thr Thr Ala Ala Thr Arg
                500                 505                 510
Phe Met Lys Asp Leu His Phe Thr Gly Thr Asn Gly Val Gly Glu Val
                515                 520                 525
Gly Arg Gly Ile Ala Leu Thr Leu Phe Asn Leu Ala Asp Thr Leu Leu
530                 535                 540
```

Gly Gly Leu Pro Thr Glu Leu Ile Ser Ser Ala Gly Gly Gln Leu Phe
545                 550                 555                 560

Tyr Ser Arg Pro Val Val Ser Ala Asn Gly Glu Pro Thr Val Lys Leu
                565                 570                 575

Tyr Thr Ser Val Glu Asn Ala Gln Gln Asp Lys Gly Ile Ala Ile Pro
            580                 585                 590

His Asp Ile Asp Leu Gly Glu Ser Arg Val Val Ile Gln Asp Tyr Asp
        595                 600                 605

Asn Gln His Glu Gln Asp Arg Pro Thr Pro Ser Pro Ala Pro Ser Arg
    610                 615                 620

Pro Leu Ser Val Leu Arg Ala Asn Asp Val Leu Trp Leu Ser Leu Thr
625                 630                 635                 640

Ala Ala Glu Tyr Asp Gln Thr Thr Tyr Gly Ser Ser Thr Asn Pro Met
                645                 650                 655

Tyr Val Ser Asp Thr Val Thr Phe Val Asn Val Ala Thr Gly Ala Gln
                660                 665                 670

Gly Val Ser Arg Ser Leu Asp Trp Ser Lys Val Thr Leu Asp Gly Arg
            675                 680                 685

Pro Leu Met Thr Ile Gln Gln Tyr Ser Lys Thr Phe Phe Val Leu Pro
    690                 695                 700

Leu Arg Gly Lys Leu Ser Phe Trp Glu Ala Gly Thr Thr Lys Ala Gly
705                 710                 715                 720

Tyr Pro Tyr Asn Tyr Asn Thr Thr Ala Ser Asp Gln Ile Leu Ile Glu
                725                 730                 735

Asn Ala Ala Gly His Arg Val Cys Ile Ser Thr Tyr Thr Thr Asn Leu
            740                 745                 750

Gly Ser Gly Pro Val Ser Ile Ser Ala Val Gly Val Leu Ala Pro His
        755                 760                 765

Ser Ala Pro Gly Glu Asn Leu Tyr Phe Gln Gly Pro Gly Gly Gly Ser
    770                 775                 780

His His His His His His
785                 790

<210> SEQ ID NO 174
<211> LENGTH: 1195
<212> TYPE: DNA
<213> ORGANISM: Artificial Sequence
<220> FEATURE:
<223> OTHER INFORMATION: Nucleotide sequence of a SNAP construct
      containing the C gene of Hepatitis C

<400> SEQUENCE: 174
tcgcgagcta gcaccatgaa actatgtatt ctacttgcag ttgttgcgtt cgtaggattg 60
tccttaccta cagctctggc aagatctgac aaagactgcg aaatgaaaag aactacattg 120
gattcaccac ttgggaagtt ggaactgagt ggatgcgagc aaggattgca tgaaattaag 180
ctactgggaa aaggaacttc tgctgctgat gcagttgaag ttccagcacc agcagctgtt 240
cttggaggtc ctgagcccct catgcaagcc acagcctggc ttaacgcata tttccaccag 300
cctgaggcca ttgaggaatt tccagtcccc gcccttcacc atcctgtgtt tcagcaggag 360
agcttcaccc gccaggtcct gtggaaattg ctgaaggtgg tcaagtttgg tgaagtgatt 420
tcatatcagc aacttgctgc attggccggt aaccccgcag ctacagctgc cgtgaaaact 480
gctctcagcg gaaatcctgt gcccatcctg atcccttgtc acagagtcgt ttcatcttcc 540
ggagctgtag gtggctatga aggaggactg gcagttaagg agtggctgct ggctcatgaa 600

```
ggtcatagac ttggaaagcc tgggctgggt cctgctggta taggcgcgcc agggtcccta      660
ggtggcggat ccgaaaacct gtacttccag agcgatatcg agtttacct attgccgcga       720 agaggtcctc gtttaggtgt tcgagcaact agaaagactt ctgaacgatc acaacctcgt      780
ggaagacgac aacctatttt taaggctcgt cgtcctgaag gtagaactat ggctcagcct      840
ggttatccta tgcctctata tggtaatgaa ggatgcggta atgcaggaat gctactatca     900
cctcgtggtt ctcgacctag ttggggtcct actgaccctc gacgaagatc acgtaattta      960
ggtagagtaa ttgatacact tacatgtggt tttgctgatc ttatgggata tattccacta    1020
gtaggtgctc cactaggtgg agctgcaaga gctcttgcac atggtgtacg agttcttgaa    1080
gatggagtga actatgcaac aggtaatctc ccgggagaga atctatattt tcaagggccc    1140
ggcggaggta gtcaccatca tcaccatcac taatgaccgg tgcggccgca agctt           1195
```

<210> SEQ ID NO 175
<211> LENGTH: 390
<212> TYPE: PRT
<213> ORGANISM: Artificial Sequence
<220> FEATURE:
<223> OTHER INFORMATION: Amino acid sequence of a SNAP construct containing the C gene of Hepatitis C.

<400> SEQUENCE: 175

```
Ser Arg Ala Ser Thr Met Lys Leu Cys Ile Leu Leu Ala Val Val Ala
1               5                  10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Ser
    210                 215                 220

Glu Asn Leu Tyr Phe Gln Ser Asp Ile Gly Val Tyr Leu Leu Pro Arg
225                 230                 235                 240

Arg Gly Pro Arg Leu Gly Val Arg Ala Thr Arg Lys Thr Ser Glu Arg
                245                 250                 255
```

```
Ser Gln Pro Arg Gly Arg Arg Gln Pro Ile Phe Lys Ala Arg Arg Pro
            260                 265                 270

Glu Gly Arg Thr Met Ala Gln Pro Gly Tyr Pro Met Pro Leu Tyr Gly
            275                 280                 285

Asn Glu Gly Cys Gly Asn Ala Gly Met Leu Leu Ser Pro Arg Gly Ser
            290                 295                 300

Arg Pro Ser Trp Gly Pro Thr Asp Pro Arg Arg Ser Arg Asn Leu
305                 310                 315                 320

Gly Arg Val Ile Asp Thr Leu Thr Cys Gly Phe Ala Asp Leu Met Gly
                325                 330                 335

Tyr Ile Pro Leu Val Gly Ala Pro Leu Gly Gly Ala Ala Arg Ala Leu
                340                 345                 350

Ala His Gly Val Arg Val Leu Glu Asp Gly Val Asn Tyr Ala Thr Gly
            355                 360                 365

Asn Leu Pro Gly Glu Asn Leu Tyr Phe Gln Gly Pro Gly Gly Gly Ser
            370                 375                 380

His His His His His His
385                 390

<210> SEQ ID NO 176
<211> LENGTH: 1288
<212> TYPE: DNA
<213> ORGANISM: Artificial Sequence
<220> FEATURE:
<223> OTHER INFORMATION: Nucleotide sequence of a SNAP construct
      containing the core sequence of the C gene of Hepatitis C

<400> SEQUENCE: 176
tcgcgagcta gcaccatgaa actatgtatt ctacttgcag ttgttgcgtt cgtaggattg      60
tccttaccta cagctctggc aagatctgac aaagactgcg aaatgaaaag aactacattg     120
gattcaccac ttgggaagtt ggaactgagt ggatgcgagc aaggattgca tgaaattaag     180
ctactgggaa aaggaacttc tgctgctgat gcagttgaag ttccagcacc agcagctgtt     240
cttggaggtc ctgagcccct catgcaagcc acagcctggc ttaacgcata tttccaccag     300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt     420
tcatatcagc aacttgctgc attggccggt aaccccgcag ctacagctgc cgtgaaaact     480
gctctcagcg gaaatcctgt gcccatcctg atcccttgtc acagagtcgt ttcatcttcc     540
ggagctgtag gtggctatga aggaggactg gcagttaagg agtggctgct ggctcatgaa     600
ggtcatagac ttggaaagcc tgggctgggt cctgctggta taggcgcgcc agggtcccta     660
ggtggcggat ccgaaaacct gtacttccag agcgatatca gtacgaatcc taagcctcaa     720
cgtaagacta gcgcaatac taatcgtcgt ccacaagatg ttaagtttcc gggtggcggt     780
caaattgttg gtggagttta cctattgccg cgaagaggtc ctcgtttagg tgttcgagca     840
actagaaaga cttctgaacg atcacaacct cgtggaagac gacaacctat ttttaaggct     900
cgtcgtcctg aaggtagaac tatggctcag cctggttatc ctatgcctct atatggtaat     960
gaaggatgcg gtaatgcagg aatgctacta tcacctcgtg gttctcgacc tagttggggt    1020
cctactgacc ctcgacgaag atcacgtaat ttaggtagag taattgatac acttacatgt    1080
ggttttgctg atcttatggg atatattcca ctagtaggtg ctccactagg tggagctgca    1140
agagctcttg cacatggtgt acgagttctt gaagatggag tgaactatgc aacaggtaat    1200
```

```
ctcccgggag agaatctata ttttcaaggg cccggcggag gtagtcacca tcatcaccat    1260
cactaatgac cggtgcggcc gcaagctt                                       1288
```

<210> SEQ ID NO 177
<211> LENGTH: 421
<212> TYPE: PRT
<213> ORGANISM: Artificial Sequence
<220> FEATURE:
<223> OTHER INFORMATION: Amino acid sequence of a SNAP construct
      containing the core sequence of the C gene of Hepatitis C

<400> SEQUENCE: 177

```
Ser Arg Ala Ser Thr Met Lys Leu Cys Ile Leu Leu Ala Val Val Ala
1

```
Pro Ser Trp Gly Pro Thr Asp Pro Arg Arg Ser Arg Asn Leu Gly
            340                 345                 350

Arg Val Ile Asp Thr Leu Thr Cys Gly Phe Ala Asp Leu Met Gly Tyr
            355                 360                 365

Ile Pro Leu Val Gly Ala Pro Leu Gly Gly Ala Ala Arg Ala Leu Ala
            370                 375                 380

His Gly Val Arg Val Leu Glu Asp Gly Val Asn Tyr Ala Thr Gly Asn
385                 390                 395                 400

Leu Pro Gly Glu Asn Leu Tyr Phe Gln Gly Pro Gly Gly Gly Ser His
                405                 410                 415

His His His His His
            420

<210> SEQ ID NO 178
<211> LENGTH: 1054
<212> TYPE: DNA
<213> ORGANISM: Artificial Sequence
<220> FEATURE:
<223> OTHER INFORMATION: Nucleotide sequence of a SNAP construct
      containing sequences encoding the NSs protein from Schmallenberg
      virus

<400> SEQUENCE: 178
tcgcgagcta gcaccatgaa actatgtatt ctacttgcag ttgttgcgtt cgtaggattg      60
tccttaccta cagctctggc aagatctgac aaagactgcg aaatgaaaag aactacattg     120 gattccaccac ttgggaagtt ggaactgagt ggatgcgagc aaggattgca tgaaattaag    180
ctactgggaa aaggaacttc tgctgctgat gcagttgaag ttccagcacc agcagctgtt    240
cttggaggtc ctgagcccct catgcaagcc acagcctggc ttaacgcata tttccaccag    300
cctgaggcca ttgaggaatt ccagtcccc gcccttcacc atcctgtgtt tcagcaggag     360
agcttcaccc gccaggtcct gtggaaattg ctgaaggtgg tcaagtttgg tgaagtgatt    420
tcatatcagc aacttgctgc attggccggt aaccccgcag ctacagctgc cgtgaaaact    480
gctctcagcg gaaatcctgt gcccatcctg atcccttgtc acagagtcgt ttcatcttcc    540
ggagctgtag gtggctatga aggaggactg gcagttaagg agtggctgct ggctcatgaa    600
ggtcatagac ttgaaaagcc tgggctgggt cctgctggta taggcgcgcc agggtcccta    660
ggtggcggat ccgaaaacct gtacttccag agcgatatct accacaacgg aatgcagcta    720
catttaaccc ggaggtcggg tatgtggcat ttattggtaa gtatgggcaa caactcaact    780
tcggtgttgc tagagtcttc ttcctcaacc agaagaaggc caagatggtc ctacataaga    840
cggcacaacc aagtgtcgat cttactttttg gtggggtcaa atttacagtg gttaataacc    900
attttcccca atatgtctca aatcctgtgc cagacaatgc cattacactt cacaggatgt    960
caggttatcc cgggagagaa tctatatttt caagggcccg gcggaggtag tcaccatcat   1020
caccatcact aatgaccggt gcggccgcaa gctt                               1054

<210> SEQ ID NO 179
<211> LENGTH: 343
<212> TYPE: PRT
<213> ORGANISM: Artificial Sequence
<220> FEATURE:
<223> OTHER INFORMATION: Amino acid sequence of a SNAP construct
      containing sequences encoding the NSs protein from Schmallenberg
      virus
```

```
<400> SEQUENCE: 179

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
            35                  40                  45

Leu Ser Gly Cys Glu Gln Gly Leu His Glu Ile Lys Leu Leu Gly Lys
        50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Tyr His Asn Gly Met Gln Leu
225                 230                 235                 240

His Leu Thr Arg Arg Ser Gly Met Trp His Leu Leu Val Ser Met Gly
                245                 250                 255

Asn Asn Ser Thr Ser Val Leu Leu Glu Ser Ser Ser Ser Thr Arg Arg
            260                 265                 270

Arg Pro Arg Trp Ser Tyr Ile Arg Arg His Asn Gln Val Ser Ile Leu
        275                 280                 285

Leu Leu Val Gly Ser Asn Leu Gln Trp Leu Ile Thr Ile Phe Pro Asn
    290                 295                 300

Met Ser Gln Ile Leu Cys Gln Thr Met Pro Leu His Phe Thr Gly Cys
305                 310                 315                 320

Gln Val Ile Pro Gly Glu Asn Leu Tyr Phe Gln Gly Pro Gly Gly Gly
                325                 330                 335

Ser His His His His His His
            340
```

MULTIPLEX IMMUNO SCREENING ASSAY

The instant application contains a Sequence Listing which has been submitted electronically in ASCII format and is hereby incorporated by reference in its entirety. Said ASCII copy, created on May 27, 2013, is named eolf-seql.txt and is 515,031 bytes in size.

BACKGROUND OF THE INVENTION

Infectious diseases caused by pathogenic agents, such as bacteria, viruses (e.g., viral hemorrhagic fevers (VHFs)), and parasites pose a significant public health problem, due to the severity of the diseases, high lethality, inter-human contagiousness of certain agents, and lack of effective treatment for most of them.

Control of epidemics crucially depends on the rapid detection and accurate identification of the agent, in order to define and implement timely and appropriate action. In this context, it is essential to produce and validate tools for early detection of outbreaks, precise identification of the etiologic agent, and improved disease surveillance.

In this respect, detection of antibodies in body fluids constitutes a major part of the diagnosis of virally induced diseases, other diseases caused by infectious organisms, autoimmune diseases and the detection of cancer. As a matter of fact, certain antibodies can serve as markers in diagnosis and can lead to prognosis and treatment, as their presence are known to correlate with the outbreak of a pathogen. This is particularly the case for the antibodies targeting viral antigens exclusively.

Current methods for detecting the presence of antibodies include diverse techniques such as immunofluorescence microscopy, chemiluminescence assay, Western blotting, Radio Immuno-Precipitation assay (RIP) and ELISA. The parallel detection of several antibodies simultaneously may be particularly useful by minimizing the matrix effects that exist between individual assays, such as in ELISAs, because the calibrators and the antibodies are analyzed under the same conditions; it therefore will generate comparable results for the measurement of multiple antibodies present within the same sample. One such assay is the Luminex multiplex assay utilizing antigens bound to beads. Pickering et al., Clinical and Diagnostic Laboratory Immunology 9:872-876 (2002).

Complicating the straightforward identification of pathogenically relevant antibodies, however, is that normal sera contain large amounts of natural antibodies which manifest themselves in complex staining patterns (Avrameas S. Immunol. Today 1991). The presence of these natural antibodies can complicate the differentiation of disease-associated antibodies from the complex background of "autoimmune noise", i.e. naturally occurring autoantibodies. As noted in Anderson et al., Methods Mol. Biol. 723:227-238 (2011), cross-talk and interference remain a concern with multiplex assays.

Binding of human antibodies directly to the beads in a multiplex assay has also been reported as a problem. Tainsky et al., Biomarker Insights 2:261-267 (2007); Waterboer et al., J. Immunol Methods 309:200-204 (2006).

Moreover, a low difference between positive and control samples can limit the utility of multiplex assays. Burbelo et al., Exp. Rev Vaccines, 9:567-578 (2010).

Another complication is that ELISA and multiplex assays do not necessary give the same results. For example, Pickering et al., 2002, noted numerous discrepancies between the two assays when measuring protective antibodies against various viral and bacterial antigens. This may reflect alterations in antigenicity relating to how the antigen is attached to the substrate. Ambrosino et al., Malaria Journal 9:317 (2010). Similarly, Cham et al., Malaria Journal 7:108 (2008), reported that some samples showed a marked difference between the ELISA and bead-based assay readings, some of which had higher ELISA readings. This could be due to the fact that different parts of the recombinant proteins are accessible by antibodies when the proteins are bound to a surface or a sphere. Id.

The preparation of sufficient quantities of the antigen for commercial applications (i.e., kits) is also required. Burbelo et al., Exp. Rev Vaccines, 9:567-578 (2010).

In view of the foregoing, there exists a need for addressable systems and methods, which can provide additional improvements in high throughput, cost-effectiveness, and accuracy for molecular diagnosis of antibody-generating diseases. The present invention satisfies these and other needs.

FIGURE LEGENDS

FIG. 1 represents the oriented coupling of chimeric AGT-antigen proteins to substrate-coated microspheres. First step of coupling consists of coupling the AGT substrate BG-PEG-NH2 to the activated microspheres by amine coupling. The second step consists of contacting the substrate-coated microspheres with fusion proteins containing AGT (for example the SNAP mutant), said enzyme being intended to covalently attach to its BG-PEG-NH2 substrate, that is, to the microspheres.

Figure 2:
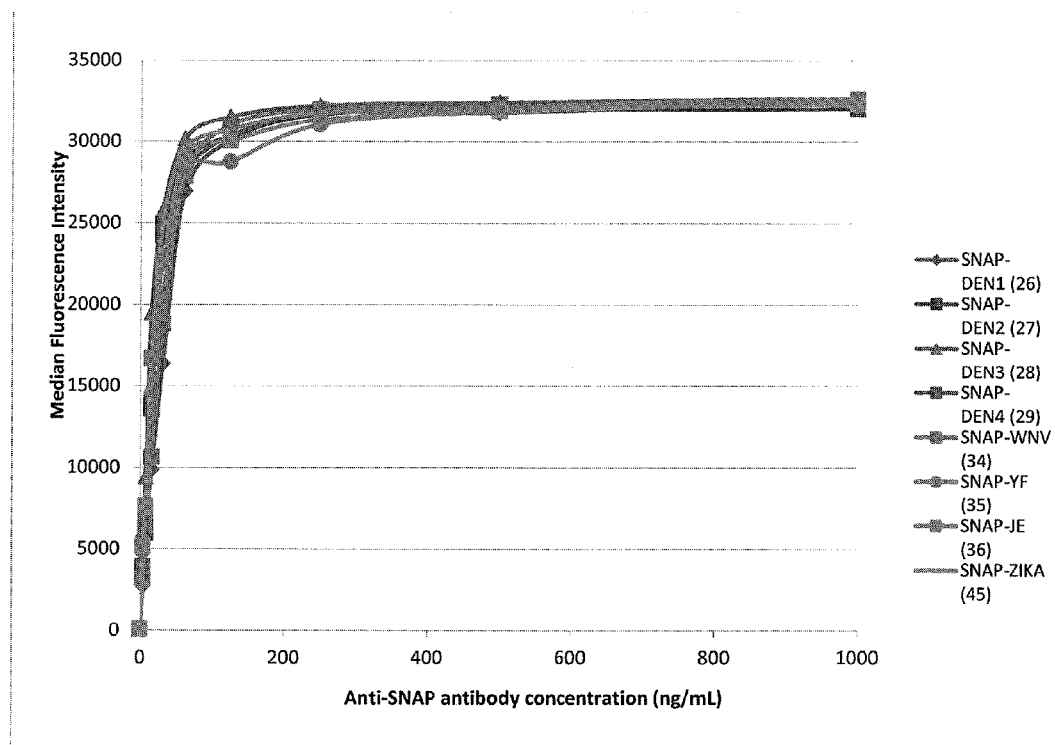

FIG. 2 shows the coupling efficiency of chimeric SNAP-viral antigens proteins (SNAP-DV1.EDIII, SNAP-DV2.EDIII, SNAP.DV3.EDIII, SNAP.DV4.EDIII, SNAP-WNV.EDIII, SNAP-YF.EDIII, SNAP-JE.EDIII, SNAP-ZIKA.EDIII), as followed by anti-SNAP antibody.

Figure 3:
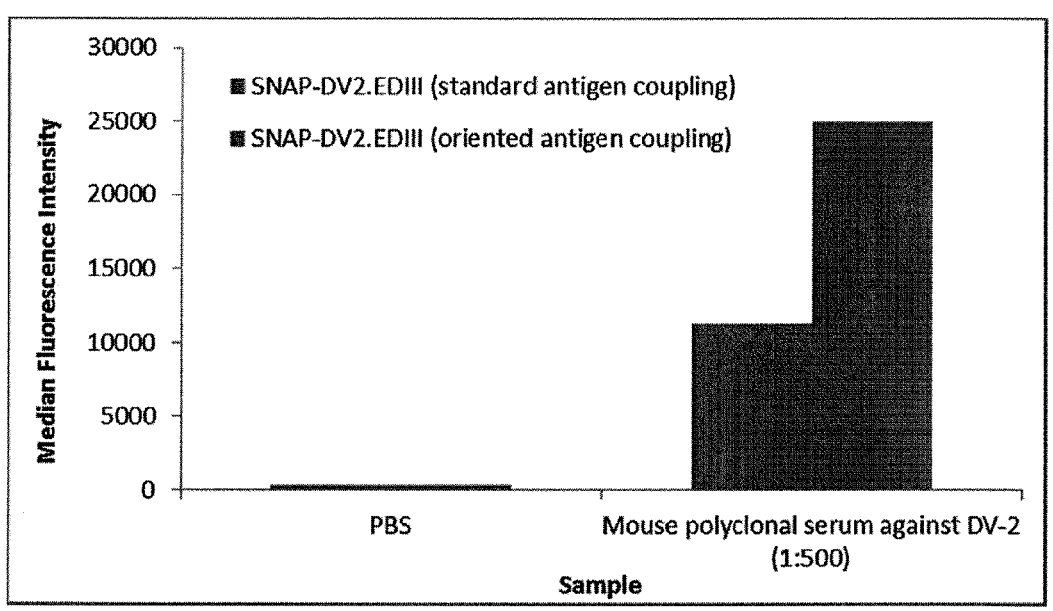

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through a standard amine coupling procedure, e.g. Bio-Plex Amine Coupling Kit, BIORAD.

Figure 4:
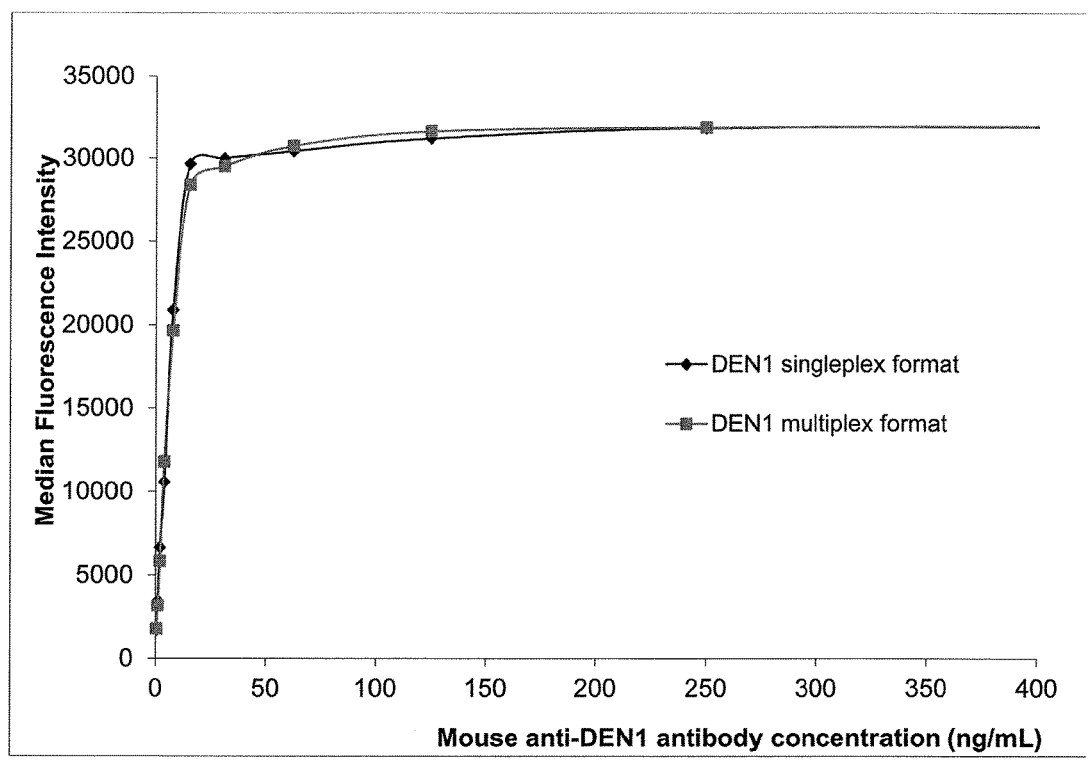

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex fomat with other chimeric SNAP-viral Ags proteins (SNAP-DV2.EDIII, SNAP.DV3.EDIII, SNAP.DV4.EDIII, SNAP-WNV.EDIII, SNAP-YF.EDIII, SNAP-JE.EDIII, SNAP-TBE.EDIII) coupled to microspheres.

Figure 5:
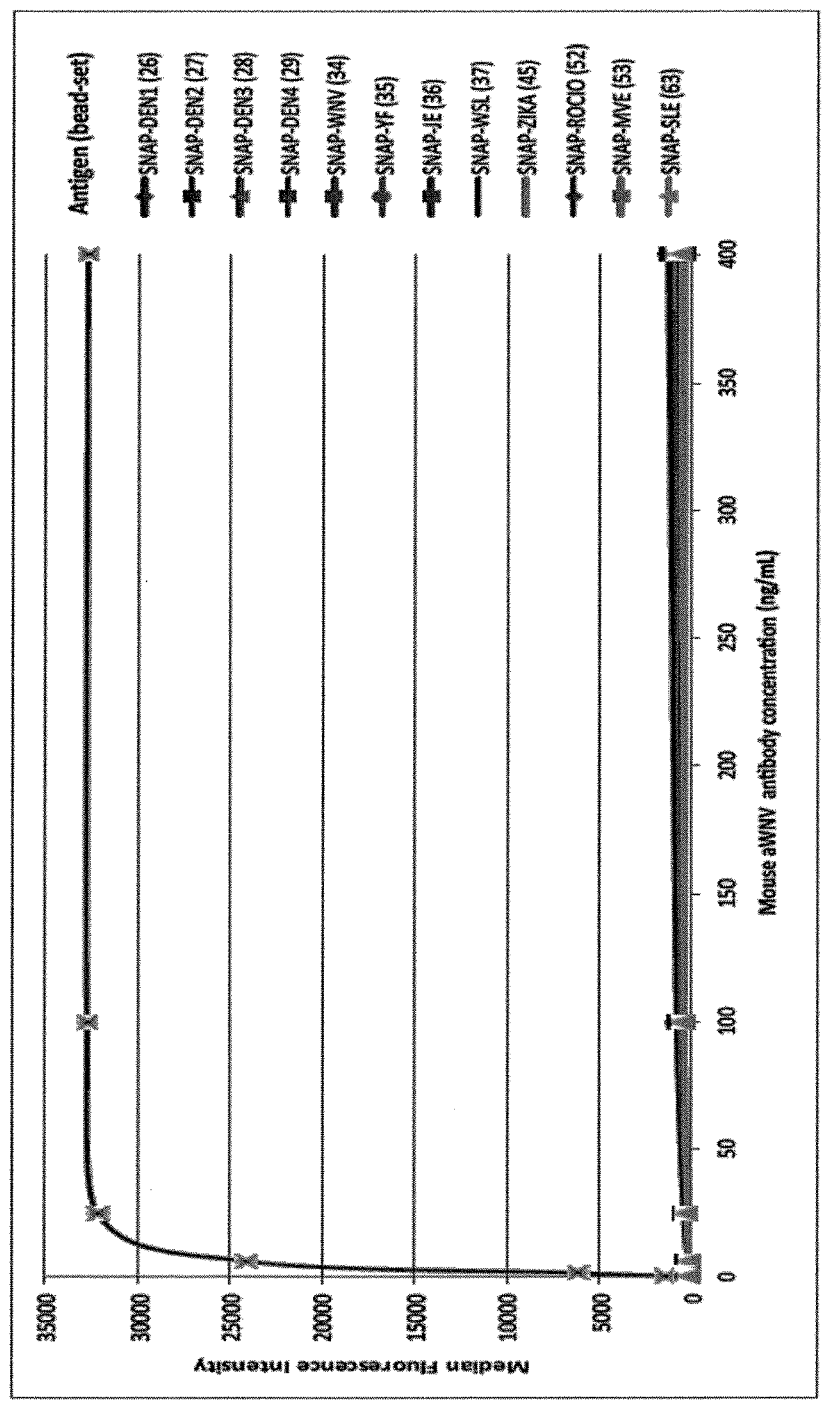

FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV.EDIII, SNAP-YF.EDIII, SNAP-JE.EDIII, SNAP-TBE.EDIII) coupled to microspheres.

Figure 6:
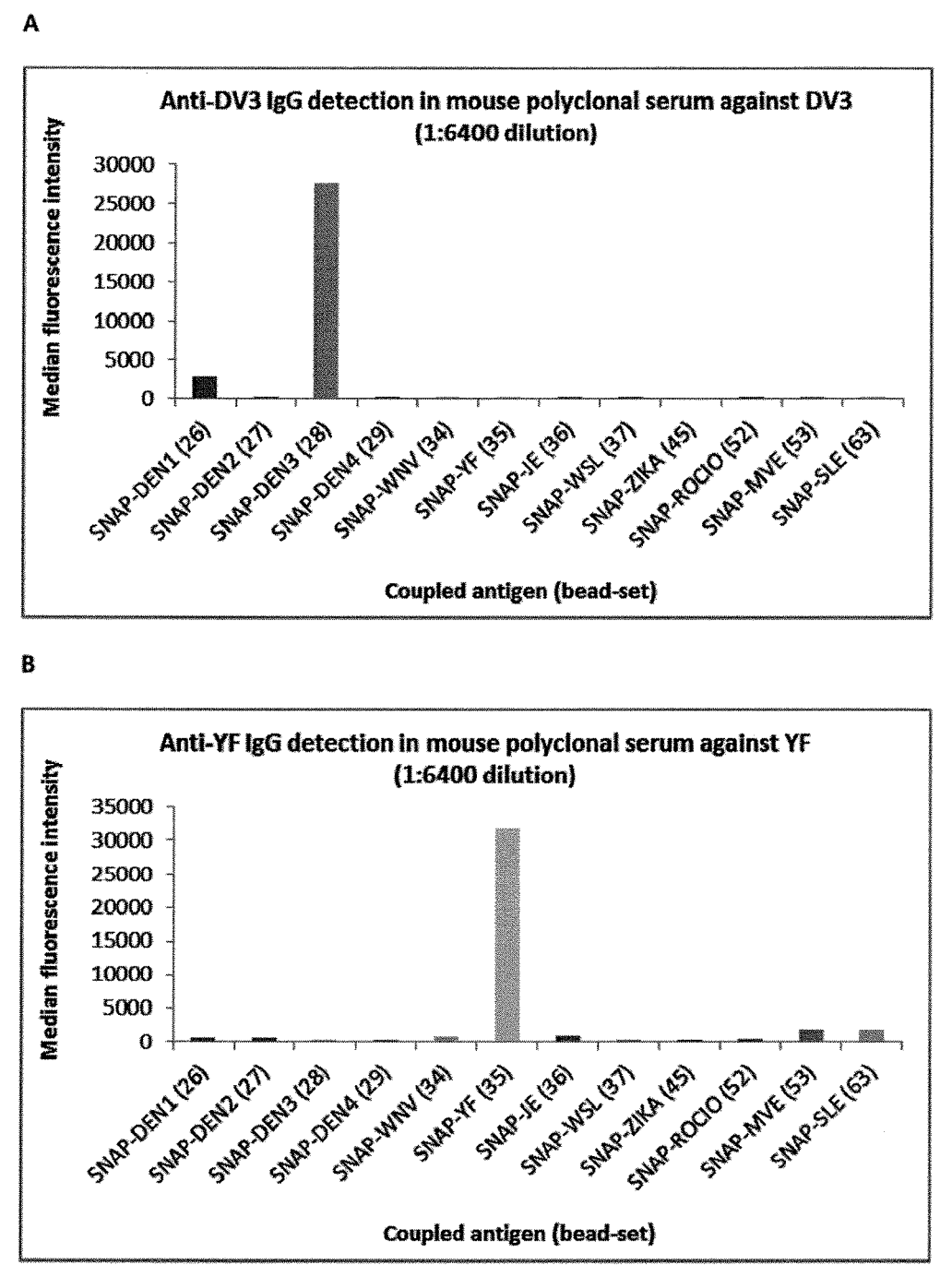

FIG. 6 shows the reactivity and specificity of anti-DV3 IgG detection in mouse polyclonal serum against DV3 (A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV.EDIII, SNAP-YF.EDIII, SNAP-JE.EDIII, SNAP- WSL.EDIII, SNAP-ROCIO.EDIII, SNAP-MVE.EDIII, SNAP-SLE.EDIII, SNAP-ZIKA.EDIII) coupled to microspheres FIG. 7 shows the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV.EDIII, SNAP-YF.EDIII, SNAP-JE.EDIII, SNAP-WSL.EDIII, SNAP-ROCIO.EDIII, SNAP-MVE.EDIII, SNAP-SLE.EDIII, SNAP-ZIKA.EDIII, SNAP-TBE.EDIII) coupled to microspheres.

FIG. 8 discloses the structure of the pDeSNAPuniv cassette. DNA sequences are nt 3-20 (5') and 774-798 (3') of SEQ ID NO:34. Amino acid sequence of signal sequence is aa 2-22 of SEQ ID NO:24. Amino acid sequence of SNAP-like sequence is aa 3-193 of SEQ ID NO:2.

FIG. 9 discloses the structure of the pDeSNAPuniv/SBV.N cassette. DNA sequences are nt 3-20 (5') and 774-798 (3') of SEQ ID NO:34. Amino acid sequence of signal sequence is aa 2-22 of SEQ ID NO:24.

FIGS. 10A and B show (A) an immunoblot assay performed on the supernatants of S2/SNAP-SBV.N cells induced for 10 days with $Cd^{2-}$ (+) or non induced (−). The secreted chimeric protein SNAP-SBV.N (theorical MW 50 kDa) was detected using an anti-$His_{tag}$ antibody, in comparison to define amounts of highly purified chimeric protein SNAP-TOS.N (theorical MW 49 kDa). (B) Direct visualization of proteins on each fraction of size-exclusion chromatography column (Coomassie blue staining of PAGE-SDS) corresponding to the final purification step of secreted SNAP+SBV.N protein from induced S2/SNAP+SBV.N cells for 10 days.

FIG. 11 shows an example of a device containing the antigen-coated microspheres of the invention.

FIGS. 12A-F show coding nucleotide (SEQ ID NO:154) and amino acid sequence (SEQ ID NO:155) of a SNAP construct containing the SARS virus N gene.

FIGS. 13A-D show coding nucleotide (SEQ ID NO:156) and amino acid sequence (SEQ ID NO:157) of a SNAP construct containing the SARS virus S gene receptor binding domain.

FIGS. 14A-E show coding nucleotide (SEQ ID NO:158) and amino acid sequence (SEQ ID NO:159). of a SNAP construct containing the human coronavirus N gene.

Figure 15E:
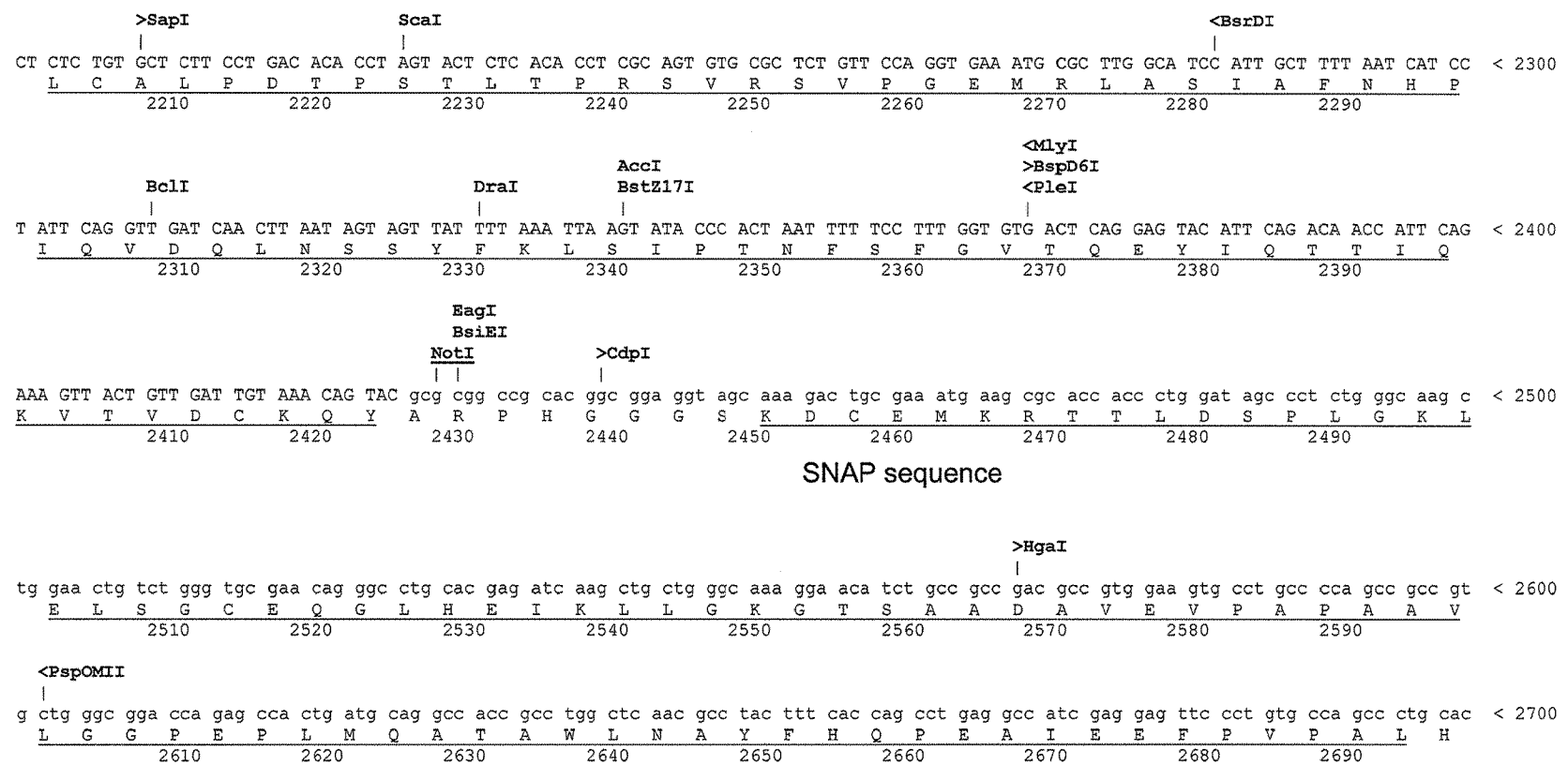
Figure 15F:
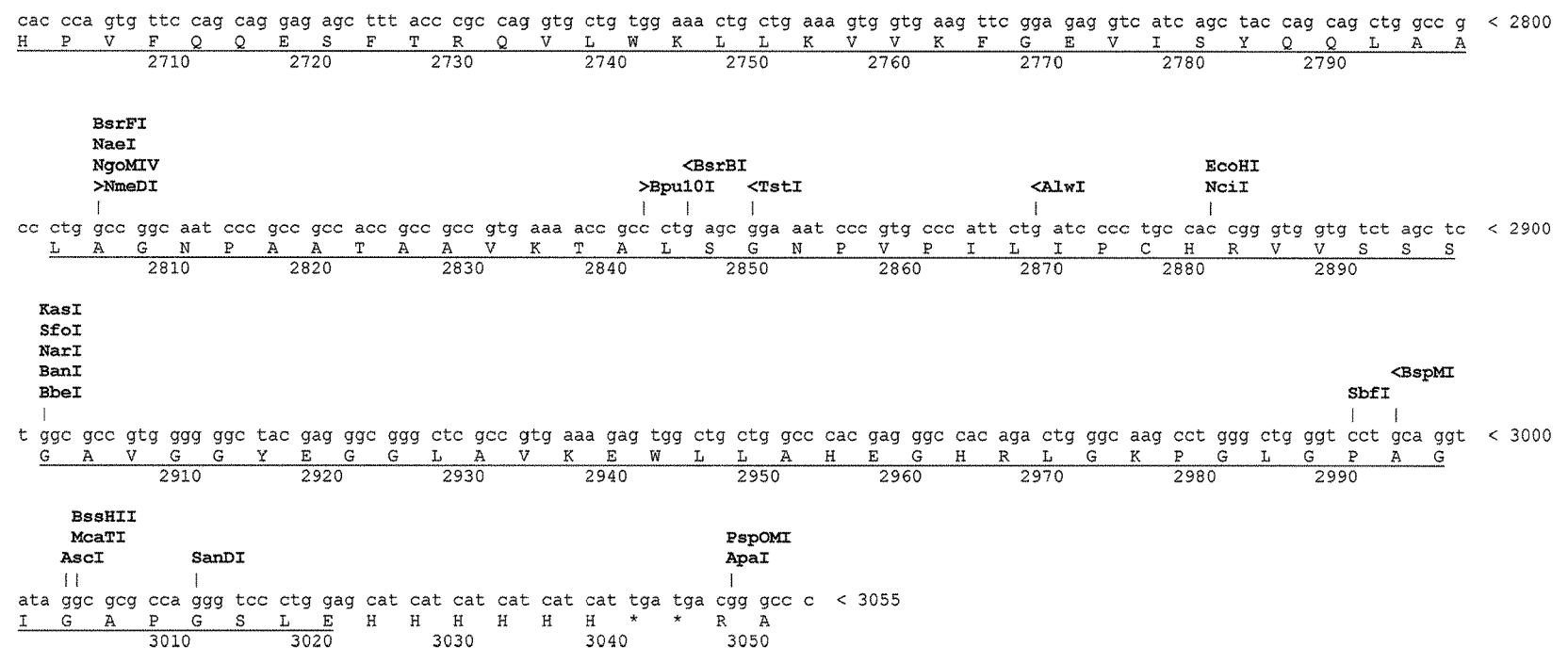

FIGS. 15A-G show coding nucleotide (SEQ ID NO:160) and amino acid sequence (SEQ ID NO:161). of a SNAP construct containing the human coronavirus S1 gene.

Figure 16C:
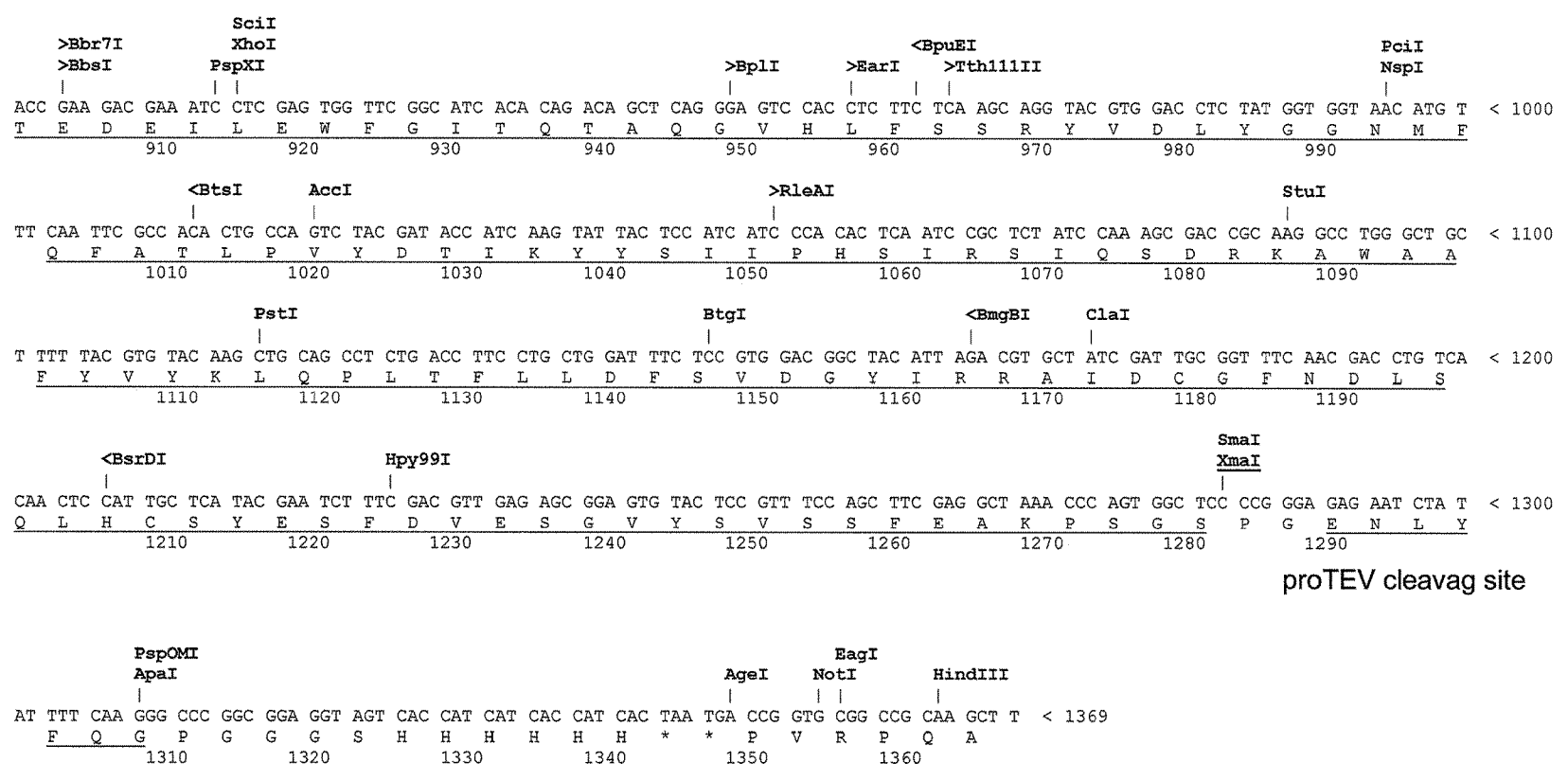

FIGS. 16A-D show coding nucleotide (SEQ ID NO:162) and amino acid sequence (SEQ ID NO:163) of a SNAP construct containing the human coronavirus S1 gene receptor binding domain (RBD).

FIGS. 17A-D show coding nucleotide (SEQ ID NO:164) and amino acid sequence (SEQ ID NO:165) of a SNAP construct containing the LruA gene of Leptospirosis.

FIGS. 18A-D show coding nucleotide (SEQ ID NO:166) and amino acid sequence (SEQ ID NO:167) of a SNAP construct containing the LruB gene of Leptospirosis.

FIGS. 19A-D show coding nucleotide (SEQ ID NO:168) and amino acid sequence (SEQ ID NO:169) of a SNAP construct containing the LipL32 gene of Leptospirosis.

FIGS. 20A-F show coding nucleotide (SEQ ID NO:170) and amino acid sequence (SEQ ID NO:171) of a SNAP construct containing the C gene of Hepatitis E.

Figure 21B:
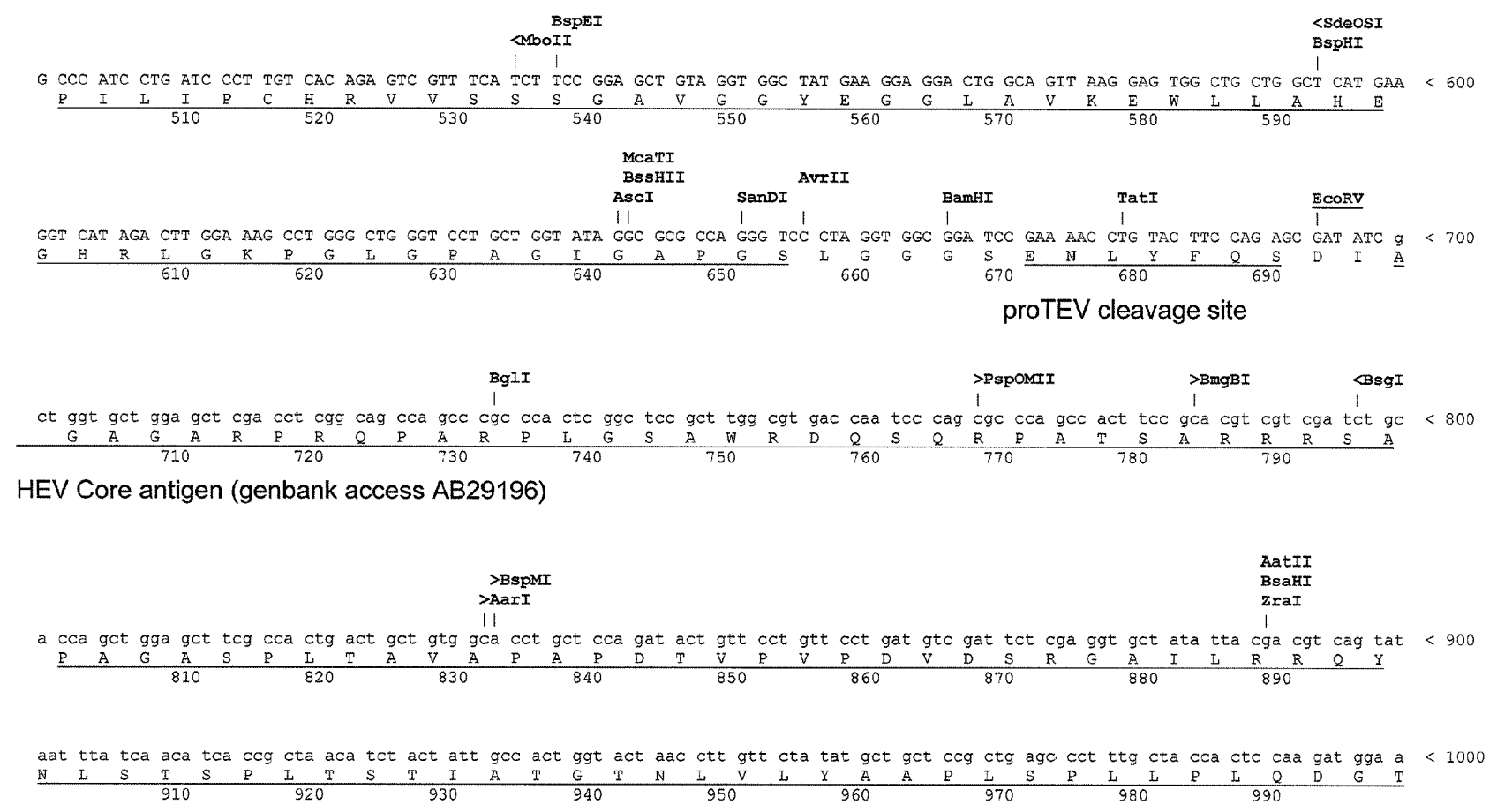
Figure 21C:
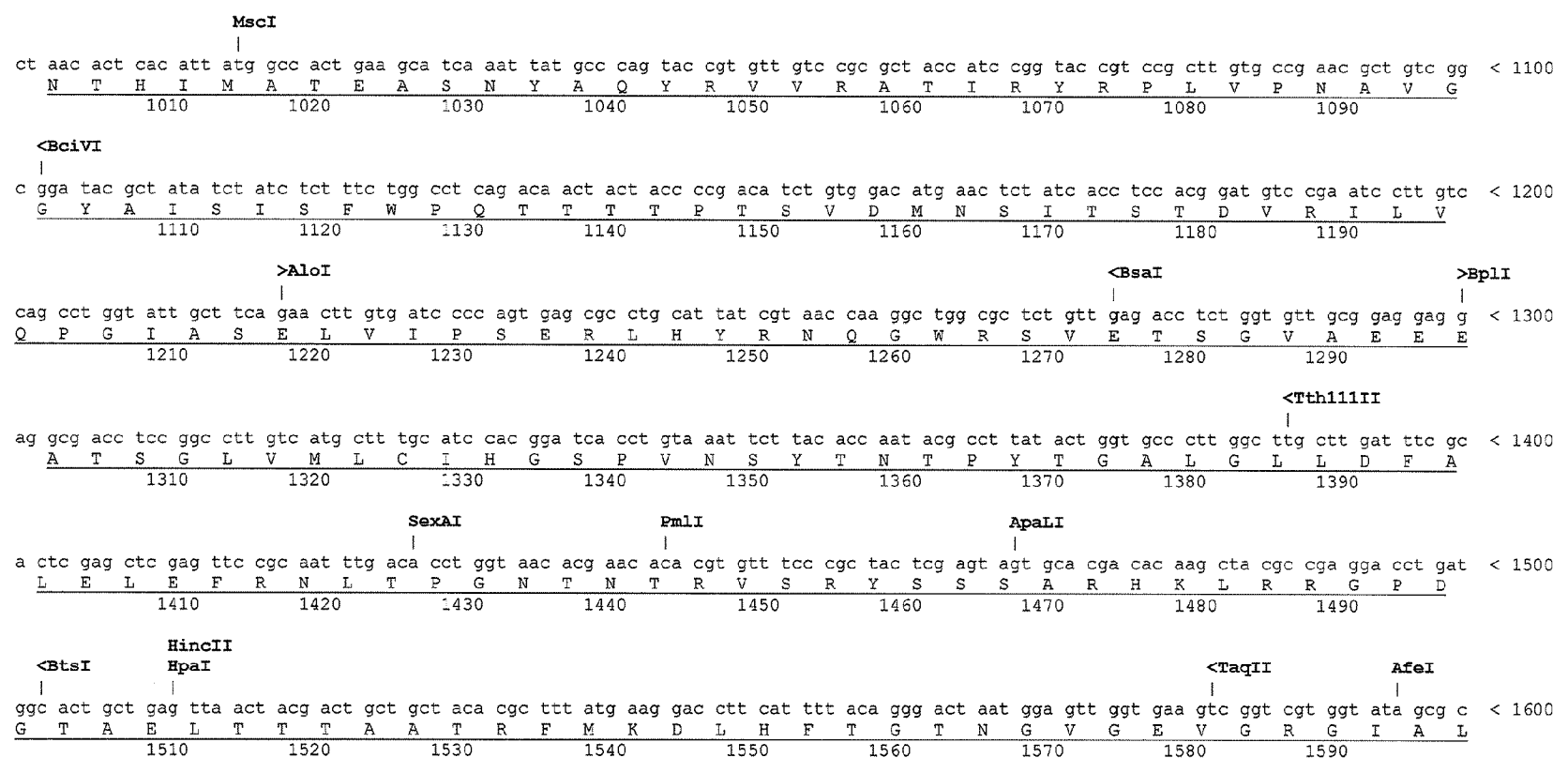
Figure 21D:
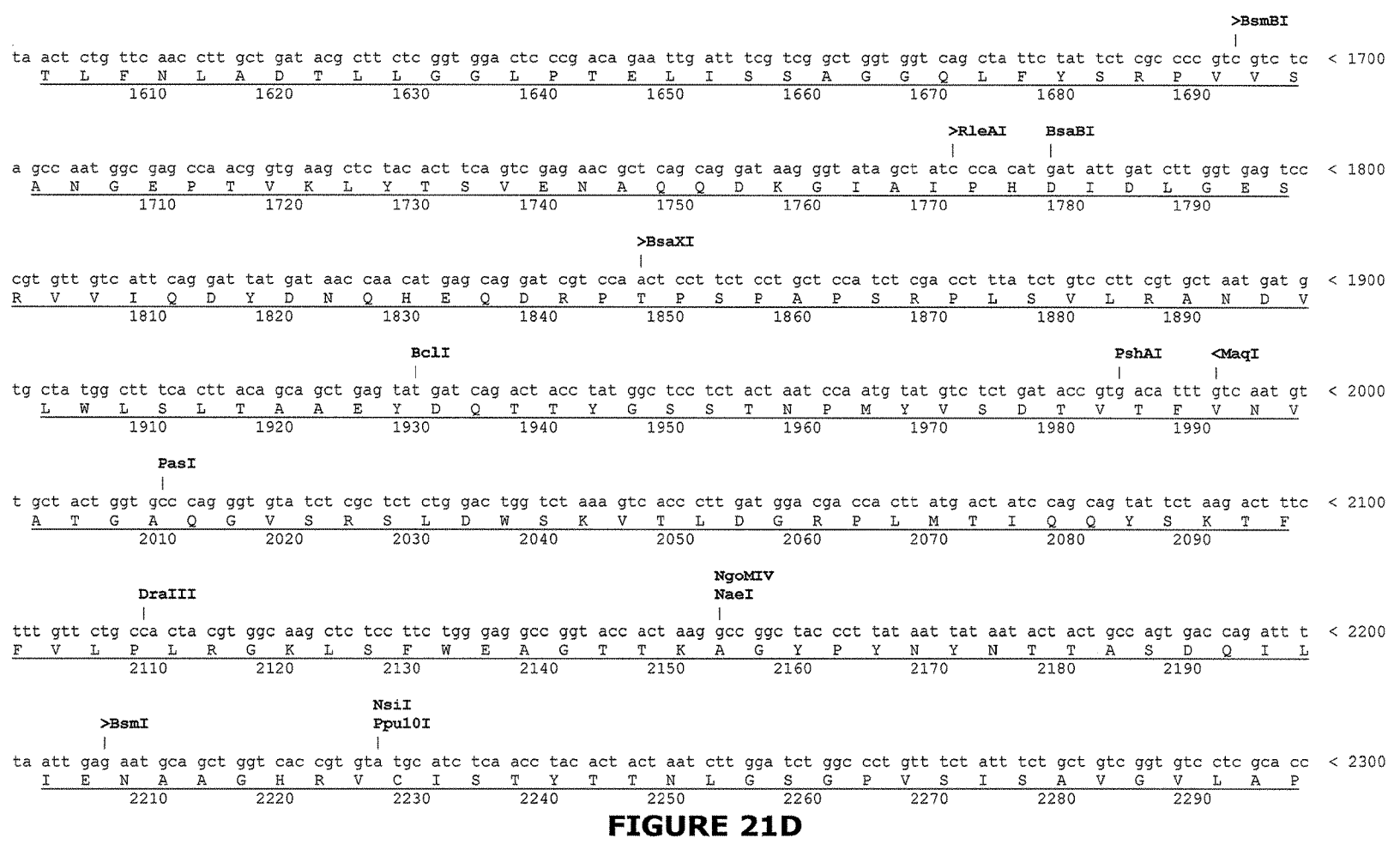

FIGS. 21A-E show coding nucleotide (SEQ ID NO:172) and amino acid sequence (SEQ ID NO:173) of a SNAP construct containing the core sequence of the C gene of Hepatitis E.

Figure 22C:
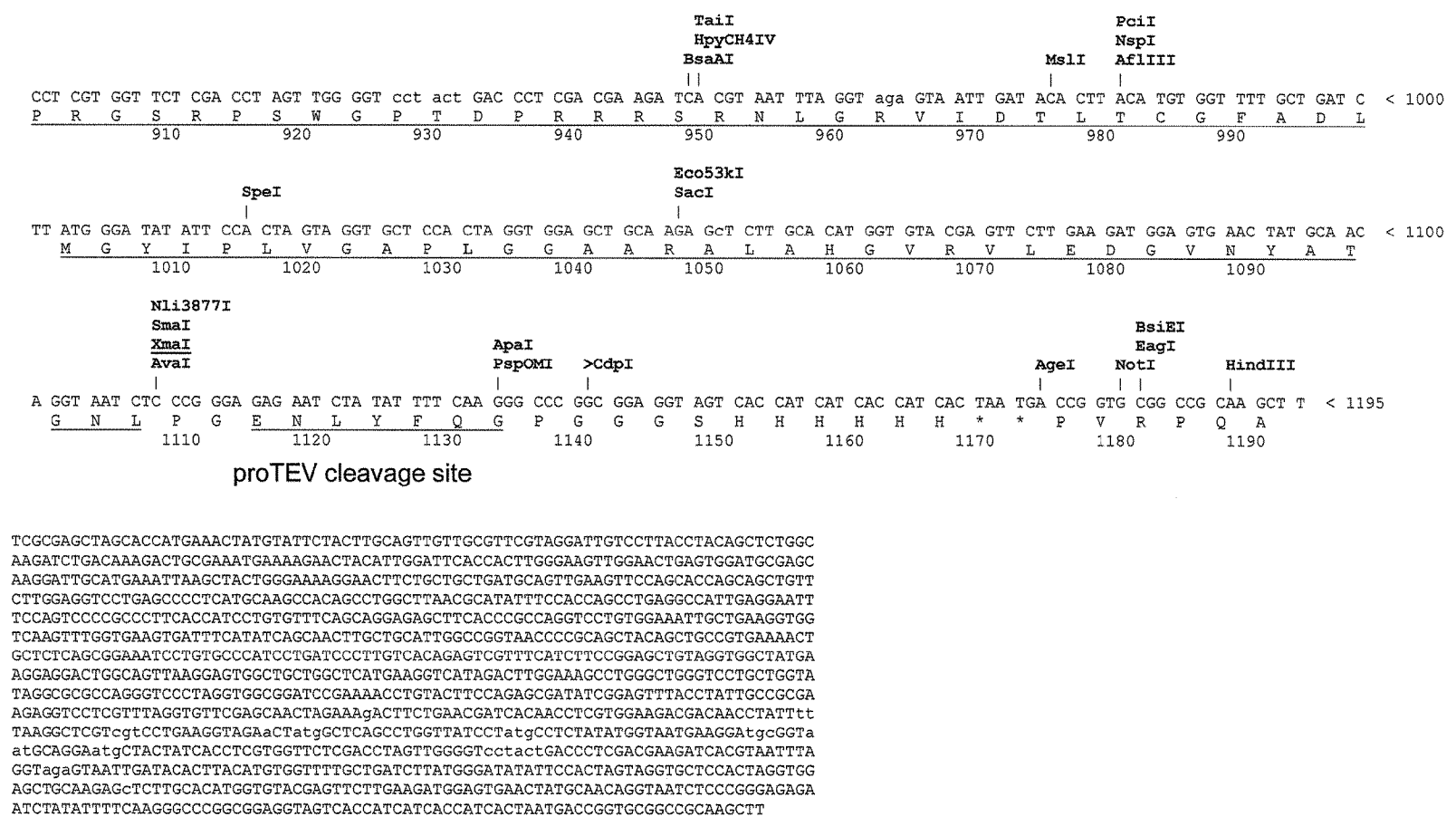

FIGS. 22A-C show coding nucleotide (SEQ ID NO:174) and amino acid sequence (SEQ ID NO:175) of a SNAP construct containing the C gene of Hepatitis C.

FIGS. 23A-D show coding nucleotide (SEQ ID NO:176) and amino acid sequence (SEQ ID NO:177) of a SNAP construct containing the core sequence of the C gene of Hepatitis C.

FIGS. 24A-C show coding nucleotide (SEQ ID NO:178) and amino acid sequence (SEQ ID NO:179) of a SNAP construct containing sequences encoding the NSs protein from Schmallenberg virus.

FIGS. 25A-B show advantageous combinations of antigen-coupled microspheres to be included in the kit of the invention.

DETAILED DESCRIPTION OF THE INVENTION

The present invention allows for the simultaneous screening for multiple antigens in a biological sample with higher sensitivity and specificity using an oriented antigen coupling procedure for the antigens. The present inventors have developed and validated immunoassays leading to rapid and simultaneous detection of several antibodies generated by a wide range of diseases, in particular arboviral diseases and VHFs, in biological fluids.

To achieve optimal sensitivity and specificity for the detection of low amount of antibodies using minimal antigen, an oriented antigen coupling procedure has been developed. This oriented antigen coupling procedure is based on the covalent interaction between the AGT enzymes and their substrates, the O6-benzylguanine derivatives, which irreversibly react with AGT enzymes by transferring their benzyl group to the active site cysteine of the enzyme. Accordingly, a number of target antigens can be fused to an AGT enzyme moiety, resulting in different chimeric fusion proteins (hereafter referred to as [AGT-Antigen] fusion proteins), that can be used as capture reagents for the antibodies present in a biological sample. The present inventors have shown that this antibody capture is unexpectedly enhanced when these fusion proteins are bound to solid supports thanks to the specific AGT-substrate interaction.

As shown in the examples, the inventors have generated a number of different antigen-coated fluorescent microspheres with the oriented antigen coupling procedure. Sixteen distinct sets of microspheres coupled with 16 purified chimeric [AGT-Antigen] fusion proteins were used in a titration of 16 serum antibodies specific to different proteins of the dengue serotypes 1 to 4, West Nile, yellow fever, Japanese encephalitis, tick-borne encephalitis, Saint-Louis encephalitis, Murray Valley encephalitis, Wesselsbron, Zika, Rocio, Usutu, Rift Valley fever, and chikungunya virus. Unexpectedly, these 16 distinct sets of microspheres have been mixed in a single sample without affecting the sensitivity and specificity of the detection (see FIG. 5). The production of this system is highly time- and cost-effective, as only a very small amount of recombinant antigen (<50 μg) is required to produce one set of antigen-coupled microspheres (~$1.25\times10^6$ microspheres), such set being sufficient to perform 1000 individual assays.

Consequently, the invention encompasses methods and kits for performing multiplex assays based on the oriented antigen coupling of a solid support, preferably a labeled microparticle, to an AGT substrate, which is coupled to chimeric fusion proteins, i.e., AGT-Antigen. This oriented coupling allows for increased interaction of the antigen with antibodies in a biological sample. A solid support coated with AGT-substrate can be coupled with the AGT-Antigen through the enzymatic activity of the AGT enzyme in these immunoassays.

The 6-alkylguanine-DNA-alkyltransferase enzyme (AGT, also known as ATase or MGMT, and hereafter referred to as "AGT") is numbered EC 2.1.1.63 in the IUBMB enzyme nomenclature. It is a 6-alkylguanine-DNA-alkyltransferase DNA repair enzyme of 207 amino acid residues whose function in the cells is to repair alkylated DNA. More precisely, AGT acts on $O^6$-methylated guanine in DNA by irreversibly transferring the methyl group in an $S_N2$ reaction to a reactive cysteine residue (Cys 145). Recently, a number of O6-benzylguanine derivatives have been shown to irreversibly react with said enzyme by transferring their benzyl group to the active site cysteine of the AGT enzyme (cf. Damoiseaux et al., *ChemBiochem.*, 2001, WO 2004/031404 and WO 2005/085470). Thus, the AGT-Antigen can be coupled to an AGT substrate through this enzymatic reaction.

The solid supports coupled to the AGT-Antigen can be incubated with a biological sample containing immunoglobulins. After immunoglobulins have been bound to the solid supports, detection of the solid supports which are effectively bound to immunoglobulins can be accomplished. The identification of immunoglobulin-coated solid support(s) enables to diagnose which pathogen was infecting the patient (as each solid support matches with a defined pathogenic antigen). This detection step is performed by any usual means, for example by using labeled detection antibodies and by identifying the nature of the solid support.

Advantageously, the method of the invention involves only the detection of the presence of antibodies in diseased patients, but knowledge about the identity of those antibodies is not required.

Methods for Detecting Multiple Target Antibodies

The present invention relates to a method for detecting at least 2 target antibodies in a biological sample. The invention encompasses detecting the presence or absence of at least 2, 3, 4, 5, 6, 7, 8, 9, 10, 11, 12, 13, 14, 15, 16, 20, 25, 30, 40, 50, 100, etc. different target antibodies. Thus, the invention comprises a method comprising at least 2, 3, 4, 5, 6, 7, 8, 9, 10, 11, 12, 13, 14, 15, 16, 20, 25, 30, 40, 50, 100, etc. solid supports and a method comprising at least 2, 3, 4, 5, 6, 7, 8, 9, 10, 11, 12, 13, 14, 15, 16, 20, 25, 30, 40, 50, 100, etc. different epitopes. The method can comprise at least 2, 3, 4, 5, 6, 7, 8, 9, 10, 11, 12, 13, 14, 15, 16, 20, 25, 30, 40, 50, 100, etc. solid supports mixed together prior to addition of the biological sample. The epitopes can be recognized by target antibodies.

In one embodiment, the method comprises:
(a) contacting a mixture of at least 2 solid supports with a biological sample; wherein at least one of the solid supports comprises a first AGT-Antigen fusion protein covalently coupled to an AGT substrate, and wherein at least one of the solid supports comprises a second AGT-Antigen fusion protein covalently coupled to an AGT substrate;
(b) detecting the presence or absence of binding of antibodies to the first AGT-Antigen; and
(c) detecting the presence or absence of binding of antibodies to the second AGT-Antigen.

In one embodiment, the method comprises:
(a) contacting a mixture of at least 10 solid supports with a biological sample;
wherein a first solid support comprises a first AGT-Antigen fusion protein covalently coupled to an AGT substrate,
wherein a second solid support comprises a second AGT-Antigen fusion protein covalently coupled to an AGT substrate;
wherein a third solid support comprises a third AGT-Antigen fusion protein covalently coupled to an AGT substrate;
wherein a fourth solid support comprises a fourth AGT-Antigen fusion protein covalently coupled to an AGT substrate;
wherein a fifth solid support comprises a fifth AGT-Antigen fusion protein covalently coupled to an AGT substrate;
wherein a sixth solid support comprises a sixth AGT-Antigen fusion protein covalently coupled to an AGT substrate;
wherein a seventh solid support comprises a seventh AGT-Antigen fusion protein covalently coupled to an AGT substrate;
wherein an eighth solid support comprises an eighth AGT-Antigen fusion protein covalently coupled to an AGT substrate;
wherein a ninth solid support comprises a ninth AGT-Antigen fusion protein covalently coupled to an AGT substrate;
wherein a tenth solid support comprises a tenth AGT-Antigen fusion protein covalently coupled to an AGT substrate; and
(b) detecting the presence or absence of binding of antibodies to the each of the AGT-Antigens.

In one embodiment, the method comprises:
(a) contacting a first solid support comprising an AGT substrate covalently coupled to a first fusion protein comprising an AGT polypeptide having a O6-alkylguanine-DNA alkyltransferase activity and a first epitope that is recognized by a first target antibody with the biological sample;
(b) contacting a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody with the biological sample; and
(c) detecting the presence or absence of the two target antibodies.

Preferably, the first and second, etc., solid supports are microspheres. Most preferably, the microspheres are labeled. Preferably, the first and second solid supports are labeled with different labels.

The invention encompasses an in vitro assay method for detecting at least two different target antibodies present in a biological sample from a subject, said method comprising the steps of:
(a) providing a first fusion protein comprising:
a polypeptide comprising a first epitope that is recognized by a first target antibody and
a AGT polypeptide having a O6-alkylguanine-DNA alkyltransferase activity,
(b) contacting said first fusion protein with a first solid support, said support being covalently coupled with a substrate of said AGT polypeptide, (c) obtaining a first solid support covalently coupled with a first epitope that is recognized by the first target antibody, (d) providing a second fusion protein comprising:
   a polypeptide comprising a second epitope, said second epitope being recognized by a second target antibody but not by said first target antibody, and
   a AGT polypeptide having a O6-alkylguanine-DNA alkyltransferase activity, (e) contacting said second fusion protein with a second solid support, said support being covalently coupled with a substrate of said AGT polypeptide, (f) obtaining a second solid support covalently coupled with a second epitope that is recognized by the second target antibody, but not by said first target antibody, wherein said first and second solid supports can be specifically identified from each other, (g) contacting said biological sample with the first and second solid supports obtained in steps (c) and (f), (h) detecting the presence of said at least two target antibodies.

As used hereafter, the terms "an antibody", "a fusion protein", "an epitope", "an antigen", "an AGT polypeptide", "a solid support" and the like have obviously to be understood as usual in the art, that is, in a broad manner. In particular, they encompass not only particular single molecules but a number of said molecules. For example, the term "solid support" encompasses a subset of numerous identical solid supports, the term "microparticle" encompasses a subset of numerous identical microparticles, and the term "fusion protein" encompasses a number of identical single protein molecules. In the context of the present invention, it is noteworthy that a solid support carries a number of identical fusion proteins, said fusion proteins containing, apart from the AGT polypeptide, identical antigen, and therefore identical epitopes, so that the antibodies which will be detected on the solid support can be unambiguously identified.

As used herein, the term "fusion protein" means a polypeptide containing a protein or a polypeptide created through the artificial joining of two or more polypeptides (see Wikipedia: peptide). In the immunoassays of the invention, said fusion proteins contain a AGT polypeptide and an antigen, containing at least one epitope. Fusion proteins can be obtained through genetic engineering (see Wikipedia: Genetic_engineering) of a fusion gene. This typically involves removing the stop codon (see Wikipedia: Codon) from a cDNA sequence (see Wikipedia: CDNA) coding for the first protein, then appending the cDNA sequence of the second protein in frame (see Wikipedia: Reading frame) through ligation (see Wikipedia: Ligase) or overlap extension PCR (see Wikipedia: PCR). That DNA sequence will then be expressed (see Wikipedia: Protein expression) by a cell (see Wikipedia: Cell (biology)) as a single protein. The protein can be engineered to include the full sequence of both original proteins, or only a portion of either. If the two entities are proteins, a linker (or "spacer") peptides can be added, which makes it more likely that the proteins fold independently and behave as expected. In particular, the fusion proteins of the invention can be obtained by providing vectors comprising AGT encoding sequences in frame with an epitope or antigen encoding sequences, either attached to the N-terminal or to the C-terminal side of the AGT DNA sequence. These vectors may be introduced in prokaryotic hosts, including eubacteria such as $E.\ coli$ bacteria, or eukaryotic hosts, e.g., yeast, insect cells or mammalian cells and the recombinant fusion proteins may be produced under appropriate conditions. Typical constructions are presented in the experimental part of this application.

The term "antibody" as used herein is intended to include monoclonal antibodies, polyclonal antibodies, and chimeric antibodies. Preferably, the antibodies which are to be detected by the immunoassays of the invention are polyclonal antibodies, which are present in biological samples of diseased patients, and have therefore been generated from different B cell sources. As such, they recognize different epitopes exhibited by a pathogenic antigen (on the other hand, monoclonal antibodies are derived from a single cell line and recognize the same epitope).

An antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (C1q) of the classical complement system.

Antibody can be of different isotypes (namely IgA, IgD, IgE, IgG or IgM). Both IgG and IgM type antibodies can be detected by the present method. Of note, these isotypes are composed of two identical heavy chains and two identical light chains that are joined by disulfide bonds. Importantly, IgM antibodies form polymers where multiple immunoglobulins are covalently linked together with disulfide bonds, mostly as a pentamer but also as a hexamer, so that they have a molecular mass of approximately 900 kDa (in their pentamer form). Because each monomer has two antigen binding sites, a pentameric IgM has 10 binding sites. Typically, however, IgM antibodies cannot bind 10 antigens at the same time because the large size of most antigens hinders binding to nearby sites. Due to its polymeric nature, IgM possesses high avidity. Different isotypes of antibodies (e.g., IgG or IgM) can be detected with the same antigen, allowing the temporal discrimination of the antibody response, such as whether the antibody response is an early or later response against an antigen/infection. This can discrimination can provide information as to the timing of infection or exposure to the antigen.

Antibody fragments can also be detected thanks to the present method. This term is intended to include Fab, Fab', F(ab')2, scFv, dsFv, ds-scFv, dimers, minibodies, diabodies, and multimers thereof and bispecific antibody fragments.

Monoclonal antibodies can be used in the present immunoassays; for example for detecting the immunoglobulins that are bound to the solid supports. As used herein, "monoclonal antibody" defines an antibody arising from a homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

The term "antigen" herein means any substance that causes the immune system to produce antibodies against the said substance. An "immunogenic" antigen is a specific type of antigen which is able to stimulate an adaptive immune response if injected on its own. At the molecular level, an antigen is thus characterized by its ability to be "bound" to the antigen-binding site of an antibody.

In the context of the present invention, an antibody is said to "bind" a define antigen (or epitope) or to "recognize" said antigen (or epitope) if said antibody has an affinity constant $K_a$ (which is the inverted dissociation constant, i.e. $1/K_d$) higher than $10^5$ $M^{-1}$, preferably higher than $10^6$ $M^{-1}$, more preferably higher than $10^7$ $M^{-1}$ for said antigen (or epitope). This affinity can be measured for example by equilibrium dialysis or by fluorescence quenching, both technologies being routinely used in the art.

The methods of the invention can be coupled with other techniques for the detection of proteins, nucleic acids, antibodies, immune responses, polysaccharides, etc., for example, in the detection of allergens.

Antigens for Use In Multiplex Immunoassays

In the context of the invention, antigens or epitopes include proteins, lipoproteins, polysaccharides, and glycoproteins. Said proteins include viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, linear peptides, oligopeptides etc. The antigens and epitopes include cancer, cytokine, and allergen antigens and epitopes. The antigens can be antigens involved in autoimmune diseases.

The antigens can be tumor associated antigens such as Alphafetoprotein (AFP, see Wikipedia: Alphafetoprotein), carcinoembryonic antigen (CEA), CA 15-3, CA27-29, CA 125, CA 19-9, Calrefinin, prostate specific antigen (PSA), MUC-1 (see Wikipedia: MUC1), Epithelial membrane protein (EMA), Epithelial tumor antigen (ETA), Tyrosinase (see Wikipedia: Tyrosinase), Melanoma-associated antigen (MAGE), TAA complexes, SSX2 or NERCMSL, ras (see Wikipedia: Ras_subfamily), P53, CD34,CD99, CD117, Chromogranin, Cytokeratin, Desmin, Factor VIII (see Wikipedia: Factor_VIII), CD31 (see Wikipedia: CD31), FL1 (see Wikipedia: FL1), GFAP, GCDFP-15, HMB-45, hCG, inhibin, keratin, PTPRC (CD45), MART-1, MyoD1, MSA, NSE, PLAP, S100 protein, SMA, synaptophysin, Thyroglobulin, thyroid transcription factor-1, Tumor M2-PK, and vimentin.

The antigens can be cancer biomarkers such as Angiopoietin-2, sCD40L, EGF, Endoglin, sFASL, IIB-EGF, IGFBP-1, IL-6, IL-8, IL-18, PAI-1, PLGF, TGF-α, TNF-α, uPA, VEGF-A, VEGF-C, VEGF-D, sEGFR, FGF-basic, Follistatin, G-CSF, HGF, sHER-2/neu, sIL-6Rα, Leptin, Osteopontin, PECAM-1, PDGF-AB/BB, Prolactin, SCF, sTIE-2, sVEGFR-1, and sVEGFR-2.

The antigens can be Kidney toxicity markers such as Calbindin, Clusterin, GST-π, IL-18, KIM-1, MCP-1, Albumin, B2M, Cystatin C, NGAL, Osteopontin, and TFF3.

The antigens can be cytokine, chemokines, and growth factors such as TGF-β1, TGF-β2, TGF-β3, IL-1β, IL-1ra, IL-2, IL-4, IL-5, IL-6, IL-7, IL-8, IL-9, IL-10, IL-12 (p70), IL-13, IL-15, IL-17, basic FGF, eotaxin, G-CSF, GM-CSF, IFN-γ, IP-10, MCP-1 (MCAF), MIP-1α, MIP-1β, PDGF-BB, RANTES, TNF-α, VEGF, IL-1α, IL-2Rα, IL-3, IL-12 (p40), IL-16, IL-18, CTACK, GRO-α, HGF, IFN-α2, LIF, MCP-3, M-CSF, MIF, MIG, β-NGF, SCF, SCGF-β, SDF-1α, TNF-β, and TRAIL.

The antigens can be haptens, and other moieties comprising low molecular weight molecules, such as saccharides, oligosaccharides, polysaccharides, peptides, mucins, toxins, and allergens (pollen, egg white).

The antigens can be allergens, such as food, grass, tree, weed, insect, mold, epidermal, or dust mite allergens. The antigens can be animal, shellfish, milk (see Wikipedia: Milk), soy (see Wikipedia: Soy), eggs (see Wikipedia: Egg_(food)), wheat (see Wikipedia: Wheat), peanuts (see Wikipedia: Peanuts), tree nuts (see Wikipedia: Tree_nuts), fish (see Wikipedia: Fish), or seed allergens.

The antigens can be involved in autoimmune diseases, and are preferably human antigens. Preferred antigens are Thyroglobulin, thyroid peroxidase, Rheumatoid Factor (IgA, IgG, IgM), Citrullinated Peptide, histtidyl-tRNA synthetase (Jo-1), PM-Scl, complement, complement components C4c and C3c; total complement (CH50), Sm/RNP, SS-A and —B (Sjogren a and b), Scl-70, topoisomerase, Ribosomal P protein, Actin, Tissue transglutaminase, Myeloperoxidase, Proteinase-3, M-type phospholipase A, liver kidney microsomal antigen type-1 (anti-LKM1), anti-liver cytosol type 1 (anti-LC1), SMA, pyruvate dehydrogenase complex E2 subunit, nuclear pore gp210, nuclear body sp100, High mobility group box 1, Collagen, Collagen type II, Collagen type IV, Collagen VII, hLAMP-2, voltage-gated potassium channel (VGKC), N-methyl-D-aspartic acid receptor (NMDAR), Hu, Yo, Ri, Ma 1/2, CRMP-5, Ampiphysin, heat shock proteins (HSPs), HSP60, clotting factor VIII, proliferating cell nuclear antigen (PCNA), DNA polymerase, recoverin, α-enolase, transducin-α, myelin basic protein (MBP), factor VIII (FVIII), factor IX (FIX), Amyloid β peptide (Aβ), myelin oligodendrocyte glycoprotein (MOG; see www.discoverymedicine.com/category/species-and-cell-types/human/brain/oligodendrocyte/), myelin basic protein (MBP), granulocyte macrophage-colony stimulating factor (GM-CSF), interferon (IFN)-γ, interleukin-(IL)-6, IL-17A, IL-17F, IL-22, histone H1,cytochrome P450, myelin, aquaporin-4 (AQP-4), Ro, La, muscle-specific kinase (MuSK), actinin-α4, α-enolase, elongation factor 2, glutamate receptor (NR2), laminin, myosin, smD1, PM-Scl, fibrillarin, RNA polymerase I, NOR), Scl-70, cyclin I and II, liver-specific protein, formiminotransferase-cyclodeaminase (LC-1), soluble liver antigen/liver-pancreas antigen (SLA/LP), desmoglein 1 or 3, envoplakin, BP180 protein, BP230 protein, myelin-associated glycoprotein, glutamic acid decarboxylase (GAD), tyrosine phosphatase (IA2), insulin, H+/K+-ATPase, elastase, kathepsin G, kactoferrin, BPI, rPAg1 (CUZD1) and rPAg2 (GP2), Phospholipase A2 receptor, Gliadin-analogue fusion peptide, glutamic acid decarboxylase (GAD65), and thyrotropin receptor antigens.

The antigens can be toxins, for example, the botulinum neurotoxins, the *Clostridium* perfringens epsilon toxin, ricin, saxitoxin, shigatoxin, tetrodotoxin, *staphylococcal* enterotoxins, etc. Mucins are also well known in the art. MUC5AC, MUC5B and MUC2 are examples thereof. In particular, they can be naturally-occurring polysaccharides such as Group *B. steptococcal* and *pneumococcal* capsular polysaccharides (including type III), *Pseudomonas aeruginosa* mucoexopolysaccharide, and capsular polysaccharides (including fisher type I), and *Haemophilus influenzae* polysaccharides.

In a preferred embodiment, said antigen or epitope is expressed by a virus which is selected from the group consisting of: the influenza virus, the hepatitis A virus, the Hepatitis B virus, the Hepatitis C virus, the Hepatitis E virus, the Hepatitis G virus, the HIV virus, the yellow fever virus, the dengue virus, the Japanese encephalitis virus, the tick-borne encephalitis virus, the Usutu or West Nile viruses, the Rift Valley fever or Toscana viruses, the chikungunya virus, the Omsk hemorrhagic fever virus, the Alkhurma hemorrhagic fever virus, the Kyasanur forest disease virus, the Venezuelan Equine Encephalitis virus, the Eastern Equine Encephalitis virus, the Western Equine Encephalitis virus, the Ross River virus, the Mayaro virus, the respiratory synticial virus, the Rocio virus, the morbillivirus, the Murray Valley encephalitis virus, the Wesselbron virus, the Zika virus, the lymphocytic choreomeningitis virus, the Ebola virus, the Marburg virus, the Crimean-Congo hemorrhagic fever virus, the Lassa virus, the Junin virus, the Machupo virus (see Wikipedia: Machupo_virus), the Sabia virus, the Guanarito virus, the mumps virus, the rabies virus, the rubella virus, the varicella zoster virus, the herpes simplex virus types 1 and 2, more generally an alphavirus, an adenovirus, a hantavirus, an echovirus, a rotavirus, a flavivirus, a rhinovirus, an orthobunyavirus, a poliovirus, a poxvirus (e.g., smallpox (see Wikipedia: Smallpox), monkeypox, blackpox, or canarypox), an orthomyxovirus (e.g., Influenzavirus A, Influenzavirus B, Influenzavirus C, see Wikipedia: Influenza_A_virus; see Wikipedia: Influenzavirus_B; see Wikipedia: Influenzavirus_C), a picornavirus, (e.g., foot and mouth disease virus, FMDV, see Wikipedia: Picornavirus), a human parvovirus, an enterovirus, a coronavirus (e.g., SARS or human betacoronavirus), a human papillomavirus, a herpes virus, the human cytomegalovirus, the Epstein-Barr virus, a paramyxovirus (see Wikipedia: Paramyxovirus), such as the parainfluenzae viruses from types 1, 2 and 3, or any identified virus.

In a preferred embodiment, said antigen or epitope is expressed by a virus belonging to a family which is selected from the group consisting of: the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg).

In another preferred embodiment, said antigen or epitope is expressed by a parasitic protozoa (such as those from the *Leishmania* genus, or *Toxoplasma Entamoeba histolytica*, *Plasmodium falciparum* (e.g., MSP1 (19)+AMA-1 (III) antigens, separately or co-expressed), *Pneumocystis carinii*, *Cryptosporidium, Naegleria fowleri* (see Wikipedia: *Naegleria_fowleri*), or *Giardia lamblia*), worms (such as *Trypanosoma cruzi*, nematodes, cestodes, or trematodes), or arthropods (such as crustaceans, insects, arachnids).

In another preferred embodiment, said antigen or epitope is expressed by an infectious bacterium, for example of the genera *Salmonella, Shigella, Streptococcus, Staphylococcus, Mycoplasma, Diptheriae, Lotospirosa, Rickettsia* or *Escherichia*. In a further preferred embodiment, the said bacterium belongs to one of the species selected from *Treponema pallidum* (see Wikipedia: *Treponema_*paffidum), *Helicobacter pylori, Campylobacter jejuni, Borrelia burgdorferi, Legionella pneumophila, Yersinia pestis, Yersinia enterocolitica, Brucella abortus, Burkholderia mallei* (see Wikipedia: *Burkholderia_mallei*), *Burkholderia pseudomallei* (see Wikipedia: *Burkholderia_pseudomallei*), *Chlamydia pneumonia, Francisella tularensis, Mycoplasma pneumonia, H. influenzae, S. pneumoniae, Klebsiella pneumoniae, S. aureus, Bacillus anthracis, Clostridium botulinum* (see Wikipedia: *Clostridium botulinum*), *Clostridium perfringens* (see Wikipedia: *Clostridium perfringens*), *Listeria monocytogenes, Bordetella pertussis, Clostridium tetani, Neisseria meningitidis* (see Wikipedia: *Neisselia_meningitidis*), *S. epidermidis, N. meningitidis, Pseudomonas aeruginosa, Chlamydia trachomatis, Mycobacterium tuberculosis, Coxiella bumetii, Rickettsia prowazekii* (see Wikipedia: *Rickettsia_prowazekii*), *Chlamydia psittaci* see Wikipedia: *Chlamyidia_psittaci*), *Leptospirosa interrogans* and *E. coli*, (e.g. *E. coli* 0157:H7(see Wikipedia: *Escherichia coli* 0157:H7)).

In another preferred embodiment, said antigen or epitope is expressed by a fungus or yeast (e.g. from the species *Candida, Aspergillus, Cryptococcus, Histoplasma, Pneumocystis,* or *Stachybolrys*).

The antigen or epitope can be from Prion protein (PrPc).

The epitope can be from a specific immunoglobulin, such as IgD, IgG1, IgG2, IgG3, IgG4, IgA, IgM, IgE, or IgG total.

Antigens usually present several surface features that can act as points of interaction for specific antibodies. Any such distinct molecular feature constitutes an epitope. As used herein, the term "epitope" therefore designates a particular molecular surface feature of an antigen, for example a fragment of an antigen, which is capable of being bound by at least one antibody. On a molecular level, an epitope therefore corresponds to a particular molecular surface feature of an antigen (for example a fragment of an antigen) which is recognized and bound by a specific antibody. In the context of the present invention, the "fusion proteins" contain at least one epitope that is recognized by a target antibody. Preferably, said fusion proteins contain whole antigens, comprising several epitopes (see Wikipedia: Epitope). These epitopes can be linear or conformational epitopes. As used herein, a linear (or sequential) epitope is an epitope that is recognized by antibodies (see Wikipedia: Antibody) by its linear sequence of amino acids (see Wikipedia: Amino_acid), or primary structure (see Wikipedia: Primary_structure). In contrast, a conformational epitope (see Wikipedia: Conformational_epitope) is recognized by its specific three-dimensional shape. Preferably, the fusion proteins of the invention contain conformational epitopes, as most polyclonal antibodies recognize same.

It is important however that such antigens do not present cross-reactive epitopes, i.e. epitopes that are recognized by non-specific antibodies that will bind thereto. If it was the case, the specificity of the method of the invention would be decreased.

In a preferred embodiment, said epitope is present on a viral protein, preferably an EDIII protein, which is selected from the group consisting of dengue virus 1, dengue virus 2, dengue virus 3, dengue virus 4, West Nile virus, yellow fever virus, Japanese encephalitis virus, Zika virus, Wesselbron virus, Rocio virus, Murray encephalitis virus, Saint-Louis encephalitis virus, Japanese encephalitis virus of genotype 1, Japanese encephalitis virus of genotype 2, Japanese encephalitis virus of genotype 4, Japanese encephalitis virus of genotype 5, and Rabensburg virus proteins.

In a more preferred embodiment, said epitope is present on a viral protein which is selected from the group consisting of: the EDIII protein of the dengue virus 1 encoded by SEQ ID NO:3, the EDIII protein of the dengue virus 2 encoded by SEQ ID NO:4, the EDIII protein of the dengue virus 3 encoded by SEQ ID NO:5, the EDIII protein of the dengue virus 4 encoded by SEQ ID NO:6, the EDIII protein of the West Nile virus encoded by SEQ ID NO:7, the EDIII protein of the yellow fever virus encoded by SEQ ID NO:8, the EDIII protein of the Japanese encephalitis virus encoded by SEQ ID NO:9, the EDIII protein of the Zika virus encoded by SEQ ID NO:10, the EDIII protein of the Wesselbron virus encoded by SEQ ID NO:11, the EDIII protein of the Rocio virus encoded by SEQ ID NO:12, the EDIII protein of the Murray encephalitis virus encoded by SEQ ID NO:13, the EDIII protein of the Saint-Louis encephalitis virus encoded by SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, and the EDIII protein of the Rabensburg virus encoded by SEQ ID NO:58 and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

In a preferred embodiment, the first and second epitopes (or antigens) that are fused with the hAGT enzyme in the fusion proteins used in the method of the invention belong to the same taxonomic level, i.e. they belong to the same family (e.g. the *Flaviviridae* family, the Bunyaviridae family, the Arenaviridae family or the Filoviridae family) or genus or species, but which have different serotypes. In other words, the said first and second epitopes can be expressed by closely related viruses, e.g. belong to the same family, genus or species but having different serotypes such as the dengue virus 1, 2, 3, or 4.

Alternatively, in another preferred embodiment, said first and second epitopes (or antigens) belong to unrelated biological families or genus or species.

The epitopes can be viral epitopes. Preferably, at least 1, 2, 3, 4, 5, 6, 7, 8, 9, 10, 11, 12, 13, 14, 15, or 16 of the epitopes are selected from viral epitopes. Preferably, at least 1, 2, 3, 4, 5, 6, 7, 8, 9, 10, 11, 12, 13, 14, 15, or 16 of the epitopes are selected from Dengue virus (serotypes 1, 2, 3, or 4), West Nile virus, yellow fever virus, Japanese encephalitis virus, tick-borne encephalitis virus, Saint-Louis encephalitis virus, Murray Valley encephalitis virus, Wesselsbron virus, Zika virus, Rocio virus, Usutu virus, Rift Valley fever virus, and chikungunya virus epitopes. More preferably, at least 1, 2, 3, 4, 5, 6, 7, 8, 9, 10, 11, 12, 13, 14, 15, or 16 of the epitopes are selected from Dengue virus (serotypes 1, 2, 3, or 4), West Nile virus, yellow fever virus, Japanese encephalitis virus, tick-borne encephalitis virus, Saint-Louis encephalitis virus, Murray Valley encephalitis virus, Wesselbron virus, Zika virus, Rocio virus, Usutu virus, Rift Valley fever virus, chikungunya virus, SARS coronavirus, human coronavirus, Hepatitic C virus (HCV), Hepatitis E virus (HEV), or Schmallenberg virus epitopes.

Preferably, at least 1, 2, 3, 4, 5, 6, 7, 8, 9, 10, 11, 12, 13, 14, 15, or 16 of the epitopes are selected from Dengue virus (serotypes 1, 2, 3, or 4), West Nile virus, yellow fever virus, Japanese encephalitis virus, tick-borne encephalitis virus, Saint-Louis encephalitis virus, Murray Valley encephalitis virus, Wesselsbron virus, Zika virus, Rocio virus, Usutu virus, Rift Valley fever virus, chikungunya virus, SARS coronavirus, human coronavirus, Hepatitic C virus (HCV), Hepatitis E virus (HEV), Schmallenberg virus, HIV1, HIV2, Hepatitis B virus, and HPV epitopes. The at least 1, 2, 3, 4, 5, 6, 7, 8, 9, 10, 11, 12, 13, 14, 15, or 16 of the epitopes can alternately be chosen from any group of 1, 2, 3, 4, 5, 6, 7, 8, 9, 10, 11, 12, 13, 14, 15, or 16 of the above-mentioned viruses.

Preferably, at least 1, 2, 3, 4, 5, 6, 7, 8, 9, 10, 11, 12, 13, 14, 15, or 16 of the epitopes are selected from Flaviviridae epitopes. Preferably, at least 1, 2, 3, 4, 5, 6, 7, 8, 9, 10, 11, 12, 13, 14, 15, or 16 of the epitopes are selected from Togaviridae eitopes. Preferably, at least 1, 2, 3, 4, 5, 6, 7, 8, 9, 10, 11, 12, 13, 14, 15, or 16 of the epitopes are selected from Bunyaviridae epitopes. Preferably, at least 1, 2, 3, 4, 5, 6, 7, 8, 9, 10, 11, 12, 13, 14, 15, or 16 of the epitopes are selected from Caliciviridae epitopes. Preferably, at least 1, 2, 3, 4, 5, 6, 7, 8, 9, 10, 11, 12, 13, 14, 15, or 16 of the epitopes are selected from Arenaviridae epitopes. Preferably, at least 1, 2, 3, 4, 5, 6, 7, 8, 9, 10, 11, 12, 13, 14, 15, or 16 of the epitopes are selected from Filoviridae epitopes. Preferably, at least 1, 2, 3, 4, 5, 6, 7, 8, 9, 10, 11, 12, 13, 14, 15, or 16 of the epitopes are selected from *Poxviridae* epitopes.

The epitopes can be bacterial epitopes. Preferably, at least 1, 2, 3, 4, 5, 6, 7, 8, 9, 10, 11, 12, 13, 14, 15, or 16 of the epitopes are selected from bacterial epitopes. Preferably, at least 1, 2, 3, 4, 5, 6, 7, 8, 9, 10, 11, 12, 13, 14, 15, or 16 of the epitopes are selected from *Treponema pallidum* (see Wikipedia: *Treponema_pallidum*), *Helicobacter pylori*, *Campylobacter jejuni*, *Borrelia burgdorferi*, *Legionella pneumophila*, *Yersinia pestis* (see Wikipedia: *Nersinia_pestis*), *Yersinia enterocolitica*, *Brucella abortus*, *Burkholderia mallei*, *Burkholderia pseudomallei*, *Chlamydia pneumonia*, *Francisella tularensis*, *Mycoplasma pneumonia*, *H. influenzae*, *S. pneumoniae*, *Klebsiella pneumoniae*, *S. aureus*, *Bacillus anthracis*, *Clostridium botulinum*, *Clostridium perfringens*, *Listeria monocytogenes*, *Bordetella pertussis*, *Clostridium tetani*, *Neisseria meningitidis*, *S. epidermidis*, *N. meningiditis*, *Pseudomonas aeruginosa*, *Chlamydia trachomatis*, *Mycobacterium tuberculosis*, *Coxiella bumetii*, *Rickettsia prowazekii*, *Chlamydia psittaci*, *Leptospirosa interrogans* and *E. coli* (e.g., *E. coli*, O157:H7) epitopes. The at least 1, 2, 3, 4, 5, 6, 7, 8, 9, 10, 11, 12, 13, 14, 15, or 16 of the epitopes can alternately be chosen from any group of 1, 2, 3, 4, 5, 6, 7, 8, 9, 10, 11, 12, 13, 14, 15, or 16 of the above-mentioned bacteria.

Preferably, at least 1, 2, 3, or 4 epitopes are selected from *Leptospira* epitopes, most preferably LruA, LruB, HbpA, or LipL32 epitopes.

In some embodiments, the first or second fusion protein comprises at least one amino acid sequence encoded by any of SEQ ID NOs 3-14 and 54-58, or at least 10, 15, 20, 25, 30, 40, 50, 60, 100, 200, or 300 consecutive amino acids thereof.

In some embodiments, the first or second fusion protein comprises at least one amino acid sequence selected from SEQ ID NOs: 155, 157, 159, 161, 163, 165, 167, 171, 173, 175, 177, and 179, or at least 10, 15, 20, 25, 30, 40, 50, 60, 100, 200, or 300 consecutive amino acids thereof.

In some embodiments, the first or second fusion protein comprises at least one amino acid sequence encoded by any of SEQ ID NOs 3-14 and 54-58 and/or comprises at least one amino acid sequence selected from SEQ ID NOs: 155, 157, 159, 161, 163, 165, 167, 171, 173, 175, 177, and 179 or at least 10, 15, 20, 25, 30, 40, 50, 60, 100, 200, or 300 consecutive amino acids thereof.

In some embodiments, the first or second fusion protein comprises at least one amino acid sequence selected from a mutated N protein from SARS coronavirus, an RBD of S protein from SARS coronavirus, a N protein from human betacoronavirus, an S1 protein from human betacoronavirus, an RBD of S protein from human betacoronavirus, a mutated C protein from Hepatitis C (HCV) virus, an HEV core antigen, an HCV core antigen, a short form of the HCV core antigen, the NSs protein from Schmallenberg virus.

In some embodiments, the first or second fusion protein comprises at least 10, 15, 20, 25, 30, 40, 50, 60, 100, 200, or 300 consecutive amino acids of the viral amino acid sequences shown in FIGS. 12-16 and 21-24.

In some embodiments, the first or second fusion protein comprises at least one amino acid sequence selected from a LruA, LruB, or LipL32 protein. Preferably, the first or second fusion protein comprises at least 10, 15, 20, 25, 30, 40, 50, 60, 100, 200, or 300 consecutive amino acids of the LruA, LruB, or LipL32 amino acid sequences shown in FIG. 17, 18, or 19.

Figure 17A:
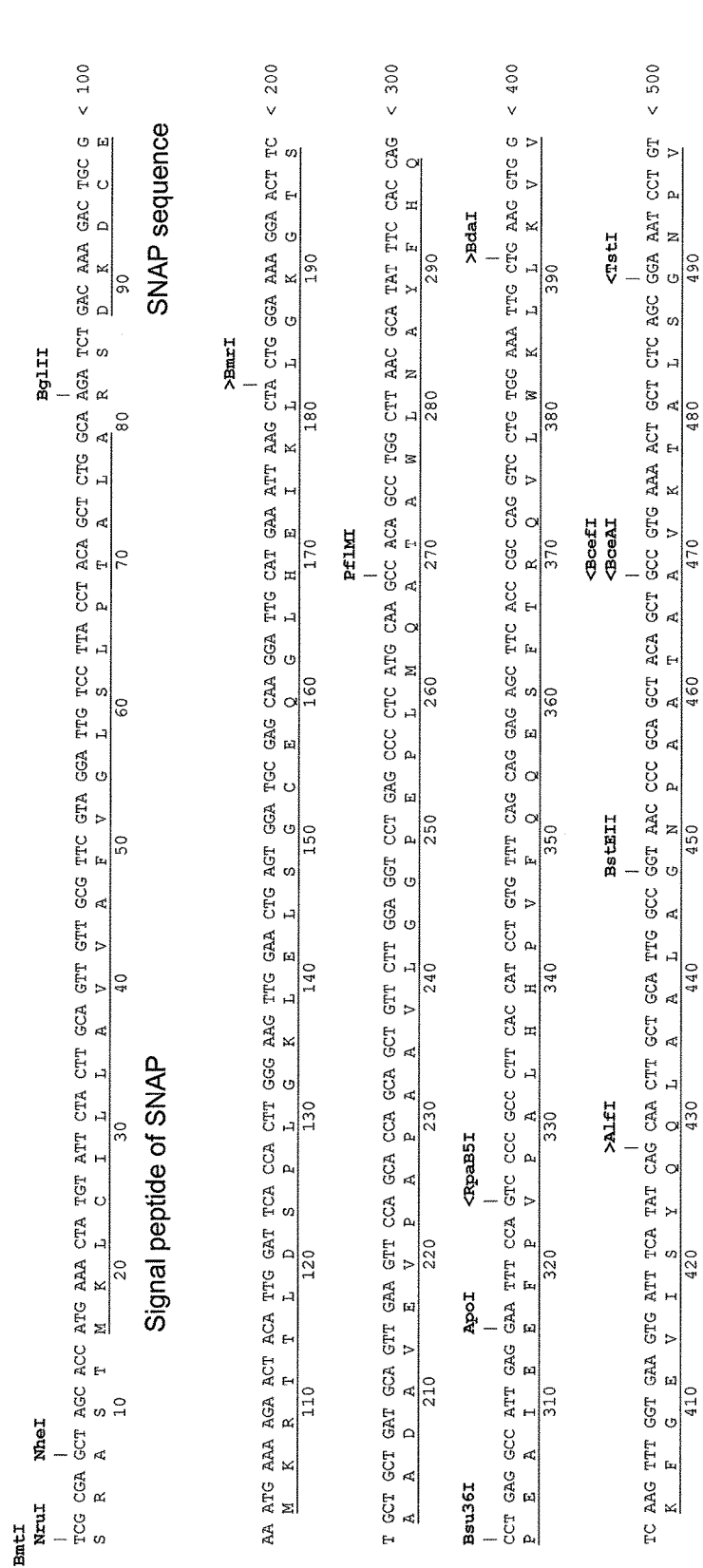
Figure 18B:
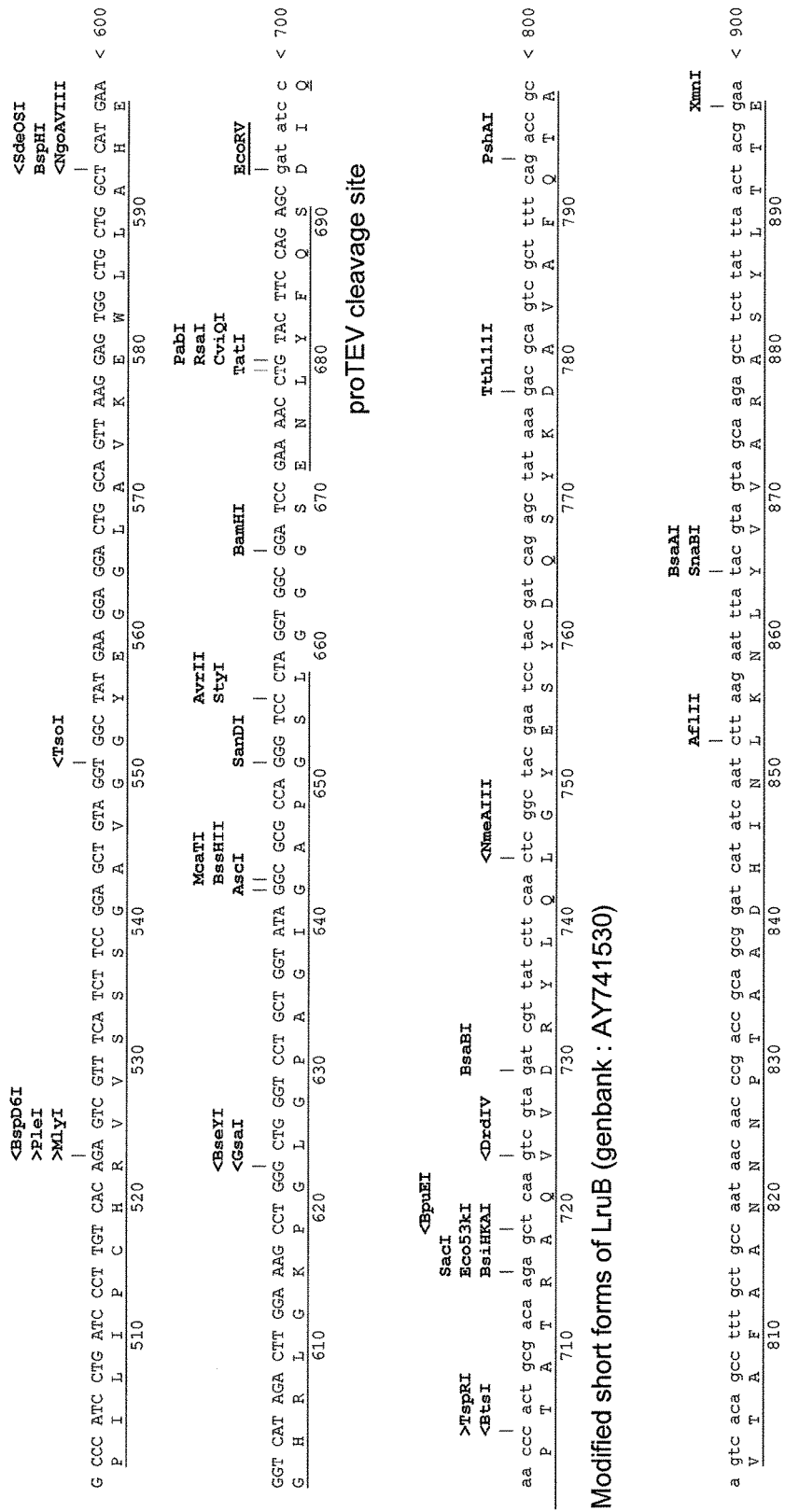
Figure 18D:
Figure 22B:
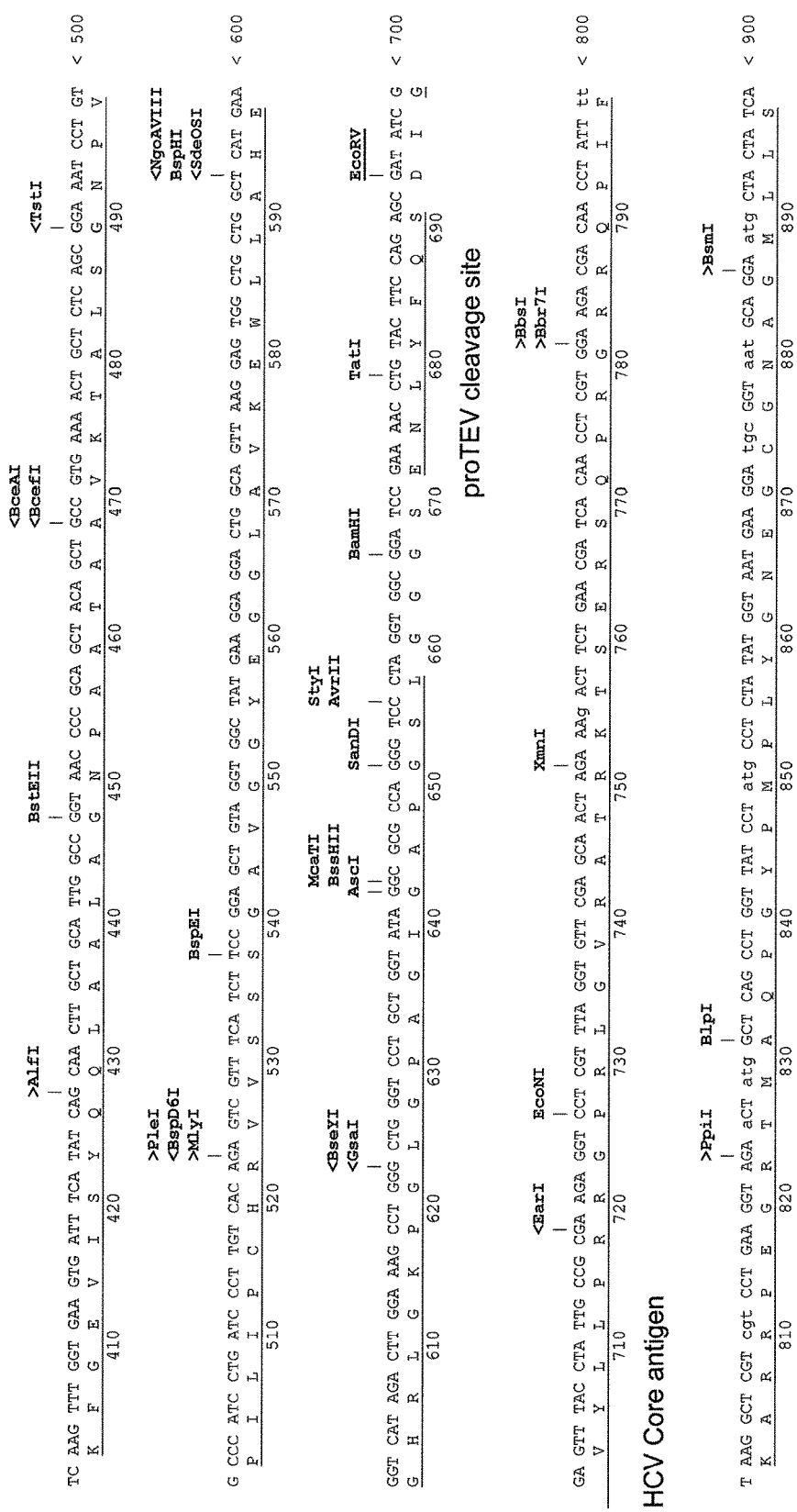
Figure 23C:
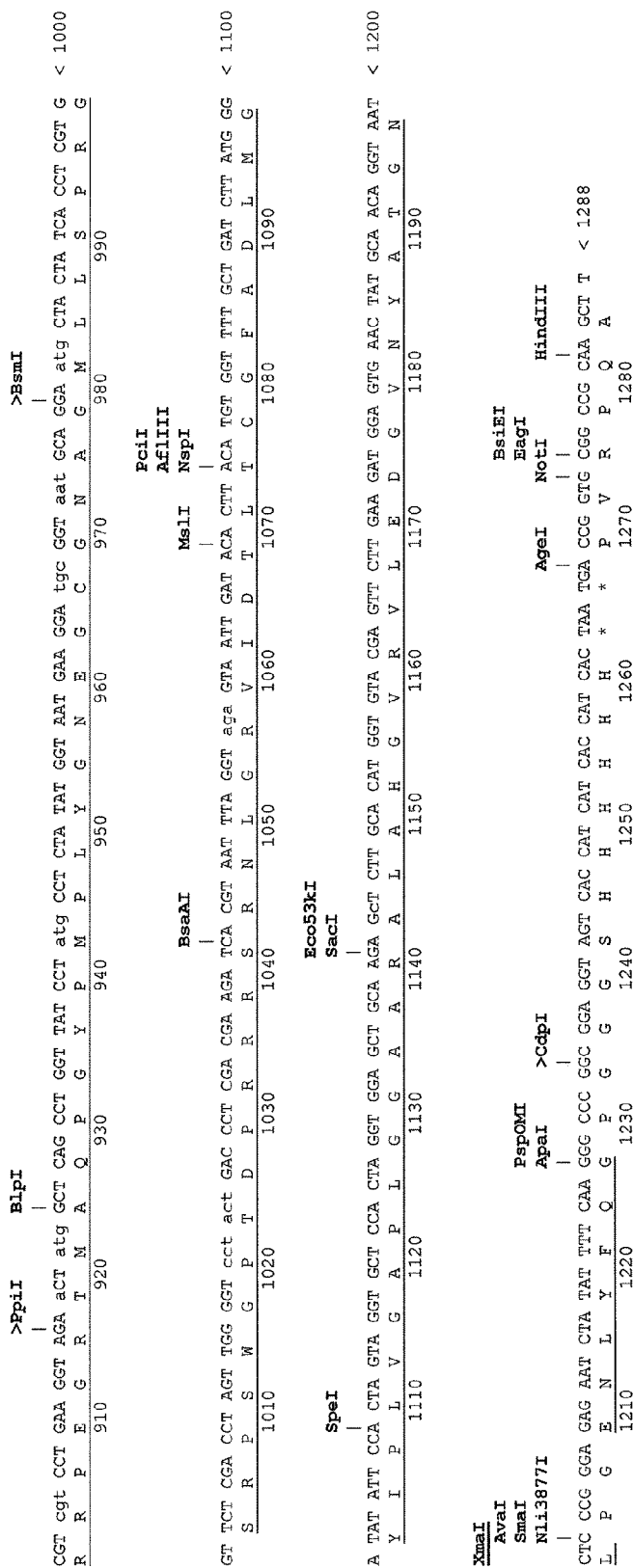
Figure 24B:
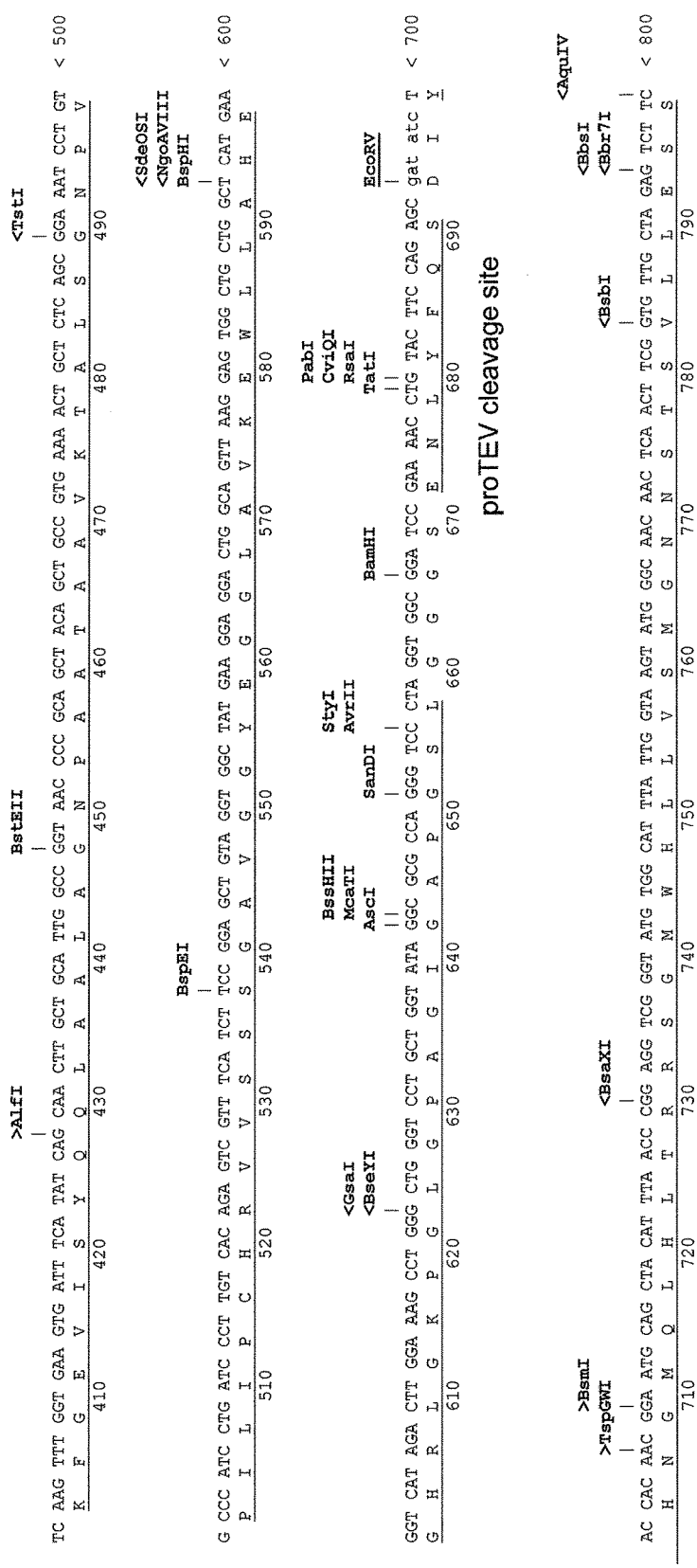
Figure 24C:
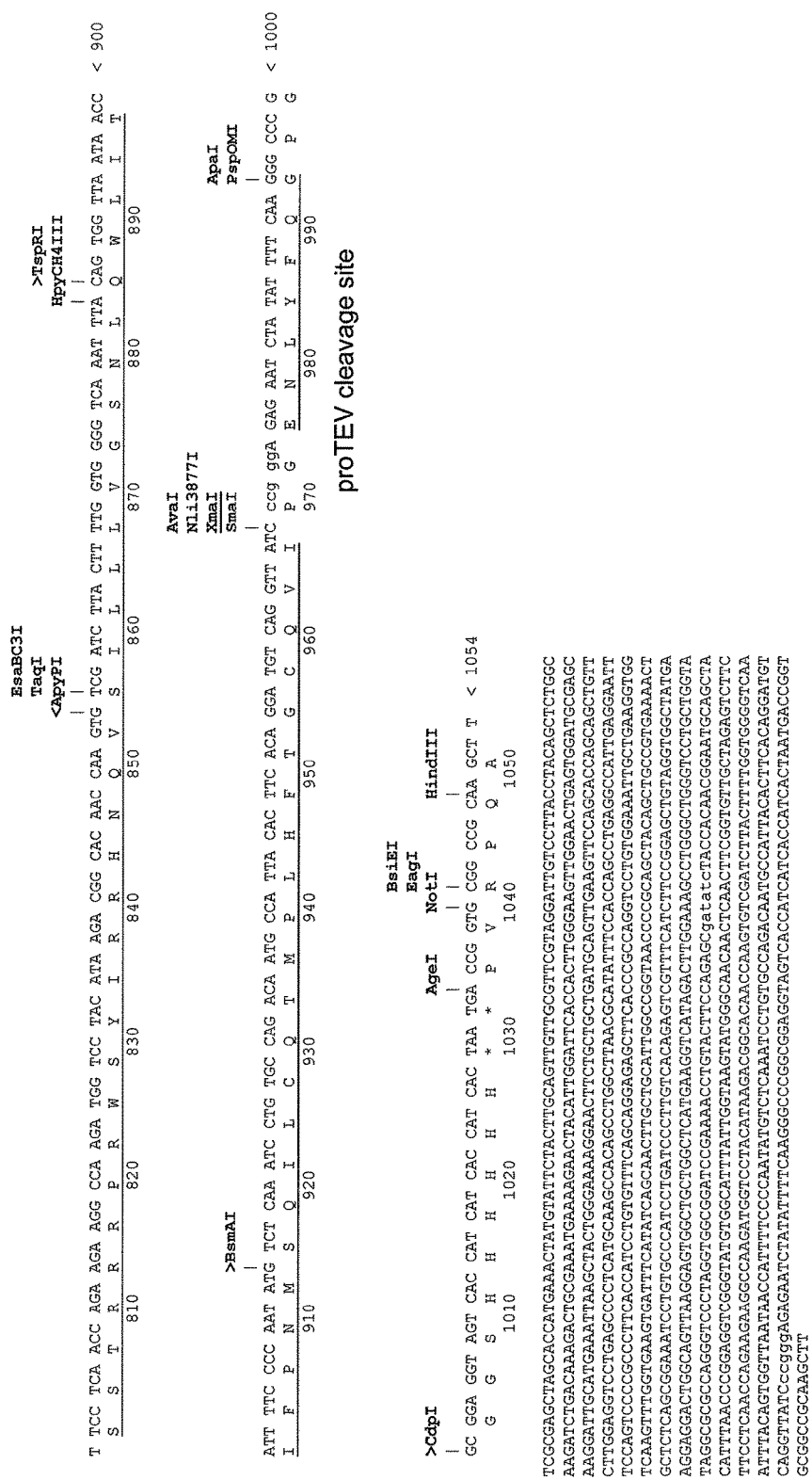

In some embodiments, the epitope comprises at least 10, 15, 20, 25, 30, 40, 50, 60, 100, 200, or 300 consecutive LruA, LruB, or LipL32 amino acids of the sequences shown in FIG. 17, 18, or 19.

The immunoassays of the invention can detect a large number of antibodies at the same time, which are known or unknown. By "large number", it is herein understood at least 5, more preferably at least 15, more preferably at least 50 and even more preferably at least 100 antibodies. Therefore, in a preferred embodiment, the assay method of the invention is used to detect at least 5, more preferably at least 15, and preferably at least 50 and even more preferably at least 100 target antibodies in a biological sample from a subject. It is of no relevance for the method of the invention whether the particular antibodies are properly characterized, since the procedure relies only on the detection of the presence of said antibodies, and not on their nature.

In a preferred embodiment of the invention, the said first and second fusion proteins that are coupled with the said first and second solid supports are selected from the group consisting of:

SEQ ID NO:21 (corresponding to the fusion protein [SNAP-DEN1EDIII])
SEQ ID NO:42 (corresponding to the fusion protein [SNAP-SBV.N])
SEQ ID NO:49 (corresponding to the fusion protein [SNAP-EV71.VP1])
SEQ ID NO:51 (corresponding to the fusion protein [JE.sE-SNAP])
SEQ ID NO:53 (corresponding to the fusion protein [SNAPJE-1.EDIII])
SEQ ID NO:60 (corresponding to the fusion protein [SNAP-JE-2.EDIII])
SEQ ID NO:62 (corresponding to the fusion protein [SNAP-JE-4.EDIII])
SEQ ID NO:64 (corresponding to the fusion protein [SNAP-JE-5.EDIII])
SEQ ID NO:66 (corresponding to the fusion protein [SNAP-RabV.EDIII])
SEQ ID NO:68 (corresponding to the fusion protein [SNAP-flavivirus.EDIII])
SEQ ID NO:70 (corresponding to the fusion protein [RR.sE2-SNAP])
SEQ ID NO:72 (corresponding to the fusion protein [MAY.sE2-SNAP])
SEQ ID NO:74 (corresponding to the fusion protein [WEE.sE2-SNAP])
SEQ ID NO:76 (corresponding to the fusion protein [EEE.sE2-SNAP])
SEQ ID NO:78 (corresponding to the fusion protein [VEE.sE2-SNAP])
SEQ ID NO:80 (corresponding to the fusion protein [SNAP-AKA.N])
SEQ ID NO:82 (corresponding to the fusion protein [SNAP-AIN.N])
SEQ ID NO:84 (corresponding to the fusion protein [SNAP-SHA.N])
SEQ ID NO:86 (corresponding to the fusion protein [SNAP-huCOV.N])
SEQ ID NO:88 (corresponding to the fusion protein [SNAP-huCOV.S])
SEQ ID NO:90 (corresponding to the fusion protein [SNAP-HCV.C])
SEQ ID NO:92 (corresponding to the fusion protein [SNAP-MSP+AMA])
SEQ ID NO:94 (corresponding to the fusion protein [SNAP-HbpA1])
SEQ ID NO:96 (corresponding to the fusion protein [SNAP-MUB40])
SEQ ID NO:98 (corresponding to the fusion protein [SNAP-moCLEC5A])
SEQ ID NO:100 (corresponding to the fusion protein [SNAP-huCLEC5A])
SEQ ID NO:102 (corresponding to the fusion protein [SNAP-cxVAGO])
SEQ ID NO:104 (corresponding to the fusion protein [SNAP-aaVAGO])
SEQ ID NO:109 (corresponding to the fusion protein [SNAP-CCHF.N])
SEQ ID NO:111 (corresponding to the fusion protein [SNAP-EBO.N])
SEQ ID NO:113 (corresponding to the fusion protein [SNAP-MAR.N])
SEQ ID NO:115 (corresponding to the fusion protein [SNAP-LAS.N])
SEQ ID NO:117 (corresponding to the fusion protein [SNAP-JUN.N])
SEQ ID NO:119 (corresponding to the fusion protein [SNAP-MAC.N])
SEQ ID NO:121 (corresponding to the fusion protein [SNAP-GUA.N])
SEQ ID NO:123 (corresponding to the fusion protein [SNAP-SAB.N])
SEQ ID NO:125 (corresponding to the fusion protein [SNAP-OMSK.EDIII])
SEQ ID NO:127 (corresponding to the fusion protein [SNAP-KYA.EDIII])
SEQ ID NO:129 (corresponding to the fusion protein [SNAP-ALK.EDIII])
SEQ ID NO:131 (corresponding to the fusion protein [LAS.ectoGP1-SNAP])
SEQ ID NO:133 (corresponding to the fusion protein [JUN.ectoGP1-SNAP])

SEQ ID NO:135 (corresponding to the fusion protein [MAC.ectoGP1-SNAP])

SEQ ID NO:137 (corresponding to the fusion protein [GUA.ectoGP1-SNAP])

SEQ ID NO:139 (corresponding to the fusion protein [SAB.ectoGP1-SNAP])

SEQ ID NO:141 (corresponding to the fusion protein [LAS.ectoGP2-SNAP])

SEQ ID NO:143 (corresponding to the fusion protein [JUN.ectoGP2-SNAP])

SEQ ID NO:145 (corresponding to the fusion protein [MAC.ectoGP2-SNAP])

SEQ ID NO:147 (corresponding to the fusion protein [GUA.ectoGP2-SNAP])

SEQ ID NO:149 (corresponding to the fusion protein [SAB.ectoGP2-SNAP]), and

SEQ ID NO:151 (corresponding to the fusion protein [SNAP-HEV.C]).

Consequently, the in vitro method of the invention enables to detect target disease(s) that is (are) viral, bacterial, yeast or fungi-mediated infection. Preferably said viral infection is caused by a Papillomavirus or RNA viruses from the families of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa see Wikipedia: Lassa_virus) and the Filoviridae (Ebola see Wikipedia: Ebola_virus, Marburg see Wikipedia: Marburg_virus). Preferably, said bacterial infection is caused by *Leptospirosa Interrogans*. Preferably, said infection is caused by *Plasmodium falciparum*.

As used herein, the term "biological sample" refers to any samples which have been obtained from a patient and which might contain antibodies. Preferably, said biological sample is a biological fluid, for example an unfiltered biological fluid such as urine, cerebrospinal fluid, pleural fluid, synovial fluid, peritoneal fluid, amniotic fluid, gastric fluid, blood, serum, plasma, lymph fluid, interstitial fluid, saliva, physiological secretions, tears, mucus, sweat, milk, semen, seminal fluid, vaginal secretions, fluid from ulcers and other surface eruptions, blisters, and abscesses. It also refers to an extract of tissues including biopsies of normal, malignant, and suspect tissues or any other constituents of the body which may contain antibodies. The said biological sample can be pre-treated prior to use, such as preparing plasma from blood, diluting viscous fluids, or the like; methods of treatment can involve filtration, distillation, concentration, inactivation of interfering compounds, and the addition of reagents. In a preferred embodiment, said biological sample is chosen from whole blood, serum, plasma, urine, seminal fluid, cerebrospinal fluid and saliva.

AGT Polypeptides

Any polypeptide having $O^6$-alkylguanine-DNA alkyltransferase activity can be used in the method of the present invention. For the purpose of the invention, these polypeptides will be referred to as "AGT polypeptides".

AGT irreversibly transfers the alkyl group from its substrate, $O^6$-alkylguanine-DNA, to one of its cysteine residues. A substrate analogue that rapidly reacts with AGT is $O^6$-benzyl-guanine, the second order rate constant being approximately $10^3$ $sec^{-1}$ $M^{-1}$.

In the context of the invention, a polypeptide is said to have "$O^6$-alkylguanine-DNA alkyltransferase activity" (or "AGT activity") if it is capable of irreversibly transferring an alkyl group from a $O^6$-alkylguanine-containing molecule to one of its own cysteine residues. The "$O^6$-alkylguanine-DNA alkyltransferase activity" of the said polypeptide can be demonstrated by, for example, contacting known labeled $O^6$-benzyl-guanine derivatives and monitoring the transfer of said label on to the tested polypeptide. If the assay is performed in cellulo or in cell extracts, the reaction of the endogenous AGT of the host cells should be controlled, so that endogenous AGT does not interfere with the said polypeptide. Therefore, known AGT-deficient cell lines are preferably used. Assays for identifying AGT activity are now well described. Several $O^6$-benzyl-guanine derivatives are commercially available ($O^6$-benzyl-guanine is distributed for example by Santa Cruz biotechnology, and fluorescently-labeled $O^6$-benzyl-guanine derivatives can be obtained from New England Biolabs NEB). Some of these assays are disclosed in WO 2005/085470 and in WO 2004/031405.

In the context of the invention, the "catalytic domain" of the AGT polypeptide corresponds to the active site of said enzyme, or, in other words, to the part of the enzyme at which the transfer of the alkyl group from its substrate, $O^6$-alkylguanine-DNA, to a reactive cysteine residue, occurs. In the structure of hAGT bound with $O^6$-benzylguanine in its active site, four amino acids are in proximity to either the benzyl ring (Pro140, Ser159, Gly160), or could make contact with the N9 of the nucleobase (Asn157). Mutations at position Pro140 and Gly160 have previously been shown to affect the reaction of hAGT with $O^6$-benzyl-guanine (Xu-Welliver et al., Biochemical Pharmacology 1999): a proline at position 140 is believed to be essential for its interaction with the benzyl ring, and the mutation Gly160Trp has been shown to increase the reactivity of hAGT towards $O^6$-benzylguanine.

In a preferred embodiment, the AGT polypeptide having $O^6$-alkylguanine-DNA alkyltransferase activity is the human AGT polypeptide (referenced as NP_002403.2) of sequence SEQ ID NO: 1, the mouse AGT identified as NP_032624.1 (SEQ ID NO: 18), the rat MGMT identified as NP_036993.1 (SEQ ID NO: 19) or a homologous sequence thereof, said homologous sequence having $O^6$-alkylguanine-DNA alkyltransferase activity.

As used herein, the term "homologous" refers to sequences that have sequence similarity. The term "sequence similarity", in all its grammatical forms, refers to the degree of identity or correspondence between nucleic acid or amino acid sequences. In the context of the invention, two amino acid sequences are "homologous" when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of the amino acids are similar. Preferably the similar or homologous polypeptide sequences are identified by using the algorithm of Needleman and Wunsch.

Preferably, the homologous sequence to the AGT enzyme shares at least 64% amino acid sequence identity, preferably at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77 amino acid sequence identity, alternatively at least about 78% amino acid sequence identity, alternatively at least about 79% amino acid sequence identity, alternatively at least about 80% amino acid identity, alternatively at least about 81% amino acid sequence identity, alternatively at least about 82% amino acid sequence identity, alternatively at least about 83 amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity with SEQ ID NO: 1. In a preferred embodiment, an homologous sequence of SEQ ID NO: 1 is at least 64%, preferably 70%, and more preferably 80% identical to SEQ ID NO: 1.

In a preferred embodiment, the said homologous polypeptide is a fragment or a mutant of the hAGT polypeptide of SEQ ID NO: 1, said fragment or mutant having a $O^6$-alkylguanine-DNA alkyltransferase activity.

Said fragments can have a size of at least 50, preferably 100, and more preferably 150 amino acids, and contain at least the "catalytic domain" of the AGT polypeptide as defined above, which is responsible of the $O^6$-alkylguanine-DNA alkyltransferase activity of the AGT enzyme. These fragments can be obtained using common techniques which are known by the skilled person.

Different mutant enzymes derived from native AGT have been described so far (Lim A. et al, 1996; Daniels D. S. et al, 2000; Juillerat A. et al, 2003, WO 2005/085470, WO 2004/031405). In particular, a mutant protein of 20 kDa containing the mutations Cys62Ala, Lys 125Ala, Ala127Thr, Arg128Ala, Gly131Lys, Gly132Thr, Met134Leu, Arg135Ser, Cys150Ser, Asn157Gly, Ser159Glu truncated at amino acid 182 has been obtained (the so-called "AGT26" mutant in WO 2005/085470, also called "SNAP 26" in WO 2006/114409). This particular mutant "SNAP26" has been shown to have enhanced labelling activity.

In the context of the present invention, the sequence of a more preferred AGT polypeptide contains the mutations described in WO 2005/085470, which positions can be easily transposed in view of SEQ ID NO: 1, the starting methionine residue of SNAP26 corresponding to the methionine residue in position 32 of SEQ ID NO: 1 (31 amino acids should therefore be added to the positions disclosed in WO 2005/085470 so as to obtain the corresponding ones in SEQ ID NO: 1).

In a preferred embodiment, the AGT homologous sequence useful in the invention corresponds to the native AGT sequence of SEQ ID NO: 1, in which between 1 and 30, preferably between 6 and 25, and in particular 14, 15, 16, 17, 18, 19, 20, 21, 22, or 23 amino acids are substituted by other amino acids, and/or 1 to 40, preferably 1 to 20, in particular 10 to 20 amino acids, more preferably 15 amino acids at the C-terminus are deleted.

In a more preferred embodiment, the AGT homologous sequence contains the following mutations as compared with SEQ ID NO: 1:

(A) Lys31 replaced by Arg, or Met32 replaced by Ser, or Cys93 replaced by Ala, or Lys156 replaced by Ala, or Ala158 replaced by Thr, or Arg159 replaced by Ala, or Gly162 replaced by Lys, or Gly163 replaced by Thr, or Met165 replaced by Leu, or Arg166 replaced by Ser, or Cys181 replaced by Ser, or Asn188 replaced by Gly, or Ser190 replaced by Glu, or Gly214 replaced by Pro, or Ser215 replaced by Ala, or Ser216 replaced by Gly, or Gly217 replaced by Ile, or Leu218 replaced by Gly, or Gly220 replaced by Pro, or Ala221 replaced by Gly, or Trp222 replaced by Ser, or (B) Lys31-Met32 replaced by Arg-Ser, or Ala158-Arg159 replaced by Thr-Ala, or Gly162-Gly163 replaced by Lys-Thr, or Met165-Arg166 replaced by Leu-Ser, or Gly162-Gly163Met165-Arg166 replaced by Lys-Thr/Leu-Ser, or Asn188/Ser190 replaced by Gly/Glu, or Gly214-Ser215-Ser216-Gly217-Leu218 replaced by Pro-Ala-Gly-Ile-Gly, or Gly220-Ala221-Trp222 replaced by Pro-Gly-Ser, preferably in combination with any other amino acid replacements cited in (A), or (C) Truncation after Leu223 (amino acids 224-238 are deleted), preferably in combination with any other amino acid replacement cited in (A) or (B).

Preferred AGT homologous sequences are those being truncated after Leu223.

Preferred AGT homologous sequences are those wherein two out of the modifications (B) are present, and optionally truncation after Leu223.

Preferred AGT homologous sequences are those wherein three out of the modifications (B) are present, and optionally truncation after Leu223.

Preferred AGT homologous sequences are those wherein four out of the modifications (B) are present, and optionally truncation after Leu223.

Preferred AGT homologous sequences are those wherein five out of the modifications (B) are present, and optionally truncation after Leu223.

Preferred AGT homologous sequences are those wherein six out of the modifications (B) are present, and optionally truncation after Leu223.

Other preferred AGT homologous sequences are those containing a combination of 2, 3, 4, 5, 6, 7, 8, 9, 10, 11, 12, 13, 14, 15, 16, 17, 18, 19, or 20 mutations chosen among the modifications disclosed in (A), and optionally truncated after Leu223.

In a far more preferred embodiment, the AGT polypeptide of the invention is the SNAP mutant of SEQ ID NO: 2, which is homologous to the hAGT enzyme and contains the mutations Lys31Arg, Met32Ser, Cys93Ala, Lys156Ala, Ala158Thr, Arg159Ala, Gly162Lys, Gly163Thr, Met165Leu, Arg166Ser, Cys181Ser, Asn188Gly, Ser190Glu, Gly214Pro, Ser215Ala, Ser216Gly, Gly217Ile, Leu218Gly, Gly220Pro, Ala221Gly, Trp222Ser and truncation after Leu223 as compared with SEQ ID NO: 1. The SNAP mutant of SEQ ID NO: 2 shares 77% homology with the amino acid sequence of the human 6-methylguanine-DNA-methyltransferase (NP_002403.2, SEQ ID NO: 1), and 70% homology with the amino acid sequence of the mouse 6-methylguanine-DNA-methyltransferase (NP_032624.1, SEQ ID NO: 18).

In an even more preferred embodiment, the AGT enzyme is the SNAP mutant protein of SEQ ID NO: 2 or a homologous thereof, having $O^6$-alkylguanine-DNA alkyltransferase activity. Preferably, said homologous sequence to the SNAP mutant protein is at least identical at more than 80%, preferably 81%, more preferably 82%, more preferably 83%, more preferably 84%, more preferably 85%, preferably 86%, more preferably 87%, more preferably 88%, more preferably 89%, more preferably 90%, more preferably 91%, more preferably 92%, more preferably 93%, more preferably 94%, more preferably 95%, more preferably 96% to the and even more preferably 97% to the SNAP mutant protein of sequence SEQ ID NO: 2, and has $O^6$-alkylguanine-DNA alkyltransferase activity as defined above.

Said homologous polypeptides having $O^6$-alkylguanine-DNA alkyltransferase activity can be produced using protein engineering techniques known to the skilled person and/or using molecular evolution to generate and select new $O^6$-alkylguanine-DNA alkyltransferases. Such techniques are e.g. targeted mutagenesis, phage display methods, saturation mutagenesis, error prone PCR to introduce variations anywhere in the sequence, DNA shuffling used after saturation mutagenesis and/or error prone PCR, or family shuffling using genes from several species.

In the most preferred embodiment, the AGT polypeptide used in the method of the invention is the SNAP mutant of SEQ ID NO: 2.

AGT Substrates

The AGT enzyme irreversibly transfers the alkyl group from its substrate, $O^6$-alkylguanine-DNA, to one of its cysteine residues. However, substitutions of $O^6$-benzylguanine at the C4 of the benzyl ring do not significantly affect the reactivity of AGT against $O^6$-benzylguanine derivatives. This property has been used to transfer a label attached to the C4 of the benzyl ring to AGT (see WO 2004/031404 and WO 2005/085470).

A number of $O^6$-benzylguanine derivatives have been shown to react with the AGT enzyme by transferring their benzyl group to the active site cysteine of the AGT enzyme (cf. Damoiseaux et al., ChemBiochem., 2001, WO 2004/031404 and WO 2005/085470).

In a preferred embodiment, the AGT substrates used in the method of the invention are $O^6$ benzyl guanine derivatives having the formula I:

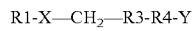

wherein:
R1 is a group recognized by said AGT polypeptide as a substrate, such as a heteroaromatic group containing 1 to 5 nitrogen atoms, and preferably a purine radical of the formula:

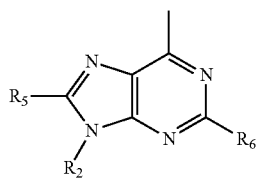

wherein R5 is hydrogen, halogen, e. g. chloro or bromo, trifluoromethyl, or hydroxy; R6 is hydrogen, hydroxy or unsubstituted or substituted amino; and R2 is hydrogen, an alkyl of 1 to 10 carbon atoms, or a saccharide moiety;

X is an oxygen or sulfur atom; preferably an oxygen atom;

R3 is an aromatic or a heteroaromatic group, or an optionally substituted unsaturated alkyl, cycloalkyl or heterocyclyl group with the double bond connected to $CH_2$; preferably a phenyl, e.g. a phenyl substituted by R4 in para or meta position, R4 is a linker moiety, Y is a reactive group, preferably an amino group.

In a preferred embodiment, said linker moiety $R_4$ is a flexible linker. Linker units are chosen in the context of the envisioned application, i.e. in the transfer of the substrate to a fusion protein comprising AGT. The linker does not interfere with the reaction with AGT nor with the target antibody.

For example, it can be a straight or branched chain alkylene group with 1 to 20 carbon atoms, preferably 5 to 15 carbon atoms, wherein:
(a) one or more carbon atoms are replaced by oxygen, in particular wherein every third carbon atom is replaced by oxygen, e.g. a poylethyleneoxy group with 1 to 5 ethyleneoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH═CH— or —C≡C—;
(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;
(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

In a preferred embodiment, R4 is a polyethyleneoxy group with 1 to 8 ethyleneoxy units, further comprising one to four nitrogen atoms carrying a hydrogen atom, which adjacent carbon atoms are substituted by oxo, representing an amide function —NH—CO—.

In a more preferred embodiment, R4 is —$CH_2$—NH—CO—NH—[$C_2H_4$—O]$_n$—, wherein n is comprised between 1 to 8, preferably 2 to 6, and is most preferably 3.

In a preferred embodiment, said reactive group is a functional group that facilitates the attachment and bonding of the substrate on the solid support. Such functional groups are well-known in the art. They include amine, activated esters, acrylamides, acyl azides, acyl halides, acyl nitriles, aldehydes, ketones, alkyl halides, anhydrides, aryl halides, aziridines, boronates, activated carnoxylic acids, carbodiimides, diazoalkanes, epoxides, haloacetamides, haloplatinate, halotriazines, imido esters, isocyanates, is othiocyanates, maleimides, phosphoramidites, solyl halides, sulfonate esters and sulfonyl halides. It is preferably the amine group —$NH_2$.

On the opposite side, the solid support should be functionalized by complementary groups corresponding to such reactive groups. The complementary groups corresponding to each of these reactive groups are well-known in the art. They are given for example on the table I of WO 2010/107433.

In a preferred embodiment, the AGT substrate used in the method of the invention is:

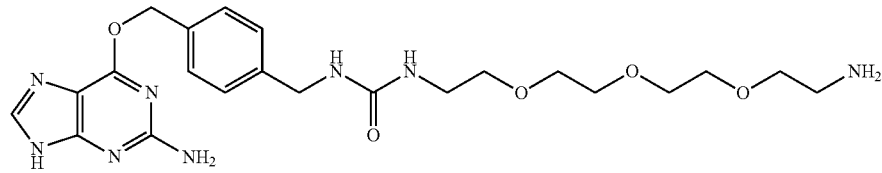 [SMILES: NCCOCCOCCOCCNC(=O)NCc1ccc(COc2nc(N)nc3[nH]cnc23)cc1]

In another preferred embodiment, the AGT substrate used in the method of the invention is the fluorescent linker designated "SNAP-Cell® 505", having the following formula:

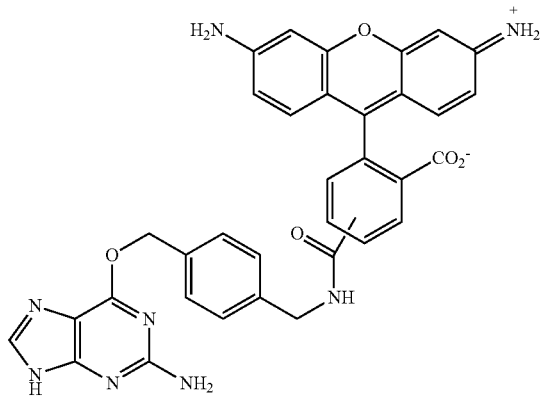

This benzylguanine derivative possesses one benzyl purine group (guanine) for the specific interaction with the SNAP domain, as well as one free amine group for the covalent coupling to the microsphere surface. It is commercialized by New England BioLabs and has been successfully coupled to the surface of the microparticles of the invention.

Substrates of the invention are generally prepared by standard methods known in the art. Particular methods are explained e.g. in patent application WO 2005/085470.

Coupling of AGT Substrates to Solid Supports

The invention encompasses AGT substrates covalently coupled to solid supports. In the context of the present invention, an AGT substrate is "covalently coupled" to a solid support if it is permanently attached to the said solid support, and will not desorb or leach over time. According to the invention, an AGT substrate is permanently attached to the said solid support if it stays attached for a long period of storage, e.g., typically, at least 6 months of storage. A number of coupling proceedings have been described so far. Any of these coupling proceedings can be used in the immunoassay of the invention, provided that the AGT substrate becomes permanently attached to the solid support.

Coupling of AGT-Antigen Fusion Proteins to Solid Supports

The invention further encompasses methods for coupling antigens to solid supports comprises the two following steps:

i) the coating of solid surfaces with an AGT substrate (e.g. BG-PEG-amino), and ii) the covalent immobilization of chimeric [AGT-Antigen] fusion proteins using the AGT substrate as an anchor (see FIG. 1). Before being coated with said AGT substrate, the solid surfaces are advantageously functionalized, preferably by using an optimized two-step carbodiimide process (Kufer S K, *Eur. Biophys. J.* 2005), so that the AGT substrate is covalently attached to the solid surfaces. Once these steps have been performed, the solid surfaces carry AGT substrates that are irreversibly linked to the chimeric [AGT-antigen] fusion proteins. Due to the high specificity of this reaction, the fusion protein is exclusively coupled via the cysteine-containing domain of the AGT enzyme, thus leaving the antigen accessible for its interactions with antibodies.

This coupling procedure is very advantageous as it allows the binding of the antigen in an oriented manner on the solid supports. Also, this antigen coupling procedure advantageously enables to obtain a multimeric antigen organization on a solid surface, so as to enhance immunoglobulin G, and potentially immunoglobulin M, capture efficiency.

Consequently, the antigen-coupled microspheres developed in the experimental part of the application have shown enhanced capture of specific antibodies as compared to antigen-coupled microspheres produced by standard non-oriented amine coupling procedures (see the experimental part below and FIG. 3). Finally, this antigen coupling procedure enables to obtain a high coupling efficiency and a long-term stability of the antigen-conjugated microspheres (>6 months at 4° C.).

In the immunoassay of the invention, the covalent coupling is preferably performed by contacting the AGT substrates (which contain a reactive group Y, as mentioned above) with solid supports which have been previously functionalized with a complementary group such as those disclosed in table I of WO 2010/107433, the disclosure of which is incorporated herein by reference.

Thus, in a preferred embodiment, the methods of the invention use solid supports that have been functionalized with a group which is complementary to the reactive group of the AGT substrate, before being contacted with the AGT substrate.

A preferred and conventional procedure for covalently coupling an AGT substrate to the surface of solid supports is based on the carbodiimide reaction and uses water-soluble carbodiimide. According to this procedure, solid supports have surface carboxyl groups available for attachment of the reactive amine- or sulfhydryl-containing AGT substrate. Thus, in this preferred embodiment, the methods of the invention use solid supports that have been functionalized with surface carboxyl groups prior to be contacted with the AGT substrate.

In this case, the first step of the method of the invention is to activate the carboxyl groups coating the solid supports. This activation is usually performed by adding a so-called "activation buffer", for example a 50 mg/mL EDAC solution or a 50 mg/mL S-NHS solution. These solutions are commercially available. Activation of the solid supports is typically performed by incubating said supports with the activation buffer at room temperature for a few minutes (e.g. 5 minutes to 30 minutes), according to the manufacturer's instructions.

Importantly, covalent coupling of the AGT substrate to the solid support has to be performed under particular conditions, so as to preserve the AGT substrate solubility and the integrity of the bead (internal fluorochrome). The inventors have observed that the AGT substrates should be suspended in a "covalent coupling" buffer containing between 0 and 20% of dimethylsulfoxide (DMSO). In particular, the inventors have observed that concentrations of DMSO above 20% may affect the detection step of the methods of the invention. Preferably, said buffer is a PBS buffer containing between 0 and 20% of DMSO, more preferably between 10% and 20% of DMSO.

Advantageously, the unspecific sites on the solid supports that have not been covalently attached to the AGT substrate can be further blocked by any conventional means, for example, by using a blocking buffer containing 1% of bovine serum albumin (BSA) or any saturating protein (e.g. casein).

Once the solid supports of the invention have been covalently coupled with the AGT substrate (preferably through a carbodiimide covalent linkage), the solid supports are then contacted by the fusion proteins of the invention, so as to couple the epitopes that are specifically recognized by the target antibodies to said supports.

Again, this coupling step has to be performed under particular conditions. As a matter of fact, the catalytic site of the AGT enzyme and the conformational structure of the antigens/epitopes which are carried by the fusion proteins have to be conserved during the coupling proceedings. The inventors identified that the fusion protein should be suspended in a dithiothreitol (DTT)-containing buffer, preferably a PBS/DTT buffer, for the coupling to be efficient. Advantageously, the said coupling buffer contains tween 20; indeed, it has been observed by the present inventors that addition of tween 20 to the coupling medium helps avoiding bead aggregation. Preferably, the coupling buffer contains 0.02% tween 20. More preferably, the covalent coupling buffer of the invention is a PBS buffer of pH 7,4, containing 0.02% tween 20, and 1 mM DTT.

Other coupling conditions are usual ones. Preferably, the covalent coupling of the AGT substrate and the coupling of the fusion protein to the solid supports are performed at room temperature. If the solid supports are fluorescently labeled, said proceedings are more preferably performed in darkness.

The invention encompasses methods for covalently coupling a AGT polypeptide having $O^6$-alkylguanine-DNA alkyltransferase activity, on a functionalized solid support, comprising the following steps:
 a) activating the said functionalized solid support,
 b) adding a substrate of said AGT polypeptide, said substrate being suspended in a buffer containing between 0 and 20% of DMSO, in appropriate conditions so that the substrate is covalently attached to said support,
 c) contacting the said AGT polypeptide with the substrate-coated support of step b) in a PBS/DTT buffer,
 wherein unbound molecules are washed out after steps b) and c).

Washings can be performed by using any kind of appropriate washing buffers. Such buffers are routinely used by the person of skills in the art and need not be further detailed here. Preferably, a PBS buffer is used.

As used herein, "appropriate conditions" are usual ones. Preferably, the covalent coupling of the AGT substrate is performed at room temperature and, if the solid supports are fluorescently labeled, in darkness.

The functionalization of the solid support can be performed by any conventional means (as those reminded above). The activation of said functionalized solid support is performed accordingly. In a preferred embodiment, the said solid supports are functionalized with surface carboxyl groups and further activated with a classical activation buffer, for example a 50 mg/mL EDAC solution or a 50 mg/mL S—NHS solution.

In a preferred embodiment, DTT is at a concentration of 1 mM in the PBS/DTT buffer.

The present invention is also drawn to a solid support which has been obtained by the said method, and to the use of said solid support in the immunoassay of the invention.

Said solid supports can then be stored in conventional storage buffers, for example containing 0.5 g/L sodium azide, 0.1% BSA, 0.02% tween 20, and/or 1 mM DTT.

All these coupling steps are preferably performed in vitro, in buffers which are devoid of living cells, so that there is no need to take into account the reaction with endogenous AGT enzymes, and the reaction of the (exogenous) AGT fusion protein is therefore highly specific.

Solid Supports

The solid supports that can be used in the methods of the invention can be of any kind, e.g. test tubes, microtiter wells, sheets, beads, chips, and/or microparticles, provided that they can be specifically identified from each other. Such identification is possible for example when they are separately located in space (e.g. the wells in a microtiter plate, or different locations on a chip) or when they are differently labeled. A "solid support" has therefore to be understood in a broad meaning, that is, by designating either discrete small parts of a whole solid supports (in case of a plate or a biochip) or a large number of identical microparticles that share common detectable characteristics (hereafter referred to as microparticles "subset").

In preferred embodiments, the solid supports used in the immunoassays of the invention should be intrinsically identifiable, so that it is possible to determine precisely which antigen is carried by which solid support. The antigen-coupled and identifiable solid supports are then used as capture reagents for specific human immunoglobulins and are therefore contacted with the biological sample of the patient.

In a preferred embodiment, the solid supports used in this invention can be specifically identified by their specific location, size, diameter, weight, granulometry, and/or labeling. Such labeling is for example a fluorochrome, a fluorophore, a chromophore, a radioisotope, a mass tag, or any kind of detectable tag which is known in the art.

The solid supports used in the invention can be made of any material, for example in polystyrene, cellulose, nitrocellulose, glass, ceramic, resin, rubber, plastic, silica, silicone, metal, and/or polymer. Polymeric materials include brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactideco-glycolide), polyanhydride, polyorthoester, polyphosphazene, polyphosophaze, polysulfone, or combinations thereof, that are acceptable as well. Most of these supports are commercially available. For example, beads from synthetic polymers such as polystyrene, polyacrylamide, polyacrylate, or latex are commercially available from numerous sources such as Bio-Rad Laboratories (Richmond, Calif.) and LKB Produkter (Stockholm, Sweden). Beads formed from natural macromolecules and particles such as agarose, cross-linked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia.

When polymeric supports were used, carboxyl groups can be added to the surface of the solid support by incorporating monomers containing such groups into the polymers (for example, acrylic acid, methacrylic acid, itaconic acid, and the like). Alternatively, they can be added to the support by further chemical reaction of a polymer having other precursor reactive groups which can be converted to carboxyl groups (for example, by hydrolysis of anhydrides, such as maleic anhydride, or by oxidation of surface methylol or aldehyde end groups), as already described.

In a preferred embodiment, the solid supports used in the invention are microparticles. Said microparticles have preferably a diameter of less than one millimeter, preferably a diameter ranging from about 0.1 to about 1,000 micrometers (μm). Even though the microparticles can be of any size, the preferred size is 1-100 μm, more preferably 2-50 μm, more preferably 3-25 μm, and even more preferably about 6-12 μm. Microparticles are made of any regularly shaped material. The preferred shape is spherical; however, particles of any other shape can be employed since this parameter is immaterial to the nature of the invention. The shape of the particle can serve as an additional distinction parameter, which is discriminated by flow cytometry, e.g., by a high-resolution slit-scanning method.

As used hereinafter the terms "microparticles", "microspheres", or "microbeads" are used interchangeably and bear equivalent meanings as they refer to small particles with overall diameter that falls essentially in the micrometer range. The terms "nanospheres", "nanoparticles", or "nanobeads" refer to smaller particles with overall size that falls essentially in the nanometer range. As used hereinafter the general term particles, spheres, or "beads" refers both to microparticles and nanoparticles, which can effectively serve as solid supports in the methods of the invention.

In the context of the present invention, a "subset" of microparticles corresponds to numerous identical microparticles having the same characteristics and that have been coated with the same epitope. Importantly, each subset of microparticles should be distinguishable from other subsets of the population by at least one characteristic (e.g. location, size, diameter, weight, granulometry, and/or labeling).

In a preferred embodiment, the different subsets of microparticles can be distinguished as they are differently labeled (e.g. with a fluorochrome, a fluorophore, a chromophore, a radioisotope, a mass tag, or any kind of detectable tag which is known in the art).

In a more preferred embodiment, the different subsets of microparticles can be distinguished as they are differently fluorescently labeled, as proposed in U.S. Pat. No. 5,736,330, U.S. Pat. No. 5,981,180, U.S. Pat. No. 6,057,107, U.S. Pat. No. 6,268,222, U.S. Pat. No. 6,449,562, U.S. Pat. No. 6,514,295, U.S. Pat. No. 6,524,793 and U.S. Pat. No. 6,528,165. More precisely, these different subsets can be dyed with different fluorescent dyes, and/or different concentrations of one or more fluorescent dyes. As such, the different subsets can have different fluorescent signatures (e.g. different fluorescent wavelength(s), different fluorescent intensities, etc.) that can be measured and used by a measurement system to determine the subset that individual microparticles belong to (i.e., to classify the microparticles according to the subset).

In a preferred embodiment, the microparticles used in the invention are internally labeled with fluorescent dyes, as described in EP 1 204 869, which is hereby incorporated by reference.

These microparticles may also incorporate magnet or magnetically responsive metal oxides selected from the group consisting of superparamagnetic, paramagnetic, and ferromagnetic metal oxide. Magnetic beads are for example commercially available from sources such as Dynal Inc. (Great Neck, N.Y.) or can be prepared using known in the art methods as disclosed for example in U.S. Pat. No. 4,358,388; U.S. Pat. No. 4,654,267; U.S. Pat. No. 4,774,265; U.S. Pat. No. 5,320,944; and U.S. Pat. No. 5,356,713. In a preferred embodiment, the solid supports used in the invention are therefore magnetic.

In a more preferred embodiment, the solid supports used in the invention are microparticles internally labeled with fluorescent dyes with magnetite encapsulated in a functional polymer outer coat containing surface carboxyl groups for covalent coupling of ligands, such as those marketed by Luminex Corp under the trade name MagPlex.

It is also possible to use MicroPlex microspheres (sold by Luminex) that are carboxylated polystyrene micro-particles that have been color coded into spectrally distinct regions. These regions can be quickly distinguished by an xMAP Instrument allowing for the interrogation of up to 100 different analytes simultaneously from one single sample volume.

It is also possible to use SeroMAP microspheres (sold by Luminex) which are a special formulation of MicroPlex microspheres which have been optimized to reduce non-specific binding in serology assays.

Detection of Bound Antibodies

The invention encompasses detecting the presence of antibodies that are bound to the epitopes and therefore to the detectable solid support. By analyzing to which subset of microparticles antibodies are bound, it can be easily inferred which antibodies were present in the biological sample, and therefore by which pathogen the tested subject was infected.

Any known technology can be used to detect the presence of the antibodies that are bound to the solid supports. For example, labeled secondary antibodies recognizing specifically the constant part of the subject immunoglobulins can be used, as shown in the experimental part below. It is important to note that the labeling of the detecting-antibodies should be different from the one of the solid support, so as to distinguish between the solid supports that are coupled to antibodies, and those that are not.

Alternatively, immunoglobulins present in sera from infected animals or humans can be directly conjugated to R-phycoerythrin (R-PE), using a one-step antibody labeling protocol (Lightning-Link™ R-Phycoerythrin Conjugation Kit—Innova Biosciences). The hands-on time for the entire procedure is usually 20-30 seconds, and allows the labeling of small quantities of immunoglobulins with 100% recovery. This procedure eliminates the need for secondary reagents, such as conjugated anti-species antibodies and streptavidin-R-phycoerythrin, in multiplex-immunoassay experiments.

When microparticles internally labeled with fluorescent dyes are used, the fluorescent detection instrument should be equipped with a first laser for detecting the type of microsphere, and a second laser to ensure the quantification of captured IgM or IgG by exciting the fluorophore which is conjugated to the specific detection antibody.

With its extensive multiplexing capabilities and lower limit of detection, this approach offers substantial cost and sample savings over traditional ELISA measurements. Moreover, the selected sets of microspheres are adaptable to an affordable, compact, and robust fluorescent detection system such as the MagPix (Luminex Corporation).

In this embodiment, the method of the invention makes it possible to simultaneously analyze up to 100 types of coupled microspheres per well by using a flow analysis tool, and affords greatly enhanced sensitivity that is expected to be on the order of several orders of magnitude larger than that of currently used systems and methods.

Interestingly, the method of the invention enables to perform high throughput serological screening to diagnose multiple infections in an individual, either a human or an animal.

Multiplex immunoassay Kits

The invention encompasses kits suitable for use in the detection of antibodies against multiple antigens. Any of the antigens or epitopes disclosed herein can be incorporated into the kits.

The invention encompasses kits for the detection of antibodies against viral, bacterial, parasitic, animal, prion, yeast, and fungal proteins.

The kit comprises at least two solid supports. The invention encompasses a kit comprising at least 2, 3, 4, 5, 6, 7, 8, 9, 10, 11, 12, 13, 14, 15, 16, 20, 25, 30, 40, 50, 100, etc. solid supports and a kit comprising at least 2, 3, 4, 5, 6, 7, 8, 9, 10, 11, 12, 13, 14, 15, 16, 20, 25, 30, 40, 50, 100, etc. different epitopes. The kit can comprise at least 2, 3, 4, 5, 6, 7, 8, 9, 10, 11, 12, 13, 14, 15, 16, 20, 25, 30, 40, 50, 100, etc. solid supports mixed together. The epitopes can be recognized by target antibodies.

In one embodiment, the kit comprises a first solid support comprising a first AGT-Antigen fusion protein covalently coupled to an AGT substrate, and a second solid support comprising a second AGT-Antigen fusion protein covalently coupled to an AGT substrate.

In one embodiment, the kit comprises:
a first solid support comprising a first AGT-Antigen fusion protein covalently coupled to an AGT substrate,
a second solid support comprising a second AGT-Antigen fusion protein covalently coupled to an AGT substrate;
a third solid support comprising a third AGT-Antigen fusion protein covalently coupled to an AGT substrate;
a fourth solid support comprising a fourth AGT-Antigen fusion protein covalently coupled to an AGT substrate;
a fifth solid support comprising a fifth AGT-Antigen fusion protein covalently coupled to an AGT substrate;
a sixth solid support comprising a sixth AGT-Antigen fusion protein covalently coupled to an AGT substrate;
a seventh solid support comprising a seventh AGT-Antigen fusion protein covalently coupled to an AGT substrate;
an eighth solid support comprising an eighth AGT-Antigen fusion protein covalently coupled to an AGT substrate;
a ninth solid support comprising a ninth AGT-Antigen fusion protein covalently coupled to an AGT substrate;
a tenth solid support comprising a tenth AGT-Antigen fusion protein covalently coupled to an AGT substrate.

In other embodiments, the kit can comprise 2, 3, 4, 5, 6, 7, 8, 9, 11, 12, 13, 14, 15, 16, 20, 25, 30, 40, 50, or 100 solid supports comprising 2, 3, 4, 5, 6, 7, 8, 9, 11, 12, 13, 14, 15, 16, 20, 25, 30, 40, 50, or 100 AGT-Antigen fusion proteins covalently coupled to an AGT substrate.

In one embodiment, the kit comprises a first solid support covalently coupled with a first epitope that is recognized by the first target antibody, a second solid support covalently coupled with a second epitope that is recognized by a second target antibody, and not by said first target antibody, wherein the at least two solid supports can be specifically identified from each other and enable the detection of two different target antibodies.

In a preferred embodiment, the invention encompasses a kit for the detection of at least two target antibodies in a biological sample comprising:
(a) a first solid support comprising an AGT substrate covalently coupled to a first fusion protein comprising an AGT polypeptide having a O6-alkylguanine-DNA alkyltransferase activity and a first epitope that is recognized by a first target antibody; and
b) a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody.

In preferred embodiments, the kit comprises at least 2, 3, 4, 5, 6, 7, 8, 9, 10, 11, 12, 13, 14, 15, 16, 20, 25, 30, 40, 50, 100, etc. different viral epitopes.

In preferred embodiments, the kit comprises at least 2, 3, 4, 5, 6, 7, 8, 9, 10, 11, 12, 13, 14, 15, 16, 20, 25, 30, 40, 50, 100, etc. different bacterial epitopes.

The kit can be specific for viruses, bacteria, and/or parasites.

The kit can be specific for a family of viruses or bacteria, or can be based on similar associated clinical symptoms (i.e., childhood diseases, respiratory or hemorrhagic syndromes, etc.).

The kit can be specific for immunoglobulins, wherein the kit detects antibodies to at least 2, 3, 4, or 5 immunoglobulins selected from IgD, IgG1, IgG2, IgG3, IgG4, IgA, IgM, IgE, and IgG total.

The kit can be specific for a bioterrorism pathogen, wherein the kit detects antibodies to at least 2, 3, 4, or 5 proteins selected from *Francisella tularensis*, *Bacillus anthracia*, *Clostridium botuLinum*, *Yersinia pestis*, Smallpox, Marburg virus, Ebola virus, Lassa virus, and Machupo virus proteins.

The kit can be specific for a flu virus, wherein the kit detects antibodies to at least 2, 3, 4, 5, 6, 7, 8, 9, 10, 11, 12, 13, 14, 15, or 16 different influenza or SARS proteins.

The kit can be specific for a poxvirus, wherein it detects antibodies to at least 2, 3, 4, 5, 6, 7, 8, 9, 10, 11, 12, 13, 14, 15, or 16 different poxviruses. The poxvirus can be an orthopox (smallpox virus/variola, vaccinia virus (see Wikipedia: Vaccinia), cowpox virus (see Wikipedia: Cowpox), or monkeypox virus (see Wikipedia: Monkeypox), parapox (orf virus, pseudocowpox, bovine papular stomatitis virus), yatapox (tanapox virus (see Wikipedia: Tanapox), yaba monkey tumor virus (see Wikipedia: Yaba_monkey_tumor_virus)), or molluscipox (see Wikipedia: *Molluscum_contagiosum*).

The invention encompasses kits for the detection of antibodies against human proteins including cancer and tumor antigens, kidney toxicity markers, cytokines, chemokines, growth factors, antigens be involved in autoimmune diseases, and immunoglobulins.

The invention encompasses kits for the detection of antibodies against allergens.

In a preferred embodiment, at least one epitope is a viral epitope. Ina preferred embodiment, said first and/or second epitope is present on a viral protein chosen in the group consisting of: the EDIII protein of the dengue virus 1 of SEQ ID NO:3, the EDIII protein of the dengue virus 2 of SEQ ID NO:4, the EDIII protein of the dengue virus 3 of SEQ ID NO:5, the EDIII protein of the dengue virus 4 of SEQ ID NO:6, the EDIII protein of the West Nile virus of SEQ ID NO:7, the EDIII protein of the Yellow Fever virus of SEQ ID NO:8, the EDIII protein of the Japanese encephalitis virus of SEQ ID NO:9, the EDIII protein of the Zika virus of SEQ ID NO:10, the EDIII protein of the Wesselbron virus of SEQ ID NO:11, the EDIII protein of the Rocio virus of SEQ ID NO:12, the EDIII protein of the Murray encephalitis virus of SEQ ID NO:13, and the EDIII protein of the Saint-Louis encephalitis virus of SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, the EDIII protein of the Rabensburg virus encoded by SEQ ID NO:58, and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

Preferably, this kit also contains the means to detect the at least two target antibodies which are bound to the solid supports. Said means are more preferably secondary antibodies recognizing the constant part of the target antibodies. Said secondary antibodies can be labeled, provided that the labeling is not the same as the ones that are present on the solid support. However, it is possible to use the same labeling for all the secondary antibodies that are used for detecting the antibodies bound to solid support(s), since the information concerning the infectious pathogen(s) are given only by the identification of the solid support which is bound to the antibodies.

The kit of the invention may contain other ingredients that are accepted as standard reagents such as a wash buffer, necessary plasticware, and the like.

In a preferred embodiment, the kit of the invention comprises at least 10, preferably at least 50, more preferably at least 100 differently coupled-solid supports, said solid supports being for example subsets of microparticles as defined above.

In a more preferred embodiment, the said solid supports are microspheres, for example those which are internally labeled with a fluorescent dye with magnetite encapsulated in a functional polymer outer coat containing surface carboxyl groups.

In another preferred embodiment, in the kit of the invention, the said solid supports are mixed together in at least one single compartment.

Figure 11:
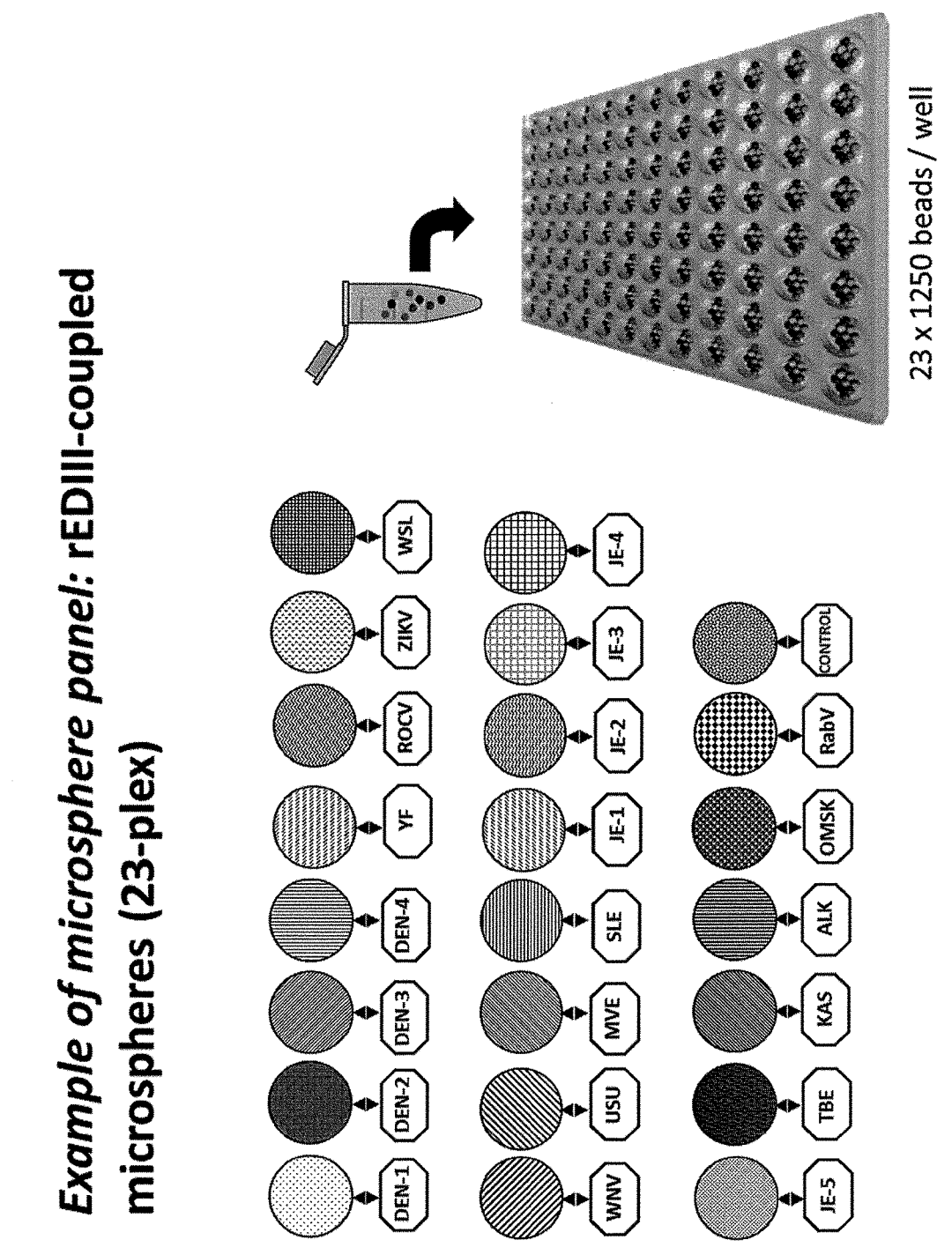

Advantageously, the kit of the invention contains conventional support(s), e.g., microtiter plates, containing the different antigen-coated microparticles subsets defined above. In a preferred embodiment, the said microparticles subsets are mixed together in at least one single compartment (e.g. a well or a tube). Such a device is disclosed on FIG. 11.

The kit of the invention may also contain recipients (e.g., tubes) containing the said subsets of antigen-coated microparticles.

The present invention also targets the use of the kit of the invention for detecting at least two, preferably at least 10, more preferably at least 50 and even more preferably at least 100 target antibodies in a biological sample from a subject.

In a preferred embodiment, the kit of the invention is used for detecting at least two, preferably at least 3, 4, 5, 6, 7, 8, 9, 10, 11, 12, 13, 14, 15, 16, 20, 25, 30, 40, 50, or 100 target antibodies that are generated upon infection by endemic viruses or parasites of the same geographic region. For example, the kit of the invention could contain microparticles that are coated with antigens of viruses or parasites that are specific of Africa regions, such as the Dengue virus type 1, type 2, type 3, type 4, the Yellow fever virus, the West-Nile virus, the Usutu virus, the Zika virus, the Wesselsbron virus, the Shamonda virus, the Rift Valley fever virus, the Chikungunya virus, the Crimean-Congo hemorrhagic fever virus, the Ebola virus, the Marburg virus, the Lassa virus, the Hepatitis C virus, the Hepatitis E virus, the Enterovirus 71, *Plasmodium falciparum*, or *Leptospira interrogans*.

FIG. 25 discloses examples of antigen-coupled microspheres combinations which can be included in the kit of the invention depending on the geographic region it is intended for (Asia, Europa, America, Oceania, or Africa).

The kit of the invention may alternatively contain antigen-coupled microspheres that enable the diagnosis of viruses or parasites inducing specific symptoms (flu-like, encephalitis, or hemorrhagic fever) or infecting specific animals, so that it can be adapted to each patient/animal.

FIG. 25 discloses examples of antigen-coupled microspheres combinations which can be included in the kit of the invention depending on the symptoms of the patient or of the animal.

Kits containing antigen combinations that are proposed by national sanitary agencies are obviously also encompassed in the present invention.

In particular, the kit of the invention comprises at least two solid supports coated with at least two fusion proteins that are selected from the group consisting of: SEQ ID NO:21, SEQ ID NO:42, SEQ ID NO:49, SEQ ID NO:51, SEQ ID NO:53, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149 and SEQ ID NO:151.

In a preferred embodiment, the kit of the invention contains a combination of at least 2, 3, 4, 5, 6, 7, 8, 9, 10, 11, 12, 13, 14, 15, 16, 20, 25, 30, 40, 50, or 100 solid supports coated with said fusion proteins.

In a more preferred embodiment, the kit of the invention contains a combination of at least five solid supports (e.g., microsphere subsets) that are coated with at least five different fusion proteins containing antigens as recommended by the Food and Drug Administration, namely, antigens from the HBV, HCV, HIV1, HIV2 and West Nile viruses.

The invention encompasses methods for manufacturing the kits of the invention.

In one embodiment, the invention encompasses a method for manufacturing a kit, said method comprising the steps of:

(a) providing a first AGT-Antigen fusion protein that is recognized by a first target antibody, (b) contacting said first AGT-Antigen fusion protein with a first solid support, said support being covalently coupled with a substrate of said AGT-Antigen fusion protein, (c) obtaining a first solid support covalently coupled with the first AGT-Antigen fusion protein, (d) providing at a second AGT-Antigen fusion protein that is recognized by a second target antibody, but not by said first target antibody, and (e) contacting said second AGT-Antigen fusion protein with a second solid support, said support being covalently coupled with a substrate of said AGT-Antigen fusion protein, and (f) obtaining a second solid support covalently coupled with the second AGT-Antigen fusion protein, wherein said first and at second solid supports can be specifically identified from each other.

In one embodiment, the solid supports covalently coupled with the AGT-Antigen fusion proteins are mixed together.

The above steps a)-c) can be repeated with at least 3, 4, 5, 6, 7, 8, 9, 10, 11, 12, 13, 14, 15, 16, 20, 25, 30, 40, 50, or 100 different AGT-Antigen fusion proteins to generate at least 3, 4, 5, 6, 7, 8, 9, 10, 11, 12, 13, 14, 15, 16, 20, 25, 30, 40, 50, or 100 solid supports covalently coupled with 3, 4, 5, 6, 7, 8, 9, 10, 11, 12, 13, 14, 15, 16, 20, 25, 30, 40, 50, or 100 different AGT-Antigen fusion proteins.

In another aspect, the present invention relates to a method for manufacturing the kit of the invention as defined above, said method comprising the steps of:

(a) providing a least a first fusion protein comprising:

a polypeptide comprising a first epitope that is recognized by a first target antibody and a AGT polypeptide having a O6-alkylguanine-DNA alkyltransferase activity, (b) contacting said first fusion protein with a first solid support, said support being covalently coupled with a substrate of said AGT polypeptide, (c) obtaining a first solid support covalently coupled with a first epitope that is recognized by the first target antibody, (d) providing at least a second fusion protein comprising:

a polypeptide comprising a second epitope, said second epitope being recognized by a second target antibody but not by said first target antibody, and a AGT polypeptide having a O6-alkylguanine-DNA alkyltransferase activity, (e) contacting said second fusion protein with a second solid support, said support being covalently coupled with a substrate of said AGT polypeptide, (f) obtaining a second solid support covalently coupled with a second epitope that is recognized by the second target antibody, but not by said first target antibody, wherein said at least first and at least second solid supports can be specifically identified from each other, the kit of the invention comprising at least said first and second supports.

In another aspect, the present invention relates to a multiplex immuno screening assay comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 96 solid supports as defined above and wherein each of said solid supports emits a different and distinguishable wave length after excitation.

In another aspect, the present invention relates to a multiplex immuno screening assay method comprising:

a) contacting one or several biological sample(s) with at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 96 solid supports as defined above and wherein each of the solid supports emits a different and distinguishable wave length after excitation, and b) detecting the presence or absence of target antibodies.

In a preferred embodiment, said target antibodies are specific to antigen from viruses to be detected in blood bank according to WHO or FDA guidelines, such as for example viruses selected from HBV, HCV, HIV1, HIV2, and WNV.

In another preferred embodiment, said target antibodies are specific to oncogenic HPV strains such as HPV 16, 18, 31, 33, 35, 39, 45, 51, 52, 56, 58, 59, 66 and 68.

In another preferred embodiment, each of said target antibodies are labeled with a detectable label.

In another aspect, the present invention relates to an apparatus for carrying out the method for manufacturing the kit of the invention as defined above, comprising a technical device for detecting the light sources emitted from the solid supports and the light source emitted from the target antibodies or labeled antibodies binding to the target antibodies, and a calculating or computer device for identifying which solid supports are bound with target antibodies, thereby indicating the presence or absence of antigens, bacteria, virus, or parasites in the analyzed sample.

In another aspect, the present invention relates to an in vitro method for diagnosing at least one target disease in a subject, said target disease being known to induce the synthesis of at least one target antibody in said subject, comprising performing the immunoassay of the invention, wherein said subject is diagnosed to be suffering from said at least one target disease if the amount of said at least one target antibody is higher than a control value.

This diagnosing method preferably enables to diagnose two, preferably three, and more preferably four target diseases in a subject in need thereof. This number is however not limiting: it is indeed possible to diagnose until 100 target diseases in so far as it is possible to detect 100 different antibodies with the detecting method of the invention.

In a preferred embodiment, said at least one target disease is a viral, a bacterial, a yeast or a fungi-mediated infection, preferably a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum*.

In a preferred embodiment, said in vitro method is used to diagnose at least 5, 6, 7, 8,9, 10, 11, 12, 13, or 15, more preferably at least 15, 16, 17, 18, 19, 20, 21, 22, 23, 24, 25, 30, 35, 40, or 45, more preferably at least 50, 60, 70, 80, or 90, and even more preferably at least 100 viral and/or bacterial and/or parasite infections in said subject.

In a preferred embodiment, the control value used in said method represents the amount of said target antibody in a sample from a subject which is not suffering from said target disease, preferably, a healthy subject.

The methods of the invention can be used to diagnose infections in animals.

In particular, they can be used for the diagnosis of animal diseases, as well as a DIVA (Differentiating Infected from Vaccinated Animals) approach to differentiate naturally infected animals from vaccinated animals. The use of a DIVA strategy complementing novel vaccines would allow the implementation of vaccination as targeted control strategy alongside conventional strategies (test, slaughter and meat inspection). Moreover, increased test specificity would have a major economic benefit by reducing the numbers of false-positive animals that may be slaughtered needlessly. Lastly, improved sensitivity, particularly when novel diagnostic assays are used, would have a further benefit in reducing the economic burden of disease control even in the absence of vaccination In a preferred embodiment, the methods of the invention are applied to human individuals.

The present invention relates to the use of the kit of the invention for diagnosing at least two target diseases in a subject, wherein said target disease is a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum*.

A new emerging arbovirus has been recently sequenced and affects cattle in Germany, Benelux and France. This virus is called Schmallenberg virus (SBV), and is related to the Akabane virus belonging to the Simbu serogroup of the *Orthobunyavirus* genus of the Bunyaviridae family. The viral genome of the Schmallenberg virus comprises three single-stranded RNA segments known as S, L and M. The S segment encodes the N nucleoprotein and the NSs non-structural protein. The N nucleoprotein shares antigenic determinants with different Bunyaviruses. The three RNA viral sequences of the BH80/11-4 strain of the Schmallenberg virus are available under the numbers HE649913.1, HE649914.1, and HE649912.1.

Use of AGT to Enhance Production of AGT Fusion Protein

The present inventors observed that the fusion as a chimeric protein of the 6-alkylguanine-DNA-alkyltransferase enzyme (AGT) with the SBV N protein greatly improves the production of recombinant N protein, in particular in invertebrate cells such as S2 cells.

The present inventors propose here for the first time to use the AGT enzyme (EC 2.1.1.63), a mutant thereof, a catalytic domain thereof or sub-fragments thereof, for enhancing the production of the N nucleoprotein from SBV in host cells, in particular in non-vertebrate cells. The enhancing effect is observed when the host cells express a fusion polypeptide comprising at least i) a secretion signal peptide which is functional in said host cells, ii) the AGT enzyme, mutant, catalytic domain or sub-fragments thereof, and iii) the N nucleoprotein of SBV. For the enhancing effect to occur, the AGT enzyme has to be physically linked, directly or indirectly (spacers and other amino acids might be introduced), to the protein of interest. Without being bound by theory, it is contemplated that the AGT enzyme acts as a chaperone protein, for example by facilitating the secretion from the host cell and stabilising the synthesised fusion polypeptide in the supernatant of the host cells, or for preventing it to be metabolised during and after its synthesis and secretion from the host cells. In addition, it has been observed that AGT has a 3D globular structure comprising α helix (Wibley J. E. A. et al, 2000), which is compatible with a scaffolding role of AGT.

In the context of the present invention, "host" cells are any cells which can be used for producing recombinant proteins, such as "non-vertebrate" (or invertebrate) cells, vertebrate cells, plant cells, yeast cells, or prokaryote cells. They are preferably non-vertebrate and vertebrate cells.

Non-vertebrate (also known as invertebrate) comprises different phyla, the most famous being the Insect, Arachnida, Crustacea, Mollusca, Annelida, Cirripedia, Radiata, Coelenterata and Infusoria. They are now classified into over 30 phyla, from simple organisms such as sea sponges and flatworms to complex animals such as arthropods and molluscs. In the context of the invention, non-vertebrate cells are preferably insect cells, such as Drosophila or Mosquito cells, more preferably Drosophila S2 cells.

Examples of cells derived from vertebrate organisms that are useful as host cell lines include non-human embryonic stem cells or derivative thereof, for example avian EBX cells; monkey kidney CVI line transformed by SV40 sequences (COS-7, ATCC CRL 1651); a human embryonic kidney line (293); baby hamster kidney cells (BHK, ATCC CCL 10); Chinese hamster ovary cells (CHO); mouse sertoli cells [TM4]; monkey kidney cells (CVI, ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells [HTC, M1.5]; YB2/O (ATCC n° CRL1662); NIH3T3; HEK and TRI cells. In the context of the invention, vertebrate cells are preferably EBX, CHO, YB2/O, COS, HEK, NIH3T3 cells or derivatives thereof.

Plant cells which can be used in the context of the invention are the tobacco cultivars Bright Yellow 2 (BY2) and *Nicotiana tabaccum* 1 (NT-1).

Yeast cells which can be used in the context of the invention are: *Saccharomyces cerevisiae*, *Schiosaccharomyces pombe*, and *Hansenula polymorpha*, as well as methylotropic yeasts like *Pichia pastoris* and *Pichia methanolica*.

Prokaryote cells which can be used in the context of the invention are typically *E. coli* bacteria or *Bacillus subtilis* bacteria.

In another aspect, the present invention is thus drawn to a vector for expressing the N nucleoprotein from SBV in an host cell (SBV.N), comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the N nucleoprotein of SBV of SEQ ID NO: 16.

The N nucleoprotein from SBV will be referred to hereafter as the "heterologous protein", the "protein of interest", "chimeric protein", or the "recombinant protein".

The term "vector" herein means the vehicle by which a DNA or RNA sequence of a foreign gene can be introduced into a host cell so as to transform it and promote expression of the introduced sequence. As understood herein, a vector is a nucleic acid molecule, such as, for example, plasmids, phages, and viruses. They are discussed in greater detail below. Any type of plasmid, cosmid, YAC or viral vector may be used to prepare a recombinant nucleic acid construct which can be introduced to a host cell where expression of the protein of interest is desired. When expression of the protein of interest in a particular type of host cell is desired, viral vectors that selectively infect the desired cell type or tissue type can be used. Also important in the context of the invention are vectors for use in gene therapy (i.e. which are capable of delivering the nucleic acid molecule to a host organism).

For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques*, 7:980-990, 1992).

Viral vectors that are actually preferred in the present invention are those that are well suited for use in vertebrate and non-vertebrate cells.

For non-vertebrate cells, preferred vectors are the arboviruses, the West Nile virus being particularly preferred, which are arthropod vectors. Other vectors that are known to efficiently be expressed in non-vertebrate cells are the baculoviruses.

For vertebrate cells, lentiviral, AAV, baculoviral and adenoviral vectors are preferred. The vectors suited for expression in mammalian host cells can also be of non-viral (e.g. plasmid DNA) origin. Suitable plasmid vectors include, without limitation, pREP4, pCEP4 (Invitrogen), pCI (Promega), pCDM8 and pMT2PC, pVAX and pgWiz.

For prokaryotic cells, plasmid, bacteriophage and cosmid vectors are preferred. Suitable vectors for use in prokaryotic systems include without limitation pBR322 (Gibco BRL), pUC (Gibco BRL), pBluescript (Stratagene), p Poly, pTrc; pET 11d; pIN; and pGEX vectors.

For plant cells, plasmid expression vectors such as Ti plasmids, and virus expression vectors such as Cauliflower mosaic virus (CaMV) and tobacco mosaic virus TMV are preferred.

Expression of recombinant proteins in yeast cells can be performed using three types of vectors: integration vectors (YIp), episomal plasmids (YEp), and centromeric plasmids (YCp): Suitable vectors for expression in yeast (e.g. *S. cerevisiae*) include, but are not limited to pYepSec1, pMFa, pJRY88, pYES2 (Invitrogen Corporation, San Diego, Calif.) and pTEF-MF (Dualsystems Biotech Product code: P03303).

Vectors which can be used for gene therapy are well-known in the art. They are for example lentivirus, retrovirus, adenovirus, poxvirus, herpes virus, measles virus, foamy virus or adeno-associated virus (AAV). Viral vectors can be replication-competent, or can be genetically disabled so as to be replication-defective or replication-impaired. Preferred gene therapy vector are the DNA Flap vectors as described in WO 99/055892, U.S. Pat. No. 6,682,507 and WO 01/27300.

A sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

The vector of the invention contains a nucleotide sequence encoding a 6-alkylguanine-DNA-alkyltransferase enzyme (AGT), a mutant, a fragment or a catalytic domain thereof. These polypeptides have been defined above. Preferably, said AGT mutant is the SNAP enzyme of SEQ ID NO: 2, and is encoded for example by SEQ ID NO:15 or SEQ ID NO: 31, the latter having a G/C content of 51%.

Preferably, the nucleotide expression vector of the invention further comprises cloning sites enabling the in-frame insertion of a heterologous DNA sequence encoding the protein of interest.

As meant in the present invention, the term "secretion signal peptide" designates a short (3-60 amino acids long) peptide chain that directs the transport of the N nucleoprotein outside the host cells.

Examples of secretion signals appropriate for the present invention include, but are not limited to, the signal peptide sequences of the mating factor (MF) alpha (U.S. Pat. No. 5,879,926); invertase (WO 84/01153); PHOS (DK 3614/83); YAP3 (yeast aspartic protease 3; WO 95/02059); and BAR1 (WO 87/02670).

In the context of the invention, this secretion signal peptide is preferably functional either in non-vertebrate cells or in vertebrate cells, or both.

Examples of secretion signal peptides which are functional in insect cells are: the insect ssBiP (SEQ ID NO: 37, for example encoded by the DNA sequence SEQ ID NO: 22), the BiP-like peptide signal of SEQ ID NO: 24 (for example encoded by the DNA sequence SEQ ID NO: 23), the BiP-like peptide signal of SEQ ID NO:153 (for example encoded by the DNA sequence SEQ ID NO:152) and any peptide signal present in an arbovirus, for example the envelop E protein of the West-Nile virus (SEQ ID NO: 38).

Interestingly, the above-mentioned BiP-like peptide signal of SEQ ID NO:24 is functional in both non-vertebrate and vertebrate cells. This BiP-like signal corresponds to the BiP peptide signal of SEQ ID NO: 37 in which the last Glycine amino acid has been replaced by the amino acid sequence Pro Thr Ala Leu Ala (SEQ ID NO: 39) which corresponds to the cleavage site of the E protein of the Dengue virus. Accordingly, the BiP-like signal will be advantageously cleaved once the protein will be translated and secreted in the supernatant of the host cells.

A variety of secretion signals is also available for expression in yeast host cells, e.g. in *S. cerevisiae*. These include the prepro-alpha factor, HSp150, PHO1, SUC2, KILM1 (killer toxin type 1), and GGP1.

A cloning site is a sequence which facilitates cloning of a gene encoding a protein of interest into the expression system. It contains restriction sites, or restriction recognition sites, i.e. locations on a DNA molecule containing specific sequences of nucleotides, which are recognized by restriction enzymes (see for example in the figures). These are generally palindromic sequences (because restriction enzymes usually bind as homodimers), and a particular restriction enzyme may cut the sequence between two nucleotides within its recognition site, or somewhere nearby. The cloning sites are well known for the man skilled in the art.

In a preferred embodiment of the invention, the DNA sequence encoding said AGT enzyme is located in 5' or in 3' of the DNA sequence encoding said heterologous protein of interest, preferably in 5'. Therefore, the AGT enzyme is directly or indirectly linked to the heterologous protein/polypeptide of interest, and preferably located at the N-terminal end of the heterologous protein/polypeptide of interest. The DNA sequence encoding the fusion polypeptide comprising said peptide signal, said AGT enzyme, mutant or catalytic domain, and said recombinant protein of interest, can be operatively associated with an inducible promoter which is functional in the same host cells as the peptide signal is.

More preferably, in the vector of the invention, said open reading frame is operatively associated with an inducible promoter which is functional in the same host cell as the peptide signal is.

A coding sequence is "operatively associated with" an expression control sequence (i.e. transcriptional and translational control sequences) in a cell, when RNA polymerase transcribes the coding sequence into RNA, which is then trans-RNA spliced (if it contains introns) and, if the sequence encodes a protein, is translated into that protein.

A "promoter" is a sequence of nucleotides from which transcription may be initiated of DNA operably linked downstream (i.e. in the 3' direction on the sense strand of double-stranded DNA). Within the promoter sequence will be found a transcription initiation site (conveniently found, for example, by mapping with nuclease S1), as well as protein binding domains (consensus sequences) responsible for the binding of RNA polymerase.

Promoters which may be used to control gene expression in the context of the present invention are for example the one that are functional in non-vertebrate cells or in vertebrate cells. For example, for non-vertebrate cells, the regulatory sequences of the metallothionein gene can be used (Brinster et al., Nature, 296:39-42, 1982).

Preferably, the inducible promoter which is present in the vector of the invention has a promoter activity in an insect cell, and more preferably in a *Drosophila* cell. It is for example the *Drosophila metallothionein* promoter pMT (Lastowski-Perry et al, *J. Biol. Chem.* 260:1527 (1985)), which directs high level transcription of the gene in the presence of metals, e.g. $CuSO_4$. Alternatively, the Drosophila actin 5C gene promoter, which is a constitutive promoter and does not require addition of a metal, can be used (B. J. Bond et al, *Mol. Biol.* 6:2080 (1986)). Examples of other known *Drosophila* promoters include, e.g. the inducible heatshock (Hsp70) and COPIA LTR promoters. The SV40 early promoter gives lower level of expression than the *Drosophila metallothionein* promoter.

Preferably, the inducible promoter which is present in the vector of the invention has a promoter activity in a *Drosophila melanogaster* cell, preferably in *Drosophila* S2 cells. It is for example the metallothionein promoter which is thoroughly described in Lastowski-Perry et al, *J. Biol. Chem.* 260: 1527 (1985).

Promoters suitable for constitutive expression in mammalian cells include the cytomegalovirus (CMV) immediate early promoter, the adenovirus major late promoter, the phosphoglycero kinase (PGK) promoter, and the thymidine kinase (TK) promoter of herpes simplex virus (HSV)-1. Inducible eukaryotic promoters regulated by exogenously supplied compounds, include without limitation, the zinc-inducible metallothionein (MT) promoter, the dexamethasone (Dex)-inducible mouse mammary tumor virus (MMTV) promoter, the T7 polymerase promoter system (WO 98/10088), the ecdysone insect promoter, the tetracycline-repressible promoter, the tetracycline-inducible promoter, the RU486-inducible promoter and the rapamycin-inducible promoter.

Preferably, the promoter which is present in the vector of the invention has a promoter activity in a mammal cell, preferably in HeLa cells. It is for example the SV 40 promoter.

A range of yeast promoters is available for protein expression in yeast host cells. Some like ADH2, SUC2 are inducible and others like GAPDH are constitutive in expression. Other promoters suitable for expression in yeast include the TEF, PGK, MF alpha, CYC-1, GAL-1, GAL4, GAL10, PHOS, glyceraldehyde-3-phosphate dehydrogenase (GAP or GAPDH), and alcohol dehydrogenase (ADH) promoters.

For use in plant cells, the most commonly used promoter is the cauliflower mosaic virus (CaMV) 35S promoter or its enhanced version, but a number of alternative promoter can be used, such as the hybrid (ocs)3mas promoter or the ubiquitin promoter from maize and *Arabidopsis thaliana*. In contrast to these constitutive promoters, the rice α-amylase RAmy3D promoter is induced by sugar deprivation (Hellwig S et al., *Nat. Biotechnol.* 2004; 22(11):1415-22).

Promoters suitable for expression in *E. coli* host cell include, but are not limited to, the bacteriophage lamba pL promoter, the lac, TRP and IPTG-inducible pTAC promoters.

It is preferred that the secretion signal peptide and the inducible promoter are functional in the same host cell.

More preferably, the secretion signal peptide and the inducible promoter are functional in both *Drosophila* S2 cells and vertebrate cells.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Once an appropriate vector has been constructed and transfected into the selected host cell, preferably a Drosophila cell line, the expression of a heterologous protein is induced by the addition of an appropriate inducing agent for the inducible promoter. For example cadmium or copper are inducing agents for the Hsp70 promoter. For constitutive promoters, such as the actin 5C promoter, no inducing agent is required for expression.

In another embodiment of the invention, the nucleotide expression vector encodes at least one peptide cleavage site, which is preferably located between the AGT enzyme or its catalytic domain and the recombinant protein of interest.

A peptide cleavage site (also called "peptide cleavage site") is an amino acid sequence which is recognized by at least one protease enzyme (for example serine protease, cysteine protease, among others). An example of a peptide cleavage site is the enterokinase cleavage site of SEQ ID NO: 40 (AspAspAspAspLys/Asp). The enterokinase is a serine protease enzyme (EC 3.4.21.9) which is known to convert inactive trypsinogen into active trypsin by cleavage at the C-terminal end of the sequence: Val-$(Asp)_4$-Lys-Ile-Val~(trypsinogen)→Val-$(Asp)_4$-Lys (hexapeptide)+Ile-Val~(trypsin). Enterokinase cleaves after lysine if the Lys is preceded by four Asp and not followed by a proline residue.

Another useful peptide cleavage site is the cleavage site of the so-called "TEV protease", having the amino acid sequence SEQ ID NO: 32 (pro-TEV1) or SEQ ID NO: 33 (pro-TEV2) (Glu Asn Leu Tyr Phe Gln Ser or Gly respectively). Such cleavage sites can be encoded for example by SEQ ID NO:29 and 30. TEV protease is the common name for the 27 kDa catalytic domain of the nuclear inclusion protein encoded by the tobacco etch virus. It is commercially available (Invitrogen).

The cleavage site from the membrane precursor prM from Dengue virus serotype 1 (SEQ ID NO: 39) may also be used in the vector of the invention.

In another embodiment, the nucleotide expression vector of the invention further encodes a label, preferably located at the C-terminal end of the recombinant protein in the fusion polypeptide of the invention (comprising the peptide signal, the AGT protein or homologous thereof, and the recombinant protein). In the context of the invention, a "label" is dedicated to facilitate the recovery of the polypeptide from the crude lysate of the host cell, and is preferably selected from the group comprising: fluorescent proteins, poly-histidine (poly-his) or poly-histidine-glycine (poly-his-gly) tags; flu HA tags; c-myc tag Herpes simplex virus glycoprotein D (gD) tags, Flag-peptides, alpha-tubulin epitopes, or T7 gene 10 protein peptide tags. However, any other label might be used. In a preferred embodiment of the invention, the vectors comprise the DNA of SEQ ID NO: 28 encoding a hexa-histidine tag which has the SEQ ID NO: 27.

In another embodiment, the nucleotide expression vector of the invention further encodes spacer sequence(s), located preferably between the AGT enzyme (or its catalytic domain) and the recombinant protein of interest and/or between the recombinant protein of interest and the label. In the context of the invention, a spacer sequence is an amino acid sequence comprising at least three amino acids, dedicated to spatially separate two linked polypeptides (these polypeptides being then indirectly linked). Such spacer can be for example the amino acid sequence Glycine-Glycine-Glycine-Serine (GGGS, SEQ ID NO: 25) and the DNA spacer sequence encoding it can be SEQ ID NO: 26. In the context of this invention, this DNA sequence is hereafter designated as "DNA spacer sequence" and is located between the DNA encoding AGT or its catalytic domain, and the recombinant DNA sequence, preferably upstream from the DNA sequence encoding the peptide cleavage site.

SNAP Cassettes and Antigen Expression

As used herein, the term "pDeSNAPUniv" designates a DNA cassette encoding, in a single open reading frame, from 5' to 3':
 a) a secretion signal peptide,
 b) an AGT protein of SEQ ID NO:1, a mutant, a fragment or a catalytic domain thereof, in particular the SNAP mutant of SEQ ID NO:2,
 c) at least one peptide cleavage site,
 d) at least one label, and
 e) at least one spacer sequence.

This pDeSNAPUniv DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

Figure 8:
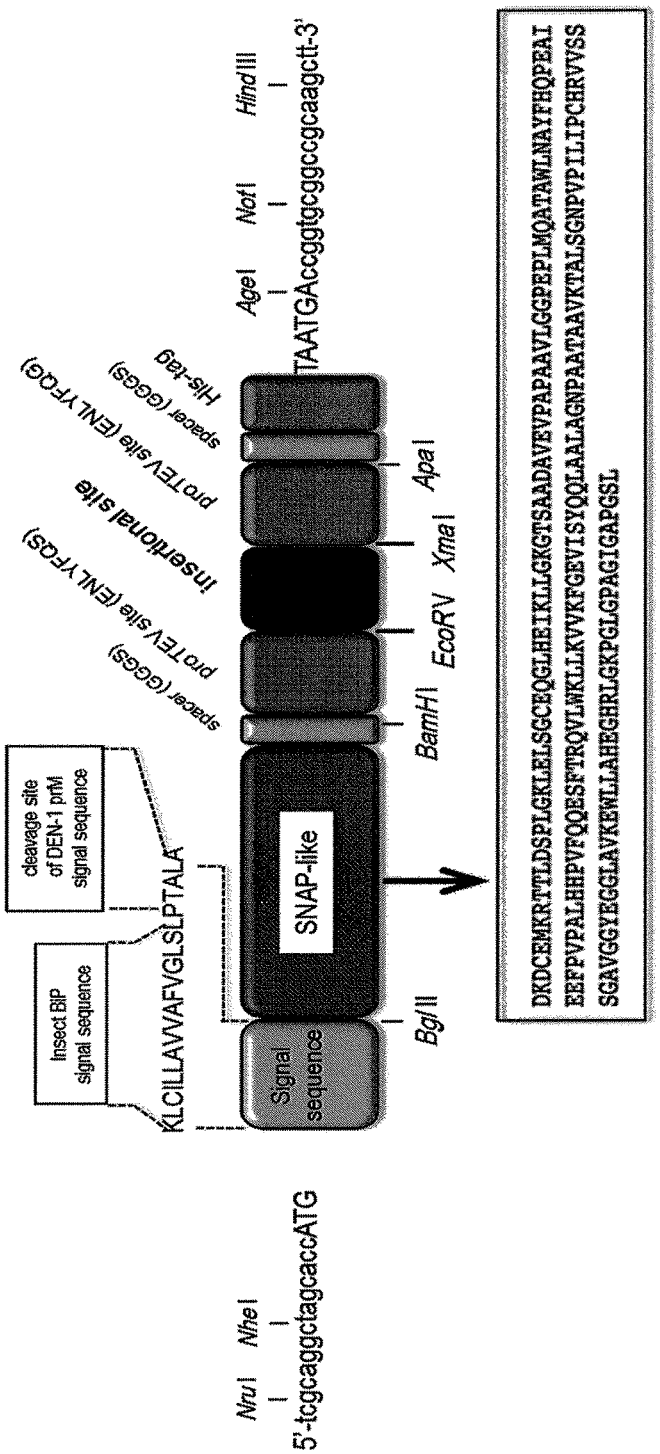

More preferably, the pDeSNAPUniv DNA cassette comprises, from 5' to 3', the sequence SEQ ID NO:23 encoding the BiP-like secretion signal, the SEQ ID NO:15 or 31 encoding the SNAP mutant, the spacer sequence of SEQ ID NO:26, the peptide cleavage site pro-TEV of SEQ ID NO:29, the peptide cleavage site pro-TEV of SEQ ID NO:30, the spacer sequence of SEQ ID NO:26 and the sequence SEQ ID NO:28 encoding the His-tag label (see FIG. 8, showing the structure of the pDeSNAPUniv cassette). Such a pDeSNAPUniv DNA cassette is for example SEQ ID NO:34.

This "pDeSNAPUniv" cassette is held as "universal" since it can be inserted in any kind of vectors dedicated to transfect host cells in order to produce heterologous proteins, namely vertebrate vectors (such as pcDNA3 or pCIneo vectors) as well as non-vertebrate vectors (such as pMT/BiP/V5-HisA which is useful in the DES system from Invitrogen). Examples of plasmid comprising said universal sequence is SEQ ID NO:43 (pMT/BiP/V5-HisA from Invitrogen comprising the pDeSNAP Univ cassette), SEQ ID NO:44 (pUC57 from Invitrogen comprising the pDeSNAP Univ cassette) or SEQ ID NO:45 (pcDNA3 from Invitrogen comprising the pDeSNAP Univ cassette).

Another example of plasmid comprising said universal sequence is SEQ ID NO:105 which is a pUC57 plasmid comprising, from 5' to 3', the constitutive promoter of *Orgyia pseudotsugata* multicapsid nucleoprotein virus-immediate-early 2 promoter (OpIE2SP) the BiPlike signal peptide of SEQ ID NO:152, the SNAP-like sequence of SEQ ID NO:31, the spacer sequence of SEQ ID NO:26, the pro-TEV1 sequence SEQ ID NO:29, and the C-term peptide tag of SEQ ID NO:106.

Once the heterologous sequence of a protein of interest such as SBV.N is cloned herein, such a vector can be advantageously transfected in either vertebrate or non-vertebrate host cells, so as to produce the protein of interest in high amounts.

In a preferred embodiment, the vector of the invention comprises a so-called "pDeSNAP Univ/SBV.N cassette" i.e., a pDeSNAPUniv DNA cassette in which the sequence of the N nucleoprotein of SBV has been inserted, said pDeSNAP Univ/SBV.N cassette comprising a nucleotide sequence encoding, in a single open reading frame, from 5' to 3':
 a) a secretion signal peptide,
 b) an AGT protein of SEQ ID NO:1, a mutant, a fragment or a catalytic domain thereof, in particular the SNAP mutant of SEQ ID NO:2,
 c) at least one peptide cleavage site,
 d) the N nucleoprotein of SBV of SEQ ID NO: 16,
 e) at least one label, and
 f) at least one spacer sequence.

This pDeSNAP Univ/SBV.N DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, the N nucleoprotein of SBV of SEQ ID NO:16, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

More preferably, the pDeSNAP Univ/SBV.N DNA cassette comprises, from 5' to 3', the sequence SEQ ID NO:23 encoding the BiP-like secretion signal or the SEQ ID NO:22 encoding the ssBiP secretion signal, the SEQ ID NO:15 or 31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label.

Even more preferably, the pDeSNAP Univ/SBV.N DNA cassette comprises, from 5' to 3', the sequence SEQ ID NO:22 encoding the ssBiP secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:35.

Figure 9:
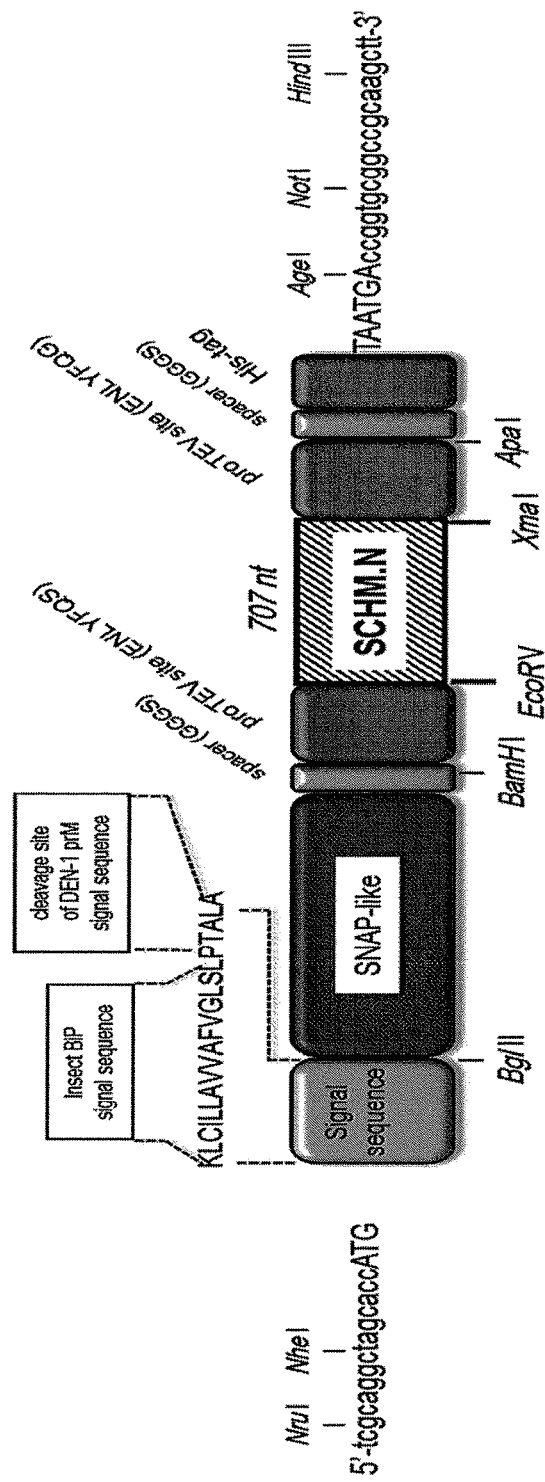
Figure 12E:
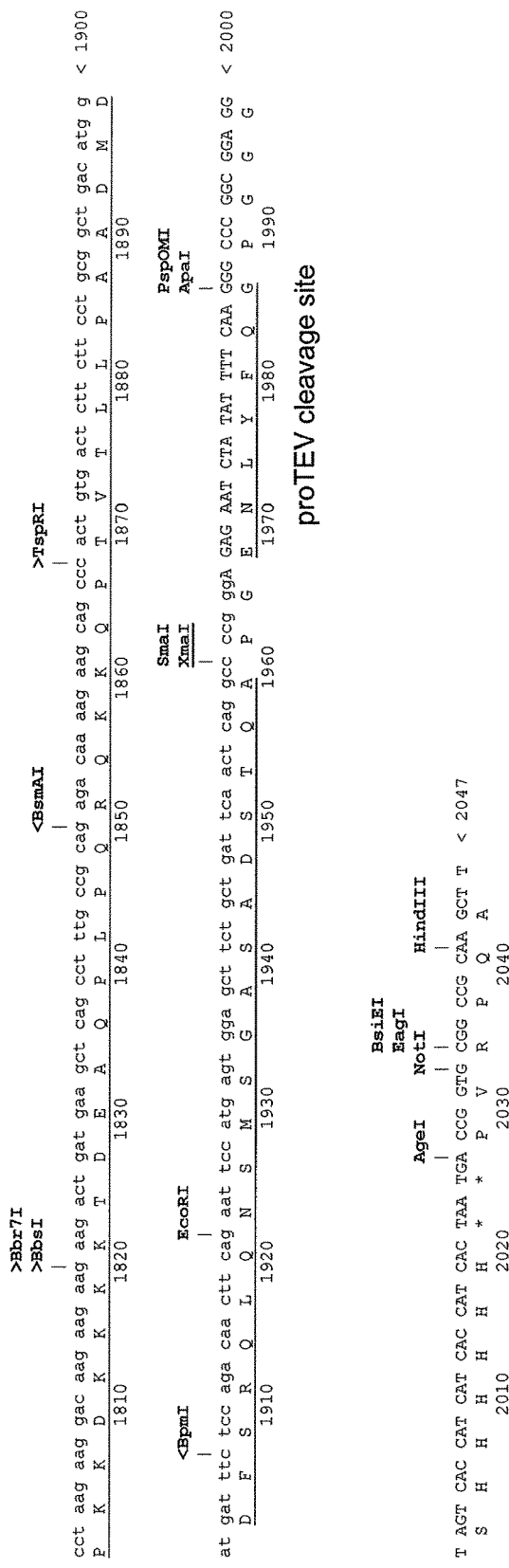
Figure 13B:
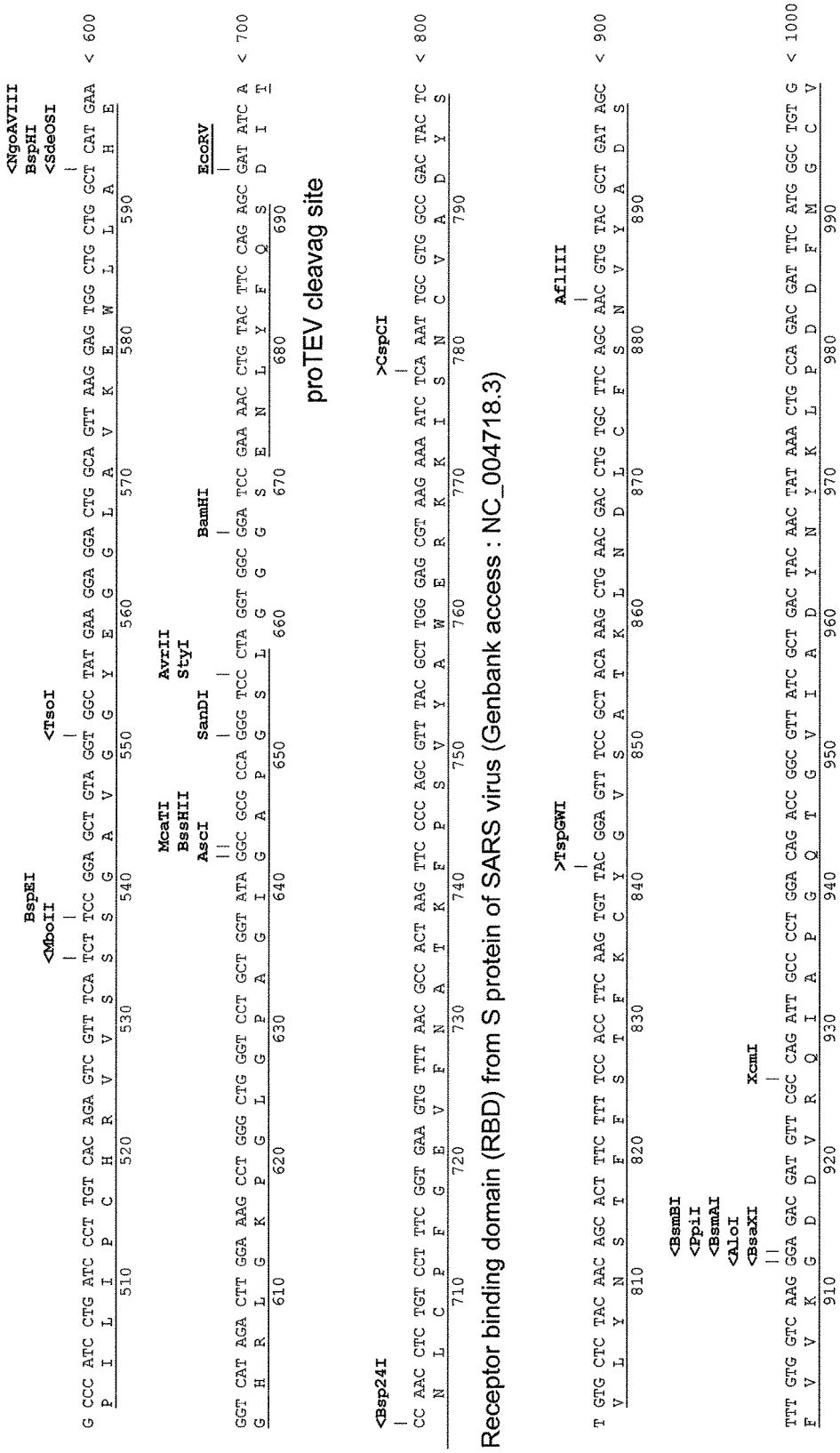
Figure 13C:
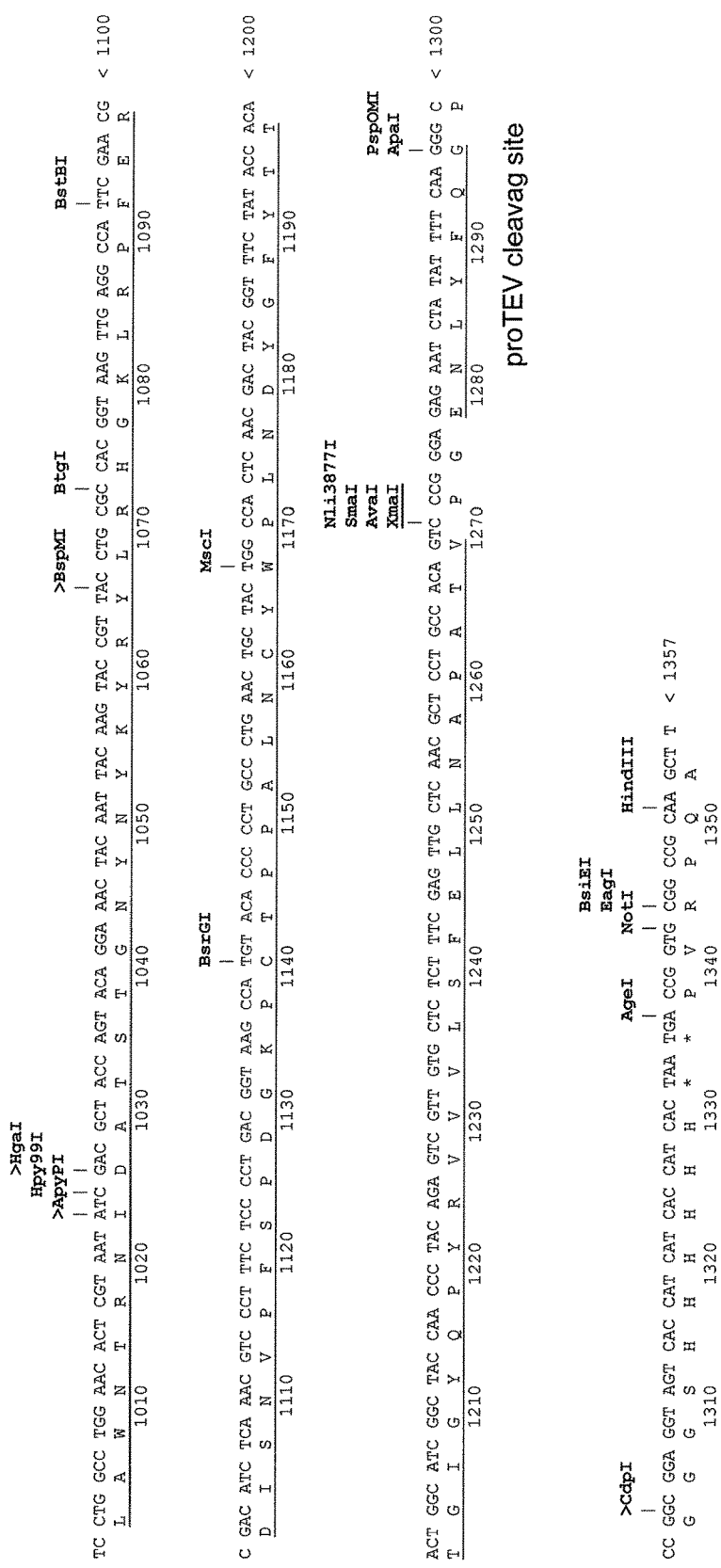
Figure 14B:
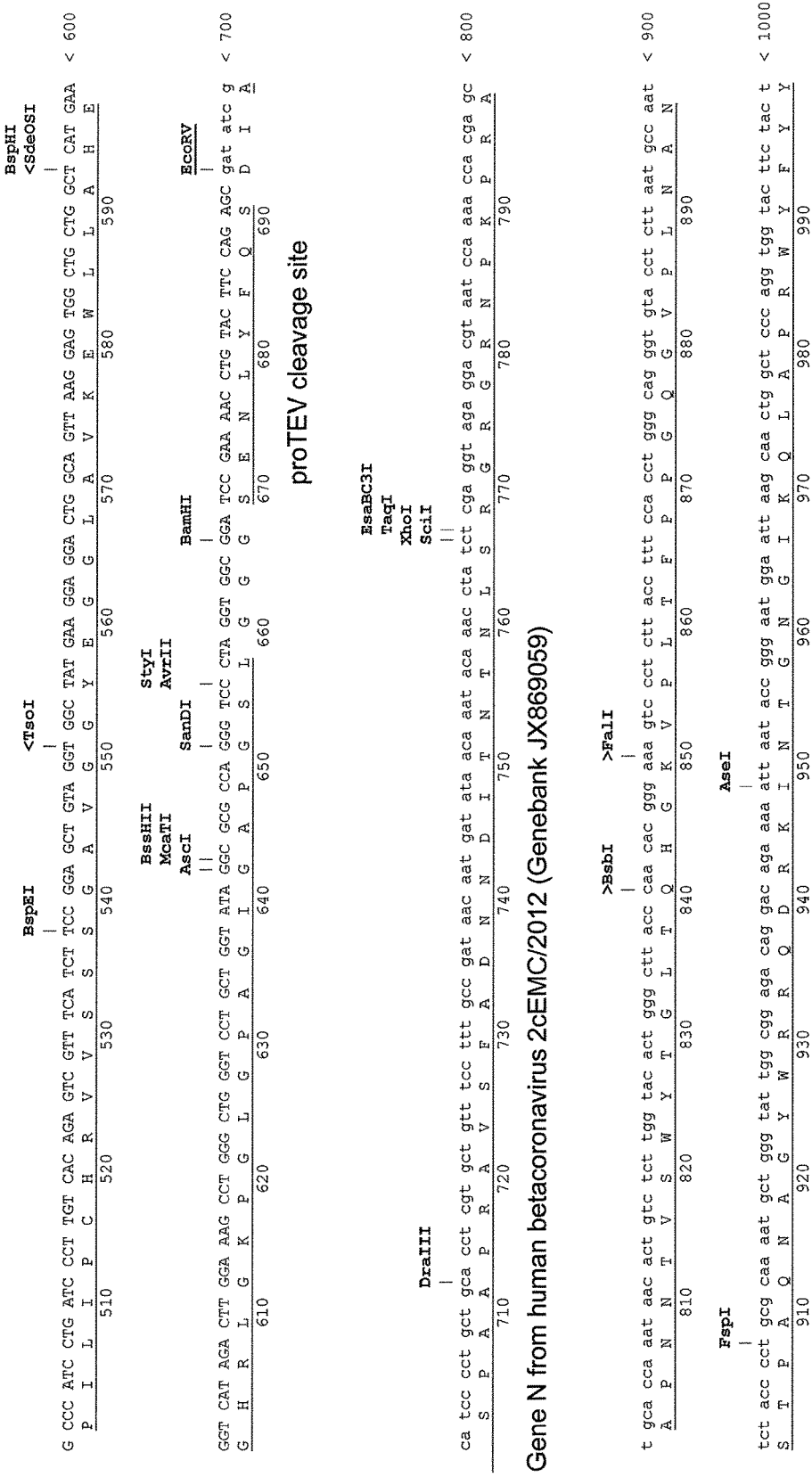
Figure 15B:
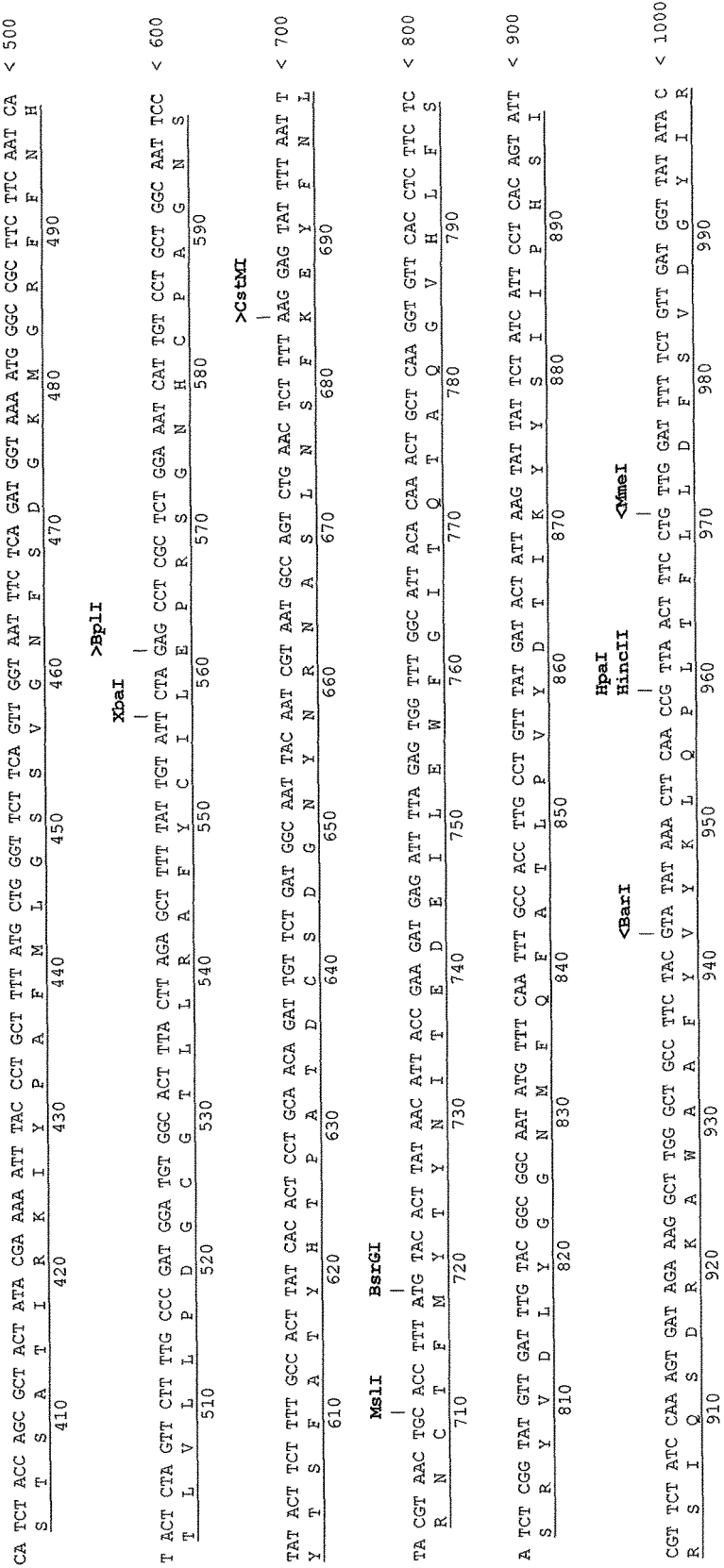
Figure 16B:
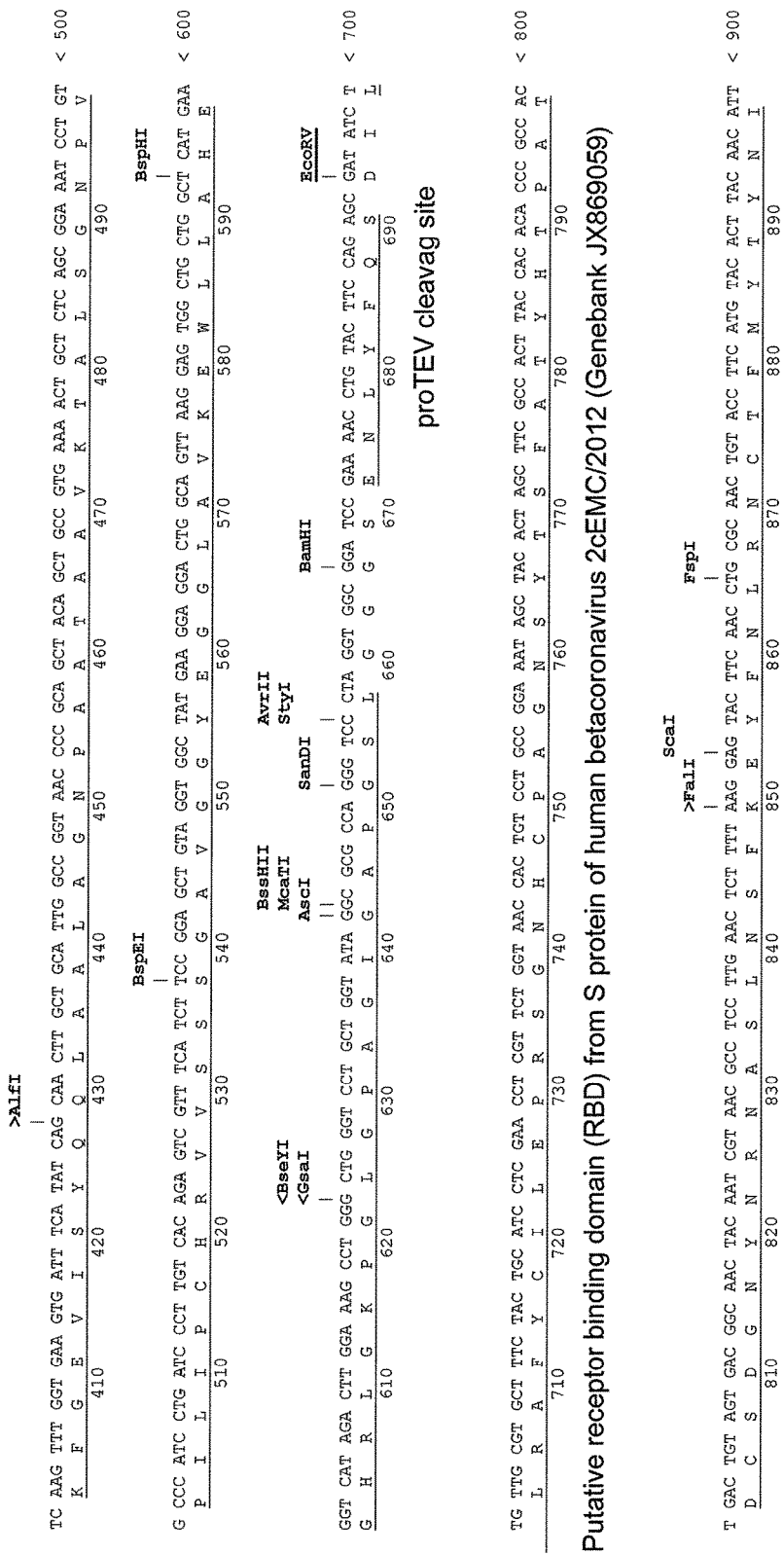

Alternatively, the pDeSNAP Univ/SBV.N DNA cassette can comprise, from 5' to 3', the sequence SEQ ID NO:23 encoding the BiP-like secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:36 (whose structure is shown on FIG. 9).

Thus, in a preferred embodiment, the vector of the invention comprises the pDeSNAP Univ/SBV.N cassette having the nucleotide sequence SEQ ID NO: 35 or the nucleotide sequence SEQ ID NO:36.

More precisely, the pDeSNAP Univ/SBV.N cassette nucleotide sequence of SEQ ID NO:35 comprises:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

And the pDeSNAP Univ/SBV.N cassette nucleotide sequence SEQ ID NO:36 comprises (see also FIG. 9):

- an insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

Interestingly, the pDeSNAP Univ/SBV.N cassette nucleotide sequence of SEQ ID NO:36 cassette also comprises in addition an NheI site upstream of the ATG, a Bg/II site between the BiP-like sequence and the SNAP-like sequence, and an AgeI site and a HindIII site which are both located downstream of the stop codon.

Vectors of the invention are for example SEQ ID NO:43 (which is the pMT/BiP/V5-HisA plasmid from Invitrogen comprising the pDeSNAP Univ cassette) in which the SBV.N DNA sequence SEQ ID NO: 17 has been inserted, SEQ ID NO:44 (which is the pUC57 plasmid from Invitrogen comprising the pDeSNAP Univ cassette) in which the SBV.N DNA sequence SEQ ID NO: 17 has been inserted or SEQ ID NO:45 (which is the pcDNA3 plasmid from Invitrogen comprising the pDeSNAP Univ cassette) in which the SBV.N DNA sequence SEQ ID NO: 17 has been inserted.

Vectors of the invention are also provided in the S2 cells which have been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another aspect, the present invention targets a recombinant cell which is stably transfected by a vector of the invention, preferably a vector comprising the nucleotide sequence SEQ ID NO: 35 or SEQ ID NO: 36.

Preferably, in this aspect of the invention, said recombinant cell is a non-vertebrate cell, preferably an insect cell, and more preferably a S2 cell.

Non-vertebrate cells can be any cells from the Insect, Arachnida, Crustacea, Mollusca, Annelida, Cirripedia, Radiata, Coelenterata and Infusoria. In the context of the invention, non-vertebrate cells are preferably insect cells, such as Drosophila or Mosquito cells. They are more preferably a *Drosophila* S2 cells. In this case, the expression vector of the invention comprises for example SEQ ID NO: 35.

*Drosophila* S2 cells have been widely described. They are especially suited to high-yield production of protein, because they can be maintained in suspension cultures at room temperature (24±1° C.). Culture medium is $M_3$ supplemented with between 5 and 10% (v/v) heat-inactivated fetal bovine serum (FBS). In the preferred embodiment of the invention, the culture medium contains 5% FBS. After induction, the cells are cultured in serum-free media. In this media, the S2 cells can be grown in suspension cultures, for example in 250 mL to 2000 mL spinner flasks, with stirring at 50-60 rpm. Cells densities are typically maintained between $10^6$ and $10^7$ cells per mL.

In a preferred embodiment, the recombinant cell of the invention is the S2 cell which has been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another preferred embodiment, said recombinant cell is a vertebrate cell.

Preferably, said vertebrate recombinant cell is a mammal cell, a preferably CHO, YB2/O, COS, HEK, NIH3T3, HeLa cell or derivatives thereof. More preferably, in this case, the expression vector of the invention comprises SEQ ID NO: 36.

In another aspect of the present invention, the said recombinant cell is used to amplify and purify the expression vectors of the invention, preferably those comprising SEQ ID NO: 35 or 36.

In this aim, the nucleotide expression vectors of the invention may also comprise a gene encoding a selection marker, and/or a terminator sequence. Selection markers genes that can be included in the construct are typically those that confer selectable phenotypes such as resistance to antibiotics (e.g. blasticidin, ampicillin, kanamycin, hygromycin, puromycin, chloramphenicol).

Methods for producing expression vectors are well-known in the art.

In another aspect, the recombinant cell of the invention is used so as to produce the N nucleoprotein of the Schmallenberg virus in high amounts.

Thus, in a particular embodiment, the present invention is also drawn to a method for the production of the N nucleoprotein of the Schmallenberg virus, the method comprising the steps of:

(a) obtaining the vector of the invention, said vector comprising for example the DNA sequence SEQ ID NO:35 or SEQ ID NO:36, (b) transfecting an host cell (preferably an insect cell or a mammal cell) with the polynucleotide obtained under step (a);

(c) allowing for the expression of said polynucleotide obtained under step (b) to produce the N nucleoprotein of the Schmallenberg virus;

(d) optionally, cleaving the AGT polypeptide, (e) recovering the N nucleoprotein of the Schmallenberg virus, (f) optionally, purifying the N nucleoprotein of the Schmallenberg virus.

For performing the different steps of the method of the present invention, there may be employed conventional molecular biology, microbiology and recombinant DNA techniques within the skills of the person of the art. Such techniques are fully explained in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization(B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

The term "transfection" means the introduction of a foreign nucleic acid into a eukaryotic host cell so that the host cell will express the introduced gene or sequence to produce the N nucleoprotein of Schmallenberg virus. A host cell that receives and expresses introduced DNA or RNA has been "transfected" and is a "transfectant" or a "clone". The DNA or RNA introduced to a host cell can come from any source, including cells of the same genus or species as the host cell or cells of a different genus or species.

In the context of the invention, the transfection of the host cells with the polynucleotides can be performed by a classical method in the art, for example by transfection, infection, or electroporation. In another embodiment, the vector of the invention can be introduced in vivo by lipofection (as naked DNA), or with other transfection facilitating agents (peptides, polymers, etc.). Synthetic cationic lipids can be used to prepare liposomes for in vivo transfection of a gene encoding a marker (Felgner et al., Proc. Natl. Acad. Sci. U.S.A., 84:7413-7417, 1987). Useful lipid compounds and compositions for transfer of nucleic acids are described in WO 95/18863 and WO 96/17823, and in U.S. Pat. No. 5,459,127. Lipids may be chemically coupled to other molecules for the purpose of targeting (see, Mackey et al., Proc. Natl. Acad. Sci. U.S.A., 85:8027-8031, 1988). Targeted peptides, such as hormones or neurotransmitters, and proteins such as antibodies, or non-peptide molecules could be coupled to liposomes chemically. Other molecules are also useful for facilitating transfection of a nucleic acid in vivo, such as a cationic oligopeptides (see WO 95/21931), peptides derived from DNA binding proteins (see WO 96/25508), or a cationic polymer (see WO 95/21931). It is also possible to introduce the vector in vivo as a naked DNA plasmid. Naked DNA vectors for gene therapy can be introduced into the desired host cells by methods known in the art, such as electroporation, microinjection, cell fusion, DEAE dextran, calcium phosphate precipitation, use of a gene gun, or use of a DNA vector transporter (see, Wu et al., J. Biol. Chem., 267:963-967, 1992; Wu and Wu, J. Biol. Chem., 263:14621-14624, 1988; Williams et al., Proc. Natl. Acad. Sci. U.S.A., 88:2726-2730, 1991).

The term "allowing for the expression" of a polynucleotide herein means that the stimulus of the regulatory sequences that are present in the vector (e.g. the stimulus activating the inducible promoter), and all the required components are present in a sufficient amount for the translation of the polynucleotide to occur.

If need be, the AGT/SNAP polypeptide can be cleaved off the produced fusion protein by adding a protease having a defined cleavage site to the supernatant of or into the recombinant cells. For example, when a vector comprising the pDeSNAP Univ cassette of SEQ ID NO: 35 or 36 is used, the cleavage of the pro-TEV cleavage site ENLKYFQ/G(S) is obtained by adding the TEV protease to the supernatant of the recombinant cells. Alternatively, the AGT/SNAP polypeptide can be maintained so as to enhance the life-span of the N nucleoprotein from SBV.

Moreover, the skilled artisan will appreciate that an expressed or secreted protein or polypeptide can be detected in the culture medium used to maintain or grow the present host cells. The culture medium can be separated from the host cells by known procedures, such as centrifugation or filtration. The protein or polypeptide can then be detected in the cell-free culture medium by taking advantage of known properties characteristic of the protein or polypeptide. Such properties can include the distinct immunological, enzymatic or physical properties of the protein or polypeptide. For example, if a protein or polypeptide has a unique enzyme activity an assay for that activity can be performed on the culture medium used by the host cells. Moreover, when antibodies reactive against a given protein or polypeptide are available, such antibodies can be used to detect the protein or polypeptide in any known immunological assay (for example as in Harlowe, et al., 1988, Antibodies: A Laboratory Manual, Cold Spring Harbor Laboratory Press).

Recovery of the nucleoprotein N from SBV is mediated by the means well-known in the art, including, but not limited to, preparative disc-gel electrophoresis, isoelectric focusing, HPLC, reversed-phase HPLC, gel filtration, ion exchange and partition chromatography, precipitation and salting-out chromatography, extraction, and countercurrent distribution, and the like. As it is preferable to produce the protein of interest in the recombinant system of the invention linked with a label, said label will facilitate the recovery of the polypeptide from the crude lysate of the host cell by chromatography on an appropriate solid-phase matrix. Alternatively, antibodies produced against the protein or against peptides derived therefrom can be used as recovery reagents.

The present Inventors discovered that the fusion proteins generated with the method of the invention generally do not need to be further purified. However, a further step (g) of purification may be performed, if required.

A purified material may contain less than about 50%, preferably less than about 75%, and most preferably less than about 90%, of the cellular components with which it was originally associated. The term "substantially pure" indicates the highest degree of purity which can be achieved using conventional purification techniques known in the art.

In an embodiment of the invention, the methods of the invention enable to obtain at least 40 mg/L, preferably at least 50 mg/L, more preferably at least 60 mg/L of the substantially pure N nucleoprotein of the Schmallenberg virus (SBV) in the recovered cell culture supernatant.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein of Schmallenberg virus of SEQ ID NO: 16.

In this fusion polypeptide, said AGT enzyme is preferably the protein of SEQ ID NO: 2, or a homologue thereof (said homologous being as defined above).

This fusion polypeptide preferably further comprises a label, as defined above. This label is preferably a polyhistidine label, and is preferably located at the C terminal end of the N nucleoprotein of the Schmallenberg virus.

The fusion polypeptide of the invention is for example the amino acid sequence of SEQ ID NO: 41 (corresponding to the BiPlike/SNAP/SBV.N/Histag fusion protein) or SEQ ID NO: 46 (corresponding to the ssBiP/SNAP/SBV.N/Histag fusion protein) or SEQ ID NO:42 (corresponding to the SNAP/SBV.N fusion protein).

The invention encompasses a vector comprising the DeSNAPuniv-Schmallenberg NSs protein cassette having the nucleotide sequence of SEQ ID NO: 178 and/or encoding the amino acid sequence of SEQ ID NO: 179. The vector can comprise a DNA sequence encoding the signal peptide of SNAP, the SNAP sequence, the pro-TEV sites, or the NSs protein from Schmallenberg virus depicted in FIG. 24, or at least 10, 15, 20, 25, 30, 40, 50, 60, 100, 200, or 300 consecutive amino acids thereof, alone or in combination.

Finally, the chimeric protein SNAP-SBV.N may be useful as a diagnostic agent for the detection of the viral infection by the Schmallenberg virus, or for the detection of antibodies specific of the said virus in biological fluids, such as blood, serum, saliva, and the like.

Thus, in another aspect, the present invention is also drawn to the use of the fusion protein [SNAP-SBV.N] obtained by any method of the invention for identifying the presence of said pathogenic or non-pathogenic microorganisms in a biological sample, for example thanks to the immunoassay of the present invention.

In other aspects, the present invention also relates to vectors expressing fusion proteins of particular interest, said fusion proteins comprising a 6-alkylguanine-DNA-alkyltransferase enzyme (AGT), a mutant, a fragment or a catalytic domain thereof, that is fused in frame with interesting antigens, such as viral or bacterial antigens, microbial peptides and/or polypeptides of interest. These vectors are detailed below.

Echovirus Antigen

In another aspect, the present invention relates to a vector for expressing an echovirus antigen, for example the VP1 protein of the enterovirus 71 (*Picornaviridae*), in a host cell. In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VP1 protein of the enterovirus 71 (EV71, see for example Kolpe A. B. et al, Virus Research 2012).

In a preferred embodiment, this vector comprises a so-called "pDeSNAP Univ/EV71.VP1 cassette" i.e., a pDeSNAPUniv DNA cassette as defined above, in which the sequence SEQ ID NO:47 encoding the VP1 protein from the EV71 virus strain JL-AFP-EV71-07-03 (Genebank#JQ715713) has been inserted.

In a preferred embodiment, this vector comprises the pDeSNAP Univ/EV71.VP1 cassette having the nucleotide sequence SEQ ID NO: 48 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence SEQ ID NO:47 encoding the VP1 protein from the EV71 virus strain JL-AFP-EV71-07-03 (Genebank#JQ715713),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VP1 protein from the EV71 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 49 (corresponding to the SNAP-like/proTEV1/EV71.VP1/proTEV2/Histag fusion protein). High levels (30 mg/l) of this protein were produced after induction of S2/.

Thus, in another aspect, the present invention is also drawn to the use of this fusion protein [SNAP-EV71.VP1] for identifying the presence of the enterovirus 71 in a biological sample, for example in the immunoassay of the present invention.

Flavivirus Antigens

In another aspect, the present invention relates to vectors for expressing particular Flavivirus antigens in a host cell.

In a preferred embodiment, said Flavivirus antigen is the soluble E protein (sE) from the Japanese Encephalitis virus (JEV.sE). More particularly, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE protein from the Japanese Encephalitis virus.

In a preferred embodiment, this vector comprises a so-called "pDeSNAP Univ/JEV.sE cassette" i.e., a pDeSNAPUniv DNA cassette as defined above, in which the sequences of gene encoding the soluble E protein (sE) from the Japanese Encephalitis virus (JEV) have been inserted.

In a preferred embodiment, this vector comprises the pDeSNAP Univ/JEV.sE cassette having the nucleotide sequence SEQ ID NO: 50 comprising, from 5' to 3':
- an insect BiP sequence of SEQ ID NO: 22,
- the DNA sequence encoding the prM/M sequence from JEV strain SA-14 (Genbank#M55506),
- the DNA sequence encoding the E[1-395] sequence from JEV strain SA-14 (Genbank#M55506),
- a DNA sequence SEQ ID NO: 26 encoding the spacer sequence GGGS (SEQ ID NO: 25), the SNAP-like sequence of SEQ ID NO: 31,
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble E protein (sE) from the Japanese Encephalitis virus (JEV.sE). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 51 (corresponding to the JEV.sE/SNAP-like/Histag fusion protein).

Thus, in another aspect, the present invention is also drawn to the use of this fusion protein [SNAPJEV.sE] for identifying the presence of the Japanese Encephalitis virus (JEV) in a biological sample, for example thanks to the immunoassay of the present invention.

In a preferred embodiment, said Flavivirus antigen is the domain III of the envelope E protein (EDIII protein) from the Japanese encephalitis virus of genotype 1 (JE-1.EDIII), of genotype 2 (JE-3.EDIII), of genotype 4 (JE-4.EDIII), or of genotype 5 (JE-5.EDIII).

In another aspect, the present invention therefore relates to a vector for expressing the domain III of the envelope E protein (EDIII protein) from the Japanese encephalitis virus of genotype I (JE-LEDIII), of genotype 2 (JE-2.EDIII), of genotype 4 (JE-4.EDIII), or of genotype 5 (JE-5.EDIII) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the EDIII protein from the Japanese encephalitis virus of genotype 1 (JE-LEDIII), of genotype 2 (JE-2.EDIII), of genotype 4 (JE-4.EDIII), or of genotype 5 (JE-5.EDIII).

In a preferred embodiment, this vector comprises a so-called "pDeSNAP Univ/JE-LEDIII cassette" i.e., a pDeSNAPUniv DNA cassette as defined above, in which the sequence of gene encoding the domain III of the envelope E protein (EDIII protein) from the Japanese encephalitis virus of genotype 1 (JE-1.EDIII) has been inserted.

In a preferred embodiment, this vector comprises the pDeSNAP Univ/JE-1.EDIII cassette having the nucleotide sequence SEQ ID NO: 52 comprising:
an insect BiP-like sequence of SEQ ID NO: 23,
the SNAP-like sequence of SEQ ID NO: 31,
the DNA sequence SEQ ID NO:54 encoding the domain III of the envelope E protein (EDIII protein) from the Japanese encephalitis virus of genotype 1 (Genebank#AY377577),
a DNA sequence SEQ ID NO: 28 encoding a HisTag sequence.

In a preferred embodiment, this vector comprises a so-called "pDeSNAP Univ/JE-2.EDIII cassette" i.e., a pDeSNAPUniv DNA cassette as defined above, in which the sequence of the domain III of the envelope E protein (EDIII protein) from the Japanese encephalitis virus of genotype 2 (JE-2.EDIII) has been inserted.

In a preferred embodiment, this vector comprises the pDeSNAP Univ/JE-2.EDIII cassette having the nucleotide sequence SEQ ID NO: 59 comprising:
an insect BiP-like sequence of SEQ ID NO: 23,
the SNAP-like sequence of SEQ ID NO: 31,
the DNA sequence SEQ ID NO:55 encoding the domain III of the envelope E protein (EDIII protein) from the Japanese encephalitis virus of genotype 2 (Genebank#L-43566),
a DNA sequence SEQ ID NO: 28 encoding a HisTag sequence.

In a preferred embodiment, this vector comprises a so-called "pDeSNAP Univ/JE-4.EDIII cassette" i.e., a pDeSNAPUniv DNA cassette as defined above, in which the sequence of the domain III of the envelope E protein (EDIII protein) from the Japanese encephalitis virus of genotype 4 (JE-4.EDIII) has been inserted.

In a preferred embodiment, this vector comprises the pDeSNAP Univ/JE-4.EDIII cassette having the nucleotide sequence SEQ ID NO: 61 comprising:
an insect BiP-like sequence of SEQ ID NO: 23,
the SNAP-like sequence of SEQ ID NO: 31,
the DNA sequence SEQ ID NO:56 encoding the domain III of the envelope E protein (EDIII protein) from the Japanese encephalitis virus of genotype 4 (Genebank#U70408),
a DNA sequence SEQ ID NO: 28 encoding a HisTag sequence.

In a preferred embodiment, this vector comprises a so-called "pDeSNAP Univ/JE-5.EDIII cassette" i.e., a pDeSNAPUniv DNA cassette as defined above, in which the sequence of the gene encoding the domain III of the envelope E protein (EDIII protein) from the Japanese encephalitis virus of genotype 5 (JE-5.EDIII) has been inserted.

In a preferred embodiment, this vector comprises the pDeSNAP Univ/JE-5.EDIII cassette having the nucleotide sequence SEQ ID NO: 63 comprising:
an insect BiP-like sequence of SEQ ID NO: 23,
the SNAP-like sequence of SEQ ID NO: 31,
the DNA sequence SEQ ID NO:57 encoding the domain III of the envelope E protein (EDIII protein) from the Japanese encephalitis virus of genotype 5 (Genebank#JN587258),
a DNA sequence SEQ ID NO: 28 encoding a HisTag sequence.

In another aspect, the present invention relates to recombinant cells which are stably transfected by said vectors.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the JE-1, JE-2, JE-4, or JE-5 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 53 (corresponding to the SNAP-like/JE-1.EDIII/Histag fusion protein), SEQ ID NO: 60 (corresponding to the SNAP-like/JE-2.EDIII/Histag fusion protein) SEQ ID NO: 62 (corresponding to the SNAP-like/JE-4.EDIII/Histag fusion protein) or SEQ ID NO: 64 (corresponding to the SNAP-like/JE-5.EDIII/Histag fusion protein).

Thus, in another aspect, the present invention is also drawn to the use of any of these fusion proteins [SNAP-JE-1.EDIII], [SNAP-JE-2.EDIII], [SNAP-JE-4.EDIII] or [SNAP-JE-5.EDIII] for identifying the presence of the Japanese encephalitis virus of genotype 1, 2, 4 or 5 respectively in a biological sample, for example thanks to the immunoassay of the present invention.

In another aspect, the present invention is drawn to a vector for expressing the domain III of the envelope E protein (EDIII protein) from the Rabensburg virus (RabV) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the envelope E protein (EDIII protein) from the Rabensburg virus (RabV).

In a preferred embodiment, this vector comprises a so-called "pDeSNAP Univ/RabV.EDIII cassette" i.e., a pDeSNAPUniv DNA cassette as defined above, in which the sequence of the EDIII protein from the Rabensburg virus has been inserted.

In a preferred embodiment, this vector comprises the pDeSNAP Univ/RabV.EDIII cassette having the nucleotide sequence SEQ ID NO: 65 comprising:
an insect BiP-like sequence of SEQ ID NO: 23,
the SNAP-like sequence of SEQ ID NO: 31,
the DNA sequence SEQ ID NO:58 encoding the domain III of the envelope E protein (EDIII protein) from the Rabensburg virus (Genebank#AY65264),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Rabensburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 66 (corresponding to the SNAP-like/RabV.EDIII/Histag fusion protein).

Thus, in another aspect, the present invention is also drawn to the use of this fusion protein [SNAP-RabV.EDIII] for identifying the presence of the Rabensburg virus in a biological sample, for example thanks to the immunoassay of the present invention.

Alphavirus Antigens

In another aspect, the present invention is relates to vectors for expressing particular alphavirus antigens, for example the soluble E2 protein from the Ross River virus (RR.sE2) or from the Mayaro virus (MAY.sE2), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Ross River virus.

In a preferred embodiment, this vector comprises a so-called "pDeSNAP Univ/RR.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/RR.sE2 cassette having the nucleotide sequence SEQ ID NO: 69 comprising:
an insect BiP sequence of SEQ ID NO: 22,
the DNA sequence encoding the sE2 protein of the Ross River virus strain QML1 (Genebank#GQ433354),
the SNAP-like sequence of SEQ ID NO: 31,
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Ross River virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 70 (corresponding to the RR.sE2/SNAP-like/Histag fusion protein).

Thus, in another aspect, the present invention is also drawn to the use of this fusion protein [SNAP-RR.sE2] for identifying the presence of the Ross River virus in a biological sample, for example thanks to the immunoassay of the present invention.

The present invention is also drawn to a vector for expressing the soluble E2 protein from the Mayaro virus (MAY.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Mayaro virus.

In a preferred embodiment, this vector comprises a so-called "pDeSNAP Univ/MAY.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/MAY.sE2 cassette having the nucleotide sequence SEQ ID NO: 71 comprising:
an insect BiP sequence of SEQ ID NO: 22,
the DNA sequence encoding the corrected sE2 protein (E2-S203C) of the Mayaro virus strain IQD2668 (Genbank#DQ487429.1),
the SNAP-like sequence of SEQ ID NO: 31,
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Mayaro virus (MAY.sE2). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 72 (corresponding to the MAY.sE2/SNAP-like/Histag fusion protein).

Thus, in another aspect, the present invention is also drawn to the use of this fusion protein [SNAP-MAY.sE2] for identifying the presence of the Mayaro virus in a biological sample, for example thanks to the immunoassay of the present invention.

Equine Encephalitis Virus Antigens

In another aspect, the present invention relates to vectors for expressing particular Equine Encephalitis virus antigens, for example the soluble E2 protein from the Western Equine Encephalitis virus (WEE.sE2), the Eastern Equine Encephalitis virus (EEE.sE2) or the Venezuelan Equine Encephalitis virus (VEE.sE2) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Western Equine Encephalitis virus.

In a preferred embodiment, this vector comprises a so-called "pDeSNAP Univ/WEE.sE2 cassette" i.e., a pDeSNAPUniv DNA cassette as defined above, in which the sequence of the sE2 gene from the Western Equine Encephalitis virus has been inserted.

In a preferred embodiment, this vector comprises the pDeSNAP Univ/WEE.sE2 cassette having the nucleotide sequence SEQ ID NO: 73 comprising:
- an insect BiP sequence of SEQ ID NO: 22,
- the DNA sequence encoding the sE2 protein from Western Equine Encephalitis virus strain (Genbank#NC00390808),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the WEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 74 (corresponding to the WEE.sE2/SNAP-like/Histag fusion protein).

Thus, in another aspect, the present invention is also drawn to the use of this fusion protein [SNAP-WEE.sE2] for identifying the presence of the Western Equine Encephalitis virus in a biological sample, for example thanks to the immunoassay of the present invention.

In another embodiment, the present invention is also drawn to a vector for expressing the soluble E2 protein from the Eastern Equine Encephalitis virus (EEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Eastern Equine Encephalitis virus.

In a preferred embodiment, this vector comprises a so-called "pDeSNAP Univ/EEE.sE2 cassette" i.e., a pDeSNAPUniv DNA cassette as defined above, in which the sequence of the sE2 gene from the Eastern Equine Encephalitis virus has been inserted.

In a preferred embodiment, this vector comprises the pDeSNAP Univ/EEE.sE2 cassette having the nucleotide sequence SEQ ID NO: 75 comprising:
- an insect BiP sequence of SEQ ID NO: 22,
- the DNA sequence encoding the sE2 protein from Eastern Equine Encephalitis virus strain (Genbank#EF151502),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the EEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 76 (corresponding to the EEE.sE2/SNAP-like/Histag fusion protein).

Thus, in another aspect, the present invention is also drawn to the use of this fusion protein [SNAP-EEE.sE2] for identifying the presence of the Eastern Equine Encephalitis virus in a biological sample, for example thanks to the immunoassay of the present invention.

In another embodiment, the present invention is also drawn to a vector for expressing the soluble E2 protein from the Venezuelan Equine Encephalitis virus (VEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Venezuelan Equine Encephalitis virus.

In a preferred embodiment, this vector comprises a so-called "pDeSNAP Univ/VEE.sE2 cassette" i.e., a pDeSNAPUniv DNA cassette as defined above, in which the sequence of the sE2 gene from the Venezuelan Equine Encephalitis virus has been inserted.

In a preferred embodiment, this vector comprises the pDeSNAP Univ/VEE.sE2 cassette having the nucleotide sequence SEQ ID NO: 77 comprising:
- an insect BiP sequence of SEQ ID NO: 22,
- the DNA sequence encoding the sE2 protein from Venezuelan Equine Encephalitis virus strain (Genbank#AY973944),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the VEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 78 (corresponding to the VEE.sE2/SNAP-like/Histag fusion protein).

Thus, in another aspect, the present invention is also drawn to the use of this fusion protein [SNAP-VEE.sE2] for identifying the presence of the Venezuelan Equine Encephalitis virus in a biological sample, for example thanks to the immunoassay of the present invention.

*Orthobunyavirus* Antigens

In another aspect, the present invention relates to vectors for expressing particular orthobunyavirus antigens, for example the Nucleoprotein N from the Akabane virus (AKA.N), from the Aino virus (AIN.N) or from the Shamonda virus (SHA.N), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Akabane virus.

In a preferred embodiment, this vector comprises a so-called "pDeSNAP Univ/AKA.N cassette" i.e., a pDeSNAPUniv DNA cassette as defined above, in which the sequence of the gene encoding the Nucleoprotein N from the Akabane virus has been inserted.

In a preferred embodiment, this vector comprises the pDeSNAP Univ/AKA.N cassette having the nucleotide sequence SEQ ID NO: 79 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Akabane virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Akabane virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 80 (corresponding to the SNAP-like/proTEV1/AKA.N/pro-TEV2/Histag fusion protein).

Thus, in another aspect, the present invention is also drawn to the use of this fusion protein [SNAP-AKA.N] for identifying the presence of the Akabane virus in a biological sample, for example thanks to the immunoassay of the present invention.

In another embodiment, the present invention is drawn to a vector for expressing the Nucleoprotein N from the Aino virus (AIN.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Aino virus.

In a preferred embodiment, this vector comprises a so-called "pDeSNAP Univ/AIN.N cassette" i.e., a pDeSNAPUniv DNA cassette as defined above, in which the sequence of the gene encoding the Nucleoprotein N from the Aino virus has been inserted.

In a preferred embodiment, this vector comprises the pDeSNAP Univ/AIN.N cassette having the nucleotide sequence SEQ ID NO: 81 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Aino virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Aino virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 82 (corresponding to the SNAP-like/proTEV1/AIN.N/pro-TEV2/Histag fusion protein).

Thus, in another aspect, the present invention is also drawn to the use of this fusion protein [SNAP-AIN.N] for identifying the presence of the Aino virus in a biological sample, for example thanks to the immunoassay of the present invention.

In another embodiment, the present invention is drawn to a vector for expressing the Nucleoprotein N from the Shamonda virus (SHA.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Shamonda virus.

In a preferred embodiment, this vector comprises a so-called "pDeSNAP Univ/SHA.N cassette" i.e., a pDeSNAPUniv DNA cassette as defined above, in which the sequence of the gene encoding the Nucleoprotein N from the Shamonda virus has been inserted.

In a preferred embodiment, this vector comprises the pDeSNAP Univ/SHA.N cassette having the nucleotide sequence SEQ ID NO: 83 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Shamonda virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Shamonda virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 84 (corresponding to the SNAP-like/proTEV1/SHA.N/pro-TEV2/Histag fusion protein).

Thus, in another aspect, the present invention is also drawn to the use of this fusion protein [SNAP-SHA.N] for identifying the presence of the Shamonda virus in a biological sample, for example thanks to the immunoassay of the present invention.

Betacoronavirus Antigens

In another aspect, the present invention relates to vectors for expressing particular betacoronavirus antigens, for example the Nucleoprotein N from human betacoronavirus (huCOV.N) or the protein S of the human betacoronavirus (huCOV.S), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from human betacoronavirus.

In a preferred embodiment, this vector comprises a so-called "pDeSNAP Univ/huCOV.N cassette" i.e., a pDeSNAPUniv DNA cassette as defined above, in which the sequence of the gene encoding the Nucleoprotein N from human betacoronavirus has been inserted.

In a preferred embodiment, this vector comprises the pDeSNAP Univ/huCOV.N cassette having the nucleotide sequence SEQ ID NO: 85 comprising:

an insect BiP sequence of SEQ ID NO: 22,
the SNAP-like sequence of SEQ ID NO: 31,
a DNA sequence SEQ ID NO: 29 encoding a pro-TEV1 cleavage site of sequence ENLYFQS (SEQ ID NO: 32),
the DNA sequence encoding the gene N from human betacoronavirus 2cEMC/2012 (Genbank#JX869059),
a DNA sequence SEQ ID NO: 30 encoding a pro-TEV2 cleavage site of sequence ENLYFQG (SEQ ID NO: 33),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant, or a catalytic domain thereof and b) the Nucleoprotein N from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 86 (corresponding to the SNAP-like/proTEV1/huCOV.N/proTEV2/Histag fusion protein).

Thus, in another aspect, the present invention is also drawn to the use of this fusion protein [SNAP-huCOV.N] for identifying the presence of the human betacoronavirus in a biological sample, for example thanks to the immunoassay of the present invention.

In another embodiment, the present invention is drawn to a vector for expressing the soluble form of the spike S protein from human betacoronavirus (huCOV.S) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble form of the spike S protein from human betacoronavirus.

In a preferred embodiment, this vector comprises a so-called "pDeSNAP Univ/huCOV.S cassette" i.e., a pDeSNAPUniv DNA cassette as defined above, in which the sequence of the gene S from human betacoronavirus has been inserted.

In a preferred embodiment, this vector comprises the pDeSNAP Univ/huCOV.S cassette having the nucleotide sequence SEQ ID NO: 87 comprising:

an insect BiP sequence of SEQ ID NO: 22,
the DNA sequence encoding the gene S from human betacoronavirus 2cEMC/2012 (Genbank#JX869059),
a DNA sequence SEQ ID NO: 26 encoding the spacer sequence GGGS (SEQ ID NO: 25),
the SNAP-like sequence of SEQ ID NO: 31,
a DNA sequence SEQ ID NO: 28 encoding a HisTag sequence.

In another embodiment, the vector comprises the DeSNAPuniv-SARS virus N protein cassette having the nucleotide sequence of SEQ ID NO: 154 and/or encoding the amino acid sequence of SEQ ID NO: 155. The vector can comprise a DNA sequence encoding the signal peptide of SNAP, the SNAP sequence, the pro-TEV sites, or the mutated protein from SARS coronavirus depicted in FIG. 12, or at least 10, 15, 20, 25, 30, 40, 50, 60, 100, 200, or 300 consecutive amino acids thereof, alone or in combination.

In another embodiment, the vector comprises the DeSNAP+SARS S-RDB cassette having the nucleotide sequence of SEQ ID NO: 156 and/or encoding the amino acid sequence of SEQ ID NO: 157. The vector can comprise a DNA sequence encoding the signal peptide of SNAP, the SNAP sequence, the pro-TEV sites, or the receptor binding domain from S protein of SARS virus depicted in FIG. 13, or at least 10, 15, 20, 25, 30, 40, 50, 60, 100, 200, or 300 consecutive amino acids thereof, alone or in combination In another embodiment, the vector comprises the DeSNAPuniv-huCOV.N (human coronavirus) cassette having the nucleotide sequence of SEQ ID NO: 158 and/or encoding the amino acid sequence of SEQ ID NO: 159. The vector can comprise a DNA sequence encoding the signal peptide of SNAP, the SNAP sequence, the pro-TEV sites, or the gene N from human betacoronavirus depicted in FIG. 14, or at least 10, 15, 20, 25, 30, 40, 50, 60, 100, 200, or 300 consecutive amino acids thereof, alone or in combination.

In another embodiment, the vector comprises the—huCOV.S1+DeSNAP (human coronavirus) cassette having the nucleotide sequence of SEQ ID NO: 160 and/or encoding the amino acid sequence of SEQ ID NO: 161. The vector can comprise a DNA sequence encoding the signal peptide of chimeric protein, the SNAP sequence, or the gene S1 from human betacoronavirus depicted in FIG. 15, or at least 10, 15, 20, 25, 30, 40, 50, 60, 100, 200, or 300 consecutive amino acids thereof, alone or in combination.

In another embodiment, the vector comprises the DeSNAPuniv-huCoV.S-RDB cassette having the nucleotide sequence of SEQ ID NO: 162 and/or encoding the amino acid sequence of SEQ ID NO: 163. The vector can comprise a DNA sequence encoding the signal peptide of chimeric protein, the SNAP sequence, the pro-TEV sites, or the RBD from S protein of human betacoronavirus depicted in FIG. 16, or at least 10, 15, 20, 25, 30, 40, 50, 60, 100, 200, or 300 consecutive amino acids thereof, alone or in combination.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble form of the spike S protein from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 88 (corresponding to the huCOV.S/SNAP-like/Histag fusion protein).

Thus, in another aspect, the present invention is also drawn to the use of this fusion protein [SNAP-huCOV.S] for identifying the presence of the human betacoronavirus in a biological sample, for example thanks to the immunoassay of the present invention.

Hepacivirus Antigen

In another aspect, the present invention relates to vectors for expressing particular hepacivirus antigens, for example the protein C from Hepatitis C virus (HCV.C) or from Hepatitis E virus (HEV.C), in a host cell.

In one embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis C virus.

In a preferred embodiment, this vector comprises a so-called "pDeSNAP Univ/HCV.C cassette" i.e., a pDeSNAPUniv DNA cassette as defined above, in which the sequence of the gene of the protein C from Hepatitis C virus has been inserted.

In a preferred embodiment, this vector comprises the pDeSNAP Univ/HCV.C cassette having the nucleotide sequence SEQ ID NO: 89 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the C protein from hepatitis C virus genotype 1b (strain TCHM-R2/03),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

In another embodiment, the vector comprises the DeSNAPuniv-HEV.C cassette having the nucleotide sequence of SEQ ID NO: 170 and/or encoding the amino acid sequence of SEQ ID NO: 171. The vector can comprise a DNA sequence encoding the signal peptide of SNAP, the SNAP sequence, the pro-TEV sites, or the mutated C protein from Hepatitis E virus depicted in FIG. 20, or at least 10, 15, 20, 25, 30, 40, 50, 60, 100, 200, or 300 consecutive amino acids thereof, alone or in combination.

In another embodiment, the vector comprises the DeSNAPuniv-HEV.C protein central domain cassette having the nucleotide sequence of SEQ ID NO: 172 and/or encoding the amino acid sequence of SEQ ID NO: 173. The vector can comprise a DNA sequence encoding the signal peptide of SNAP, the SNAP sequence, the pro-TEV sites, or the HEV core antigen depicted in FIG. 21, or at least 10, 15, 20, 25, 30, 40, 50, 60, 100, 200, or 300 consecutive amino acids thereof, alone or in combination.

In another embodiment, the vector comprises the DeSNAPuniv-HCV Core antigen cassette having the nucleotide sequence of SEQ ID NO: 174 and/or encoding the amino acid sequence of SEQ ID NO: 175. The vector can comprise a DNA sequence encoding the signal peptide of SNAP, the SNAP sequence, the pro-TEV sites, or the HCV core antigen depicted in FIG. 22, or at least 10, 15, 20, 25, 30, 40, 50, 60, 100, 200, or 300 consecutive amino acids thereof, alone or in combination.

In another embodiment, the vector comprises the DeSNAPuniv-short HCV Core (C) cassette having the nucleotide sequence of SEQ ID NO: 176 and/or encoding the amino acid sequence of SEQ ID NO: 177. The vector can comprise a DNA sequence encoding the signal peptide of SNAP, the SNAP sequence, the pro-TEV sites, or the short form of the HCV core protein depicted in FIG. 23, or at least 10, 15, 20, 25, 30, 40, 50, 60, 100, 200, or 300 consecutive amino acids thereof, alone or in combination.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis C virus (HCV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 90 (corresponding to the SNAP-like/proTEV1/HCV.C/proTEV2/Histag fusion protein).

Thus, in another aspect, the present invention is also drawn to the use of this fusion protein [SNAP-HCV.C] for identifying the presence of the Hepatitis C virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis E virus (HEV.C).

In a preferred embodiment, this vector comprises a so-called "pDeSNAP Univ/HEV.C cassette" i.e., a pDeSNAPUniv DNA cassette as defined above, in which the sequence of the gene of the protein C from Hepatitis E virus has been inserted.

In a preferred embodiment, this vector comprises the pDeSNAP Univ/HEV.C cassette having the nucleotide sequence SEQ ID NO: 150 comprising:

- an insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the C protein from hepatitis E virus (Genbank#AB29196),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis E virus (HEV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 151 (corresponding to the SNAP-like/proTEV1/HEV.C/proTEV2/Histag fusion protein).

Thus, in another aspect, the present invention is also drawn to the use of this fusion protein [SNAP-HEV.C] for identifying the presence of the Hepatitis E virus in a biological sample, for example thanks to the immunoassay of the present invention.

Malaria Antigens In another aspect, the present invention is drawn to a vector for expressing particular Malaria antigens, for example, the MSP-1 and the AMA-1 proteins from *Plasmodium falciparum* (MSP-1+AMA-1) (see Pan W. et al, *The Journal of Immunology*, 2004), in an host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MSP-1 and the AMA-1 proteins from the parasite *Plasmodium falciparum*.

In a preferred embodiment, this vector comprises a so-called "pDeSNAP Univ/MSP-1+AMA-1cassette" i.e., a pDeSNAPUniv DNA cassette as defined above, in which the sequence encoding the MSP-1 and the AMA-1 proteins from the parasite *Plasmodium falciparum* has been inserted.

In a preferred embodiment, this vector comprises the pDeSNAP Univ/MSP-1+AMA-1cassette having the nucleotide sequence SEQ ID NO: 91 comprising:
  an insect BiP sequence of SEQ ID NO: 22,
  the SNAP-like sequence of SEQ ID NO: 31,
  a first DNA sequence SEQ ID NO: 26 encoding the spacer sequence GGGS (SEQ ID NO: 25),
  the DNA sequence encoding the MSP-1 (19) sequence (50% G+C) from *Plasmodium falciparum*,
  a DNA sequence SEQ ID NO: 30 encoding a pro-TEV2 cleavage site of sequence ENLYFQG (SEQ ID NO: 33),
  the DNA sequence encoding the AMA-1 (III) sequence (50% G+C) from *Plasmodium falciparum*,
  a second DNA sequence SEQ ID NO: 26 encoding the spacer sequence GGGS (SEQ ID NO: 25),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MSP-1+AMA-1 protein from *Plasmodium falciparum*. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 92 (corresponding to the SNAP-like/MSP-1/proTEV2/AMA-1/Histag fusion protein).

Thus, in another aspect, the present invention is also drawn to the use of this fusion protein [SNAP-MSP-1+AMA-1] for identifying the presence of the parasite *Plasmodium falciparum* in a biological sample, for example thanks to the immunoassay of the present invention.

Leptospirosis Antigens

In another aspect, the present invention is drawn to a vector for expressing a particular leptospirosis antigen, such as the HbpA, LruA, LruB, or LipL32 protein of *Leptospira* bacteria (see Sivakolundu S. et al, *Journal of Medical Microbiology*, 2012), in a host cell. Preferred vectors are SNAP-Lru A and SNAP-Lru B. Particularly preferred are S2 cell lines containing these vectors. S2/SNAP-Lru A and S2/SNAP-Lru B cell lines were deposited on May 2, 2013, at the Collection Nationale de Cultures de Microorganismes (CNCM), 25, Rue du Docteur Roux, 75724 Paris Cedex 15, France, under numbers CNCM I-4745 and CNCM I-4746, respectively.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the HbpA protein from *Leptospira interrogans* bacteria.

In a preferred embodiment, this vector comprises a so-called "pDeSNAP Univ/HbpA cassette" i.e., a pDeSNAPUniv DNA cassette as defined above, in which the sequence encoding the HbpA protein from *Leptospira* bacteria has been inserted.

In a preferred embodiment, this vector comprises the pDeSNAP Univ/HbpA cassette having the nucleotide sequence SEQ ID NO: 93 comprising:
  an insect BiP sequence of SEQ ID NO: 22,
  the SNAP-like sequence of SEQ ID NO: 31,
  a first DNA sequence SEQ ID NO: 26 encoding the spacer sequence GGGS (SEQ ID NO: 25),
  a DNA sequence SEQ ID NO: 29 encoding a pro-TEV1 cleavage site of sequence ENLYFQS (SEQ ID NO: 32),
  the DNA sequence encoding the modified short form of HbpA (TonB-dependent outer membrane receptor or LB191) from *Leptospira interrogans* serovar Lai str.56601 (Genbank#AA51750.1),
  a DNA sequence SEQ ID NO: 30 encoding a pro-TEV2 cleavage site of sequence ENLYFQG (SEQ ID NO: 33),
  a second DNA sequence SEQ ID NO: 26 encoding the spacer sequence GGGS (SEQ ID NO: 25),
  a DNA sequence SEQ ID NO: 28 encoding a HisTag sequence.

In another embodiment, the vector comprises the DeSNAPuniv-shortLruA (leptospirosis) cassette having the nucleotide sequence of SEQ ID NO: 164 and/or encoding the amino acid sequence of SEQ ID NO: 165. The vector can comprise a DNA sequence encoding the signal peptide of SNAP, the SNAP sequence, the pro-TEV sites, or the modified short forms of LruA depicted in FIG. 17, or at least 10, 15, 20, 25, 30, 40, 50, 60, 100, 200, or 300 consecutive amino acids thereof, alone or in combination.

In another embodiment, the vector comprises the DeSNAPuniv-shortLruB (leptospirosis) cassette having the nucleotide sequence of SEQ ID NO: 166 and/or encoding the amino acid sequence of SEQ ID NO: 167. The vector can comprise a DNA sequence encoding the signal peptide of SNAP, the SNAP sequence, the pro-TEV sites, or the modified short forms of LruB depicted in FIG. 18, or at least 10, 15, 20, 25, 30, 40, 50, 60, 100, 200, or 300 consecutive amino acids thereof, alone or in combination.

In another embodiment, the vector comprises the DeSNAPuniv-LipL32 (leptospirosis) cassette having the nucleotide sequence of SEQ ID NO: 168 and/or encoding the amino acid sequence of SEQ ID NO: 169. The vector can comprise a DNA sequence encoding the signal peptide of SNAP, the SNAP sequence, the pro-TEV sites, or the modified short forms of LipL32 depicted in FIG. 19, or at least 10, 15, 20, 25, 30, 40, 50, 60, 100, 200, or 300 consecutive amino acids thereof, alone or in combination.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the HbpA protein from *Leptospira interrogans* bacteria. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 94 (corresponding to the SNAP-like/proTEV1/HbpA/proTEV2/Histag fusion protein).

Thus, in another aspect, the present invention is also drawn to the use of this fusion protein [SNAP-HbpA] for identifying the presence of the *Leptospira* bacteria in a biological sample, for example thanks to the immunoassay of the present invention.

Microbial Peptides

In another aspect, the present invention is drawn to a vector for expressing a microbial peptide, for example the microbial peptide MUB-40, in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MUB-40 peptide.

In a preferred embodiment, this vector comprises a so-called "pDeSNAP Univ/MUB40 cassette" i.e., a pDeSNAPUniv DNA cassette as defined above, in which the sequence encoding the MUB40 peptide has been inserted.

In a preferred embodiment, this vector comprises the pDeSNAP Univ/MUB40 cassette having the nucleotide sequence SEQ ID NO: 95 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the MUB-40 peptide,
- a DNA sequence SEQ ID NO: 30 encoding a pro-TEV2 cleavage site of sequence ENLYFQG (SEQ ID NO: 33), and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MUB 40 peptide. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 96 (corresponding to the SNAP-like/proTEV1/MUB40/proTEV2/Histag fusion protein).

Thus, in another aspect, the present invention is also drawn to the use of this fusion protein [SNAP-MUB40] for identifying the presence of a ligand in a biological sample, for example thanks to the immunoassay of the present invention.

Lectins Involved in Flavivirus Pathogenesis

In another aspect, the present invention is drawn to vectors for expressing particular lectins involved in Flavivirus pathogenesis, for example the mouse or the human soluble form of C-type like lectin (CLEC5A), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the mouse CLEC5A (mo-CLEC5A) or the human CLEC5A (hu-CLEC5A).

In a preferred embodiment, this vector comprises a so-called "pDeSNAP Univ/mo-CLEC5A cassette" i.e., a pDeSNAPUniv DNA cassette as defined above, in which the sequence encoding the mouse soluble form of C-type like lectin has been inserted.

In a preferred embodiment, this vector comprises the pDeSNAP Univ/mo-CLEC5A cassette having the nucleotide sequence SEQ ID NO: 97 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the mouse soluble form of C-type like lectin (CLEC5A),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25), and
- a DNA sequence SEQ ID NO: 28 encoding a HisTag sequence.

In another aspect, the present invention relates to a recombinant cell which is stably transfected by said vector.

In another preferred embodiment, this vector comprises a so-called "pDeSNAP Univ/hu-CLEC5A cassette" i.e., a pDeSNAPUniv DNA cassette as defined above, in which the sequence encoding the human soluble form of C-type like lectin has been inserted.

In a preferred embodiment, this vector comprises the pDeSNAP Univ/hu-CLEC5A cassette having the nucleotide sequence SEQ ID NO: 99 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the human soluble form of C-type like lectin (CLEC5A),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25), and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the mouse or the human soluble form of C-type like lectin (CLEC5A). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 98 (corresponding to the SNAP-like/proTEV1/mo-CLEC5A/proTEV2/Histag fusion protein) or the amino acid sequence of SEQ ID NO: 100 (corresponding to the SNAP-like/proTEV1/hu-CLEC5A/proTEV2/Histag fusion protein).

Thus, in another aspect, the present invention is also drawn to the use of this fusion protein [SNAP-mo-CLEC5A] or [SNAP-hu-CLEC5A] for detection of presence of flaviviruses in a biological sample, for example thanks to the immunoassay of the present invention.

Anti-Flaviviral Mosquito Proteins

In another aspect, the present invention is drawn to vectors for expressing particular antiviral mosquito proteins, for example the VAGO protein from the Culex species (cxVAGO) or from the *Aedes* species (aaVAGO) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Aedes albopictus* mosquito.

In a preferred embodiment, this vector comprises a so-called "pDeSNAP Univ/aaVAGO cassette" i.e., a pDeSNAPUniv DNA cassette as defined above, in which the sequence encoding the VAGO protein from the *Aedes albopictus* mosquito has been inserted.

In a preferred embodiment, this vector comprises the pDeSNAP Univ/aaVAGO cassette having the nucleotide sequence SEQ ID NO: 103 comprising:
  an insect BiP-like sequence of SEQ ID NO: 152,
  the SNAP-like sequence of SEQ ID NO: 31,
  a DNA sequence SEQ ID NO: 26 encoding the spacer sequence GGGS (SEQ ID NO: 25),
  the DNA sequence encoding the VAGO protein from the *Aedes albopictus* mosquito, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Aedes albopictus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 104 (corresponding to the SNAP-like/aaVAGO/Histag fusion protein).

Thus, in another aspect, the present invention is also drawn to the use of this fusion protein [SNAP-aaVAGO] for identifying the presence of a ligand in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Culex quinquefasciatus* mosquito.

In a preferred embodiment, this vector comprises a so-called "pDeSNAP Univ/cxVAGO cassette" i.e., a pDeSNAPUniv DNA cassette as defined above, in which the sequence encoding the VAGO protein from the *Culex quinquefasciatus* mosquito has been inserted.

In a preferred embodiment, this vector comprises the pDeSNAP Univ/cxVAGO cassette having the nucleotide sequence SEQ ID NO: 101 comprising:
  an insect BiP-like sequence of SEQ ID NO: 152,
  the SNAP-like sequence of SEQ ID NO: 31,
  a DNA sequence SEQ ID NO: 26 encoding the spacer sequence GGGS (SEQ ID NO: 25),
  the DNA sequence encoding the VAGO protein from the *Culex quinquefasciatus* mosquito, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Culex quinquefasciatus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 102 (corresponding to the SNAP-like/cxVAGO/Histag fusion protein).

Thus, in another aspect, the present invention is also drawn to the use of this fusion protein [SNAP-cxVAGO] for identifying the presence of a ligand in a biological sample, for example thanks to the immunoassay of the present invention.

Viral Hemorragic Fever Antigens

In another aspect, the present invention is drawn to vectors for expressing particular viral hemorrhagic fever antigens such as:
  the Nucleoprotein N from the Crimean-Congo virus (CCHF.N), from the Ebola virus (EBO.N), from the Marburg virus (MAR.N), from the Lassa virus (LAS.N), from the Junin virus (JUN.N), from the Machupo virus (MAC.N), from the Sabia virus (SAB.N), or from the Guanarito virus (GUA.N),
  the Ectodomain of GP1 from the Lassa virus (LAS.ectoGP1), from the Junin virus (JUN.ectoGP1), from the Machupo virus (MAC.ectoGP1), from the Sabia virus (SAB.ectoGP1), or from the Guanarito virus (GUA.ectoGP1),
  the Ectodomain of GP2 from the Lassa virus (LAS.ectoGP2), from the Junin virus (JUN.ectoGP2), from the Machupo virus (MAC.ectoGP2), from the Sabia virus (SAB.ectoGP2), or from the Guanarito virus (GUA.ectoGP2),
  the domain III of the envelope E protein from the Omsk virus (OMSK.EDIII), from the Kasyanur virus (KAS.EDIII), or from the Alkhurma virus (ALK.EDIII).

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Crimean-Congo virus (CCHF.N).

In a preferred embodiment, this vector comprises a so-called "pDeSNAP Univ/CCHF.N cassette" i.e., a pDeSNAPUniv DNA cassette as defined above, in which the sequence encoding the Nucleoprotein N from the Crimean-Congo virus has been inserted.

In a preferred embodiment, this vector comprises the pDeSNAP Univ/CCHF.N cassette having the nucleotide sequence SEQ ID NO: 108 comprising:
  an insect BiP sequence of SEQ ID NO: 22,
  the SNAP-like sequence of SEQ ID NO: 31,
  a first DNA sequence SEQ ID NO: 26 encoding the spacer sequence GGGS (SEQ ID NO: 25),
  a DNA sequence SEQ ID NO: 29 encoding a pro-TEV1 cleavage site of sequence ENLYFQS (SEQ ID NO: 32),
  the DNA sequence encoding the Nucleoprotein N from the Crimean-Congo virus, a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Crimean-Congo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 109 (corresponding to the SNAP-like/proTEV1/CCHF.N/proTEV2/Histag fusion protein).

Thus, in another aspect, the present invention is also drawn to the use of this fusion protein [SNAP-CCHF.N] for identifying the presence of the Crimean-Congo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Ebola virus (EBO.N).

In a preferred embodiment, this vector comprises a so-called "pDeSNAP Univ/EBO.N cassette" i.e., a pDeSNAPUniv DNA cassette as defined above, in which the sequence encoding the Nucleoprotein N from the Ebola virus has been inserted.

In a preferred embodiment, this vector comprises the pDeSNAP Univ/EBO.N cassette having the nucleotide sequence SEQ ID NO: 110 comprising:

an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the Nucleoprotein N from the Ebola virus (Genbank#NC_002549),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Ebola virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 111 (corresponding to the SNAP-like/proTEV1/EBO.N/proTEV2/Histag fusion protein).

Thus, in another aspect, the present invention is also drawn to the use of this fusion protein [SNAP-EBO.N] for identifying the presence of the Ebola virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Marburg virus (MAR.N).

In a preferred embodiment, this vector comprises a so-called "pDeSNAP Univ/MAR.N cassette" i.e., a pDeSNAPUniv DNA cassette as defined above, in which the sequence encoding the Nucleoprotein N from the Marburg virus has been inserted.

In a preferred embodiment, this vector comprises the pDeSNAP Univ/MAR.N cassette having the nucleotide sequence SEQ ID NO: 112 comprising:

an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the Nucleoprotein N from the Marburg virus (Genbank#NC_001608),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Marburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 113 (corresponding to the SNAP-like/proTEV1/MAR.N/proTEV2/Histag fusion protein).

Thus, in another aspect, the present invention is also drawn to the use of this fusion protein [SNAP-MAR.N] for identifying the presence of the Marburg virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Lassa virus (LAS.N).

In a preferred embodiment, this vector comprises a so-called "pDeSNAP Univ/LAS.N cassette" i.e., a pDeSNAPUniv DNA cassette as defined above, in which the sequence encoding the Nucleoprotein N from the Lassa virus has been inserted.

In a preferred embodiment, this vector comprises the pDeSNAP Univ/LAS.N cassette having the nucleotide sequence SEQ ID NO: 114 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Lassa virus (Genbank#NC_004296),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 115 (corresponding to the SNAP-like/proTEV1/LAS.N/proTEV2/Histag fusion protein).

Thus, in another aspect, the present invention is also drawn to the use of this fusion protein [SNAP-LAS.N] for identifying the presence of the Lassa virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Junin virus (JUN.N).

In a preferred embodiment, this vector comprises a so-called "pDeSNAP Univ/JUN.N cassette" i.e., a pDeSNAPUniv DNA cassette as defined above, in which the sequence encoding the Nucleoprotein N from the Junin virus has been inserted.

In a preferred embodiment, this vector comprises the pDeSNAP Univ/JUN.N cassette having the nucleotide sequence SEQ ID NO: 116 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Junin virus (Genbank#NC_005081),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 117 (corresponding to the SNAP-like/proTEV1/JUN.N/proTEV2/Histag fusion protein).

Thus, in another aspect, the present invention is also drawn to the use of this fusion protein [SNAPJUN.N] for identifying the presence of the Junin virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Machupo virus (MAC.N).

In a preferred embodiment, this vector comprises a so-called "pDeSNAP Univ/MAC.N cassette" i.e., a pDeSNAPUniv DNA cassette as defined above, in which the sequence encoding the Nucleoprotein N from the Machupo virus has been inserted.

In a preferred embodiment, this vector comprises the pDeSNAP Univ/MAC.N cassette having the nucleotide sequence SEQ ID NO: 118 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Machupo virus (Genbank#NC_005078),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 119 (corresponding to the SNAP-like/proTEV1/MAC.N/proTEV2/Histag fusion protein).

Thus, in another aspect, the present invention is also drawn to the use of this fusion protein [SNAP-MAC.N] for identifying the presence of the Machupo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Guanarito virus (GUA.N).

In a preferred embodiment, this vector comprises a so-called "pDeSNAP Univ/GUA.N cassette" i.e., a pDeSNAPUniv DNA cassette as defined above, in which the sequence encoding the Nucleoprotein N from the Guanarito virus has been inserted.

In a preferred embodiment, this vector comprises the pDeSNAP Univ/GUA.N cassette having the nucleotide sequence SEQ ID NO: 120 comprising:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the Nucleoprotein N from the Guanarito virus (Genbank#NC_005077),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 121 (corresponding to the SNAP-like/proTEV1/GUA.N/proTEV2/Histag fusion protein).

Thus, in another aspect, the present invention is also drawn to the use of this fusion protein [SNAP-GUA.N] for identifying the presence of the Guanarito virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Sabia virus (SAB.N).

In a preferred embodiment, this vector comprises a so-called "pDeSNAP Univ/SAB.N cassette" i.e., a pDeSNAPUniv DNA cassette as defined above, in which the sequence encoding the Nucleoprotein N from the Sabia virus has been inserted.

In a preferred embodiment, this vector comprises the pDeSNAP Univ/SAB.N cassette having the nucleotide sequence SEQ ID NO: 122 comprising:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the Nucleoprotein N from the Sabia virus (Genbank#NC_006317),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 123 (corresponding to the SNAP-like/proTEV1/SAB.N/proTEV2/Histag fusion protein).

Thus, in another aspect, the present invention is also drawn to the use of this fusion protein [SNAP-SAB.N] for identifying the presence of the Sabia virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Omsk virus (OMSK.EDIII).

In a preferred embodiment, this vector comprises a so-called "pDeSNAP Univ/OMSK.EDIII cassette" i.e., a pDeSNAPUniv DNA cassette as defined above, in which the sequence encoding the EDIII protein from the Omsk virus has been inserted.

In a preferred embodiment, this vector comprises the pDeSNAP Univ/OMSK.EDIII cassette having the nucleotide sequence SEQ ID NO: 124 comprising:
an insect BiP-like sequence of SEQ ID NO: 152,
the SNAP-like sequence of SEQ ID NO: 31,
the DNA sequence encoding the EDIII protein of the Omsk virus (Genbank#NC_005062),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Omsk virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 125 (corresponding to the SNAP-like/OMSK.EDIII/Histag fusion protein).

Thus, in another aspect, the present invention is also drawn to the use of this fusion protein [SNAP-OMSK.EDIII] for identifying the presence of the Omsk virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Kyasanur Forest Disease virus (KYA.EDIII).

In a preferred embodiment, this vector comprises a so-called "pDeSNAP Univ/KYA.EDIII cassette" i.e., a pDeSNAPUniv DNA cassette as defined above, in which the sequence encoding the EDIII protein from the Kyasanur Forest Disease virus has been inserted.

In a preferred embodiment, this vector comprises the pDeSNAP Univ/KYA.EDIII cassette having the nucleotide sequence SEQ ID NO: 126 comprising:
  an insect BiP-like sequence of SEQ ID NO: 152,
  the SNAP-like sequence of SEQ ID NO: 31,
  the DNA sequence encoding the EDIII protein of the Kyasanur Forest Disease virus (Genbank#JF416958),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Kyasanur Forest Disease virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 127 (corresponding to the SNAP-like/KYA.EDIII/Histag fusion protein).

Thus, in another aspect, the present invention is also drawn to the use of this fusion protein [SNAP-KYA.EDIII] for identifying the presence of the Kyasanur Forest Disease virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Alkhurma virus (ALK.EDIII).

In a preferred embodiment, this vector comprises a so-called "pDeSNAP Univ/ALK.EDIII cassette" i.e., a pDeSNAPUniv DNA cassette as defined above, in which the sequence encoding the EDIII protein from the Alkhurma virus has been inserted.

In a preferred embodiment, this vector comprises the pDeSNAP Univ/ALK.EDIII cassette having the nucleotide sequence SEQ ID NO: 128 comprising:
  an insect BiP-like sequence of SEQ ID NO: 152,
  the SNAP-like sequence of SEQ ID NO: 31,
  the DNA sequence encoding the EDIII protein of the Alkhurma virus (Genbank#NC_004355),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Alkhurma virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 129 (corresponding to the SNAP-like/ALK.EDIII/Histag fusion protein).

Thus, in another aspect, the present invention is also drawn to the use of this fusion protein [SNAP-ALK.EDIII] for identifying the presence of the Alkhurma virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Lassa virus (LAS.ectoGP1).

In a preferred embodiment, this vector comprises a so-called "pDeSNAP Univ/LAS.ectoGP1 cassette" i.e., a pDeSNAPUniv DNA cassette as defined above, in which the sequence encoding the Glycoprotein GP1 ectodomain from the Lassa virus has been inserted.

In a preferred embodiment, this vector comprises the pDeSNAP Univ/LAS.ectoGP1 cassette having the nucleotide sequence SEQ ID NO: 130 comprising:
  an insect BiP sequence of SEQ ID NO: 22,
  the DNA sequence encoding the Glycoprotein GP1 ectodomain from the Lassa virus (Genbank#NC_004296),
  the SNAP-like sequence of SEQ ID NO: 31, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 131 (corresponding to the SNAP-like/LAS.ectoGP1/Histag fusion protein).

Thus, in another aspect, the present invention is also drawn to the use of this fusion protein [SNAP-LAS.ectoGP1] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Junin virus (JUN.ectoGP1).

In a preferred embodiment, this vector comprises a so-called "pDeSNAP Univ/JUN.ectoGP1 cassette" i.e., a pDeSNAPUniv DNA cassette as defined above, in which the sequence encoding the Glycoprotein GP1 ectodomain from the Junin virus has been inserted.

In a preferred embodiment, this vector comprises the pDeSNAP Univ/JUN.ectoGP1 cassette having the nucleotide sequence SEQ ID NO: 132 comprising:
  an insect BiP sequence of SEQ ID NO: 22,
  the DNA sequence encoding the Glycoprotein GP1 ectodomain from the Junin virus (Genbank#NC_005081), the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 133 (corresponding to the SNAP-like/JUN.ectoGP1/Histag fusion protein).

Thus, in another aspect, the present invention is also drawn to the use of this fusion protein [SNAP-JUN.ectoGP1] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Machupo virus (MAC.ectoGP1).

In a preferred embodiment, this vector comprises a so-called "pDeSNAP Univ/MAC.ectoGP1 cassette" i.e., a pDeSNAPUniv DNA cassette as defined above, in which the sequence encoding the Glycoprotein GP1 ectodomain from the Machupo virus has been inserted.

In a preferred embodiment, this vector comprises the pDeSNAP Univ/MAC.ectoGP1 cassette having the nucleotide sequence SEQ ID NO: 134 comprising:
an insect BiP sequence of SEQ ID NO: 22,
the DNA sequence encoding the Glycoprotein GP1 ectodomain from the Machupo virus (Genbank#NC_005078),
the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 135 (corresponding to the SNAP-like/MAC.ectoGP1/Histag fusion protein).

Thus, in another aspect, the present invention is also drawn to the use of this fusion protein [SNAP-MAC.ectoGP1] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Guanarito virus (GUA.ectoGP1).

In a preferred embodiment, this vector comprises a so-called "pDeSNAP Univ/GUA.ectoGP1 cassette" i.e., a pDeSNAPUniv DNA cassette as defined above, in which the sequence encoding the Glycoprotein GP1 ectodomain from the Guanarito virus has been inserted.

In a preferred embodiment, this vector comprises the pDeSNAP Univ/GUA.ectoGP1 cassette having the nucleotide sequence SEQ ID NO: 136 comprising:
an insect BiP sequence of SEQ ID NO: 22,
the DNA sequence encoding the Glycoprotein GP1 ectodomain from the Guanarito virus (Genbank#NC_005077),
the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 137 (corresponding to the SNAP-like/GUA.ectoGP1/Histag fusion protein).

Thus, in another aspect, the present invention is also drawn to the use of this fusion protein [SNAP-GUA.ectoGP1] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Sabia virus (SAB.ectoGP1).

In a preferred embodiment, this vector comprises a so-called "pDeSNAP Univ/SAB.ectoGP1 cassette" i.e., a pDeSNAPUniv DNA cassette as defined above, in which the sequence encoding the Glycoprotein GP1 ectodomain from the Sabia virus has been inserted.

In a preferred embodiment, this vector comprises the pDeSNAP Univ/SAB.ectoGP1 cassette having the nucleotide sequence SEQ ID NO: 138 comprising:
an insect BiP sequence of SEQ ID NO: 22,
the DNA sequence encoding the Glycoprotein GP1 ectodomain from the Guanarito virus (Genbank#NC_006317),
the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 139 (corresponding to the SNAP-like/SAB.ectoGP1/Histag fusion protein).

Thus, in another aspect, the present invention is also drawn to the use of this fusion protein [SNAP-SAB.ectoGP1] for identifying the presence of the Sabia virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Lassa virus (LAS.ectoGP2).

In a preferred embodiment, this vector comprises a so-called "pDeSNAP Univ/LAS.ectoGP2 cassette" i.e., a pDeSNAPUniv DNA cassette as defined above, in which the sequence encoding the Glycoprotein GP2 ectodomain from the Lassa virus has been inserted.

In a preferred embodiment, this vector comprises the pDeSNAP Univ/LAS.ectoGP2 cassette having the nucleotide sequence SEQ ID NO: 140 comprising:
- an insect BiP sequence of SEQ ID NO: 22,
- the DNA sequence encoding the Glycoprotein GP2 ectodomain from the Lassa virus (Genbank#NC_004296),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 141 (corresponding to the SNAP-like/LAS.ectoGP2/Histag fusion protein).

Thus, in another aspect, the present invention is also drawn to the use of this fusion protein [SNAP-LAS.ectoGP2] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Junin virus (JUN.ectoGP2).

In a preferred embodiment, this vector comprises a so-called "pDeSNAP Univ/JUN.ectoGP2 cassette" i.e., a pDeSNAPUniv DNA cassette as defined above, in which the sequence encoding the Glycoprotein GP2 ectodomain from the Junin virus has been inserted.

In a preferred embodiment, this vector comprises the pDeSNAP Univ/JUN.ectoGP2 cassette having the nucleotide sequence SEQ ID NO: 142 comprising:
- an insect BiP sequence of SEQ ID NO: 22,
- the DNA sequence encoding the Glycoprotein GP2 ectodomain from the Junin virus (Genbank#NC_005081),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 143 (corresponding to the SNAP-like/JUN.ectoGP2/Histag fusion protein).

Thus, in another aspect, the present invention is also drawn to the use of this fusion protein [SNAPJUN.ectoGP2] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Machupo virus (MAC.ectoGP2).

In a preferred embodiment, this vector comprises a so-called "pDeSNAP Univ/MAC.ectoGP2 cassette" i.e., a pDeSNAPUniv DNA cassette as defined above, in which the sequence encoding the Glycoprotein GP2 ectodomain from the Machupo virus has been inserted.

In a preferred embodiment, this vector comprises the pDeSNAP Univ/MAC.ectoGP2 cassette having the nucleotide sequence SEQ ID NO: 144 comprising:
- an insect BiP sequence of SEQ ID NO: 22,
- the DNA sequence encoding the Glycoprotein GP2 ectodomain from the Machupo virus (Genbank#NC_005078),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 145 (corresponding to the SNAP-like/MAC.ectoGP2/Histag fusion protein).

Thus, in another aspect, the present invention is also drawn to the use of this fusion protein [SNAP-MAC.ectoGP2] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Guanarito virus (GUA.ectoGP2).

In a preferred embodiment, this vector comprises a so-called "pDeSNAP Univ/GUA.ectoGP2 cassette" i.e., a pDeSNAPUniv DNA cassette as defined above, in which the sequence encoding the Glycoprotein GP2 ectodomain from the Guanarito virus has been inserted.

In a preferred embodiment, this vector comprises the pDeSNAP Univ/GUA.ectoGP2 cassette having the nucleotide sequence SEQ ID NO: 146 comprising:

an insect BiP sequence of SEQ ID NO: 22,
the DNA sequence encoding the Glycoprotein GP2 ectodomain from the Guanarito virus (Genbank#NC_005077),
the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 147 (corresponding to the SNAP-like/GUA.ectoGP2/Histag fusion protein).

Thus, in another aspect, the present invention is also drawn to the use of this fusion protein [SNAP-GUA.ectoGP2] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Sabia virus (SAB.ectoGP2).

In a preferred embodiment, this vector comprises a so-called "pDeSNAP Univ/SAB.ectoGP2 cassette" i.e., a pDeSNAPUniv DNA cassette as defined above, in which the sequence encoding the Glycoprotein GP2 ectodomain from the Sabia virus has been inserted.

In a preferred embodiment, this vector comprises the pDeSNAP Univ/MAC.ectoGP2 cassette having the nucleotide sequence SEQ ID NO: 148 comprising:
an insect BiP sequence of SEQ ID NO: 22,
the DNA sequence encoding the Glycoprotein GP2 ectodomain from the Sabia virus (Genbank#NC_006317),
the SNAP-like sequence of SEQ ID NO: 31, and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 149 (corresponding to the SNAP-like/SAB.ectoGP2/Histag fusion protein).

Thus, in another aspect, the present invention is also drawn to the use of this fusion protein [SNAP-SAB.ectoGP2] for identifying the presence of the Sabia virus in a biological sample, for example thanks to the immunoassay of the present invention.

EXAMPLES

In the context of the invention, a multiplex bead-based immunoassay was developed for rapid and simultaneous detection of antibodies to arboviruses in biological fluids.

The system is based on the xMAP technology (Luminex corporation) and uses a mixture of antigen-coated microspheres as capture reagents for specific human immunoglobulins. Distinct sets of microspheres (Magplex, Luminex corporation) were coupled with purified AGT fusion proteins, namely the SNAP-tagged viral recombinant proteins: sSNAP-DV1.EDIII, sSNAP-DV2.EDIII, sSNAP-DV3.EDIII, sSNAP-DV4.EDIII, sSNAP-WN.EDIII, sSNAP-JE.EDIII, sSNAP-USU.EDIII, sSNAP-TBE.EDIII, sSNAP-YF.EDIII, sSNAP-MVE.EDIII, sSNAP-Rocio.EDIII, sSNAP-WSL.EDIII, sSNAP-ZIKA.EDIII, SNAP-DV1ectoM, sSNAP-N.RVF, sSNAP-N.TOS, and CHIK.sE2-SNAP. Recombinant antigens were covalently coupled to the carboxyl microsphere surface using a substrate of the AGT protein as linker (BG-PEG-NH2, New England Biolabs), thereby enhancing antibody capture efficiency as compared to standard amine coupling procedures.

Technical validation using anti-SNAP-tag antibodies and specific mouse monoclonal antibodies confirmed coupling efficiency and demonstrated long-term antigen stability (up to six month). This application is not limited to viral antigens as any peptide or polypeptide can be used for bead coating and subsequent antibody capture.

I. Material and Methods
1. The following buffers and solutions are used:
a) PBS buffer: 100 mL of 10×PBS, pH 7.4 in 1 L H2O sterile
b) SNAP coupling buffer (PBS-DTT): 100 mL of 10×PBS, pH 7.4, 0.5 mL 10% tween 20, 1 mL of 1.0 M DTT, in 1 L H$_2$O sterile
c) blocking/assay buffer (PBS-B): PBS, 1% BSA, pH 7.4 in 1 L H$_2$O sterile
d) storage buffer (PBS-TBN): 100 mL of 10×PBS, 1 g of BSA, 2 mL of 10% tween 20, 500 mg of sodium azide, 1 mL of 1.0M DTT, in 1 L H$_2$O sterile
e) Substrate solution (4 mg/mL): 2 mg of BG-PEG-NH$_2$, DMSO 200 µL.
f) Activation solution (EDAC/SNHS): 50 mg/mL of EDAC solution or 50 mg/mL of SNSHS in distilled water
2. The following materials were used:
2.1. MagPlex Luminex microspheres: MC 100XX-ID (where XX is the fluorescence region), XX can be e.g. 26, 27, 28, 29, 34, 35, 36, 37, 45, 52, 53, 63, 64, as mentioned on FIG. 7B
2.2. hAGT substrate: PEG-BG-NH$_2$ (NEB S9150S)

2.3. Fusion proteins SNAP-viral EDIII:

The generation of a fusion protein comprising AGT and viral EDIII moieties is well-known to the skilled person. Every known synthesis process can be used for this purpose, provided that the AGT enzyme remains active in the fusion protein.

In the present case, the AGT mutant SNAP of SEQ ID NO: 2 has been used and SNAP-viral EDIII fusion proteins have been generated.

The *Drosophila* S2 inducible expression system (DES, Invitrogen), has been chosen for the mass production of individual EDIII from flaviviruses in non-vertebrate cells and the plasmid pMT/BiP/V5-HisA from Invitrogen has been used.

This plasmid contains:
The metallothionein promoter pMT,
An insect ssBiP sequence of SEQ ID NO: 22,
Bgl II and Age I restriction sites,
the DNA of SEQ ID NO: 28 encoding a $His_6$tag located downstream of the AgeI restriction site, and
the DNA spacer sequence of SEQ ID NO: 26 located between the AgeI restriction site and the DNA encoding a $His_6$tag.

The synthetic genes coding for the full-length domain III of the E proteins from flaviviruses WN, USU, JE, TBE, DEN-1 to DEN-4, YF, Rocio, MVE, Zika, SLE, and WSL are listed in SEQ ID NO: 3 to SEQ ID NO: 14. The ED III amino acid sequences were fused in frame to the C-terminus of the SNAP protein, with both moieties being separated by a linker GGGS (SEQ ID NO: 25). The DNA sequences encoding SNAP-EDIII were inserted in the plasmid pMT/BiP/V5-Histag (Invitrogen) to generate the plasmids pMT/BiP/SNAP/EDIII/Histag.

The resulting plasmids pMT/BiP/SNAP-EDIII-Histag, which can drive the expression of secreted SNAP-EDIII-$His_6$ fusion proteins, were co-transfected with selection marker pCo-Blast into S2 cells to generate the stable S2/sS-NAP-ED III-Histag cell line showing resistance to blasticidine.

Stable S2 cell lines grown in spinner (1000 ml) were stimulated 10 days with heavy metal cadmium ($Cd^{2+}$) and proteins from extracellular medium were concentrated and purified.

Accumulation of secreted SNAP-tagged EDIII protein was observed in the supernatants of stable S2/sSNAP-EDIII-Histag cells after 10 days of induction with heavy metal cadmium.

The proteins SNAP-DEN1.EDIII of SEQ ID NO: 21, SNAP-DEN2.EDIII of SEQ ID NO:X, SNAP-DEN3.EDIII of SEQ ID NO:X, SNAP-DEN4.EDIII of SEQ ID NO:X, SNAP-WN.EDIII of SEQ ID NO:X, SNAP-JE.EDIII of SEQ ID NO:X, SNAP-YF.EDIII of SEQ ID NO:X, SNAP-MVE.EDIII of SEQ ID NO:X, SNAP-Rocio.EDIII of SEQ ID NO:X, SNAP-WSL.EDIII of SEQ ID NO:X, SNAP-ZIKA.EDIII of SEQ ID NO:X, SNAP-SLE.EDIII of SEQ ID NO:X have been produced accordingly.

3. Preparation of the Antigen-Coupled Beads

The production of antigen-coupled beads comprised two steps: functionalization of microsphere surfaces with an $O^6$-benzylguanine derivative (BG-PEG-amino), and covalent immobilization of the chimeric SNAP-viral Ags proteins using the BG-PEG-amino as an anchor (FIG. 1). The carboxyl microsphere surfaces were covalently coated with BG-PEG-amino substrate using an optimized two-step carbodiimide process (Wong et al *Journal of Clinical Microbiology* 42(1): 65-72, 2004). Subsequently, coupled BG-PEG-amino compounds were irreversibly linked to the chimeric SNAP-viral Ags proteins by transfer of the benzyl group to the active site cysteine of the SNAP protein. Due to the high specificity of this reaction, the fusion protein is exclusively coupled via the SNAP domain, leaving the viral antigen accessible for interactions with antibodies.

3.1. First, the commercial beads were activated as per the manufacturer instructions (by using the EDAC and SNHS activation solutions), and washed in a PBS buffer. All the steps were performed in darkness so as to prevent the fluorescent quenching of the beads, according to the manufacturer instructions.

About $1.25 \times 10^6$ beads were used for each coupling process.

3.2. The AGT substrate PEG-BG-$NH_2$ in the DMSO solution was then added overnight at room temperature on the activated beads, and subsequently washed with PBS buffer.

3.3. The unbound carboxylic sites were then blocked with the blocking buffer for 30 minutes at room temperature, and the beads subsequently washed with the SNAP coupling buffer.

3.4. SNAP-EDIII proteins resuspended in the SNAP coupling buffer (100 µg/mL) were incubated with the thus obtained beads for two hours at room temperature, and then washed once with the SNAP coupling buffer, and three times with the storage buffer (PBS-TBN).

4. Microsphere Fluorescence Immunoassays

The bead sets, conjugated with different SNAP-viral Ags, were mixed by vortex to ensure total bead dispersal. After adjusting the bead density to 100 beads/µL, 25 µl of each of the bead sets (containing 2500 microspheres) were transferred to a 96-well microtiter plate (Bio-Plex Pro flat bottom plate, BioRad) in separate wells for singleplex assays, or mixed in the same wells for multiplex assays. The microspheres were washed 2 times with 100 µL washing buffer (BioPlex Wash buffer, BioRad) using a microplate wash station for magnetic beads (BioPlex Pro Wash Station, BioRad). The samples (antibodies or sera) were diluted in assay buffer (PBS-BSA) and 50 µl, of the resulting solutions were added to the test wells containing the conjugated beads. After incubation in darkness on a plate shaker for 30 min, the plate was washed 3 times. Subsequently, a fluorochrome-labeled secondary antibody was diluted in assay buffer (PBS-BSA) at 2 µg/mL, and 50 µL of the resulting solutions were added to the test wells containing the conjugated beads. After incubation in darkness on a plate shaker for 30 min, the plate was washed as previously. Finally, streptavidin-phycoerythrin (SAPE, Invitrogen Molecular Probes) was diluted in assay buffer (PBS-BSA) at 2 µg/ml, and 50 µL of the resulting solution was added to the microplate wells. The plate was incubated in darkness on a plate shaker for 10 min and washed as previously, before resuspending the contents of the wells in 125 µl of assay buffer. The median fluorescence intensity (MFI) of the detection antibody bound to the individual microspheres was evaluated from flow analysis of 50 microspheres per well using a dual-laser flow analyzer (BioPlex 200 instrument, BioRad). The fluorescent detection instrument is equipped with a first laser for detecting the type of bead, and a second to ensure the quantification of captured IgM or IgG by exciting the fluorophore (red-phycoerythrin) conjugated to the specific detection antibody.

4.1 Confirmation of Antigen Coupling

Antigen coupling was confirmed by testing the antigen-coupled microspheres with dilutions of rabbit anti-SNAP-tag polyclonal antibody (GenScript). The fluorescence immunoassays were performed in singleplex format, as described above. A two-fold dilution series of anti-SNAP antibody starting at 4000 ng/mL and ending at 3.9 ng/mL was performed in PBS-BSA, and volumes of each dilution were added to the test wells containing the beads. A biotin-conjugated goat anti-rabbit IgG (2 µg/mL in 50 µl, PBS-BSA) was used as secondary antibody to detect bound anti-SNAP antibodies.

FIG. 2 shows the fluorescence results observed for the detection of anti-SNAP antibody on 8 different sets of microspheres coupled to chimeric SNAP-viral antigens proteins (SNAP-DV1.EDIII, SNAP-DV2.EDIII, SNAP.DV3.EDIII, SNAP.DV4.EDIII, SNAP-WNV.EDIII, SNAP-YF.EDIII, SNAP-JE.EDIII, SNAP-TBE.EDIII).

4.2 Detection of Specific Antibodies

The capture and detection of specific antibodies by the antigen-conjugated microspheres was assessed using purified monoclonal mouse antibodies (anti-WNV, anti-DV1 and anti-DV2) and polyclonal mouse sera (anti-DV3, anti-DV4, anti-YF and anti-JE) or human sera (anti-DV1). The fluorescence immunoassays were performed in singleplex and multiplex format, as described above. A four-fold dilution series of purified mouse monoclonal antibodies starting at 400 ng/mL and ending at 0.1 ng/mL, and of mouse and human sera starting at 1:25 and ending at 1:102400, was performed in PBS-BSA, and volumes of each dilution were added to the test wells containing the beads. A biotin-conjugated goat anti-mouse IgG (2 µg/mL in 50 µl, PBS-BSA), was used as secondary antibody to detect bound monoclonal and polyclonal mouse antibodies. A biotin-conjugated goat anti-human IgM (2 µg/mL in 50 µl, PBS-BSA) or a biotin-conjugated goat anti-human IgG (2 µg/mL in 50 µl, PBS-BSA), was used to detect bound IgM or IgG antibodies in human serum, respectively.

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through Bio-Plex Amine Coupling Kit, BIORAD.

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex format with other chimeric SNAP-viral Ags proteins (SNAP-DV2.EDIII, SNAP.DV3.EDIII, SNAP.DV4.EDIII, SNAP-WNV, SNAP-YF, SNAP-JE, SNAP-TBE) coupled to microspheres.

FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE) coupled to microspheres.

FIG. 6 shows the reactivity and specificity of anti-DV3 IgG detection in mouse polyclonal serum against DV3 (A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA) coupled to microspheres.

FIG. 7 shows the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA, SNAP-TBE) coupled to microspheres.

II. Results

The system of the invention uses a mixture of antigen-coated Magplex microspheres (Luminex Corporation) as capture reagents for specific human immunoglobulins. Each set of internally color-coded microspheres have been coupled to a specific recombinant antigen and mixed with other types of microspheres in a small sample volume. The power of this system lies in the fact that it is possible to simultaneously analyze up to 100 types of coupled microspheres per well using a flow analysis tool. The fluorescent detection instrument is equipped with a first laser for detecting the type of bead, and a second to ensure the quantification of captured IgM or IgG by exciting the fluorophore (phycoerythrin) conjugated to the specific detection antibody. With its extensive multiplexing capabilities and lower limit of detection, this approach offers substantial cost and sample savings over traditional ELISA measurements.

Presently, 16 distinct sets of microspheres have been coupled with purified chimeric SNAP-viral Ags proteins, allowing titration of serum antibodies specific to dengue serotypes 1 to 4, West Nile, Yellow fever, Japanese encephalitis, tick-borne encephalitis, Saint-Louis encephalitis, Murray Valley encephalitis, Wesselsbron, Zika, Rocio, Usutu, Rift Valley fever, and Chikungunya virus. The production of the system is highly time- and cost-effective, as only a very small amount of recombinant antigen (<50 µg) is required to produce one set of antigen-coupled microspheres (~1.25× $10^6$ microspheres), sufficient to perform 1000 individual assays. Moreover, the selected sets of microspheres are adaptable to an affordable, compact, and robust fluorescent detection system such as the MagPix (Luminex Corporation).

The evaluation of antigen coupling using an anti-SNAP antibody (FIG. 2) confirmed the coupling efficiency and demonstrated that the relative quantities of bound antigens are comparable between the different coupled microsphere sets. The assessment of antibody capture and detection using purified mouse antibodies showed enhanced capture of specific antibodies by the produced antigen-coupled microspheres as compared to antigen-coupled microspheres obtained by standard amine coupling procedures (FIG. 3). In addition, it demonstrated the low detection limit of the method and confirmed that multiplexing does not affect antibody detection (FIG. 4). Additionally, the antigen-conjugated microspheres exhibited long-term stability when stored at 4° C. (>6 months). Finally, the specificity of each set of coupled microspheres in multiplex immunoassays was demonstrated for purified mouse monoclonal antibodies (FIG. 5), for IgG antibodies in polyclonal mouse sera (FIGS. 6A-B) and for both IgM and IgG antibodies in polyclonal sera from infected humans (FIG. 7).

With its extensive multiplexing capabilities (up to 100 types of coupled microspheres per well) and lower limit of detection, this approach offers substantial cost and sample savings over traditional ELISA measurements.

III. Generation of a Fusion Protein Comprising SNAP and the N Nucleoprotein of the Schmallenberg Virus 1. Construction of the vectors Encoding the Fusion Protein SNAP-SBV.N The chimeric fusion protein comprising SNAP and the N nucleoprotein of the Schmallenberg virus has been obtained as follows:

In a first step, the sequence of the open reading frame of the S segment encoding the N nucleoprotein and the NSs protein of the BH80/11-4 strain was mutated by inserting an EcoRV restriction site at its 5' terminus and an XmaI restriction site at its 3' terminus. In addition, the internal EcoRV restriction site was removed by mutating the 294T nucleotide into 294A. This mutated sequence is shown on SEQ ID NO: 17.

This mutated sequence was then inserted into the EcoRV and XmaI restriction sites of the pDeSNAP Univ cassette of SEQ ID NO: 34, generating the "pDeSNAP Univ/SBV.N" DNA cassette of SEQ ID NO: 36.

The so-called "pDeSNAP Univ/SBV.N" DNA cassette comprises (see FIG. 9 and SEQ ID NO: 36):
- the insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

Note that this cassette comprises in addition an NheI site upstream of the ATG, a Bg/II site between the BiP-like sequence and the SNAP-like sequence, and an AgeI site and a HindIII site which are both located downstream of the stop codon.

The sequence comprised between the Bg/II and AgeI restriction sites of the pDeSNAPUniv/SBV.N cassette (see FIG. 9) was excised by enzymatic digestion, then cloned into the pMT/BiP/V5-A plasmid (Invitrogen) to generate the pMT/BiP/SNAP-SBV.N vector. This vector has been used to generate stable S2 cells secreting the SNAP-SBV.N fusion protein.

The sequence comprised between the NheI and NotI restriction sites of the pDeSNAPUniv/SBV.N cassette is then cloned into the pcDNA3 plasmid (Invitrogen) to generate the pcDNA3/SNAP-SBV.N vector. This vector is then used to generate stable mammalian cells secreting the SNAP-SBV.N fusion protein.

2. Production of the Fusion Protein SNAP-SBV.N

The resulting plasmids pMT/BiP/SNAP-SBV.N that allow the production of SNAP-tagged SBV.N proteins as secreted fusion proteins, were co-transfected with selection marker pCo-Blast into S2 cells to generate the stable S2/SNAP-SBV.N cell line showing resistance to blasticidine.

This cell line has been deposited to the Collection Nationale de Cultures de Microorganismes (CNCM) of the Institut Pasteur, 25, rue du Docteur Roux, 75724 PARIS CEDEX 15, under the number CNCM 1-4616.

Stable S2 cell lines grown in spinner (1000 ml) were stimulated 10 days with heavy metal cadmium ($Cd^{2+}$).

Accumulation of secreted SNAP-SBV.N protein was observed in the supernatants of the S2/SNAP-SBV.N cells after 10 days of induction with heavy metal cadmium.

Figure 10A:
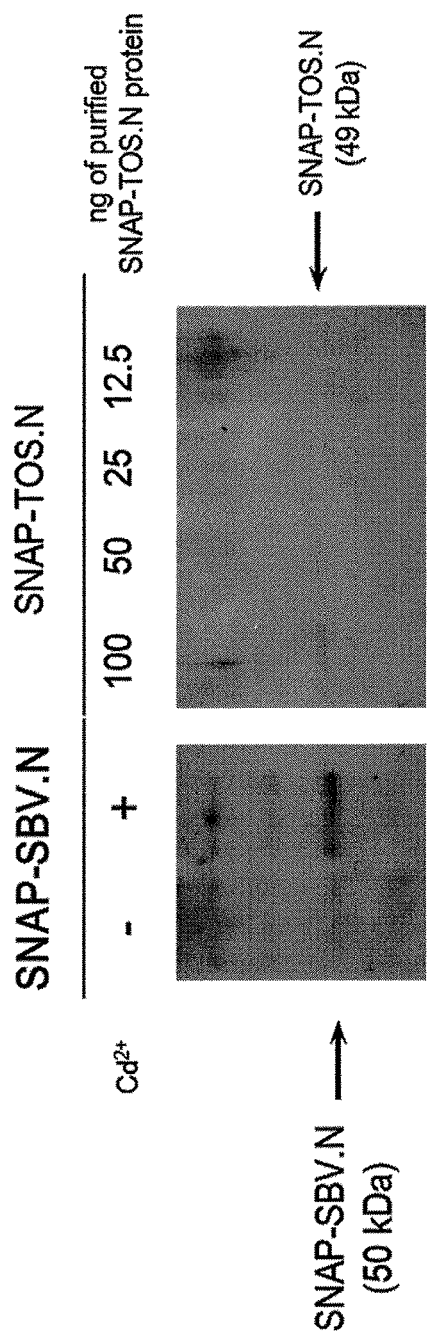

0.01 mL from 4 mL of supernatant of S2/SNAP-SBV.N cells induced 10 days with $Cd^{2+}$ were tested by immunoblot assay using anti-Histag antibody (dilution 1:1,000) (see FIG. 10).

The chimeric protein SNAP-SBV.N was compared with defined amounts of the SNAP-TOS.N chimeric protein (corresponding to the fusion protein comprising SNAP and the N nucleoprotein from the Toscana virus, which is a phlebovirus).

Figure 10B:
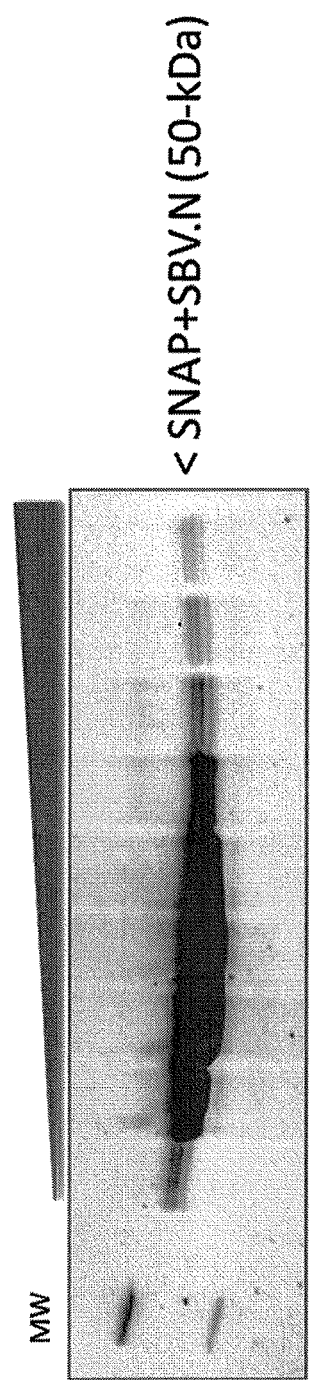

The production of purified SNAP-SBV.N from induced S2/SNAP+SBV.N cells for 10 days is 18 mg per liter of cell culture (FIG. 10B).

BIBLIOGRAPHIC REFERENCES

Avrameas S. *Immunol. Today* 1991 May; 12(5):154-9.
Zimmerman C W, *Electrophoresis* 1995; June; 16(6):941-7.
Kim H-J. *The Journal of Veterinary Medical Science*, 2011
Damoiseaux et al., *ChemBiochem.* 4:285-287, 2001
Xu-Welliver et al., Biochemical Pharmacology 58: 1279-85, 1999
Lim A. et al, EMBO J. 15: 4050-4060, 1996;
Daniels D. S. et al, EMBO J. 19: 1719-1730, 2000;
Juillerat A. et al, *Chemisty & Biology*, vol.10, 313-317, 2003
Wong et al Journal of Clinical Microbiology 42, no. 1 (January 2004): 65-72
Wibley J. E. A. et al, 2000
Felgner et al., *Proc. Natl. Acad. Sci. U.S.A.*, 84:7413-7417, 1987
Mackey et al., *Proc. Natl. Acad. Sci. U.S.A.*, 85:8027-8031, 1988
Wu et al., *J. Biol. Chem.*, 267:963-967, 1992;
Wu and Wu, *J. Biol. Chem.*, 263:14621-14624, 1988;
Williams et al., *Proc. Natl. Acad. Sci. U.S.A.*, 88:2726-2730, 1991
Kolpe A. B. et al, *Virus Research* 2012; 168:64-72
Pan W. et al, *The Journal of Immunology*, 2004), 172: 6167-6174
Sivakolundu S. et al, *Journal of Medical Microbiology*, 2012

---

The invention claimed is:

1. An in vitro assay method for detecting at least two different target antibodies present in a biological sample from a subject, said method comprising the steps of:
(a) contacting a mixture of at least 2 solid supports with a biological sample from a subject comprising a mixture of human antibodies;
wherein one of the solid supports comprises a first 6-alkylguanine-DNA-alkyltransferase-antigen fusion protein covalently coupled to a 6-alkylguanine-DNA-alkyltransferase-antigen substrate, and
wherein another of the solid supports comprises a second 6-alkylguanine-DNA-alkyltransferase-antigen fusion protein covalently coupled to a 6-alkylguanine-DNA-alkyltransferase-antigen substrate;
wherein said antigen is an epitope of a viral protein from a virus selected from: Dengue virus 1, Dengue virus 2, Dengue virus 3, Dengue virus 4, West Nile virus, Yellow Fever virus, Japanese encephalitis virus of genotype 1, 2, 4, or 5, Zika virus, Wesselbron virus, Rocio virus, Murray encephalitis virus Saint-Louis encephalitis virus, and Rabensburg virus;

(b) detecting the presence or absence of binding of antibodies to the first 6-alkylguanine-DNA-alkyltransferase-antigen fusion protein by detecting the binding or lack of binding of one of the two target antibodies to the first fusion protein; and (c) detecting the presence or absence of binding of antibodies to the second 6-alkylguanine-DNA-alkyltransferase-antigen fusion protein by detecting the binding or lack of binding of the second of the two target antibodies to the second fusion protein.

2. The assay method of claim 1, wherein a mixture of at least 15 solid supports is used in step (a).

3. The assay method of claim 1, wherein both 6-alkylguanine-DNA-alkyltransferase-antigen fusion proteins comprise the amino acid sequence of SEQ ID NO:2.

4. The assay method of claim 1, wherein said solid supports are microparticles.

5. The assay method of claim 1, wherein said solid supports are magnetic.

6. The assay method of claim 1, wherein said solid supports are microparticles internally labeled with fluorescent dyes.

7. The assay method of claim 1, wherein each of the solid supports emits a different and distinguishable wave length after excitation.

8. The assay method of claim 1, wherein the mixture of at least 2 solid supports further comprises a third solid support comprising a 6-alkylguanine-DNA-alkyltransferase-antigen fusion protein comprising an epitope of the E2 protein of the Chikungunya virus.

9. The assay method of claim 1, wherein said biological sample is serum or plasma.

* * * * *